(12) United States Patent
Mason

(10) Patent No.: US 8,722,587 B2
(45) Date of Patent: May 13, 2014

(54) SINGLE CHAIN FRAGMENT VARIABLE ANTIBODY LIBRARIES AND USES THEREOF

(75) Inventor: Nicola Mason, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 313 days.

(21) Appl. No.: 12/936,981

(22) PCT Filed: Apr. 8, 2009

(86) PCT No.: PCT/US2009/039941
§ 371 (c)(1),
(2), (4) Date: Dec. 28, 2010

(87) PCT Pub. No.: WO2009/126730
PCT Pub. Date: Oct. 15, 2009

(65) Prior Publication Data
US 2011/0158997 A1     Jun. 30, 2011

Related U.S. Application Data

(60) Provisional application No. 61/071,040, filed on Apr. 9, 2008.

(51) Int. Cl.
*C40B 50/06*     (2006.01)
(52) U.S. Cl.
USPC .......................................................... 506/26
(58) Field of Classification Search
None
See application file for complete search history.

(56) References Cited

U.S. PATENT DOCUMENTS 6,342,587 B1     1/2002    Barbas et al.

FOREIGN PATENT DOCUMENTS

WO     WO 01/42308 A1     6/2001

OTHER PUBLICATIONS

Tang et al. (2001) Veterinary Immunology and Immunopathology vol. 80 pp. 259 to 270.*
Kho et al. Genbank: D1157191. Feb. 21, 2008 [Retrieved on Oct. 12, 2009]. Retrieved from the internet: <URL:http://www.ncbi.nlm.nih.gov/nuccore/168448552>.. Especially p. 1 nucleotides 337-411.

* cited by examiner

*Primary Examiner* — Christian Boesen
(74) *Attorney, Agent, or Firm* — Mark S. Cohen; Pearl Cohen Zedek Latzer Baratz LLP

(57) ABSTRACT

The invention is generally directed to antibody variable domains or antibodies, libraries of antibody variable domains or antibodies, methods of making said antibodies and libraries, and methods of treatment comprising administering the generated antibody variable domains or antibodies. Specifically, the invention is directed to novel primer nucleotide sequences that are used to amplify all rearranged sequences of canine variable heavy (VH) and variable light (VL) immunoglobulin chains that have been used in naturally occurring antibody responses. These novel sequences contain canine framework regions and complementarity determining regions which may be used to canine-ize antibodies. Further, these sequences are useful for the identification and targeting of viral and bacterial pathogens, and tumor-associated antigens.

11 Claims, 4 Drawing Sheets

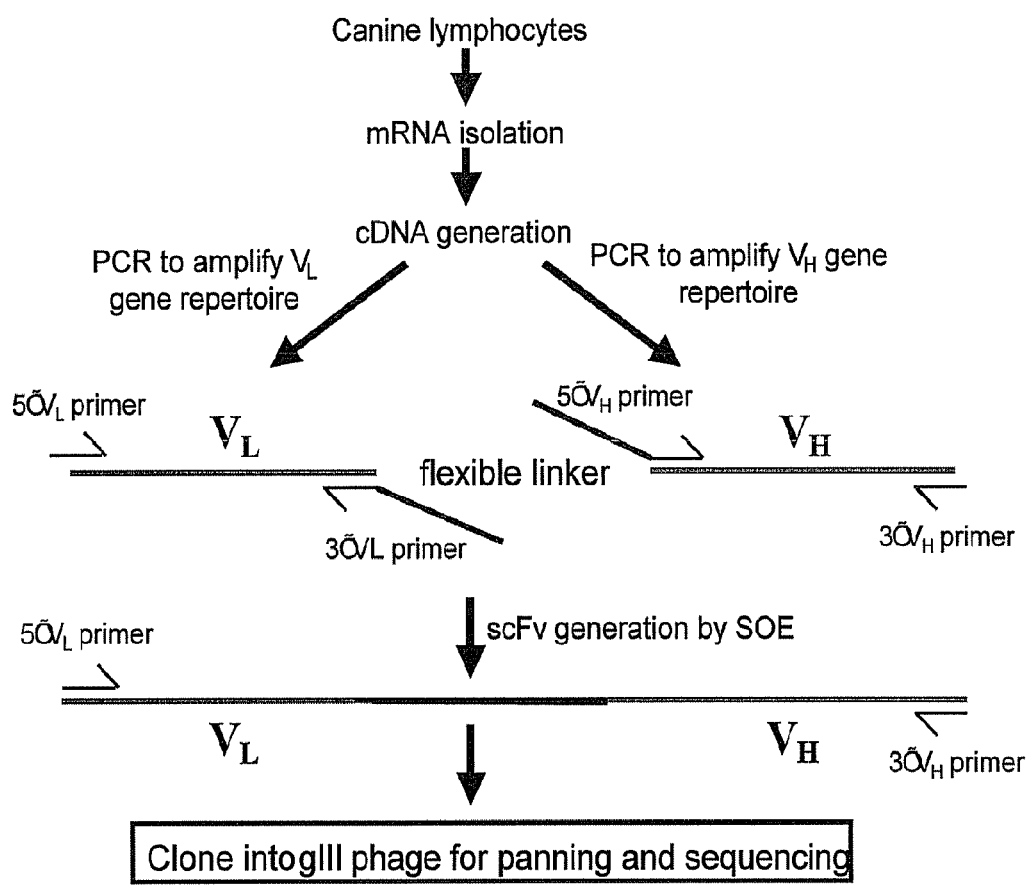
Figure 3
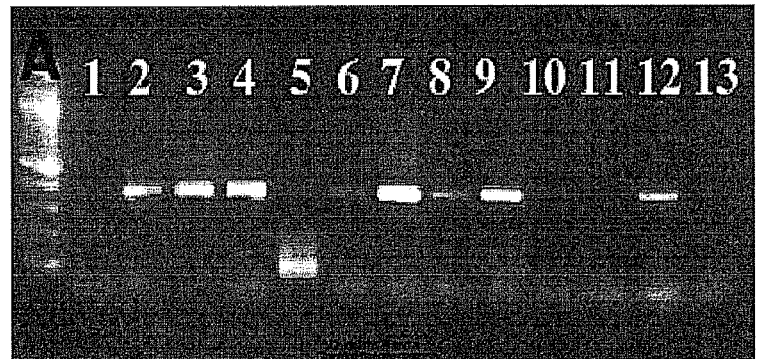
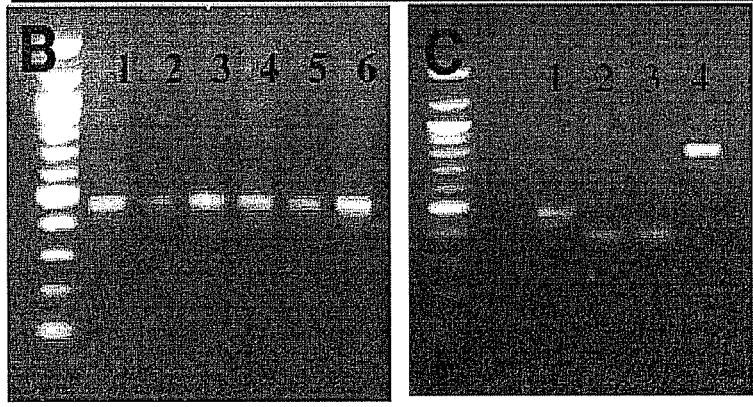
Figure 4

```
                                                         FR2
                                    FR1
Dog     MESVFCWVFLVVILKGVQGEVQLVESGGDLVKPGGSLRLSCVASGFTFSSYYMHWIRQAP  60
Human   MELGLSWVFLVAILEGVQCEVQLVESGGGLVQPGGSLRLSCVVSGFTFSSYWMSWVRQAP  60
Mouse   MDSRLNLVFLVLLVLFIKGVQCEVQLVESGGGLVKPGGSRKLSCAASGFTFSDYGMHWVRQAP 60
Rat     MDISLSLVFLVLFIKGVQLVETGGGLVQPGRSLKLSCVASGFTFSSYWMYWIRQAP  60
        *:  :    ::::*  :***   *.**:*** .**:*** * * **:*****

FR3
Dog     GKGLQRVAHIRGDGRTTHYADAMKGRFTISRDNAKNTLYLQMNSLTVEDTAIYYCVKD--  118
Human   GKGLEWVANIKQDGSEKYYVDSVKGRFTISRDNAKNSLYLQMNSLRAEDTAVYYCARDGS  120
Mouse   EKGLEWVAYINSGSTTIYYADTVKGRFTISRDNAKNTLFLQMTSLRSEDTAMYYCAR--E  118
Rat     GKGLEWVSSINTDGGSTYYPDSVKGRFTISRDNAENTVYLQMNSLRSEDTATYYCAKGGE  120
        ***:  *:   .*   * *.*.* ***********: **:**.**.****:****    ::

FR4         CγR
Dog     -IYYG-VGDYWGQGTLVTVSSASTTAPSVFPLAPSCGSTSGSTVALACLVSGYFPEPVTV  176
Human   SWYRD-WFDPWGQGTLVTVSSASTKGPSVFPLAPSSKSTSGGTAALGCLVKDYFPEPVTV  179
Mouse   LWLR--RIDYWGQGTTITVSSAKTTPPSVYPLAPGCGDTTGSSVTLGCLVKGYFPESVTV  176
Rat     YYGYNYPFDYWGQGVMVTVSSAETTAPSVYPLAPGTALKSNSMVTLGCLVKGYFPEPVTV  180
         :           *.*  ***** .*.  . *.****:           .: .   .: :. . *.* ****.****
```

Figure 5

SEQUENCE LISTING

```
<160> NUMBER OF SEQ ID NOS: 516

<210> SEQ ID NO 1
<211> LENGTH: 75
<212> TYPE: DNA
<213> ORGANISM: Artificial
<220> FEATURE:
<223> OTHER INFORMATION: Primer for the VH chain

<400> SEQUENCE: 1
ggtggttcct ctagatcttc ctcctctggt ggcggtggct cgggcggtgg tggggaggtv      60
carctggtgs artct                                                       75

<210> SEQ ID NO 2
<211> LENGTH: 75
<212> TYPE: DNA
<213> ORGANISM: Artificial
<220> FEATURE:
<223> OTHER INFORMATION: Primer for the VH chain

<400> SEQUENCE: 2
ggtggttcct ctagatcttc ctcctctggt ggcggtggct cgggcggtgg tggggaggtr      60
mvdytggtgg artct                                                       75

<210> SEQ ID NO 3
<211> LENGTH: 75
<212> TYPE: DNA
<213> ORGANISM: Artificial
<220> FEATURE:
<223> OTHER INFORMATION: Primer for the VH chain

<400> SEQUENCE: 3
ggtggttcct ctagatcttc ctcctctggt ggcggtggct cgggcggtgg tggggrsgtg      60
cagctggtgg agtct                                                       75

<210> SEQ ID NO 4
<211> LENGTH: 75
<212> TYPE: DNA
<213> ORGANISM: Artificial
<220> FEATURE:
<223> OTHER INFORMATION: Primer for the VH chain

<400> SEQUENCE: 4
ggtggttcct ctagatcttc ctcctctggt ggcggtggct cgggcggtgg tggggaggtr      60
cagctgstgg agwmt                                                       75

<210> SEQ ID NO 5
<211> LENGTH: 75
<212> TYPE: DNA
<213> ORGANISM: Artificial
<220> FEATURE:
<223> OTHER INFORMATION: Primer for the VH chain

<400> SEQUENCE: 5
```

-continued

```
ggtggttcct ctagatcttc ctcctctggt ggcggtggct cgggcggtgg tggggarkwg      60
carctggtgg agytt                                                       75
```

<210> SEQ ID NO 6
<211> LENGTH: 75
<212> TYPE: DNA
<213> ORGANISM: Artificial
<220> FEATURE:
<223> OTHER INFORMATION: Primer for the VH chain

<400> SEQUENCE: 6

```
ggtggttcct ctagatcttc ctcctctggt ggcggtggct cgggcggtgg tggggagggg      60
cagctggcgg agtct                                                       75
```

<210> SEQ ID NO 7
<211> LENGTH: 75
<212> TYPE: DNA
<213> ORGANISM: Artificial
<220> FEATURE:
<223> OTHER INFORMATION: Primer for the VH chain
<220> FEATURE:
<221> NAME/KEY: misc_feature
<222> LOCATION: (60)..(60)
<223> OTHER INFORMATION: n is a, c, g, t or u
<220> FEATURE:
<221> NAME/KEY: misc_feature
<222> LOCATION: (69)..(69)
<223> OTHER INFORMATION: n is a, c, g, t or u
<220> FEATURE:
<221> NAME/KEY: misc_feature
<222> LOCATION: (75)..(75)
<223> OTHER INFORMATION: n is a, c, g, t or u

<400> SEQUENCE: 7

```
ggtggttcct ctagatcttc ctcctctggt ggcggtggct cgggcggtgg tggggarbtn      60
marytggtng arwsn                                                       75
```

<210> SEQ ID NO 8
<211> LENGTH: 42
<212> TYPE: DNA
<213> ORGANISM: Artificial
<220> FEATURE:
<223> OTHER INFORMATION: Primer for the VH chain

<400> SEQUENCE: 8

```
cctggccggc ctggccacta gaaccgaggg ggccgtggtg ga                         42
```

<210> SEQ ID NO 9
<211> LENGTH: 41
<212> TYPE: DNA
<213> ORGANISM: Artificial
<220> FEATURE:
<223> OTHER INFORMATION: Primer for the VL lamda chain

<400> SEQUENCE: 9

```
gggcccaggc ggccgagctc gtgctgamtc mgcyrssytc d                          41
```

<210> SEQ ID NO 10
<211> LENGTH: 41
<212> TYPE: DNA
<213> ORGANISM: Artificial
<220> FEATURE:
<223> OTHER INFORMATION: Primer for the VL lamda chain

<400> SEQUENCE: 10

```
gggcccaggc ggccgagctc rysctgactc armmgscctc m                          41
```

```
<210> SEQ ID NO 11
<211> LENGTH: 41
<212> TYPE: DNA
<213> ORGANISM: Artificial
<220> FEATURE:
<223> OTHER INFORMATION: Primer for the VL lamda chain

<400> SEQUENCE: 11
gggcccaggc ggccgagctc gtsctgactc agcydvcctc a                     41

<210> SEQ ID NO 12
<211> LENGTH: 41
<212> TYPE: DNA
<213> ORGANISM: Artificial
<220> FEATURE:
<223> OTHER INFORMATION: Primer for the VL lamda chain

<400> SEQUENCE: 12
gggcccaggc ggccgagctc gygytgacyc arcyrgcctc m                     41

<210> SEQ ID NO 13
<211> LENGTH: 41
<212> TYPE: DNA
<213> ORGANISM: Artificial
<220> FEATURE:
<223> OTHER INFORMATION: Primer for the VL lamda chain

<400> SEQUENCE: 13
gggcccaggc ggccgagctc gccctgactc aaccttcctc g                     41

<210> SEQ ID NO 14
<211> LENGTH: 41
<212> TYPE: DNA
<213> ORGANISM: Artificial
<220> FEATURE:
<223> OTHER INFORMATION: Primer for the VL lamda chain

<400> SEQUENCE: 14
gggcccaggc ggccgagctc gtgctgwcwc agcygccatc m                     41

<210> SEQ ID NO 15
<211> LENGTH: 40
<212> TYPE: DNA
<213> ORGANISM: Artificial
<220> FEATURE:
<223> OTHER INFORMATION: Primer for the VL lamda chain

<400> SEQUENCE: 15
gggcccaggc ggccgagctc gtgctgactc agcctccytc                       40

<210> SEQ ID NO 16
<211> LENGTH: 40
<212> TYPE: DNA
<213> ORGANISM: Artificial
<220> FEATURE:
<223> OTHER INFORMATION: Primer for the VL lamda chain

<400> SEQUENCE: 16
gggcccaggc ggccgagctc grgytgactc agcyrccwtc                       40

<210> SEQ ID NO 17
<211> LENGTH: 40
<212> TYPE: DNA
<213> ORGANISM: Artificial
<220> FEATURE:
<223> OTHER INFORMATION: Primer for the VL lamda chain
```

-continued

```
<400> SEQUENCE: 17
gggcccaggc ggccgagctc gggytgaatc agsctyccte                    40

<210> SEQ ID NO 18
<211> LENGTH: 41
<212> TYPE: DNA
<213> ORGANISM: Artificial
<220> FEATURE:
<223> OTHER INFORMATION: Primer for the VL lamda chain

<400> SEQUENCE: 18
gggcccaggc ggccgagctc gtrctgacyc arcckccktc w                  41

<210> SEQ ID NO 19
<211> LENGTH: 41
<212> TYPE: DNA
<213> ORGANISM: Artificial
<220> FEATURE:
<223> OTHER INFORMATION: Primer for the VL lamda chain

<400> SEQUENCE: 19
gggcccaggc ggccgagctc gtrmgsaayc arcckccktc w                  41

<210> SEQ ID NO 20
<211> LENGTH: 41
<212> TYPE: DNA
<213> ORGANISM: Artificial
<220> FEATURE:
<223> OTHER INFORMATION: Primer for the VL lamda chain

<400> SEQUENCE: 20
gggcccaggc ggccgagctc ctgctgacyc arcckgcytc w                  41

<210> SEQ ID NO 21
<211> LENGTH: 41
<212> TYPE: DNA
<213> ORGANISM: Artificial
<220> FEATURE:
<223> OTHER INFORMATION: Primer for the VL lamda chain

<400> SEQUENCE: 21
gggcccaggc ggccgagctc gtrctgaayc arcckccktc w                  41

<210> SEQ ID NO 22
<211> LENGTH: 48
<212> TYPE: DNA
<213> ORGANISM: Artificial
<220> FEATURE:
<223> OTHER INFORMATION: Primer for the VL lamda chain

<400> SEQUENCE: 22
ggaagatcta gaggaaccac cgccaccgag gacggtcags tgggtscc           48

<210> SEQ ID NO 23
<211> LENGTH: 48
<212> TYPE: DNA
<213> ORGANISM: Artificial
<220> FEATURE:
<223> OTHER INFORMATION: Primer for the VL lamda chain

<400> SEQUENCE: 23
ggaagatcta gaggaaccac cgccaccwag gacggtsagy tsgrttcc           48

<210> SEQ ID NO 24
<211> LENGTH: 39
<212> TYPE: DNA
```

```
<213> ORGANISM: Artificial
<220> FEATURE:
<223> OTHER INFORMATION: Primer for the VL kappa chain

<400> SEQUENCE: 24
gggcccaggc ggccgagctc cagatgaccc agtccccaa                              39

<210> SEQ ID NO 25
<211> LENGTH: 39
<212> TYPE: DNA
<213> ORGANISM: Artificial
<220> FEATURE:
<223> OTHER INFORMATION: Primer for the VL kappa chain

<400> SEQUENCE: 25
gggcccaggc ggccgagctc gtsatgayrc agacyccac                              39

<210> SEQ ID NO 26
<211> LENGTH: 39
<212> TYPE: DNA
<213> ORGANISM: Artificial
<220> FEATURE:
<223> OTHER INFORMATION: Primer for the VL kappa chain

<400> SEQUENCE: 26
gggcccaggc ggccgagctc gtgatgacmc agtctccag                              39

<210> SEQ ID NO 27
<211> LENGTH: 39
<212> TYPE: DNA
<213> ORGANISM: Artificial
<220> FEATURE:
<223> OTHER INFORMATION: Primer for the VL kappa chain

<400> SEQUENCE: 27
gggcccaggc ggccgagctc aysmtgacyc agtkyccag                              39

<210> SEQ ID NO 28
<211> LENGTH: 42
<212> TYPE: DNA
<213> ORGANISM: Artificial
<220> FEATURE:
<223> OTHER INFORMATION: Primer for the VL kappa chain

<400> SEQUENCE: 28
ggaagatcta gaggaaccac ctttgagytc cacctkggtw cc                          42

<210> SEQ ID NO 29
<211> LENGTH: 42
<212> TYPE: DNA
<213> ORGANISM: Artificial
<220> FEATURE:
<223> OTHER INFORMATION: Primer for the VL kappa chain

<400> SEQUENCE: 29
ggaagatcta gaggaaccac ctttgagctc ctccttggtt cg                          42

<210> SEQ ID NO 30
<211> LENGTH: 42
<212> TYPE: DNA
<213> ORGANISM: Artificial
<220> FEATURE:
<223> OTHER INFORMATION: Primer for the VL kappa chain

<400> SEQUENCE: 30
ggaagatcta gaggaaccac ctttgaggtc caccttggtt cc                          42
```

```
<210> SEQ ID NO 31
<211> LENGTH: 42
<212> TYPE: DNA
<213> ORGANISM: Artificial
<220> FEATURE:
<223> OTHER INFORMATION: Primer for the VL kappa chain

<400> SEQUENCE: 31
ggaagatcta gaggaaccac ctttkatctc cavcttggty cc                          42

<210> SEQ ID NO 32
<211> LENGTH: 9
<212> TYPE: PRT
<213> ORGANISM: Artificial
<220> FEATURE:
<223> OTHER INFORMATION: conserved FR1 sequence of VL lamda chains

<400> SEQUENCE: 32

Gln Ser Val Leu Thr Gln Pro Ala Ser
1               5

<210> SEQ ID NO 33
<211> LENGTH: 15
<212> TYPE: PRT
<213> ORGANISM: Artificial
<220> FEATURE:
<223> OTHER INFORMATION: flexible serine-glycine linker

<400> SEQUENCE: 33

Gly Gly Gly Gly Ser Gly Gly Gly Gly Ser Gly Gly Gly Gly Ser
1               5                   10                  15

<210> SEQ ID NO 34
<211> LENGTH: 369
<212> TYPE: DNA
<213> ORGANISM: Artificial
<220> FEATURE:
<223> OTHER INFORMATION: VH chain

<400> SEQUENCE: 34
gacgtgcagc tggtggagtc tgggggagac ctggtgaagc ctggggggtc cctgagactg        60
tcctgtgtgg cctctggaat caccctcagc aactactaca tgtgctgggt ccgccaggct       120
ccagggaagg ggcttcagtg gtcgcacgg attagttatg atggaggtat cacagagtac        180
gcagacgctg tgaagggccg attcaccatc tccagagaca tgccaagaa cacgctgtat        240 ctgcagatga acagcctgag agccgacgac acggctatgt actactgtac ccagggcata       300
gatggaccct attggggcca gggaaccctg gtcaccgtct cctcagcctc caccacggcc       360
ccctcggtt                                                              369

<210> SEQ ID NO 35
<211> LENGTH: 123
<212> TYPE: PRT
<213> ORGANISM: Artificial
<220> FEATURE:
<223> OTHER INFORMATION: VH chain

<400> SEQUENCE: 35

Asp Val Gln Leu Val Glu Ser Gly Gly Asp Leu Val Lys Pro Gly Gly
1               5                   10                  15

Ser Leu Arg Leu Ser Cys Val Ala Ser Gly Ile Thr Leu Ser Asn Tyr
            20                  25                  30

Tyr Met Cys Trp Val Arg Gln Ala Pro Gly Lys Gly Leu Gln Trp Val
        35                  40                  45
```

```
Ala Arg Ile Ser Tyr Asp Gly Ile Thr Glu Tyr Ala Asp Ala Val
     50                  55                  60

Lys Gly Arg Phe Thr Ile Ser Arg Asp Asn Ala Lys Asn Thr Leu Tyr
 65                  70                  75                  80

Leu Gln Met Asn Ser Leu Arg Ala Asp Asp Thr Ala Met Tyr Tyr Cys
                 85                  90                  95

Thr Gln Gly Ile Asp Gly Pro Tyr Trp Gly Gln Gly Thr Leu Val Thr
            100                 105                 110

Val Ser Ser Ala Ser Thr Thr Ala Pro Ser Val
            115                 120
```

<210> SEQ ID NO 36
<211> LENGTH: 360
<212> TYPE: DNA
<213> ORGANISM: Artificial
<220> FEATURE:
<223> OTHER INFORMATION: VH chain

<400> SEQUENCE: 36

```
gagggqcagc tggcggagtc tgggggagac ctggtgaagc ctgcggggtc cctgactctg     60
tcctgtgtgg cctctggaat caccttcagt aaatacgacg tgatatgggt ccgcctggct    120
cctgggaagg gactgcagtg ggtcgcaggt attagcaaca atggaaacac agcctacgca    180
gacgctgtgg tggggcgatt caccacgtcc agagacatcg ccaagaacac agtgtatctg    240
cggatgaaca gcctgacagc cgaggacacg gccgtatatt actgtgtcgc gggccttaag    300
tactggggcc agggcaccct ggtcaccgtc tcctcagcct ccaccacggc cccctcggtt    360
```

<210> SEQ ID NO 37
<211> LENGTH: 120
<212> TYPE: PRT
<213> ORGANISM: Artificial
<220> FEATURE:
<223> OTHER INFORMATION: VH chain

<400> SEQUENCE: 37

```
Glu Gly Gln Leu Ala Glu Ser Gly Gly Asp Leu Val Lys Pro Ala Gly
  1               5                  10                  15

Ser Leu Thr Leu Ser Cys Val Ala Ser Gly Ile Thr Phe Ser Lys Tyr
             20                  25                  30

Asp Val Ile Trp Val Arg Leu Ala Pro Gly Lys Gly Leu Gln Trp Val
         35                  40                  45

Ala Gly Ile Ser Asn Asn Gly Asn Thr Ala Tyr Ala Asp Ala Val Val
     50                  55                  60

Gly Arg Phe Thr Thr Ser Arg Asp Ile Ala Lys Asn Thr Val Tyr Leu
 65                  70                  75                  80

Arg Met Asn Ser Leu Thr Ala Glu Asp Thr Ala Val Tyr Tyr Cys Val
                 85                  90                  95

Ala Gly Leu Lys Tyr Trp Gly Gln Gly Thr Leu Val Thr Val Ser Ser
            100                 105                 110

Ala Ser Thr Thr Ala Pro Ser Val
            115                 120
```

<210> SEQ ID NO 38
<211> LENGTH: 384
<212> TYPE: DNA
<213> ORGANISM: Artificial
<220> FEATURE:
<223> OTHER INFORMATION: VH chain

<400> SEQUENCE: 38

```
gaggggcagc tggcggagtc tgggggagac ctggtgaagc ctgcggggtc cctgagactg      60
tcctgtgtgg cctctggatt caccttcagc agctacgaca tgagctgggt ccgccaggct     120
cctgggaagg gctgcagtg gtcgcaggt attatggccg atggaagtac atactacgca      180
gacgctgtga agggccgatt caccatctcc agagacaacg ccaagaacac agtgtatctg     240
cagatggaca gcctgagagc cgaggacacg gccatgtatt actgtgcgaa ggataggttg     300
agctactaca tttattgcct tgagtactgg ggccagggca ccctggtcac cgtctcctca     360
gcctccacca cggccccctc ggtt                                            384
```

<210> SEQ ID NO 39
<211> LENGTH: 372
<212> TYPE: PRT
<213> ORGANISM: Artificial
<220> FEATURE:
<223> OTHER INFORMATION: VH chain

<400> SEQUENCE: 39

```
Gly Ala Gly Gly Thr Ala Cys Ala Gly Cys Thr Gly Gly Thr Gly
  1               5                  10                  15
Ala Gly Thr Cys Thr Gly Gly Gly Gly Ala Gly Ala Cys Cys Thr
                 20                  25                  30
Gly Gly Thr Gly Ala Ala Gly Cys Cys Gly Gly Gly Gly Gly Gly
                 35                  40                  45
Thr Cys Cys Cys Thr Gly Ala Gly Ala Cys Thr Gly Thr Cys Cys
 50                  55                  60
Gly Thr Gly Thr Gly Gly Cys Cys Thr Cys Thr Gly Gly Ala Thr
 65                  70                  75                  80
Cys Gly Cys Thr Thr Thr Cys Ala Gly Thr Ala Gly Thr Ala Thr
                 85                  90                  95
Gly Gly Cys Ala Thr Gly Ala Gly Thr Thr Gly Gly Thr Cys Cys
                100                 105                 110
Gly Thr Cys Ala Gly Thr Cys Thr Cys Ala Gly Gly Gly Ala Ala
                115                 120                 125
Gly Gly Gly Gly Cys Thr Gly Cys Ala Gly Gly Gly Thr Cys
                130                 135                 140
Gly Cys Ala Gly Ala Thr Thr Ala Gly Gly Ala Gly Thr Ala
145                 150                 155                 160
Cys Thr Gly Gly Ala Gly Ala Cys Ala Cys Thr Ala Cys Thr Ala
                165                 170                 175
Cys Gly Cys Ala Gly Ala Cys Gly Cys Thr Gly Thr Gly Ala Ala
                180                 185                 190
Gly Gly Cys Cys Gly Ala Thr Thr Cys Ala Cys Cys Ala Thr Cys
                195                 200                 205
Cys Cys Ala Gly Ala Gly Ala Cys Ala Cys Gly Cys Cys Gly Ala
                210                 215                 220
Gly Ala Ala Cys Ala Cys Gly Cys Thr Gly Thr Ala Thr Cys Thr
225                 230                 235                 240
Cys Ala Gly Ala Thr Gly Ala Gly Cys Ala Gly Cys Thr Gly Ala
                245                 250                 255
Gly Ala Gly Thr Cys Gly Ala Gly Ala Cys Ala Cys Gly Gly Cys
                260                 265                 270
Cys Ala Thr Ala Thr Ala Thr Thr Ala Thr Gly Thr Gly Cys Cys
                275                 280                 285
```

```
Thr Cys Ala Gly Gly Ala Cys Cys Ala Gly Thr Ala Gly Ala Thr Ala
        290                 295                 300
Cys Gly Ala Cys Thr Gly Ala Ala Cys Ala Cys Thr Gly Gly Gly
305                 310                 315                 320
Cys Cys Ala Gly Gly Cys Ala Cys Cys Thr Gly Gly Thr Cys
                325                 330                 335
Ala Cys Cys Gly Cys Cys Thr Cys Cys Thr Cys Ala Gly Cys Tyr Thr
                340                 345                 350
Cys Cys Ala Cys Cys Ala Cys Gly Cys Cys Cys Cys Thr Cys
                355                 360                 365
Gly Gly Thr Thr
        370

<210> SEQ ID NO 40
<211> LENGTH: 372
<212> TYPE: DNA
<213> ORGANISM: Artificial
<220> FEATURE:
<223> OTHER INFORMATION: VH chain

<400> SEQUENCE: 40
gaggtacagc tggtggagtc tgggggagac ctggtgaagc cggggggtc cctgagactg      60
tcctgtgtgg cctctggatt cgctttcagt agttatggca tgagttgggt ccgtcagtct    120
ccagggaagg ggctgcagtg ggtcgcagat attaggagta ctggagacac atactacgca    180
gacgctgtga aggccgatt caccatctcc agagacaacg ccgagaacac gctgtatctg     240
cagatgagca gcctgagagt cgaggacacg gccatatatt attgtgcctc aggaccagta    300
gatacgactg aacactgggg ccagggcacc ctggtcaccg cctcctcagc ytccaccacg    360
gccccctcgg tt                                                        372

<210> SEQ ID NO 41
<211> LENGTH: 124
<212> TYPE: PRT
<213> ORGANISM: Artificial
<220> FEATURE:
<223> OTHER INFORMATION: VH chain

<400> SEQUENCE: 41

Glu Val Gln Leu Val Glu Ser Gly Gly Asp Leu Val Lys Pro Gly Gly
1               5                   10                  15
Ser Leu Arg Leu Ser Cys Val Ala Ser Gly Phe Ala Phe Ser Ser Tyr
            20                  25                  30
Gly Met Ser Trp Val Arg Gln Ser Pro Gly Lys Gly Leu Gln Trp Val
        35                  40                  45
Ala Asp Ile Arg Ser Thr Gly Asp Thr Tyr Tyr Ala Asp Ala Val Lys
    50                  55                  60
Gly Arg Phe Thr Ile Ser Arg Asp Asn Ala Glu Asn Thr Leu Tyr Leu
65                  70                  75                  80
Gln Met Ser Ser Leu Arg Val Glu Asp Thr Ala Ile Tyr Tyr Cys Ala
                85                  90                  95
Ser Gly Pro Val Asp Thr Thr Glu His Trp Gly Gln Gly Thr Leu Val
            100                 105                 110
Thr Ala Ser Ser Ala Ser Thr Thr Ala Pro Ser Val
        115                 120

<210> SEQ ID NO 42
<211> LENGTH: 396
<212> TYPE: DNA
```

-continued

<213> ORGANISM: Artificial
<220> FEATURE:
<223> OTHER INFORMATION: VH chain

<400> SEQUENCE: 42

```
gagttgcaac tggtggagct tggaggaaac ctggtgaagc ctgggggtc cctgagactc      60
tcttgtgtgg cctctggatc caccttcaag aactattata tggactgggt ccgccaggct    120
ccagggaaga ctctggagtg ggtcgcaggg attagtagtg atggctataa gacgtattat    180
ggacaggctg tgcagggccg tttcaccatc tctagagaca acgccaagaa tacactctat    240
ctacaaatgg acggcctgac agtcgaggac tctgctgtat attactgtgc gatggaaggg    300
ggtgtacaca gtgaaagttg gttcgcggat tttgactctt ggggccaggg aaccctggtc    360
accgtctcct cagcctccac cacggcccc tcggtt                                396
```

<210> SEQ ID NO 43
<211> LENGTH: 132
<212> TYPE: PRT
<213> ORGANISM: Artificial
<220> FEATURE:
<223> OTHER INFORMATION: VH chain

<400> SEQUENCE: 43

```
Glu Leu Gln Leu Val Glu Leu Gly Gly Asn Leu Val Lys Pro Gly Gly
1               5                   10                  15
Ser Leu Arg Leu Ser Cys Val Ala Ser Gly Ser Thr Phe Lys Asn Tyr
            20                  25                  30
Tyr Met Asp Trp Val Arg Gln Ala Pro Gly Lys Thr Leu Glu Trp Val
        35                  40                  45
Ala Gly Ile Ser Ser Asp Gly Tyr Lys Thr Tyr Tyr Gly Gln Ala Val
    50                  55                  60
Gln Gly Arg Phe Thr Ile Ser Arg Asp Asn Ala Lys Asn Thr Leu Tyr
65                  70                  75                  80
Leu Gln Met Asp Gly Leu Thr Val Glu Asp Ser Ala Val Tyr Tyr Cys
                85                  90                  95
Ala Met Glu Gly Gly Val His Ser Glu Ser Trp Phe Ala Asp Phe Asp
            100                 105                 110
Ser Trp Gly Gln Gly Thr Leu Val Thr Val Ser Ser Ala Ser Thr Thr
        115                 120                 125
Ala Pro Ser Val
    130
```

<210> SEQ ID NO 44
<211> LENGTH: 378
<212> TYPE: DNA
<213> ORGANISM: Artificial
<220> FEATURE:
<223> OTHER INFORMATION: VH chain

<400> SEQUENCE: 44

```
gaggtgcaac tggtggagct tgggggagac ctggtgaagc ctggagaatc cctaagactg     60
tcctgttttgg cctccgatat cacattcagt gcctatgcga tgttctgggt ccgccaggct   120
ccagggaagg gcttggactg ggtcgcgact attagtggag atggagacac cacatactac   180
ggagacgctg tgaagggccg attcaccgtc tccagagaca cgccagaa cacagtttat      240
ctacagatga acagcctgag agccgaggac acggccgtgt attactgtgt ccctactacg   300
gtgactactc agcttgcata ctggggccag ggcaccctgg tcaccgtctc ctcagcctcc   360
accacggccc cctcggtt                                                   378
```

<210> SEQ ID NO 45
<211> LENGTH: 126
<212> TYPE: PRT
<213> ORGANISM: Artificial
<220> FEATURE:
<223> OTHER INFORMATION: VH chain

<400> SEQUENCE: 45

```
Glu Val Gln Leu Val Glu Leu Gly Gly Asp Leu Val Lys Pro Gly Glu
1               5                   10                  15

Ser Leu Arg Leu Ser Cys Leu Ala Ser Asp Ile Thr Phe Ser Ala Tyr
            20                  25                  30

Ala Met Phe Trp Val Arg Gln Ala Pro Gly Lys Gly Leu Asp Trp Val
        35                  40                  45

Ala Thr Ile Ser Gly Asp Gly Asp Thr Thr Tyr Tyr Gly Asp Ala Val
    50                  55                  60

Lys Gly Arg Phe Thr Val Ser Arg Asp Asn Ala Gln Asn Thr Val Tyr
65                  70                  75                  80

Leu Gln Met Asn Ser Leu Arg Ala Glu Asp Thr Ala Val Tyr Tyr Cys
                85                  90                  95

Val Pro Thr Thr Val Thr Thr Gln Leu Ala Tyr Trp Gly Gln Gly Thr
            100                 105                 110

Leu Val Thr Val Ser Ser Ala Ser Thr Thr Ala Pro Ser Val
        115                 120                 125
```

<210> SEQ ID NO 46
<211> LENGTH: 381
<212> TYPE: DNA
<213> ORGANISM: Artificial
<220> FEATURE:
<223> OTHER INFORMATION: VH chain

<400> SEQUENCE: 46

```
gaggtgcagc tggtggagtc tgggggagac ctggtgaagc ctggggagtc cctgagactc    60
tcctgtgtgg cctctacttt cactctccgt aaatacgacg tatattgggt ccgccaggtt   120 ccagggggcag gcctagaatg ggtcgcacgg atttctgaca gtggaagcac acattctat   180 gcagaatacg tagagggccg cttcaccatt accagagaca cggcaagaa catggcattt   240 ttacagatga acagcctgag agccgaggac acggccctt attactgtgc gatcagtctc   300
agttggcggt ggggttttga ctactggggc cagggaaccc tggtcaccgt ctcctcagcc   360
tccaccacgg cccctcggt t                                              381
```

<210> SEQ ID NO 47
<211> LENGTH: 127
<212> TYPE: PRT
<213> ORGANISM: Artificial
<220> FEATURE:
<223> OTHER INFORMATION: VH chain

<400> SEQUENCE: 47

```
Glu Val Gln Leu Val Glu Ser Gly Gly Asp Leu Val Lys Pro Gly Glu
1               5                   10                  15

Ser Leu Arg Leu Ser Cys Val Ala Ser Thr Phe Thr Leu Arg Lys Tyr
            20                  25                  30

Asp Val Tyr Trp Val Arg Gln Val Pro Gly Ala Gly Leu Glu Trp Val
        35                  40                  45

Ala Arg Ile Ser Asp Ser Gly Ser Thr Thr Phe Tyr Ala Glu Tyr Val
    50                  55                  60
```

```
Glu Gly Arg Phe Thr Ile Thr Arg Asp Asn Gly Lys Asn Met Ala Phe
 65                  70                  75                  80

Leu Gln Met Asn Ser Leu Arg Ala Glu Asp Thr Ala Leu Tyr Tyr Cys
                 85                  90                  95

Ala Ile Ser Leu Ser Trp Arg Trp Gly Phe Asp Tyr Trp Gly Gln Gly
            100                 105                 110

Thr Leu Val Thr Val Ser Ser Ala Ser Thr Thr Ala Pro Ser Val
        115                 120                 125

<210> SEQ ID NO 48
<211> LENGTH: 357
<212> TYPE: DNA
<213> ORGANISM: Artificial
<220> FEATURE:
<223> OTHER INFORMATION: VH chain

<400> SEQUENCE: 48
cagctggtgg agcttggggg agacctggtg aagcctgcgg ggtccctgag actgtcctgt        60
gtggcctctg gactcaccat cagtaactac ggcatgagat gggtccgcca gggtcctggg       120
aaggggctgc agtgggtcgc aggtattagc ggcgatggaa ccacaaactc cgcagacgct       180
gtgaagggcc gattcaccat ctccagagac aactctaaga acacagtgta tctgcagatg       240
cacagcctga gtcgagga cacggccgtg tattactgtg tgagtgggtc atggagtac          300 tggggccagg gcaccctggt caccgtctcc tcagcctcca ccacggcccc ctcggtt          357

<210> SEQ ID NO 49
<211> LENGTH: 119
<212> TYPE: PRT
<213> ORGANISM: Artificial
<220> FEATURE:
<223> OTHER INFORMATION: VH chain

<400> SEQUENCE: 49

Gln Leu Val Glu Leu Gly Gly Asp Leu Val Lys Pro Ala Gly Ser Leu
  1               5                  10                  15

Arg Leu Ser Cys Val Ala Ser Gly Leu Thr Ile Ser Asn Tyr Gly Met
             20                  25                  30

Arg Trp Val Arg Gln Gly Pro Gly Lys Gly Leu Gln Trp Val Ala Gly
         35                  40                  45

Ile Ser Gly Asp Gly Thr Thr Asn Ser Ala Asp Ala Val Lys Gly Arg
     50                  55                  60

Phe Thr Ile Ser Arg Asp Asn Ser Lys Asn Thr Val Tyr Leu Gln Met
 65                  70                  75                  80

His Ser Leu Arg Val Glu Asp Thr Ala Val Tyr Tyr Cys Val Ser Gly
                 85                  90                  95

Ser Trp Glu Tyr Trp Gly Gln Gly Thr Leu Val Thr Val Ser Ser Ala
            100                 105                 110

Ser Thr Thr Ala Pro Ser Val
        115

<210> SEQ ID NO 50
<211> LENGTH: 381
<212> TYPE: DNA
<213> ORGANISM: Artificial
<220> FEATURE:
<223> OTHER INFORMATION: VH chain

<400> SEQUENCE: 50
gacgtgcagc tggtggagtc tgggggagac ctggtgaagc ctgggggtc cttgagactg        60
```

```
tcctgtgtgg cctctggatt caccttcagt aactatggca tgagctgggt ccgtcagtct      120
ccagggaagg ggctgcagtc ggtcgcagtt attaacaatg gtggagatta catacactac      180
acaggcgctg tgaagggccg attcaccatc tccagagaca acgccaagaa cacgctgtat      240
ctgcagatga acagcctgag agccgaggac acggccgtct attactgtgc gaaggcgacg      300
attttgggtt ttggacacga gtcttggggc cagggcaccc tggtcaccgt ctcctcagcc      360
tccaccacgg ccccctcggt t                                                381
```

<210> SEQ ID NO 51
<211> LENGTH: 127
<212> TYPE: PRT
<213> ORGANISM: Artificial
<220> FEATURE:
<223> OTHER INFORMATION: VH chain

<400> SEQUENCE: 51

```
Asp Val Gln Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Asn Tyr
            20                  25                  30

Gly Met Ser Trp Val Arg Gln Ser Pro Gly Lys Gly Leu Gln Ser Val
        35                  40                  45

Ala Val Ile Asn Asn Gly Gly Asp Tyr Ile His Tyr Thr Gly Ala Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Thr Ile Leu Gly Phe Gly His Glu Ser Trp Gly Gln Gly
            100                 105                 110

Thr Leu Val Thr Val Ser Ser Ala Ser Thr Thr Ala Pro Ser Val
        115                 120                 125
```

<210> SEQ ID NO 52
<211> LENGTH: 378
<212> TYPE: DNA
<213> ORGANISM: Artificial
<220> FEATURE:
<223> OTHER INFORMATION: VH chain

<400> SEQUENCE: 52

```
gaggtgcagc tggtggagac tgggggggggc ctggcgaagc cgggggggtc cctaagactc      60
tcctgtgtgg cctctggatt gtccttcagt agttatagta tgagttgggt ccgccaggct      120
cctgggaagg gtctgcagtg gtcacagcc atcgactatc atggacgtga cactttctac      180
actgacactg tgaagggccg cttcaccatc tccagagacg atgccaggaa cacgatgtat      240
ctgcacatgg acggcctgag agccgaagac acagctgtct attactgtat ggtctacggt      300
agccacctga cctttgactt ctggggccag ggaaccctgg tcaccgtctc ctcagcctcc      360
accacggccc cctcggtt                                                    378
```

<210> SEQ ID NO 53
<211> LENGTH: 126
<212> TYPE: PRT
<213> ORGANISM: Artificial
<220> FEATURE:
<223> OTHER INFORMATION: VH chain

<400> SEQUENCE: 53

```
Glu Val Gln Leu Val Glu Thr Gly Gly Leu Ala Lys Pro Gly Gly
1               5                   10                  15

Ser Leu Arg Leu Ser Cys Val Ala Ser Gly Leu Ser Phe Ser Ser Tyr
            20                  25                  30

Ser Met Ser Trp Val Arg Gln Ala Pro Gly Lys Gly Leu Gln Trp Val
        35                  40                  45

Thr Ala Ile Asp Tyr His Gly Arg Asp Thr Phe Tyr Thr Asp Thr Val
    50                  55                  60

Lys Gly Arg Phe Thr Ile Ser Arg Asp Ala Arg Asn Thr Met Tyr
65                  70                  75                  80

Leu His Met Asp Gly Leu Arg Ala Glu Asp Thr Ala Val Tyr Tyr Cys
                85                  90                  95

Met Val Tyr Gly Ser His Leu Thr Phe Asp Phe Trp Gly Gln Gly Thr
            100                 105                 110

Leu Val Thr Val Ser Ser Ala Ser Thr Thr Ala Pro Ser Val
        115                 120                 125
```

<210> SEQ ID NO 54
<211> LENGTH: 390
<212> TYPE: DNA
<213> ORGANISM: Artificial
<220> FEATURE:
<223> OTHER INFORMATION: VH chain

<400> SEQUENCE: 54

```
gaggtgcagc tggtggagtt tggaggagac ctggtgaagc ctgggggtc cctgagactt      60 tcctgtgtgg cctctggatt caccttcagt agctatgaca tggactgggt ccgccaggct    120
ccagggaagg gctgcaatg gctctcagaa attagcagta gtggaagtag cacatactac    180
gcagacgctg tgaagggccg attcaccatc tccagagaca cgccaagaa cacactctat    240 ctgcacatga acagcctgcg acccgaggac acggccgtgt attactgtac aaagggcggg    300
gtcaaagcgc cctataaaag tggtgtggac tactggggcc ctggcacctc agtcctcgtg    360
tcctcagcct ccaccacggc cccctcggtt                                     390
```

<210> SEQ ID NO 55
<211> LENGTH: 130
<212> TYPE: PRT
<213> ORGANISM: Artificial
<220> FEATURE:
<223> OTHER INFORMATION: VH chain

<400> SEQUENCE: 55

```
Glu Val Gln Leu Val Glu Phe Gly Gly Asp Leu Val Lys Pro Gly Gly
1               5                   10                  15

Ser Leu Arg Leu Ser Cys Val Ala Ser Gly Phe Thr Phe Ser Ser Tyr
            20                  25                  30

Asp Met Asp Trp Val Arg Gln Ala Pro Gly Lys Gly Leu Gln Trp Leu
        35                  40                  45

Ser Glu Ile Ser Ser Ser Gly Ser Ser Thr Tyr Tyr Ala Asp Ala Val
    50                  55                  60

Lys Gly Arg Phe Thr Ile Ser Arg Asp Asn Ala Lys Asn Thr Leu Tyr
65                  70                  75                  80

Leu His Met Asn Ser Leu Arg Pro Glu Asp Thr Ala Val Tyr Tyr Cys
                85                  90                  95

Thr Lys Gly Gly Val Lys Ala Pro Tyr Lys Ser Gly Val Asp Tyr Trp
            100                 105                 110
```

```
Gly Pro Gly Thr Ser Val Leu Val Ser Ser Ala Ser Thr Thr Ala Pro
        115                 120                 125
Ser Val
    130

<210> SEQ ID NO 56
<211> LENGTH: 387
<212> TYPE: DNA
<213> ORGANISM: Artificial
<220> FEATURE:
<223> OTHER INFORMATION: VH chain

<400> SEQUENCE: 56
gaggtaaagc tggtggaatc tgggggagac ctggcgaagc ctgggggggtc cctgagactc     60 tcctgtgcgg cctctggact agccttcagt agccacagca tgaactgggt ccgccaggct    120
cctgggaagg gcctgcagtg ggtcactgct atcagttatg atggaagaag aatctactat    180
agtgacgatg tgaagggccg attcgccgtc tcccgcgata tgccaggaa caccatgtat    240 cttcagatga cgggcctgac agtcgcggac acaggtctct attactgtgc aatagtgggc    300
ttaggatggc agctggccaa ttttgagttc tggggccagg gagcccaggt catcgtcgcc    360
tcagcctcca ccacggcccc ctcggtt                                          387

<210> SEQ ID NO 57
<211> LENGTH: 129
<212> TYPE: PRT
<213> ORGANISM: Artificial
<220> FEATURE:
<223> OTHER INFORMATION: VH chain

<400> SEQUENCE: 57

Glu Val Lys Leu Val Glu Ser Gly Gly Asp Leu Ala Lys Pro Gly Gly
1               5                   10                  15
Ser Leu Arg Leu Ser Cys Ala Ala Ser Gly Leu Ala Phe Ser Ser His
            20                  25                  30
Ser Met Asn Trp Val Arg Gln Ala Pro Gly Lys Gly Leu Gln Trp Val
        35                  40                  45
Thr Ala Ile Ser Tyr Asp Gly Arg Arg Ile Tyr Tyr Ser Asp Asp Val
    50                  55                  60
Lys Gly Arg Phe Ala Val Ser Arg Asp Asn Ala Arg Asn Thr Met Tyr
65                  70                  75                  80
Leu Gln Met Thr Gly Leu Thr Val Ala Asp Thr Gly Leu Tyr Tyr Cys
                85                  90                  95
Ala Ile Val Gly Leu Gly Trp Gln Leu Ala Asn Phe Glu Phe Trp Gly
            100                 105                 110
Gln Gly Ala Gln Val Ile Val Ala Ser Ala Ser Thr Thr Ala Pro Ser
        115                 120                 125
Val

<210> SEQ ID NO 58
<211> LENGTH: 387
<212> TYPE: DNA
<213> ORGANISM: Artificial
<220> FEATURE:
<223> OTHER INFORMATION: VH chain

<400> SEQUENCE: 58
gaggtgcagc tggtggagtc tgggggagac cttgtgaagc ctgggggggtc cctgagactc     60 tcctgtgtgg cctctggatt caccttagt agctatgaca tgagctgggt ccgtcaggct    120
```

```
cctggaaagg ggctgcagtg gatcacagct attaagtcag atggaactac tacatactac    180
attgacgctg tgaagggccg attcaccgtc tccagagaca tgccaggaa cacagtgtat     240 ctgcagatga acagtctgag agccgaggac acggccatgt attactgtgc gagggacgat    300
atatttatgg atagagttgg tatggactac tggggccgtg gcacctcact cttcgtgtcc    360
tcagcctcca ccacggcccc ctcggtt                                        387

<210> SEQ ID NO 59
<211> LENGTH: 129
<212> TYPE: PRT
<213> ORGANISM: Artificial
<220> FEATURE:
<223> OTHER INFORMATION: VH chain

<400> SEQUENCE: 59

Glu Val Gln Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Ser Tyr
            20                  25                  30

Asp Met Ser Trp Val Arg Gln Ala Pro Gly Lys Gly Leu Gln Trp Ile
        35                  40                  45

Thr Ala Ile Lys Ser Asp Gly Thr Thr Thr Tyr Tyr Ile Asp Ala Val
    50                  55                  60

Lys Gly Arg Phe Thr Val Ser Arg Asp Asn Ala Arg Asn Thr Val Tyr
65                  70                  75                  80

Leu Gln Met Asn Ser Leu Arg Ala Glu Asp Thr Ala Met Tyr Tyr Cys
                85                  90                  95

Ala Arg Asp Asp Ile Phe Met Asp Arg Val Gly Met Asp Tyr Trp Gly
            100                 105                 110

Arg Gly Thr Ser Leu Phe Val Ser Ser Ala Ser Thr Thr Ala Pro Ser
        115                 120                 125

Val

<210> SEQ ID NO 60
<211> LENGTH: 399
<212> TYPE: DNA
<213> ORGANISM: Artificial
<220> FEATURE:
<223> OTHER INFORMATION: VH chain

<400> SEQUENCE: 60
gaggtgcgtc tggtggagtc tgggggagac ctggtgaagc cgggggggtc cctgagactc    60
tcctgtctag cctctggatt caccttcagt gactacgaca tgagctgggt ccgccaggct    120
cctggaaagg ggctgcagtg gtcgcaggt attagctatg aggaagtag tacatactac     180 aatgacgctg tgaagggccg actcaccatc tccagagaca tgccaggaa tacattatat    240 ctgcagatga atagcctgag agccgatgac acgctgttt attactgtgc gagatttcga    300
gcgaactacg gtaacatcta tggcaactcc tattttgcct attggggcca gggaaccctg    360
gtcaccgtct cctcagcctc caccacggcc ccctcggtt                          399

<210> SEQ ID NO 61
<211> LENGTH: 133
<212> TYPE: PRT
<213> ORGANISM: Artificial
<220> FEATURE:
<223> OTHER INFORMATION: VH chain

<400> SEQUENCE: 61
```

```
Glu Val Arg Leu Val Glu Ser Gly Gly Asp Leu Val Lys Pro Gly Gly
1               5                   10                  15

Ser Leu Arg Leu Ser Cys Leu Ala Ser Gly Phe Thr Phe Ser Asp Tyr
            20                  25                  30

Asp Met Ser Trp Val Arg Gln Ala Pro Gly Lys Gly Leu Gln Trp Val
            35                  40                  45

Ala Gly Ile Ser Tyr Glu Gly Ser Ser Thr Tyr Tyr Asn Asp Ala Val
        50                  55                  60

Lys Gly Arg Leu Thr Ile Ser Arg Asp Asn Ala Arg Asn Thr Leu Tyr
65                  70                  75                  80

Leu Gln Met Asn Ser Leu Arg Ala Asp Asp Thr Ala Val Tyr Tyr Cys
                85                  90                  95

Ala Arg Phe Arg Ala Asn Tyr Gly Asn Ile Tyr Gly Asn Ser Tyr Phe
            100                 105                 110

Ala Tyr Trp Gly Gln Gly Thr Leu Val Thr Val Ser Ser Ala Ser Thr
            115                 120                 125

Thr Ala Pro Ser Val
        130

<210> SEQ ID NO 62
<211> LENGTH: 384
<212> TYPE: DNA
<213> ORGANISM: Artificial
<220> FEATURE:
<223> OTHER INFORMATION: VH chain

<400> SEQUENCE: 62
ggggtgcagc tggtggagtc tgggggagac gtggtgaagc ctgggggtc cctgagactc      60
tcctgtgtgg cctctggatt taccttcagt agttactaca tgtattgggc ccgccaggct    120
ccagggaagg ggcttcagtg gtctcacac attaagagag atggaagtag cacaagctat     180
gcagacgctg tgaagggccg attcaccatc tccagagaca acgcaaagaa cacgctgtat    240
ctgcagatga acagtttgag agctgaggac acagcggtgt attactgtgc aaaggacctg    300
gggacatatg gatacaacct tgagtactgg ggccggggca ccctggtcac cgtctcctca    360
gcctccacca cggcccccctc ggtt                                          384

<210> SEQ ID NO 63
<211> LENGTH: 128
<212> TYPE: PRT
<213> ORGANISM: Artificial
<220> FEATURE:
<223> OTHER INFORMATION: VH chain

<400> SEQUENCE: 63

Gly Val Gln Leu Val Glu Ser Gly Gly Asp Val Val Lys Pro Gly Gly
1               5                   10                  15

Ser Leu Arg Leu Ser Cys Val Ala Ser Gly Phe Thr Phe Ser Ser Tyr
            20                  25                  30

Tyr Met Tyr Trp Ala Arg Gln Ala Pro Gly Lys Gly Leu Gln Trp Val
            35                  40                  45

Ser His Ile Lys Arg Asp Gly Ser Ser Thr Ser Tyr Ala Asp Ala Val
        50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Leu Gly Thr Tyr Gly Tyr Asn Leu Glu Tyr Trp Gly Arg
```

```
                  100                 105                 110
Gly Thr Leu Val Thr Val Ser Ser Ala Ser Thr Thr Ala Pro Ser Val
            115                 120                 125

<210> SEQ ID NO 64
<211> LENGTH: 375
<212> TYPE: DNA
<213> ORGANISM: Artificial
<220> FEATURE:
<223> OTHER INFORMATION: VH chain

<400> SEQUENCE: 64
gaggtccaac tggtggagtc tgggggggac ctggtgaagc ctggggagtc cctgaggctg      60
tcgtgtgtgg cctctggttt cattctaaga agtattatc tacactgggt ccgccaggct     120
ccagggaagg gtcctcagtg gtcgcacgg atcagtggcg aaggttataa gacctactac     180
gcggacgcgg tgaggggccg attcaccatc tccagagaca atgccaagag cacgatttat     240
ctacaaatgg acaccctgac agccgaggac gcgggaatct attattgtgt gaaggattca     300
gatgcacctc ttcatagttg gggcgacggt accctggttg ccgtctcttc agcctccacc     360
acggccccct cggtt                                                      375

<210> SEQ ID NO 65
<211> LENGTH: 125
<212> TYPE: PRT
<213> ORGANISM: Artificial
<220> FEATURE:
<223> OTHER INFORMATION: VH chain

<400> SEQUENCE: 65

Glu Val Gln Leu Val Glu Ser Gly Gly Asp Leu Val Lys Pro Gly Glu
1               5                   10                  15

Ser Leu Arg Leu Ser Cys Val Ala Ser Gly Phe Ile Leu Arg Lys Tyr
            20                  25                  30

Tyr Leu His Trp Val Arg Gln Ala Pro Gly Lys Gly Pro Gln Trp Val
        35                  40                  45

Ala Arg Ile Ser Gly Glu Gly Tyr Lys Thr Tyr Tyr Ala Asp Ala Val
    50                  55                  60

Arg Gly Arg Phe Thr Ile Ser Arg Asp Asn Ala Lys Ser Thr Ile Tyr
65                  70                  75                  80

Leu Gln Met Asp Thr Leu Thr Ala Glu Asp Ala Gly Ile Tyr Tyr Cys
                85                  90                  95

Val Lys Asp Ser Asp Ala Pro Leu His Ser Trp Gly Asp Gly Thr Leu
            100                 105                 110

Val Ala Val Ser Ser Ala Ser Thr Thr Ala Pro Ser Val
        115                 120                 125

<210> SEQ ID NO 66
<211> LENGTH: 375
<212> TYPE: DNA
<213> ORGANISM: Artificial
<220> FEATURE:
<223> OTHER INFORMATION: VH chain

<400> SEQUENCE: 66
gaggtgcagc tgctggagtc tggggggagac ctggtgaagc cggggggggtc cctgagactc     60 tcctgtgtgg cctctggtct caccttcagt agtcacgaca tggactgggt ccgccaggct    120
ccagggaagg gactgcagtg gctcacacgg atcaccaatg atggaaggag cacagactac    180
gcagatgctg tgaagggccg attcaccatc tccagagaca acgccaagaa cacgctgtat    240
```

```
ctgcagatga acagcctgag agccgaggac acggccctgt attactgtgc gagggggcggc      300 acgatgtctc cttggtactg gggccagggc actttggtca ccgtctcctc agcctccacc      360 acggcccccct cggtt                                                       375
```

<210> SEQ ID NO 67
<211> LENGTH: 125
<212> TYPE: PRT
<213> ORGANISM: Artificial
<220> FEATURE:
<223> OTHER INFORMATION: VH chain

<400> SEQUENCE: 67

```
Glu Val Gln Leu Leu Glu Ser Gly Gly Asp Leu Val Lys Pro Gly Gly
1               5                   10                  15

Ser Leu Arg Leu Ser Cys Val Ala Ser Gly Leu Thr Phe Ser Ser His
            20                  25                  30

Asp Met Asp Trp Val Arg Gln Ala Pro Gly Lys Gly Leu Gln Trp Leu
        35                  40                  45

Thr Arg Ile Thr Asn Asp Gly Arg Ser Thr Tyr Ala Asp Ala Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Leu Tyr Tyr Cys
                85                  90                  95

Ala Arg Gly Gly Thr Met Ser Pro Trp Tyr Trp Gly Gln Gly Thr Leu
            100                 105                 110

Val Thr Val Ser Ser Ala Ser Thr Thr Ala Pro Ser Val
        115                 120                 125
```

<210> SEQ ID NO 68
<211> LENGTH: 390
<212> TYPE: DNA
<213> ORGANISM: Artificial
<220> FEATURE:
<223> OTHER INFORMATION: VH chain

<400> SEQUENCE: 68

```
gaggtgcagc tgctggagtc tgggggagac ctggtgaggc ctggggagtc cctgagactc      60
tcctgcatag cctctggatt caccttcaat acgtatacca tggcctgggt ccgccagggt      120
cctgggaagg ggctggagtg ggtcgcaggt atcagttctg atggaagtag cccatatcac      180
agtgccgctg tgaagggccg attcaccatc tccaggaca gcgccaggag cacagtctat      240
ctgcagatga acagcctgag agccgaggac acggctgtgt attactgtgc gaaggacgct      300
ctcagtagtt ggggcccca taactttgat cattggggcc agggaacccct ggtcaccgtc      360 tcctcagcct ccaccacggc cccctcggtt                                       390
```

<210> SEQ ID NO 69
<211> LENGTH: 130
<212> TYPE: PRT
<213> ORGANISM: Artificial
<220> FEATURE:
<223> OTHER INFORMATION: VH chain

<400> SEQUENCE: 69

```
Glu Val Gln Leu Leu Glu Ser Gly Gly Asp Leu Val Arg Pro Gly Glu
1               5                   10                  15

Ser Leu Arg Leu Ser Cys Ile Ala Ser Gly Phe Thr Phe Asn Thr Tyr
            20                  25                  30
```

```
Thr Met Ala Trp Val Arg Gln Gly Pro Gly Lys Gly Leu Glu Trp Val
             35                  40                  45

Ala Gly Ile Ser Ser Asp Gly Ser Ser Pro Tyr His Ser Ala Ala Val
 50                  55                  60

Lys Gly Arg Phe Thr Ile Ser Arg Asp Ser Ala Arg Ser Thr Val Tyr
 65                  70                  75                  80

Leu Gln Met Asn Ser Leu Arg Ala Glu Asp Thr Ala Val Tyr Tyr Cys
                 85                  90                  95

Ala Lys Asp Ala Leu Ser Ser Trp Gly Pro His Asn Phe Asp His Trp
            100                 105                 110

Gly Gln Gly Thr Leu Val Thr Val Ser Ser Ala Ser Thr Thr Ala Pro
            115                 120                 125

Ser Val
    130
```

<210> SEQ ID NO 70
<211> LENGTH: 387
<212> TYPE: DNA
<213> ORGANISM: Artificial
<220> FEATURE:
<223> OTHER INFORMATION: VH chain

<400> SEQUENCE: 70

```
gaggtgcagc tggtgcagtc tgggggagac ctggtgaagc ctggggggcc cctgagactg      60
tcctgtgtgg cctctggatt caccttcagt aactactaca tgcactgggt ccgccaggct     120
ccagggaagg gactgcagtg ggtcggatac attagtagtg atggaagtgg cacatggtac     180
gcggacgctg tgaagggccg cttcaccatc tccagagaca cgccaagaa cacactgtat      240
ctgcagatga acagcctgag agccgaggac acggccgtgt attactgtgc gaccacgggg     300
aataccgtct cccactggac tatggaatac tggggccctg gcacctcact cttcgtgtcc     360
tcagcctcca ccacggcccc ctcggtt                                         387
```

<210> SEQ ID NO 71
<211> LENGTH: 129
<212> TYPE: PRT
<213> ORGANISM: Artificial
<220> FEATURE:
<223> OTHER INFORMATION: VH chain

<400> SEQUENCE: 71

```
Glu Val Gln Leu Val Gln Ser Gly Gly Asp Leu Val Lys Pro Gly Gly
  1               5                  10                  15

Pro Leu Arg Leu Ser Cys Val Ala Ser Gly Phe Thr Phe Ser Asn Tyr
             20                  25                  30

Tyr Met His Trp Val Arg Gln Ala Pro Gly Lys Gly Leu Gln Trp Val
             35                  40                  45

Gly Tyr Ile Ser Ser Asp Gly Ser Gly Thr Trp Tyr Ala Asp Ala Val
 50                  55                  60

Lys Gly Arg Phe Thr Ile Ser Arg Asp Asn Ala Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Thr Thr Gly Asn Thr Val Ser His Trp Thr Met Glu Tyr Trp Gly
            100                 105                 110

Pro Gly Thr Ser Leu Phe Val Ser Ser Ala Ser Thr Thr Ala Pro Ser
            115                 120                 125
```

Val

<210> SEQ ID NO 72
<211> LENGTH: 387
<212> TYPE: DNA
<213> ORGANISM: Artificial
<220> FEATURE:
<223> OTHER INFORMATION: VH chain

<400> SEQUENCE: 72

```
gaggggcagc tggcggagtc tgggggagac ctggtgaagc ctgcggggtc cctgagactg      60
tcctgtgtgg cctctggatt caccttcagt acctacggca tggactgggt ccgccaggct     120
cctgggaagg ggccgcaatg ggtcggacat atcagaacca gtggagacac acggtacgca    180
gacgctgtga aggccgatt caccatctcc agagacaacg ccaaaaacac agtgtatctg      240
cagatggaca gcctgacagt cgaggacacg gccttctatt tctgtgcgaa ggatggacta     300
agatatggat acgtccctga ctttgaacac tggggccagg gtaccctggt caccgtctct     360
ttagcctcca ccacggcccc ctcggtt                                          387
```

<210> SEQ ID NO 73
<211> LENGTH: 129
<212> TYPE: PRT
<213> ORGANISM: Artificial
<220> FEATURE:
<223> OTHER INFORMATION: VH chain

<400> SEQUENCE: 73

```
Glu Gly Gln Leu Ala Glu Ser Gly Gly Asp Leu Val Lys Pro Ala Gly
1               5                   10                  15
Ser Leu Arg Leu Ser Cys Val Ala Ser Gly Phe Thr Phe Ser Thr Tyr
            20                  25                  30
Gly Met Asp Trp Val Arg Gln Ala Pro Gly Lys Gly Pro Gln Trp Val
        35                  40                  45
Gly His Ile Arg Thr Ser Gly Asp Thr Arg Tyr Ala Asp Ala Val Lys
    50                  55                  60
Gly Arg Phe Thr Ile Ser Arg Asp Asn Ala Lys Asn Thr Val Tyr Leu
65                  70                  75                  80
Gln Met Asp Ser Leu Thr Val Glu Asp Thr Ala Phe Tyr Phe Cys Ala
                85                  90                  95
Lys Asp Gly Leu Arg Tyr Gly Tyr Val Pro Asp Phe Glu His Trp Gly
            100                 105                 110
Gln Gly Thr Leu Val Thr Val Ser Leu Ala Ser Thr Thr Ala Pro Ser
        115                 120                 125
Val
```

<210> SEQ ID NO 74
<211> LENGTH: 369
<212> TYPE: DNA
<213> ORGANISM: Artificial
<220> FEATURE:
<223> OTHER INFORMATION: VH chain

<400> SEQUENCE: 74

```
gaggtgcaac tggtggagtt tgggggagac ctggtgaagc ctgcggggtc cctgaaattg      60
tcctgtgtgg cctctggatt caccttcagg cactacgaca tacactgggt ccgccaggct    120
cctgggaggc ggctgcaata tgtcgcaggt attcactatg atggaagtta catatactac    180
attgacgctg tgaagggccg attcaccatc tccagagaca cgccaggaa cacagtgtat      240
ctgcagatga acagtctgag agtcgaggac acggctgtgt attattgtgt gaaggctccg     300
ggcctagagt actggggcca gggaaccctg gtcaccgtct cctcagcctc cacacggcc      360
ccctcggtt                                                              369
```

```
Lys Gly Arg Phe Thr Ile Ser Arg Asp Asn Ala Arg Asn Thr Val Tyr
 65                  70                  75                  80

Leu Gln Met Asn Ser Leu Arg Val Glu Asp Thr Ala Val Tyr Tyr Cys
                 85                  90                  95

Val Lys Ala Pro Gly Leu Glu Tyr Trp Gly Gln Gly Thr Leu Val Thr
            100                 105                 110

Val Ser Ser Ala Ser Thr Thr Ala Pro Ser Val
        115                 120
```

<210> SEQ ID NO 76
<211> LENGTH: 393
<212> TYPE: DNA
<213> ORGANISM: Artificial
<220> FEATURE:
<223> OTHER INFORMATION: VH chain

<400> SEQUENCE: 76

```
gaggtccagc tggtggagtc tgggggagac ctggtgaagc ctgggggtc cctgagactt      60
tcctgtgtgg cctctggatt caccttcggt gactattaca tgaactgggt ccgccaggct    120
ccagggaagg ggcttcagtg ggtcgcatac attcacagtg gtggaggtag cacgacttat    180
gcagacgctg tgaagggccg attcaccatc tccagagaca cgccaaaaa cacactatat     240
cttcagatga acggcctgag agccgaggac acggccctat attactgtgc gagcgggtcg    300
ctgggaacct acggtcgtta ctactccttt gactactggg gccagggaac cctggtcacc    360
gtctcctcag cctccaccac ggccccctcg gtt                                  393
```

<210> SEQ ID NO 77
<211> LENGTH: 131
<212> TYPE: PRT
<213> ORGANISM: Artificial
<220> FEATURE:
<223> OTHER INFORMATION: VH chain

<400> SEQUENCE: 77

```
Glu Val Gln Leu Val Glu Ser Gly Gly Asp Leu Val Lys Pro Gly Gly
  1               5                  10                  15

Ser Leu Arg Leu Ser Cys Val Ala Ser Gly Phe Thr Phe Gly Asp Tyr
             20                  25                  30

Tyr Met Asn Trp Val Arg Gln Ala Pro Gly Lys Gly Leu Gln Trp Val
             35                  40                  45

Ala Tyr Ile His Ser Gly Gly Gly Ser Thr Thr Tyr Ala Asp Ala Val
         50                  55                  60

Lys Gly Arg Phe Thr Ile Ser Arg Asp Asn Ala Lys Asn Thr Leu Tyr
 65                  70                  75                  80

Leu Gln Met Asn Gly Leu Arg Ala Glu Asp Thr Ala Leu Tyr Tyr Cys
                 85                  90                  95

Ala Ser Gly Ser Leu Gly Thr Tyr Gly Arg Tyr Tyr Ser Phe Asp Tyr
            100                 105                 110

Trp Gly Gln Gly Thr Leu Val Thr Val Ser Ser Ala Ser Thr Thr Ala
            115                 120                 125

Pro Ser Val
        130
```

<210> SEQ ID NO 78
<211> LENGTH: 390
<212> TYPE: DNA
<213> ORGANISM: Artificial
<220> FEATURE:
<223> OTHER INFORMATION: VH chain

<400> SEQUENCE: 78

```
gagataccgc tggtggagtc tgggggagac ctggtgaagc ctgcagggtc cctgagactg      60
tcctgtgtgg cctctggatt caccttctcc agctatgtca tgagctgggt ccgccagact     120
cctgggaagg gctgcagtg gtcgcaact attaacagtg gtggaagtag cacgagctac       180
gcagacgctg tgaagggccg attcaccatc tccagagaca atgtcaagaa cacactgtat    240
ctgcagatga acagcctgag agccgaggac acggccgtgt attactgtgt gacgccgtta    300
tatgatagtt actacggcta tggtatggac tactggggcc ctggcaccct cactcttcgtg   360
tcctcagcct ccaccacggc ccctcggtt                                      390
```

<210> SEQ ID NO 79
<211> LENGTH: 130
<212> TYPE: PRT
<213> ORGANISM: Artificial
<220> FEATURE:
<223> OTHER INFORMATION: VH chain

<400> SEQUENCE: 79

```
Glu Ile Pro Leu Val Glu Ser Gly Gly Asp Leu Val Lys Pro Ala Gly
1               5                  10                  15

Ser Leu Arg Leu Ser Cys Val Ala Ser Gly Phe Thr Phe Ser Ser Tyr
            20                  25                  30

Val Met Ser Trp Val Arg Gln Thr Pro Gly Lys Gly Leu Gln Trp Val
        35                  40                  45

Ala Thr Ile Asn Ser Gly Gly Ser Ser Thr Ser Tyr Ala Asp Ala Val
    50                  55                  60

Lys Gly Arg Phe Thr Ile Ser Arg Asp Asn Val Lys Asn Thr Leu Tyr
65                  70                  75                  80

Leu Gln Met Asn Ser Leu Arg Ala Glu Asp Thr Ala Val Tyr Tyr Cys
                85                  90                  95

Val Thr Pro Leu Tyr Asp Ser Tyr Tyr Gly Tyr Gly Met Asp Tyr Trp
            100                 105                 110

Gly Pro Gly Thr Ser Leu Phe Val Ser Ser Ala Ser Thr Thr Ala Pro
        115                 120                 125

Ser Val
    130
```

<210> SEQ ID NO 80
<211> LENGTH: 387
<212> TYPE: DNA
<213> ORGANISM: Artificial
<220> FEATURE:
<223> OTHER INFORMATION: VH chain

<400> SEQUENCE: 80

```
gaggtgcagc tggtggagtc tgggggagac ctggtgaagc ctggggggtc cctgagattg     60
tcctgtgtgg cctctggatt catcttcagt agttattata tatattgggt ccgccagagt    120
ccagggaagg ggcttcagtg gtcgcacga atcaacaatg atggaagtag gatatactac     180
gcagacgctg tgaagggccg attcaccatc tccagagaca tcgccaagga cacgctctac   240
ctgcagctgg acaggctcgg ggccgaggac acggccgtgt attattgtgt cccgccgaga   300
gtacacgttt ggttaggaga ttttgactcc tggggccagg ggaccctggt caccgtctcc   360
tcagcctcca ccacggcccc ctcggtt                                       387
```

<210> SEQ ID NO 81

```
<211> LENGTH: 129
<212> TYPE: PRT
<213> ORGANISM: Artificial
<220> FEATURE:
<223> OTHER INFORMATION: VH chain

<400> SEQUENCE: 81

Glu Val Gln Leu Val Glu Ser Gly Gly Asp Leu Val Lys Pro Gly Gly
1               5                   10                  15

Ser Leu Arg Leu Ser Cys Val Ala Ser Gly Phe Ile Phe Ser Ser Tyr
            20                  25                  30

Tyr Ile Tyr Trp Val Arg Gln Ser Pro Gly Lys Gly Leu Gln Trp Val
        35                  40                  45

Ala Arg Ile Asn Asn Asp Gly Ser Arg Ile Tyr Tyr Ala Asp Ala Val
    50                  55                  60

Lys Gly Arg Phe Thr Ile Ser Arg Asp Ile Ala Lys Asp Thr Leu Tyr
65                  70                  75                  80

Leu Gln Leu Asp Arg Leu Gly Ala Glu Asp Thr Ala Val Tyr Tyr Cys
                85                  90                  95

Val Pro Pro Arg Val His Val Trp Leu Gly Asp Phe Asp Ser Trp Gly
            100                 105                 110

Gln Gly Thr Leu Val Thr Val Ser Ser Ala Ser Thr Thr Ala Pro Ser
        115                 120                 125

Val

<210> SEQ ID NO 82
<211> LENGTH: 390
<212> TYPE: DNA
<213> ORGANISM: Artificial
<220> FEATURE:
<223> OTHER INFORMATION: VH chain

<400> SEQUENCE: 82
gggGtgcagc tggtggagtc tgggggagac cgggtgaacc ctgcggggtc cctgagactg      60
tcctgtgtgg cctctggatt caccttcagt agtcacgata tgaattgggt ccgccaggct    120
cctggaaagg gactgcagtg gtcgcatct attaacagtg gtggcagcgg tctgcattac     180
gcagacagtg tgaggggccg attcaccgtc tccagagaca acgccaagaa caccctttat    240
ctggacttga cgatgtgag agacgaagac acggccatgt attattgtac gacagagaag    300
ttgggttacc acaaccccctt cggtttctgg gattggggcc agggcaccct ggtcaccgtc    360
tcctcagcct ccaccacggc cccctcggtt                                      390

<210> SEQ ID NO 83
<211> LENGTH: 130
<212> TYPE: PRT
<213> ORGANISM: Artificial
<220> FEATURE:
<223> OTHER INFORMATION: VH chain

<400> SEQUENCE: 83

Gly Val Gln Leu Val Glu Ser Gly Gly Asp Arg Val Asn Pro Ala Gly
1               5                   10                  15

Ser Leu Arg Leu Ser Cys Val Ala Ser Gly Phe Thr Phe Ser Ser His
            20                  25                  30

Asp Met Asn Trp Val Arg Gln Ala Pro Gly Lys Gly Leu Gln Trp Val
        35                  40                  45

Ala Ser Ile Asn Ser Gly Gly Ser Gly Leu His Tyr Ala Asp Ser Val
    50                  55                  60
```

```
Arg Gly Arg Phe Thr Val Ser Arg Asp Asn Ala Lys Asn Thr Leu Tyr
65                  70                  75                  80

Leu Asp Leu Asn Asp Val Arg Asp Glu Asp Thr Ala Met Tyr Tyr Cys
                85                  90                  95

Thr Thr Glu Lys Leu Gly Tyr His Asn Pro Phe Gly Phe Trp Asp Trp
            100                 105                 110

Gly Gln Gly Thr Leu Val Thr Val Ser Ser Ala Ser Thr Thr Ala Pro
        115                 120                 125

Ser Val
    130

<210> SEQ ID NO 84
<211> LENGTH: 390
<212> TYPE: DNA
<213> ORGANISM: Artificial
<220> FEATURE:
<223> OTHER INFORMATION: VH chain

<400> SEQUENCE: 84
gagttgcaac tggtggagtt tggggagac ctggtgaagc ctgggggtc cctgagactc      60 tcctgtgtag cctctggatt caccttcagt aactacgaca tggcctgggt ccgccaggct    120
cctgggaagg ggctgcagtg ggtctcagct attagctatg atggaaggag tacatataac    180
actgacgatg tgaagggccg attcaccatc tccagagaca cgccaggaa cacactgtat     240 ctgcagatga acagcctgag agccgaggac acggctgtac attactgtgt ccctaccacc    300
tgtactgatg attactgtct ctcttttgcc tactggggcc agggaaccct ggtcacgtc     360 tcytcagcyt ccaccacggc cccytcggtt                                     390

<210> SEQ ID NO 85
<211> LENGTH: 130
<212> TYPE: PRT
<213> ORGANISM: Artificial
<220> FEATURE:
<223> OTHER INFORMATION: VH chain

<400> SEQUENCE: 85

Glu Leu Gln Leu Val Glu Phe Gly Gly Asp Leu Val Lys Pro Gly Gly
1               5                   10                  15

Ser Leu Arg Leu Ser Cys Val Ala Ser Gly Phe Thr Phe Ser Asn Tyr
            20                  25                  30

Asp Met Ala Trp Val Arg Gln Ala Pro Gly Lys Gly Leu Gln Trp Val
        35                  40                  45

Ser Ala Ile Ser Tyr Asp Gly Arg Ser Thr Tyr Asn Thr Asp Asp Val
    50                  55                  60

Lys Gly Arg Phe Thr Ile Ser Arg Asp Asn Ala Arg Asn Thr Leu Tyr
65                  70                  75                  80

Leu Gln Met Asn Ser Leu Arg Ala Glu Asp Thr Ala Val His Tyr Cys
                85                  90                  95

Val Pro Thr Thr Cys Thr Asp Asp Tyr Cys Leu Ser Phe Ala Tyr Trp
            100                 105                 110

Gly Gln Gly Thr Leu Val Thr Val Ser Ser Ala Ser Thr Thr Ala Pro
        115                 120                 125

Ser Val
    130

<210> SEQ ID NO 86
<211> LENGTH: 369
<212> TYPE: DNA
```

-continued

<213> ORGANISM: Artificial
<220> FEATURE:
<223> OTHER INFORMATION: VH chain

<400> SEQUENCE: 86

```
gaggggcagc tggcggagtc tgggggagac ctggtgaagc ctgcggggtc cctgagactg      60
tcctgtgtgg cctctggatt caccatcagc agccacgaca tgagctgggt ccgccaggct    120
cctgggaagg gctgcagtg gtcgcaggt attaacagtg gtggaaccag gacaggctac      180
acagacgctg tgaaggcccg attcaccatc tccagagaca acgccaagaa cacactgtat    240
ctgcagatga acagcctgag agccgaggac acggccgtat attactgtgt gttgagtatt    300
gtaacgacta attggggccg gggaaccctg gtcaccgtct cctcagcctc caccacggcc    360
ccctcggtt                                                            369
```

<210> SEQ ID NO 87
<211> LENGTH: 123
<212> TYPE: PRT
<213> ORGANISM: Artificial
<220> FEATURE:
<223> OTHER INFORMATION: VH chain

<400> SEQUENCE: 87

```
Glu Gly Gln Leu Ala Glu Ser Gly Gly Asp Leu Val Lys Pro Ala Gly
1               5                   10                  15
Ser Leu Arg Leu Ser Cys Val Ala Ser Gly Phe Thr Ile Ser Ser His
            20                  25                  30
Asp Met Ser Trp Val Arg Gln Ala Pro Gly Lys Gly Leu Gln Trp Val
        35                  40                  45
Ala Gly Ile Asn Ser Gly Gly Thr Arg Thr Gly Tyr Thr Asp Ala Val
    50                  55                  60
Lys Ala Arg Phe Thr Ile Ser Arg Asp Asn Ala Lys Asn Thr Leu Tyr
65                  70                  75                  80
Leu Gln Met Asn Ser Leu Arg Ala Glu Asp Thr Ala Val Tyr Tyr Cys
                85                  90                  95
Val Leu Ser Ile Val Thr Thr Asn Trp Gly Arg Gly Thr Leu Val Thr
            100                 105                 110
Val Ser Ser Ala Ser Thr Thr Ala Pro Ser Val
        115                 120
```

<210> SEQ ID NO 88
<211> LENGTH: 393
<212> TYPE: DNA
<213> ORGANISM: Artificial
<220> FEATURE:
<223> OTHER INFORMATION: VH chain

<400> SEQUENCE: 88

```
gaggtgcagc tggtgcagtc tgaggagac ctggtgaagc ctgggggtc cctgagactt       60
tcctgtgtgg cctctggatt caccttcagt cgctatcgca tggcctgggt ccgccaacca    120
ccggggaggg gacttcagtg gtcgcattc attaatagtg atggagatcg cacgacctat    180
tcagacactg tgaagggccg attcaccatt tccagagaca acgccaacga cacgctatat    240
cttcagatga acagcctgag agacgaagac acggcccttt atttctgtgc gagtgacgcc    300
ctctacggca ccagttggta ttccatcctt gactactggg gccagggaac cctggtcacc    360
gtctcctccg cctccaccac ggccccctcg gtt                                  393
```

<210> SEQ ID NO 89

```
<211> LENGTH: 131
<212> TYPE: PRT
<213> ORGANISM: Artificial
<220> FEATURE:
<223> OTHER INFORMATION: VH chain

<400> SEQUENCE: 89

Glu Val Gln Leu Val Gln Ser Gly Gly Asp Leu Val Lys Pro Gly Gly
1               5                   10                  15

Ser Leu Arg Leu Ser Cys Val Ala Ser Gly Phe Thr Phe Ser Arg Tyr
            20                  25                  30

Arg Met Ala Trp Val Arg Gln Pro Pro Gly Arg Gly Leu Gln Trp Val
        35                  40                  45

Ala Phe Ile Asn Ser Asp Gly Asp Arg Thr Thr Tyr Ser Asp Thr Val
    50                  55                  60

Lys Gly Arg Phe Thr Ile Ser Arg Asp Asn Ala Asn Asp Thr Leu Tyr
65                  70                  75                  80

Leu Gln Met Asn Ser Leu Arg Asp Glu Asp Thr Ala Leu Tyr Phe Cys
                85                  90                  95

Ala Ser Asp Ala Leu Tyr Gly Thr Ser Trp Tyr Ser Ile Leu Asp Tyr
            100                 105                 110

Trp Gly Gln Gly Thr Leu Val Thr Val Ser Ser Ala Ser Thr Thr Ala
        115                 120                 125

Pro Ser Val
    130

<210> SEQ ID NO 90
<211> LENGTH: 387
<212> TYPE: DNA
<213> ORGANISM: Artificial
<220> FEATURE:
<223> OTHER INFORMATION: VH chain

<400> SEQUENCE: 90
ggggtgcagc tggtggagtc tgggggagcc ctggtgaagc ctgcggggtc cctgagactg      60
tcctgtgtga cctctggctt catcttcaca tactatggca tgagctgggt ccgccaggct     120
cctgggaagg ggctgcagtg ggtcgcgcat atttacagtg atggaagtgg cacaacttac     180
gcagacgctg tgaaggggcg attcaccata tccagggaca cgccaagaa cacagtgcat      240 ctgcaaatga acagcctgag agccgaggac acggccgtgt attactgtgc gagggatatg     300
gactggggcg cgtgggtcga ccttgagtac tggggccagg gcaccctggt cacygtctcy     360
tcagcytcca ccacggcccc ytcggtt                                         387

<210> SEQ ID NO 91
<211> LENGTH: 129
<212> TYPE: PRT
<213> ORGANISM: Artificial
<220> FEATURE:
<223> OTHER INFORMATION: VH chain

<400> SEQUENCE: 91

Gly Val Gln Leu Val Glu Ser Gly Gly Ala Leu Val Lys Pro Ala Gly
1               5                   10                  15

Ser Leu Arg Leu Ser Cys Val Thr Ser Gly Phe Ile Phe Thr Tyr Tyr
            20                  25                  30

Gly Met Ser Trp Val Arg Gln Ala Pro Gly Lys Gly Leu Gln Trp Val
        35                  40                  45

Ala His Ile Tyr Ser Asp Gly Ser Gly Thr Thr Tyr Ala Asp Ala Val
    50                  55                  60
```

-continued

Lys Gly Arg Phe Thr Ile Ser Arg Asp Asn Ala Lys Asn Thr Val His
 65                  70                  75                  80

Leu Gln Met Asn Ser Leu Arg Ala Glu Asp Thr Ala Val Tyr Tyr Cys
                 85                  90                  95

Ala Arg Asp Met Asp Trp Gly Ala Trp Val Asp Leu Glu Tyr Trp Gly
            100                 105                 110

Gln Gly Thr Leu Val Thr Val Ser Ser Ala Ser Thr Thr Ala Pro Ser
        115                 120                 125

Val

<210> SEQ ID NO 92
<211> LENGTH: 384
<212> TYPE: DNA
<213> ORGANISM: Artificial
<220> FEATURE:
<223> OTHER INFORMATION: VH chain

<400> SEQUENCE: 92
gaggtgcagc tggtggagtc tgggggagac ctggtgaagc cggggggtc cctgagactc        60 tcctgtgtag cctctggatt caccttcagt aactacgaca tgacctgggt ccgccaggct       120
cctgggaagg gctgcagtg gtcgcagct gttagttttg ttggaggtag tacatattac         180
actgacgctc tgaagggccg attcaccatc tccagagaca cgccaggaa cacagtgtat        240 ctgcagatga acgacctgag agccgaggac acggctgtgt atttctgtgc ggacaatact       300
tacaactggg gtgggggc ggaatactgg ggccaggca ccctggtcac cgtctcctca          360
gcctccacca cggccccctc ggtt                                              384

<210> SEQ ID NO 93
<211> LENGTH: 128
<212> TYPE: PRT
<213> ORGANISM: Artificial
<220> FEATURE:
<223> OTHER INFORMATION: VH chain

<400> SEQUENCE: 93

Glu Val Gln Leu Val Glu Ser Gly Gly Asp Leu Val Lys Pro Gly Gly
 1               5                  10                  15

Ser Leu Arg Leu Ser Cys Val Ala Ser Gly Phe Thr Phe Ser Asn Tyr
            20                  25                  30

Asp Met Thr Trp Val Arg Gln Ala Pro Gly Lys Gly Leu Gln Trp Val
        35                  40                  45

Ala Ala Val Ser Phe Val Gly Gly Ser Thr Tyr Tyr Thr Asp Ala Leu
    50                  55                  60

Lys Gly Arg Phe Thr Ile Ser Arg Asp Asn Ala Arg Asn Thr Val Tyr
 65                  70                  75                  80

Leu Gln Met Asn Asp Leu Arg Ala Glu Asp Thr Ala Val Tyr Phe Cys
                 85                  90                  95

Ala Asp Asn Thr Tyr Asn Trp Gly Trp Gly Ala Glu Tyr Trp Gly Gln
            100                 105                 110

Gly Thr Leu Val Thr Val Ser Ser Ala Ser Thr Thr Ala Pro Ser Val
        115                 120                 125

<210> SEQ ID NO 94
<211> LENGTH: 378
<212> TYPE: DNA
<213> ORGANISM: Artificial
<220> FEATURE:
<223> OTHER INFORMATION: VH chain

<400> SEQUENCE: 94

```
gagttgcaac tggtggagtt tgggggagac ctggtgaagc ctgggggggtc cttgagactg      60
tcctgtgtgg cctctggatt caccttcagt agctatggca tgacctgggt ccgtcagtct     120
ccagggaagg ggctacagtg gtcgcagat attagcagta gtggaaccac ataccacgca     180
gacgctgtga agggccgatt taccatctcc agagacaacg ccaagaacac gctgtatctg     240
cagatgaaca gcctgagagc cgaggacacg gccgtctatt actgtgcaaa acaggtacag     300
ggatccttgc caccggacca ctggggccag ggcaccctgg tcaccgtctc ctcagcctcc     360
accacggccc cctcggtt                                                   378
```

<210> SEQ ID NO 95
<211> LENGTH: 126
<212> TYPE: PRT
<213> ORGANISM: Artificial
<220> FEATURE:
<223> OTHER INFORMATION: VH chain

<400> SEQUENCE: 95

Glu Leu Gln Leu Val Glu Phe Gly Gly Asp Leu Val Lys Pro Gly Gly
1               5                   10                  15

Ser Leu Arg Leu Ser Cys Val Ala Ser Gly Phe Thr Phe Ser Ser Tyr
            20                  25                  30

Gly Met Thr Trp Val Arg Gln Ser Pro Gly Lys Gly Leu Gln Trp Val
        35                  40                  45

Ala Asp Ile Ser Ser Gly Thr Thr Tyr His Ala Asp Ala Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Gln Val Gln Gly Ser Leu Pro Pro Asp His Trp Gly Gln Gly Thr
            100                 105                 110

Leu Val Thr Val Ser Ser Ala Ser Thr Thr Ala Pro Ser Val
        115                 120                 125

<210> SEQ ID NO 96
<211> LENGTH: 393
<212> TYPE: DNA
<213> ORGANISM: Artificial
<220> FEATURE:
<223> OTHER INFORMATION: VH chain

<400> SEQUENCE: 96

```
gaggtgcaac tggtggaatc tgggggagac ctagtgaagc ctggggggtc cttgagactg      60
tcctgtgtgg cctccggatt caccttcagt gactatggca tgatctgggt ccgtcagtct     120
ccagggaagg ggctgcagtg gtcgcggct cttagcagta gtggaagtag cacatactac     180
gcagacgctg tgaagggccg attcaccatc tccagagaca acgccgagaa cacgctgcat     240
ctgcagatga agagcctgag agccgaggac acggccgtct attactgtgc gaagggattc     300
gggggactat atatacgcat ggataatatt gaatactggg ccagggcac cctggtcgcc     360
gtctcctcag cctccaccac ggcccctcg gtt                                   393
```

<210> SEQ ID NO 97
<211> LENGTH: 131
<212> TYPE: PRT
<213> ORGANISM: Artificial

<220> FEATURE:
<223> OTHER INFORMATION: VH chain

<400> SEQUENCE: 97

```
Glu Val Gln Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Asp Tyr
            20                  25                  30

Gly Met Ile Trp Val Arg Gln Ser Pro Gly Lys Gly Leu Gln Trp Val
        35                  40                  45

Ala Ala Leu Ser Ser Ser Gly Ser Ser Thr Tyr Tyr Ala Asp Ala Val
    50                  55                  60

Lys Gly Arg Phe Thr Ile Ser Arg Asp Asn Ala Glu Asn Thr Leu His
65                  70                  75                  80

Leu Gln Met Lys Ser Leu Arg Ala Glu Asp Thr Ala Val Tyr Tyr Cys
                85                  90                  95

Ala Lys Gly Phe Gly Leu Tyr Ile Arg Met Asp Asn Ile Glu Tyr
            100                 105                 110

Trp Gly Gln Gly Thr Leu Val Ala Val Ser Ser Ala Ser Thr Thr Ala
        115                 120                 125

Pro Ser Val
    130
```

<210> SEQ ID NO 98
<211> LENGTH: 366
<212> TYPE: DNA
<213> ORGANISM: Artificial
<220> FEATURE:
<223> OTHER INFORMATION: VH chain

<400> SEQUENCE: 98

```
gaggtgcagc tggtggagtc tgggggagac ctggtgaagc ctggggggtc cctgagagtc    60
tcctgtgtgg cctctggaat caccctcagt agttacagca tgcaatgggt ccgtcaggct   120
ccaggaaagg ggctgcagtg ggtcgcatac attaatagtg gtggaagtac acatactac   180
gcagacgctg tgaagggccg attcaccatc tccagagaca cgccgagaa cacggtgtat   240
ctgcagatga acagcctgag acccgaagac acggccgtgt attactgtag tccccctgcc   300
cttgagttct ggggccaggg caccctactc accgtctcct cagcctccac cacggccccc   360
tcggtt                                                              366
```

<210> SEQ ID NO 99
<211> LENGTH: 122
<212> TYPE: PRT
<213> ORGANISM: Artificial
<220> FEATURE:
<223> OTHER INFORMATION: VH chain

<400> SEQUENCE: 99

```
Glu Val Gln Leu Val Glu Ser Gly Gly Asp Leu Val Lys Pro Gly Gly
1               5                   10                  15

Ser Leu Arg Val Ser Cys Val Ala Ser Gly Ile Thr Leu Ser Ser Tyr
            20                  25                  30

Ser Met Gln Trp Val Arg Gln Ala Pro Gly Lys Gly Leu Gln Trp Val
        35                  40                  45

Ala Tyr Ile Asn Ser Gly Gly Ser Thr Thr Tyr Tyr Ala Asp Ala Val
    50                  55                  60

Lys Gly Arg Phe Thr Ile Ser Arg Asp Asn Ala Glu Asn Thr Val Tyr
65                  70                  75                  80
```

```
Leu Gln Met Asn Ser Leu Arg Pro Glu Asp Thr Ala Val Tyr Tyr Cys
                85                  90                  95

Ser Pro Pro Ala Leu Glu Phe Trp Gly Gln Gly Thr Leu Leu Thr Val
            100                 105                 110

Ser Ser Ala Ser Thr Thr Ala Pro Ser Val
            115                 120
```

<210> SEQ ID NO 100
<211> LENGTH: 387
<212> TYPE: DNA
<213> ORGANISM: Artificial
<220> FEATURE:
<223> OTHER INFORMATION: VH chain

<400> SEQUENCE: 100

```
gaggtgcgtt tggtggagtc tggaggagac ctggtgaagc cggggggggtc cctgagactt    60 tcctgtgtgg cctctggatt caccttcagt gactatgaca tggactgggt ccgccaggct   120
ccagggaagg ggctgcagtg gctctcagag atcaacagca gtggaagtaa cacattctac   180
gcagacgctg tgaggggccg attcaccgtc tccagagaca tgccaagca tacggtgtat   240 ctgcagatga acggcctgag agccgaggac acggccgtgt attattgtgc aaggggttgg   300
ggcaagaata cgttcgcccc ttttgactac tggggccagg gaaccctggt caccgtctcc   360
tcagcctcca ccacggcccc ctcggtt                                       387
```

<210> SEQ ID NO 101
<211> LENGTH: 129
<212> TYPE: PRT
<213> ORGANISM: Artificial
<220> FEATURE:
<223> OTHER INFORMATION: VH chain

<400> SEQUENCE: 101

```
Glu Val Arg Leu Val Glu Ser Gly Gly Asp Leu Val Lys Pro Gly Gly
1               5                  10                  15

Ser Leu Arg Leu Ser Cys Val Ala Ser Gly Phe Thr Phe Ser Asp Tyr
            20                  25                  30

Asp Met Asp Trp Val Arg Gln Ala Pro Gly Lys Gly Leu Gln Trp Leu
        35                  40                  45

Ser Glu Ile Asn Ser Ser Gly Ser Asn Thr Phe Tyr Ala Asp Ala Val
    50                  55                  60

Arg Gly Arg Phe Thr Val Ser Arg Asp Asn Ala Lys His Thr Val Tyr
65                  70                  75                  80

Leu Gln Met Asn Gly Leu Arg Ala Glu Asp Thr Ala Val Tyr Tyr Cys
                85                  90                  95

Ala Arg Gly Trp Gly Lys Asn Thr Phe Ala Pro Phe Asp Tyr Trp Gly
            100                 105                 110

Gln Gly Thr Leu Val Thr Val Ser Ser Ala Ser Thr Thr Ala Pro Ser
        115                 120                 125

Val
```

<210> SEQ ID NO 102
<211> LENGTH: 378
<212> TYPE: DNA
<213> ORGANISM: Artificial
<220> FEATURE:
<223> OTHER INFORMATION: VH chain

<400> SEQUENCE: 102

```
gaattgcaac tggtggagtt tgggggagac ctggtgaagc ctggggggtc cctgaaactc      60
tcctgtgtgg cctctggatt catgctcggt aattacgaga tttactgggt ccgccaggct     120
ccagggagag gtctggagtg ggtcgcaagg atctatgaga ctggaactac acatactac     180 gcagaatctg tgaatggccg cttcaccgtg tccagaaaca cgccaatga cattgcgtac     240 ctacagatgg acagcctgag agccgacgac acggccgtat attactgtgc aaacgaccta    300
actagtactc ggggcccct ctggggccag ggaaccctgg tcaccgtctc ctcggcctcc     360
accacggccc cctcggtt                                                 378
```

<210> SEQ ID NO 103
<211> LENGTH: 126
<212> TYPE: PRT
<213> ORGANISM: Artificial
<220> FEATURE:
<223> OTHER INFORMATION: VH chain

<400> SEQUENCE: 103

```
Glu Leu Gln Leu Val Glu Phe Gly Gly Asp Leu Val Lys Pro Gly Gly
1               5                   10                  15

Ser Leu Lys Leu Ser Cys Val Ala Ser Gly Phe Met Leu Gly Asn Tyr
            20                  25                  30

Glu Ile Tyr Trp Val Arg Gln Ala Pro Gly Arg Gly Leu Glu Trp Val
        35                  40                  45

Ala Arg Ile Tyr Glu Thr Gly Thr Thr Thr Tyr Tyr Ala Glu Ser Val
    50                  55                  60

Asn Gly Arg Phe Thr Val Ser Arg Asn Asn Ala Asn Asp Ile Ala Tyr
65                  70                  75                  80

Leu Gln Met Asp Ser Leu Arg Ala Asp Asp Thr Ala Val Tyr Tyr Cys
                85                  90                  95

Ala Asn Asp Leu Thr Ser Thr Arg Gly Pro Leu Trp Gly Gln Gly Thr
            100                 105                 110

Leu Val Thr Val Ser Ser Ala Ser Thr Thr Ala Pro Ser Val
        115                 120                 125
```

<210> SEQ ID NO 104
<211> LENGTH: 390
<212> TYPE: DNA
<213> ORGANISM: Artificial
<220> FEATURE:
<223> OTHER INFORMATION: VH chain

<400> SEQUENCE: 104

```
gacgtgcagc tggtggagtc tgggggagac ttggtgaggc ctggggggtc cctgacactc      60
tcctgtgtgg cctctggatt caccttcact aactacgata tgtactgggt ccgccaacct     120
ccagggaaag gactggagtg ggtcgctagg atttatgaga ctggaagtac acatactat     180 gcagaagttg taaagggccg attcaccatg tccagagaca cgccaagag catggcatac     240 ctacagatga acagcctgag agccgaggac acggccgttt attactgtgc gaatctcact     300
ccgcagcggg atatctatgg accaggggac tactggggcc agggaaccct ggtcaccgtc     360
tcctcagcct ccaccacggc ccctcggtt                                      390
```

<210> SEQ ID NO 105
<211> LENGTH: 130
<212> TYPE: PRT
<213> ORGANISM: Artificial
<220> FEATURE:
<223> OTHER INFORMATION: VH chain -continued

<400> SEQUENCE: 105

Asp Val Gln Leu Val Glu Ser Gly Gly Asp Leu Val Arg Pro Gly Gly
1               5                   10                  15

Ser Leu Thr Leu Ser Cys Val Ala Ser Gly Phe Thr Phe Thr Asn Tyr
            20                  25                  30

Asp Met Tyr Trp Val Arg Gln Pro Pro Gly Lys Gly Leu Glu Trp Val
        35                  40                  45

Ala Arg Ile Tyr Glu Thr Gly Ser Thr Thr Tyr Tyr Ala Glu Val Val
    50                  55                  60

Lys Gly Arg Phe Thr Met Ser Arg Asp Asn Ala Lys Ser Met Ala Tyr
65                  70                  75                  80

Leu Gln Met Asn Ser Leu Arg Ala Glu Asp Thr Ala Val Tyr Tyr Cys
                85                  90                  95

Ala Asn Leu Thr Pro Gln Arg Asp Ile Tyr Gly Pro Gly Asp Tyr Trp
            100                 105                 110

Gly Gln Gly Thr Leu Val Thr Val Ser Ser Ala Ser Thr Thr Ala Pro
        115                 120                 125

Ser Val
    130

<210> SEQ ID NO 106
<211> LENGTH: 378
<212> TYPE: DNA
<213> ORGANISM: artificial
<220> FEATURE:
<223> OTHER INFORMATION: VH chain

<400> SEQUENCE: 106
gaggagcaac tggtggagtt tgggggagag ctggtgaagc ctgcggggtc cctgagactg      60
tcctgtgtgg cctctggatt tcccttcagc aattacgaca taaactgggt ccgccaggct     120
cctgggaagg ggctgcagtg ggtcgcaggt attaagagtg atggaagtag acatggtac      180 gcagacgctg tgaagggccg attcaccatt tccagagaca tgccaagaa tacagtgtat      240 ctgcagatga acagcctgag agacgaggac acggccgtgt attattgtgt ggacttagga      300
tggggccctg atatggacca ctggggccct ggcacctcac tcttcgtgtc ctcagcctcc      360
accacggccc cctcggtt                                                    378

<210> SEQ ID NO 107
<211> LENGTH: 126
<212> TYPE: PRT
<213> ORGANISM: artificial
<220> FEATURE:
<223> OTHER INFORMATION: VH chain

<400> SEQUENCE: 107

Glu Glu Gln Leu Val Glu Phe Gly Gly Glu Leu Val Lys Pro Ala Gly
1               5                   10                  15

Ser Leu Arg Leu Ser Cys Val Ala Ser Gly Phe Pro Phe Ser Asn Tyr
            20                  25                  30

Asp Ile Asn Trp Val Arg Gln Ala Pro Gly Lys Gly Leu Gln Trp Val
        35                  40                  45

Ala Gly Ile Lys Ser Asp Gly Ser Arg Thr Trp Tyr Ala Asp Ala Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Arg Asp Glu Asp Thr Ala Val Tyr Tyr Cys
                85                  90                  95

Val Asp Leu Gly Trp Gly Pro Asp Met Asp His Trp Gly Pro Gly Thr
            100                 105                 110

Ser Leu Phe Val Ser Ser Ala Ser Thr Thr Ala Pro Ser Val
        115                 120                 125

<210> SEQ ID NO 108
<211> LENGTH: 390
<212> TYPE: DNA
<213> ORGANISM: artificial
<220> FEATURE:
<223> OTHER INFORMATION: VH chain

<400> SEQUENCE: 108
gaggtgcagc tggcggagtc tgggggagac ctggtgaagc ctgggggtc cctgagactg      60 tcctgtgtgg cctctggatt caccttcagt agttactaca tgtactgggt ccgccaggct    120
cctgggaagg ggcttcagtg ggtcgcacgg attaacactg atggaagtaa tacatactac    180
acagacgctg tgaagggccg cttcaccatc tccagagaca tgccaagaa cacgctgtat    240 ctgcagatga acagcctgag agccgaggac acggctatgt atttctgtgc aaagacccgg    300
ccatacggta cctcctggct gggttttgac ttctggggcc agggaaccct ggtcaccgtc    360
tcctcagcct ccaccacggc cccctcggtt                                     390

<210> SEQ ID NO 109
<211> LENGTH: 130
<212> TYPE: PRT
<213> ORGANISM: artificial
<220> FEATURE:
<223> OTHER INFORMATION: VH chain

<400> SEQUENCE: 109

Glu Val Gln Leu Ala Glu Ser Gly Gly Asp Leu Val Lys Pro Gly Gly
1               5                   10                  15

Ser Leu Arg Leu Ser Cys Val Ala Ser Gly Phe Thr Phe Ser Ser Tyr
            20                  25                  30

Tyr Met Tyr Trp Val Arg Gln Ala Pro Gly Lys Gly Leu Gln Trp Val
        35                  40                  45

Ala Arg Ile Asn Thr Asp Gly Ser Asn Thr Tyr Tyr Thr Asp Ala Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Met Tyr Phe Cys
                85                  90                  95

Ala Lys Thr Arg Pro Tyr Gly Thr Ser Trp Leu Gly Phe Asp Phe Trp
            100                 105                 110

Gly Gln Gly Thr Leu Val Thr Val Ser Ser Ala Ser Thr Thr Ala Pro
        115                 120                 125

Ser Val
    130

<210> SEQ ID NO 110
<211> LENGTH: 378
<212> TYPE: DNA
<213> ORGANISM: artificial
<220> FEATURE:
<223> OTHER INFORMATION: VH chain

<400> SEQUENCE: 110
gaggagcagc tggtggagct tgggggagac ctggtgaagc ctgggggtc cttgagactg      60

```
tcctgtgtgg cctctgaatc gaccttcggt gtctttgtca tgacctgggt ccgtcagtct      120
cccgggaagg gtctgcagtg ggtcgctgat tatagtagta ctggaagtac ctactacatg      180
gacgctgtga ggggccgctt caccatctcc agagacaacg ccaagaacac gctgtatctt      240
cagatgaaca gcctgagagc cgaagacacg gccgtatatt actgtgcgag cccccaggag      300
atgggacttt tcaccgcctc ctggggccag ggaaccctgg tcaccgtctc ctcagcctcc      360
accacggccc cctcggtt                                                    378
```

<210> SEQ ID NO 111
<211> LENGTH: 126
<212> TYPE: PRT
<213> ORGANISM: artificial
<220> FEATURE:
<223> OTHER INFORMATION: VH chain

<400> SEQUENCE: 111

```
Glu Glu Gln Leu Val Glu Leu Gly Gly Asp Leu Val Lys Pro Gly Gly
1               5                   10                  15

Ser Leu Arg Leu Ser Cys Val Ala Ser Glu Ser Thr Phe Gly Val Phe
            20                  25                  30

Val Met Thr Trp Val Arg Gln Ser Pro Gly Lys Gly Leu Gln Trp Val
        35                  40                  45

Ala Asp Tyr Ser Ser Thr Gly Ser Thr Tyr Tyr Met Asp Ala Val Arg
    50                  55                  60

Gly Arg Phe Thr Ile Ser Arg Asp Asn Ala Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Ser Pro Gln Glu Met Gly Leu Phe Thr Ala Ser Trp Gly Gln Gly Thr
            100                 105                 110

Leu Val Thr Val Ser Ser Ala Ser Thr Thr Ala Pro Ser Val
        115                 120                 125
```

<210> SEQ ID NO 112
<211> LENGTH: 378
<212> TYPE: DNA
<213> ORGANISM: artificial
<220> FEATURE:
<223> OTHER INFORMATION: VH chain

<400> SEQUENCE: 112

```
gaggtgcagc tggtggagtc tgggggagac ctggtgaagc ctgcggggtc cctgagactg       60
tcctgtgtgg cctccggatt caccttcagt agctccacca tggcctgggt acgccagtct      120
cctgggaagg ggctgcagtt ggtcgctgct attaacagag tggaaataa cacatattac      180 tcagacgctg taaagggccg attcaccatc tccagagaca tgccaagaa tacagtgtat      240 ctacagatga acagcctcag agacgaggac acggccatgt attattgtgc aaaggggtgg      300
ggaagtgacg accttgagta ctggggccag ggcaccctgg tcaccgtctc ctcagcctcc      360
accacggccc cctcggtt                                                    378
```

<210> SEQ ID NO 113
<211> LENGTH: 126
<212> TYPE: PRT
<213> ORGANISM: artificial
<220> FEATURE:
<223> OTHER INFORMATION: VH chain

<400> SEQUENCE: 113

```
Glu Val Gln Leu Val Glu Ser Gly Gly Asp Leu Val Lys Pro Ala Gly
1               5                   10                  15

Ser Leu Arg Leu Ser Cys Val Ala Ser Gly Phe Thr Phe Ser Ser Ser
                20                  25                  30

Thr Met Ala Trp Val Arg Gln Ser Pro Gly Lys Gly Leu Gln Leu Val
            35                  40                  45

Ala Ala Ile Asn Arg Gly Gly Asn Asn Thr Tyr Tyr Ser Asp Ala Val
        50                  55                  60

Lys Gly Arg Phe Thr Ile Ser Arg Asp Asn Ala Lys Asn Thr Val Tyr
65                  70                  75                  80

Leu Gln Met Asn Ser Leu Arg Asp Glu Asp Thr Ala Met Tyr Tyr Cys
                85                  90                  95

Ala Lys Gly Trp Gly Ser Asp Asp Leu Glu Tyr Trp Gly Gln Gly Thr
            100                 105                 110

Leu Val Thr Val Ser Ser Ala Ser Thr Thr Ala Pro Ser Val
        115                 120                 125
```

<210> SEQ ID NO 114
<211> LENGTH: 393
<212> TYPE: DNA
<213> ORGANISM: artificial
<220> FEATURE:
<223> OTHER INFORMATION: VH chain

<400> SEQUENCE: 114

```
gaggggcagc tggcggagtc tgggggagcc ctggtaaaac ctggggcatc cctgagactc    60
tcctgtgtgg cctctggatt caccttcagt gactatgaca tgagttgggt ccgccaggct   120
ccagggaagg gactacagtg ggtcgcagtt atttcgtctg atgcaagtac cacatacacc   180
gcagacgttg tgaggggccg attcaccatc tccagagaca cgccaagaa ttcgatgtat    240
ctggagatga atggcctgag agacgaggac acagccgtat attattgtgg gaagggatcc   300
ctgactagta actggtggac ggatggtatg gactactggg gccctggcac ttcactcttc   360
gtgtcctcag cctccaccac ggccccctcg gtt                               393
```

<210> SEQ ID NO 115
<211> LENGTH: 131
<212> TYPE: PRT
<213> ORGANISM: artificial
<220> FEATURE:
<223> OTHER INFORMATION: VH chain

<400> SEQUENCE: 115

```
Glu Gly Gln Leu Ala Glu Ser Gly Gly Ala Leu Val Lys Pro Gly Ala
1               5                   10                  15

Ser Leu Arg Leu Ser Cys Val Ala Ser Gly Phe Thr Phe Ser Asp Tyr
                20                  25                  30

Asp Met Ser Trp Val Arg Gln Ala Pro Gly Lys Gly Leu Gln Trp Val
            35                  40                  45

Ala Val Ile Ser Ser Asp Ala Ser Thr Thr Tyr Thr Ala Asp Val Val
        50                  55                  60

Arg Gly Arg Phe Thr Ile Ser Arg Asp Asn Ala Lys Asn Ser Met Tyr
65                  70                  75                  80

Leu Glu Met Asn Gly Leu Arg Asp Glu Asp Thr Ala Val Tyr Tyr Cys
                85                  90                  95

Gly Lys Gly Ser Leu Thr Ser Asn Trp Trp Thr Asp Gly Met Asp Tyr
            100                 105                 110

Trp Gly Pro Gly Thr Ser Leu Phe Val Ser Ser Ala Ser Thr Thr Ala
```

```
                   115                 120                 125
Pro Ser Val
        130

<210> SEQ ID NO 116
<211> LENGTH: 390
<212> TYPE: DNA
<213> ORGANISM: artificial
<220> FEATURE:
<223> OTHER INFORMATION: VH chain

<400> SEQUENCE: 116
gaggtgcagc tggtggagtc tgggggagac ctggtgaagc ctgcggggtc cctgagactg        60
tcctgtgtgg cctctggatt caccttcagt agctacagta tgagctgggt acgccaggct       120
cctgggaagg ggctgcaatt ggtcgcaggt attatcagcg gtggaagtag cacatactac       180
acagacgctg tgaagggccg attcaccgtc tccagagaca atgccaagaa cacagtgttt       240
ctgcagatga acagcctgag agccgaggac acggccatgt attactgtgc aaaggagaag       300
tatacatatg gatacggggc cggacttgag tactggggcc agggcaccct ggtcaccgtc       360
tcctcagcct ccaccacggc cccctcggtt                                        390

<210> SEQ ID NO 117
<211> LENGTH: 130
<212> TYPE: PRT
<213> ORGANISM: artificial
<220> FEATURE:
<223> OTHER INFORMATION: VH chain

<400> SEQUENCE: 117

Glu Val Gln Leu Val Glu Ser Gly Gly Asp Leu Val Lys Pro Ala Gly
1               5                   10                  15

Ser Leu Arg Leu Ser Cys Val Ala Ser Gly Phe Thr Phe Ser Ser Tyr
            20                  25                  30

Ser Met Ser Trp Val Arg Gln Ala Pro Gly Lys Gly Leu Gln Leu Val
        35                  40                  45

Ala Gly Ile Ile Ser Gly Gly Ser Ser Thr Tyr Tyr Thr Asp Ala Val
    50                  55                  60

Lys Gly Arg Phe Thr Val Ser Arg Asp Asn Ala Lys Asn Thr Val Phe
65                  70                  75                  80

Leu Gln Met Asn Ser Leu Arg Ala Glu Asp Thr Ala Met Tyr Tyr Cys
                85                  90                  95

Ala Lys Glu Lys Tyr Thr Tyr Gly Tyr Gly Ala Gly Leu Glu Tyr Trp
            100                 105                 110

Gly Gln Gly Thr Leu Val Thr Val Ser Ser Ala Ser Thr Thr Ala Pro
        115                 120                 125

Ser Val
    130

<210> SEQ ID NO 118
<211> LENGTH: 384
<212> TYPE: DNA
<213> ORGANISM: artificial
<220> FEATURE:
<223> OTHER INFORMATION: VH chain

<400> SEQUENCE: 118
ggggtgcagc tggtggagtc tgggggagac ctggtgaagc ctgggggtc cttgagattg         60 tcctgtgtag tctctggaat caccatcaat acatatacct atgcatgag ttgggtccgt        120
```

```
ctgtccccag ggaggggact gcagtccgtc gctcatctta gtcgggctgg ttacacatac      180
tacgcggacg ctgtaaaggg ccgattcacc atctccagag acaacggcaa gagtacgcta      240
tatttacaga tgaacagcct gacagtcgag gacacggccg tatattattg tgtgaaggcc      300
ccccttaggt ccggtggcgt cgactactgg ggccagggca ccctggtcac cgtctcctca      360
gcctccacca cggccccctc ggtt                                             384

<210> SEQ ID NO 119
<211> LENGTH: 128
<212> TYPE: PRT
<213> ORGANISM: artificial
<220> FEATURE:
<223> OTHER INFORMATION: VH chain

<400> SEQUENCE: 119

Gly Val Gln Leu Val Glu Ser Gly Gly Asp Leu Val Lys Pro Gly Gly
1               5                   10                  15

Ser Leu Arg Leu Ser Cys Val Val Ser Gly Ile Thr Ile Asn Thr Tyr
            20                  25                  30

Thr Tyr Gly Met Ser Trp Val Arg Leu Ser Pro Gly Arg Gly Leu Gln
        35                  40                  45

Ser Val Ala His Leu Ser Arg Ala Gly Tyr Thr Tyr Tyr Ala Asp Ala
    50                  55                  60

Val Lys Gly Arg Phe Thr Ile Ser Arg Asp Asn Gly Lys Ser Thr Leu
65                  70                  75                  80

Tyr Leu Gln Met Asn Ser Leu Thr Val Glu Asp Thr Ala Val Tyr Tyr
                85                  90                  95

Cys Val Lys Ala Pro Leu Arg Ser Gly Gly Val Asp Tyr Trp Gly Gln
            100                 105                 110

Gly Thr Leu Val Thr Val Ser Ser Ala Ser Thr Thr Ala Pro Ser Val
        115                 120                 125

<210> SEQ ID NO 120
<211> LENGTH: 390
<212> TYPE: DNA
<213> ORGANISM: artificial
<220> FEATURE:
<223> OTHER INFORMATION: VH chain

<400> SEQUENCE: 120
gaggggcagc tggcggagtc tgggggagac ctggtgaagc ctgggggtc cctgagactc       60 tcctgtgtag cctctggatt caccttcagt aactacgaca tgacctgggt ccgccaggct      120
cctgggaagg ggctgcagtg ggtcgcagct attagctatg atggaagtag tacatattac      180
actgacgctg tgaagggccg attcaccatc tccagagaca cgccaggaa cacactgtat       240 ctgcagatga acagcctgag agccgaggac acggctgtat attactgtgt ccctaccacc      300
tgtactgatg attactgtct ctcttttgcc tactggggcc agggaaccct ggtcaccgtc      360
tcctcagcct ccaccacggc cccctcggtt                                       390

<210> SEQ ID NO 121
<211> LENGTH: 130
<212> TYPE: PRT
<213> ORGANISM: artificial
<220> FEATURE:
<223> OTHER INFORMATION: VH chain

<400> SEQUENCE: 121

Glu Gly Gln Leu Ala Glu Ser Gly Gly Asp Leu Val Lys Pro Gly Gly
1               5                   10                  15
```

```
Ser Leu Arg Leu Ser Cys Val Ala Ser Gly Phe Thr Phe Ser Asn Tyr
            20                  25                  30

Asp Met Thr Trp Val Arg Gln Ala Pro Gly Lys Gly Leu Gln Trp Val
            35                  40                  45

Ala Ala Ile Ser Tyr Asp Gly Ser Thr Tyr Tyr Thr Asp Ala Val
 50                  55                  60

Lys Gly Arg Phe Thr Ile Ser Arg Asp Asn Ala Arg Asn Thr Leu Tyr
 65                  70                  75                  80

Leu Gln Met Asn Ser Leu Arg Ala Glu Asp Thr Ala Val Tyr Tyr Cys
                85                  90                  95

Val Pro Thr Thr Cys Thr Asp Asp Tyr Cys Leu Ser Phe Ala Tyr Trp
                100                 105                 110

Gly Gln Gly Thr Leu Val Thr Val Ser Ser Ala Ser Thr Ala Pro
            115                 120                 125

Ser Val
 130

<210> SEQ ID NO 122
<211> LENGTH: 366
<212> TYPE: DNA
<213> ORGANISM: artificial
<220> FEATURE:
<223> OTHER INFORMATION: VH chain

<400> SEQUENCE: 122
ggggtgcagc tggtgcaatc tgggggagac ctggtgaagc ctgggggtc cttgagactc      60 tcctgtgtgg cctctggttt caccttcagt agcaaccaca tggactgggt ccgccaggct    120
ccagggaagg ggctgcagtg gctcacacgg attcgcagtg atggagacat aggctacgca    180
gatgttgtga agggccgctt caccatctcc agagacaacg ccaagaacac actgtatctg    240
cagatggaca gcctgagatc tgaggacacg gctgtatatt attgtgcgag acactgggat    300
ctggactatt ggggccaggg aacccgggtg accgtctcct cagcctccac cacggccccc    360
tcggtt                                                              366

<210> SEQ ID NO 123
<211> LENGTH: 122
<212> TYPE: PRT
<213> ORGANISM: artificial
<220> FEATURE:
<223> OTHER INFORMATION: VH chain

<400> SEQUENCE: 123

Gly Val Gln Leu Val Gln Ser Gly Gly Asp Leu Val Lys Pro Gly Gly
 1               5                  10                  15

Ser Leu Arg Leu Ser Cys Val Ala Ser Gly Phe Thr Phe Ser Ser Asn
            20                  25                  30

His Met Asp Trp Val Arg Gln Ala Pro Gly Lys Gly Leu Gln Trp Leu
            35                  40                  45

Thr Arg Ile Arg Ser Asp Gly Asp Ile Gly Tyr Ala Asp Val Val Lys
 50                  55                  60

Gly Arg Phe Thr Ile Ser Arg Asp Asn Ala Lys Asn Thr Leu Tyr Leu
 65                  70                  75                  80

Gln Met Asp Ser Leu Arg Ser Glu Asp Thr Ala Val Tyr Tyr Cys Ala
                85                  90                  95

Arg His Trp Asp Leu Asp Tyr Trp Gly Gln Gly Thr Arg Val Thr Val
                100                 105                 110
```

Ser Ser Ala Ser Thr Thr Ala Pro Ser Val
        115                 120

<210> SEQ ID NO 124
<211> LENGTH: 381
<212> TYPE: DNA
<213> ORGANISM: artificial
<220> FEATURE:
<223> OTHER INFORMATION: VH chain

<400> SEQUENCE: 124
gacgtgcagc tggtggagtc tgggggagac ctggtgaagc ctgggggtc cctgagactc      60 tcctgtgtgg cctctggatt caccttcaat aattatgaga tctactgggt ccgccaggct     120
ccagggaaag gactgagtg gtcgcaaag atctatgaga gtggacgtac cacatcctac       180
gcagaagctg taaagggccg attcaccatt tccagagaca cggcgagaa catggcgtct     240 ttgcagatga atagcctgag agccgaggac acggccgtgt attactgtgc gagtgctctc    300
gacggtagcc tttatcccaa ttactggggc caggggaaccc tggtcaccgt ttcctccgcc   360
tccaccacgg ccccctcggt t                                              381

<210> SEQ ID NO 125
<211> LENGTH: 127
<212> TYPE: PRT
<213> ORGANISM: artificial
<220> FEATURE:
<223> OTHER INFORMATION: VH chain

<400> SEQUENCE: 125

Asp Val Gln Leu Val Glu Ser Gly Gly Asp Leu Val Lys Pro Gly Gly
1               5                   10                  15

Ser Leu Arg Leu Ser Cys Val Ala Ser Gly Phe Thr Phe Asn Asn Tyr
            20                  25                  30

Glu Ile Tyr Trp Val Arg Gln Ala Pro Gly Lys Gly Leu Glu Trp Val
        35                  40                  45

Ala Lys Ile Tyr Glu Ser Gly Arg Thr Thr Ser Tyr Ala Glu Ala Val
    50                  55                  60

Lys Gly Arg Phe Thr Ile Ser Arg Asp Asn Gly Glu Asn Met Ala Ser
65                  70                  75                  80

Leu Gln Met Asn Ser Leu Arg Ala Glu Asp Thr Ala Val Tyr Tyr Cys
                85                  90                  95

Ala Ser Ala Leu Asp Gly Ser Leu Tyr Pro Asn Tyr Trp Gly Gln Gly
            100                 105                 110

Thr Leu Val Thr Val Ser Ser Ala Ser Thr Thr Ala Pro Ser Val
        115                 120                 125

<210> SEQ ID NO 126
<211> LENGTH: 363
<212> TYPE: DNA
<213> ORGANISM: artificial
<220> FEATURE:
<223> OTHER INFORMATION: VH chain

<400> SEQUENCE: 126
gaggtacaac tggtgcagtc tgggggagac ctggtgaagc ctgggggtc cctgagactc      60 tcctgtgtgg cctctggatt cacccctcagt aacttcgaca tgcaatgggt ccgtcaggct   120
ccagggaagg ggctgcaatg gtcgcttac attaatagtg gtgcaaatac cacatactac     180
gcagacgctg tgaggggccg attcaccgtc tccagagaca cgccaagaa cacactctat    240 ctgcagatga acagcctgac agccgaggac acggccgttt attactgtac tgatcggggg   300

```
ggacactggg gccagggcac cctggtcacc gtctcctcag cctccaccac ggccccctcg    360
gtt                                                                 363
```

```
<210> SEQ ID NO 127
<211> LENGTH: 121
<212> TYPE: PRT
<213> ORGANISM: artificial
<220> FEATURE:
<223> OTHER INFORMATION: VH chain

<400> SEQUENCE: 127
```

Glu Val Gln Leu Val Gln Ser Gly Gly Asp Leu Val Lys Pro Gly Gly
1               5                   10                  15

Ser Leu Arg Leu Ser Cys Val Ala Ser Gly Phe Thr Leu Ser Asn Phe
            20                  25                  30

Asp Met Gln Trp Val Arg Gln Ala Pro Gly Lys Gly Leu Gln Trp Val
        35                  40                  45

Ala Tyr Ile Asn Ser Gly Ala Asn Thr Thr Tyr Tyr Ala Asp Ala Val
    50                  55                  60

Arg Gly Arg Phe Thr Val Ser Arg Asp Asn Ala Lys Asn Thr Leu Tyr
65                  70                  75                  80

Leu Gln Met Asn Ser Leu Thr Ala Glu Asp Thr Ala Val Tyr Tyr Cys
                85                  90                  95

Thr Asp Arg Gly Gly His Trp Gly Gln Gly Thr Leu Val Thr Val Ser
            100                 105                 110

Ser Ala Ser Thr Thr Ala Pro Ser Val
        115                 120

```
<210> SEQ ID NO 128
<211> LENGTH: 399
<212> TYPE: DNA
<213> ORGANISM: artificial
<220> FEATURE:
<223> OTHER INFORMATION: VH chain

<400> SEQUENCE: 128
caactggtgg agcttggggg agacctggtg aagcctgcgg ggtccctgag actgtcctgt    60
gtggcctctg gattcacctt cagttcgtac agcatgagct gggtacgcca ggctcctggg   120
aaggggctgc agttggtcgc aggtattaac agtggtggaa caagtatata ttatacagac   180
gttgtgaagg gccgattcac catctccaga gacaatgcca agaacacagt ttatctgcag   240
atgaacagcc tgagagccga ggacacggct atgtattact gtgtaaagga cgcgtactac   300
tgtaattctt attactgtcc cgcgacttat ggttgggact actggggccc aggcacttca   360
atattcgtgt cctccgcctc caccacggcc ccctcggtt                         399
```

```
<210> SEQ ID NO 129
<211> LENGTH: 133
<212> TYPE: PRT
<213> ORGANISM: artificial
<220> FEATURE:
<223> OTHER INFORMATION: VH chain

<400> SEQUENCE: 129
```

Gln Leu Val Glu Leu Gly Gly Asp Leu Val Lys Pro Ala Gly Ser Leu
1               5                   10                  15

Arg Leu Ser Cys Val Ala Ser Gly Phe Thr Phe Ser Ser Tyr Ser Met
            20                  25                  30

Ser Trp Val Arg Gln Ala Pro Gly Lys Gly Leu Gln Leu Val Ala Gly

```
                35                  40                  45
Ile Asn Ser Gly Gly Thr Ser Ile Tyr Tyr Thr Asp Val Val Lys Gly
 50                  55                  60

Arg Phe Thr Ile Ser Arg Asp Asn Ala Lys Asn Thr Val Tyr Leu Gln
 65                  70                  75                  80

Met Asn Ser Leu Arg Ala Glu Asp Thr Ala Met Tyr Tyr Cys Val Lys
                 85                  90                  95

Asp Ala Tyr Tyr Cys Asn Ser Tyr Cys Pro Ala Thr Tyr Gly Trp
                100                 105                 110

Asp Tyr Trp Gly Pro Gly Thr Ser Ile Phe Val Ser Ser Ala Ser Thr
            115                 120                 125

Thr Ala Pro Ser Val
        130

<210> SEQ ID NO 130
<211> LENGTH: 387
<212> TYPE: DNA
<213> ORGANISM: artificial
<220> FEATURE:
<223> OTHER INFORMATION: VH chain

<400> SEQUENCE: 130
gaggggcagc tggcggagtc tgggggagac ctggtgaagc ctgggggtc cctgagactg      60 tcctgtgtgg cctctggatt caccttcagt gactattata tgtattgggt ccgtctggct    120
ccagggaagg gctgcagtg gtcgcacgg attaagaatg atggaactta cacatcctac      180
gcagacgctg tggagggcca cttcaccatc tccagagaca atgccaagaa cacagtgtat    240
ctgcagatga acagcctgag agccgaggac acggccatgt attactgtgg acaatgggga    300
gttgttctag tggttggccc ttgggaatac ttgggccagg gcaccctggt caccgtctcc    360
tcagcctcca ccacggcccc ctcggtt                                        387

<210> SEQ ID NO 131
<211> LENGTH: 129
<212> TYPE: PRT
<213> ORGANISM: artificial
<220> FEATURE:
<223> OTHER INFORMATION: VH chain

<400> SEQUENCE: 131

Glu Gly Gln Leu Ala Glu Ser Gly Gly Asp Leu Val Lys Pro Gly Gly
  1               5                  10                  15

Ser Leu Arg Leu Ser Cys Val Ala Ser Gly Phe Thr Phe Ser Asp Tyr
                 20                  25                  30

Tyr Met Tyr Trp Val Arg Leu Ala Pro Gly Lys Gly Leu Gln Trp Val
             35                  40                  45

Ala Arg Ile Lys Asn Asp Gly Thr Tyr Thr Ser Tyr Ala Asp Ala Val
 50                  55                  60

Glu Gly His Phe Thr Ile Ser Arg Asp Asn Ala Lys Asn Thr Val Tyr
 65                  70                  75                  80

Leu Gln Met Asn Ser Leu Arg Ala Glu Asp Thr Ala Met Tyr Tyr Cys
                 85                  90                  95

Gly Gln Trp Gly Val Val Leu Val Val Gly Pro Trp Glu Tyr Leu Gly
                100                 105                 110

Gln Gly Thr Leu Val Thr Val Ser Ser Ala Ser Thr Thr Ala Pro Ser
            115                 120                 125

Val
```

<210> SEQ ID NO 132
<211> LENGTH: 376
<212> TYPE: DNA
<213> ORGANISM: artificial
<220> FEATURE:
<223> OTHER INFORMATION: VH chain

<400> SEQUENCE: 132

| | | | | | |
|---|---|---|---|---|---|
| gaggtgagtt | tggtggagtc | tgggggagac | ctggtgaagc | ctgcggggtc | cctgagactg | 60 |
| tcctgtgtgg | cctctggatt | caccttcagt | gactacgaca | tgtactgggt | ccgccaggct | 120 |
| ccggggaagg | ggctgcagtg | ggtcgcagtt | atcagttatg | aggaattgac | acatacagt | 180 |
| gacactgtga | agggccgatt | caccatctcc | agagacaacg | ccaggaacac | agtatatttg | 240 |
| cagatgaaca | gtctgagagc | cgaggacacg | gctgtgtatt | tctgtgcgag | gtcttccttc | 300 |
| agaactgacc | ttaactattg | gggccagggc | accctggtca | ttgtctcctc | agcctccacc | 360 |
| acggcccct | cggtta | | | | | 376 |

<210> SEQ ID NO 133
<211> LENGTH: 125
<212> TYPE: PRT
<213> ORGANISM: artificial
<220> FEATURE:
<223> OTHER INFORMATION: VH chain

<400> SEQUENCE: 133

Glu Val Ser Leu Val Glu Ser Gly Gly Asp Leu Val Lys Pro Ala Gly
1               5                   10                  15

Ser Leu Arg Leu Ser Cys Val Ala Ser Gly Phe Thr Phe Ser Asp Tyr
            20                  25                  30

Asp Met Tyr Trp Val Arg Gln Ala Pro Gly Lys Gly Leu Gln Trp Val
        35                  40                  45

Ala Val Ile Ser Tyr Gly Gly Ile Asp Thr Tyr Ser Asp Thr Val Lys
    50                  55                  60

Gly Arg Phe Thr Ile Ser Arg Asp Asn Ala Arg Asn Thr Val Tyr Leu
65                  70                  75                  80

Gln Met Asn Ser Leu Arg Ala Glu Asp Thr Ala Val Tyr Phe Cys Ala
                85                  90                  95

Arg Ser Ser Phe Arg Thr Asp Leu Asn Tyr Trp Gly Gln Gly Thr Leu
            100                 105                 110

Val Ile Val Ser Ser Ala Ser Thr Thr Ala Pro Ser Val
        115                 120                 125

<210> SEQ ID NO 134
<211> LENGTH: 384
<212> TYPE: DNA
<213> ORGANISM: artificial
<220> FEATURE:
<223> OTHER INFORMATION: VH chain

<400> SEQUENCE: 134

| | | | | | |
|---|---|---|---|---|---|
| gaggtgcagc | tggtggagct | tgggggagac | ctggtgaagc | ctgggggtc | cttgagactg | 60 |
| tcctgtgtgg | cctctggatt | caccttcagt | aactatggca | tgatctgggt | ccgtcagtct | 120 |
| ccagggaagg | ggctgcagtg | ggtcgcagct | attagcgaaa | atggaattag | tacatactac | 180 |
| gcagacgctg | tgaagggccg | attcaccatc | tccaaagaca | acgccaagag | cacgctgtat | 240 |
| ctgcagatga | acgccctgag | agccgaggac | acggccgtat | attactgtgg | gaaggcccag | 300 |
| aaaatagtag | caactggaaa | tgagtactgg | ggccagggca | ccctggtcac | cgtctcctca | 360 |

```
gcctccacca cggccccctc ggtt                                               384
```

```
<210> SEQ ID NO 135
<211> LENGTH: 128
<212> TYPE: PRT
<213> ORGANISM: artificial
<220> FEATURE:
<223> OTHER INFORMATION: VH chain

<400> SEQUENCE: 135
```

```
Glu Val Gln Leu Val Glu Leu Gly Gly Asp Leu Val Lys Pro Gly Gly
1               5                   10                  15

Ser Leu Arg Leu Ser Cys Val Ala Ser Gly Phe Thr Phe Ser Asn Tyr
            20                  25                  30

Gly Met Ile Trp Val Arg Gln Ser Pro Gly Lys Gly Leu Gln Trp Val
        35                  40                  45

Ala Ala Ile Ser Glu Asn Gly Ile Ser Thr Tyr Tyr Ala Asp Ala Val
    50                  55                  60

Lys Gly Arg Phe Thr Ile Ser Lys Asp Asn Ala Lys Ser Thr Leu Tyr
65                  70                  75                  80

Leu Gln Met Asn Ala Leu Arg Ala Glu Asp Thr Ala Val Tyr Tyr Cys
                85                  90                  95

Gly Lys Ala Gln Lys Ile Val Ala Thr Gly Asn Glu Tyr Trp Gly Gln
            100                 105                 110

Gly Thr Leu Val Thr Val Ser Ser Ala Ser Thr Thr Ala Pro Ser Val
        115                 120                 125
```

```
<210> SEQ ID NO 136
<211> LENGTH: 369
<212> TYPE: DNA
<213> ORGANISM: artificial
<220> FEATURE:
<223> OTHER INFORMATION: VH chain

<400> SEQUENCE: 136
gaggtgcagc tggtggagac tggggggagat ttggtgaaac ctggggggtc cctgagaatt    60
tcctgtgtgg cctctgggtt cgactttcat tcatcccaca tgacctgggt ccgccagact   120
ccagggaagg gactgcagtg ggtcgcaagt attaacagcg gtagaggaac aggctacgca   180
gacgctgtga aggccgatt caccatctcc agagacaacg ccaagaatac agtgtatctg    240
cggatgaaca gcctgacagc caaggacacg gccgtgtatt actgtgcgaa ggggcgtatc   300
gccgttgagt cctggggcca gggcaccctg gtcaccgtct cctcagcctc caccacggcc   360
ccctcggtt                                                          369
```

```
<210> SEQ ID NO 137
<211> LENGTH: 123
<212> TYPE: PRT
<213> ORGANISM: artificial
<220> FEATURE:
<223> OTHER INFORMATION: VH chain

<400> SEQUENCE: 137
```

```
Glu Val Gln Leu Val Glu Thr Gly Gly Asp Leu Val Lys Pro Gly Gly
1               5                   10                  15

Ser Leu Arg Ile Ser Cys Val Ala Ser Gly Phe Asp Phe His Ser Ser
            20                  25                  30

His Met Thr Trp Val Arg Gln Thr Pro Gly Lys Gly Leu Gln Trp Val
        35                  40                  45

Ala Ser Ile Asn Ser Gly Arg Gly Thr Gly Tyr Ala Asp Ala Val Lys
```

Gly Arg Phe Thr Ile Ser Arg Asp Asn Ala Lys Asn Thr Val Tyr Leu
65                  70                  75                  80

Arg Met Asn Ser Leu Thr Ala Lys Asp Thr Ala Val Tyr Tyr Cys Ala
                85                  90                  95

Lys Gly Arg Ile Ala Val Glu Ser Trp Gly Gln Gly Thr Leu Val Thr
            100                 105                 110

Val Ser Ser Ala Ser Thr Thr Ala Pro Ser Val
        115                 120

<210> SEQ ID NO 138
<211> LENGTH: 387
<212> TYPE: DNA
<213> ORGANISM: artificial
<220> FEATURE:
<223> OTHER INFORMATION: VH chain

<400> SEQUENCE: 138 gagggcagc tggcggagtc tgggggagac ctggtgaagc ctggggggtc cctgagactc      60
tcctgtgtag ctctggatt caccttcagt acctatgtca tgacctgggt ccgccaggct     120
cctgggaagg ggccgcagtg ggtcgcaagt attaacagtg gtggaactag cgctacctac    180
gcagacgctg tgaagggccg attcaccatc tccagagaca cgccaaaaa cacactttat     240
ctacagataa acagcctgag agccgaggac acggccgtat atcactgtgc gggcctttat    300
atgtatagtc catctcgcgc gcttgaattc tggggccagg gcaccctggt caccgtctcc    360
tcagcctcca ccacggcccc ctcggtt                                        387

<210> SEQ ID NO 139
<211> LENGTH: 129
<212> TYPE: PRT
<213> ORGANISM: artificial
<220> FEATURE:
<223> OTHER INFORMATION: VH chain

<400> SEQUENCE: 139

Glu Gly Gln Leu Ala Glu Ser Gly Gly Asp Leu Val Lys Pro Gly Gly
1               5                   10                  15

Ser Leu Arg Leu Ser Cys Val Gly Ser Gly Phe Thr Phe Ser Thr Tyr
            20                  25                  30

Val Met Thr Trp Val Arg Gln Ala Pro Gly Lys Gly Pro Gln Trp Val
        35                  40                  45

Ala Ser Ile Asn Ser Gly Gly Thr Ser Ala Thr Tyr Ala Asp Ala Val
    50                  55                  60

Lys Gly Arg Phe Thr Ile Ser Arg Asp Asn Ala Lys Asn Thr Leu Tyr
65                  70                  75                  80

Leu Gln Ile Asn Ser Leu Arg Ala Glu Asp Thr Ala Val Tyr His Cys
                85                  90                  95

Ala Gly Leu Tyr Met Tyr Ser Pro Ser Arg Ala Leu Glu Phe Trp Gly
            100                 105                 110

Gln Gly Thr Leu Val Thr Val Ser Ser Ala Ser Thr Thr Ala Pro Ser
        115                 120                 125

Val

<210> SEQ ID NO 140
<211> LENGTH: 378
<212> TYPE: DNA
<213> ORGANISM: artificial
<220> FEATURE:

<223> OTHER INFORMATION: VH chain

<400> SEQUENCE: 140

```
gaggagcagc tggtggagct tgggggagac ctggtgaagc ctgggggggtc cctgagactg      60
tcctgtgtgg cctctggatt caccttcagt agctattaca tgttctgggt ccgccaggct     120
ccagggaaga gactacaatg ggtcgcagat attacctatg ctggaaccgt atattacgca     180
gacattacag agggccgatt caccatttcc agagacaacg ccaaaaatac ggtgtatctg     240
cagatggcca gcctgacggc cgaggacacg gccgtctatt actgtacgaa attagggggt     300
tctagtgcct gggggggacta ttggggcccct ggcacgtcag tcttcgtgtc gtcagcctcc     360
accacggccc cctcggtt                                                   378
```

<210> SEQ ID NO 141
<211> LENGTH: 126
<212> TYPE: PRT
<213> ORGANISM: artificial
<220> FEATURE:
<223> OTHER INFORMATION: VH chain

<400> SEQUENCE: 141

```
Glu Glu Gln Leu Val Glu Leu Gly Gly Asp Leu Val Lys Pro Gly Gly
1               5                   10                  15
Ser Leu Arg Leu Ser Cys Val Ala Ser Gly Phe Thr Phe Ser Ser Tyr
            20                  25                  30
Tyr Met Phe Trp Val Arg Gln Ala Pro Gly Lys Arg Leu Gln Trp Val
        35                  40                  45
Ala Asp Ile Thr Tyr Ala Gly Thr Val Tyr Tyr Ala Asp Ile Thr Glu
    50                  55                  60
Gly Arg Phe Thr Ile Ser Arg Asp Asn Ala Lys Asn Thr Val Tyr Leu
65                  70                  75                  80
Gln Met Ala Ser Leu Thr Ala Glu Asp Thr Ala Val Tyr Tyr Cys Thr
                85                  90                  95
Lys Leu Gly Gly Ser Ser Ala Trp Gly Asp Tyr Trp Gly Pro Gly Thr
            100                 105                 110
Ser Val Phe Val Ser Ser Ala Ser Thr Thr Ala Pro Ser Val
        115                 120                 125
```

<210> SEQ ID NO 142
<211> LENGTH: 387
<212> TYPE: DNA
<213> ORGANISM: artificial
<220> FEATURE:
<223> OTHER INFORMATION: VH chain
<220> FEATURE:
<221> NAME/KEY: misc_feature
<222> LOCATION: (75)..(75)
<223> OTHER INFORMATION: n is a, c, g, or t
<220> FEATURE:
<221> NAME/KEY: misc_feature
<222> LOCATION: (360)..(360)
<223> OTHER INFORMATION: n is a, c, g, or t
<220> FEATURE:
<221> NAME/KEY: misc_feature
<222> LOCATION: (366)..(366)
<223> OTHER INFORMATION: n is a, c, g, or t

<400> SEQUENCE: 142

```
gaagagcaac tggtggagct tgggggagac ctggtgaagc ctgggggggtc cttgagactg      60
tcctgtgtgg cctcnggatt caccttcaat aactatggca tgagctgggt ccgtcagtct     120
ccagggaagg ggctgcagtg ggccgcaact attagtcttc gtggaagtac cacatactac     180
```

```
gcagacgctg tgaagggccg atgcaccatc tccagagacg acgccaagaa cacactgtat    240
ctgcagatga gcagcctgag agccgaagac acggccgtgt attactgtgc gaagggagcg    300
gacgctacct attattataa tatggaggac tggggccctg gcacctcact cttcgtgtcn    360
tgggcntcca ccacggcccc ctcggtt                                         387
```

<210> SEQ ID NO 143
<211> LENGTH: 129
<212> TYPE: PRT
<213> ORGANISM: artificial
<220> FEATURE:
<223> OTHER INFORMATION: VH chain

<400> SEQUENCE: 143

```
Glu Glu Gln Leu Val Glu Leu Gly Gly Asp Leu Val Lys Pro Gly Gly
1               5                   10                  15

Ser Leu Arg Leu Ser Cys Val Ala Ser Gly Phe Thr Phe Asn Asn Tyr
            20                  25                  30

Gly Met Ser Trp Val Arg Gln Ser Pro Gly Lys Gly Leu Gln Trp Ala
        35                  40                  45

Ala Thr Ile Ser Leu Arg Gly Ser Thr Thr Tyr Tyr Ala Asp Ala Val
    50                  55                  60

Lys Gly Arg Cys Thr Ile Ser Arg Asp Asp Ala Lys Asn Thr Leu Tyr
65                  70                  75                  80

Leu Gln Met Ser Ser Leu Arg Ala Glu Asp Thr Ala Val Tyr Tyr Cys
                85                  90                  95

Ala Lys Gly Ala Asp Ala Thr Tyr Tyr Tyr Asn Met Glu Asp Trp Gly
            100                 105                 110

Pro Gly Thr Ser Leu Phe Val Ser Trp Ala Ser Thr Thr Ala Pro Ser
        115                 120                 125

Val
```

<210> SEQ ID NO 144
<211> LENGTH: 378
<212> TYPE: DNA
<213> ORGANISM: artificial
<220> FEATURE:
<223> OTHER INFORMATION: VH chain

<400> SEQUENCE: 144

```
gaggagcagc tggtggagct tgggggagac ctggtgaagc ctggggggtc cctgagactg     60
tcctgtgtgg cctctggatt caccttcagt agctattaca tgttctgggt ccgccaggct    120
ccagggaaga gactacaatg ggtcgcagat attacctatg ctggaaccgt atattacgca    180
gacattacag agggccgatt caccatttcc agagacaacg ccaaaaatac ggtgtatctg    240
cagatggcca gcctgacggc cgaggacacg gccgtctatt actgtacgaa attagggggt    300
tctagtgcct ggggggacta ttggggcccct ggcacgtcag tcttcgtgtc gtcagcctcc    360
accacggccc cctcggtt                                                   378
```

<210> SEQ ID NO 145
<211> LENGTH: 126
<212> TYPE: PRT
<213> ORGANISM: artificial
<220> FEATURE:
<223> OTHER INFORMATION: VH chain

<400> SEQUENCE: 145

```
Glu Glu Gln Leu Val Glu Leu Gly Gly Asp Leu Val Lys Pro Gly Gly
1               5                   10                  15
```

```
Ser Leu Arg Leu Ser Cys Val Ala Ser Gly Phe Thr Phe Ser Ser Tyr
        20                  25                  30

Tyr Met Phe Trp Val Arg Gln Ala Pro Gly Lys Arg Leu Gln Trp Val
            35                  40                  45

Ala Asp Ile Thr Tyr Ala Gly Thr Val Tyr Tyr Ala Asp Ile Thr Glu
        50                  55                  60

Gly Arg Phe Thr Ile Ser Arg Asp Asn Ala Lys Asn Thr Val Tyr Leu
 65              70                  75                      80

Gln Met Ala Ser Leu Thr Ala Glu Asp Thr Ala Val Tyr Tyr Cys Thr
            85                  90                  95

Lys Leu Gly Gly Ser Ser Ala Trp Gly Asp Tyr Trp Gly Pro Gly Thr
            100                 105                 110

Ser Val Phe Val Ser Ser Ala Ser Thr Thr Ala Pro Ser Val
            115                 120                 125
```

<210> SEQ ID NO 146
<211> LENGTH: 129
<212> TYPE: PRT
<213> ORGANISM: artificial
<220> FEATURE:
<223> OTHER INFORMATION: VH chain

<400> SEQUENCE: 146

```
Glu Gly Gln Leu Ala Glu Ser Gly Gly Asp Leu Val Lys Pro Ala Gly
 1               5                  10                  15

Ser Leu Arg Leu Ser Cys Val Ala Ser Gly Phe Thr Phe Ser Asp Tyr
            20                  25                  30

Asp Met Ser Trp Val Arg Gln Ala Pro Gly Lys Gly Leu Gln Trp Val
            35                  40                  45

Ala Gly Ile Ser Tyr Asp Gly Arg Ser Thr Tyr Tyr Thr Asp Ala Val
        50                  55                  60

Lys Gly Arg Phe Thr Val Ser Arg Asp Asn Ala Arg Asn Thr Leu Phe
 65              70                  75                      80

Leu Gln Met Asn Ser Leu Arg Ala Glu Asp Thr Ala Met Tyr Tyr Cys
            85                  90                  95

Ala Lys Val Asp Trp Phe Thr Arg Asn Trp Tyr Ile Asp Phe Trp Gly
            100                 105                 110

Gln Gly Thr Leu Val Thr Val Ser Ser Ala Ser Thr Thr Ala Pro Ser
            115                 120                 125

Val
```

<210> SEQ ID NO 147
<211> LENGTH: 391
<212> TYPE: DNA
<213> ORGANISM: artificial
<220> FEATURE:
<223> OTHER INFORMATION: VH chain

<400> SEQUENCE: 147

```
gaggtgcctt tggtggaatc tgggggaggg ttggtgaagc cggggggctt cctgagactg      60
tcctgtgtgg cctccggatt caccttcagt aactccacca tgacctggct acgccaggct     120
cctgggaagg ggctgcagtt ggtcgcatat atttcctatg gtggaggtac cacatactat     180
gtagaggatg ttaagggccg gttcaccatc tccagagaca cgccaagaa cacgctctct      240 ctgcagatgg acagcctgag agccgaggac acgccgtat attttgtgc ggcacagagt       300 tctagtggtt ggggctattt cgtcagtgag tactgggggcc agggcaccct ggtcaccgtc    360
```

-continued tcatcggcct ccaccacggc cccctcggtt t    391

<210> SEQ ID NO 148
<211> LENGTH: 130
<212> TYPE: PRT
<213> ORGANISM: artificial
<220> FEATURE:
<223> OTHER INFORMATION: VH chain

<400> SEQUENCE: 148

Glu Val Pro Leu Val Glu Ser Gly Gly Gly Leu Val Lys Pro Gly Gly
1               5                   10                  15

Phe Leu Arg Leu Ser Cys Val Ala Ser Gly Phe Thr Phe Ser Asn Ser
            20                  25                  30

Thr Met Thr Trp Leu Arg Gln Ala Pro Gly Lys Gly Leu Gln Leu Val
        35                  40                  45

Ala Tyr Ile Ser Tyr Gly Gly Thr Thr Tyr Tyr Val Glu Asp Val
    50                  55                  60

Lys Gly Arg Phe Thr Ile Ser Arg Asp Asn Ala Lys Asn Thr Leu Ser
65                  70                  75                  80

Leu Gln Met Asp Ser Leu Arg Ala Glu Asp Thr Ala Val Tyr Phe Cys
                85                  90                  95

Ala Ala Gln Ser Ser Ser Gly Trp Gly Tyr Phe Val Ser Glu Tyr Trp
            100                 105                 110

Gly Gln Gly Thr Leu Val Thr Val Ser Ser Ala Ser Thr Thr Ala Pro
        115                 120                 125

Ser Val
    130

<210> SEQ ID NO 149
<211> LENGTH: 393
<212> TYPE: DNA
<213> ORGANISM: artificial
<220> FEATURE:
<223> OTHER INFORMATION: VH chain

<400> SEQUENCE: 149
gaggtgcagc tggtggagtc tgggggagac ctggtgaagc tgggggggtc cctaagactc    60
tcctgtgcgg cctctggatt caccttcagt acctacttca gtcctgggt ccgccaggct   120 ccagggaagg ggcttcagtg gtcgcacgg ataaccgagg atggaagtag cgcaaactac   180
gcagacgctg tgaggggccg attcaccatc tccagagaca acgccgaaaa cacgctctat   240
cttcagatga acagcctgag agccgacgac acggccgtgt attactgtgt gaaactggta   300
cctggttctt atcgtctctt ctatggtgtg gactactggg gccctggcac ctcactcttc   360
gtgtcctcgg cctccaccac ggccccctcg gtt    393

<210> SEQ ID NO 150
<211> LENGTH: 131
<212> TYPE: PRT
<213> ORGANISM: artificial
<220> FEATURE:
<223> OTHER INFORMATION: VH chain

<400> SEQUENCE: 150

Glu Val Gln Leu Val Glu Ser Gly Gly Asp Leu Val Lys Pro Gly Gly
1               5                   10                  15

Ser Leu Arg Leu Ser Cys Ala Ala Ser Gly Phe Thr Phe Ser Thr Tyr
            20                  25                  30

Phe Met Ser Trp Val Arg Gln Ala Pro Gly Lys Gly Leu Gln Trp Val

```
                35                  40                  45
Ala Arg Ile Thr Glu Asp Gly Ser Ser Ala Asn Tyr Ala Asp Ala Val
 50                  55                  60

Arg Gly Arg Phe Thr Ile Ser Arg Asp Asn Ala Glu Asn Thr Leu Tyr
 65                  70                  75                  80

Leu Gln Met Asn Ser Leu Arg Ala Asp Asp Thr Ala Val Tyr Tyr Cys
                 85                  90                  95

Val Lys Leu Val Pro Gly Ser Tyr Arg Leu Phe Tyr Gly Val Asp Tyr
            100                 105                 110

Trp Gly Pro Gly Thr Ser Leu Phe Val Ser Ser Ala Ser Thr Thr Ala
            115                 120                 125

Pro Ser Val
        130

<210> SEQ ID NO 151
<211> LENGTH: 381
<212> TYPE: DNA
<213> ORGANISM: artificial
<220> FEATURE:
<223> OTHER INFORMATION: VH chain

<400> SEQUENCE: 151
gaggtacagc tggtgcagtc tgggggagac ctggtaaacc ctgggggtc cttgagactg      60 tcctgtctgg cctctggatt cgcctttagt tctcatgcca tgagctgggt ccgtcagtct   120
ccagggaagg gctgcagtg gtcgcagcc atttggaata atggacatac tgcacattac     180
accgacgctg tcaagggccg attcaccatc tccagggacg acgccaagaa cacggtatat   240
ctccagatga acagcctgag agccgaggac acagccgtat attactgtgt ggcccgggg   300 ggtaattggc aaccttttga ctactggggc cagggaaccc aggtcaccgt ctcctcagcc   360
tccaccacgg ccccctcggt t                                             381

<210> SEQ ID NO 152
<211> LENGTH: 127
<212> TYPE: PRT
<213> ORGANISM: artificial
<220> FEATURE:
<223> OTHER INFORMATION: VH chain

<400> SEQUENCE: 152

Glu Val Gln Leu Val Gln Ser Gly Gly Asp Leu Val Asn Pro Gly Gly
 1               5                  10                  15

Ser Leu Arg Leu Ser Cys Leu Ala Ser Gly Phe Ala Phe Ser Ser His
             20                  25                  30

Ala Met Ser Trp Val Arg Gln Ser Pro Gly Lys Gly Leu Gln Trp Val
         35                  40                  45

Ala Ala Ile Trp Asn Asn Gly His Thr Ala His Tyr Thr Asp Ala Val
 50                  55                  60

Lys Gly Arg Phe Thr Ile Ser Arg Asp Asp Ala Lys Asn Thr Val Tyr
 65                  70                  75                  80

Leu Gln Met Asn Ser Leu Arg Ala Glu Asp Thr Ala Val Tyr Tyr Cys
                 85                  90                  95

Val Ala Arg Gly Gly Asn Trp Gln Pro Phe Asp Tyr Trp Gly Gln Gly
            100                 105                 110

Thr Gln Val Thr Val Ser Ser Ala Ser Thr Thr Ala Pro Ser Val
            115                 120                 125

<210> SEQ ID NO 153
```

```
<211> LENGTH: 387
<212> TYPE: DNA
<213> ORGANISM: artificial
<220> FEATURE:
<223> OTHER INFORMATION: VH chain

<400> SEQUENCE: 153 gagggcagc tggcggagtc tgggggagac ctggtgaagc ctgcggggtc cctgagactc        60
tcctgtgtag cctctggatt caccttcagt gactacgaca tgagttgggt ccgccaggct      120
cctgggaagg ggctgcagtg ggtcgcaggt attagttatg atggaaggag cacatactac      180
actgacgctg tgaagggccg attcaccgtg tccagagaca cgccaggaa cacgttgttt       240 ctgcagatga acagcctgag agctgaggac acggccatgt attattgtgc gaaggtcgac      300
tggtttacta ggaattggta cattgacttc tggggccagg gcaccctggt caccgtctcc      360
tcagcctcca ccacggcccc ctcggtt                                          387

<210> SEQ ID NO 154
<211> LENGTH: 129
<212> TYPE: PRT
<213> ORGANISM: artificial
<220> FEATURE:
<223> OTHER INFORMATION: VH chain

<400> SEQUENCE: 154

Glu Gly Gln Leu Ala Glu Ser Gly Gly Asp Leu Val Lys Pro Ala Gly
1               5                   10                  15

Ser Leu Arg Leu Ser Cys Val Ala Ser Gly Phe Thr Phe Ser Asp Tyr
            20                  25                  30

Asp Met Ser Trp Val Arg Gln Ala Pro Gly Lys Gly Leu Gln Trp Val
        35                  40                  45

Ala Gly Ile Ser Tyr Asp Gly Arg Ser Thr Tyr Tyr Thr Asp Ala Val
    50                  55                  60

Lys Gly Arg Phe Thr Val Ser Arg Asp Asn Ala Arg Asn Thr Leu Phe
65                  70                  75                  80

Leu Gln Met Asn Ser Leu Arg Ala Glu Asp Thr Ala Met Tyr Tyr Cys
                85                  90                  95

Ala Lys Val Asp Trp Phe Thr Arg Asn Trp Tyr Ile Asp Phe Trp Gly
            100                 105                 110

Gln Gly Thr Leu Val Thr Val Ser Ser Ala Ser Thr Thr Ala Pro Ser
        115                 120                 125

Val

<210> SEQ ID NO 155
<211> LENGTH: 369
<212> TYPE: DNA
<213> ORGANISM: artificial
<220> FEATURE:
<223> OTHER INFORMATION: VH chain

<400> SEQUENCE: 155
gaggtgcgtt tggtggagtc tgggggagac ctggtgaagc tgggggggtc cctgagactc       60
tcctgtgtgg cctctggatt caccttcagt agatacggca tgagttgggt ccgccaggct      120
cctgggaagg ggctgcagtg ggtcacgatt attaaccatg atggaagtag cacattctac      180
actgacgctg tgaagggccg attcaccatc tccagagaca cgccaggaa cacagtggtt       240 ctgcagatga gcagcctgag agccgaggac acggctgtgt attactgtgt ggcttcgggt      300
tcttttggtc attgggggcca gggcaccctg gtcactgtct cctcagcctc caccacggcc    360
```

```
ccctcggtt                                                             369
```

<210> SEQ ID NO 156
<211> LENGTH: 123
<212> TYPE: PRT
<213> ORGANISM: artificial
<220> FEATURE:
<223> OTHER INFORMATION: VH chain

<400> SEQUENCE: 156

```
Glu Val Arg Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Arg Tyr
            20                  25                  30

Gly Met Ser Trp Val Arg Gln Ala Pro Gly Lys Gly Leu Gln Trp Val
        35                  40                  45

Thr Ile Ile Asn His Asp Gly Ser Ser Thr Phe Tyr Thr Asp Ala Val
    50                  55                  60

Lys Gly Arg Phe Thr Ile Ser Arg Asp Asn Ala Arg Asn Thr Val Val
65                  70                  75                  80

Leu Gln Met Ser Ser Leu Arg Ala Glu Asp Thr Ala Val Tyr Tyr Cys
                85                  90                  95

Val Ala Ser Gly Ser Phe Gly His Trp Gly Gln Gly Thr Leu Val Thr
            100                 105                 110

Val Ser Ser Ala Ser Thr Thr Ala Pro Ser Val
        115                 120
```

<210> SEQ ID NO 157
<211> LENGTH: 393
<212> TYPE: DNA
<213> ORGANISM: artificial
<220> FEATURE:
<223> OTHER INFORMATION: VH chain

<400> SEQUENCE: 157

```
gaggtgcagc tgctggagta tgggggagac ctggtgaagc ctgggggggtc cctgagactc       60 tcctgtgtgg cctctggatt caccttcagt cagtacgaaa tgtactgggt ccgccaggct      120
ccagggaaag gctggagtg gtcgcaagg atttatggga atggaaagac cacatactat       180
ggagaatctg taaagggccg attcaccatt tccagacgg acgccaacaa catggcgttt       240
ctgcagatga acagcctgcg agccgaggac acggccgtat attactgtgc gagtggtaga       300
tatttcggta gtttcgccca tcccagtttt gactattggg gccagggaac cctggtcacc       360
gtctcctcag cctccaccac ggccccctcg gtt                                   393
```

<210> SEQ ID NO 158
<211> LENGTH: 131
<212> TYPE: PRT
<213> ORGANISM: artificial
<220> FEATURE:
<223> OTHER INFORMATION: VH chain

<400> SEQUENCE: 158

```
Glu Val Gln Leu Leu Glu Tyr Gly Gly Asp Leu Val Lys Pro Gly Gly
1               5                   10                  15

Ser Leu Arg Leu Ser Cys Val Ala Ser Gly Phe Thr Phe Ser Gln Tyr
            20                  25                  30

Glu Met Tyr Trp Val Arg Gln Ala Pro Gly Lys Gly Leu Glu Trp Val
        35                  40                  45

Ala Arg Ile Tyr Gly Asn Gly Lys Thr Thr Tyr Tyr Gly Glu Ser Val
```

-continued

```
                50                  55                  60
Lys Gly Arg Phe Thr Ile Ser Arg Asp Asp Ala Asn Asn Met Ala Phe
 65                  70                  75                  80

Leu Gln Met Asn Ser Leu Arg Ala Glu Asp Thr Ala Val Tyr Tyr Cys
                 85                  90                  95

Ala Ser Gly Arg Tyr Phe Gly Ser Phe Ala His Pro Ser Phe Asp Tyr
            100                 105                 110

Trp Gly Gln Gly Thr Leu Val Thr Val Ser Ser Ala Ser Thr Thr Ala
            115                 120                 125

Pro Ser Val
    130

<210> SEQ ID NO 159
<211> LENGTH: 391
<212> TYPE: DNA
<213> ORGANISM: artificial
<220> FEATURE:
<223> OTHER INFORMATION: VH chain

<400> SEQUENCE: 159
gaggtacgat tggtggaatc tgggggagac ctggtgaagc tggggggtc cctgagactc      60 tcctgtgtgg cctctggatt caccttcagt gaatataaca tgggctgggt ccgccagggt    120
ccagggaagg gactgcaatg ggtcgcgtgg atttatgcca gtggaactag tacaaggtat    180
gcagacactg tgcagggccg cctcaccata tccagagaca cgccaagaa cacgttgtat     240 ctacagatgg acaggttgag aggtgaagac acggctgtgt attattgtgc gaggagtcat    300
catacatttg gatttggata caaccttgac tattggggcc agggcaaccc tggtcaccgt    360
ctcctcagcc tccaccacgg ccccctcggt t                                   391

<210> SEQ ID NO 160
<211> LENGTH: 130
<212> TYPE: PRT
<213> ORGANISM: artificial
<220> FEATURE:
<223> OTHER INFORMATION: VH chain

<400> SEQUENCE: 160

Glu Val Arg Leu Val Glu Ser Gly Gly Asp Leu Val Lys Pro Gly Gly
 1               5                  10                  15

Ser Leu Arg Leu Ser Cys Val Ala Ser Gly Phe Thr Phe Ser Glu Tyr
                20                  25                  30

Asn Met Gly Trp Val Arg Gln Gly Pro Gly Lys Gly Leu Gln Trp Val
            35                  40                  45

Ala Trp Ile Tyr Ala Ser Gly Thr Ser Thr Arg Tyr Ala Asp Thr Val
 50                  55                  60

Gln Gly Arg Leu Thr Ile Ser Arg Asp Asn Ala Lys Asn Thr Leu Tyr
 65                  70                  75                  80

Leu Gln Met Asp Arg Leu Arg Gly Glu Asp Thr Ala Val Tyr Tyr Cys
                 85                  90                  95

Ala Arg Ser His His Thr Phe Gly Phe Gly Tyr Asn Leu Asp Tyr Trp
            100                 105                 110

Gly Gln Gly Asn Pro Gly His Arg Leu Leu Ser Leu His His Gly Pro
            115                 120                 125

Leu Gly
    130

<210> SEQ ID NO 161
```

<211> LENGTH: 405
<212> TYPE: DNA
<213> ORGANISM: artificial
<220> FEATURE:
<223> OTHER INFORMATION: VH chain
<220> FEATURE:
<221> NAME/KEY: misc_feature
<222> LOCATION: (378)..(378)
<223> OTHER INFORMATION: n is a, c, g, or t

<400> SEQUENCE: 161

```
gaggtgcagc tgctggagac tgggggagac ctggtgaagc ctggggagtc cctgagactt      60
tcctgtgtgg cctctggatt cagttttagt aattattaca tgacctgggt ccgccaggct     120
ccagggaagg gtcttcagtg ggtcggatat attgacaatg atggcagcgg cacggactat     180
gcagactctg tgaagggccg attcaccatc tccagagaca acgccaggaa cacgctatat     240
cttcagatga ccagcctgag agtcgaggat acggccgttt attactgtgc gagtgacctt     300
tggggacact acggtagtta tcgtggtccc agactacttc ttgacaactg gggacaggga     360
accctggtca ccgtctcntc ggcctccacc acggccccct cggtt                     405
```

<210> SEQ ID NO 162
<211> LENGTH: 135
<212> TYPE: PRT
<213> ORGANISM: artificial
<220> FEATURE:
<223> OTHER INFORMATION: VH chain

<400> SEQUENCE: 162

```
Glu Val Gln Leu Leu Glu Thr Gly Gly Asp Leu Val Lys Pro Gly Glu
 1               5                  10                  15
Ser Leu Arg Leu Ser Cys Val Ala Ser Gly Phe Ser Phe Ser Asn Tyr
            20                  25                  30
Tyr Met Thr Trp Val Arg Gln Ala Pro Gly Lys Gly Leu Gln Trp Val
        35                  40                  45
Gly Tyr Ile Asp Asn Asp Gly Ser Gly Thr Asp Tyr Ala Asp Ser Val
    50                  55                  60
Lys Gly Arg Phe Thr Ile Ser Arg Asp Asn Ala Arg Asn Thr Leu Tyr
65                  70                  75                  80
Leu Gln Met Thr Ser Leu Arg Val Glu Asp Thr Ala Val Tyr Tyr Cys
                85                  90                  95
Ala Ser Asp Leu Trp Gly His Tyr Gly Ser Tyr Arg Gly Pro Arg Leu
            100                 105                 110
Leu Leu Asp Asn Trp Gly Gln Gly Thr Leu Val Thr Val Ser Ser Ala
        115                 120                 125
Ser Thr Thr Ala Pro Ser Val
    130                 135
```

<210> SEQ ID NO 163
<211> LENGTH: 381
<212> TYPE: DNA
<213> ORGANISM: artificial
<220> FEATURE:
<223> OTHER INFORMATION: VH chain

<400> SEQUENCE: 163

```
gaggtgaggt tggtggagtc tgggggagac ctggtgaagc ctgcggggtc cctgagactg      60
tcctgtgtgg cctctggatt caccttcagt agctacacca tgagctgggt acgccaggct     120
cctgggaagg gcctgcagtt ggtcgctaat attaagagcg tggaacttac acatactac     180
acagacgctg tgcagggccg attcaccatc tccagagaca atgccaagaa cacagtgtat     240
```

```
ctccagatga acagcctgag agccgaggac acggccatgt attactgtac aaaggagggc      300
tactacgata ctttctttga ctgctggggc cagggcaccc tggtcaccgt ctcctcagcc      360
tccaccacgg ccccctcggt t                                                381
```

<210> SEQ ID NO 164
<211> LENGTH: 127
<212> TYPE: PRT
<213> ORGANISM: artificial
<220> FEATURE:
<223> OTHER INFORMATION: VH chain

<400> SEQUENCE: 164

```
Glu Val Arg Leu Val Glu Ser Gly Gly Asp Leu Val Lys Pro Ala Gly
1               5                   10                  15

Ser Leu Arg Leu Ser Cys Val Ala Ser Gly Phe Thr Phe Ser Ser Tyr
            20                  25                  30

Thr Met Ser Trp Val Arg Gln Ala Pro Gly Lys Gly Leu Gln Leu Val
        35                  40                  45

Ala Asn Ile Lys Ser Gly Gly Thr Tyr Thr Tyr Tyr Thr Asp Ala Val
    50                  55                  60

Gln Gly Arg Phe Thr Ile Ser Arg Asp Asn Ala Lys Asn Thr Val Tyr
65                  70                  75                  80

Leu Gln Met Asn Ser Leu Arg Ala Glu Asp Thr Ala Met Tyr Tyr Cys
                85                  90                  95

Thr Lys Glu Gly Tyr Tyr Asp Thr Phe Phe Asp Cys Trp Gly Gln Gly
            100                 105                 110

Thr Leu Val Thr Val Ser Ser Ala Ser Thr Thr Ala Pro Ser Val
        115                 120                 125
```

<210> SEQ ID NO 165
<211> LENGTH: 384
<212> TYPE: DNA
<213> ORGANISM: artificial
<220> FEATURE:
<223> OTHER INFORMATION: VH chain

<400> SEQUENCE: 165

```
gagttgcaac tggtggagct tggggggagac ctggtgaagc ctgggggatc cctgacactg      60
tcctgtgtga cctctggatt caccttcagt gactatgcca tgacctgggt ccgccaggct     120
ccagggaagg ggctgcagtg ggtcgcatac attaacactg gtgggactac aacatactac     180
gcagatgctg tgaagggccg cttcaccatt tccagagacg atgccaggaa cacactgtat     240
ctgcaaatga acagcctgag atccgaggat acagccgttt attactgtct ggggctacg      300 gtggcttatt tctatggtct ggactactgg ggccatggca cctcagtctt cgtgtcctca     360
gcctccacca cggccccctc ggtt                                            384
```

<210> SEQ ID NO 166
<211> LENGTH: 128
<212> TYPE: PRT
<213> ORGANISM: artificial
<220> FEATURE:
<223> OTHER INFORMATION: VH chain

<400> SEQUENCE: 166

```
Glu Leu Gln Leu Val Glu Leu Gly Gly Asp Leu Val Lys Pro Gly Gly
1               5                   10                  15

Ser Leu Thr Leu Ser Cys Val Thr Ser Gly Phe Thr Phe Ser Asp Tyr
            20                  25                  30
```

```
Ala Met Thr Trp Val Arg Gln Ala Pro Gly Lys Gly Leu Gln Trp Val
        35                  40                  45

Ala Tyr Ile Asn Thr Gly Gly Thr Thr Thr Tyr Tyr Ala Asp Ala Val
 50                  55                  60

Lys Gly Arg Phe Thr Ile Ser Arg Asp Asp Ala Arg Asn Thr Leu Tyr
 65                  70                  75                  80

Leu Gln Met Asn Ser Leu Arg Ser Glu Asp Thr Ala Val Tyr Tyr Cys
                 85                  90                  95

Leu Gly Ala Thr Val Ala Tyr Phe Tyr Gly Leu Asp Tyr Trp Gly His
                100                 105                 110

Gly Thr Ser Val Phe Val Ser Ser Ala Ser Thr Thr Ala Pro Ser Val
                115                 120                 125
```

<210> SEQ ID NO 167
<211> LENGTH: 360
<212> TYPE: DNA
<213> ORGANISM: artificial
<220> FEATURE:
<223> OTHER INFORMATION: VH chain

<400> SEQUENCE: 167

```
gaggggcagc tggcggagtc tgggggagac ctggtgaagc ctgggggtc  cttgagactg      60
tcctgtgtgg cctctggatt caccttcagt aaggacatga cctgggtccg tcagtctcca     120
gggcagggcc tgcaatgggt cgcagatatc acccctgatg gaaggacgga ctattcagac     180
gctgtcaggg gccgattcac catctccagc gacatcgcca agaccacgct ctatctgcag     240
atggacagtc tgagagtcga agactcggcc gtctattatt gtgcctcggg gccattagac     300
ctctggggcc agggcaccct ggtcaccgtc tcctcagcct ccaccacggc cccctcggtt     360
```

<210> SEQ ID NO 168
<211> LENGTH: 120
<212> TYPE: PRT
<213> ORGANISM: artificial
<220> FEATURE:
<223> OTHER INFORMATION: VH chain

<400> SEQUENCE: 168

```
Glu Gly Gln Leu Ala Glu Ser Gly Gly Asp Leu Val Lys Pro Gly Gly
 1               5                  10                  15

Ser Leu Arg Leu Ser Cys Val Ala Ser Gly Phe Thr Phe Ser Lys Asp
                 20                  25                  30

Met Thr Trp Val Arg Gln Ser Pro Gly Gln Gly Leu Gln Trp Val Ala
         35                  40                  45

Asp Ile Thr Pro Asp Gly Arg Thr Asp Tyr Ser Asp Ala Val Arg Gly
 50                  55                  60

Arg Phe Thr Ile Ser Ser Asp Ile Ala Lys Thr Thr Leu Tyr Leu Gln
 65                  70                  75                  80

Met Asp Ser Leu Arg Val Glu Asp Ser Ala Val Tyr Tyr Cys Ala Ser
                 85                  90                  95

Gly Pro Leu Asp Leu Trp Gly Gln Gly Thr Leu Val Thr Val Ser Ser
                100                 105                 110

Ala Ser Thr Thr Ala Pro Ser Val
                115                 120
```

<210> SEQ ID NO 169
<211> LENGTH: 369
<212> TYPE: DNA
<213> ORGANISM: artificial

```
<220> FEATURE:
<223> OTHER INFORMATION: VH chain

<400> SEQUENCE: 169
aaccgagggg gccgtggtgg aggctgagga cacggtgacc agggttccct ggccccaata    60
gtcaatgctc cccaccgcac agtaataaag acccgtgtcg tcggctctca ggctgttcat   120
ctgcagatag actgtccttt tggcggtgtc tctggaaatg gtgaatcggc ccttcacagc   180
gtcaatatag tatgtgctga ttccatcaac actgattcca gcgacccact gtagtcgctt   240
cccaggagcc aggcggaccc agttcgtgtc ggagtcagag aaggtgaatc caggggctac   300
acaggagagt ctcagggacc ccccggcttt caccaggtct cccccagatt ccaccagctg   360
caccctcccc                                                          369

<210> SEQ ID NO 170
<211> LENGTH: 123
<212> TYPE: PRT
<213> ORGANISM: artificial
<220> FEATURE:
<223> OTHER INFORMATION: VH chain

<400> SEQUENCE: 170

Gly Glu Val Gln Leu Val Glu Ser Gly Gly Asp Leu Val Lys Pro Gly
1               5                   10                  15

Gly Ser Leu Arg Leu Ser Cys Val Ala Pro Gly Phe Thr Phe Ser Asp
            20                  25                  30

Ser Asp Thr Asn Trp Val Arg Leu Ala Pro Gly Lys Arg Leu Gln Trp
        35                  40                  45

Val Ala Gly Ile Ser Val Asp Gly Ile Ser Thr Tyr Tyr Ile Asp Ala
    50                  55                  60

Val Lys Gly Arg Phe Thr Ile Ser Arg Asp Thr Ala Lys Arg Thr Val
65                  70                  75                  80

Tyr Leu Gln Met Asn Ser Leu Arg Ala Asp Thr Gly Leu Tyr Tyr
                85                  90                  95

Cys Ala Val Gly Ser Ile Asp Tyr Trp Gly Gln Gly Thr Leu Val Thr
                100                 105                 110

Val Ser Ser Ala Ser Thr Thr Ala Pro Ser Val
            115                 120

<210> SEQ ID NO 171
<211> LENGTH: 376
<212> TYPE: DNA
<213> ORGANISM: artificial
<220> FEATURE:
<223> OTHER INFORMATION: VH chain

<400> SEQUENCE: 171
aaccgagggg gccgtggtgg aggctgagga cacgaagagt gaggtgccat ggccccagta    60
gtcaaaagcc accgcccgcc tcgcacagta atacacagcc gtgtcctcag ctctcaagct   120
gttcatctgc agatacagtg tgttcttggc gttgtctctg gagatggtga atcggccctt   180
cacagcgtct gcatacccttg tgttacttcc actatccata atccatgcga cccactgcag   240
tcccttccct ggagcctggc ggacccagcc catgttgtag ctactgaagg ggaatccaga   300
ggccacacag gagagtctca gggacccccc aggcctcacc aagtctcccc cagactccgc   360
cagctgcccc tcccca                                                   376

<210> SEQ ID NO 172
<211> LENGTH: 125
```

```
<212> TYPE: PRT
<213> ORGANISM: artificial
<220> FEATURE:
<223> OTHER INFORMATION: VH chain

<400> SEQUENCE: 172

Gly Glu Gly Gln Leu Ala Glu Ser Gly Gly Asp Leu Val Arg Pro Gly
1               5                   10                  15

Gly Ser Leu Arg Leu Ser Cys Val Ala Ser Gly Phe Pro Phe Ser Ser
            20                  25                  30

Tyr Asn Met Gly Trp Val Arg Gln Ala Pro Gly Lys Gly Leu Gln Trp
        35                  40                  45

Val Ala Trp Ile Tyr Asp Ser Gly Ser Asn Thr Arg Tyr Ala Asp Ala
50                  55                  60

Val Lys Gly Arg Phe Thr Ile Ser Arg Asp Asn Ala Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Arg Ala Val Ala Phe Asp Tyr Trp Gly His Gly Thr Ser
            100                 105                 110

Leu Phe Val Ser Ser Ala Ser Thr Thr Ala Pro Ser Val
        115                 120                 125

<210> SEQ ID NO 173
<211> LENGTH: 366
<212> TYPE: DNA
<213> ORGANISM: artificial
<220> FEATURE:
<223> OTHER INFORMATION: VH chain

<400> SEQUENCE: 173
aaccgagggg gccgtggtgg aggctgarga gacggtgacc agggttccct ggctccaata      60
cctccaggta gcgggggcac agtaatatac ggccgtgtcc tcgactttca ggctgttcat     120
ctggagatat agcgtgtttt tggcgtcgtc tctggaaatg gtgaatcggc ccttcacagc     180
gtctgcgtag tatgtggtac ttccatcata ccaaatactt gcgacccact gcagtccctt     240
tcctggagac tgacggaccc agctcatgtc agagccacta aggtgaatc agaggccac      300
acaggacagt ctcaaggtcc ccccaggctt caccaggtct cccccagact ccaccagctg     360
cacctc                                                                366

<210> SEQ ID NO 174
<211> LENGTH: 122
<212> TYPE: PRT
<213> ORGANISM: artificial
<220> FEATURE:
<223> OTHER INFORMATION: VH chain

<400> SEQUENCE: 174

Glu Val Gln Leu Val Glu Ser Gly Gly Asp Leu Val Lys Pro Gly Gly
1               5                   10                  15

Thr Leu Arg Leu Ser Cys Val Ala Ser Gly Phe Thr Phe Ser Gly Ser
            20                  25                  30

Asp Met Ser Trp Val Arg Gln Ser Pro Gly Lys Gly Leu Gln Trp Val
        35                  40                  45

Ala Ser Ile Trp Tyr Asp Gly Ser Thr Thr Tyr Tyr Ala Asp Ala Val
50                  55                  60

Lys Gly Arg Phe Thr Ile Ser Arg Asp Asp Ala Lys Asn Thr Leu Tyr
65                  70                  75                  80
```

```
Leu Gln Met Asn Ser Leu Lys Val Glu Asp Thr Ala Val Tyr Tyr Cys
                 85                  90                  95

Ala Pro Ala Thr Trp Arg Tyr Trp Ser Gln Gly Thr Leu Val Thr Val
            100                 105                 110

Ser Ser Ala Ser Thr Thr Ala Pro Ser Val
        115                 120
```

<210> SEQ ID NO 175
<211> LENGTH: 390
<212> TYPE: DNA
<213> ORGANISM: artificial
<220> FEATURE:
<223> OTHER INFORMATION: VH chain

<400> SEQUENCE: 175

```
aaccgagggg gccgtggtgg aggcagagga gacggtgacc agggttccat ggccccagta      60
ggtcagatga tatctattca aatatatcag accaagccca gtcgcacagt agtagacagc     120
cgtgtcctcg gttctcagac tgtccatctg cagatacact gtgttccggc cattgtctct     180
ggagacggtg actcggccct tcacagagtc actatgataa gtgattccat cataagtaag     240
agctgcgacc cactgcagcc ccttcccagg agcctggcgg acccaggtca tgtcgtggga     300
actgaaggcg agtccagaga ctagacagga gagtctcagg gacccccccag gcttcaccag    360 gtctccccca gactccacca gctgcacctc                                      390
```

<210> SEQ ID NO 176
<211> LENGTH: 130
<212> TYPE: PRT
<213> ORGANISM: artificial
<220> FEATURE:
<223> OTHER INFORMATION: VH chain

<400> SEQUENCE: 176

```
Glu Val Gln Leu Val Glu Ser Gly Gly Asp Leu Val Lys Pro Gly Gly
1               5                   10                  15

Ser Leu Arg Leu Ser Cys Leu Val Ser Gly Leu Ala Phe Ser Ser His
            20                  25                  30

Asp Met Thr Trp Val Arg Gln Ala Pro Gly Lys Gly Leu Gln Trp Val
        35                  40                  45

Ala Ala Leu Thr Tyr Asp Gly Ile Thr Tyr His Ser Asp Ser Val Lys
    50                  55                  60

Gly Arg Val Thr Val Ser Arg Asp Asn Gly Arg Asn Thr Val Tyr Leu
65                  70                  75                  80

Gln Met Asp Ser Leu Arg Thr Glu Asp Thr Ala Val Tyr Tyr Cys Ala
                85                  90                  95

Thr Gly Leu Gly Leu Ile Tyr Leu Asn Arg Tyr His Leu Thr Tyr Trp
            100                 105                 110

Gly His Gly Thr Leu Val Thr Val Ser Ser Ala Ser Thr Thr Ala Pro
        115                 120                 125

Ser Val
    130
```

<210> SEQ ID NO 177
<211> LENGTH: 381
<212> TYPE: DNA
<213> ORGANISM: artificial
<220> FEATURE:
<223> OTHER INFORMATION: VH chain

<400> SEQUENCE: 177

```
aaccgagggg gccgtggtgg aggctgagga cgggtgacc agagttccct ggccccagta      60
gtcaaactca tagtcggtac cgaaattgtt cgcacagtaa tatacagccg tgtcctcagt    120
ggtcaacctg ttcatatgca aaaacagtgt gttcttggcg ttgtctctgg agacggtgaa    180
tcggcccttc acagcgtctg cataggttgt ggtacttcca ctatcataaa tccatgcgac    240
ccactgcagt cccttccctg gagcctggcg acccagacc atgttgtagg tagtgaaggt     300
gaatccagag ccacacagg agagtctcag ggaccccca ggcttcacca agtctccccc      360
agactccgcc agctgcccct c                                              381
```

<210> SEQ ID NO 178
<211> LENGTH: 127
<212> TYPE: PRT
<213> ORGANISM: artificial
<220> FEATURE:
<223> OTHER INFORMATION: VH chain

<400> SEQUENCE: 178

```
Glu Gly Gln Leu Ala Glu Ser Gly Gly Asp Leu Val Lys Pro Gly Gly
1               5                  10                  15

Ser Leu Arg Leu Ser Cys Val Ala Ser Gly Phe Thr Phe Thr Thr Tyr
            20                  25                  30

Asn Met Val Trp Val Arg Gln Ala Pro Gly Lys Gly Leu Gln Trp Val
        35                  40                  45

Ala Trp Ile Tyr Asp Ser Gly Ser Thr Thr Tyr Ala Asp Ala Val
    50                  55                  60

Lys Gly Arg Phe Thr Val Ser Arg Asp Asn Ala Lys Asn Thr Leu Phe
65                  70                  75                  80

Leu His Met Asn Arg Leu Thr Thr Glu Asp Thr Ala Val Tyr Tyr Cys
                85                  90                  95

Ala Asn Asn Phe Gly Thr Asp Tyr Glu Phe Asp Tyr Trp Gly Gln Gly
            100                 105                 110

Thr Leu Val Thr Val Ser Ser Ala Ser Thr Thr Ala Pro Ser Val
        115                 120                 125
```

<210> SEQ ID NO 179
<211> LENGTH: 393
<212> TYPE: DNA
<213> ORGANISM: artificial
<220> FEATURE:
<223> OTHER INFORMATION: VH chain

<400> SEQUENCE: 179

```
aaccgagggg gccgtggtgg aggctgagga cgggtgacc agggttccct ggccccagta      60
gtcaaatccc tccagtacc agctgctact atacgttccg gttgcacagt aatacacggc    120
cgtgtcctcg gctctcaggc tgttcatctg cagatacagc atgttcttgg cgttgtctct    180
ggagatggtg aatcggccct tcacagcgtc tgcgtagtat gtgctacttc cactactgct    240
aatttctgag agccactgca gccccttccc tggagcctgg cggacccagt ccatgtcata    300
gctactgaag gtgaatccag aggccacaca ggaaagtctc agggaccccc caggcttcac    360
caggtctcct ccagactcca ccagctgcac ccc                                 393
```

<210> SEQ ID NO 180
<211> LENGTH: 131
<212> TYPE: PRT
<213> ORGANISM: artificial
<220> FEATURE:
<223> OTHER INFORMATION: VH chain -continued

<400> SEQUENCE: 180

```
Gly Val Gln Leu Val Glu Ser Gly Gly Asp Leu Val Lys Pro Gly Gly
 1               5                  10                  15
Ser Leu Arg Leu Ser Cys Val Ala Ser Gly Phe Thr Phe Ser Ser Tyr
            20                  25                  30
Asp Met Asp Trp Val Arg Gln Ala Pro Gly Lys Gly Leu Gln Trp Leu
        35                  40                  45
Ser Glu Ile Ser Ser Ser Gly Ser Ser Thr Tyr Tyr Ala Asp Ala Val
    50                  55                  60
Lys Gly Arg Phe Thr Ile Ser Arg Asp Asn Ala Lys Asn Met Leu Tyr
65                  70                  75                  80
Leu Gln Met Asn Ser Leu Arg Ala Glu Asp Thr Ala Val Tyr Tyr Cys
                85                  90                  95
Ala Thr Gly Thr Tyr Ser Ser Trp Tyr Trp Glu Gly Phe Asp Tyr
            100                 105                 110
Trp Gly Gln Gly Thr Leu Val Thr Val Ser Ser Ala Ser Thr Thr Ala
        115                 120                 125
Pro Ser Val
    130
```

<210> SEQ ID NO 181
<211> LENGTH: 396
<212> TYPE: DNA
<213> ORGANISM: artificial
<220> FEATURE:
<223> OTHER INFORMATION: VH chain

<400> SEQUENCE: 181

```
aaccgagggg gccgtggtgg aggctgcgga gacggtgacc aggcttccct ggccccagta      60
gtcaaaaccc tcttggtagc gaccggagta gcggaacaga aggtttacac agtaatatac    120
ggccgtgtct tcggctctca ggctgttcat ctgcagatac agcgtgttct tggcgtcgtc    180
tctggagatg gtgaatcggc ccttcacagc gtctgcgtag tatgtgctac ttccactact    240
gttaatttcc gagagccact gcagcccctt ccctggagcc tggcggaccc agttcatgtc    300
atagttatta aggtgaatc cagaggccac acaggaaagt ctcagggacc cccaggctt      360
caccaggtct cctccaaact ccaccagctg ctcctc                              396
```

<210> SEQ ID NO 182
<211> LENGTH: 132
<212> TYPE: PRT
<213> ORGANISM: artificial
<220> FEATURE:
<223> OTHER INFORMATION: VH chain

<400> SEQUENCE: 182

```
Glu Glu Gln Leu Val Glu Phe Gly Gly Asp Leu Val Lys Pro Gly Gly
 1               5                  10                  15
Ser Leu Arg Leu Ser Cys Val Ala Ser Gly Phe Thr Phe Asn Asn Tyr
            20                  25                  30
Asp Met Asn Trp Val Arg Gln Ala Pro Gly Lys Gly Leu Gln Trp Leu
        35                  40                  45
Ser Glu Ile Asn Ser Ser Gly Ser Ser Thr Tyr Tyr Ala Asp Ala Val
    50                  55                  60
Lys Gly Arg Phe Thr Ile Ser Arg Asp Asp Ala Lys Asn Thr Leu Tyr
65                  70                  75                  80
Leu Gln Met Asn Ser Leu Arg Ala Glu Asp Thr Ala Val Tyr Tyr Cys
                85                  90                  95
```

Val Asn Leu Leu Phe Arg Tyr Ser Gly Arg Tyr Gln Glu Gly Phe Asp
                100                 105                 110

Tyr Trp Gly Gln Gly Ser Leu Val Thr Val Ser Ala Ala Ser Thr Thr
            115                 120                 125

Ala Pro Ser Val
        130

<210> SEQ ID NO 183
<211> LENGTH: 363
<212> TYPE: DNA
<213> ORGANISM: artificial
<220> FEATURE:
<223> OTHER INFORMATION: VH chain

<400> SEQUENCE: 183
aaccgagggg gccgtggtgg aggctgagga gacgatgacc agggttccct ggccccaata       60
gtcaaaacgg taataactcc ctcctttttcc cccggaactc gcacaatgat acacggccgt    120
gtcctcggct ctcagactgt tcatctgaag ataccgta ttcctggcat tgtctctgga      180
gacggtgaat cggcccctca cagcgtctgc ataggttgtc ttatctccac cactattaat    240
gtatgtgacc cactgaaacc ccttccctgg agcctggcgg acccaggtca tgtgatggtc    300
actgagggtg aatccagagg ccgcacagga aagtctcagg gaccccccag gcttcaccag    360
gtc                                                                   363

<210> SEQ ID NO 184
<211> LENGTH: 121
<212> TYPE: PRT
<213> ORGANISM: artificial
<220> FEATURE:
<223> OTHER INFORMATION: VH chain

<400> SEQUENCE: 184

Asp Leu Val Lys Pro Gly Gly Ser Leu Arg Leu Ser Cys Ala Ala Ser
1               5                   10                  15

Gly Phe Thr Leu Ser Asp His His Met Thr Trp Val Arg Gln Ala Pro
            20                  25                  30

Gly Lys Gly Phe Gln Trp Val Thr Tyr Ile Asn Ser Gly Gly Asp Lys
        35                  40                  45

Thr Thr Tyr Ala Asp Ala Val Arg Gly Arg Phe Thr Val Ser Arg Asp
    50                  55                  60

Asn Ala Arg Asn Thr Val Tyr Leu Gln Met Asn Ser Leu Arg Ala Glu
65                  70                  75                  80

Asp Thr Ala Val Tyr His Cys Ala Ser Ser Gly Gly Lys Gly Gly Ser
                85                  90                  95

Tyr Tyr Arg Phe Asp Tyr Trp Gly Gln Gly Thr Leu Val Ile Val Ser
                100                 105                 110

Ser Ala Ser Thr Thr Ala Pro Ser Val
            115                 120

<210> SEQ ID NO 185
<211> LENGTH: 381
<212> TYPE: DNA
<213> ORGANISM: artificial
<220> FEATURE:
<223> OTHER INFORMATION: VH chain

<400> SEQUENCE: 185
aaccgagggg gccgtggtgg aggctgagga gacggtgacc agggttccct ggccccactc       60

```
gtccccccct gtaatgtcgt agccatgccg acacagtaa tacacggccg tgtcctcggc      120
tctcaggctg ttcatctgca gatacagcgt gttcttggcg ttgtctctgg agatggtgaa      180
tcggcccttc acagcgtctc cataatatgt gctaaatcca tcattccaaa taatcgcgac      240
ccactgcagc cccttccctg gagactgacg gacccagctc atgtcagagc tactaaaggt      300
gaatccagag gccacacagg acagtctcaa ggtccccca ggcttcacca ggtctccccc      360
agattccacc aaactcacct c                                                381
```

<210> SEQ ID NO 186
<211> LENGTH: 127
<212> TYPE: PRT
<213> ORGANISM: artificial
<220> FEATURE:
<223> OTHER INFORMATION: VH chain

<400> SEQUENCE: 186

```
Glu Val Ser Leu Val Glu Ser Gly Gly Asp Leu Val Lys Pro Gly Gly
1               5                   10                  15

Thr Leu Arg Leu Ser Cys Val Ala Ser Gly Phe Thr Phe Ser Ser Ser
            20                  25                  30

Asp Met Ser Trp Val Arg Gln Ser Pro Gly Lys Gly Leu Gln Trp Val
        35                  40                  45

Ala Ile Ile Trp Asn Asp Gly Phe Ser Thr Tyr Tyr Gly Asp Ala Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg His Gly Tyr Asp Ile Thr Gly Gly Asp Glu Trp Gly Gln Gly
            100                 105                 110

Thr Leu Val Thr Val Ser Ser Ala Ser Thr Thr Ala Pro Ser Val
        115                 120                 125
```

<210> SEQ ID NO 187
<211> LENGTH: 391
<212> TYPE: DNA
<213> ORGANISM: artificial
<220> FEATURE:
<223> OTHER INFORMATION: VH chain

<400> SEQUENCE: 187

```
aaccgagggg gccgtggtgg aggcggagga gacggtgacc agggttccct ggccccagta       60
gtcaaagtac caggaaccac catagcccaa tttcctcgcg cagtaataga cggccgtgtc      120
ttcggctctc agactgttca tctgcagata caggtgttc ctggcgttgt ctctggagat      180
ggtgaatcgg cccttcacag cgtctccata ttttgtgaga gatccatcac tccaaataag      240
tgcgacccat gcagcccct cccctggaga ctgacggacc cagttcatgt cagaactact      300
gaaggtgaat ccagaggcca cacaggacag tctcaaggtc cccccaggct tcaccaggtc      360
tcccccagat tccaccagtt gtacctcccc a                                    391
```

<210> SEQ ID NO 188
<211> LENGTH: 130
<212> TYPE: PRT
<213> ORGANISM: artificial
<220> FEATURE:
<223> OTHER INFORMATION: VH chain

<400> SEQUENCE: 188

Gly Glu Val Gln Leu Val Glu Ser Gly Gly Asp Leu Val Lys Pro Gly
1               5                   10                  15

Gly Thr Leu Arg Leu Ser Cys Val Ala Ser Gly Phe Thr Phe Ser Ser
            20                  25                  30

Ser Asp Met Asn Trp Val Arg Gln Ser Pro Gly Glu Gly Leu Gln Trp
        35                  40                  45

Val Ala Leu Ile Trp Ser Asp Gly Ser Leu Thr Lys Tyr Gly Asp Ala
    50                  55                  60

Val Lys Gly Arg Phe Thr Ile Ser Arg Asp Asn Ala Arg Asn Thr Leu
65              70                  75                  80

Tyr Leu Gln Met Asn Ser Leu Arg Ala Glu Asp Thr Ala Val Tyr Tyr
                85                  90                  95

Cys Ala Arg Lys Leu Gly Tyr Gly Gly Ser Trp Tyr Phe Asp Tyr Trp
            100                 105                 110

Gly Gln Gly Thr Leu Val Thr Val Ser Ser Ala Ser Thr Thr Ala Pro
            115                 120                 125

Ser Val
    130

<210> SEQ ID NO 189
<211> LENGTH: 360
<212> TYPE: DNA
<213> ORGANISM: artificial
<220> FEATURE:
<223> OTHER INFORMATION: VH chain

<400> SEQUENCE: 189
aaccgagggg gccgtggtgg aggctgagga cacggtgacc agggttccct ggccccaata    60
gtcaatgctc cccaccgcac agtaatacag agccgtgtcg tcggctctca ggctgttcat   120
ctgtagatag actgtctttc tggcggtgtc tctggaaatg gtgaatcggc ccttcacagc   180
gtcaatatag tatgtgctga ttccatcgac actgattcca gcgacccact gcagccgctt   240
cccaggagcc aggcggaccc agttcgtgtc ggagtcagag aaggtgaatc cagggggctac   300 acaggagagt ctcagggacc ccccggctt caccaggtct cccccagact ccaccagctg    360

<210> SEQ ID NO 190
<211> LENGTH: 120
<212> TYPE: PRT
<213> ORGANISM: artificial
<220> FEATURE:
<223> OTHER INFORMATION: VH chain

<400> SEQUENCE: 190

Gln Leu Val Glu Ser Gly Gly Asp Leu Val Lys Pro Gly Gly Ser Leu
1               5                   10                  15

Arg Leu Ser Cys Val Ala Pro Gly Phe Thr Phe Ser Asp Ser Asp Thr
            20                  25                  30

Asn Trp Val Arg Leu Ala Pro Gly Lys Arg Leu Gln Trp Val Ala Gly
        35                  40                  45

Ile Ser Val Asp Gly Ile Ser Thr Tyr Tyr Ile Asp Ala Val Lys Gly
    50                  55                  60

Arg Phe Thr Ile Ser Arg Asp Thr Ala Arg Lys Thr Val Tyr Leu Gln
65              70                  75                  80

Met Asn Ser Leu Arg Ala Asp Asp Thr Ala Leu Tyr Tyr Cys Ala Val
                85                  90                  95

Gly Ser Ile Asp Tyr Trp Gly Gln Gly Thr Leu Val Thr Val Ser Ser
            100                 105                 110

```
Ala Ser Thr Thr Ala Pro Ser Val
        115                 120
```

<210> SEQ ID NO 191
<211> LENGTH: 363
<212> TYPE: DNA
<213> ORGANISM: artificial
<220> FEATURE:
<223> OTHER INFORMATION: VH chain

<400> SEQUENCE: 191

```
aaccgagggg gccgtggtgg aggctgagga cggtgacc agggtgccct ggccccagta    60
gtcataacag gaccagacgg accaggcact attatccttg cacagtaat acatagccgt   120
gtcctcggct ctcagactgt tcatccgcag atacagtgtg ttgttggcat tgtctctgga  180
gacggtgaat cggcccttca cagcgtctcc ataatatgta gtctttccat caatactaat  240
ccgtgcgacc cactgaagcc ccttccctgg agcctggcgg acccaataca tataataatt  300
cttgaaggta atccagagg ccacacagga cagtgtcagg acccccccag gcttcaccag   360
gtc                                                                363
```

<210> SEQ ID NO 192
<211> LENGTH: 122
<212> TYPE: PRT
<213> ORGANISM: artificial
<220> FEATURE:
<223> OTHER INFORMATION: VH chain

<400> SEQUENCE: 192

```
Asp Leu Val Lys Pro Gly Gly Ser Leu Thr Leu Ser Cys Val Ala Ser
1               5                   10                  15
Gly Phe Thr Phe Lys Asn Tyr Tyr Met Tyr Trp Val Arg Gln Ala Pro
            20                  25                  30
Gly Lys Gly Leu Gln Trp Val Ala Arg Ile Ser Ile Asp Gly Lys Thr
        35                  40                  45
Thr Tyr Tyr Gly Asp Ala Val Lys Gly Arg Phe Thr Val Ser Arg Asp
    50                  55                  60
Asn Ala Asn Asn Thr Leu Tyr Leu Arg Met Asn Ser Leu Arg Ala Glu
65                  70                  75                  80
Asp Thr Ala Met Tyr Tyr Cys Ala Lys Asp Asn Ser Ala Trp Ser Val
                85                  90                  95
Trp Ser Cys Tyr Asp Tyr Trp Gly Gln Gly Thr Leu Val Thr Val Ser
            100                 105                 110
Ser Ala Ser Thr Thr Ala Pro Ser Val Val
        115                 120
```

<210> SEQ ID NO 193
<211> LENGTH: 366
<212> TYPE: DNA
<213> ORGANISM: artificial
<220> FEATURE:
<223> OTHER INFORMATION: VH chain

<400> SEQUENCE: 193

```
aaccgagggg gccgtggtgg aggctgarga cggtgacc agggttccct ggccccagta    60
caccgggacc tgctcctttg cacagtaata catagccgtg tcctcggctc tcaggctgtt  120
catctgcaga tacagcgtgt ttttggcatt gtctctggag atggtgaatc ggcccttcac  180
agcgtctgta ttatatgtgc tactcccatc actgctaatc cgtgcgaccc actgaagccc  240
cttccctgga gcctggcgga cccagtagta gtaacttctg aaggtaaatc cagaggccac  300
```

```
acaggacagt ctcagggacc ccccaggctt caccaggtct cccccagact ccaccagctg    360
cacctc                                                               366

<210> SEQ ID NO 194
<211> LENGTH: 122
<212> TYPE: PRT
<213> ORGANISM: artificial
<220> FEATURE:
<223> OTHER INFORMATION: VH chain

<400> SEQUENCE: 194

Glu Val Gln Leu Val Glu Ser Gly Gly Asp Leu Val Lys Pro Gly Gly
1               5                   10                  15

Ser Leu Arg Leu Ser Cys Val Ala Ser Gly Phe Thr Phe Arg Ser Tyr
            20                  25                  30

Tyr Tyr Trp Val Arg Gln Ala Pro Gly Lys Gly Leu Gln Trp Val Ala
        35                  40                  45

Arg Ile Ser Ser Asp Gly Ser Ser Thr Tyr Asn Thr Asp Ala Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Ala Glu Asp Thr Ala Met Tyr Tyr Cys Ala
                85                  90                  95

Lys Glu Gln Val Pro Val Tyr Trp Gly Gln Gly Thr Leu Val Thr Val
            100                 105                 110

Ser Ser Ala Ser Thr Thr Ala Pro Ser Val
        115                 120

<210> SEQ ID NO 195
<211> LENGTH: 396
<212> TYPE: DNA
<213> ORGANISM: artificial
<220> FEATURE:
<223> OTHER INFORMATION: VH chain

<400> SEQUENCE: 195
aaccgagggg gccgtggtgg aggctgagga gacggtgacc agggttccct ggccccagta    60
gtcaaaaaac tccactatcg aagagtagct gctaccccca tccctcgcac agtaatattg   120
agccatgtcc tcaactctca atctgttcat ctgcagatat aatgtgttcc tggcgttgtc   180
tctggagatg gtgaatcggc ccttcacagc gtctgcatac cttgtgccac ttccactatc   240
ataaatccaa gcgacccact gcagtcccct ccctggagcc tggcggaccc agcccatgtt   300
gtagctactg aaggtgaatc cagaggccac acaggagagt ctcagggacc ccccaggctt   360
caccaggtct cccccagact ccgccagctg cccctc                             396

<210> SEQ ID NO 196
<211> LENGTH: 132
<212> TYPE: PRT
<213> ORGANISM: artificial
<220> FEATURE:
<223> OTHER INFORMATION: VH chain

<400> SEQUENCE: 196

Glu Gly Gln Leu Ala Glu Ser Gly Gly Asp Leu Val Lys Pro Gly Gly
1               5                   10                  15

Ser Leu Arg Leu Ser Cys Val Ala Ser Gly Phe Thr Phe Ser Ser Tyr
            20                  25                  30

Asn Met Gly Trp Val Arg Gln Ala Pro Gly Arg Gly Leu Gln Trp Val
```

```
                35                  40                  45
Ala Trp Ile Tyr Asp Ser Gly Ser Gly Thr Arg Tyr Ala Asp Ala Val
 50                  55                  60
Lys Gly Arg Phe Thr Ile Ser Arg Asp Asn Ala Arg Asn Thr Leu Tyr
 65                  70                  75                  80
Leu Gln Met Asn Arg Leu Arg Val Glu Asp Met Ala Gln Tyr Tyr Cys
                 85                  90                  95
Ala Arg Asp Gly Gly Ser Ser Tyr Ser Ser Ile Val Glu Phe Phe Asp
                100                 105                 110
Tyr Trp Gly Gln Gly Thr Leu Val Thr Val Ser Ser Ala Ser Thr Thr
            115                 120                 125
Ala Pro Ser Val
        130

<210> SEQ ID NO 197
<211> LENGTH: 348
<212> TYPE: DNA
<213> ORGANISM: artificial
<220> FEATURE:
<223> OTHER INFORMATION: VH chain

<400> SEQUENCE: 197
aaccgagggg gccgtggtgg argctgagga gacggtgacc agggttccct ggccccaggc    60
ggaataacta ccggcaatat catccctcgt acagtaataa atgcccgtgt cctcggctct   120
caggctgttc atctgcagat aaagcgtgtt cttggcgttg tctctggaga tggtgaatcg   180
gcccttcaca gcgtctgcgt agtatgtgct acttccatca ctgctaatcc gtgcgaccca   240
ctgaagcccc ctccctggag cctggcggac ccagtagtag taacttctga aggtaaatcc   300
agaggccaca caggacagtc tcagggaccc cccaggcttc accaggtc                348

<210> SEQ ID NO 198
<211> LENGTH: 116
<212> TYPE: PRT
<213> ORGANISM: artificial
<220> FEATURE:
<223> OTHER INFORMATION: VH chain

<400> SEQUENCE: 198

Asp Leu Val Lys Pro Gly Gly Ser Leu Arg Leu Ser Cys Val Ala Ser
 1               5                  10                  15
Gly Phe Thr Phe Arg Ser Tyr Tyr Tyr Trp Val Arg Gln Ala Pro Gly
                20                  25                  30
Arg Gly Leu Gln Trp Val Ala Arg Ile Ser Ser Asp Gly Ser Ser Thr
            35                  40                  45
Tyr Tyr Ala Asp Ala Val Lys Gly Arg Phe Thr Ile Ser Arg Asp Asn
 50                  55                  60
Ala Lys Asn Thr Leu Tyr Leu Gln Met Asn Ser Leu Arg Ala Glu Asp
 65                  70                  75                  80
Thr Gly Ile Tyr Tyr Cys Thr Arg Asp Asp Ile Ala Gly Ser Tyr Ser
                 85                  90                  95
Ala Trp Gly Gln Gly Thr Leu Val Thr Val Ser Ser Ala Ser Thr Thr
                100                 105                 110
Ala Pro Ser Val
        115

<210> SEQ ID NO 199
<211> LENGTH: 372
<212> TYPE: DNA
```

<213> ORGANISM: artificial
<220> FEATURE:
<223> OTHER INFORMATION: VH chain

<400> SEQUENCE: 199

```
aaccgagggg gccgtggtgg aggctgagga gacggtgacc agggttccct ggccccaaaa      60
gtcaaaattc aacaaggtgc cccgacagta atacacagct gtgtcctcga ctctcaggct     120
gttcatctgc agatacactg tgttcctggc gttgtctctg gaaatggtga atcggccctt     180
cacagcggca gtgtagtatg tacttctccc atcatagtca ataccgtgtga cccactgcag     240
ccccttccca ggggcctggc ggacccagga catgctgtag cttccgatac ttaatccaga     300
ggccacacag gagagtctca gggaccccccc aggcttcgcc aggtctcccc cagactccac     360
cagctgcacg cc                                                          372
```

<210> SEQ ID NO 200
<211> LENGTH: 124
<212> TYPE: PRT
<213> ORGANISM: artificial
<220> FEATURE:
<223> OTHER INFORMATION: VH chain

<400> SEQUENCE: 200

```
Gly Val Gln Leu Val Glu Ser Gly Gly Asp Leu Ala Lys Pro Gly Gly
  1               5                  10                  15
Ser Leu Arg Leu Ser Cys Val Ala Ser Gly Leu Ser Ile Gly Ser Tyr
             20                  25                  30
Ser Met Ser Trp Val Arg Gln Ala Pro Gly Lys Gly Leu Gln Trp Val
         35                  40                  45
Thr Gly Ile Asp Tyr Asp Gly Arg Ser Thr Tyr Tyr Thr Ala Ala Val
     50                  55                  60
Lys Gly Arg Phe Thr Ile Ser Arg Asp Asn Ala Arg Asn Thr Val Tyr
 65                  70                  75                  80
Leu Gln Met Asn Ser Leu Arg Val Glu Asp Thr Ala Val Tyr Tyr Cys
                 85                  90                  95
Arg Gly Thr Leu Leu Asn Phe Asp Phe Trp Gly Gln Gly Thr Leu Val
            100                 105                 110
Thr Val Ser Ser Ala Ser Thr Thr Ala Pro Ser Val
        115                 120
```

<210> SEQ ID NO 201
<211> LENGTH: 372
<212> TYPE: DNA
<213> ORGANISM: artificial
<220> FEATURE:
<223> OTHER INFORMATION: VH chain

<400> SEQUENCE: 201

```
aaccgagggg gccgtggtgg aggctgarga gacggtgacc agggttccct ggccccaaaa      60
gtcaaaattc aacaaggtgc cccgacagta atacacagct gtgtcctcga ctctcaggct     120
gttcatctgc agatacactg tgttcctggc gttgtctctg gaaatggtga atcggccctt     180
cacagcggca gtgtagtatg tacttctccc atcatagtca ataccgtgtga cccactgcag     240
ccccttccca ggggcctggc ggacccagga catgctgtag cttccgatac ttaatccaga     300
ggccacacag gagagtctca gggaccccccc aggcttcgcc aggtctcccc cagactccac     360
cagctgcacg cc                                                          372
```

<210> SEQ ID NO 202

<211> LENGTH: 124
<212> TYPE: PRT
<213> ORGANISM: artificial
<220> FEATURE:
<223> OTHER INFORMATION: VH chain

<400> SEQUENCE: 202

Gly Val Gln Leu Val Glu Ser Gly Gly Asp Leu Ala Lys Pro Gly Gly
1               5                   10                  15

Ser Leu Arg Leu Ser Cys Val Ala Ser Gly Leu Ser Ile Gly Ser Tyr
            20                  25                  30

Ser Met Ser Trp Val Arg Gln Ala Pro Gly Lys Gly Leu Gln Trp Val
        35                  40                  45

Thr Gly Ile Asp Tyr Asp Gly Arg Ser Thr Tyr Tyr Thr Ala Ala Val
    50                  55                  60

Lys Gly Arg Phe Thr Ile Ser Arg Asp Asn Ala Arg Asn Thr Val Tyr
65                  70                  75                  80

Leu Gln Met Asn Ser Leu Arg Val Glu Asp Thr Ala Val Tyr Tyr Cys
                85                  90                  95

Arg Gly Thr Leu Leu Asn Phe Asp Phe Trp Gly Gln Gly Thr Leu Val
            100                 105                 110

Thr Val Ser Ser Ala Ser Thr Thr Ala Pro Ser Val
        115                 120

<210> SEQ ID NO 203
<211> LENGTH: 393
<212> TYPE: DNA
<213> ORGANISM: artificial
<220> FEATURE:
<223> OTHER INFORMATION: VH chain

<400> SEQUENCE: 203
aaccgagggg gccgtggtgg aggctgagga cggtgacc agggttccct ggccccagta      60
gtcaaatccc tcccagtacc agctgctact atacgttccg gttgcacagt aatacacggc    120
cgtgtcctcg gctctcaggc tgttcatctg cagatacagc atgttcttgg cgttgtctct    180
ggagatggtg aatcggccct tcacagcgtc tgcgtagtat gtgctacttc cactactgct    240
aatttctgag agccactgca gcccttccc tggagcctgg cggacccagt ccatgtcata     300
gctactgaag gtgaatccag aggccacaca ggaaagtctc agggaccccc caggcttcac    360
caggtctcct ccagactcca ccagctgcac ccc                                  393

<210> SEQ ID NO 204
<211> LENGTH: 131
<212> TYPE: PRT
<213> ORGANISM: artificial
<220> FEATURE:
<223> OTHER INFORMATION: VH chain

<400> SEQUENCE: 204

Gly Val Gln Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Ser Tyr
            20                  25                  30

Asp Met Asp Trp Val Arg Gln Ala Pro Gly Lys Gly Leu Gln Trp Leu
        35                  40                  45

Ser Glu Ile Ser Ser Ser Gly Ser Ser Thr Tyr Tyr Ala Asp Ala Val
    50                  55                  60

Lys Gly Arg Phe Thr Ile Ser Arg Asp Asn Ala Lys Asn Met Leu Tyr
65                  70                  75                  80

```
Leu Gln Met Asn Ser Leu Arg Ala Glu Asp Thr Ala Val Tyr Tyr Cys
                85                  90                  95

Ala Thr Gly Thr Tyr Ser Ser Ser Trp Tyr Trp Glu Gly Phe Asp Tyr
            100                 105                 110

Trp Gly Gln Gly Thr Leu Val Thr Val Ser Ser Ala Ser Thr Thr Ala
        115                 120                 125

Pro Ser Val
    130

<210> SEQ ID NO 205
<211> LENGTH: 384
<212> TYPE: DNA
<213> ORGANISM: artificial
<220> FEATURE:
<223> OTHER INFORMATION: VH chain

<400> SEQUENCE: 205
aaccgagggg gccgtggtgg aggctgarga dacggtgacc agggttccct ggccccagta      60
gtcaaagccg tagtagctac cgtaatctct agggacacag taatacacgg ctgtgtcctc    120
ggatctcagg ctgttcatct gcagatacag tgtgttcctg tcattgtctc tggagatggt    180
gaaccggccc ttcacagcat ctgcgtagta tgtgacactt ccaccactgt taatgatgc     240 gacccactgc agccccttcc ctggagcctg gcggacccag ttcatggtat agggactgaa    300
ggtgaatcca gaggccacac aggacagtct cagggatccc ccaggcttca ccaggtctcc    360
cccagattcc accagctgca cctc                                            384

<210> SEQ ID NO 206
<211> LENGTH: 128
<212> TYPE: PRT
<213> ORGANISM: artificial
<220> FEATURE:
<223> OTHER INFORMATION: VH chain

<400> SEQUENCE: 206

Glu Val Gln Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Pro Tyr
            20                  25                  30

Thr Met Asn Trp Val Arg Gln Ala Pro Gly Lys Gly Leu Gln Trp Val
            35                  40                  45

Ala Ser Ile Asn Ser Gly Gly Ser Val Thr Tyr Tyr Ala Asp Ala Val
        50                  55                  60

Lys Gly Arg Phe Thr Ile Ser Arg Asp Asn Asp Arg Asn Thr Leu Tyr
65                  70                  75                  80

Leu Gln Met Asn Ser Leu Arg Ser Glu Asp Thr Ala Val Tyr Tyr Cys
                85                  90                  95

Val Pro Arg Asp Tyr Gly Ser Tyr Tyr Gly Phe Asp Tyr Trp Gly Gln
            100                 105                 110

Gly Thr Leu Val Thr Val Ser Ser Ala Ser Thr Thr Ala Pro Ser Val
        115                 120                 125

<210> SEQ ID NO 207
<211> LENGTH: 387
<212> TYPE: DNA
<213> ORGANISM: artificial
<220> FEATURE:
<223> OTHER INFORMATION: VH chain

<400> SEQUENCE: 207
```

```
aaccgagggg gccgtggtgg aggctgagga cggtgacc agggttccct ggccccagta    60
gtcaaaagat ggtatccata tatattcacc ccctcgtgca cagtaataca tagccgtgtc   120
ctcggctctc aggctgttca tctgcagata cagcgttttc ttggcattgt ctctggagat   180
ggtgaatcgg cccttcatag cgtctgcata gtatgtgcta cttccatcac cgctaatccg   240
tgcgacccac tgaagcccct tcctagagc ctggcggacc cagtacatgt agtagctgct   300
gaaggtgaat ccagaggcca cacaggacag tctcagggac cccccaggct tcaccaggtc   360
tcccccagat tccaccaatc ttacctc                                      387
```

<210> SEQ ID NO 208
<211> LENGTH: 129
<212> TYPE: PRT
<213> ORGANISM: artificial
<220> FEATURE:
<223> OTHER INFORMATION: VH chain

<400> SEQUENCE: 208

```
Glu Val Arg Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Ser Tyr
            20                  25                  30

Tyr Met Tyr Trp Val Arg Gln Ala Leu Gly Lys Gly Leu Gln Trp Val
        35                  40                  45

Ala Arg Ile Ser Gly Asp Gly Ser Ser Thr Tyr Tyr Ala Asp Ala Met
    50                  55                  60

Lys Gly Arg Phe Thr Ile Ser Arg Asp Asn Ala Lys Lys Thr Leu Tyr
65                  70                  75                  80

Leu Gln Met Asn Ser Leu Arg Ala Glu Asp Thr Ala Met Tyr Tyr Cys
                85                  90                  95

Ala Arg Gly Gly Glu Tyr Ile Trp Ile Pro Ser Phe Asp Tyr Trp Gly
            100                 105                 110

Gln Gly Thr Leu Val Thr Val Ser Ser Ala Ser Thr Thr Ala Pro Ser
        115                 120                 125

Val
```

<210> SEQ ID NO 209
<211> LENGTH: 384
<212> TYPE: DNA
<213> ORGANISM: artificial
<220> FEATURE:
<223> OTHER INFORMATION: VH chain

<400> SEQUENCE: 209

```
aaccgagggg gccgtggtgg argctgagga cggtgacc agggttccct ggccccagtc    60
gccaaagtat tggccacttc taccccggac atccacacag taatatacag ctgtgtcctc   120
ggctctcagg ccggtcatct gcagagaaac tgtgttcctg gcgttgtctc tggagatggt   180
gaatcggccc ttcacagcgt cagtgtagta tgtgctactt ccatcatagc taatagctgc   240
gacccactgc agccccttcc caggagcctg gcggacccac tcatgtcgt aatcactgaa   300 ggtgaatcca gagcctacac aggagagtct cagggacccc ccggcttca cctggtctcc   360 cccagattcc accagctgca cctc                                         384
```

<210> SEQ ID NO 210
<211> LENGTH: 128
<212> TYPE: PRT
<213> ORGANISM: artificial
<220> FEATURE:
<223> OTHER INFORMATION: VH chain

<400> SEQUENCE: 210

```
Glu Val Gln Leu Val Glu Ser Gly Gly Asp Gln Val Lys Pro Gly Gly
1               5                   10                  15
Ser Leu Arg Leu Ser Cys Val Gly Ser Gly Phe Thr Phe Ser Asp Tyr
            20                  25                  30
Asp Met Ser Trp Val Arg Gln Ala Pro Gly Lys Gly Leu Gln Trp Val
        35                  40                  45
Ala Ala Ile Ser Tyr Asp Gly Ser Ser Thr Tyr Tyr Thr Asp Ala Val
    50                  55                  60
Lys Gly Arg Phe Thr Ile Ser Arg Asp Asn Ala Arg Asn Thr Val Ser
65                  70                  75                  80
Leu Gln Met Thr Gly Leu Arg Ala Glu Asp Thr Ala Val Tyr Tyr Cys
                85                  90                  95
Val Asp Val Arg Gly Arg Ser Gly Gln Tyr Phe Gly Asp Trp Gly Gln
            100                 105                 110
Gly Thr Leu Val Thr Val Ser Ser Ala Ser Thr Thr Ala Pro Ser Val
        115                 120                 125
```

<210> SEQ ID NO 211
<211> LENGTH: 387
<212> TYPE: DNA
<213> ORGANISM: artificial
<220> FEATURE:
<223> OTHER INFORMATION: VH chain

<400> SEQUENCE: 211

```
aaccgagggg gccgtggtgg aggctgagga cggtgacc agggttccct ggccccagta      60
gtcaaaatcc cagccccaag tagtagaata atccctcgca cagtaataca cagccgtgtc   120
ctcagctctc aagttgttca tctgcagata cagtgtgttc ttggcattgt ctctggagat   180
ggtgaatcgg cccttcacag cgtctgcgta gcttgtccta gttccaccag tataaatcca   240
tgcgacccac tgcagtccct tcctggagc ctggcggacc cagcccatgt tgtagctact    300
gaaggtgaat ccagaggcca cacaggagag tctcagggac ccccccggct tcaccaggtc   360
tcccccagac tccaccagct gcatgtc                                        387
```

<210> SEQ ID NO 212
<211> LENGTH: 129
<212> TYPE: PRT
<213> ORGANISM: artificial
<220> FEATURE:
<223> OTHER INFORMATION: VH chain

<400> SEQUENCE: 212

```
Asp Met Gln Leu Val Glu Ser Gly Gly Asp Leu Val Lys Pro Gly Gly
1               5                   10                  15
Ser Leu Arg Leu Ser Cys Val Ala Ser Gly Phe Thr Phe Ser Ser Tyr
            20                  25                  30
Asn Met Gly Trp Val Arg Gln Ala Pro Gly Lys Gly Leu Gln Trp Val
        35                  40                  45
Ala Trp Ile Tyr Thr Gly Gly Thr Arg Thr Ser Tyr Ala Asp Ala Val
    50                  55                  60
Lys Gly Arg Phe Thr Ile Ser Arg Asp Asn Ala Lys Asn Thr Leu Tyr
65                  70                  75                  80
Leu Gln Met Asn Asn Leu Arg Ala Glu Asp Thr Ala Val Tyr Tyr Cys
                85                  90                  95
```

```
Ala Arg Asp Tyr Ser Thr Thr Trp Gly Trp Asp Phe Asp Tyr Trp Gly
            100                 105                 110

Gln Gly Thr Leu Val Thr Val Ser Ser Ala Ser Thr Thr Ala Pro Ser
        115                 120                 125

Val

<210> SEQ ID NO 213
<211> LENGTH: 366
<212> TYPE: DNA
<213> ORGANISM: artificial
<220> FEATURE:
<223> OTHER INFORMATION: VH chain

<400> SEQUENCE: 213
aaccgagggg gccgtggtgg aggctgagga gacggtgacc agggttccct ggccccagta      60
gtagccactg ccgggtccac aataatatac ggccgtgtcc tcggctctga ggcggtccat    120
ctgcagatag agcgcgttct tggcgttgtc tctggagatg gtgaatcggc ccttcacagc    180
gtctgcgtag ctatgttag ttggataagg gcctatgtat gcgacccact gaagcccctt    240
tcctggagcc tggcggatcc agctcatgcc ggaactactg aaggcgaatc agaggctac    300 acaggagagt ctcagggacc ccccaggctt cwccaggtct cccccagact ccaccagctg    360
cacctc                                                               366

<210> SEQ ID NO 214
<211> LENGTH: 122
<212> TYPE: PRT
<213> ORGANISM: artificial
<220> FEATURE:
<223> OTHER INFORMATION: VH chain
<220> FEATURE:
<221> NAME/KEY: misc_feature
<222> LOCATION: (12)..(12)
<223> OTHER INFORMATION: Xaa can be any naturally occurring amino acid

<400> SEQUENCE: 214

Glu Val Gln Leu Val Glu Ser Gly Gly Asp Leu Xaa Lys Pro Gly Gly
1               5                   10                  15

Ser Leu Arg Leu Ser Cys Val Ala Ser Gly Phe Ala Phe Ser Ser Ser
            20                  25                  30

Gly Met Ser Trp Ile Arg Gln Ala Pro Gly Lys Gly Leu Gln Trp Val
        35                  40                  45

Ala Tyr Ile Gly Pro Tyr Pro Thr Asn Ile Ala Tyr Ala Asp Ala Val
    50                  55                  60

Lys Gly Arg Phe Thr Ile Ser Arg Asp Asn Ala Lys Asn Ala Leu Tyr
65                  70                  75                  80

Leu Gln Met Asp Arg Leu Arg Ala Glu Asp Thr Ala Val Tyr Tyr Cys
                85                  90                  95

Gly Pro Gly Ser Gly Tyr Tyr Trp Gly Gln Gly Thr Leu Val Thr Val
            100                 105                 110

Ser Ser Ala Ser Thr Thr Ala Pro Ser Val
        115                 120

<210> SEQ ID NO 215
<211> LENGTH: 378
<212> TYPE: DNA
<213> ORGANISM: artificial
<220> FEATURE:
<223> OTHER INFORMATION: VH chain

<400> SEQUENCE: 215
```

```
aaccgagggg gccgtggtgg aggctgagga cacggtgacc agggttccct ggccccagta    60
gtcaaattga tatgcgtaga ctggggcgac acaataatac atagccgtgt cctcggctct   120
caggctgtcc atctgcagat acagcgtgtt cttggcgttg tctctggaga tggtgaatcg   180
gcccttcaca gtgtctccgt aggatgtggt aaatccatca ctgctaattc gtgcgaccca   240
ctgaagcccc ttcccaggag cctggcggac ccagtatatg tacaagcgac tgaaggcgaa   300
tccagaggcc acacaggaca gtgtcagaga ccccccaggc ttcaccaggt ctcccccaga   360
ttccaccagc tgcacctc                                                 378
```

```
<210> SEQ ID NO 216
<211> LENGTH: 126
<212> TYPE: PRT
<213> ORGANISM: artificial
<220> FEATURE:
<223> OTHER INFORMATION: VH chain

<400> SEQUENCE: 216
```

| Glu | Val | Gln | Leu | Val | Glu | Ser | Gly | Gly | Asp | Leu | Val | Lys | Pro | Gly | Gly |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ser | Leu | Thr | Leu | Ser | Cys | Val | Ala | Ser | Gly | Phe | Ala | Phe | Ser | Arg | Leu |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Tyr | Ile | Tyr | Trp | Val | Arg | Gln | Ala | Pro | Gly | Lys | Gly | Leu | Gln | Trp | Val |
|-----|-----|-----|-----|-----|-----|-----|-----|-----|-----|-----|-----|-----|-----|-----|-----|
|     |     |     | 35  |     |     |     |     | 40  |     |     |     |     | 45  |     |     |

| Ala | Arg | Ile | Ser | Ser | Asp | Gly | Phe | Thr | Thr | Ser | Tyr | Gly | Asp | Thr | Val |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Lys | Gly | Arg | Phe | Thr | Ile | Ser | Arg | Asp | Asn | Ala | Lys | Asn | Thr | Leu | Tyr |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Leu | Gln | Met | Asp | Ser | Leu | Arg | Ala | Glu | Asp | Thr | Ala | Met | Tyr | Tyr | Cys |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Val | Ala | Pro | Val | Tyr | Ala | Tyr | Gln | Phe | Asp | Tyr | Trp | Gly | Gln | Gly | Thr |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| Leu | Val | Thr | Val | Ser | Ser | Ala | Ser | Thr | Thr | Ala | Pro | Ser | Val |
|-----|-----|-----|-----|-----|-----|-----|-----|-----|-----|-----|-----|-----|-----|
|     |     |     | 115 |     |     |     |     | 120 |     |     |     |     | 125 |

```
<210> SEQ ID NO 217
<211> LENGTH: 396
<212> TYPE: DNA
<213> ORGANISM: artificial
<220> FEATURE:
<223> OTHER INFORMATION: VH chain

<400> SEQUENCE: 217
aaccgagggg gccgtggtgg aggctgagga cacggtgacc agggttccct ggccccagga    60
gtcaaaaaag ttgtagtcgg caccggtcag gaccttcgca cagtaataga cagccgtgtc   120
ctcggctttc agactgtcca tctgcagata caccgtgttc tggaattgtc tctggaaat    180 ggtgaatcgg cccttcacag cgtcagtgta gtatgttata gttccatcat ccttaatagt   240
agcgacccac tgcagtccct tcccaggagc ctggcggacc caggtcatgt aacggttttt   300
gaaggtgaga ctagtgagtc cagaggctac acaggagagt ctcagggacc ccccaggctt   360
caccaggtct cccccagact ccaccagctg tacctc                             396
```

```
<210> SEQ ID NO 218
<211> LENGTH: 132
<212> TYPE: PRT
<213> ORGANISM: artificial
<220> FEATURE:
<223> OTHER INFORMATION: VH chain
```

<400> SEQUENCE: 218

Glu Val Gln Leu Val Glu Ser Gly Gly Asp Leu Val Lys Pro Gly Gly
1               5                   10                  15

Ser Leu Arg Leu Ser Cys Val Ala Ser Gly Leu Thr Ser Leu Thr Phe
            20                  25                  30

Lys Asn Arg Tyr Met Thr Trp Val Arg Gln Ala Pro Gly Lys Gly Leu
        35                  40                  45

Gln Trp Val Ala Thr Ile Lys Asp Asp Gly Thr Ile Thr Tyr Tyr Thr
    50                  55                  60

Asp Ala Val Lys Gly Arg Phe Thr Ile Ser Arg Asp Asn Ser Arg Asn
65                  70                  75                  80

Thr Val Tyr Leu Gln Met Asp Ser Leu Lys Ala Glu Asp Thr Ala Val
                85                  90                  95

Tyr Tyr Cys Ala Lys Val Leu Thr Gly Ala Asp Tyr Asn Phe Phe Asp
            100                 105                 110

Ser Trp Gly Gln Gly Thr Leu Val Thr Val Ser Ser Ala Ser Thr Thr
        115                 120                 125

Ala Pro Ser Val
    130

<210> SEQ ID NO 219
<211> LENGTH: 387
<212> TYPE: DNA
<213> ORGANISM: artificial
<220> FEATURE:
<223> OTHER INFORMATION: VH chain

<400> SEQUENCE: 219
aaccgagggg gccgtggtgg aggctgagga cggtgacc agggttccct ggccccagtg      60
gtcaccgtaa tagctaccgt ggtaggccag tccagccgca caataataca cggccgtgtc   120
ctcgactctc agattgttca tctgcagata cagcgtgttc ttggcgccgt ctctggagag   180
agtgaatcgg tccttcacag cgtctgcaaa cctcgtcaca gctccaccac tgttaatgta   240
gccgaccac tgaggcccct tcccgggagc caggcggatc caggtcatgt ggtaggcact    300
gagggtgaat ccagaggcca cacaggaaag tctcagggac cccccaggct tcaccaggtc   360
tcccccagac tccaccagct gcacctc                                       387

<210> SEQ ID NO 220
<211> LENGTH: 129
<212> TYPE: PRT
<213> ORGANISM: artificial
<220> FEATURE:
<223> OTHER INFORMATION: VH chain

<400> SEQUENCE: 220

Glu Val Gln Leu Val Glu Ser Gly Gly Asp Leu Val Lys Pro Gly Gly
1               5                   10                  15

Ser Leu Arg Leu Ser Cys Val Ala Ser Gly Phe Thr Leu Ser Ala Tyr
            20                  25                  30

His Met Thr Trp Ile Arg Leu Ala Pro Gly Lys Gly Pro Gln Trp Val
        35                  40                  45

Gly Tyr Ile Asn Ser Gly Gly Ala Val Thr Arg Phe Ala Asp Ala Val
    50                  55                  60

Lys Asp Arg Phe Thr Leu Ser Arg Asp Gly Ala Lys Asn Thr Leu Tyr
65                  70                  75                  80

Leu Gln Met Asn Asn Leu Arg Val Glu Asp Thr Ala Val Tyr Tyr Cys

Ala Ala Gly Leu Ala Tyr His Gly Ser Tyr Tyr Gly Asp His Trp Gly
                100                 105                 110

Gln Gly Thr Leu Val Thr Val Ser Ser Ala Ser Thr Thr Ala Pro Ser
            115                 120                 125

Val

<210> SEQ ID NO 221
<211> LENGTH: 372
<212> TYPE: DNA
<213> ORGANISM: artificial
<220> FEATURE:
<223> OTHER INFORMATION: VH chain

<400> SEQUENCE: 221
aaccgagggg gccgtggtgg argctgarga cacggtgacc agrgttccct ggccccaaaa      60
gtcaaaattc aacaaggtgc cccgacagta atacacagct gtgtcctcga ctctcaggct     120
gttcatctgc agatacactg tgttcctggc gttgtctctg gaaatggtga atcggccctt     180
cacagcggca gtagtatg tacttctccc atcatagtca atacctgtga cccactgcag       240
ccccttccca ggggcctggc ggacccagga catgctgtag cttccgatac ttaatccaga     300
ggccacacag gagagtctca gggaccccc tggcttcgcc aggtctcccc cagactccac      360
cagctgcacc cc                                                         372

<210> SEQ ID NO 222
<211> LENGTH: 124
<212> TYPE: PRT
<213> ORGANISM: artificial
<220> FEATURE:
<223> OTHER INFORMATION: VH chain

<400> SEQUENCE: 222

Gly Val Gln Leu Val Glu Ser Gly Gly Asp Leu Ala Lys Pro Gly Gly
1               5                   10                  15

Ser Leu Arg Leu Ser Cys Val Ala Ser Gly Leu Ser Ile Gly Ser Tyr
            20                  25                  30

Ser Met Ser Trp Val Arg Gln Ala Pro Gly Lys Gly Leu Gln Trp Val
        35                  40                  45

Thr Gly Ile Asp Tyr Asp Gly Arg Ser Thr Tyr Tyr Thr Ala Ala Val
    50                  55                  60

Lys Gly Arg Phe Thr Ile Ser Arg Asp Asn Ala Arg Asn Thr Val Tyr
65                  70                  75                  80

Leu Gln Met Asn Ser Leu Arg Val Glu Asp Thr Ala Val Tyr Tyr Cys
                85                  90                  95

Arg Gly Thr Leu Leu Asn Phe Asp Phe Trp Gly Gln Gly Thr Leu Val
            100                 105                 110

Thr Val Ser Ser Ala Ser Thr Thr Ala Pro Ser Val
        115                 120

<210> SEQ ID NO 223
<211> LENGTH: 384
<212> TYPE: DNA
<213> ORGANISM: artificial
<220> FEATURE:
<223> OTHER INFORMATION: VH chain

<400> SEQUENCE: 223
aaccgagggg gccgtggtgg aggctgggga gacggtgacc aggggttccct ggccccagtt     60

```
gtccgcgatc gtatccatat atatataacc gctcgaacag aaatacacgg ccgtgtcttc      120
gactcccagg ctgtccatct gaagatacac cgtgttcttg gcgttgtctc tggagatggt      180
gaatcggccc ttcacagcgt ctgcaaaggc tatgtccttt ccatcattgt tgatgtaagc      240
gacccactga agcccttcc  caggaggctg gcggacccag ttgacgtggt ggtcattgaa      300
ggcgaatcca gaggccacac aggaaagtct cagggacccc ccaggcttca cgaggtctcc      360
cccagattcc accagctgca cctc                                            384

<210> SEQ ID NO 224
<211> LENGTH: 128
<212> TYPE: PRT
<213> ORGANISM: artificial
<220> FEATURE:
<223> OTHER INFORMATION: VH chain

<400> SEQUENCE: 224

Glu Val Gln Leu Val Glu Ser Gly Gly Asp Leu Val Lys Pro Gly Gly
1               5                   10                  15

Ser Leu Arg Leu Ser Cys Val Ala Ser Gly Phe Ala Phe Asn Asp His
            20                  25                  30

His Val Asn Trp Val Arg Gln Pro Pro Gly Lys Gly Leu Gln Trp Val
        35                  40                  45

Ala Tyr Ile Asn Asn Asp Gly Lys Asp Ile Ala Phe Ala Asp Ala Val
    50                  55                  60

Lys Gly Arg Phe Thr Ile Ser Arg Asp Asn Ala Lys Asn Thr Val Tyr
65                  70                  75                  80

Leu Gln Met Asp Ser Leu Gly Val Glu Asp Thr Ala Val Tyr Phe Cys
                85                  90                  95

Ser Ser Gly Tyr Ile Tyr Met Asp Thr Ile Ala Asp Asn Trp Gly Gln
            100                 105                 110

Gly Thr Leu Val Thr Val Ser Pro Ala Ser Thr Thr Ala Pro Ser Val
        115                 120                 125

<210> SEQ ID NO 225
<211> LENGTH: 339
<212> TYPE: DNA
<213> ORGANISM: artificial
<220> FEATURE:
<223> OTHER INFORMATION: VH chain

<400> SEQUENCE: 225
aaccgagggg gccgtggtgg aggctgagga cacggtgacc agggttccct ggccccagta       60
agacacgtat ccatatatat atatatcccc cgccacacag taatacacag ctgtgtcctc      120
ggctctcagg ctgttcatct gcagatacac tgtgttcctg gcgttgtctc tggagatggt      180
gaatcggccc ttcacagcgt cactatagta tgtgttactt ccatcatagc taatagttgt      240
gacccactgc agcccttcc  caggagcctg gcggacccag ttcatgctgt agctactgaa      300
ggttaatcca gaggccacac aggagagtct cagggaccc                             339

<210> SEQ ID NO 226
<211> LENGTH: 113
<212> TYPE: PRT
<213> ORGANISM: artificial
<220> FEATURE:
<223> OTHER INFORMATION: VH chain

<400> SEQUENCE: 226

Gly Ser Leu Arg Leu Ser Cys Val Ala Ser Gly Leu Thr Phe Ser Ser
1               5                   10                  15
```

Tyr Ser Met Asn Trp Val Arg Gln Ala Pro Gly Lys Gly Leu Gln Trp
                20                  25                  30

Val Thr Thr Ile Ser Tyr Asp Gly Ser Asn Thr Tyr Tyr Ser Asp Ala
            35                  40                  45

Val Lys Gly Arg Phe Thr Ile Ser Arg Asp Asn Ala Arg Asn Thr Val
50                  55                  60

Tyr Leu Gln Met Asn Ser Leu Arg Ala Glu Asp Thr Ala Val Tyr Tyr
65                  70                  75                  80

Cys Val Ala Gly Asp Ile Tyr Ile Tyr Gly Tyr Val Ser Tyr Trp Gly
                85                  90                  95

Gln Gly Thr Leu Val Thr Val Ser Ser Ala Ser Thr Thr Ala Pro Ser
                100                 105                 110

Val

<210> SEQ ID NO 227
<211> LENGTH: 329
<212> TYPE: DNA
<213> ORGANISM: artificial
<220> FEATURE:
<223> OTHER INFORMATION: VH chain

<400> SEQUENCE: 227
gtgatgatgc agactccact gtccctgtcc gtcagccctg gagagccggc ctccatctcc     60
tgcaaggcca gtcagagcct cctgtacagt aacgggaaca cctatttgta ttggttccga    120
cagaagccag gccagtctcc acagcgcctg atctatttgg tttccaatag agacgctggg    180
gtcccagaca ggttcagtgg cagcgggtca gggacagatt tcactctgac aatcagcaga    240
gtggaggctg atgatgctgg agtttattat tgcgggcaag gtatacaaga tcctcctact    300
ttcagccagg aaccaagctg gagataaaa                                      329

<210> SEQ ID NO 228
<211> LENGTH: 108
<212> TYPE: PRT
<213> ORGANISM: artificial
<220> FEATURE:
<223> OTHER INFORMATION: VH chain

<400> SEQUENCE: 228

Val Met Met Gln Thr Pro Leu Ser Leu Ser Val Ser Pro Gly Glu Pro
1               5                   10                  15

Ala Ser Ile Ser Cys Lys Ala Ser Gln Ser Leu Leu Tyr Ser Asn Gly
                20                  25                  30

Asn Thr Tyr Leu Tyr Trp Phe Arg Gln Lys Pro Gly Gln Ser Pro Gln
            35                  40                  45

Arg Leu Ile Tyr Leu Val Ser Asn Arg Asp Ala Gly Val Pro Asp Arg
50                  55                  60

Phe Ser Gly Ser Gly Ser Gly Thr Asp Phe Thr Leu Thr Ile Ser Arg
65                  70                  75                  80

Val Glu Ala Asp Asp Ala Gly Val Tyr Tyr Cys Gly Gln Gly Ile Gln
                85                  90                  95

Asp Pro Pro Thr Phe Ser Gln Glu Pro Ser Trp Arg
                100                 105

<210> SEQ ID NO 229
<211> LENGTH: 312
<212> TYPE: DNA
<213> ORGANISM: artificial
<220> FEATURE:

```
<223> OTHER INFORMATION: VH chain

<400> SEQUENCE: 229
gtgatgacac agtctccagc ctccctctcc ttgtctcagg aggaaaaagt caccatcacc      60
tgccgggcca gtcagagtgt tagcagctac ttagcctggt accagcaaaa acctgggcag     120
gctcccaagc tcctcatcta tggtacatcc aacagggcca ctggtgtccc atcccggttc     180
agtggcagtg gtctgggac agacttcagc ttcaccatca gcagcctgga gcctgaagat      240
gttgcagttt attactgtca gcagtataat agcgggtgga cgttcggagc aggaaccaag     300
gtggacctca aa                                                         312

<210> SEQ ID NO 230
<211> LENGTH: 104
<212> TYPE: PRT
<213> ORGANISM: artificial
<220> FEATURE:
<223> OTHER INFORMATION: VH chain

<400> SEQUENCE: 230

Val Met Thr Gln Ser Pro Ala Ser Leu Ser Leu Ser Gln Glu Glu Lys
1               5                   10                  15

Val Thr Ile Thr Cys Arg Ala Ser Gln Ser Val Ser Ser Tyr Leu Ala
            20                  25                  30

Trp Tyr Gln Gln Lys Pro Gly Gln Ala Pro Lys Leu Leu Ile Tyr Gly
        35                  40                  45

Thr Ser Asn Arg Ala Thr Gly Val Pro Ser Arg Phe Ser Gly Ser Gly
    50                  55                  60

Ser Gly Thr Asp Phe Ser Phe Thr Ile Ser Ser Leu Glu Pro Glu Asp
65                  70                  75                  80

Val Ala Val Tyr Tyr Cys Gln Gln Tyr Asn Ser Gly Trp Thr Phe Gly
                85                  90                  95

Ala Gly Thr Lys Val Asp Leu Lys
            100

<210> SEQ ID NO 231
<211> LENGTH: 330
<212> TYPE: DNA
<213> ORGANISM: artificial
<220> FEATURE:
<223> OTHER INFORMATION: VH chain

<400> SEQUENCE: 231
gtgatgatgc agaccccact gtccctgtcc gtcagccctg ggaaccggc ctccatctcc       60 tgcaaggcca gtcagagcct cctgtcaagt aatgggaaca cctatttgta ttggttccga    120
cagaagccag gccagtctcc gcagcgtttg atttatgagg tctccaacag agaccctggg    180
gttccagaca ggttcagtgg cagcgggtca gggacagatt tcaccctgag aatcagcgga    240
gtggaggctg atgatgctgg aatttattac tgcgggcaag tatacagga tccgtggacg     300 ttcggagcag gaaccaaggt ggacctcaaa                                     330

<210> SEQ ID NO 232
<211> LENGTH: 110
<212> TYPE: PRT
<213> ORGANISM: artificial
<220> FEATURE:
<223> OTHER INFORMATION: VH chain

<400> SEQUENCE: 232

Val Met Met Gln Thr Pro Leu Ser Leu Ser Val Ser Pro Gly Glu Pro
```

```
            1               5                  10                 15
Ala Ser Ile Ser Cys Lys Ala Ser Gln Ser Leu Leu Ser Asn Gly
                 20                  25                  30

Asn Thr Tyr Leu Tyr Trp Phe Arg Gln Lys Pro Gly Gln Ser Pro Gln
                 35                  40                  45

Arg Leu Ile Tyr Glu Val Ser Asn Arg Asp Pro Gly Val Pro Asp Arg
 50                  55                  60

Phe Ser Gly Ser Gly Ser Gly Thr Asp Phe Thr Leu Arg Ile Ser Gly
 65                  70                  75                  80

Val Glu Ala Asp Asp Ala Gly Ile Tyr Tyr Cys Gly Gln Gly Ile Gln
                 85                  90                  95

Asp Pro Trp Thr Phe Gly Ala Gly Thr Lys Val Asp Leu Lys
                 100                 105                 110

<210> SEQ ID NO 233
<211> LENGTH: 327
<212> TYPE: DNA
<213> ORGANISM: artificial
<220> FEATURE:
<223> OTHER INFORMATION: VH chain

<400> SEQUENCE: 233
gtgatgatgc agactccact gtccctgtcc gtcagccctg gagagactgc ctccatctcc    60
tgcaaggcca gtcagagcct cctgcacagt aacgggaaca cctatttgtt ttggttgcga   120
cagaggccag gccagtctcc acagcgcctg atcaacttgg tttccaacag agaccctggg   180
gtcccagaca ggttcagtgg cagcgggtca gggacagatt tcaccctgag aatcagcaga   240
gtggaggctg acgatgctgg agtttattac tgcgggcaag gtatacaagg ttatagtttc   300
agccagggaa ccaagctgga gatcaaa                                       327

<210> SEQ ID NO 234
<211> LENGTH: 109
<212> TYPE: PRT
<213> ORGANISM: artificial
<220> FEATURE:
<223> OTHER INFORMATION: VH chain

<400> SEQUENCE: 234

Val Met Met Gln Thr Pro Leu Ser Leu Ser Val Ser Pro Gly Glu Thr
 1               5                  10                  15

Ala Ser Ile Ser Cys Lys Ala Ser Gln Ser Leu Leu His Ser Asn Gly
                 20                  25                  30

Asn Thr Tyr Leu Phe Trp Leu Arg Gln Arg Pro Gly Gln Ser Pro Gln
                 35                  40                  45

Arg Leu Ile Asn Leu Val Ser Asn Arg Asp Pro Gly Val Pro Asp Arg
 50                  55                  60

Phe Ser Gly Ser Gly Ser Gly Thr Asp Phe Thr Leu Arg Ile Ser Arg
 65                  70                  75                  80

Val Glu Ala Asp Asp Ala Gly Val Tyr Tyr Cys Gly Gln Gly Ile Gln
                 85                  90                  95

Gly Tyr Ser Phe Ser Gln Gly Thr Lys Leu Glu Ile Lys
                 100                 105

<210> SEQ ID NO 235
<211> LENGTH: 317
<212> TYPE: DNA
<213> ORGANISM: artificial
<220> FEATURE:
<223> OTHER INFORMATION: VH chain
```

<400> SEQUENCE: 235

```
gtgatgatgc agactccact gtccctgtcc gtcagccctg gagagccggc ctccatctcc      60
tgcaaggcca gtcagagcct cctgcacagt aatgggaaca cctatttgta ttggttccga     120
cagaagccag gccagtctcc acagcgtttg atctatgggg tctccaacag agaccctggg     180
gtcccagaca ggttcagtgg cagcgggtca gggacagatt tcaccctgag aatcagcgga     240
gtggaggctg atgatgctgg agtttattac tgcgggcaag gtatacaaga tccgtggacg     300
ttcggagcag gaaccaa                                                    317
```

<210> SEQ ID NO 236
<211> LENGTH: 105
<212> TYPE: PRT
<213> ORGANISM: artificial
<220> FEATURE:
<223> OTHER INFORMATION: VH chain

<400> SEQUENCE: 236

```
Val Met Met Gln Thr Pro Leu Ser Leu Ser Val Ser Pro Gly Glu Pro
1               5                   10                  15
Ala Ser Ile Ser Cys Lys Ala Ser Gln Ser Leu Leu His Ser Asn Gly
            20                  25                  30
Asn Thr Tyr Leu Tyr Trp Phe Arg Gln Lys Pro Gly Gln Ser Pro Gln
        35                  40                  45
Arg Leu Ile Tyr Gly Val Ser Asn Arg Asp Pro Gly Val Pro Asp Arg
    50                  55                  60
Phe Ser Gly Ser Gly Ser Gly Thr Asp Phe Thr Leu Arg Ile Ser Gly
65                  70                  75                  80
Val Glu Ala Asp Asp Ala Gly Val Tyr Tyr Cys Gly Gln Gly Ile Gln
                85                  90                  95
Asp Pro Trp Thr Phe Gly Ala Gly Thr
            100                 105
```

<210> SEQ ID NO 237
<211> LENGTH: 317
<212> TYPE: DNA
<213> ORGANISM: artificial
<220> FEATURE:
<223> OTHER INFORMATION: VH chain

<400> SEQUENCE: 237

```
gtgatgatgc agactccact gtccctgtcc gtcagccctg gagagccggc ctccatctcc      60
tgcaaggcca gtcagagcct cctggacagt aatggaaaca ccttttttgtc ttggttccga    120
cagaagccag gccagtctcc acagcgtttg atctataagg tctccaacag agaccctggg     180
gtcccagaca ggttcagtgg cagcgggtca gggacagatt tcaccctgag aatcagcgga     240
gtggaggctg atgatgctgg aatttattac tgcgggcaag gtttacaaga tccgtggacg     300
ttcggagcag gaaccca                                                    317
```

<210> SEQ ID NO 238
<211> LENGTH: 105
<212> TYPE: PRT
<213> ORGANISM: artificial
<220> FEATURE:
<223> OTHER INFORMATION: VH chain

<400> SEQUENCE: 238

```
Val Met Met Gln Thr Pro Leu Ser Leu Ser Val Ser Pro Gly Glu Pro
1               5                   10                  15
```

```
Ala Ser Ile Ser Cys Lys Ala Ser Gln Ser Leu Leu Asp Ser Asn Gly
            20                  25                  30

Asn Thr Phe Leu Ser Trp Phe Arg Gln Lys Pro Gly Gln Ser Pro Gln
         35                  40                  45

Arg Leu Ile Tyr Lys Val Ser Asn Arg Asp Pro Gly Val Pro Asp Arg
     50                  55                  60

Phe Ser Gly Ser Gly Ser Gly Thr Asp Phe Thr Leu Arg Ile Ser Gly
65                  70                  75                  80

Val Glu Ala Asp Asp Ala Gly Ile Tyr Tyr Cys Gly Gln Gly Leu Gln
                 85                  90                  95

Asp Pro Trp Thr Phe Gly Ala Gly Thr
            100                 105
```

<210> SEQ ID NO 239
<211> LENGTH: 317
<212> TYPE: DNA
<213> ORGANISM: artificial
<220> FEATURE:
<223> OTHER INFORMATION: VH chain

<400> SEQUENCE: 239

```
gtgatgatac agactccact gtccctgtcc gtcagccctg gagagccggc ctccatctcc    60
tgcaaggcca gtcagagcct cctggacagt aatggaaaca ccttttttgtc ttggttccga   120
cagaagccag gccagtctcc acagcgtttg atctataagg tctccaacag agaccctggg   180
gtcccagaca ggttcagtgg cagcgggtca gggacagatt tcaccctgag aatcagcgga   240
gtggaggctg atgatgctgg aatttattac tgcgggcaag gtatacagga tccgtggacg   300
ttcggagcag gaaccaa                                                   317
```

<210> SEQ ID NO 240
<211> LENGTH: 105
<212> TYPE: PRT
<213> ORGANISM: artificial
<220> FEATURE:
<223> OTHER INFORMATION: VH chain

<400> SEQUENCE: 240

```
Val Met Ile Gln Thr Pro Leu Ser Leu Ser Val Ser Pro Gly Glu Pro
1               5                   10                  15

Ala Ser Ile Ser Cys Lys Ala Ser Gln Ser Leu Leu Asp Ser Asn Gly
            20                  25                  30

Asn Thr Phe Leu Ser Trp Phe Arg Gln Lys Pro Gly Gln Ser Pro Gln
         35                  40                  45

Arg Leu Ile Tyr Lys Val Ser Asn Arg Asp Pro Gly Val Pro Asp Arg
     50                  55                  60

Phe Ser Gly Ser Gly Ser Gly Thr Asp Phe Thr Leu Arg Ile Ser Gly
65                  70                  75                  80

Val Glu Ala Asp Asp Ala Gly Ile Tyr Tyr Cys Gly Gln Gly Ile Gln
                 85                  90                  95

Asp Pro Trp Thr Phe Gly Ala Gly Thr
            100                 105
```

<210> SEQ ID NO 241
<211> LENGTH: 312
<212> TYPE: DNA
<213> ORGANISM: artificial
<220> FEATURE:
<223> OTHER INFORMATION: VH chain

<400> SEQUENCE: 241

```
gtgatgaccc agtctccagc ctccctctcc ttgtctcagg aggaaaaagt caccatcacc      60
tgccgggcca gtcaaagtct taacaattac ttggcctggt accagcaaaa acctgggcag     120
gctcccaagc tcctcatcta tgatacattt aaaagggcca ctggtgtccc atcccggttc     180
agtggcagtg ggtctggggc agagttcacc ttcaccatca gcagcctgga gcctgaagat     240
gttgcagttt attactgtca gcaatattat gacggttgca cgttcggacc aggaaccaag     300
gtggacctca aa                                                        312
```

<210> SEQ ID NO 242
<211> LENGTH: 104
<212> TYPE: PRT
<213> ORGANISM: artificial
<220> FEATURE:
<223> OTHER INFORMATION: VH chain

<400> SEQUENCE: 242

```
Val Met Thr Gln Ser Pro Ala Ser Leu Ser Leu Ser Gln Glu Glu Lys
1               5                   10                  15
Val Thr Ile Thr Cys Arg Ala Ser Gln Ser Leu Asn Asn Tyr Leu Ala
            20                  25                  30
Trp Tyr Gln Gln Lys Pro Gly Gln Ala Pro Lys Leu Leu Ile Tyr Asp
        35                  40                  45
Thr Phe Lys Arg Ala Thr Gly Val Pro Ser Arg Phe Ser Gly Ser Gly
    50                  55                  60
Ser Gly Ala Glu Phe Thr Phe Thr Ile Ser Ser Leu Glu Pro Glu Asp
65                  70                  75                  80
Val Ala Val Tyr Tyr Cys Gln Gln Tyr Tyr Asp Gly Cys Thr Phe Gly
                85                  90                  95
Pro Gly Thr Lys Val Asp Leu Lys
            100
```

<210> SEQ ID NO 243
<211> LENGTH: 330
<212> TYPE: DNA
<213> ORGANISM: artificial
<220> FEATURE:
<223> OTHER INFORMATION: VH chain

<400> SEQUENCE: 243

```
gtgatgatgc agactccact gtccctgtcc gtcagccctg gagagccggc ctccatctcc      60
tgcaaggcca gtcagagcct cctgcacagt aatgggaaca cctatttgta ttggttccga     120
cagaagccag gccagtctcc acagcgtttg atctatgggg tctccaacag agaccctggg     180
gtcccagaca ggttcagtgg cagcgggtca gggacagatt tcaccctgag aatcagcgga     240
gtggaggctg atgatgctgg agtttattac tgcgggcaag gtatacaaga tccgtggacg     300
ttcggagcag gaaccaaggt ggacctcaaa                                     330
```

<210> SEQ ID NO 244
<211> LENGTH: 110
<212> TYPE: PRT
<213> ORGANISM: artificial
<220> FEATURE:
<223> OTHER INFORMATION: VH chain

<400> SEQUENCE: 244

```
Val Met Met Gln Thr Pro Leu Ser Leu Ser Val Ser Pro Gly Glu Pro
1               5                   10                  15
```

```
Ala Ser Ile Ser Cys Lys Ala Ser Gln Ser Leu Leu His Ser Asn Gly
            20                  25                  30

Asn Thr Tyr Leu Tyr Trp Phe Arg Gln Lys Pro Gly Gln Ser Pro Gln
        35                  40                  45

Arg Leu Ile Tyr Gly Val Ser Asn Arg Asp Pro Gly Val Pro Asp Arg
    50                  55                  60

Phe Ser Gly Ser Gly Ser Gly Thr Asp Phe Thr Leu Arg Ile Ser Gly
65                  70                  75                  80

Val Glu Ala Asp Asp Ala Gly Val Tyr Tyr Cys Gln Gly Ile Gln
                85                  90                  95

Asp Pro Trp Thr Phe Gly Ala Gly Thr Lys Val Asp Leu Lys
            100                 105                 110
```

<210> SEQ ID NO 245
<211> LENGTH: 330
<212> TYPE: DNA
<213> ORGANISM: artificial
<220> FEATURE:
<223> OTHER INFORMATION: VH chain

<400> SEQUENCE: 245

```
gtcatgatgc agactccact gtccctgtcc gtcagccctg gagagccggc ctccatctcc      60
tgcaaggcca gtcagagcct cctggaaagt gatgggaaca ccttttttgtc ttggttccga   120
cagaagccag gccagtctcc acagcgtttg atctataagg tctccaacag agaccctggg    180
gtcccagaca ggttcagtgg cagcgggtca gggacagatt tcaccctgag aatcagcaga    240
gtggaggctg acgatgctgg agtttattac tgcatgcaag gtactcagtt tcctcggacg    300
ttcggagcag gaaccaaggt ggaccctcaaa                                     330
```

<210> SEQ ID NO 246
<211> LENGTH: 110
<212> TYPE: PRT
<213> ORGANISM: artificial
<220> FEATURE:
<223> OTHER INFORMATION: VH chain

<400> SEQUENCE: 246

```
Val Met Met Gln Thr Pro Leu Ser Leu Ser Val Ser Pro Gly Glu Pro
1               5                   10                  15

Ala Ser Ile Ser Cys Lys Ala Ser Gln Ser Leu Leu Glu Ser Asp Gly
            20                  25                  30

Asn Thr Phe Leu Ser Trp Phe Arg Gln Lys Pro Gly Gln Ser Pro Gln
        35                  40                  45

Arg Leu Ile Tyr Lys Val Ser Asn Arg Asp Pro Gly Val Pro Asp Arg
    50                  55                  60

Phe Ser Gly Ser Gly Ser Gly Thr Asp Phe Thr Leu Arg Ile Ser Arg
65                  70                  75                  80

Val Glu Ala Asp Asp Ala Gly Val Tyr Tyr Cys Met Gln Gly Thr Gln
                85                  90                  95

Phe Pro Arg Thr Phe Gly Ala Gly Thr Lys Val Asp Leu Lys
            100                 105                 110
```

<210> SEQ ID NO 247
<211> LENGTH: 330
<212> TYPE: DNA
<213> ORGANISM: artificial
<220> FEATURE:
<223> OTHER INFORMATION: VH chain

<400> SEQUENCE: 247

```
gtgatgatgc agaccccact gtccctgtcc gtcagccctg gggaaccggc ctccatctcc    60
tgcaaggcca gtcagagcct cctgtcaagt aatgggaaca cctatttgta ttggttccga   120
cagaagccag gccagtctcc gcagcgtttg atttatgagg tctccaacag agaccctggg   180
gttccagaca ggttcagtgg cagcgggtca gggacagatt tcaccctgag aatcagcgga   240
gtggaggctg atgatgctgg aatttattac tgcgggcaag gtatacagga tccgtggacg   300
ttcggagcag gaaccaaggt ggacctcaaa                                    330
```

<210> SEQ ID NO 248
<211> LENGTH: 110
<212> TYPE: PRT
<213> ORGANISM: artificial
<220> FEATURE:
<223> OTHER INFORMATION: VH chain

<400> SEQUENCE: 248

Val Met Met Gln Thr Pro Leu Ser Leu Ser Val Ser Pro Gly Glu Pro
1               5                   10                  15

Ala Ser Ile Ser Cys Lys Ala Ser Gln Ser Leu Leu Ser Ser Asn Gly
            20                  25                  30

Asn Thr Tyr Leu Tyr Trp Phe Arg Gln Lys Pro Gly Gln Ser Pro Gln
        35                  40                  45

Arg Leu Ile Tyr Glu Val Ser Asn Arg Asp Pro Gly Val Pro Asp Arg
    50                  55                  60

Phe Ser Gly Ser Gly Ser Gly Thr Asp Phe Thr Leu Arg Ile Ser Gly
65                  70                  75                  80

Val Glu Ala Asp Asp Ala Gly Ile Tyr Tyr Cys Gly Gln Gly Ile Gln
                85                  90                  95

Asp Pro Trp Thr Phe Gly Ala Gly Thr Lys Val Asp Leu Lys
            100                 105                 110

<210> SEQ ID NO 249
<211> LENGTH: 330
<212> TYPE: DNA
<213> ORGANISM: artificial
<220> FEATURE:
<223> OTHER INFORMATION: VH chain

<400> SEQUENCE: 249

```
gtcatgacgc agactccact gtccctggcc gtcaccctg gagagctggc cactatctcc     60
tgcagggcca gtcagagtct cctgcgcagt gatggaaaat cctatttgaa ttggtaccta   120
cagaagccag gccagactcc tcggccgctg atttatgagg cttccaagcg tttctctggg   180
gtctcagaca ggttcagtgg cagcgggtca gggacagatt tcacccttaa aatcagcagg   240
gtggaggctg aggatgttgg agtttattac tgccagcaaa gtctacattt tcctccgacg   300
ttcggagcag gaaccaaggt ggagctcaaa                                    330
```

<210> SEQ ID NO 250
<211> LENGTH: 110
<212> TYPE: PRT
<213> ORGANISM: artificial
<220> FEATURE:
<223> OTHER INFORMATION: VH chain

<400> SEQUENCE: 250

Val Met Thr Gln Thr Pro Leu Ser Leu Ala Val Thr Pro Gly Glu Leu
1               5                   10                  15

Ala Thr Ile Ser Cys Arg Ala Ser Gln Ser Leu Leu Arg Ser Asp Gly

-continued

```
                    20                  25                  30
Lys Ser Tyr Leu Asn Trp Tyr Leu Gln Lys Pro Gly Gln Thr Pro Arg
            35                  40                  45

Pro Leu Ile Tyr Glu Ala Ser Lys Arg Phe Ser Gly Val Ser Asp Arg
 50                  55                  60

Phe Ser Gly Ser Gly Ser Gly Thr Asp Phe Thr Leu Lys Ile Ser Arg
 65                  70                  75                  80

Val Glu Ala Glu Asp Val Gly Val Tyr Tyr Cys Gln Gln Ser Leu His
                 85                  90                  95

Phe Pro Pro Thr Phe Gly Ala Gly Thr Lys Val Glu Leu Lys
                100                 105                 110
```

<210> SEQ ID NO 251
<211> LENGTH: 330
<212> TYPE: DNA
<213> ORGANISM: artificial
<220> FEATURE:
<223> OTHER INFORMATION: VH chain

<400> SEQUENCE: 251

```
gtgatgatgc agactccact gtccctgtcc gtcagccctg gagagccggc ctccatctcc    60
tgcaaggcca gtcagagcct cctgcacagt agcgggaaca cctatttgta ttggtttcga   120
cagaagccag gccagtctcc acagcgtttg atctataagg tctccaacag agaccctggg   180
gtcccagaca ggttcagtgg cagcgggtca gggacagatt tcaccctgag aatcagcgga   240
gtggaggctg atgatgctgg aatttattac tgcgggcaag gtatacagga tccgtggacg   300
ttcggagcag gaaccaaggt ggacctcaaa                                    330
```

<210> SEQ ID NO 252
<211> LENGTH: 110
<212> TYPE: PRT
<213> ORGANISM: artificial
<220> FEATURE:
<223> OTHER INFORMATION: VH chain

<400> SEQUENCE: 252

```
Val Met Met Gln Thr Pro Leu Ser Leu Ser Val Ser Pro Gly Glu Pro
 1               5                  10                  15

Ala Ser Ile Ser Cys Lys Ala Ser Gln Ser Leu Leu His Ser Ser Gly
                20                  25                  30

Asn Thr Tyr Leu Tyr Trp Phe Arg Gln Lys Pro Gly Gln Ser Pro Gln
            35                  40                  45

Arg Leu Ile Tyr Lys Val Ser Asn Arg Asp Pro Gly Val Pro Asp Arg
 50                  55                  60

Phe Ser Gly Ser Gly Ser Gly Thr Asp Phe Thr Leu Arg Ile Ser Gly
 65                  70                  75                  80

Val Glu Ala Asp Asp Ala Gly Ile Tyr Tyr Cys Gly Gln Gly Ile Gln
                 85                  90                  95

Asp Pro Trp Thr Phe Gly Ala Gly Thr Lys Val Asp Leu Lys
                100                 105                 110
```

<210> SEQ ID NO 253
<211> LENGTH: 312
<212> TYPE: DNA
<213> ORGANISM: artificial
<220> FEATURE:
<223> OTHER INFORMATION: VH chain

<400> SEQUENCE: 253

```
gtgatgacac agtctccagc ctccctctcc ttgtctcagg acgaaaaagt caccatcacc    60
tgccgggcca gtcagagtat tagcagctac ttagcctggt atcagcaaaa acctgggcag   120
gctcccaagc tcctcatcta tggtacatcc aacagggcca ctggtgtccc atcccggttc   180
agtggcagtg gtctgggac agacttcagc ctcaccatca gcaccctgga gcctgaggat   240
gttgcagttt attactgtca acagtattat atctggtgga cgttcggagc aggaacccag   300
gtggaactca aa                                                      312
```

<210> SEQ ID NO 254
<211> LENGTH: 104
<212> TYPE: PRT
<213> ORGANISM: artificial
<220> FEATURE:
<223> OTHER INFORMATION: VH chain

<400> SEQUENCE: 254

```
Val Met Thr Gln Ser Pro Ala Ser Leu Ser Leu Ser Gln Asp Glu Lys
1               5                   10                  15

Val Thr Ile Thr Cys Arg Ala Ser Gln Ser Ile Ser Ser Tyr Leu Ala
            20                  25                  30

Trp Tyr Gln Gln Lys Pro Gly Gln Ala Pro Lys Leu Leu Ile Tyr Gly
        35                  40                  45

Thr Ser Asn Arg Ala Thr Gly Val Pro Ser Arg Phe Ser Gly Ser Gly
    50                  55                  60

Ser Gly Thr Asp Phe Ser Leu Thr Ile Ser Thr Leu Glu Pro Glu Asp
65                  70                  75                  80

Val Ala Val Tyr Tyr Cys Gln Gln Tyr Tyr Ile Trp Trp Thr Phe Gly
                85                  90                  95

Ala Gly Thr Gln Val Glu Leu Lys
            100
```

<210> SEQ ID NO 255
<211> LENGTH: 330
<212> TYPE: DNA
<213> ORGANISM: artificial
<220> FEATURE:
<223> OTHER INFORMATION: VH chain

<400> SEQUENCE: 255

```
gtgatgatgc agactccact gtccctgtcc gtcagccctg gagagccggc ctccatctcc    60
tgcaaggcca gtcagagcct cctgcacagt aatgggaaca cctatttgta ttggttccga   120
cagaagccag gccagtctcc acagcgtttg atctctaatg tctccaacag agaccctggg   180
gtcccagaca gggtcagtgg cagcgggtca gggacagatt tcaccctgag aatcagcaga   240
gtggaggctg atgatgctgg agtttattac tgcgggcaag ctatacagga tccgcggacg   300
ttcggagcag gaaccaaggt ggacctcaaa                                    330
```

<210> SEQ ID NO 256
<211> LENGTH: 110
<212> TYPE: PRT
<213> ORGANISM: artificial
<220> FEATURE:
<223> OTHER INFORMATION: VH chain

<400> SEQUENCE: 256

```
Val Met Met Gln Thr Pro Leu Ser Leu Ser Val Ser Pro Gly Glu Pro
1               5                   10                  15

Ala Ser Ile Ser Cys Lys Ala Ser Gln Ser Leu Leu His Ser Asn Gly
            20                  25                  30
```

Asn Thr Tyr Leu Tyr Trp Phe Arg Gln Lys Pro Gly Gln Ser Pro Gln
         35                  40                  45

Arg Leu Ile Ser Asn Val Ser Asn Arg Asp Pro Gly Val Pro Asp Arg
 50                  55                  60

Val Ser Gly Ser Gly Ser Gly Thr Asp Phe Thr Leu Arg Ile Ser Arg
 65                  70                  75                  80

Val Glu Ala Asp Asp Ala Gly Val Tyr Tyr Cys Gly Gln Ala Ile Gln
                 85                  90                  95

Asp Pro Arg Thr Phe Gly Ala Gly Thr Lys Val Asp Leu Lys
             100                 105                 110

<210> SEQ ID NO 257
<211> LENGTH: 330
<212> TYPE: DNA
<213> ORGANISM: artificial
<220> FEATURE:
<223> OTHER INFORMATION: VH chain

<400> SEQUENCE: 257
gtgatgatgc agactccact gtccctgtcc gtcagccctg gagagactgc ctccatctcc      60
tgcaaggcca gtcagagcct cctgtatagt gatggaaaca cgtatttgca ttggttccga     120
cagaagccag gccagcctcc acagcgtttg atctttcagg tctccaaaag agaccctggg     180
gtcccagaca ggctcagtgg cagcgggtca gggacagact tcaccctgag aatcagcaga     240
gtggaggctg gcgatactgg agtttattac tgcatgcaag caacaaagtc tcctctcact     300
ttcagccagg ggaccaaggt ggagataaaa                                      330

<210> SEQ ID NO 258
<211> LENGTH: 110
<212> TYPE: PRT
<213> ORGANISM: artificial
<220> FEATURE:
<223> OTHER INFORMATION: VH chain

<400> SEQUENCE: 258

Val Met Met Gln Thr Pro Leu Ser Leu Ser Val Ser Pro Gly Glu Thr
 1                5                  10                  15

Ala Ser Ile Ser Cys Lys Ala Ser Gln Ser Leu Leu Tyr Ser Asp Gly
                 20                  25                  30

Asn Thr Tyr Leu His Trp Phe Arg Gln Lys Pro Gly Gln Pro Pro Gln
             35                  40                  45

Arg Leu Ile Phe Gln Val Ser Lys Arg Asp Pro Gly Val Pro Asp Arg
 50                  55                  60

Leu Ser Gly Ser Gly Ser Gly Thr Asp Phe Thr Leu Arg Ile Ser Arg
 65                  70                  75                  80

Val Glu Ala Gly Asp Thr Gly Val Tyr Tyr Cys Met Gln Ala Thr Lys
                 85                  90                  95

Ser Pro Leu Thr Phe Ser Gln Gly Thr Lys Val Glu Ile Lys
             100                 105                 110

<210> SEQ ID NO 259
<211> LENGTH: 312
<212> TYPE: DNA
<213> ORGANISM: artificial
<220> FEATURE:
<223> OTHER INFORMATION: VH chain

<400> SEQUENCE: 259
gtgatgaccc agtctccagc ctccctctcc ttgtctcagg aggaaaaagt caccatcacc      60

```
tgccgggcca gtcagagtgt tagcagctac ttagcctggt accagcaaaa acctgggcag    120
gctcccaagc tcctcatcta tggtacatcc aacagggcca ctggtgtccc atcccggttc    180
agtggcagtg ggtctgggac agacttcagc ttcaccatca gcagcctgga gcctgaagat    240
gttgcagttt attactgtca gcagtataat agcggatata cgttcggcca aggaaccaag    300
gtggagctca aa                                                       312
```

```
<210> SEQ ID NO 260
<211> LENGTH: 104
<212> TYPE: PRT
<213> ORGANISM: artificial
<220> FEATURE:
<223> OTHER INFORMATION: VH chain

<400> SEQUENCE: 260

Val Met Thr Gln Ser Pro Ala Ser Leu Ser Leu Ser Gln Glu Glu Lys
1               5                   10                  15

Val Thr Ile Thr Cys Arg Ala Ser Gln Ser Val Ser Ser Tyr Leu Ala
            20                  25                  30

Trp Tyr Gln Gln Lys Pro Gly Gln Ala Pro Lys Leu Leu Ile Tyr Gly
        35                  40                  45

Thr Ser Asn Arg Ala Thr Gly Val Pro Ser Arg Phe Ser Gly Ser Gly
    50                  55                  60

Ser Gly Thr Asp Phe Ser Phe Thr Ile Ser Ser Leu Glu Pro Glu Asp
65                  70                  75                  80

Val Ala Val Tyr Tyr Cys Gln Gln Tyr Asn Ser Gly Tyr Thr Phe Gly
                85                  90                  95

Gln Gly Thr Lys Val Glu Leu Lys
            100
```

```
<210> SEQ ID NO 261
<211> LENGTH: 330
<212> TYPE: DNA
<213> ORGANISM: artificial
<220> FEATURE:
<223> OTHER INFORMATION: VH chain

<400> SEQUENCE: 261
gtcatgatgc agactccact gtccctgtcc gtcagccctg gagagccggc ctccatctcc     60
tgcaaggcca gtcagagcct cctggacagt aatggaaaca ccttttttgtc ttggttccga   120 cagaagccag gccagtctcc acagcgtttg atctataagg tctccaacag agaccctggg   180
gtcccagaca ggttcagtgg cagcgggtca gggacagatt tcaccctgag aatcagcgga   240
gtggaggctg atgatgctgg aatttattac tgcgggcaag gtttacaaga tccgtggacg   300
ttcggagcag gaaccaaggt ggacctcaaa                                     330
```

```
<210> SEQ ID NO 262
<211> LENGTH: 110
<212> TYPE: PRT
<213> ORGANISM: artificial
<220> FEATURE:
<223> OTHER INFORMATION: VH chain

<400> SEQUENCE: 262

Val Met Met Gln Thr Pro Leu Ser Leu Ser Val Ser Pro Gly Glu Pro
1               5                   10                  15

Ala Ser Ile Ser Cys Lys Ala Ser Gln Ser Leu Leu Asp Ser Asn Gly
            20                  25                  30
```

Asn Thr Phe Leu Ser Trp Phe Arg Gln Lys Pro Gly Gln Ser Pro Gln
        35                  40                  45

Arg Leu Ile Tyr Lys Val Ser Asn Arg Asp Pro Gly Val Pro Asp Arg
    50                  55                  60

Phe Ser Gly Ser Gly Ser Gly Thr Asp Phe Thr Leu Arg Ile Ser Gly
65                  70                  75                  80

Val Glu Ala Asp Asp Ala Gly Ile Tyr Tyr Cys Gly Gln Gly Leu Gln
                85                  90                  95

Asp Pro Trp Thr Phe Gly Ala Gly Thr Lys Val Asp Leu Lys
            100                 105                 110

<210> SEQ ID NO 263
<211> LENGTH: 330
<212> TYPE: DNA
<213> ORGANISM: artificial
<220> FEATURE:
<223> OTHER INFORMATION: VH chain

<400> SEQUENCE: 263
gtgatgatgc agactccact gtccctgtcc gtcagccctg gagagccggc ctccatctcc      60
tgcaaggcca gtcagagcct cctacacagt aatgggaaca tcttgttgta ttggttccga     120
cagaagccag gccagtctcc acagcctttg atctataagg tctccaacag agaccctggg     180
gtcccagaca ggttcagtgg cagcgggtca gggacagatt tcaccctgag aatcagcaga     240
gtggaggctg acgatactgg aatttattac tgcgggcaaa ttatacagtt tcctcggacg     300
ttcggagcag gtacccaggt ggaactcaaa                                       330

<210> SEQ ID NO 264
<211> LENGTH: 110
<212> TYPE: PRT
<213> ORGANISM: artificial
<220> FEATURE:
<223> OTHER INFORMATION: VH chain

<400> SEQUENCE: 264

Val Met Met Gln Thr Pro Leu Ser Leu Ser Val Ser Pro Gly Glu Pro
1               5                   10                  15

Ala Ser Ile Ser Cys Lys Ala Ser Gln Ser Leu Leu His Ser Asn Gly
                20                  25                  30

Asn Ile Leu Leu Tyr Trp Phe Arg Gln Lys Pro Gly Gln Ser Pro Gln
        35                  40                  45

Pro Leu Ile Tyr Lys Val Ser Asn Arg Asp Pro Gly Val Pro Asp Arg
    50                  55                  60

Phe Ser Gly Ser Gly Ser Gly Thr Asp Phe Thr Leu Arg Ile Ser Arg
65                  70                  75                  80

Val Glu Ala Asp Asp Thr Gly Ile Tyr Tyr Cys Gly Gln Ile Ile Gln
                85                  90                  95

Phe Pro Arg Thr Phe Gly Ala Gly Thr Gln Val Glu Leu Lys
            100                 105                 110

<210> SEQ ID NO 265
<211> LENGTH: 330
<212> TYPE: DNA
<213> ORGANISM: artificial
<220> FEATURE:
<223> OTHER INFORMATION: VH chain

<400> SEQUENCE: 265
gtgatgatgc agactccact gtccctgtcc gtcagccctg gagagccggc ctccatctcc      60

```
tgcaaggcca gtcagagcct cgtggacagt aatggaaaca ccttttttgtc ttggttccga    120 cagaagccag ccagtctcc acagcgtttg atctataagg tctccaacag agaccctggg     180
gtcccagaca ggttcagtgg cagcgggtca gggacagatt tcaccctgag aatcagcgga    240
gtggaggctg atgatggtgg aatttattac tgcgggcaag gtttacaaga tccgtggacg    300
ttcggagcag gaaccaaggt ggacctcaaa                                     330
```

```
<210> SEQ ID NO 266
<211> LENGTH: 110
<212> TYPE: PRT
<213> ORGANISM: artificial
<220> FEATURE:
<223> OTHER INFORMATION: VH chain

<400> SEQUENCE: 266
```

Val Met Met Gln Thr Pro Leu Ser Leu Ser Val Ser Pro Gly Glu Pro
1               5                   10                  15

Ala Ser Ile Ser Cys Lys Ala Ser Gln Ser Leu Val Asp Ser Asn Gly
            20                  25                  30

Asn Thr Phe Leu Ser Trp Phe Arg Gln Lys Pro Gly Gln Ser Pro Gln
        35                  40                  45

Arg Leu Ile Tyr Lys Val Ser Asn Arg Asp Pro Gly Val Pro Asp Arg
    50                  55                  60

Phe Ser Gly Ser Gly Ser Gly Thr Asp Phe Thr Leu Arg Ile Ser Gly
65                  70                  75                  80

Val Glu Ala Asp Asp Gly Gly Ile Tyr Tyr Cys Gly Gln Gly Leu Gln
                85                  90                  95

Asp Pro Trp Thr Phe Gly Ala Gly Thr Lys Val Asp Leu Lys
            100                 105                 110

```
<210> SEQ ID NO 267
<211> LENGTH: 312
<212> TYPE: DNA
<213> ORGANISM: artificial
<220> FEATURE:
<223> OTHER INFORMATION: VH chain

<400> SEQUENCE: 267
gtgatgaccc agtctccagc ctccctctcc ttgtctcggg aggaagaggt caccatcacc    60
tgccgggcca gtcagactat taccaactcc ttagcctggt accagcaaaa acctgggcag    120
gctcccaagc tcctcatcta tgctacatcc aacagggcca ctggtgtccc atcccggttc    180
agtggcagtg ggtctgggac agacttcagg ttcaccatca gcagcctgga gcctgaagat    240
gttggagttt attactgtca gcagtataat agcggatgga cgttcggagc agggaccaag    300
gtggagataa aa                                                       312
```

```
<210> SEQ ID NO 268
<211> LENGTH: 104
<212> TYPE: PRT
<213> ORGANISM: artificial
<220> FEATURE:
<223> OTHER INFORMATION: VH chain

<400> SEQUENCE: 268
```

Val Met Thr Gln Ser Pro Ala Ser Leu Ser Leu Ser Arg Glu Glu Glu
1               5                   10                  15

Val Thr Ile Thr Cys Arg Ala Ser Gln Thr Ile Thr Asn Ser Leu Ala
            20                  25                  30

Trp Tyr Gln Gln Lys Pro Gly Gln Ala Pro Lys Leu Leu Ile Tyr Ala

```
                35                  40                  45
Thr Ser Asn Arg Ala Thr Gly Val Pro Ser Arg Phe Ser Gly Ser Gly
 50                  55                  60

Ser Gly Thr Asp Phe Arg Phe Thr Ile Ser Ser Leu Glu Pro Glu Asp
 65                  70                  75                  80

Val Gly Val Tyr Tyr Cys Gln Gln Tyr Asn Ser Gly Trp Thr Phe Gly
                 85                  90                  95

Ala Gly Thr Lys Val Glu Ile Lys
            100

<210> SEQ ID NO 269
<211> LENGTH: 330
<212> TYPE: DNA
<213> ORGANISM: artificial
<220> FEATURE:
<223> OTHER INFORMATION: VH chain

<400> SEQUENCE: 269
gtcatgatgc agacccact  gtccctgtcc gtcagccctg gagagctggc ctccatctcc    60
tgcaaggcca gtcagagcct cctggacagt aatggaaaca ccttttttgtc ttggttccga   120 cagaagccag ccagtctccc acagcgtttg atctataagg tctccaacag agaccctggg   180
gtcccagaca ggttcagtgg cagcgggtca gggacagatt tcaccctgag aatcagcgga   240
gtggaggctg atgatgctgg aatttattac tgcgggcaag gtatacagga tccgtggacg   300
ttcggagcag gaaccaaggt ggacctcaaa                                    330

<210> SEQ ID NO 270
<211> LENGTH: 110
<212> TYPE: PRT
<213> ORGANISM: artificial
<220> FEATURE:
<223> OTHER INFORMATION: VH chain

<400> SEQUENCE: 270

Val Met Met Gln Thr Pro Leu Ser Leu Ser Val Ser Pro Gly Glu Leu
 1               5                  10                  15

Ala Ser Ile Ser Cys Lys Ala Ser Gln Ser Leu Leu Asp Ser Asn Gly
                 20                  25                  30

Asn Thr Phe Leu Ser Trp Phe Arg Gln Lys Pro Gly Gln Ser Pro Gln
            35                  40                  45

Arg Leu Ile Tyr Lys Val Ser Asn Arg Asp Pro Gly Val Pro Asp Arg
 50                  55                  60

Phe Ser Gly Ser Gly Ser Gly Thr Asp Phe Thr Leu Arg Ile Ser Gly
 65                  70                  75                  80

Val Glu Ala Asp Asp Ala Gly Ile Tyr Tyr Cys Gly Gln Gly Ile Gln
                 85                  90                  95

Asp Pro Trp Thr Phe Gly Ala Gly Thr Lys Val Asp Leu Lys
            100                 105                 110

<210> SEQ ID NO 271
<211> LENGTH: 330
<212> TYPE: DNA
<213> ORGANISM: artificial
<220> FEATURE:
<223> OTHER INFORMATION: VH chain

<400> SEQUENCE: 271
gtgatgatgc agactccact gtccctgtcc gtcagccctg gagagactgt ctccatctcc    60
tgcaaggcca gtcagagcct cctgcacagt aacgggaaca cccatttgtt ttggttccga   120
```

```
cagaagccag gccagtctcc acagcgcctg atcaacttgg tttccaacag agaccctggg    180
gtcccagaca ggttcagtgg cagcgggtca gggacagatt tcaccctgag aatcagcaga    240
gtggaggctg acgatgctgg tgtttattac tgcgggcaag gtacacaaga tcctccgacg    300
ttcggagcag gaaccaaggt ggacctcaaa                                     330
```

<210> SEQ ID NO 272
<211> LENGTH: 110
<212> TYPE: PRT
<213> ORGANISM: artificial
<220> FEATURE:
<223> OTHER INFORMATION: VH chain

<400> SEQUENCE: 272

```
Val Met Met Gln Thr Pro Leu Ser Leu Ser Val Ser Pro Gly Glu Thr
1               5                   10                  15

Val Ser Ile Ser Cys Lys Ala Ser Gln Ser Leu Leu His Ser Asn Gly
            20                  25                  30

Asn Thr His Leu Phe Trp Phe Arg Gln Lys Pro Gly Gln Ser Pro Gln
        35                  40                  45

Arg Leu Ile Asn Leu Val Ser Asn Arg Asp Pro Gly Val Pro Asp Arg
    50                  55                  60

Phe Ser Gly Ser Gly Ser Gly Thr Asp Phe Thr Leu Arg Ile Ser Arg
65                  70                  75                  80

Val Glu Ala Asp Asp Ala Gly Val Tyr Tyr Cys Gly Gln Gly Thr Gln
                85                  90                  95

Asp Pro Pro Thr Phe Gly Ala Gly Thr Lys Val Asp Leu Lys
            100                 105                 110
```

<210> SEQ ID NO 273
<211> LENGTH: 330
<212> TYPE: DNA
<213> ORGANISM: artificial
<220> FEATURE:
<223> OTHER INFORMATION: VH chain

<400> SEQUENCE: 273

```
gtgatgatgc agactccact gtccctgtcc gtcagccctg gagagccggc ctccatctcc     60
tgcaaggcca gtcagagcct cctgcacagt aacgggaaca cctatttgtc ttggtttcga    120
cagaagccag gccagtctcc acagtctttg atctataagg tctccaacag agaccctggg    180
gccccagaca ggttcagtgg cagcgggtca gggacagatt tcaccctgag aatcagcgga    240
gtggaggctg atgatgttgg aatttattac tgcgggcaag gtatacagga tccgtggacg    300
ttcggagcag gaaccaaggt ggacctcaaa                                     330
```

<210> SEQ ID NO 274
<211> LENGTH: 110
<212> TYPE: PRT
<213> ORGANISM: artificial
<220> FEATURE:
<223> OTHER INFORMATION: VH chain

<400> SEQUENCE: 274

```
Val Met Met Gln Thr Pro Leu Ser Leu Ser Val Ser Pro Gly Glu Pro
1               5                   10                  15

Ala Ser Ile Ser Cys Lys Ala Ser Gln Ser Leu Leu His Ser Asn Gly
            20                  25                  30

Asn Thr Tyr Leu Ser Trp Phe Arg Gln Lys Pro Gly Gln Ser Pro Gln
        35                  40                  45
```

```
Ser Leu Ile Tyr Lys Val Ser Asn Arg Asp Pro Gly Ala Pro Asp Arg
    50                  55                  60

Phe Ser Gly Ser Gly Ser Gly Thr Asp Phe Thr Leu Arg Ile Ser Gly
 65              70                  75                  80

Val Glu Ala Asp Asp Val Gly Ile Tyr Tyr Cys Gly Gln Gly Ile Gln
                 85                  90                  95

Asp Pro Trp Thr Phe Gly Ala Gly Thr Lys Val Asp Leu Lys
            100                 105                 110

<210> SEQ ID NO 275
<211> LENGTH: 330
<212> TYPE: DNA
<213> ORGANISM: artificial
<220> FEATURE:
<223> OTHER INFORMATION: VH chain

<400> SEQUENCE: 275
gtgatgatgc agactccact gtccctgtcc gtcagccctg gagagccggc ctccatctcc      60
tgcaaggcca gtcagagcct cctggacagt aatggaaaca cctttttgtc ttggttccga     120
cagaagccag gccagtctcc acagcgtttg atctataagg tctccaacag agaccctggg     180
gtcccagaca ggttcagtgg cagcgggtca gggacagatt tcaccctgag aatcagcgga     240
gtggaggctg atgatgctgg aatttattac tgtgggcaag gtatacagga tccgtggacg     300
ttcggagcag gaaccaaggt ggacctcaaa                                      330

<210> SEQ ID NO 276
<211> LENGTH: 110
<212> TYPE: PRT
<213> ORGANISM: artificial
<220> FEATURE:
<223> OTHER INFORMATION: VH chain

<400> SEQUENCE: 276

Val Met Met Gln Thr Pro Leu Ser Leu Ser Val Ser Pro Gly Glu Pro
 1               5                  10                  15

Ala Ser Ile Ser Cys Lys Ala Ser Gln Ser Leu Leu Asp Ser Asn Gly
            20                  25                  30

Asn Thr Phe Leu Ser Trp Phe Arg Gln Lys Pro Gly Gln Ser Pro Gln
            35                  40                  45

Arg Leu Ile Tyr Lys Val Ser Asn Arg Asp Pro Gly Val Pro Asp Arg
    50                  55                  60

Phe Ser Gly Ser Gly Ser Gly Thr Asp Phe Thr Leu Arg Ile Ser Gly
 65              70                  75                  80

Val Glu Ala Asp Asp Ala Gly Ile Tyr Tyr Cys Gly Gln Gly Ile Gln
                 85                  90                  95

Asp Pro Trp Thr Phe Gly Ala Gly Thr Lys Val Asp Leu Lys
            100                 105                 110

<210> SEQ ID NO 277
<211> LENGTH: 330
<212> TYPE: DNA
<213> ORGANISM: artificial
<220> FEATURE:
<223> OTHER INFORMATION: VH chain

<400> SEQUENCE: 277
gtgatgatgc agactccact gtccctgtcc gtcagccctg gagagccggc ctccatctcc      60
tgcaaggcca gtcagagcct cctggacagt aatggaaaca cctttttgtc ttggttccga     120
```

```
cagaagccag gccagtctcc acagcgtttg atctataagg tctccaacag agaccctggg      180
gtcccagaca ggttcagtgg cagcgggtca ggggcagatt tcaccctgag aatcagcgga      240
gtggaggctg acgatactgg agtttattac tgcatgcaag gtatacagtt cctcggacg       300 ttcggagcag gaaccaaggt ggacctcaaa                                       330
```

<210> SEQ ID NO 278
<211> LENGTH: 110
<212> TYPE: PRT
<213> ORGANISM: artificial
<220> FEATURE:
<223> OTHER INFORMATION: VH chain

<400> SEQUENCE: 278

Val Met Met Gln Thr Pro Leu Ser Leu Ser Val Ser Pro Gly Glu Pro
1               5                   10                  15

Ala Ser Ile Ser Cys Lys Ala Ser Gln Ser Leu Leu Asp Ser Asn Gly
            20                  25                  30

Asn Thr Phe Leu Ser Trp Phe Arg Gln Lys Pro Gly Gln Ser Pro Gln
        35                  40                  45

Arg Leu Ile Tyr Lys Val Ser Asn Arg Asp Pro Gly Val Pro Asp Arg
    50                  55                  60

Phe Ser Gly Ser Gly Ser Gly Ala Asp Phe Thr Leu Arg Ile Ser Gly
65                  70                  75                  80

Val Glu Ala Asp Asp Thr Gly Val Tyr Tyr Cys Met Gln Gly Ile Gln
                85                  90                  95

Phe Pro Arg Thr Phe Gly Ala Gly Thr Lys Val Asp Leu Lys
            100                 105                 110

<210> SEQ ID NO 279
<211> LENGTH: 330
<212> TYPE: DNA
<213> ORGANISM: artificial
<220> FEATURE:
<223> OTHER INFORMATION: VH chain

<400> SEQUENCE: 279

```
gtgatgacgc agaccccact gtccctgtcc gtcagccctg gagagccggc ctccatctcc       60
tgcaaggcca gtcagagcct cctggacagt aatggaaaca ccttttttgtc ttggttccga     120 cagaagccag gccagtctcc acagcgtttg atctttaagg tctccaacag agaccctggg     180
gtcccagaca ggttcagtgg cagcgggtca gggacagatt tcaccctgag aatcagcgga    240
gtggaggctg atgatgttgg aatttattac tgcgggcaag gtatacagga tccgtggacg    300
ttcggagcag gtacccaggt ggaactcaaa                                      330
```

<210> SEQ ID NO 280
<211> LENGTH: 110
<212> TYPE: PRT
<213> ORGANISM: artificial
<220> FEATURE:
<223> OTHER INFORMATION: VH chain

<400> SEQUENCE: 280

Val Met Thr Gln Thr Pro Leu Ser Leu Ser Val Ser Pro Gly Glu Pro
1               5                   10                  15

Ala Ser Ile Ser Cys Lys Ala Ser Gln Ser Leu Leu Asp Ser Asn Gly
            20                  25                  30

Asn Thr Phe Leu Ser Trp Phe Arg Gln Lys Pro Gly Gln Ser Pro Gln
        35                  40                  45

```
Arg Leu Ile Phe Lys Val Ser Asn Arg Asp Pro Gly Val Pro Asp Arg
        50                  55                  60

Phe Ser Gly Ser Gly Ser Gly Thr Asp Phe Thr Leu Arg Ile Ser Gly
 65                  70                  75                  80

Val Glu Ala Asp Asp Val Gly Ile Tyr Tyr Cys Gly Gln Gly Ile Gln
                 85                  90                  95

Asp Pro Trp Thr Phe Gly Ala Gly Thr Gln Val Glu Leu Lys
            100                 105                 110

<210> SEQ ID NO 281
<211> LENGTH: 330
<212> TYPE: DNA
<213> ORGANISM: artificial
<220> FEATURE:
<223> OTHER INFORMATION: VH chain

<400> SEQUENCE: 281
gtcatgacgc agacccccact gtccctgtcc gtcascccctg gagagccggc ctccatctcc     60
tgcaaggcca gtcagagcct cctggacagt aatggaaaca ccttttttgtc ttggttccga    120 cagaagccag gccagtctcc acagcgtttg atctataagg tctccaacag agaccctggg    180
gtcccagaca ggttcagtgg cagcgggtca gggacagatt tcaccctgag aatcagcgga    240
gtggaggctg atgatgctgg aatttattac tgcgggcaag gtatacagga tccgtggacg    300
ttcggagcag gtaccccaggt ggagctcaaa                                     330

<210> SEQ ID NO 282
<211> LENGTH: 110
<212> TYPE: PRT
<213> ORGANISM: artificial
<220> FEATURE:
<223> OTHER INFORMATION: VH chain
<220> FEATURE:
<221> NAME/KEY: misc_feature
<222> LOCATION: (12)..(12)
<223> OTHER INFORMATION: Xaa can be any naturally occurring amino acid

<400> SEQUENCE: 282

Val Met Thr Gln Thr Pro Leu Ser Leu Ser Val Xaa Pro Gly Glu Pro
 1               5                  10                  15

Ala Ser Ile Ser Cys Lys Ala Ser Gln Ser Leu Leu Asp Ser Asn Gly
                20                  25                  30

Asn Thr Phe Leu Ser Trp Phe Arg Gln Lys Pro Gly Gln Ser Pro Gln
            35                  40                  45

Arg Leu Ile Tyr Lys Val Ser Asn Arg Asp Pro Gly Val Pro Asp Arg
        50                  55                  60

Phe Ser Gly Ser Gly Ser Gly Thr Asp Phe Thr Leu Arg Ile Ser Gly
 65                  70                  75                  80

Val Glu Ala Asp Asp Ala Gly Ile Tyr Tyr Cys Gly Gln Gly Ile Gln
                 85                  90                  95

Asp Pro Trp Thr Phe Gly Ala Gly Thr Gln Val Glu Leu Lys
            100                 105                 110

<210> SEQ ID NO 283
<211> LENGTH: 312
<212> TYPE: DNA
<213> ORGANISM: artificial
<220> FEATURE:
<223> OTHER INFORMATION: VH chain

<400> SEQUENCE: 283
gtgatgacac agtctccagc ctccctctcc ttgtctcagg aggaagaagt caccatcacc      60
```

```
tgccgggcca gtcagagtgt tagcagctac ttagcctggt accagcaaaa acctgggcag      120
gctcccaagc tcctcatcta tggtacatcc aacagggcca ctggtgtccc atcccggttc      180
agtggcagtg ggtctgggac agacttcagc ttcaccatca gcagcctgga gcctgaagat      240
gttgcagttt attactgtca gcactataat ggcgggtgga cgttcggagc aggaaccaag      300
gtggaactca aa                                                          312

<210> SEQ ID NO 284
<211> LENGTH: 104
<212> TYPE: PRT
<213> ORGANISM: artificial
<220> FEATURE:
<223> OTHER INFORMATION: VH chain

<400> SEQUENCE: 284

Val Met Thr Gln Ser Pro Ala Ser Leu Ser Leu Ser Gln Glu Glu Glu
1               5                   10                  15

Val Thr Ile Thr Cys Arg Ala Ser Gln Ser Val Ser Ser Tyr Leu Ala
            20                  25                  30

Trp Tyr Gln Gln Lys Pro Gly Gln Ala Pro Lys Leu Leu Ile Tyr Gly
        35                  40                  45

Thr Ser Asn Arg Ala Thr Gly Val Pro Ser Arg Phe Ser Gly Ser Gly
    50                  55                  60

Ser Gly Thr Asp Phe Ser Phe Thr Ile Ser Ser Leu Glu Pro Glu Asp
65                  70                  75                  80

Val Ala Val Tyr Tyr Cys Gln His Tyr Asn Gly Gly Trp Thr Phe Gly
                85                  90                  95

Ala Gly Thr Lys Val Glu Leu Lys
            100

<210> SEQ ID NO 285
<211> LENGTH: 330
<212> TYPE: DNA
<213> ORGANISM: artificial
<220> FEATURE:
<223> OTHER INFORMATION: VH chain

<400> SEQUENCE: 285
gtgatgatgc agactccact gtccctgtcc gtcagccctg gagagccggc ctccatctcc       60
tgcaaggcca gtcagagcct cctggacagt aatggaaaca cctttttgtc ttggttccga      120
cagaagccag gccagtctcc acagcgtttg atctataagg tctccaacag agaccctggg      180
gtcccagaca ggttcagtgg cagcgggtca gggacagatt tcaccctgag aatcagcgga      240
gtggaggctg atgatgctgg aatttattac tgcgggcaag tatacagga tccgtggacg      300 ttcggagcag gaaccaaggt ggacctcaaa                                       330

<210> SEQ ID NO 286
<211> LENGTH: 110
<212> TYPE: PRT
<213> ORGANISM: artificial
<220> FEATURE:
<223> OTHER INFORMATION: VH chain

<400> SEQUENCE: 286

Val Met Met Gln Thr Pro Leu Ser Leu Ser Val Ser Pro Gly Glu Pro
1               5                   10                  15

Ala Ser Ile Ser Cys Lys Ala Ser Gln Ser Leu Leu Asp Ser Asn Gly
            20                  25                  30
```

```
Asn Thr Phe Leu Ser Trp Phe Arg Gln Lys Pro Gly Gln Ser Pro Gln
        35                  40                  45

Arg Leu Ile Tyr Lys Val Ser Asn Arg Asp Pro Gly Val Pro Asp Arg
    50                  55                  60

Phe Ser Gly Ser Gly Ser Gly Thr Asp Phe Thr Leu Arg Ile Ser Gly
65                  70                  75                  80

Val Glu Ala Asp Asp Ala Gly Ile Tyr Tyr Cys Gly Gln Gly Ile Gln
                85                  90                  95

Asp Pro Trp Thr Phe Gly Ala Gly Thr Lys Val Asp Leu Lys
            100                 105                 110

<210> SEQ ID NO 287
<211> LENGTH: 330
<212> TYPE: DNA
<213> ORGANISM: artificial
<220> FEATURE:
<223> OTHER INFORMATION: VH chain

<400> SEQUENCE: 287
gtgatgacac agaccccact gtccctgtcc gtcagccctg gagagccggc ctccatctcc      60
tgcaaggcca gtcagagcct cctgcacagt aatgggaaca cctatttgta ttggttccga     120
cagaagccag gccagtctcc acagcgtttg atctataagg tctccaacag agaccctggg     180
gtcccagaca ggttcagtgg cagcgggtca gggacagatt tcaccctgag aatcagcaga     240
gtggaggctg atgatgctgg agtttattac tgcgggcaag gtttccaaga tccgtggacg     300
ttcggagcag gaaccaaggt ggacctcaaa                                      330

<210> SEQ ID NO 288
<211> LENGTH: 110
<212> TYPE: PRT
<213> ORGANISM: artificial
<220> FEATURE:
<223> OTHER INFORMATION: VH chain

<400> SEQUENCE: 288

Val Met Thr Gln Thr Pro Leu Ser Leu Ser Val Ser Pro Gly Glu Pro
1               5                   10                  15

Ala Ser Ile Ser Cys Lys Ala Ser Gln Ser Leu Leu His Ser Asn Gly
            20                  25                  30

Asn Thr Tyr Leu Tyr Trp Phe Arg Gln Lys Pro Gly Gln Ser Pro Gln
        35                  40                  45

Arg Leu Ile Tyr Lys Val Ser Asn Arg Asp Pro Gly Val Pro Asp Arg
    50                  55                  60

Phe Ser Gly Ser Gly Ser Gly Thr Asp Phe Thr Leu Arg Ile Ser Arg
65                  70                  75                  80

Val Glu Ala Asp Asp Ala Gly Val Tyr Tyr Cys Gly Gln Gly Phe Gln
                85                  90                  95

Asp Pro Trp Thr Phe Gly Ala Gly Thr Lys Val Asp Leu Lys
            100                 105                 110

<210> SEQ ID NO 289
<211> LENGTH: 330
<212> TYPE: DNA
<213> ORGANISM: artificial
<220> FEATURE:
<223> OTHER INFORMATION: VH chain

<400> SEQUENCE: 289
gtgatgatac agactccact gtccctggcc gtcacccctg gagagctggc cactatctcc      60
```

```
tgcagggcca gtcagagtct cctgcacagt gatggaaaat cctatttgaa ttggtacctg    120
cagaagccag gccagactcc tcggccgctg atttatgagg cttccaagcg tttctctggg    180
gtctcagaca ggttcagtgg cagcgggtca gggacagatt tcacccttaa aatcagcagg    240
gtggaggctg aggatgttgg agtttattac tgccagcaaa gtctacattt tcctcctgcg    300
ttcggagcag aaccaaggt ggacctcaaa                                       330
```

<210> SEQ ID NO 290
<211> LENGTH: 110
<212> TYPE: PRT
<213> ORGANISM: artificial
<220> FEATURE:
<223> OTHER INFORMATION: VH chain

<400> SEQUENCE: 290

Val Met Ile Gln Thr Pro Leu Ser Leu Ala Val Thr Pro Gly Glu Leu
1               5                   10                  15

Ala Thr Ile Ser Cys Arg Ala Ser Gln Ser Leu Leu His Ser Asp Gly
            20                  25                  30

Lys Ser Tyr Leu Asn Trp Tyr Leu Gln Lys Pro Gly Gln Thr Pro Arg
        35                  40                  45

Pro Leu Ile Tyr Glu Ala Ser Lys Arg Phe Ser Gly Val Ser Asp Arg
    50                  55                  60

Phe Ser Gly Ser Gly Ser Gly Thr Asp Phe Thr Leu Lys Ile Ser Arg
65                  70                  75                  80

Val Glu Ala Glu Asp Val Gly Val Tyr Tyr Cys Gln Gln Ser Leu His
                85                  90                  95

Phe Pro Pro Ala Phe Gly Ala Gly Thr Lys Val Asp Leu Lys
            100                 105                 110

<210> SEQ ID NO 291
<211> LENGTH: 330
<212> TYPE: DNA
<213> ORGANISM: artificial
<220> FEATURE:
<223> OTHER INFORMATION: VH chain

<400> SEQUENCE: 291

```
gtcatgatgc agactccact gtccctgtcc gtcagccctg gagagccggc ctccatctcc    60
tgcaaggcca gtcagagcct cctgcacagt aacgggaaca cctatttgtt ttggtttcga    120
cagaagccag gccagtctcc acagcgtttg atctataagg tctccaacag agaccctggg    180
gtcccagaca ggttcagtgg cagcgggtca gggacagatt tcacccctgac aatcagcaga    240 gtggaggctg acgatactgg agtttattac tgcgggcaag gtatacagtt tcctcggacg    300
ttcggagcag gtacccaggt ggagctcaaa                                      330
```

<210> SEQ ID NO 292
<211> LENGTH: 110
<212> TYPE: PRT
<213> ORGANISM: artificial
<220> FEATURE:
<223> OTHER INFORMATION: VH chain

<400> SEQUENCE: 292

Val Met Met Gln Thr Pro Leu Ser Leu Ser Val Ser Pro Gly Glu Pro
1               5                   10                  15

Ala Ser Ile Ser Cys Lys Ala Ser Gln Ser Leu Leu His Ser Asn Gly
            20                  25                  30

Asn Thr Tyr Leu Phe Trp Phe Arg Gln Lys Pro Gly Gln Ser Pro Gln

```
                35                  40                  45
Arg Leu Ile Tyr Lys Val Ser Asn Arg Asp Pro Gly Val Pro Asp Arg
 50                  55                  60

Phe Ser Gly Ser Gly Ser Gly Thr Asp Phe Thr Leu Thr Ile Ser Arg
 65                  70                  75                  80

Val Glu Ala Asp Asp Thr Gly Val Tyr Tyr Cys Gly Gln Gly Ile Gln
                 85                  90                  95

Phe Pro Arg Thr Phe Gly Ala Gly Thr Gln Val Glu Leu Lys
                100                 105                 110

<210> SEQ ID NO 293
<211> LENGTH: 330
<212> TYPE: DNA
<213> ORGANISM: artificial
<220> FEATURE:
<223> OTHER INFORMATION: VH chain

<400> SEQUENCE: 293
gtgatgatgc agactccact gtccctgtcc gtcagccctg gagagactgc ctccatttcc      60
tgcacggcca gtcagagcct cctccacagt gatggaaaca cgtatttgaa ttggatccga     120
cagaagccag gccagtctcc acagcgtttg atcgaaaagg tctccaagag agaccctggg     180
gtcccagaca ggttcagtgg cagcgggtca gggacagatt tcaccctgag aatcagcaga     240
gtggaggctg gcgatgttgg agtttattac tgcctgcaag gcacacagtc tccgtggacg     300
ttcggaacag ggaccaagct ggagatcaaa                                      330

<210> SEQ ID NO 294
<211> LENGTH: 110
<212> TYPE: PRT
<213> ORGANISM: artificial
<220> FEATURE:
<223> OTHER INFORMATION: VH chain

<400> SEQUENCE: 294

Val Met Met Gln Thr Pro Leu Ser Leu Ser Val Ser Pro Gly Glu Thr
 1               5                  10                  15

Ala Ser Ile Ser Cys Thr Ala Ser Gln Ser Leu Leu His Ser Asp Gly
                 20                  25                  30

Asn Thr Tyr Leu Asn Trp Ile Arg Gln Lys Pro Gly Gln Ser Pro Gln
                 35                  40                  45

Arg Leu Ile Glu Lys Val Ser Lys Arg Asp Pro Gly Val Pro Asp Arg
 50                  55                  60

Phe Ser Gly Ser Gly Ser Gly Thr Asp Phe Thr Leu Arg Ile Ser Arg
 65                  70                  75                  80

Val Glu Ala Gly Asp Val Gly Val Tyr Tyr Cys Leu Gln Gly Thr Gln
                 85                  90                  95

Ser Pro Trp Thr Phe Gly Thr Gly Thr Lys Leu Glu Ile Lys
                100                 105                 110

<210> SEQ ID NO 295
<211> LENGTH: 330
<212> TYPE: DNA
<213> ORGANISM: artificial
<220> FEATURE:
<223> OTHER INFORMATION: VH chain

<400> SEQUENCE: 295
gtcatgatgc agactccact gtccctgtcc gtcagccctg gagagccggc ctccatctcc      60
tacaaggcca gtcagagcct cctggaaagt gatgggaaca ccttttttgtc ttggttccga    120
```

```
cagaagccag gccagtctcc acagcgtttg atctataagg tctccaacag agaccctggg      180
gtcccagaca ggttcagtgg cagcgggtca gggacagatt tcaccctgag aatcagcgga      240
gtggaggctg atgatgctgg aatttattac tgcgggcaag gtatacagga tccgtggacg      300
ttcggagcag gaaccaaggt ggacctcaaa                                       330
```

<210> SEQ ID NO 296
<211> LENGTH: 110
<212> TYPE: PRT
<213> ORGANISM: artificial
<220> FEATURE:
<223> OTHER INFORMATION: VH chain

<400> SEQUENCE: 296

Val Met Met Gln Thr Pro Leu Ser Leu Ser Val Ser Pro Gly Glu Pro
1               5                   10                  15

Ala Ser Ile Ser Tyr Lys Ala Ser Gln Ser Leu Leu Glu Ser Asp Gly
            20                  25                  30

Asn Thr Phe Leu Ser Trp Phe Arg Gln Lys Pro Gly Gln Ser Pro Gln
        35                  40                  45

Arg Leu Ile Tyr Lys Val Ser Asn Arg Asp Pro Gly Val Pro Asp Arg
    50                  55                  60

Phe Ser Gly Ser Gly Ser Gly Thr Asp Phe Thr Leu Arg Ile Ser Gly
65                  70                  75                  80

Val Glu Ala Asp Asp Ala Gly Ile Tyr Tyr Cys Gly Gln Gly Ile Gln
                85                  90                  95

Asp Pro Trp Thr Phe Gly Ala Gly Thr Lys Val Asp Leu Lys
            100                 105                 110

<210> SEQ ID NO 297
<211> LENGTH: 330
<212> TYPE: DNA
<213> ORGANISM: artificial
<220> FEATURE:
<223> OTHER INFORMATION: VH chain

<400> SEQUENCE: 297

```
gtgatgatgc agaccccact gtccctgtcc gtcagccctg gagagccggc ctccatctcc      60
tgcaaggcca gtcagagtct cctgcgcagt gatggaaaat cctatttgaa ttggtacctg      120
cagaagccag accagactcc tcggccgctg atttatgagg cttccaagcg tttctctggg      180
gtctcagaca ggttcagtgg cagcgggtca gggacagatt tcaccctgag aatcagcaga      240
gtggaggctg acgatactgg agtttattat tgtgggcaag ttatagaaga tccgtggacg      300
ttcggagcag gaaccaaggt ggacctcaaa                                       330
```

<210> SEQ ID NO 298
<211> LENGTH: 110
<212> TYPE: PRT
<213> ORGANISM: artificial
<220> FEATURE:
<223> OTHER INFORMATION: VH chain

<400> SEQUENCE: 298

Val Met Met Gln Thr Pro Leu Ser Leu Ser Val Ser Pro Gly Glu Pro
1               5                   10                  15

Ala Ser Ile Ser Cys Lys Ala Ser Gln Ser Leu Leu Arg Ser Asp Gly
            20                  25                  30

Lys Ser Tyr Leu Asn Trp Tyr Leu Gln Lys Pro Asp Gln Thr Pro Arg
        35                  40                  45

```
Pro Leu Ile Tyr Glu Ala Ser Lys Arg Phe Ser Gly Val Ser Asp Arg
    50                  55                  60

Phe Ser Gly Ser Gly Ser Gly Thr Asp Phe Thr Leu Arg Ile Ser Arg
65                  70                  75                  80

Val Glu Ala Asp Asp Thr Gly Val Tyr Tyr Cys Gly Gln Val Ile Glu
                85                  90                  95

Asp Pro Trp Thr Phe Gly Ala Gly Thr Lys Val Asp Leu Lys
            100                 105                 110

<210> SEQ ID NO 299
<211> LENGTH: 330
<212> TYPE: DNA
<213> ORGANISM: artificial
<220> FEATURE:
<223> OTHER INFORMATION: VH chain

<400> SEQUENCE: 299
gtcatgacac agactccact gtccctgtcc gtcagccctg gagagccggc ctccatctcc      60
tgcaaggcca gtcagagcct cctgcacagt aatgggaaca cctatttgta ttggtttcga    120
cagaaggcag gccagtctcc acagcgtttg atctataagg tctccaacag agaccctggg    180
gtcccagaca ggttcagtgg cagcgggtca gggacagatt tcaccctgag aatcagcaga    240
gtggaggctg atgatgctgg agtttattat tgcgggcaag gtatacaaga tcctccgacg    300
ttcggagcag gaacccaggt ggagctcaaa                                     330

<210> SEQ ID NO 300
<211> LENGTH: 110
<212> TYPE: PRT
<213> ORGANISM: artificial
<220> FEATURE:
<223> OTHER INFORMATION: VH chain

<400> SEQUENCE: 300

Val Met Thr Gln Thr Pro Leu Ser Leu Ser Val Ser Pro Gly Glu Pro
1               5                   10                  15

Ala Ser Ile Ser Cys Lys Ala Ser Gln Ser Leu Leu His Ser Asn Gly
                20                  25                  30

Asn Thr Tyr Leu Tyr Trp Phe Arg Gln Lys Ala Gly Gln Ser Pro Gln
            35                  40                  45

Arg Leu Ile Tyr Lys Val Ser Asn Arg Asp Pro Gly Val Pro Asp Arg
    50                  55                  60

Phe Ser Gly Ser Gly Ser Gly Thr Asp Phe Thr Leu Arg Ile Ser Arg
65                  70                  75                  80

Val Glu Ala Asp Asp Ala Gly Val Tyr Tyr Cys Gly Gln Gly Ile Gln
                85                  90                  95

Asp Pro Pro Thr Phe Gly Ala Gly Thr Gln Val Glu Leu Lys
            100                 105                 110

<210> SEQ ID NO 301
<211> LENGTH: 315
<212> TYPE: DNA
<213> ORGANISM: artificial
<220> FEATURE:
<223> OTHER INFORMATION: VH chain

<400> SEQUENCE: 301
gggttgactc agctgccttc cgtgaatgtg accctgaggc agacggccca catcacctgt      60
gggggagaca ggattggaag taaatatgtt caatggaccc agcagaatcc aggccaggcc    120
```

```
cccgtggtga ttatctataa ggataccaac aggccgagag ggatccctga gcgattctct      180
ggcgccaact cagggaacac ggctaccctg accatcagcg gggccctcgc cgaagacgag      240
gctgactatt actgccaggt gtgggacacc agtgctaagg ctgtgttcgg cggaggcacc      300
cacctgaccg tcctt                                                      315

<210> SEQ ID NO 302
<211> LENGTH: 105
<212> TYPE: PRT
<213> ORGANISM: artificial
<220> FEATURE:
<223> OTHER INFORMATION: VH chain

<400> SEQUENCE: 302

Gly Leu Thr Gln Leu Pro Ser Val Asn Val Thr Leu Arg Gln Thr Ala
1               5                   10                  15

His Ile Thr Cys Gly Gly Asp Arg Ile Gly Ser Lys Tyr Val Gln Trp
            20                  25                  30

Thr Gln Gln Asn Pro Gly Gln Ala Pro Val Val Ile Ile Tyr Lys Asp
        35                  40                  45

Thr Asn Arg Pro Arg Gly Ile Pro Glu Arg Phe Ser Gly Ala Asn Ser
    50                  55                  60

Gly Asn Thr Ala Thr Leu Thr Ile Ser Gly Ala Leu Ala Glu Asp Glu
65                  70                  75                  80

Ala Asp Tyr Tyr Cys Gln Val Trp Asp Thr Ser Ala Lys Ala Val Phe
                85                  90                  95

Gly Gly Gly Thr His Leu Thr Val Leu
            100                 105

<210> SEQ ID NO 303
<211> LENGTH: 325
<212> TYPE: DNA
<213> ORGANISM: artificial
<220> FEATURE:
<223> OTHER INFORMATION: VH chain

<400> SEQUENCE: 303
gtgttgactc agctggcctc agtgtctggg tccctgwggc cagagggtca ccatctcctg      60
cactggcagc agctccaaca tcggtagatt tagtgttggc tggttccagc aactcccggg     120
aaaaggcccc agaaccgtca tctatagtag tagtaaccga ccctcagggg tccctgatcg     180
attctctggc tccaagtcag gcagcacaac caccctgact atctctggcc tccaggctga     240
ggacgaggct gattattact gttcaacata cgacgacagt ctcactatta ctgtgttcgg     300
cggaggcacc cacctgaccg tcctc                                           325

<210> SEQ ID NO 304
<211> LENGTH: 106
<212> TYPE: PRT
<213> ORGANISM: artificial
<220> FEATURE:
<223> OTHER INFORMATION: VH chain
<220> FEATURE:
<221> NAME/KEY: misc_feature
<222> LOCATION: (10)..(10)
<223> OTHER INFORMATION: Xaa can be any naturally occurring amino acid

<400> SEQUENCE: 304

Leu Ser Trp Pro Gln Cys Leu Gly Pro Xaa Gly Gln Arg Val Thr Ile
1               5                   10                  15

Ser Cys Thr Gly Ser Ser Ser Asn Ile Gly Arg Phe Ser Val Gly Trp
            20                  25                  30
```

```
Phe Gln Gln Leu Pro Gly Lys Gly Pro Arg Thr Val Ile Tyr Ser Ser
            35                  40                  45

Ser Asn Arg Pro Ser Gly Val Pro Asp Arg Phe Ser Gly Ser Lys Ser
 50                  55                  60

Gly Ser Thr Thr Thr Leu Thr Ile Ser Gly Leu Gln Ala Glu Asp Glu
 65                  70                  75                  80

Ala Asp Tyr Tyr Cys Ser Thr Tyr Asp Asp Ser Leu Thr Ile Thr Val
                85                  90                  95

Phe Gly Gly Gly Thr His Leu Thr Val Leu
            100                 105

<210> SEQ ID NO 305
<211> LENGTH: 324
<212> TYPE: DNA
<213> ORGANISM: artificial
<220> FEATURE:
<223> OTHER INFORMATION: VH chain

<400> SEQUENCE: 305
gtgctgactc agctggcctc agtggctggg tccctgggcc agagggtcac catctcctgc      60
actggaagca gttccaacat cggtggatat catgttggct ggttccagca ggtcccggaa     120
acaggcccca gaatcgtcat ctatagtagt ggtcagcgac cctcgggggt cccagatcga     180
ttctctggct ccaggtcagg cagcacagcc accctgacca tatctgggct ccaggctgag     240
gacgaggctg agtattactg ctcaacatgg gacgacagtc tcaaagcgcc tgtgttcggc     300
agaggcaccc agctgaccgt cctc                                            324

<210> SEQ ID NO 306
<211> LENGTH: 108
<212> TYPE: PRT
<213> ORGANISM: artificial
<220> FEATURE:
<223> OTHER INFORMATION: VH chain

<400> SEQUENCE: 306

Val Leu Thr Gln Leu Ala Ser Val Ala Gly Ser Leu Gly Gln Arg Val
 1               5                  10                  15

Thr Ile Ser Cys Thr Gly Ser Ser Ser Asn Ile Gly Gly Tyr His Val
                20                  25                  30

Gly Trp Phe Gln Gln Val Pro Glu Thr Gly Pro Arg Ile Val Ile Tyr
            35                  40                  45

Ser Ser Gly Gln Arg Pro Ser Gly Val Pro Asp Arg Phe Ser Gly Ser
 50                  55                  60

Arg Ser Gly Ser Thr Ala Thr Leu Thr Ile Ser Gly Leu Gln Ala Glu
 65                  70                  75                  80

Asp Glu Ala Glu Tyr Tyr Cys Ser Thr Trp Asp Asp Ser Leu Lys Ala
                85                  90                  95

Pro Val Phe Gly Arg Gly Thr Gln Leu Thr Val Leu
            100                 105

<210> SEQ ID NO 307
<211> LENGTH: 321
<212> TYPE: DNA
<213> ORGANISM: artificial
<220> FEATURE:
<223> OTHER INFORMATION: VH chain

<400> SEQUENCE: 307
gtgctgactc agcttacctc agtgtctggg tccctgggcc agaggctcac catctcctgc      60
```

```
actggaagca gttctaacgt cggtcgatat aatgttggct ggttccagca ggtcccggga      120
aaaggcccca aaccgtcat ctataatact tctacccgac cctcaggggt ccctgatcga       180
ttctctgggt ccaagtcagg caataccgcc accctgacca tctctggcct ccaacctgag      240
gacgaagctg attattactg ctcaacatac gacagctttc tcattactgt cttcggcgga     300
ggcacccacc tgaccgtcct c                                                321
```

<210> SEQ ID NO 308
<211> LENGTH: 107
<212> TYPE: PRT
<213> ORGANISM: artificial
<220> FEATURE:
<223> OTHER INFORMATION: VH chain

<400> SEQUENCE: 308

Val Leu Thr Gln Leu Thr Ser Val Ser Gly Ser Leu Gly Gln Arg Leu
1               5                   10                  15

Thr Ile Ser Cys Thr Gly Ser Ser Asn Val Gly Arg Tyr Asn Val
            20                  25                  30

Gly Trp Phe Gln Gln Val Pro Gly Lys Gly Pro Lys Thr Val Ile Tyr
        35                  40                  45

Asn Thr Ser Thr Arg Pro Ser Gly Val Pro Asp Arg Phe Ser Gly Ser
    50                  55                  60

Lys Ser Gly Asn Thr Ala Thr Leu Thr Ile Ser Gly Leu Gln Pro Glu
65                  70                  75                  80

Asp Glu Ala Asp Tyr Tyr Cys Ser Thr Tyr Asp Ser Phe Leu Ile Thr
                85                  90                  95

Val Phe Gly Gly Gly Thr His Leu Thr Val Leu
            100                 105

<210> SEQ ID NO 309
<211> LENGTH: 324
<212> TYPE: DNA
<213> ORGANISM: artificial
<220> FEATURE:
<223> OTHER INFORMATION: VH chain

<400> SEQUENCE: 309

```
gtgctgactc agctgacctc agtgtcgggg tcccttggcc agagggtcac cctgtcctgc      60
tctggaagca cgaacaacat cggtcttttt ggtgcgacct ggtaccaaca gttcccagga    120 aaggcccta aactcctcat gtacactgat ggggatcgac cgtccggggt ccctgaccgg      180
ttttccggct ccaagtcagg cgactcagcc accctgacca tcactgggct tcaggctgag    240
gacgaggctg attatcactg tcaatccgct gatcccacgc ttagagttta tgtgttcggc    300
tcaggcaccc agctgaccgt cctc                                            324
```

<210> SEQ ID NO 310
<211> LENGTH: 108
<212> TYPE: PRT
<213> ORGANISM: artificial
<220> FEATURE:
<223> OTHER INFORMATION: VH chain

<400> SEQUENCE: 310

Val Leu Thr Gln Leu Thr Ser Val Ser Gly Ser Leu Gly Gln Arg Val
1               5                   10                  15

Thr Leu Ser Cys Ser Gly Ser Thr Asn Asn Ile Gly Leu Phe Gly Ala
            20                  25                  30

```
Thr Trp Tyr Gln Gln Phe Pro Gly Lys Ala Pro Lys Leu Leu Met Tyr
        35                  40                  45

Thr Asp Gly Asp Arg Pro Ser Gly Val Pro Asp Arg Phe Ser Gly Ser
 50                  55                  60

Lys Ser Gly Asp Ser Ala Thr Leu Thr Ile Thr Gly Leu Gln Ala Glu
65                   70                  75                  80

Asp Glu Ala Asp Tyr His Cys Gln Ser Ala Asp Pro Thr Leu Arg Val
                85                  90                  95

Tyr Val Phe Gly Ser Gly Thr Gln Leu Thr Val Leu
                100                 105

<210> SEQ ID NO 311
<211> LENGTH: 324
<212> TYPE: DNA
<213> ORGANISM: artificial
<220> FEATURE:
<223> OTHER INFORMATION: VH chain

<400> SEQUENCE: 311
gtgctgactc agcctccttc agtgtcccgg tacctgggcc agagtgtcac catctcttgt      60
aatggaagct cttccaatat cggtcgacct tatgtacact ggtaccaaca attcccggga     120
accgccccca gaaccctcat ctatggtgtt agtaatcgac tctcaggggt ccccgatcga     180
ttctctgcct ccaggtcggg cactacagcg actctgacga tctttgggct ccaggctgag     240
gatgagactg attattattg ttcatcctgg gacagcagtc tcaatggtta cgtgttcggc     300
tcgggaatcg aactcaccgt ccta                                            324

<210> SEQ ID NO 312
<211> LENGTH: 108
<212> TYPE: PRT
<213> ORGANISM: artificial
<220> FEATURE:
<223> OTHER INFORMATION: VH chain

<400> SEQUENCE: 312

Val Leu Thr Gln Pro Pro Ser Val Ser Arg Tyr Leu Gly Gln Ser Val
1               5                   10                  15

Thr Ile Ser Cys Asn Gly Ser Ser Asn Ile Gly Arg Pro Tyr Val
                20                  25                  30

His Trp Tyr Gln Gln Phe Pro Gly Thr Ala Pro Arg Thr Leu Ile Tyr
        35                  40                  45

Gly Val Ser Asn Arg Leu Ser Gly Val Pro Asp Arg Phe Ser Ala Ser
 50                  55                  60

Arg Ser Gly Thr Thr Ala Thr Leu Thr Ile Phe Gly Leu Gln Ala Glu
65                   70                  75                  80

Asp Glu Thr Asp Tyr Tyr Cys Ser Ser Trp Asp Ser Ser Leu Asn Gly
                85                  90                  95

Tyr Val Phe Gly Ser Gly Ile Glu Leu Thr Val Leu
                100                 105

<210> SEQ ID NO 313
<211> LENGTH: 324
<212> TYPE: DNA
<213> ORGANISM: artificial
<220> FEATURE:
<223> OTHER INFORMATION: VH chain

<400> SEQUENCE: 313
gtgttgactc agctggcctc agtgtctggg tccctgggcc agaaggtcac catctcctgc      60
```

```
tctggaaaca cctccaacat cggaactaat tcagtgggct ggtatcaaca gttgccaggc    120
agaggcccta gaaccgtcat ctatggtgat gattaccgcc cttcagggt cccccgatcga    180 ttctctgcct ccaagtcagg cagttcaggc tccctgacca tctctggcct ccagcctgag    240
gacgaggctg cctattactg ctcatcctgg gatgataatc tcagaggtgt tgtattcggt    300
ggaggcaccc agctgaccgt cctc                                          324
```

```
<210> SEQ ID NO 314
<211> LENGTH: 108
<212> TYPE: PRT
<213> ORGANISM: artificial
<220> FEATURE:
<223> OTHER INFORMATION: VH chain

<400> SEQUENCE: 314
```

Val Leu Thr Gln Leu Ala Ser Val Ser Gly Ser Leu Gly Gln Lys Val
1               5                   10                  15

Thr Ile Ser Cys Ser Gly Asn Thr Ser Asn Ile Gly Thr Asn Ser Val
            20                  25                  30

Gly Trp Tyr Gln Gln Leu Pro Gly Arg Gly Pro Arg Thr Val Ile Tyr
        35                  40                  45

Gly Asp Asp Tyr Arg Pro Ser Gly Val Pro Asp Arg Phe Ser Ala Ser
    50                  55                  60

Lys Ser Gly Ser Ser Gly Leu Thr Ile Ser Gly Leu Gln Pro Glu
65                  70                  75                  80

Asp Glu Ala Ala Tyr Tyr Cys Ser Ser Trp Asp Asp Asn Leu Arg Gly
                85                  90                  95

Val Val Phe Gly Gly Gly Thr Gln Leu Thr Val Leu
            100                 105

```
<210> SEQ ID NO 315
<211> LENGTH: 324
<212> TYPE: DNA
<213> ORGANISM: artificial
<220> FEATURE:
<223> OTHER INFORMATION: VH chain

<400> SEQUENCE: 315
ctgctgactc agcctgcttc tgtgtctggg tccctgggcc agagggtcac catctcctgc    60
actggaagca gttccaacat cggtggatat catgttggct ggttccagca ggtcccggaa    120
acaggcccca gaatcgtcat ccatagtagt ggtcagcgac cctcgggggt cccagatcga    180
ttctctggct ccaggtcagg cagcacagcc accctgacca tctctggct ccaggctgag    240 gacgaggctg agtattactg ttcaacatgg gacgacagtc tcaaagcgcc tgtgttcggc    300
ggaggcaccc acctgaccgt cctc                                          324
```

```
<210> SEQ ID NO 316
<211> LENGTH: 108
<212> TYPE: PRT
<213> ORGANISM: artificial
<220> FEATURE:
<223> OTHER INFORMATION: VH chain

<400> SEQUENCE: 316
```

Leu Leu Thr Gln Pro Ala Ser Val Ser Gly Ser Leu Gly Gln Arg Val
1               5                   10                  15

Thr Ile Ser Cys Thr Gly Ser Ser Asn Ile Gly Gly Tyr His Val
            20                  25                  30

Gly Trp Phe Gln Gln Val Pro Glu Thr Gly Pro Arg Ile Val Ile His

```
                35                  40                  45
Ser Ser Gly Gln Arg Pro Ser Gly Val Pro Asp Arg Phe Ser Gly Ser
 50                  55                  60
Arg Ser Gly Ser Thr Ala Thr Leu Thr Ile Ser Gly Leu Gln Ala Glu
 65                  70                  75                  80
Asp Glu Ala Glu Tyr Tyr Cys Ser Thr Trp Asp Ser Leu Lys Ala
                 85                  90                  95
Pro Val Phe Gly Gly Gly Thr His Leu Thr Val Leu
            100                 105

<210> SEQ ID NO 317
<211> LENGTH: 327
<212> TYPE: DNA
<213> ORGANISM: artificial
<220> FEATURE:
<223> OTHER INFORMATION: VH chain

<400> SEQUENCE: 317
gtgctgactc agcctccttc tgtgtctgca gccctgggac agagggtcac catctcctgc      60
actggaagtg acaccaacat cggcagtggt tatgaggtac agtggtacca actcctccca    120
ggaaagtccc cgaagactat catctatggt aatatcaatc gaccctcggg ggtcccggtt    180
cgattctctg ctccaagtc aggcactata gtcaccctgt ccatcactgg gatccaggct    240
gaggatgagg ctgattatta ctgccagtcc tatgatgaca cgtcgatgg ttacgtgttc    300 ggctcaggaa ccgaactcac cgtcctt                                        327

<210> SEQ ID NO 318
<211> LENGTH: 109
<212> TYPE: PRT
<213> ORGANISM: artificial
<220> FEATURE:
<223> OTHER INFORMATION: VH chain

<400> SEQUENCE: 318

Val Leu Thr Gln Pro Pro Ser Val Ser Ala Ala Leu Gly Gln Arg Val
 1                   5                  10                  15
Thr Ile Ser Cys Thr Gly Ser Asp Thr Asn Ile Gly Ser Gly Tyr Glu
                 20                  25                  30
Val Gln Trp Tyr Gln Leu Leu Pro Gly Lys Ser Pro Lys Thr Ile Ile
             35                  40                  45
Tyr Gly Asn Ile Asn Arg Pro Ser Gly Val Pro Val Arg Phe Ser Gly
 50                  55                  60
Ser Lys Ser Gly Thr Ile Val Thr Leu Ser Ile Thr Gly Ile Gln Ala
 65                  70                  75                  80
Glu Asp Glu Ala Asp Tyr Tyr Cys Gln Ser Tyr Asp Asp Asn Val Asp
                 85                  90                  95
Gly Tyr Val Phe Gly Ser Gly Thr Glu Leu Thr Val Leu
            100                 105

<210> SEQ ID NO 319
<211> LENGTH: 312
<212> TYPE: DNA
<213> ORGANISM: artificial
<220> FEATURE:
<223> OTHER INFORMATION: VH chain

<400> SEQUENCE: 319
gggctgactc agccgccatc cgtgaatgtg accctgaggc agacggccca catcacctgt      60
gggggagaca gtattggaag taaatatgtt caatggatcc agcagagtcc aggccaggcc    120
```

```
cccctactta tcatctataa agatagtcac agggcgacag ggatccctga gcgattctct      180
gccgccaact cagggagcac ggctaccctg accatcgccg ggccctggc cgaagacgag       240 gctgactatt actgccaggt gtgggacaac agtgtcattg cgttcggcgg aggcacccac     300
ctgaccgtcc tc                                                          312
```

```
<210> SEQ ID NO 320
<211> LENGTH: 104
<212> TYPE: PRT
<213> ORGANISM: artificial
<220> FEATURE:
<223> OTHER INFORMATION: VH chain

<400> SEQUENCE: 320
```

Gly Leu Thr Gln Pro Pro Ser Val Asn Val Thr Leu Arg Gln Thr Ala
1               5                   10                  15

His Ile Thr Cys Gly Gly Asp Ser Ile Gly Ser Lys Tyr Val Gln Trp
            20                  25                  30

Ile Gln Gln Ser Pro Gly Gln Ala Pro Leu Leu Ile Ile Tyr Lys Asp
        35                  40                  45

Ser His Arg Ala Thr Gly Ile Pro Glu Arg Phe Ser Ala Ala Asn Ser
    50                  55                  60

Gly Ser Thr Ala Thr Leu Thr Ile Ala Gly Ala Leu Ala Glu Asp Glu
65                  70                  75                  80

Ala Asp Tyr Tyr Cys Gln Val Trp Asp Asn Ser Val Ile Ala Phe Gly
                85                  90                  95

Gly Gly Thr His Leu Thr Val Leu
            100

```
<210> SEQ ID NO 321
<211> LENGTH: 324
<212> TYPE: DNA
<213> ORGANISM: artificial
<220> FEATURE:
<223> OTHER INFORMATION: VH chain

<400> SEQUENCE: 321
gcgttgactc agctagcctc agtgtctgga tccctgggcc aaagggtcac catctcctgc      60
actgtaagca caggcaatgt cggtggttat aattatgtac actggtacca gcaactccca    120
ggaaaggcac ccagtctcct catctatggt gatcataaca gagattctag gccccctgaa    180
cgattctctg gctccaagtc aggcagctca gccactctga ccatcactgg cctccaggct    240
gaggacgagg ctgattatta ttgccagtcc tacgatgaca gtttcaatgc tgtgttcggc    300
ggaggcaccc acctgaccgt cctc                                            324
```

```
<210> SEQ ID NO 322
<211> LENGTH: 108
<212> TYPE: PRT
<213> ORGANISM: artificial
<220> FEATURE:
<223> OTHER INFORMATION: VH chain

<400> SEQUENCE: 322
```

Ala Leu Thr Gln Leu Ala Ser Val Ser Gly Ser Leu Gly Gln Arg Val
1               5                   10                  15

Thr Ile Ser Cys Thr Val Ser Thr Gly Asn Val Gly Gly Tyr Asn Tyr
            20                  25                  30

Val His Trp Tyr Gln Gln Leu Pro Gly Lys Ala Pro Ser Leu Leu Ile
        35                  40                  45

```
Tyr Gly Asp His Asn Arg Asp Ser Arg Ala Pro Glu Arg Phe Ser Gly
    50                  55                  60

Ser Lys Ser Gly Ser Ser Ala Thr Leu Thr Ile Thr Gly Leu Gln Ala
65                  70                  75                  80

Glu Asp Glu Ala Asp Tyr Tyr Cys Gln Ser Tyr Asp Ser Phe Asn
                85                  90                  95

Ala Val Phe Gly Gly Gly Thr His Leu Thr Val Leu
            100                 105

<210> SEQ ID NO 323
<211> LENGTH: 324
<212> TYPE: DNA
<213> ORGANISM: artificial
<220> FEATURE:
<223> OTHER INFORMATION: VH chain

<400> SEQUENCE: 323
gcgctgactc agaaggcctc agtgtctggg tccctgggcc agagggtcac catctcctgc     60
actggaagca gctccaacat cggtagatat agtgttggtt ggttccagca gctcccggga    120
aaaggcccca gaaccgtcat ccaaagtagt agtgaccgac cctcagggt cccctgatcga    180 ttctctggct ccaagtcagg cagcacagcc accctgacca tctctgggct ccaggctgag    240
gacgaggctg attattattg ttcaacatac gatagcagtc tcagtggttg ggtatccggt    300
gaagggaccc agctgaccgt cctc                                          324

<210> SEQ ID NO 324
<211> LENGTH: 108
<212> TYPE: PRT
<213> ORGANISM: artificial
<220> FEATURE:
<223> OTHER INFORMATION: VH chain

<400> SEQUENCE: 324

Ala Leu Thr Gln Lys Ala Ser Val Ser Gly Ser Leu Gly Gln Arg Val
1               5                   10                  15

Thr Ile Ser Cys Thr Gly Ser Ser Asn Ile Gly Arg Tyr Ser Val
                20                  25                  30

Gly Trp Phe Gln Gln Leu Pro Gly Lys Gly Pro Arg Thr Val Ile Gln
            35                  40                  45

Ser Ser Ser Asp Arg Pro Ser Gly Val Pro Asp Arg Phe Ser Gly Ser
    50                  55                  60

Lys Ser Gly Ser Thr Ala Thr Leu Thr Ile Ser Gly Leu Gln Ala Glu
65                  70                  75                  80

Asp Glu Ala Asp Tyr Tyr Cys Ser Thr Tyr Asp Ser Ser Leu Ser Gly
                85                  90                  95

Trp Val Ser Gly Glu Gly Thr Gln Leu Thr Val Leu
            100                 105

<210> SEQ ID NO 325
<211> LENGTH: 327
<212> TYPE: DNA
<213> ORGANISM: artificial
<220> FEATURE:
<223> OTHER INFORMATION: VH chain

<400> SEQUENCE: 325
gtgctgactc agctaccctc agtgtctggg tccctgggcc agagggtcac catctcctgc     60
actggaagca gctccaatgt tggttatggc gcttatgtgg gctggtggca gcagctccca    120
```

```
ggaacaaggc ccagaatcct catctatgat ataactaacc gaccctcggg ggtccctgat       180
cgattctctg ctccaggtc aggctacaca gctaccctga ccatctctgg ctcccggct          240 gaggatgaag ccgattatta ctgctcaacc tatgacagca gtctcaaagg ttacgtgttc        300
ggcggaggca cccagctgac cgtcctc                                            327
```

<210> SEQ ID NO 326
<211> LENGTH: 109
<212> TYPE: PRT
<213> ORGANISM: artificial
<220> FEATURE:
<223> OTHER INFORMATION: VH chain

<400> SEQUENCE: 326

Val Leu Thr Gln Leu Pro Ser Val Ser Gly Ser Leu Gly Gln Arg Val
1               5                   10                  15

Thr Ile Ser Cys Thr Gly Ser Ser Ser Asn Val Gly Tyr Gly Ala Tyr
            20                  25                  30

Val Gly Trp Trp Gln Gln Leu Pro Gly Thr Arg Pro Arg Ile Leu Ile
        35                  40                  45

Tyr Asp Ile Thr Asn Arg Pro Ser Gly Val Pro Asp Arg Phe Ser Gly
    50                  55                  60

Ser Arg Ser Gly Tyr Thr Ala Thr Leu Thr Ile Ser Gly Leu Pro Ala
65                  70                  75                  80

Glu Asp Glu Ala Asp Tyr Tyr Cys Ser Thr Tyr Asp Ser Ser Leu Lys
                85                  90                  95

Gly Tyr Val Phe Gly Gly Gly Thr Gln Leu Thr Val Leu
            100                 105

<210> SEQ ID NO 327
<211> LENGTH: 315
<212> TYPE: DNA
<213> ORGANISM: artificial
<220> FEATURE:
<223> OTHER INFORMATION: VH chain

<400> SEQUENCE: 327

```
gggctgaatc agcctccctc ggtatcagtg tctctgggac agacagcaac catctcctgc       60
tctggagaga gtctgagtaa atattatgca caatggttcc agcagaaggc aggccaagcc       120
cctgtgttgg tcatatataa ggacactgag cggccctctg ggatccctga ccgattctct       180
ggctccagtt cagggaacac acacaccctg accatcagcg gggctcgggc cgaggacgag       240
gctgactatt actgcgagtc agcagtcagt actgatactg ctatgttcgg cggagggacc       300
cagctgaccg tcctc                                                         315
```

<210> SEQ ID NO 328
<211> LENGTH: 105
<212> TYPE: PRT
<213> ORGANISM: artificial
<220> FEATURE:
<223> OTHER INFORMATION: VH chain

<400> SEQUENCE: 328

Gly Leu Asn Gln Pro Pro Ser Val Ser Val Ser Leu Gly Gln Thr Ala
1               5                   10                  15

Thr Ile Ser Cys Ser Gly Glu Ser Leu Ser Lys Tyr Tyr Ala Gln Trp
            20                  25                  30

Phe Gln Gln Lys Ala Gly Gln Ala Pro Val Leu Val Ile Tyr Lys Asp
        35                  40                  45

```
Thr Glu Arg Pro Ser Gly Ile Pro Asp Arg Phe Ser Gly Ser Ser Ser
    50                  55                  60

Gly Asn Thr His Thr Leu Thr Ile Ser Gly Ala Arg Ala Glu Asp Glu
65                  70                  75                  80

Ala Asp Tyr Tyr Cys Glu Ser Ala Val Ser Thr Asp Thr Ala Met Phe
                85                  90                  95

Gly Gly Gly Thr Gln Leu Thr Val Leu
            100                 105
```

<210> SEQ ID NO 329
<211> LENGTH: 327
<212> TYPE: DNA
<213> ORGANISM: artificial
<220> FEATURE:
<223> OTHER INFORMATION: VH chain
<220> FEATURE:
<221> NAME/KEY: misc_feature
<222> LOCATION: (45)..(45)
<223> OTHER INFORMATION: n is a, c, g, or t

<400> SEQUENCE: 329

```
gtgctgactc agaaggcctc agttgtctgg gtccctgtgg cacanacggt caccatctcc      60
tgcactggaa gcctgtccaa catccgtgca ttcggtgttg gctggttcca gcaggtcccg     120
ggaagaggcc ccagaaccgt catctatagt acgcgtaacc gaccctcagg ggtccctgat     180
cgattctctg gctccaagtc aggcagcaca gccaccctga ccatctctgg gctccaggct     240
gaggacaagg ctgattatta ctgttcagtc tatgacagca gtctcactaa tggtctgttc     300
ggcggaggga cccacctgac cgtcctc                                         327
```

<210> SEQ ID NO 330
<211> LENGTH: 109
<212> TYPE: PRT
<213> ORGANISM: artificial
<220> FEATURE:
<223> OTHER INFORMATION: VH chain
<220> FEATURE:
<221> NAME/KEY: misc_feature
<222> LOCATION: (15)..(15)
<223> OTHER INFORMATION: Xaa can be any naturally occurring amino acid

<400> SEQUENCE: 330

```
Val Leu Thr Gln Lys Ala Ser Val Val Trp Val Pro Val Ala Xaa Thr
1               5                   10                  15

Val Thr Ile Ser Cys Thr Gly Ser Leu Ser Asn Ile Arg Ala Phe Gly
            20                  25                  30

Val Gly Trp Phe Gln Gln Val Pro Gly Arg Gly Pro Arg Thr Val Ile
        35                  40                  45

Tyr Ser Thr Arg Asn Arg Pro Ser Gly Val Pro Asp Arg Phe Ser Gly
    50                  55                  60

Ser Lys Ser Gly Ser Thr Ala Thr Leu Thr Ile Ser Gly Leu Gln Ala
65                  70                  75                  80

Glu Asp Lys Ala Asp Tyr Tyr Cys Ser Val Tyr Asp Ser Ser Leu Thr
                85                  90                  95

Asn Gly Leu Phe Gly Gly Gly Thr His Leu Thr Val Leu
            100                 105
```

<210> SEQ ID NO 331
<211> LENGTH: 318
<212> TYPE: DNA
<213> ORGANISM: artificial
<220> FEATURE:
<223> OTHER INFORMATION: VH chain

<400> SEQUENCE: 331

```
ctcagctggc ctcagatgtt ggggtccctt ggccagaggg tctccatctc ctgttctgga      60
agcacgaaca gtatcggttt tcttggtgcg agttggtacc aacagctccc aggaaaggcc     120
cctaaactcc tcgtgtacac tgatgggaat cgaccgtcag gggtccctga ccggttttcc     180
ggctccaggt ctggcgactc aggcaccctg accatcactg gctccaggc tgaggacgag      240
gctgattatt actgtcagtc tgttgattcc acgtctagtg ctattatatt cggcggaggg     300
acccacctga ccgtcctc                                                   318
```

<210> SEQ ID NO 332
<211> LENGTH: 106
<212> TYPE: PRT
<213> ORGANISM: artificial
<220> FEATURE:
<223> OTHER INFORMATION: VH chain

<400> SEQUENCE: 332

```
Leu Ser Trp Pro Gln Met Leu Gly Ser Leu Gly Gln Arg Val Ser Ile
1               5                   10                  15
Ser Cys Ser Gly Ser Thr Asn Ser Ile Gly Phe Leu Gly Ala Ser Trp
            20                  25                  30
Tyr Gln Gln Leu Pro Gly Lys Ala Pro Lys Leu Leu Val Tyr Thr Asp
        35                  40                  45
Gly Asn Arg Pro Ser Gly Val Pro Asp Arg Phe Ser Gly Ser Arg Ser
    50                  55                  60
Gly Asp Ser Gly Thr Leu Thr Ile Thr Gly Leu Gln Ala Glu Asp Glu
65                  70                  75                  80
Ala Asp Tyr Tyr Cys Gln Ser Val Asp Ser Thr Ser Ser Ala Ile Ile
                85                  90                  95
Phe Gly Gly Gly Thr His Leu Thr Val Leu
            100                 105
```

<210> SEQ ID NO 333
<211> LENGTH: 327
<212> TYPE: DNA
<213> ORGANISM: artificial
<220> FEATURE:
<223> OTHER INFORMATION: VH chain

<400> SEQUENCE: 333

```
ggggttgaatc agccttcctc ggtgtctggg actttgggcc agactgtcac catctcctgt     60
gatggaagca gcagtaacat tggcagtcat aattggatcg aatggtacca gcagttccca    120
ggcacctccc ccaaactcct gatttactat accaataatc ggccatcagg gatccctgct    180
cgcttctctg gctccaagtc tgggaatacg gcctccttga ccatctctgg cctccaggct    240
gaagatgagg ctgattatta ctgcagcgca tttgctggta gtaataacgc tgctctgttc    300
ggcggaggca cccagctgac cgtcctc                                        327
```

<210> SEQ ID NO 334
<211> LENGTH: 109
<212> TYPE: PRT
<213> ORGANISM: artificial
<220> FEATURE:
<223> OTHER INFORMATION: VH chain

<400> SEQUENCE: 334

```
Gly Leu Asn Gln Pro Ser Ser Val Ser Gly Thr Leu Gly Gln Thr Val
1               5                   10                  15
```

```
Thr Ile Ser Cys Asp Gly Ser Ser Asn Ile Gly Ser His Asn Trp
            20                  25                  30

Ile Glu Trp Tyr Gln Gln Phe Pro Gly Thr Ser Pro Lys Leu Leu Ile
        35                  40                  45

Tyr Tyr Thr Asn Asn Arg Pro Ser Gly Ile Pro Ala Arg Phe Ser Gly
    50                  55                  60

Ser Lys Ser Gly Asn Thr Ala Ser Leu Thr Ile Ser Gly Leu Gln Ala
65                  70                  75                  80

Glu Asp Glu Ala Asp Tyr Tyr Cys Ser Ala Phe Ala Gly Ser Asn Asn
                85                  90                  95

Ala Ala Leu Phe Gly Gly Gly Thr Gln Leu Thr Val Leu
            100                 105
```

<210> SEQ ID NO 335
<211> LENGTH: 323
<212> TYPE: DNA
<213> ORGANISM: artificial
<220> FEATURE:
<223> OTHER INFORMATION: VH chain

<400> SEQUENCE: 335

```
gtctgactca gccggcctcc gtgactgggt ccctgggcca gagggtcact atctcctgca    60
ctggaagcag ttccaacatc ggtggatatc atgttggctg gttccagcag gtcccggaaa   120
caggccccag aatcgtcatc catagtagtg gtcagcgacc ctcgggggtc ccagatcgat   180
tctctggctc caggtcaggc agcacagcca ccctgaccat ctctgggctc cagactgagg   240
acgaggctga gtattactgc tcaacatggg acgacagtct caaagcgcct gtgttcggca   300
gaggcaccca cctgaccgtc ctc                                           323
```

<210> SEQ ID NO 336
<211> LENGTH: 107
<212> TYPE: PRT
<213> ORGANISM: artificial
<220> FEATURE:
<223> OTHER INFORMATION: VH chain

<400> SEQUENCE: 336

```
Leu Thr Gln Pro Ala Ser Val Thr Gly Ser Leu Gly Gln Arg Val Thr
1               5                   10                  15

Ile Ser Cys Thr Gly Ser Ser Ser Asn Ile Gly Gly Tyr His Val Gly
            20                  25                  30

Trp Phe Gln Gln Val Pro Glu Thr Gly Pro Arg Ile Val Ile His Ser
        35                  40                  45

Ser Gly Gln Arg Pro Ser Gly Val Pro Asp Arg Phe Ser Gly Ser Arg
    50                  55                  60

Ser Gly Ser Thr Ala Thr Leu Thr Ile Ser Gly Leu Gln Thr Glu Asp
65                  70                  75                  80

Glu Ala Glu Tyr Tyr Cys Ser Thr Trp Asp Asp Ser Leu Lys Ala Pro
                85                  90                  95

Val Phe Gly Arg Gly Thr His Leu Thr Val Leu
            100                 105
```

<210> SEQ ID NO 337
<211> LENGTH: 330
<212> TYPE: DNA
<213> ORGANISM: artificial
<220> FEATURE:
<223> OTHER INFORMATION: VH chain

<400> SEQUENCE: 337

```
gtgctgactc agccgccctc agtgtcgggg tccctcggcc agagggtcac catgtcctgc    60
actggaagca gatccaatgt tggttatggc aacagatatg tgggctggta ccaattggtc   120
ccagggacag gccccaaaac cctcatctat gaagatagta gacgaccctc ggggtccct    180
gatcgattct caggctccag gtcaggcagc acagcaaccc tgactatctc tgggctccag   240
gctgaggatg aagccgatta ttttgttca tcctatgaca ccagtctcct tgctggcgtg   300
ttcggtggag gcacccacct gaccgtcctc                                    330
```

<210> SEQ ID NO 338
<211> LENGTH: 110
<212> TYPE: PRT
<213> ORGANISM: artificial
<220> FEATURE:
<223> OTHER INFORMATION: VH chain

<400> SEQUENCE: 338

```
Val Leu Thr Gln Pro Pro Ser Val Ser Gly Ser Leu Gly Gln Arg Val
1               5                   10                  15
Thr Met Ser Cys Thr Gly Ser Arg Ser Asn Val Gly Tyr Gly Asn Arg
            20                  25                  30
Tyr Val Gly Trp Tyr Gln Leu Val Pro Gly Thr Gly Pro Lys Thr Leu
        35                  40                  45
Ile Tyr Glu Asp Ser Arg Arg Pro Ser Gly Val Pro Asp Arg Phe Ser
    50                  55                  60
Gly Ser Arg Ser Gly Ser Thr Ala Thr Leu Thr Ile Ser Gly Leu Gln
65                  70                  75                  80
Ala Glu Asp Glu Ala Asp Tyr Phe Cys Ser Ser Tyr Asp Thr Ser Leu
                85                  90                  95
Leu Ala Gly Val Phe Gly Gly Gly Thr His Leu Thr Val Leu
            100                 105                 110
```

<210> SEQ ID NO 339
<211> LENGTH: 324
<212> TYPE: DNA
<213> ORGANISM: artificial
<220> FEATURE:
<223> OTHER INFORMATION: VH chain

<400> SEQUENCE: 339

```
gtgctgactc agccggcctc agtgtctggg tccctgggcc agagggtcac catctcctgc    60
actggaagca gctccaacat cggttggggt gatgtgggct ggtaccaaca gtacccagga   120
acaggcccca gaaccctcat ctatgatact agtcgccgac cctcgggggt ccctgatcga   180
ttttctggct ccaggtcagg cagcacagca accctgacca tctctgggct ccaggctgag   240
gacgaggctg attattactg ttcatcctct gacagcacaa ccagtggtgg cgtgttcggc   300
tcaggaatcc aactcaccgt cctt                                          324
```

<210> SEQ ID NO 340
<211> LENGTH: 108
<212> TYPE: PRT
<213> ORGANISM: artificial
<220> FEATURE:
<223> OTHER INFORMATION: VH chain

<400> SEQUENCE: 340

```
Val Leu Thr Gln Pro Ala Ser Val Ser Gly Ser Leu Gly Gln Arg Val
1               5                   10                  15
```

```
Thr Ile Ser Cys Thr Gly Ser Ser Asn Ile Gly Trp Gly Asp Val
            20                  25                  30

Gly Trp Tyr Gln Gln Tyr Pro Gly Thr Gly Pro Arg Thr Leu Ile Tyr
        35                  40                  45

Asp Thr Ser Arg Arg Pro Ser Gly Val Pro Asp Arg Phe Ser Gly Ser
    50                  55                  60

Arg Ser Gly Ser Thr Ala Thr Leu Thr Ile Ser Gly Leu Gln Ala Glu
65                  70                  75                  80

Asp Glu Ala Asp Tyr Tyr Cys Ser Ser Asp Ser Thr Ser Gly
                85                  90                  95

Gly Val Phe Gly Ser Gly Ile Gln Leu Thr Val Leu
            100                 105
```

<210> SEQ ID NO 341
<211> LENGTH: 330
<212> TYPE: DNA
<213> ORGANISM: artificial
<220> FEATURE:
<223> OTHER INFORMATION: VH chain

<400> SEQUENCE: 341

```
gtgctgtcac agctgccatc cgtgtctgcg gtcctgggac agagggtcac catctcctgc      60
actggaagta gcaccaacat tggcaaggat tatgatgtac aatggtacca gcagctccca     120
ggaaagtccc ctaaaactat cgtctatggt aatagcaatc gaccctcagg ggtcccggat     180
cgcttctctg gctccaagtc aggcagcaca gcctctctga ccatcactgg gctccaggct     240
gaggacgagg ctgattatta ctgccagtcc tctgatgaca atgtcgatga ttatattgtg     300
ttcggcagag gcacccacct gaccgtcctc                                      330
```

<210> SEQ ID NO 342
<211> LENGTH: 110
<212> TYPE: PRT
<213> ORGANISM: artificial
<220> FEATURE:
<223> OTHER INFORMATION: VH chain

<400> SEQUENCE: 342

```
Val Leu Ser Gln Leu Pro Ser Val Ser Ala Val Leu Gly Gln Arg Val
1               5                   10                  15

Thr Ile Ser Cys Thr Gly Ser Ser Thr Asn Ile Gly Lys Asp Tyr Asp
            20                  25                  30

Val Gln Trp Tyr Gln Gln Leu Pro Gly Lys Ser Pro Lys Thr Ile Val
        35                  40                  45

Tyr Gly Asn Ser Asn Arg Pro Ser Gly Val Pro Asp Arg Phe Ser Gly
    50                  55                  60

Ser Lys Ser Gly Ser Thr Ala Ser Leu Thr Ile Thr Gly Leu Gln Ala
65                  70                  75                  80

Glu Asp Glu Ala Asp Tyr Tyr Cys Gln Ser Ser Asp Asp Asn Val Asp
                85                  90                  95

Asp Tyr Ile Val Phe Gly Arg Gly Thr His Leu Thr Val Leu
            100                 105                 110
```

<210> SEQ ID NO 343
<211> LENGTH: 321
<212> TYPE: DNA
<213> ORGANISM: artificial
<220> FEATURE:
<223> OTHER INFORMATION: VH chain

<400> SEQUENCE: 343

```
ctgctgaccc agccggcctc agtgtctggg tccctgggcc agagggtcac catctcctgc    60
actggaagca gctccaacat cggtagaggt tatgtgggct ggtaccagca gctcccagga   120
acaggcccca gaaccctcat ctatgatagt agtagtcgac cctcgggggt ccctgatcga   180
ttctctggct ccaggtcagg cagcacagca accctgacca tctctgggct ccaggctgag   240
gacgaggctg attattactg ctcatcctat gacagcagtc tcagtgctgt gttcggcgga   300
ggcacccacc tgaccgtcct c                                             321
```

<210> SEQ ID NO 344
<211> LENGTH: 107
<212> TYPE: PRT
<213> ORGANISM: artificial
<220> FEATURE:
<223> OTHER INFORMATION: VH chain

<400> SEQUENCE: 344

```
Leu Leu Thr Gln Pro Ala Ser Val Ser Gly Ser Leu Gly Gln Arg Val
1               5                   10                  15

Thr Ile Ser Cys Thr Gly Ser Ser Ser Asn Ile Gly Arg Gly Tyr Val
            20                  25                  30

Gly Trp Tyr Gln Gln Leu Pro Gly Thr Gly Pro Arg Thr Leu Ile Tyr
        35                  40                  45

Asp Ser Ser Arg Pro Ser Gly Val Pro Asp Arg Phe Ser Gly Ser
    50                  55                  60

Arg Ser Gly Ser Thr Ala Thr Leu Thr Ile Ser Gly Leu Gln Ala Glu
65                  70                  75                  80

Asp Glu Ala Asp Tyr Tyr Cys Ser Ser Tyr Asp Ser Ser Leu Ser Ala
                85                  90                  95

Val Phe Gly Gly Gly Thr His Leu Thr Val Leu
            100                 105
```

<210> SEQ ID NO 345
<211> LENGTH: 324
<212> TYPE: DNA
<213> ORGANISM: artificial
<220> FEATURE:
<223> OTHER INFORMATION: VH chain

<400> SEQUENCE: 345

```
atgctgactc aacaggcctc agtgtctggg tccctgggcc agacggtcac catctcctgc    60
actggaagca cctccaacat tggtaggagt catgtggcct ggtaccagca gctcccagga   120
gcaagcccca gaaccctcat ctatgatagt actagccgac cctcgggggt ccctgatcga   180
ttctctggct ccaggtcagg cagcacagca accctgacca tctctgggct ccagtctgag   240
gacgaggctg aatattttg ttcatcatgg gataatcgtc tcagaggtgt tctgttcggc   300
ggagggaccc agctgaccgt cctc                                          324
```

<210> SEQ ID NO 346
<211> LENGTH: 108
<212> TYPE: PRT
<213> ORGANISM: artificial
<220> FEATURE:
<223> OTHER INFORMATION: VH chain

<400> SEQUENCE: 346

```
Met Leu Thr Gln Gln Ala Ser Val Ser Gly Ser Leu Gly Gln Thr Val
1               5                   10                  15

Thr Ile Ser Cys Thr Gly Ser Thr Ser Asn Ile Gly Arg Ser His Val
```

```
                    20                  25                  30
Ala Trp Tyr Gln Gln Leu Pro Gly Ala Ser Pro Arg Thr Leu Ile Tyr
                35                  40                  45

Asp Ser Thr Ser Arg Pro Ser Gly Val Pro Asp Arg Phe Ser Gly Ser
             50                  55                  60

Arg Ser Gly Ser Thr Ala Thr Leu Thr Ile Ser Gly Leu Gln Ser Glu
 65                  70                  75                  80

Asp Glu Ala Glu Tyr Phe Cys Ser Ser Trp Asp Asn Arg Leu Arg Gly
                 85                  90                  95

Val Leu Phe Gly Gly Gly Thr Gln Leu Thr Val Leu
                100                 105

<210> SEQ ID NO 347
<211> LENGTH: 324
<212> TYPE: DNA
<213> ORGANISM: artificial
<220> FEATURE:
<223> OTHER INFORMATION: VH chain

<400> SEQUENCE: 347
ctgctgactc aaccggcctc agtgtccggg ttcctgggcc agacggtcac catctcctgc    60
actggaagca gctccaacat cgaaacaggt tatgtacact ggtaccaaca gttcccagga   120
acaggcccca gaaccctcat ctatgatctt catgaccgac cctcaggggt ccccgatcgc   180
ttctctggct ccaggtccgg caacacagcc actcttacaa tctctggact ccaggctgag   240
gatgaggctg attattactg ctcagcctgg gacaccagtc tcagtgcgta cttgttcggc   300
gcaggaatcc agctcaccgt ccta                                          324

<210> SEQ ID NO 348
<211> LENGTH: 108
<212> TYPE: PRT
<213> ORGANISM: artificial
<220> FEATURE:
<223> OTHER INFORMATION: VH chain

<400> SEQUENCE: 348

Leu Leu Thr Gln Pro Ala Ser Val Ser Gly Phe Leu Gly Gln Thr Val
  1               5                  10                  15

Thr Ile Ser Cys Thr Gly Ser Ser Asn Ile Glu Thr Gly Tyr Val
                20                  25                  30

His Trp Tyr Gln Gln Phe Pro Gly Thr Gly Pro Arg Thr Leu Ile Tyr
                35                  40                  45

Asp Leu His Asp Arg Pro Ser Gly Val Pro Asp Arg Phe Ser Gly Ser
             50                  55                  60

Arg Ser Gly Asn Thr Ala Thr Leu Thr Ile Ser Gly Leu Gln Ala Glu
 65                  70                  75                  80

Asp Glu Ala Asp Tyr Tyr Cys Ser Ala Trp Asp Thr Ser Leu Ser Ala
                 85                  90                  95

Tyr Leu Phe Gly Ala Gly Ile Gln Leu Thr Val Leu
                100                 105

<210> SEQ ID NO 349
<211> LENGTH: 330
<212> TYPE: DNA
<213> ORGANISM: artificial
<220> FEATURE:
<223> OTHER INFORMATION: VH chain

<400> SEQUENCE: 349
```

```
gtgctgactc agcctccttc tgtgtctgca gccctggggc agagggtcac catctcctgc    60
actggaagta acaccaacat cggcagtggt tctgatgtac agtggtacca gcagttccca   120
ggaaagtccc ctaaacctat catttatggt aatagggatc gaccctcggg ggtcccggct   180
cgattctctg gctccaagtc aggcaacaca gccaccctga ccatcactgg gatccaggct   240
gaggatgagg ctgattatta ctgccagtcc tatgatgaca cctcgatgg tcattgcgtg    300 ttcggctcag gaacccaact caccgtcctc                                    330
```

<210> SEQ ID NO 350
<211> LENGTH: 110
<212> TYPE: PRT
<213> ORGANISM: artificial
<220> FEATURE:
<223> OTHER INFORMATION: VH chain

<400> SEQUENCE: 350

```
Val Leu Thr Gln Pro Pro Ser Val Ser Ala Ala Leu Gly Gln Arg Val
1               5                   10                  15

Thr Ile Ser Cys Thr Gly Ser Asn Thr Asn Ile Gly Ser Gly Ser Asp
            20                  25                  30

Val Gln Trp Tyr Gln Gln Phe Pro Gly Lys Ser Pro Lys Pro Ile Ile
        35                  40                  45

Tyr Gly Asn Arg Asp Arg Pro Ser Gly Val Pro Ala Arg Phe Ser Gly
    50                  55                  60

Ser Lys Ser Gly Asn Thr Ala Thr Leu Thr Ile Thr Gly Ile Gln Ala
65                  70                  75                  80

Glu Asp Glu Ala Asp Tyr Tyr Cys Gln Ser Tyr Asp Asp Asn Leu Asp
                85                  90                  95

Gly His Cys Val Phe Gly Ser Gly Thr Gln Leu Thr Val Leu
            100                 105                 110
```

<210> SEQ ID NO 351
<211> LENGTH: 324
<212> TYPE: DNA
<213> ORGANISM: artificial
<220> FEATURE:
<223> OTHER INFORMATION: VH chain
<220> FEATURE:
<221> NAME/KEY: misc_feature
<222> LOCATION: (39)..(39)
<223> OTHER INFORMATION: n is a, c, g, or t

<400> SEQUENCE: 351

```
gcgttgaccc aaccagcctc cgtgtccggg tccctgggnc agaaagtcac catctcctgc    60
actggaagca actccaacat cggtgataat tttgtgggct ggtaccaaca actcccagga   120
ataggcccta gaaccgtcat ctatggtgat gattaccgac cttcaggcat ccccgatcga   180
ttctctggct ccaagtcagg cagttcagcc accctgacca tctctgggct ccaggctgag   240
gacgaggctg attattactg ctcatcatgg gactatagtc tcagaggtcc tgtgttcggc   300
ggaggcaccc acctgaccgt cctc                                          324
```

<210> SEQ ID NO 352
<211> LENGTH: 108
<212> TYPE: PRT
<213> ORGANISM: artificial
<220> FEATURE:
<223> OTHER INFORMATION: VH chain

<400> SEQUENCE: 352

Ala Leu Thr Gln Pro Ala Ser Val Ser Gly Ser Leu Gly Gln Lys Val

```
                1               5                  10                 15
Thr Ile Ser Cys Thr Gly Ser Asn Ser Asn Ile Gly Asp Asn Phe Val
                20                 25                 30

Gly Trp Tyr Gln Gln Leu Pro Gly Ile Gly Pro Arg Thr Val Ile Tyr
         35                 40                 45

Gly Asp Asp Tyr Arg Pro Ser Gly Ile Pro Asp Arg Phe Ser Gly Ser
         50                 55                 60

Lys Ser Gly Ser Ser Ala Thr Leu Thr Ile Ser Gly Leu Gln Ala Glu
 65                 70                 75                 80

Asp Glu Ala Asp Tyr Tyr Cys Ser Ser Trp Asp Tyr Ser Leu Arg Gly
                 85                 90                 95

Pro Val Phe Gly Gly Gly Thr His Leu Thr Val Leu
             100                105
```

<210> SEQ ID NO 353
<211> LENGTH: 327
<212> TYPE: DNA
<213> ORGANISM: artificial
<220> FEATURE:
<223> OTHER INFORMATION: VH chain

<400> SEQUENCE: 353

```
gggttgaatc agcctccctc tgtgtctgca gccctggggc agagggtcac catttcctgc    60
actggaagtg acaccaacat cggcggtgat catgatgttc agtggtaccg ccaactccca   120
ggaaagtccc ctgaagctat catttacggt aataccaatc gaccctcggg ggtctcggtt   180
cgattctctg gctccaagtc aggcaacaca gccaccctga ccatcagtgg gatccaggct   240
gaggatgagg ctgattatta ctgccagtcc tatgatgaca cttcgatgg ttgggtattc   300
ggtgaaggga cccacctgac cgtcctc                                       327
```

<210> SEQ ID NO 354
<211> LENGTH: 109
<212> TYPE: PRT
<213> ORGANISM: artificial
<220> FEATURE:
<223> OTHER INFORMATION: VH chain

<400> SEQUENCE: 354

```
Gly Leu Asn Gln Pro Pro Ser Val Ser Ala Ala Leu Gly Gln Arg Val
 1               5                 10                 15

Thr Ile Ser Cys Thr Gly Ser Asp Thr Asn Ile Gly Gly Asp His Asp
                20                 25                 30

Val Gln Trp Tyr Arg Gln Leu Pro Gly Lys Ser Pro Glu Ala Ile Ile
         35                 40                 45

Tyr Gly Asn Thr Asn Arg Pro Ser Gly Val Ser Val Arg Phe Ser Gly
         50                 55                 60

Ser Lys Ser Gly Asn Thr Ala Thr Leu Thr Ile Ser Gly Ile Gln Ala
 65                 70                 75                 80

Glu Asp Glu Ala Asp Tyr Tyr Cys Gln Ser Tyr Asp Asp Asn Phe Asp
                 85                 90                 95

Gly Trp Val Phe Gly Glu Gly Thr His Leu Thr Val Leu
             100                105
```

<210> SEQ ID NO 355
<211> LENGTH: 324
<212> TYPE: DNA
<213> ORGANISM: artificial
<220> FEATURE:
<223> OTHER INFORMATION: VH chain

<400> SEQUENCE: 355

```
gtgctgactc agcttgcctc agtgactggg tccctgggcc agagggtcac catctcctgc    60
actggaagca cgccaacat cggtacatat aatgttggct ggttccagca gctcccggga    120
gcaggcccca gaaccgtcat taatagaagt gataaccgac cctcgggggt cccggatcga    180
ttctctggtt ccaggtcagg cagcacagcc accctgacca tctctgggct ccaggctgag    240
gacgaggctg agtattactg ctcaacatgg gacaaggatc tcaataccta cgtcttcggc    300
tcaggaatcg agctgaccgt ccta                                            324
```

<210> SEQ ID NO 356
<211> LENGTH: 108
<212> TYPE: PRT
<213> ORGANISM: artificial
<220> FEATURE:
<223> OTHER INFORMATION: VH chain

<400> SEQUENCE: 356

```
Val Leu Thr Gln Leu Ala Ser Val Thr Gly Ser Leu Gly Gln Arg Val
1               5                   10                  15
Thr Ile Ser Cys Thr Gly Ser Ser Ala Asn Ile Gly Thr Tyr Asn Val
            20                  25                  30
Gly Trp Phe Gln Gln Leu Pro Gly Ala Gly Pro Arg Thr Val Ile Asn
        35                  40                  45
Arg Ser Asp Asn Arg Pro Ser Gly Val Pro Asp Arg Phe Ser Gly Ser
    50                  55                  60
Arg Ser Gly Ser Thr Ala Thr Leu Thr Ile Ser Gly Leu Gln Ala Glu
65                  70                  75                  80
Asp Glu Ala Glu Tyr Tyr Cys Ser Thr Trp Asp Lys Asp Leu Asn Thr
                85                  90                  95
Tyr Val Phe Gly Ser Gly Ile Glu Leu Thr Val Leu
            100                 105
```

<210> SEQ ID NO 357
<211> LENGTH: 324
<212> TYPE: DNA
<213> ORGANISM: artificial
<220> FEATURE:
<223> OTHER INFORMATION: VH chain

<400> SEQUENCE: 357

```
gtgctgactc agcctccttc agtgtcgggg tcccttggcc agagggtcac catttcctgc    60
tccggaacta tgaataacat cgggactgtt ggtgcgagtt ggtaccaaca ggtcccagga    120
aaggccccta aactcatcgc gaacagtggt gggagtcgac cgtcagggt cccctgaccgg    180
ttttccggcg ccgactcagg cgattcagcc accctgacca tcactggact ccaggctgag    240
gacgaggctg attatttctg tcagtctatt gattccgcgc ttgatgagta cgtgttcggc    300
tcaggaaccc aactgaccgt cctt                                            324
```

<210> SEQ ID NO 358
<211> LENGTH: 108
<212> TYPE: PRT
<213> ORGANISM: artificial
<220> FEATURE:
<223> OTHER INFORMATION: VH chain

<400> SEQUENCE: 358

```
Val Leu Thr Gln Pro Pro Ser Val Ser Gly Ser Leu Gly Gln Arg Val
1               5                   10                  15
```

```
Thr Ile Ser Cys Ser Gly Thr Met Asn Asn Ile Gly Thr Val Gly Ala
            20                  25                  30

Ser Trp Tyr Gln Gln Val Pro Gly Lys Ala Pro Lys Leu Ile Ala Asn
        35                  40                  45

Ser Gly Gly Ser Arg Pro Ser Gly Val Pro Asp Arg Phe Ser Gly Ala
    50                  55                  60

Asp Ser Gly Asp Ser Ala Thr Leu Thr Ile Thr Gly Leu Gln Ala Glu
65                  70                  75                  80

Asp Glu Ala Asp Tyr Phe Cys Gln Ser Ile Asp Ser Ala Leu Asp Glu
                85                  90                  95

Tyr Val Phe Gly Ser Gly Thr Gln Leu Thr Val Leu
                100                 105

<210> SEQ ID NO 359
<211> LENGTH: 315
<212> TYPE: DNA
<213> ORGANISM: artificial
<220> FEATURE:
<223> OTHER INFORMATION: VH chain

<400> SEQUENCE: 359
gtgctgactc agcctccctc agtatcagtc tctctgggac agacagcaac catctcctgc      60
tctggagaga gtctgagtaa atattatgca caatggttcc agcagagggc aggccaagtc     120
cctgtgttgg tcatatataa ggacactgag cggccctctg ggatccctga ccgattctcc     180
ggctccagtt cagggaacac acacaccctg accatcagcg gggctcgggc cgaggacgag     240
gctgactatt actgcgagtc agaagtcagt actggtactg ctgtgttcgg cggaggcacc     300
cacctgaccg tcctc                                                      315

<210> SEQ ID NO 360
<211> LENGTH: 105
<212> TYPE: PRT
<213> ORGANISM: artificial
<220> FEATURE:
<223> OTHER INFORMATION: VH chain

<400> SEQUENCE: 360

Val Leu Thr Gln Pro Pro Ser Val Ser Val Ser Leu Gly Gln Thr Ala
1               5                   10                  15

Thr Ile Ser Cys Ser Gly Glu Ser Leu Ser Lys Tyr Tyr Ala Gln Trp
            20                  25                  30

Phe Gln Gln Arg Ala Gly Gln Val Pro Val Leu Val Ile Tyr Lys Asp
        35                  40                  45

Thr Glu Arg Pro Ser Gly Ile Pro Asp Arg Phe Ser Gly Ser Ser Ser
    50                  55                  60

Gly Asn Thr His Thr Leu Thr Ile Ser Gly Ala Arg Ala Glu Asp Glu
65                  70                  75                  80

Ala Asp Tyr Tyr Cys Glu Ser Glu Val Ser Thr Gly Thr Ala Val Phe
                85                  90                  95

Gly Gly Gly Thr His Leu Thr Val Leu
                100                 105

<210> SEQ ID NO 361
<211> LENGTH: 327
<212> TYPE: DNA
<213> ORGANISM: artificial
<220> FEATURE:
<223> OTHER INFORMATION: VH chain
```

<400> SEQUENCE: 361

```
ctgctgaccc aaccggcctc agtgtctggg tccctgggac agagggtcac catctcctgc        60
actggaagca cctccaattt tggtagctct tatgtgggct ggtaccaacg actcccagga       120
acaggccccc gaaccctcat atatagtact aatatccgac ccccgggggt ccccgatcga       180
ttttctggct ccgggtcagg caatacagcg accctgacca tatctggact ccaggctgag       240
gacgagggtg attattactg ctcagcatat gacagcaatc tcagtagtga gatcgtgttt       300
ggcggaggca cccacctgac cgtcctc                                            327
```

<210> SEQ ID NO 362
<211> LENGTH: 109
<212> TYPE: PRT
<213> ORGANISM: artificial
<220> FEATURE:
<223> OTHER INFORMATION: VH chain

<400> SEQUENCE: 362

```
Leu Leu Thr Gln Pro Ala Ser Val Ser Gly Ser Leu Gly Gln Arg Val
 1               5                  10                  15
Thr Ile Ser Cys Thr Gly Ser Ser Asn Phe Gly Ser Ser Tyr Val
            20                  25                  30
Gly Trp Tyr Gln Arg Leu Pro Gly Thr Gly Pro Arg Thr Leu Ile Tyr
        35                  40                  45
Ser Thr Asn Ile Arg Pro Pro Gly Val Pro Asp Arg Phe Ser Gly Ser
    50                  55                  60
Gly Ser Gly Asn Thr Ala Thr Leu Thr Ile Ser Gly Leu Gln Ala Glu
65                  70                  75                  80
Asp Glu Gly Asp Tyr Tyr Cys Ser Ala Tyr Asp Ser Asn Leu Ser Ser
                85                  90                  95
Glu Ile Val Phe Gly Gly Gly Thr His Leu Thr Val Leu
            100                 105
```

<210> SEQ ID NO 363
<211> LENGTH: 327
<212> TYPE: DNA
<213> ORGANISM: artificial
<220> FEATURE:
<223> OTHER INFORMATION: VH chain

<400> SEQUENCE: 363

```
gtgctgactc agcctccctc agtgtctgcg gtcctgggac agacggtcac catctcctgc        60
actggaagca gcaccaacat tggcagtggt tatgatgtac attggtacca acaggcccca       120
ggaaagtccc ctaagactat catctatggt aatagtaaac gaccctcagg gtcccggat        180
cgcttctctg gctccaagtc aggcagcaca gcctctctga ccatcactgg gctccaggct       240
gaggacgagg ctgattatta ctgccagtcc tctgatgaca cgtccataa ttacgtgttc       300
ggctcaggaa cccaactgac cgtccta                                            327
```

<210> SEQ ID NO 364
<211> LENGTH: 109
<212> TYPE: PRT
<213> ORGANISM: artificial
<220> FEATURE:
<223> OTHER INFORMATION: VH chain

<400> SEQUENCE: 364

```
Val Leu Thr Gln Pro Pro Ser Val Ser Ala Val Leu Gly Gln Thr Val
 1               5                  10                  15
```

```
Thr Ile Ser Cys Thr Gly Ser Ser Thr Asn Ile Gly Ser Gly Tyr Asp
            20                  25                  30

Val His Trp Tyr Gln Gln Ala Pro Gly Lys Ser Pro Lys Thr Ile Ile
            35                  40                  45

Tyr Gly Asn Ser Lys Arg Pro Ser Gly Val Pro Asp Arg Phe Ser Gly
 50                  55                  60

Ser Lys Ser Gly Ser Thr Ala Ser Leu Thr Ile Thr Gly Leu Gln Ala
 65                  70                  75                  80

Glu Asp Glu Ala Asp Tyr Tyr Cys Gln Ser Ser Asp Asn Val His
                85                  90                  95

Asn Tyr Val Phe Gly Ser Gly Thr Gln Leu Thr Val Leu
            100                 105
```

<210> SEQ ID NO 365
<211> LENGTH: 324
<212> TYPE: DNA
<213> ORGANISM: artificial
<220> FEATURE:
<223> OTHER INFORMATION: VH chain

<400> SEQUENCE: 365

```
ctgctgactc agcctgcctc agtgtctggg tccctgggcc agaaggtcac cctctcctgc      60
actgggagca gctccaacat cggtggtaat tatgtgggct ggtaccaaca acttccagga     120
gtaggcccta gaaccgtcat ctatgataat gataaccgac ctttaggggt ccccgatcga     180
ttctctggct ccaagtcagg gagttcagcc accctgacca tctctgggct ccaggctgag     240
gacgaggctg aatattattg ttcgtcatgg gatgatagtc tcagtcagac tgtattcggc     300
ggaggcaccc acctgaccgt cctc                                            324
```

<210> SEQ ID NO 366
<211> LENGTH: 108
<212> TYPE: PRT
<213> ORGANISM: artificial
<220> FEATURE:
<223> OTHER INFORMATION: VH chain

<400> SEQUENCE: 366

```
Leu Leu Thr Gln Pro Ala Ser Val Ser Gly Ser Leu Gly Gln Lys Val
1               5                   10                  15

Thr Leu Ser Cys Thr Gly Ser Ser Ser Asn Ile Gly Gly Asn Tyr Val
            20                  25                  30

Gly Trp Tyr Gln Gln Leu Pro Gly Val Gly Pro Arg Thr Val Ile Tyr
            35                  40                  45

Asp Asn Asp Asn Arg Pro Leu Gly Val Pro Asp Arg Phe Ser Gly Ser
 50                  55                  60

Lys Ser Gly Ser Ser Ala Thr Leu Thr Ile Ser Gly Leu Gln Ala Glu
 65                  70                  75                  80

Asp Glu Ala Glu Tyr Tyr Cys Ser Ser Trp Asp Asp Ser Leu Ser Gln
                85                  90                  95

Thr Val Phe Gly Gly Gly Thr His Leu Thr Val Leu
            100                 105
```

<210> SEQ ID NO 367
<211> LENGTH: 323
<212> TYPE: DNA
<213> ORGANISM: artificial
<220> FEATURE:
<223> OTHER INFORMATION: VL chain

<400> SEQUENCE: 367

```
gtgctgactc agctgcctca gtgtccgggt ccctgggcca gagggtcacc atctcctgct      60
ctggaagcag ctccaacatc ggtaaccatg tggcctggtt ccaacagctc ccgggaacag     120
gccccagaac cctcatctat ggtaataata accgaccctc aggggtcccc gatcggttct     180
ctggctccag gtcaggcagc acagccaccc tgaccatctc tgggctccag actgaggatg     240
aggctgatta ttactgctca tcgtgggaca ccagtctcag cggttacgtg ttcggctcag     300
gaaccgagct gaccgtcctt ggc                                             323
```

<210> SEQ ID NO 368
<211> LENGTH: 107
<212> TYPE: PRT
<213> ORGANISM: artificial
<220> FEATURE:
<223> OTHER INFORMATION: VL chain

<400> SEQUENCE: 368

Ala Asp Ser Ala Ala Ser Val Ser Gly Ser Leu Gly Gln Arg Val Thr
1               5                   10                  15

Ile Ser Cys Ser Gly Ser Ser Asn Ile Gly Asn His Val Ala Trp
            20                  25                  30

Phe Gln Gln Leu Pro Gly Thr Gly Pro Arg Thr Leu Ile Tyr Gly Asn
        35                  40                  45

Asn Asn Arg Pro Ser Gly Val Pro Asp Arg Phe Ser Gly Ser Arg Ser
    50                  55                  60

Gly Ser Thr Ala Thr Leu Thr Ile Ser Gly Leu Gln Thr Glu Asp Glu
65                  70                  75                  80

Ala Asp Tyr Tyr Cys Ser Ser Trp Asp Thr Ser Leu Ser Gly Tyr Val
                85                  90                  95

Phe Gly Ser Gly Thr Glu Leu Thr Val Leu Gly
            100                 105

<210> SEQ ID NO 369
<211> LENGTH: 329
<212> TYPE: DNA
<213> ORGANISM: artificial
<220> FEATURE:
<223> OTHER INFORMATION: VL chain

<400> SEQUENCE: 369

```
bvctgctgac ccaaccggct tcagtgtctg ggtccctggg acagaaggtc accatctcct      60
gcactggaag cagctccaac attggtagta attatgtggc ctggtaccag cagctcccag     120
gaacaggccc cagaaccctc atctatagta atactaatcg attttcgggg gtccccgatc     180
gattctctgg ctccaggtca ggcagcacag caaccctgac catctctggg ctccaggctg     240
aggacgaggc tgattattac tgctcaacat atgacaacag tctcagtggt cttgtgttcg     300 gcggggggcac ccagctgacc gtcctcggc                                      329
```

<210> SEQ ID NO 370
<211> LENGTH: 109
<212> TYPE: PRT
<213> ORGANISM: artificial
<220> FEATURE:
<223> OTHER INFORMATION: VL chain

<400> SEQUENCE: 370

Leu Leu Thr Gln Pro Ala Ser Val Ser Gly Ser Leu Gly Gln Lys Val
1               5                   10                  15

Thr Ile Ser Cys Thr Gly Ser Ser Ser Asn Ile Gly Ser Asn Tyr Val

-continued

```
                    20                  25                  30
Ala Trp Tyr Gln Gln Leu Pro Gly Thr Gly Pro Arg Thr Leu Ile Tyr
            35                  40                  45

Ser Asn Thr Asn Arg Phe Ser Gly Val Pro Asp Arg Phe Ser Gly Ser
 50                  55                  60

Arg Ser Gly Ser Thr Ala Thr Leu Thr Ile Ser Gly Leu Gln Ala Glu
 65                  70                  75                  80

Asp Glu Ala Asp Tyr Tyr Cys Ser Thr Tyr Asp Asn Ser Leu Ser Gly
                    85                  90                  95

Leu Val Phe Gly Gly Gly Thr Gln Leu Thr Val Leu Gly
                100                 105

<210> SEQ ID NO 371
<211> LENGTH: 315
<212> TYPE: DNA
<213> ORGANISM: artificial
<220> FEATURE:
<223> OTHER INFORMATION: VL chain

<400> SEQUENCE: 371
gggttgactc agctgccttc catgagtgtg ccctgaggc agacggcccg catcacctgt       60
gggggaggca acatcgaaag taaaaatgtt cattggtacc aacagaaact gggccaggcc     120
cctatacaga tcgtctatta tgatacccgg aggccggtag ggatccctga acgattctct     180
ggcgccaagt cggggaacac ggccaccctg accatcagcg gggccctggc cgaggacgag     240
gctgactatt actgtcaggt gtgggacagc ggcactctca tattcggcgg aggcacccag     300
ctgaccgtcc tcggc                                                     315

<210> SEQ ID NO 372
<211> LENGTH: 105
<212> TYPE: PRT
<213> ORGANISM: artificial
<220> FEATURE:
<223> OTHER INFORMATION: VL chain

<400> SEQUENCE: 372

Gly Leu Thr Gln Leu Pro Ser Met Ser Val Ala Leu Arg Gln Thr Ala
 1               5                  10                  15

Arg Ile Thr Cys Gly Gly Gly Asn Ile Glu Ser Lys Asn Val His Trp
                    20                  25                  30

Tyr Gln Gln Lys Leu Gly Gln Ala Pro Ile Gln Ile Val Tyr Tyr Asp
            35                  40                  45

Thr Arg Arg Pro Val Gly Ile Pro Glu Arg Phe Ser Gly Ala Lys Ser
 50                  55                  60

Gly Asn Thr Ala Thr Leu Thr Ile Ser Gly Ala Leu Ala Glu Asp Glu
 65                  70                  75                  80

Ala Asp Tyr Tyr Cys Gln Val Trp Asp Ser Gly Thr Leu Ile Phe Gly
                    85                  90                  95

Gly Gly Thr Gln Leu Thr Val Leu Gly
                100                 105

<210> SEQ ID NO 373
<211> LENGTH: 327
<212> TYPE: DNA
<213> ORGANISM: artificial
<220> FEATURE:
<223> OTHER INFORMATION: VL chain

<400> SEQUENCE: 373
```

-continued

```
gtgctgactc agcttgcctc agtgtctggg tccctgggcc agagggtcac catctcctgc    60
actggaagca gctccaatgt tgggtatggc aatgatgtgg gctggtacca gcagctccca   120
ggaacaggcc ccagaaccct catctatggt agcagtatcc gaccctcggg ggtccctgat   180
cgattctctg gctccaaatc aggcaactca gccacactga ccatctctgg gctccaggct   240
gaggatgaag ctgattatta ctgttcatcc tatgacagca gtctcggtta cgtgttcggc   300
tcaggaatcg agctcaccgt ccttggc                                       327
```

<210> SEQ ID NO 374
<211> LENGTH: 109
<212> TYPE: PRT
<213> ORGANISM: artificial
<220> FEATURE:
<223> OTHER INFORMATION: VL chain

<400> SEQUENCE: 374

```
Val Leu Thr Gln Leu Ala Ser Val Ser Gly Ser Leu Gly Gln Arg Val
 1               5                  10                  15

Thr Ile Ser Cys Thr Gly Ser Ser Asn Val Gly Tyr Gly Asn Asp
             20                  25                  30

Val Gly Trp Tyr Gln Gln Leu Pro Gly Thr Gly Pro Arg Thr Leu Ile
         35                  40                  45

Tyr Gly Ser Ser Ile Arg Pro Ser Gly Val Pro Asp Arg Phe Ser Gly
     50                  55                  60

Ser Lys Ser Gly Asn Ser Ala Thr Leu Thr Ile Ser Gly Leu Gln Ala
 65                  70                  75                  80

Glu Asp Glu Ala Asp Tyr Tyr Cys Ser Ser Tyr Asp Ser Ser Leu Gly
                 85                  90                  95

Tyr Val Phe Gly Ser Gly Ile Glu Leu Thr Val Leu Gly
            100                 105
```

<210> SEQ ID NO 375
<211> LENGTH: 324
<212> TYPE: DNA
<213> ORGANISM: artificial
<220> FEATURE:
<223> OTHER INFORMATION: VL chain

<400> SEQUENCE: 375

```
gtgctgactc agctaacctc agtgtcgggg tccctgggcc agagagtcac catctcctgc    60
tctggaagga caaacatcga taggtttggt gtgacttggt atcagcagtt cccaggaaag   120
gcccctagac tcctcgtgga cagtgatggg atcgaccgt caggtgtccc tgaccgattt    180
tccggctcca agtctgccaa ctcggccact ctgaccatca ctggtctcca tgctgaggac   240
gaggctgatt attattgtct gtctattggt cccacacttg tgtttacgt gttcggctca    300 ggaatcgagc tgaccgtcct aggc                                         324
```

<210> SEQ ID NO 376
<211> LENGTH: 108
<212> TYPE: PRT
<213> ORGANISM: artificial
<220> FEATURE:
<223> OTHER INFORMATION: VL chain

<400> SEQUENCE: 376

```
Val Leu Thr Gln Leu Thr Ser Val Ser Gly Ser Leu Gly Gln Arg Val
 1               5                  10                  15

Thr Ile Ser Cys Ser Gly Arg Thr Asn Ile Asp Arg Phe Gly Val Thr
             20                  25                  30
```

```
Trp Tyr Gln Gln Phe Pro Gly Lys Ala Pro Arg Leu Leu Val Asp Ser
            35                  40                  45

Asp Gly Asp Arg Pro Ser Gly Val Pro Asp Arg Phe Ser Gly Ser Lys
 50                  55                  60

Ser Ala Asn Ser Ala Thr Leu Thr Ile Thr Gly Leu His Ala Glu Asp
 65                  70                  75                  80

Glu Ala Asp Tyr Tyr Cys Leu Ser Ile Gly Pro Thr Leu Gly Val Tyr
                 85                  90                  95

Val Phe Gly Ser Gly Ile Glu Leu Thr Val Leu Gly
                100                 105
```

<210> SEQ ID NO 377
<211> LENGTH: 321
<212> TYPE: DNA
<213> ORGANISM: artificial
<220> FEATURE:
<223> OTHER INFORMATION: VL chain

<400> SEQUENCE: 377

```
gtgctgactc agccaccctc agtgtcgggg tcccttggcc agagggtcac catttcctgc      60
tctggaagca cgaacaacat cggcattgtt ggtgcgagct ggtaccaaca gcccccagga     120
aaggccccta aactcctcgt atacactaat ggggtcgac cgtcagggt ccctgaccgg       180 ttttccggct ccaagtctgg caactcagcc accctgacca tcactggcct tcaggctgag    240
gacgaggctg attattactg ccagtcctct gattccatgc ttgctgtgtt cggcggaggc    300
acccacctga ccgtcctcgg c                                              321
```

<210> SEQ ID NO 378
<211> LENGTH: 107
<212> TYPE: PRT
<213> ORGANISM: artificial
<220> FEATURE:
<223> OTHER INFORMATION: VL chain

<400> SEQUENCE: 378

```
Val Leu Thr Gln Pro Pro Ser Val Ser Gly Ser Leu Gly Gln Arg Val
 1               5                  10                  15

Thr Ile Ser Cys Ser Gly Ser Thr Asn Asn Ile Gly Ile Val Gly Ala
                 20                  25                  30

Ser Trp Tyr Gln Gln Pro Pro Gly Lys Ala Pro Lys Leu Leu Val Tyr
            35                  40                  45

Thr Asn Gly Gly Arg Pro Ser Gly Val Pro Asp Arg Phe Ser Gly Ser
 50                  55                  60

Lys Ser Gly Asn Ser Ala Thr Leu Thr Ile Thr Gly Leu Gln Ala Glu
 65                  70                  75                  80

Asp Glu Ala Asp Tyr Tyr Cys Gln Ser Ser Asp Ser Met Leu Ala Val
                 85                  90                  95

Phe Gly Gly Gly Thr His Leu Thr Val Leu Gly
                100                 105
```

<210> SEQ ID NO 379
<211> LENGTH: 268
<212> TYPE: DNA
<213> ORGANISM: artificial
<220> FEATURE:
<223> OTHER INFORMATION: VL chain

<400> SEQUENCE: 379

```
gtgctgactc agcctccttc agtgtcgggg tcccttggcc agaagatcac catctcctgt      60
```

```
tctggaagca cgaacaacgt cggtgttgtt ggtgcgggct ggtaccaaca gctcccagga      120
aaggccccta aactcctcgt atttagtgat ggggttcgac cgtcaggggt ccctgaccgg      180
ttttccggct ccaagtttgg cgactcacac accctgacca tcactggact tcaggctgag      240
gacgaggctg attattattg ccagtcgt                                        268

<210> SEQ ID NO 380
<211> LENGTH: 109
<212> TYPE: PRT
<213> ORGANISM: artificial
<220> FEATURE:
<223> OTHER INFORMATION: VL chain

<400> SEQUENCE: 380

Val Leu Thr Gln Pro Pro Ser Val Ser Gly Leu Gly Gln Lys Ile
1               5                   10                  15

Thr Ile Ser Cys Ser Gly Ser Thr Asn Asn Val Gly Val Gly Ala
                20                  25                  30

Gly Trp Tyr Gln Gln Leu Pro Gly Lys Ala Pro Lys Leu Leu Val Phe
            35                  40                  45

Ser Asp Gly Val Arg Pro Ser Gly Val Pro Asp Arg Phe Ser Gly Ser
        50                  55                  60

Lys Phe Gly Asp Ser His Thr Leu Thr Ile Thr Gly Leu Gln Ala Glu
65                  70                  75                  80

Asp Glu Ala Asp Tyr Tyr Cys Gln Ser Tyr Asp Thr Thr Leu His Thr
                85                  90                  95

Tyr Val Phe Gly Ser Gly Ile Glu Leu Ile Val Leu Gly
            100                 105

<210> SEQ ID NO 381
<211> LENGTH: 330
<212> TYPE: DNA
<213> ORGANISM: artificial
<220> FEATURE:
<223> OTHER INFORMATION: VL chain

<400> SEQUENCE: 381
gcgctgaccc agcctgcctc agtgtcgggg tcccttggcc agagggtcac catttcctgc      60
tctggaacca cggacaatat cggtattgtt ggtgcgaact ggtaccaaca actcccagga     120
aaggccccta aactcctcgt gtacagtgat gggaatcgac cggcaggggt ccctgaccgg     180
ttttccggct ccaagtctgg cagctcagcc accctgatca tcactgggct tcaggctgag     240
gacgagtctg attattactg tcagtctgtt gatcccacgc ttggtgctcg gtacgtcttc     300
ggctcaggaa tcgagctgac cgtcctaggc                                     330

<210> SEQ ID NO 382
<211> LENGTH: 110
<212> TYPE: PRT
<213> ORGANISM: artificial
<220> FEATURE:
<223> OTHER INFORMATION: VL chain

<400> SEQUENCE: 382

Ala Leu Thr Gln Pro Ala Ser Val Ser Gly Ser Leu Gly Gln Arg Val
1               5                   10                  15

Thr Ile Ser Cys Ser Gly Thr Thr Asp Asn Ile Gly Ile Val Gly Ala
                20                  25                  30

Asn Trp Tyr Gln Gln Leu Pro Gly Lys Ala Pro Lys Leu Leu Val Tyr
            35                  40                  45
```

Ser Asp Gly Asn Arg Pro Ala Gly Val Pro Asp Arg Phe Gly Ser
    50                  55                  60

Lys Ser Gly Ser Ser Ala Thr Leu Ile Ile Thr Gly Leu Gln Ala Glu
 65                  70                  75                  80

Asp Glu Ser Asp Tyr Tyr Cys Gln Ser Val Asp Pro Thr Leu Gly Ala
                 85                  90                  95

Arg Tyr Val Phe Gly Ser Gly Ile Glu Leu Thr Val Leu Gly
            100                 105                 110

<210> SEQ ID NO 383
<211> LENGTH: 327
<212> TYPE: DNA
<213> ORGANISM: artificial
<220> FEATURE:
<223> OTHER INFORMATION: VL chain

<400> SEQUENCE: 383
gtgctgactc agcctccctc agtgtccggg ttcctgggcc agagggtcac catctcctgc      60
actggagaca cccccaacat cggtagaggt tatgtgcact ggtaccaaca gctcccagga     120
acaggcccca gaaccctcat ctatggtgtt agtaaccgac cctcagggt ccccgatcga     180 ttctctggct ccaggtcagg cagcacaggc actctgacaa tctctgggct ccaggctgag     240
gatgaggctg attattattg ctcgtcctgg gacaccactc tcagtgctta cgtgttcggc     300
tcaggaatcg agctgaccgt ccttggc                                         327

<210> SEQ ID NO 384
<211> LENGTH: 109
<212> TYPE: PRT
<213> ORGANISM: artificial
<220> FEATURE:
<223> OTHER INFORMATION: VL chain

<400> SEQUENCE: 384

Val Leu Thr Gln Pro Pro Ser Val Ser Gly Phe Leu Gly Gln Arg Val
 1               5                  10                  15

Thr Ile Ser Cys Thr Gly Asp Thr Pro Asn Ile Gly Arg Gly Tyr Val
             20                  25                  30

His Trp Tyr Gln Gln Leu Pro Gly Thr Gly Pro Arg Thr Leu Ile Tyr
         35                  40                  45

Gly Val Ser Asn Arg Pro Ser Gly Val Pro Asp Arg Phe Ser Gly Ser
     50                  55                  60

Arg Ser Gly Ser Thr Gly Thr Leu Thr Ile Ser Gly Leu Gln Ala Glu
 65                  70                  75                  80

Asp Glu Ala Asp Tyr Tyr Cys Ser Ser Trp Asp Thr Thr Leu Ser Ala
                 85                  90                  95

Tyr Val Phe Gly Ser Gly Ile Glu Leu Thr Val Leu Gly
            100                 105

<210> SEQ ID NO 385
<211> LENGTH: 330
<212> TYPE: DNA
<213> ORGANISM: artificial
<220> FEATURE:
<223> OTHER INFORMATION: VL chain

<400> SEQUENCE: 385
gtgttgactc agccagcctc agtgtctggg tccctgggcc agagggtcac catctcctgc      60
actggaagca gttccaatgt tggttatggc aattctgtgg gttggtatca gcagctccca     120

-continued

```
ggaacaagtc ccagaaccct catcattgat agtaataacc gaccctcggg ggtccctgat        180
cggttctcta gctccaggtc aggcaacata ggaaccctga ccatatctgg gctccaggct        240
gaggatgaag ccgattattg ctgtacatgt tttgacagca gtctcaatgg tggtgttttc        300
ggcggaggca cccagctgac cgtcctcggc                                         330
```

<210> SEQ ID NO 386
<211> LENGTH: 110
<212> TYPE: PRT
<213> ORGANISM: artificial
<220> FEATURE:
<223> OTHER INFORMATION: VL chain

<400> SEQUENCE: 386

```
Val Leu Thr Gln Pro Ala Ser Val Ser Gly Ser Leu Gly Gln Arg Val
1               5                   10                  15

Thr Ile Ser Cys Thr Gly Ser Ser Ser Asn Val Gly Tyr Gly Asn Ser
            20                  25                  30

Val Gly Trp Tyr Gln Gln Leu Pro Gly Thr Ser Pro Arg Thr Leu Ile
        35                  40                  45

Ile Asp Ser Asn Asn Arg Pro Ser Gly Val Pro Asp Arg Phe Ser Ser
    50                  55                  60

Ser Arg Ser Gly Asn Ile Gly Thr Leu Thr Ile Ser Gly Leu Gln Ala
65                  70                  75                  80

Glu Asp Glu Ala Asp Tyr Cys Cys Thr Cys Phe Asp Ser Ser Leu Asn
                85                  90                  95

Gly Gly Val Phe Gly Gly Gly Thr Gln Leu Thr Val Leu Gly
            100                 105                 110
```

<210> SEQ ID NO 387
<211> LENGTH: 327
<212> TYPE: DNA
<213> ORGANISM: artificial
<220> FEATURE:
<223> OTHER INFORMATION: VL chain

<400> SEQUENCE: 387

```
gcgttgaccc aaccggcctc agtgtctggg tccctgggcc agagggtcac cgtctcctgc        60
actgggagca gctccaacat cggtagattt gttgttggct ggttccagca gctcccggga        120
aaaggcccca gaaccgtcat ctataataca gtaaccgac cctcaggggt ccctgatcga        180 tttctggct ccaagtcagg cagcacagcc accctgacca tctctgggct ccagactgag        240
gacgaggctg cttattactg ctcagtatat gacagtagtc tcaatactat tctgtttggc        300
ggaggcaccc acctgaccgt cctcggc                                            327
```

<210> SEQ ID NO 388
<211> LENGTH: 109
<212> TYPE: PRT
<213> ORGANISM: artificial
<220> FEATURE:
<223> OTHER INFORMATION: VL chain

<400> SEQUENCE: 388

```
Ala Leu Thr Gln Pro Ala Ser Val Ser Gly Ser Leu Gly Gln Arg Val
1               5                   10                  15

Thr Val Ser Cys Thr Gly Ser Ser Ser Asn Ile Gly Arg Phe Val Val
            20                  25                  30

Gly Trp Phe Gln Gln Leu Pro Gly Lys Gly Pro Arg Thr Val Ile Tyr
        35                  40                  45
```

```
Asn Thr Ser Asn Arg Pro Ser Gly Val Pro Asp Arg Phe Ser Gly Ser
            50                  55                  60

Lys Ser Gly Ser Thr Ala Thr Leu Thr Ile Ser Gly Leu Gln Thr Glu
 65                  70                  75                  80

Asp Glu Ala Ala Tyr Tyr Cys Ser Val Tyr Asp Ser Ser Leu Asn Thr
                 85                  90                  95

Ile Leu Phe Gly Gly Gly Thr His Leu Thr Val Leu Gly
            100                 105
```

<210> SEQ ID NO 389
<211> LENGTH: 320
<212> TYPE: DNA
<213> ORGANISM: artificial
<220> FEATURE:
<223> OTHER INFORMATION: VL chain

<400> SEQUENCE: 389

```
gggctgactc agctgccttc cgtgaatgtg accctgaggc agacggccca catcacctgt      60
gggggagaca gcattggaag taaatatgtt caatggatcc agcagaatcc aggccaggcc     120
cccgtgatga ttatctataa agataccaac aggccgacag ggatccctga gcgattctct     180
ggcgccaact cagggaacac ggctaccctg accatcagcg ggccctggc cgaagacgag      240 gctgactatt actgccaggt gtgggacagc aatactaaga ggattgtgtt cggcggaggc     300
acccacctga ccgtcctggg                                                 320
```

<210> SEQ ID NO 390
<211> LENGTH: 107
<212> TYPE: PRT
<213> ORGANISM: artificial
<220> FEATURE:
<223> OTHER INFORMATION: VL chain

<400> SEQUENCE: 390

```
Gly Leu Thr Gln Leu Pro Ser Val Asn Val Thr Leu Arg Gln Thr Ala
 1               5                  10                  15

His Ile Thr Cys Gly Gly Asp Ser Ile Gly Ser Lys Tyr Val Gln Trp
             20                  25                  30

Ile Gln Gln Asn Pro Gly Gln Ala Pro Val Met Ile Ile Tyr Lys Asp
         35                  40                  45

Thr Asn Arg Pro Thr Gly Ile Pro Glu Arg Phe Ser Gly Ala Asn Ser
     50                  55                  60

Gly Asn Thr Ala Thr Leu Thr Ile Ser Gly Ala Leu Ala Glu Asp Glu
 65                  70                  75                  80

Ala Asp Tyr Tyr Cys Gln Val Trp Asp Ser Asn Thr Lys Arg Ile Val
                 85                  90                  95

Phe Gly Gly Gly Thr His Leu Thr Val Leu Gly
            100                 105
```

<210> SEQ ID NO 391
<211> LENGTH: 326
<212> TYPE: DNA
<213> ORGANISM: artificial
<220> FEATURE:
<223> OTHER INFORMATION: VL chain

<400> SEQUENCE: 391

```
gggttgatca ggcttcctca gtgtccgggt cctgggcca gagggtcacc atctcctgca      60
ctgggagtag ctccaagatc ggtagaggtt tgttcactg gtaccaggta ctcccaggaa     120
caggccccag aaccctcatc tatggtgtta gtcaccgacc ctcaggggtc ccgatcgat    180
```

```
tctctgcctc caagtcaggc aagacagcca ctctgacaat ctctgggctc caggctgagg     240
atgaggctga ttattactgc tcatcctggg acagcagtct cagtagtctc gtgttcggct     300
caggaaccca gctcaccgtc cttggc                                          326
```

<210> SEQ ID NO 392
<211> LENGTH: 108
<212> TYPE: PRT
<213> ORGANISM: artificial
<220> FEATURE:
<223> OTHER INFORMATION: VL chain

<400> SEQUENCE: 392

```
Val Asp Gln Ala Ser Ser Val Ser Gly Phe Leu Gly Gln Arg Val Thr
1               5                   10                  15

Ile Ser Cys Thr Gly Ser Ser Lys Ile Gly Arg Gly Phe Val His
            20                  25                  30

Trp Tyr Gln Val Leu Pro Gly Thr Gly Pro Arg Thr Leu Ile Tyr Gly
        35                  40                  45

Val Ser His Arg Pro Ser Gly Val Pro Asp Arg Phe Ser Ala Ser Lys
    50                  55                  60

Ser Gly Lys Thr Ala Thr Leu Thr Ile Ser Gly Leu Gln Ala Glu Asp
65                  70                  75                  80

Glu Ala Asp Tyr Tyr Cys Ser Ser Trp Asp Ser Ser Leu Ser Ser Leu
                85                  90                  95

Val Phe Gly Ser Gly Thr Gln Leu Thr Val Leu Gly
            100                 105
```

<210> SEQ ID NO 393
<211> LENGTH: 330
<212> TYPE: DNA
<213> ORGANISM: artificial
<220> FEATURE:
<223> OTHER INFORMATION: VL chain

<400> SEQUENCE: 393

```
accctgactc agaagccctc cgtgtctggg tccctgggcc agagggtcac catctcctgc     60
actggaagca gctccaatgt tggttatggc gattctgtgg gctggtacca gcagctccca     120
ggaacaagcc ccagaaccct catctatgat agtagtagcc gaccctcggg ggtccctgat     180
cgattctctg gctccaggtc aggcagcaca gcaaccctga ccatctctgg gctccaggct     240
gaggatgaag ccgattatta ctgctcatcc tatgacagca gtctcagtgg tgctgtgttc     300
ggcggaggca cccacctgac cgtcctcggc                                      330
```

<210> SEQ ID NO 394
<211> LENGTH: 110
<212> TYPE: PRT
<213> ORGANISM: artificial
<220> FEATURE:
<223> OTHER INFORMATION: VL chain

<400> SEQUENCE: 394

```
Thr Leu Thr Gln Lys Pro Ser Val Ser Gly Ser Leu Gly Gln Arg Val
1               5                   10                  15

Thr Ile Ser Cys Thr Gly Ser Ser Asn Val Gly Tyr Gly Asp Ser
            20                  25                  30

Val Gly Trp Tyr Gln Gln Leu Pro Gly Thr Ser Pro Arg Thr Leu Ile
        35                  40                  45

Tyr Asp Ser Ser Ser Arg Pro Ser Gly Val Pro Asp Arg Phe Ser Gly
```

```
                    50                  55                  60
Ser Arg Ser Gly Ser Thr Ala Thr Leu Thr Ile Ser Gly Leu Gln Ala
 65                  70                  75                  80

Glu Asp Glu Ala Asp Tyr Tyr Cys Ser Ser Tyr Asp Ser Ser Leu Ser
                 85                  90                  95

Gly Ala Val Phe Gly Gly Gly Thr His Leu Thr Val Leu Gly
            100                 105                 110
```

<210> SEQ ID NO 395
<211> LENGTH: 327
<212> TYPE: DNA
<213> ORGANISM: artificial
<220> FEATURE:
<223> OTHER INFORMATION: VL chain

<400> SEQUENCE: 395

```
gtgctgactc agcctccctc agtgtcgggg tcccctggcc agagggtcac catctcctgc      60
tctggaagga cgaacaatat cggtagtgtt ggtgcgacct ggtaccgaca attcccagga     120
aaggccccta acctcctcgt atacagtgat gggaatcgac cgtcgggggt ccctgaccgg     180
ttttccgcct ccatgtctgg caactcagcc accctgacca tcactgggct cagactgag      240
gacgaggctg attattactg ccagtcctat gacacctcgc ttgatggtgc tgtgttcggc     300
ggaggcaccc acctgaccgt cctcggc                                         327
```

<210> SEQ ID NO 396
<211> LENGTH: 109
<212> TYPE: PRT
<213> ORGANISM: artificial
<220> FEATURE:
<223> OTHER INFORMATION: VL chain

<400> SEQUENCE: 396

```
Val Leu Thr Gln Pro Pro Ser Val Ser Gly Ser Pro Gly Gln Arg Val
 1               5                  10                  15

Thr Ile Ser Cys Ser Gly Arg Thr Asn Asn Ile Gly Ser Val Gly Ala
                20                  25                  30

Thr Trp Tyr Arg Gln Phe Pro Gly Lys Ala Pro Asn Leu Leu Val Tyr
            35                  40                  45

Ser Asp Gly Asn Arg Pro Ser Gly Val Pro Asp Arg Phe Ser Ala Ser
 50                  55                  60

Met Ser Gly Asn Ser Ala Thr Leu Thr Ile Thr Gly Leu Gln Thr Glu
 65                  70                  75                  80

Asp Glu Ala Asp Tyr Tyr Cys Gln Ser Tyr Asp Thr Ser Leu Asp Gly
                 85                  90                  95

Ala Val Phe Gly Gly Gly Thr His Leu Thr Val Leu Gly
            100                 105
```

<210> SEQ ID NO 397
<211> LENGTH: 327
<212> TYPE: DNA
<213> ORGANISM: artificial
<220> FEATURE:
<223> OTHER INFORMATION: VL chain

<400> SEQUENCE: 397

```
gccctgactc aaccttcctc ggtgtctggg actttgggcc agactgtcac catctcctgt      60
gatggaagca gcagtgacat tggcagttat agtatatcg cttggtacca gcagttccca     120
ggcacctccc ccaaactcct gattcaatac accgataatc ggccatcagg gatccctact     180
```

-continued

```
cgcttctctg gctccaagtc tgggaacacg gcctccttga ccatccctgg tctccaggct    240
gaagatgagg ctgattatta ctgctgcgca tatgctggta gtgatactta cgtattcggc    300
tcaggaaccc aactcaccgt cctaggc                                        327
```

<210> SEQ ID NO 398
<211> LENGTH: 109
<212> TYPE: PRT
<213> ORGANISM: artificial
<220> FEATURE:
<223> OTHER INFORMATION: VL chain

<400> SEQUENCE: 398

```
Ala Leu Thr Gln Pro Ser Ser Val Ser Gly Thr Leu Gly Gln Thr Val
1               5                   10                  15

Thr Ile Ser Cys Asp Gly Ser Ser Asp Ile Gly Ser Tyr Ser Tyr
            20                  25                  30

Ile Ala Trp Tyr Gln Gln Phe Pro Gly Thr Ser Pro Lys Leu Leu Ile
        35                  40                  45

Gln Tyr Thr Asp Asn Arg Pro Ser Gly Ile Pro Thr Arg Phe Ser Gly
    50                  55                  60

Ser Lys Ser Gly Asn Thr Ala Ser Leu Thr Ile Pro Gly Leu Gln Ala
65                  70                  75                  80

Glu Asp Glu Ala Asp Tyr Tyr Cys Cys Ala Tyr Ala Gly Ser Asp Thr
                85                  90                  95

Tyr Val Phe Gly Ser Gly Thr Gln Leu Thr Val Leu Gly
            100                 105
```

<210> SEQ ID NO 399
<211> LENGTH: 327
<212> TYPE: DNA
<213> ORGANISM: artificial
<220> FEATURE:
<223> OTHER INFORMATION: VL chain

<400> SEQUENCE: 399

```
gtgttgactc agctggcctc cgtgtctggg tccctgggcc agagggtcac catctcctgc    60
actggaagca gctccaatgt tgggtatggc aatgatgtgg gctggtacca gcagctccca    120
ggaacaggcc ccagaaccct catctatggt agcagtatcc gaccctcggg ggtccctgat    180
cgattctctg gctccaaatc aggcaactca gccacactga ccatctctgg ctccaggct    240 gaggatgaag ctgattatta ctgttcatcc tatgacagca gtctcggtta cgtgttcggc    300
tcaggaaccc aactcaccgt ccttggc                                        327
```

<210> SEQ ID NO 400
<211> LENGTH: 109
<212> TYPE: PRT
<213> ORGANISM: artificial
<220> FEATURE:
<223> OTHER INFORMATION: VL chain

<400> SEQUENCE: 400

```
Val Leu Thr Gln Leu Ala Ser Val Ser Gly Ser Leu Gly Gln Arg Val
1               5                   10                  15

Thr Ile Ser Cys Thr Gly Ser Ser Asn Val Gly Tyr Gly Asn Asp
            20                  25                  30

Val Gly Trp Tyr Gln Gln Leu Pro Gly Thr Gly Pro Arg Thr Leu Ile
        35                  40                  45

Tyr Gly Ser Ser Ile Arg Pro Ser Gly Val Pro Asp Arg Phe Ser Gly
    50                  55                  60
```

```
Ser Lys Ser Gly Asn Ser Ala Thr Leu Thr Ile Ser Gly Leu Gln Ala
 65                  70                  75                  80

Glu Asp Glu Ala Asp Tyr Tyr Cys Ser Ser Tyr Asp Ser Ser Leu Gly
                 85                  90                  95

Tyr Val Phe Gly Ser Gly Thr Gln Leu Thr Val Leu Gly
            100                 105

<210> SEQ ID NO 401
<211> LENGTH: 330
<212> TYPE: DNA
<213> ORGANISM: artificial
<220> FEATURE:
<223> OTHER INFORMATION: VL chain

<400> SEQUENCE: 401
gtgctgactc agcttgcctc agtgtctggg tccctgggcc aaagggtcac catctcctgc      60
tctggaagca gctccaatgt tggttgtggc gattatgtgg ctggttcca gcaactccca     120 ggaacgggcc ccagaaccct catctatgat actagtaccc gaccctcggg ggtccctgat    180
cgattctctg gctccaggtc tgcagcaca gcaaccctga ccatctctgg ctccaggct     240 gaggatgagg ccgattacta ctgctcatcc tatgacatga ctctcagagg tcctatgttc    300
ggcggaggga cccagctgac cgtcctcggc                                     330

<210> SEQ ID NO 402
<211> LENGTH: 110
<212> TYPE: PRT
<213> ORGANISM: artificial
<220> FEATURE:
<223> OTHER INFORMATION: VL chain

<400> SEQUENCE: 402

Val Leu Thr Gln Leu Ala Ser Val Ser Gly Ser Leu Gly Gln Arg Val
 1               5                  10                  15

Thr Ile Ser Cys Ser Gly Ser Ser Asn Val Gly Cys Gly Asp Tyr
                20                  25                  30

Val Gly Trp Phe Gln Gln Leu Pro Gly Thr Gly Pro Arg Thr Leu Ile
             35                  40                  45

Tyr Asp Thr Ser Thr Arg Pro Ser Gly Val Pro Asp Arg Phe Ser Gly
 50                  55                  60

Ser Arg Ser Gly Ser Thr Ala Thr Leu Thr Ile Ser Gly Leu Gln Ala
 65                  70                  75                  80

Glu Asp Glu Ala Asp Tyr Tyr Cys Ser Ser Tyr Asp Met Thr Leu Arg
                 85                  90                  95

Gly Pro Met Phe Gly Gly Gly Thr Gln Leu Thr Val Leu Gly
            100                 105                 110

<210> SEQ ID NO 403
<211> LENGTH: 327
<212> TYPE: DNA
<213> ORGANISM: artificial
<220> FEATURE:
<223> OTHER INFORMATION: VL chain

<400> SEQUENCE: 403
gtcctgactc agctgccctc agtgtcgggg tcccttggcc agagggtcac catctcctgc      60
tctggaagca cgaacaacat cggtattact ggtgcgacct ggtaccaaca actcccagga    120
aaggccccta cactcctcgt atacagtgat ggggatcgac cgtcagggt ccctgaccgg     180 ttttccagtt ccaactctga cttctcagac accctgacca tcactggtct tcaggctgag    240
```

```
gacgaggctg attattactg ccagtccttt gataccacgc ttgatgctta cgtgttcggt    300
tcaggaatcg agctgaccgt ccttggc                                        327
```

<210> SEQ ID NO 404
<211> LENGTH: 109
<212> TYPE: PRT
<213> ORGANISM: artificial
<220> FEATURE:
<223> OTHER INFORMATION: VL chain

<400> SEQUENCE: 404

```
Val Leu Thr Gln Leu Pro Ser Val Ser Gly Ser Leu Gly Gln Arg Val
1               5                   10                  15

Thr Ile Ser Cys Ser Gly Ser Thr Asn Asn Ile Gly Ile Thr Gly Ala
            20                  25                  30

Thr Trp Tyr Gln Gln Leu Pro Gly Lys Ala Pro Thr Leu Leu Val Tyr
        35                  40                  45

Ser Asp Gly Asp Arg Pro Ser Gly Val Pro Asp Arg Phe Ser Ser Ser
    50                  55                  60

Asn Ser Asp Phe Ser Asp Thr Leu Thr Ile Thr Gly Leu Gln Ala Glu
65                  70                  75                  80

Asp Glu Ala Asp Tyr Tyr Cys Gln Ser Phe Asp Thr Thr Leu Asp Ala
                85                  90                  95

Tyr Val Phe Gly Ser Gly Ile Glu Leu Thr Val Leu Gly
            100                 105
```

<210> SEQ ID NO 405
<211> LENGTH: 327
<212> TYPE: DNA
<213> ORGANISM: artificial
<220> FEATURE:
<223> OTHER INFORMATION: VL chain

<400> SEQUENCE: 405

```
gtgctgactc agcttgcctc agtgtctggg tccctgggcc agagggtcac catctcctgc    60
actggaagca cctccaacat cggtagaggt tatgtgacct ggtaccagca gctcccagga    120
acaggcccca gaaccctcat ctatgataat agtgaccgac cctcgggggt ccctgatcgc    180
ttctctggct ccaagtcagg cagcacagcc accctgacca tatccggcct ccaggttgag    240
gacgaggctg attatcactg ctcaacatat gacagcagtc tcggtggtcc tgtgttcggc    300
ggaggcaccc agctgaccgt cctcggc                                        327
```

<210> SEQ ID NO 406
<211> LENGTH: 109
<212> TYPE: PRT
<213> ORGANISM: artificial
<220> FEATURE:
<223> OTHER INFORMATION: VL chain

<400> SEQUENCE: 406

```
Val Leu Thr Gln Leu Ala Ser Val Ser Gly Ser Leu Gly Gln Arg Val
1               5                   10                  15

Thr Ile Ser Cys Thr Gly Ser Thr Ser Asn Ile Gly Arg Gly Tyr Val
            20                  25                  30

Thr Trp Tyr Gln Gln Leu Pro Gly Thr Gly Pro Arg Thr Leu Ile Tyr
        35                  40                  45

Asp Asn Ser Asp Arg Pro Ser Gly Val Pro Asp Arg Phe Ser Gly Ser
    50                  55                  60
```

Lys Ser Gly Ser Thr Ala Thr Leu Thr Ile Ser Gly Leu Gln Val Glu
65                  70                  75                  80

Asp Glu Ala Asp Tyr His Cys Ser Thr Tyr Asp Ser Ser Leu Gly Gly
                85                  90                  95

Pro Val Phe Gly Gly Gly Thr Gln Leu Thr Val Leu Gly
            100                 105

<210> SEQ ID NO 407
<211> LENGTH: 316
<212> TYPE: DNA
<213> ORGANISM: artificial
<220> FEATURE:
<223> OTHER INFORMATION: VL chain

<400> SEQUENCE: 407
gtgttgactc agctggcctc cgtgtcagtg aacccgggac agacagccat catcacctgt      60
gaggcagata aaatagggga taaatttgtt cactggtacc aacagaagcc tagtcaggcc     120
cccggaatga ttgtttatga ggatcacaag cgccccccag gatccctga gcgattctct     180 gcctccaact cggggaacac ggccaccctg accatcagcg gggccagggc cgaggatgag     240
gctgactatt actgtcaggt gtgggacaac ggtgctccga tgttcggcgg aggcacccac     300
cctgaccgtc ctcggc                                                    316

<210> SEQ ID NO 408
<211> LENGTH: 105
<212> TYPE: PRT
<213> ORGANISM: artificial
<220> FEATURE:
<223> OTHER INFORMATION: VL chain

<400> SEQUENCE: 408

Val Leu Thr Gln Leu Ala Ser Val Ser Val Asn Pro Gly Gln Thr Ala
1               5                   10                  15

Ile Ile Thr Cys Glu Ala Asp Lys Ile Gly Asp Lys Phe Val His Trp
                20                  25                  30

Tyr Gln Gln Lys Pro Ser Gln Ala Pro Gly Met Ile Val Tyr Glu Asp
            35                  40                  45

His Lys Arg Pro Ser Gly Ile Pro Glu Arg Phe Ser Ala Ser Asn Ser
        50                  55                  60

Gly Asn Thr Ala Thr Leu Thr Ile Ser Gly Ala Arg Ala Glu Asp Glu
65                  70                  75                  80

Ala Asp Tyr Tyr Cys Gln Val Trp Asp Asn Gly Ala Pro Met Phe Gly
                85                  90                  95

Gly Gly Thr His Pro Asp Arg Pro Arg
            100                 105

<210> SEQ ID NO 409
<211> LENGTH: 327
<212> TYPE: DNA
<213> ORGANISM: artificial
<220> FEATURE:
<223> OTHER INFORMATION: VL chain

<400> SEQUENCE: 409
gtgctgactc agcttgcctc agtgtctggg tccctgggcc agagggtcac catctcctgc      60
actggaagca gctccaatgt tggttatggc gattatgtgg gctggtatca gcagctccca     120
ggaacaggcc ccagaaccct catccatcat actactagcc gacccgcggg agtctccgat     180
cgattctctg gctccaggtc aggcaacaca gcaaccctga ccatctctgg actccaggct     240

```
gaggatgaag ccgattatta ctgctcatct tatgacacag gtctcaatgt tgtgttcggc      300
ggaggcaccc agctgaccgt cctcggc                                         327
```

<210> SEQ ID NO 410
<211> LENGTH: 109
<212> TYPE: PRT
<213> ORGANISM: artificial
<220> FEATURE:
<223> OTHER INFORMATION: VL chain

<400> SEQUENCE: 410

```
Val Leu Thr Gln Leu Ala Ser Val Ser Gly Ser Leu Gly Gln Arg Val
1               5                   10                  15

Thr Ile Ser Cys Thr Gly Ser Ser Ser Asn Val Gly Tyr Gly Asp Tyr
            20                  25                  30

Val Gly Trp Tyr Gln Gln Leu Pro Gly Thr Gly Pro Arg Thr Leu Ile
        35                  40                  45

His His Thr Thr Ser Arg Pro Ser Gly Val Ser Asp Arg Phe Ser Gly
    50                  55                  60

Ser Arg Ser Gly Asn Thr Ala Thr Leu Thr Ile Ser Gly Leu Gln Ala
65                  70                  75                  80

Glu Asp Glu Ala Asp Tyr Tyr Cys Ser Ser Tyr Asp Thr Gly Leu Asn
                85                  90                  95

Val Val Phe Gly Gly Gly Thr Gln Leu Thr Val Leu Gly
            100                 105
```

<210> SEQ ID NO 411
<211> LENGTH: 327
<212> TYPE: DNA
<213> ORGANISM: artificial
<220> FEATURE:
<223> OTHER INFORMATION: VL chain

<400> SEQUENCE: 411

```
gtgctgactc agctgacctc agtgtcgggg tcccttggcc agagggtcac catttcctgc      60
tctggaagcg cgaacaacat cggtagtttt ggtgcgatct ggtaccaaca gttcccagga     120
aaggccccta aactcctcat atacagggat gggagtcgac cgtcaggggt ccctgaccgg     180
ttttccggct ccaggtctgg caactcagcc accctgacca tcactgggct tcaggctgag     240
gacgaggctg attttactgt cagtctgtt gatcccacgc ttggtattgc tgtgttcggc     300
ggaggcaccc acctgaccgt cctcggc                                         327
```

<210> SEQ ID NO 412
<211> LENGTH: 109
<212> TYPE: PRT
<213> ORGANISM: artificial
<220> FEATURE:
<223> OTHER INFORMATION: VL chain

<400> SEQUENCE: 412

```
Val Leu Thr Gln Leu Thr Ser Val Ser Gly Ser Leu Gly Gln Arg Val
1               5                   10                  15

Thr Ile Ser Cys Ser Gly Ser Ala Asn Asn Ile Gly Ser Phe Gly Ala
            20                  25                  30

Ile Trp Tyr Gln Gln Phe Pro Gly Lys Ala Pro Lys Leu Leu Ile Tyr
        35                  40                  45

Arg Asp Gly Ser Arg Pro Ser Gly Val Pro Asp Arg Phe Ser Gly Ser
    50                  55                  60

Arg Ser Gly Asn Ser Ala Thr Leu Thr Ile Thr Gly Leu Gln Ala Glu
```

```
                 65                  70                  75                  80
Asp Glu Ala Asp Phe Tyr Cys Gln Ser Val Asp Pro Thr Leu Gly Ile
                         85                  90                  95

Ala Val Phe Gly Gly Gly Thr His Leu Thr Val Leu Gly
                100                 105
```

<210> SEQ ID NO 413
<211> LENGTH: 327
<212> TYPE: DNA
<213> ORGANISM: artificial
<220> FEATURE:
<223> OTHER INFORMATION: VL chain

<400> SEQUENCE: 413

```
gtgctgaccc agccagcctc cgtgtctggg tccctgggcc agagggtcac catctcccgc    60
actggaagca gctccaatgt tgggtatggc aatgatgtgg gctggtacca gcagctccca   120
ggaacaggcc ccagaaccct catctatggt agcagtatcc gaccctcggg ggtccctgat   180
cgattctctg gctccaaatc aggcaactca gccacactga ccatctctgg gctccaggct   240
gaggatgaag ctgattatta ctgttcatcc tatgacagca gtctcggtta cgtgttcggc   300
tcaggaaccc aactgaccgt ccttggc                                       327
```

<210> SEQ ID NO 414
<211> LENGTH: 109
<212> TYPE: PRT
<213> ORGANISM: artificial
<220> FEATURE:
<223> OTHER INFORMATION: VL chain

<400> SEQUENCE: 414

```
Val Leu Thr Gln Pro Ala Ser Val Ser Gly Ser Leu Gly Gln Arg Val
1               5                   10                  15

Thr Ile Ser Arg Thr Gly Ser Ser Ser Asn Val Gly Tyr Gly Asn Asp
            20                  25                  30

Val Gly Trp Tyr Gln Gln Leu Pro Gly Thr Gly Pro Arg Thr Leu Ile
        35                  40                  45

Tyr Gly Ser Ser Ile Arg Pro Ser Gly Val Pro Asp Arg Phe Ser Gly
    50                  55                  60

Ser Lys Ser Gly Asn Ser Ala Thr Leu Thr Ile Ser Gly Leu Gln Ala
65                  70                  75                  80

Glu Asp Glu Ala Asp Tyr Tyr Cys Ser Ser Tyr Asp Ser Ser Leu Gly
                85                  90                  95

Tyr Val Phe Gly Ser Gly Thr Gln Leu Thr Val Leu Gly
                100                 105
```

<210> SEQ ID NO 415
<211> LENGTH: 327
<212> TYPE: DNA
<213> ORGANISM: artificial
<220> FEATURE:
<223> OTHER INFORMATION: VL chain

<400> SEQUENCE: 415

```
gtgctgactc agctaacctc agtgtctggg tccctgggcc agagggtcac catctcctgc    60
tctggaagtg aattcaatgt tggtggtggc aatcatgtgg cctggtaccg gcagatccca   120
gggacaggtc ccakaaccct catctttgat actaatggtc gaccctcggg ggtccctgat   180
cgcttctctg cctccaggtc agacaataca gcgaccctga ccatctctga ctccaggct   240
gacgatgagg ccgattacta ctgttcatcc tatgacaagt ctttcagtgt tgttttcggc   300
```

```
ggargcaccc acctwaccgt cctcggc                                           327
```

<210> SEQ ID NO 416
<211> LENGTH: 109
<212> TYPE: PRT
<213> ORGANISM: artificial
<220> FEATURE:
<223> OTHER INFORMATION: VL chain
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (102)..(102)
<223> OTHER INFORMATION: Xaa can be any naturally occurring amino acid

<400> SEQUENCE: 416

Val Leu Thr Gln Leu Thr Ser Val Ser Gly Ser Leu Gly Gln Arg Val
1               5                   10                  15

Thr Ile Ser Cys Ser Gly Ser Glu Phe Asn Val Gly Gly Gly Asn His
            20                  25                  30

Val Ala Trp Tyr Arg Gln Ile Pro Gly Thr Gly Pro Xaa Thr Leu Ile
        35                  40                  45

Phe Asp Thr Asn Gly Arg Pro Ser Gly Val Pro Asp Arg Phe Ser Ala
    50                  55                  60

Ser Arg Ser Asp Asn Thr Ala Thr Leu Thr Ile Ser Glu Leu Gln Ala
65                  70                  75                  80

Asp Asp Glu Ala Asp Tyr Tyr Cys Ser Ser Tyr Asp Lys Ser Phe Ser
                85                  90                  95

Val Val Phe Gly Gly Xaa Thr His Leu Thr Val Leu Gly
            100                 105

<210> SEQ ID NO 417
<211> LENGTH: 333
<212> TYPE: DNA
<213> ORGANISM: artificial
<220> FEATURE:
<223> OTHER INFORMATION: VL chain

<400> SEQUENCE: 417

```
gtcatgatgc akaccccact gtccctgtct gtcagccctg gagagacggc ctccatctcc     60
tgcagggcca atcagagcct cctgcacagt aacgggaaca cctatttaga ttggtacata    120
cagaggccag gccagtctcc ccaggccctg atctacaggg tgtccaaccg cgccatcgcc    180
actgccgtgt cagacagatt tagtggcagc gggtcaggga cagatttcac cctgaagatc    240
agcagagtgg aggctggcga tgctggactt tattactgcg ggcaaggtac atactcttat    300
actttcagcc agggaaccaa gctggagatc aaa                                 333
```

<210> SEQ ID NO 418
<211> LENGTH: 111
<212> TYPE: PRT
<213> ORGANISM: artificial
<220> FEATURE:
<223> OTHER INFORMATION: VL chain
<220> FEATURE:
<221> NAME/KEY: misc_feature
<222> LOCATION: (4)..(4)
<223> OTHER INFORMATION: Xaa can be any naturally occurring amino acid

<400> SEQUENCE: 418

Val Met Met Xaa Thr Pro Leu Ser Leu Ser Val Ser Pro Gly Glu Thr
1               5                   10                  15

```
Ala Ser Ile Ser Cys Arg Ala Asn Gln Ser Leu Leu His Ser Asn Gly
            20                  25                  30

Asn Thr Tyr Leu Asp Trp Tyr Ile Gln Arg Pro Gly Gln Ser Pro Gln
        35                  40                  45

Ala Leu Ile Tyr Arg Val Ser Asn Arg Ala Ile Ala Thr Ala Val Ser
    50                  55                  60

Asp Arg Phe Ser Gly Ser Gly Ser Gly Thr Asp Phe Thr Leu Lys Ile
65                  70                  75                  80

Ser Arg Val Glu Ala Gly Asp Ala Gly Leu Tyr Tyr Cys Gly Gln Gly
                85                  90                  95

Thr Tyr Ser Tyr Thr Phe Ser Gln Gly Thr Lys Leu Glu Ile Lys
            100                 105                 110

<210> SEQ ID NO 419
<211> LENGTH: 333
<212> TYPE: DNA
<213> ORGANISM: artificial
<220> FEATURE:
<223> OTHER INFORMATION: VL chain

<400> SEQUENCE: 419
gtcatgatgc agaccccact gtccctgtct gtcagccctg gagagacggc ctccatctcc      60
tgcagggcca atcagagcct cctgcacagt aacgggaaca cctatttaga ttggtacata     120
cagaggccag gccagtctcc ccaggccctg atctacaggg tgtccaaccg cgccatcgcc     180
actgccgtgt cagacagatt tagtggcagc gggtcaggga cagatttcac cctgaagatc     240
agcagagtgg aggctggcga tgctggactt tattactgcg ggcaaggtac atactcttat     300
actttcagcc agggaaccaa gctggagatc aaa                                  333

<210> SEQ ID NO 420
<211> LENGTH: 111
<212> TYPE: PRT
<213> ORGANISM: artificial
<220> FEATURE:
<223> OTHER INFORMATION: VL chain

<400> SEQUENCE: 420

Val Met Met Gln Thr Pro Leu Ser Leu Ser Val Ser Pro Gly Glu Thr
1               5                   10                  15

Ala Ser Ile Ser Cys Arg Ala Asn Gln Ser Leu Leu His Ser Asn Gly
            20                  25                  30

Asn Thr Tyr Leu Asp Trp Tyr Ile Gln Arg Pro Gly Gln Ser Pro Gln
        35                  40                  45

Ala Leu Ile Tyr Arg Val Ser Asn Arg Ala Ile Ala Thr Ala Val Ser
    50                  55                  60

Asp Arg Phe Ser Gly Ser Gly Ser Gly Thr Asp Phe Thr Leu Lys Ile
65                  70                  75                  80

Ser Arg Val Glu Ala Gly Asp Ala Gly Leu Tyr Tyr Cys Gly Gln Gly
                85                  90                  95

Thr Tyr Ser Tyr Thr Phe Ser Gln Gly Thr Lys Leu Glu Ile Lys
            100                 105                 110

<210> SEQ ID NO 421
<211> LENGTH: 330
<212> TYPE: DNA
<213> ORGANISM: artificial
<220> FEATURE:
<223> OTHER INFORMATION: VL chain
```

-continued

<400> SEQUENCE: 421

```
gtgatgatgc agactccact gtccctgtcc gtcagccctg gagagacggc ctccatctcc     60
tgcaaggcca gtcagagccc cctgcacact aatgggaaca cctatttgtt ttggtttcga    120
cagaagccag gccagtctcc acagcgcttg atctcttcgg tctccaatag agaccctggg    180
gtcccagaca ggttcagtgg cagcgggtca gggacagatt tcaccctgag aatcagcaga    240
gtggaggcta acgatactgg agtttattac tgcgggcaag gtatacggtc ccttatact    300
ttcagccagg ggaccaagct ggagataaaa                                     330
```

<210> SEQ ID NO 422
<211> LENGTH: 110
<212> TYPE: PRT
<213> ORGANISM: artificial
<220> FEATURE:
<223> OTHER INFORMATION: VL chain

<400> SEQUENCE: 422

```
Val Met Met Gln Thr Pro Leu Ser Leu Ser Val Ser Pro Gly Glu Thr
1               5                   10                  15

Ala Ser Ile Ser Cys Lys Ala Ser Gln Ser Pro Leu His Thr Asn Gly
            20                  25                  30

Asn Thr Tyr Leu Phe Trp Phe Arg Gln Lys Pro Gly Gln Ser Pro Gln
        35                  40                  45

Arg Leu Ile Ser Ser Val Ser Asn Arg Asp Pro Gly Val Pro Asp Arg
    50                  55                  60

Phe Ser Gly Ser Gly Ser Gly Thr Asp Phe Thr Leu Arg Ile Ser Arg
65                  70                  75                  80

Val Glu Ala Asn Asp Thr Gly Val Tyr Tyr Cys Gly Gln Gly Ile Arg
                85                  90                  95

Ser Pro Tyr Thr Phe Ser Gln Gly Thr Lys Leu Glu Ile Lys
            100                 105                 110
```

<210> SEQ ID NO 423
<211> LENGTH: 330
<212> TYPE: DNA
<213> ORGANISM: artificial
<220> FEATURE:
<223> OTHER INFORMATION: VL chain

<400> SEQUENCE: 423

```
gtcatgatgc agactccacc gtccctgtcc gtcagccctg gagagccggc ctccatctcc     60
tgtaaggcca gtcagagcct cctgcacatt aatgggatca actatttgtc ttggttccaa    120
caaaagccag gccagtctcc acagcgtctg atcgttaggg cctccaacag agaacctgga    180
gtcccagaca ggttcagtgg cagcgggtca gggacagatt tcaccctgag aatcagcaga    240
gtggaggctg atgatgttgg agtttattac tgcggacaat atctatcaca tccgtacacg    300
ttcggaccag gaaccaaggt ggacctcaaa                                     330
```

<210> SEQ ID NO 424
<211> LENGTH: 110
<212> TYPE: PRT
<213> ORGANISM: artificial
<220> FEATURE:
<223> OTHER INFORMATION: VL chain

<400> SEQUENCE: 424

```
Val Met Met Gln Thr Pro Pro Ser Leu Ser Val Ser Pro Gly Glu Pro
1               5                   10                  15
```

-continued

```
Ala Ser Ile Ser Cys Lys Ala Ser Gln Ser Leu Leu His Ile Asn Gly
         20                  25                  30

Ile Asn Tyr Leu Ser Trp Phe Gln Gln Lys Pro Gly Gln Ser Pro Gln
     35                  40                  45

Arg Leu Ile Val Arg Ala Ser Asn Arg Glu Pro Gly Val Pro Asp Arg
 50                  55                  60

Phe Ser Gly Ser Gly Ser Gly Thr Asp Phe Thr Leu Arg Ile Ser Arg
 65                  70                  75                  80

Val Glu Ala Asp Asp Val Gly Val Tyr Tyr Cys Gly Gln Tyr Leu Ser
                 85                  90                  95

His Pro Tyr Thr Phe Gly Pro Gly Thr Lys Val Asp Leu Lys
            100                 105                 110
```

<210> SEQ ID NO 425
<211> LENGTH: 330
<212> TYPE: DNA
<213> ORGANISM: artificial
<220> FEATURE:
<223> OTHER INFORMATION: VL chain

<400> SEQUENCE: 425

```
gtgatgatgc agactccact gtccctgtcc gtcagccctg gagagactgc ctccatctcc      60
tgcaaggcca gtcagagcct cctgcacagt gatggaaaca cgtatttgaa ttggttccga     120
cagaagccag gccagtctcc acagcgtttg atctataagg tctccaacag agacactggg     180
gtcccagaca ggttcagtgg cagcgggtca gggacagatt tcaccctgag aatcagcaca     240
gtggaggctg acgatactgg aatttattac tgcgggcaag gtacacagtt tccgcttacg     300
ttcggccaag gaaccaagct ggagatcaaa                                      330
```

<210> SEQ ID NO 426
<211> LENGTH: 110
<212> TYPE: PRT
<213> ORGANISM: artificial
<220> FEATURE:
<223> OTHER INFORMATION: VL chain

<400> SEQUENCE: 426

```
Val Met Met Gln Thr Pro Leu Ser Leu Ser Val Ser Pro Gly Glu Thr
 1               5                  10                  15

Ala Ser Ile Ser Cys Lys Ala Ser Gln Ser Leu Leu His Ser Asp Gly
         20                  25                  30

Asn Thr Tyr Leu Asn Trp Phe Arg Gln Lys Pro Gly Gln Ser Pro Gln
     35                  40                  45

Arg Leu Ile Tyr Lys Val Ser Asn Arg Asp Thr Gly Val Pro Asp Arg
 50                  55                  60

Phe Ser Gly Ser Gly Ser Gly Thr Asp Phe Thr Leu Arg Ile Ser Thr
 65                  70                  75                  80

Val Glu Ala Asp Asp Thr Gly Ile Tyr Tyr Cys Gly Gln Gly Thr Gln
                 85                  90                  95

Phe Pro Leu Thr Phe Gly Gln Gly Thr Lys Leu Glu Ile Lys
            100                 105                 110
```

<210> SEQ ID NO 427
<211> LENGTH: 330
<212> TYPE: DNA
<213> ORGANISM: artificial
<220> FEATURE:
<223> OTHER INFORMATION: VL chain

<400> SEQUENCE: 427

```
gtgatgatgc agactccact gtccctgtcc gtcagtcctg gagagccggc ctccatctcc     60
tgcaaggcca gtcagagcct cctgcaccgt agtgggaaca cctatttgta ttggtttcga    120
cagaagccag gccagtctcc agagggcctg atttatcagg tgtccaaccg cctcactggc    180
gtgtcagaca ggttcagtgg cagcgggtca gggacagatt tcaccctgag gatcagcaca    240
gtggaggctg acgatactgg agtttattac tgcgggcaag tgcacagct tccgtggacg     300 ttcggagcag gaaccaaggt ggacctcaaa                                     330
```

<210> SEQ ID NO 428
<211> LENGTH: 110
<212> TYPE: PRT
<213> ORGANISM: artificial
<220> FEATURE:
<223> OTHER INFORMATION: VL chain

<400> SEQUENCE: 428

Val Met Met Gln Thr Pro Leu Ser Leu Ser Val Ser Pro Gly Glu Pro
1               5                   10                  15

Ala Ser Ile Ser Cys Lys Ala Ser Gln Ser Leu Leu His Arg Ser Gly
            20                  25                  30

Asn Thr Tyr Leu Tyr Trp Phe Arg Gln Lys Pro Gly Gln Ser Pro Glu
        35                  40                  45

Gly Leu Ile Tyr Gln Val Ser Asn Arg Leu Thr Gly Val Ser Asp Arg
    50                  55                  60

Phe Ser Gly Ser Gly Ser Gly Thr Asp Phe Thr Leu Arg Ile Ser Thr
65                  70                  75                  80

Val Glu Ala Asp Asp Thr Gly Val Tyr Tyr Cys Gly Gln Gly Ala Gln
                85                  90                  95

Leu Pro Trp Thr Phe Gly Ala Gly Thr Lys Val Asp Leu Lys
            100                 105                 110

<210> SEQ ID NO 429
<211> LENGTH: 330
<212> TYPE: DNA
<213> ORGANISM: artificial
<220> FEATURE:
<223> OTHER INFORMATION: VL chain

<400> SEQUENCE: 429

```
gtgatgatgc agactccact gtccctgtcc gtcagacctg gagagccggc ctccatctcc     60
tgcaaggcca gtcagagcct cctgcacagt aacgggaaca cctatttgtt ttggtttcga    120
cacaggccag gccagtctcc acagagtttg ttgtatctgg tctccaacag agcccctggg    180
gtcccagaca ggttcagtgc cagcgggtca gggacagatt tcaccctgag aatcagcaga    240
gtggaggctg acgatgctgg agtttattac tgcgggcata ttacacagtc tcctcctacg    300
ttcggccaag ggaccaagct ggagataaaa                                     330
```

<210> SEQ ID NO 430
<211> LENGTH: 110
<212> TYPE: PRT
<213> ORGANISM: artificial
<220> FEATURE:
<223> OTHER INFORMATION: VL chain

<400> SEQUENCE: 430

Val Met Met Gln Thr Pro Leu Ser Leu Ser Val Arg Pro Gly Glu Pro
1               5                   10                  15

Ala Ser Ile Ser Cys Lys Ala Ser Gln Ser Leu Leu His Ser Asn Gly

-continued

```
                    20                   25                   30
Asn Thr Tyr Leu Phe Trp Phe Arg His Arg Pro Gly Gln Ser Pro Gln
                35                   40                  45

Ser Leu Leu Tyr Leu Val Ser Asn Arg Ala Pro Gly Val Pro Asp Arg
     50                  55                  60

Phe Ser Ala Ser Gly Ser Gly Thr Asp Phe Thr Leu Arg Ile Ser Arg
 65                  70                  75                  80

Val Glu Ala Asp Asp Ala Gly Val Tyr Tyr Cys Gly His Ile Thr Gln
                85                  90                  95

Ser Pro Pro Thr Phe Gly Gln Gly Thr Lys Leu Glu Ile Lys
                100                  105                 110
```

<210> SEQ ID NO 431
<211> LENGTH: 330
<212> TYPE: DNA
<213> ORGANISM: artificial
<220> FEATURE:
<223> OTHER INFORMATION: VL chain

<400> SEQUENCE: 431

```
gtgatgatgc agactccact gtccctggcc gtcacccctg gagacctggc cactatttcc      60
tgcagggcca gtcagagtct cctatacact gatggaaaat cctatttgaa ttggtacctg     120
cagaggccag ccagactcc tcggccgctg atctatgaga cttccaagcg tttctctggg      180
gtctcagaca ggttcattgg cagcgggtca gggacagatt tcaccctaac aatcagcagg     240
gtggaggctg aggatgttgg agtctattac tgccagcaaa gtgtacattt tccgtggacg     300
ttcggaccag gaaccaaggt ggagatcaaa                                      330
```

<210> SEQ ID NO 432
<211> LENGTH: 110
<212> TYPE: PRT
<213> ORGANISM: artificial
<220> FEATURE:
<223> OTHER INFORMATION: VL chain

<400> SEQUENCE: 432

```
Val Met Met Gln Thr Pro Leu Ser Leu Ala Val Thr Pro Gly Asp Leu
 1               5                  10                  15

Ala Thr Ile Ser Cys Arg Ala Ser Gln Ser Leu Leu Tyr Thr Asp Gly
                20                  25                  30

Lys Ser Tyr Leu Asn Trp Tyr Leu Gln Arg Pro Gly Gln Thr Pro Arg
                35                  40                  45

Pro Leu Ile Tyr Glu Thr Ser Lys Arg Phe Ser Gly Val Ser Asp Arg
     50                  55                  60

Phe Ile Gly Ser Gly Ser Gly Thr Asp Phe Thr Leu Thr Ile Ser Arg
 65                  70                  75                  80

Val Glu Ala Glu Asp Val Gly Val Tyr Tyr Cys Gln Gln Ser Val His
                85                  90                  95

Phe Pro Trp Thr Phe Gly Pro Gly Thr Lys Val Glu Ile Lys
                100                  105                 110
```

<210> SEQ ID NO 433
<211> LENGTH: 330
<212> TYPE: DNA
<213> ORGANISM: artificial
<220> FEATURE:
<223> OTHER INFORMATION: VL chain

<400> SEQUENCE: 433

```
gtcatgacgc agaccccact gtccctgtcc gtcagtcctg gagaggcggc ctccatctcc      60
tgcaaggcca gtcagagcct cctgcacagc aatgggaata cctatttcta ttggttccga     120
cagaggccag gccagtctcc agagggcctg atctataagg tctccaaccg cttcactggc     180
gtgtcggaca ggttcagtgg cagcgggtca gggacagact tcactctgag aatcagcaga     240
gtggaggctg acgattctgg agtttattac tgcgggcaga atatacagtt tcctcttacg     300
ttcggccaag gaaccaagct ggagatcaaa                                      330
```

<210> SEQ ID NO 434
<211> LENGTH: 110
<212> TYPE: PRT
<213> ORGANISM: artificial
<220> FEATURE:
<223> OTHER INFORMATION: VL chain

<400> SEQUENCE: 434

Val Met Thr Gln Thr Pro Leu Ser Leu Ser Val Ser Pro Gly Glu Ala
1               5                   10                  15

Ala Ser Ile Ser Cys Lys Ala Ser Gln Ser Leu Leu His Ser Asn Gly
            20                  25                  30

Asn Thr Tyr Phe Tyr Trp Phe Arg Gln Arg Pro Gly Gln Ser Pro Glu
        35                  40                  45

Gly Leu Ile Tyr Lys Val Ser Asn Arg Phe Thr Gly Val Ser Asp Arg
    50                  55                  60

Phe Ser Gly Ser Gly Ser Gly Thr Asp Phe Thr Leu Arg Ile Ser Arg
65                  70                  75                  80

Val Glu Ala Asp Asp Ser Gly Val Tyr Tyr Cys Gly Gln Asn Ile Gln
                85                  90                  95

Phe Pro Leu Thr Phe Gly Gln Gly Thr Lys Leu Glu Ile Lys
            100                 105                 110

<210> SEQ ID NO 435
<211> LENGTH: 330
<212> TYPE: DNA
<213> ORGANISM: artificial
<220> FEATURE:
<223> OTHER INFORMATION: VL chain

<400> SEQUENCE: 435

```
gtgatgatgc agactccact gtccctgtcc gtcagccctg gagagccggc ctccatctcc      60
tgcaaggcca gtcagagcct cctgcacagg gatgggaaca cctatgtgta ttggttccga     120
cagaagtcag gccagtctcc agagggcctg atctatagga tgtccaaccg cttcactggc     180
gtgtcagaca ggttcagtgg cagcgggtca gggacggatt tcaccctgag aatcagcaga     240
gtggaggctg acgatgctgg agtttattac tgcgggcaag tctacacttt cctcgggca     300 ttcggagcag gaaccaaggt ggaccctcaaa                                     330
```

<210> SEQ ID NO 436
<211> LENGTH: 110
<212> TYPE: PRT
<213> ORGANISM: artificial
<220> FEATURE:
<223> OTHER INFORMATION: VL chain

<400> SEQUENCE: 436

Val Met Met Gln Thr Pro Leu Ser Leu Ser Val Ser Pro Gly Glu Pro
1               5                   10                  15

Ala Ser Ile Ser Cys Lys Ala Ser Gln Ser Leu Leu His Arg Asp Gly
            20                  25                  30

```
Asn Thr Tyr Val Tyr Trp Phe Arg Gln Lys Ser Gly Gln Ser Pro Glu
            35                  40                  45

Gly Leu Ile Tyr Arg Met Ser Asn Arg Phe Thr Gly Val Ser Asp Arg
 50                  55                  60

Phe Ser Gly Ser Gly Ser Gly Thr Asp Phe Thr Leu Arg Ile Ser Arg
 65                  70                  75                  80

Val Glu Ala Asp Asp Ala Gly Val Tyr Tyr Cys Gly Gln Gly Leu His
                 85                  90                  95

Phe Pro Arg Ala Phe Gly Ala Gly Thr Lys Val Asp Leu Lys
            100                 105                 110
```

<210> SEQ ID NO 437
<211> LENGTH: 330
<212> TYPE: DNA
<213> ORGANISM: artificial
<220> FEATURE:
<223> OTHER INFORMATION: VL chain

<400> SEQUENCE: 437

```
gtgatgatgc agactccact gtccctgtcc gtcagccctg gagagactgc ctccatctct    60
tgtaaggcca gtcagagcct cctgcacagt gatgggaaca cgtatttgaa ttggttccga   120
cagaagccag gccagtctcc acagcgtttg atctataagg tctccaacag agacaccggg   180
gtcccagaca ggttcagtgg cagcgggtca gggacagatt tcaccctgaa aatcagcaca   240
gtggaggcta tcgatactgg aatttattac tgtggacaaa atatccactt tcctcttacg   300
ttcggccaag ggaccaagct ggagatcaaa                                    330
```

<210> SEQ ID NO 438
<211> LENGTH: 110
<212> TYPE: PRT
<213> ORGANISM: artificial
<220> FEATURE:
<223> OTHER INFORMATION: VL chain

<400> SEQUENCE: 438

```
Val Met Met Gln Thr Pro Leu Ser Leu Ser Val Ser Pro Gly Glu Thr
 1               5                  10                  15

Ala Ser Ile Ser Cys Lys Ala Ser Gln Ser Leu Leu His Ser Asp Gly
            20                  25                  30

Asn Thr Tyr Leu Asn Trp Phe Arg Gln Lys Pro Gly Gln Ser Pro Gln
            35                  40                  45

Arg Leu Ile Tyr Lys Val Ser Asn Arg Asp Thr Gly Val Pro Asp Arg
 50                  55                  60

Phe Ser Gly Ser Gly Ser Gly Thr Asp Phe Thr Leu Lys Ile Ser Thr
 65                  70                  75                  80

Val Glu Ala Ile Asp Thr Gly Ile Tyr Tyr Cys Gly Gln Asn Ile His
                 85                  90                  95

Phe Pro Leu Thr Phe Gly Gln Gly Thr Lys Leu Glu Ile Lys
            100                 105                 110
```

<210> SEQ ID NO 439
<211> LENGTH: 330
<212> TYPE: DNA
<213> ORGANISM: artificial
<220> FEATURE:
<223> OTHER INFORMATION: VL chain

<400> SEQUENCE: 439

```
gtgatgatgc agacccact gtccctgtcc gtcagccctg gagagccggc ctccatctcc    60
```

```
tgcaaggcca gtcagaacct cctgcacagt aatgggaaca cctatttgta ttggttccga    120
cagaggccag gccagtctcc agagggcctg atctataagg tgtccaaccg cttcactggc    180
gtgtcagaca ggttcagtgg cagcgggtca gggacagatt tcaccctgag aatcagcaga    240
gtggaggctg acgatactgg agtttattac tgcgggcacg gtatagagtt tccttatact    300
ttcggccagg gaaccaagct ggagatcaaa                                      330
```

<210> SEQ ID NO 440
<211> LENGTH: 110
<212> TYPE: PRT
<213> ORGANISM: artificial
<220> FEATURE:
<223> OTHER INFORMATION: VL chain

<400> SEQUENCE: 440

```
Val Met Met Gln Thr Pro Leu Ser Leu Ser Val Ser Pro Gly Glu Pro
1               5                   10                  15

Ala Ser Ile Ser Cys Lys Ala Ser Gln Asn Leu Leu His Ser Asn Gly
            20                  25                  30

Asn Thr Tyr Leu Tyr Trp Phe Arg Gln Arg Pro Gly Gln Ser Pro Glu
        35                  40                  45

Gly Leu Ile Tyr Lys Val Ser Asn Arg Phe Thr Gly Val Ser Asp Arg
    50                  55                  60

Phe Ser Gly Ser Gly Ser Gly Thr Asp Phe Thr Leu Arg Ile Ser Arg
65                  70                  75                  80

Val Glu Ala Asp Asp Thr Gly Val Tyr Tyr Cys Gly His Gly Ile Glu
                85                  90                  95

Phe Pro Tyr Thr Phe Gly Gln Gly Thr Lys Leu Glu Ile Lys
            100                 105                 110
```

<210> SEQ ID NO 441
<211> LENGTH: 330
<212> TYPE: DNA
<213> ORGANISM: artificial
<220> FEATURE:
<223> OTHER INFORMATION: VL chain

<400> SEQUENCE: 441

```
gtgatgatgc agactccact gtccctgtcc gtcagccctg gagagccggc ctccatctcc     60
tgcaaggcca gtcagagcct cctgcacagg gatgggaaca cctatgtgta ttggttccga    120
cagaagtcag gccagtctcc agagggcctg atctatagga tgtccaaccg cttcactggc    180
gtgtcagaca ggttcagtgg cagcgggtca gggacggatt tcaccctgag aatcagcaga    240
gtggaggctg acgatgctgg agtttattac tgcgggcaag gtctacactt tcctcgggca    300
ttcggagcag gaaccaaggt ggacctcaaa                                      330
```

<210> SEQ ID NO 442
<211> LENGTH: 110
<212> TYPE: PRT
<213> ORGANISM: artificial
<220> FEATURE:
<223> OTHER INFORMATION: VL chain

<400> SEQUENCE: 442

```
Val Met Met Gln Thr Pro Leu Ser Leu Ser Val Ser Pro Gly Glu Pro
1               5                   10                  15

Ala Ser Ile Ser Cys Lys Ala Ser Gln Ser Leu Leu His Arg Asp Gly
            20                  25                  30
```

```
Asn Thr Tyr Val Tyr Trp Phe Arg Gln Lys Ser Gly Gln Ser Pro Glu
         35                  40                  45

Gly Leu Ile Tyr Arg Met Ser Asn Arg Phe Thr Gly Val Ser Asp Arg
     50                  55                  60

Phe Ser Gly Ser Gly Ser Gly Thr Asp Phe Thr Leu Arg Ile Ser Arg
 65                  70                  75                  80

Val Glu Ala Asp Asp Ala Gly Val Tyr Tyr Cys Gly Gln Gly Leu His
                 85                  90                  95

Phe Pro Arg Ala Phe Gly Ala Gly Thr Lys Val Asp Leu Lys
            100                 105                 110
```

```
<210> SEQ ID NO 443
<211> LENGTH: 330
<212> TYPE: DNA
<213> ORGANISM: artificial
<220> FEATURE:
<223> OTHER INFORMATION: VL chain

<400> SEQUENCE: 443
gtgatgatgc agactccact gtccctggcc gtcacccctg gagagctggc cactatctac     60
tgcagggcca gtcagagtct cctgcacagt gatggaaaat cctatttgag ttggtacctg    120
cagaagccag gccagactcc tcggccgctg atttatgagg cttccaagcg tttctctggg    180
gtctcagaca ggttcagtgg cagcgggtca gggacagatt tcacccttaa aatcagcggg    240
gtggaggctg ggatgttgg agtttattac tgccagcaaa gtctacattt tccggggact    300
ttcagccagg gaaccaagct ggagatcaaa                                     330
```

```
<210> SEQ ID NO 444
<211> LENGTH: 110
<212> TYPE: PRT
<213> ORGANISM: artificial
<220> FEATURE:
<223> OTHER INFORMATION: VL chain

<400> SEQUENCE: 444

Val Met Met Gln Thr Pro Leu Ser Leu Ala Val Thr Pro Gly Glu Leu
 1               5                  10                  15

Ala Thr Ile Tyr Cys Arg Ala Ser Gln Ser Leu Leu His Ser Asp Gly
             20                  25                  30

Lys Ser Tyr Leu Ser Trp Tyr Leu Gln Lys Pro Gly Gln Thr Pro Arg
         35                  40                  45

Pro Leu Ile Tyr Glu Ala Ser Lys Arg Phe Ser Gly Val Ser Asp Arg
     50                  55                  60

Phe Ser Gly Ser Gly Ser Gly Thr Asp Phe Thr Leu Lys Ile Ser Gly
 65                  70                  75                  80

Val Glu Ala Gly Asp Val Gly Val Tyr Tyr Cys Gln Gln Ser Leu His
                 85                  90                  95

Phe Pro Gly Thr Phe Ser Gln Gly Thr Lys Leu Glu Ile Lys
            100                 105                 110
```

```
<210> SEQ ID NO 445
<211> LENGTH: 176
<212> TYPE: PRT
<213> ORGANISM: Canis lupus

<400> SEQUENCE: 445

Met Glu Ser Val Phe Cys Trp Val Phe Leu Val Val Ile Leu Lys Gly
 1               5                  10                  15

Val Gln Gly Glu Val Gln Leu Val Glu Ser Gly Gly Asp Leu Val Lys
```

-continued

```
                20                  25                  30
Pro Gly Gly Ser Leu Arg Leu Ser Cys Val Ala Ser Gly Phe Thr Phe
                35                  40                  45

Ser Ser Tyr Tyr Met His Trp Ile Arg Gln Ala Pro Gly Lys Gly Leu
            50                  55                  60

Gln Arg Val Ala His Ile Arg Gly Asp Gly Arg Thr Thr His Tyr Ala
65                  70                  75                  80

Asp Ala Met Lys Gly Arg Phe Thr Ile Ser Arg Asp Asn Ala Lys Asn
                85                  90                  95

Thr Leu Tyr Leu Gln Met Asn Ser Leu Thr Val Glu Asp Thr Ala Ile
            100                 105                 110

Tyr Tyr Cys Val Lys Asp Ile Tyr Tyr Gly Val Gly Asp Tyr Trp Gly
                115                 120                 125

Gln Gly Thr Leu Val Thr Val Ser Ser Ala Ser Thr Thr Ala Pro Ser
            130                 135                 140

Val Phe Pro Leu Ala Pro Ser Cys Gly Ser Thr Ser Gly Ser Thr Val
145                 150                 155                 160

Ala Leu Ala Cys Leu Val Ser Gly Tyr Phe Pro Glu Pro Val Thr Val
                165                 170                 175

<210> SEQ ID NO 446
<211> LENGTH: 179
<212> TYPE: PRT
<213> ORGANISM: Homo sapiens

<400> SEQUENCE: 446

Met Glu Leu Gly Leu Ser Trp Val Phe Leu Val Ala Ile Leu Glu Gly
1               5                   10                  15

Val Gln Cys Glu Val Gln Leu Val Glu Ser Gly Gly Gly Leu Val Gln
                20                  25                  30

Pro Gly Gly Ser Leu Arg Leu Ser Cys Val Val Ser Gly Phe Thr Phe
                35                  40                  45

Ser Ser Tyr Trp Met Ser Trp Val Arg Gln Ala Pro Gly Lys Gly Leu
            50                  55                  60

Glu Trp Val Ala Asn Ile Lys Gln Asp Gly Ser Glu Lys Tyr Tyr Val
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Ala Arg Asp Gly Ser Ser Trp Tyr Arg Asp Trp Phe Asp
                115                 120                 125

Pro Trp Gly Gln Gly Thr Leu Val Thr Val Ser Ala Ser Thr Lys
            130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val

<210> SEQ ID NO 447
<211> LENGTH: 176
<212> TYPE: PRT
<213> ORGANISM: Mus musculus

<400> SEQUENCE: 447
```

```
Met Asp Ser Arg Leu Asn Leu Val Phe Leu Val Ile Leu Lys Gly
1               5                   10                  15

Val Gln Cys Glu Val Gln Leu Val Glu Ser Gly Gly Gly Leu Val Lys
            20                  25                  30

Pro Gly Gly Ser Arg Lys Leu Ser Cys Ala Ala Ser Gly Phe Thr Phe
                35                  40                  45

Ser Asp Tyr Gly Met His Trp Val Arg Gln Ala Pro Glu Lys Gly Leu
    50                  55                  60

Glu Trp Val Ala Tyr Ile Asn Ser Gly Ser Thr Ile Tyr Tyr Ala
65                  70                  75                  80

Asp Thr Val Lys Gly Arg Phe Thr Ile Ser Arg Asp Asn Ala Lys Asn
                85                  90                  95

Thr Leu Phe Leu Gln Met Thr Ser Leu Arg Ser Glu Asp Thr Ala Met
            100                 105                 110

Tyr Tyr Cys Ala Arg Glu Leu Trp Leu Arg Arg Ile Asp Tyr Trp Gly
            115                 120                 125

Gln Gly Thr Thr Ile Thr Val Ser Ser Ala Lys Thr Thr Pro Pro Ser
    130                 135                 140

Val Tyr Pro Leu Ala Pro Gly Cys Gly Asp Thr Thr Gly Ser Ser Val
145                 150                 155                 160

Thr Leu Gly Cys Leu Val Lys Gly Tyr Phe Pro Glu Ser Val Thr Val
                165                 170                 175

<210> SEQ ID NO 448
<211> LENGTH: 180
<212> TYPE: PRT
<213> ORGANISM: Rattus rattus

<400> SEQUENCE: 448

Met Asp Ile Ser Leu Ser Leu Val Phe Leu Val Leu Phe Ile Lys Gly
1               5                   10                  15

Val Gln Cys Glu Val Gln Leu Val Glu Thr Gly Gly Gly Leu Val Gln
            20                  25                  30

Pro Gly Arg Ser Leu Lys Leu Ser Cys Val Ala Ser Gly Phe Thr Phe
                35                  40                  45

Ser Ser Tyr Trp Met Tyr Trp Ile Arg Gln Ala Pro Gly Lys Gly Leu
    50                  55                  60

Glu Trp Val Ser Ser Ile Asn Thr Asp Gly Ser Thr Tyr Tyr Pro
65                  70                  75                  80

Asp Ser Val Lys Gly Arg Phe Thr Ile Ser Arg Asp Asn Ala Glu Asn
                85                  90                  95

Thr Val Tyr Leu Gln Met Asn Ser Leu Arg Ser Glu Asp Thr Ala Thr
            100                 105                 110

Tyr Tyr Cys Ala Lys Gly Gly Glu Tyr Tyr Gly Tyr Asn Tyr Pro Phe
            115                 120                 125

Asp Tyr Trp Gly Gln Gly Val Met Val Thr Val Ser Ser Ala Glu Thr
    130                 135                 140

Thr Ala Pro Ser Val Tyr Pro Leu Ala Pro Gly Thr Ala Leu Lys Ser
145                 150                 155                 160

Asn Ser Met Val Thr Leu Gly Cys Leu Val Lys Gly Tyr Phe Pro Glu
                165                 170                 175

Pro Val Thr Val
            180

<210> SEQ ID NO 449
<211> LENGTH: 128
```

```
<212> TYPE: PRT
<213> ORGANISM: Canis lupus

<400> SEQUENCE: 449

Asp Met Gln Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Ser Tyr
            20                  25                  30

Asn Met Gly Trp Val Arg Gln Ala Pro Gly Lys Gly Leu Gln Trp Val
        35                  40                  45

Ala Trp Ile Tyr Asp Ser Gly Ser Asn Thr Arg Tyr Ala Asp Ala Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Ser Thr Thr Trp Gly Trp Asp Phe Tyr Tyr Trp Gly
            100                 105                 110

Gln Gly Thr Leu Val Thr Val Ser Ser Ala Ser Thr Thr Ala Pro Ser
        115                 120                 125

<210> SEQ ID NO 450
<211> LENGTH: 131
<212> TYPE: PRT
<213> ORGANISM: Canis lupus

<400> SEQUENCE: 450

Glu Gly Gln Leu Ala Glu Ser Gly Gly Asp Leu Val Lys Pro Gly Gly
1               5                   10                  15

Ser Leu Arg Leu Ser Cys Val Ala Ser Gly Phe Pro Phe Ser Ser Tyr
            20                  25                  30

Asn Met Gly Trp Val Arg Gln Ala Pro Gly Lys Gly Leu Gln Trp Val
        35                  40                  45

Ala Trp Ile Tyr Thr Gly Gly Thr Arg Thr Tyr Ala Asp Ala Val
    50                  55                  60

Lys Gly Arg Phe Thr Ile Ser Arg Asp Asn Ala Lys Asn Thr Leu Tyr
65                  70                  75                  80

Leu Gln Met Asn Asn Leu Arg Val Glu Asp Met Ala Gln Tyr Tyr Cys
                85                  90                  95

Ala Arg Asp Gly Gly Ser Ser Tyr Ser Ser Ile Val Glu Phe Phe Asp
            100                 105                 110

Tyr Trp Gly Gln Gly Thr Leu Val Thr Val Ser Ser Ala Ser Thr Thr
        115                 120                 125

Ala Pro Ser
    130

<210> SEQ ID NO 451
<211> LENGTH: 123
<212> TYPE: PRT
<213> ORGANISM: Canis lupus

<400> SEQUENCE: 451

Glu Val Gln Leu Val Glu Ser Gly Gly Asp Leu Val Lys Pro Ala Gly
1               5                   10                  15

Ser Leu Arg Leu Ser Cys Val Ala Ser Arg Ala Thr Phe Ser Ser Tyr
            20                  25                  30

Asn Met Gly Trp Val Arg Gln Ala Pro Gly Arg Gly Leu Gln Trp Val
        35                  40                  45
```

```
Ala Trp Ile Tyr Asp Ser Gly Ser Gly Thr Arg Tyr Ala Asp Ala Val
    50                  55                  60

Lys Gly Arg Phe Thr Ile Ser Arg Asp Asn Ala Arg Asn Thr Leu Tyr
 65                  70                  75                  80

Leu Gln Met Asn Arg Leu Arg Val Glu Asp Thr Ala Met Tyr Tyr Cys
                 85                  90                  95

Ala Arg Glu Asn Trp Ser Val Asp Ala Trp Gly Gln Gly Thr Leu Val
                100                 105                 110

Thr Val Ser Ser Ala Ser Thr Thr Ala Pro Ser
            115                 120

<210> SEQ ID NO 452
<211> LENGTH: 128
<212> TYPE: PRT
<213> ORGANISM: Canis lupus

<400> SEQUENCE: 452

Glu Val Gln Leu Val Glu Ser Gly Gly Asn Leu Val Lys Pro Gly Gly
  1               5                  10                  15

Ser Leu Arg Leu Ser Cys Val Ala Ser Gly Phe Thr Phe Ser Ala His
                 20                  25                  30

Thr Met Ser Trp Val Arg Gln Ala Pro Glu Thr Gly Leu Gln Leu Val
             35                  40                  45

Ala Ala Ile Lys Ser Asp Gly Arg Lys Thr Tyr Tyr Thr Asp Ala Val
    50                  55                  60

Arg Gly Arg Phe Thr Ile Ser Arg Asp Asn Val Lys Asn Thr Leu Tyr
 65                  70                  75                  80

Leu Gln Met Asn Asp Leu Arg Thr Glu Asp Thr Ala Met Tyr Tyr Cys
                 85                  90                  95

Ala Thr Asn Glu Gly Asp Ser Arg Tyr Val Gly Phe Asp Tyr Trp Gly
                100                 105                 110

Gln Gly Thr Leu Val Thr Val Ser Pro Ala Ser Thr Thr Ala Pro Ser
            115                 120                 125

<210> SEQ ID NO 453
<211> LENGTH: 126
<212> TYPE: PRT
<213> ORGANISM: Canis lupus

<400> SEQUENCE: 453

Glu Val Ser Leu Val Glu Ser Gly Gly Asp Leu Val Lys Pro Gly Gly
  1               5                  10                  15

Thr Leu Arg Leu Ser Cys Val Ala Ser Gly Phe Thr Phe Ser Phe Asn
                 20                  25                  30

Asn Met Gly Trp Val Arg Gln Ala Pro Gly Lys Gly Leu Gln Trp Val
             35                  40                  45

Ala Trp Ile Tyr Asn Asp Gly Thr Thr Thr Tyr Ala Asp Ala Val
    50                  55                  60

Lys Gly Arg Phe Thr Ile Ser Arg Asp Asn Ala Lys Asn Thr Leu Tyr
 65                  70                  75                  80

Leu Gln Met Asn Pro Leu Arg Ala Glu Asp Thr Ala Val Tyr Tyr Cys
                 85                  90                  95

Val Arg His Gly Tyr Asp Ile Thr Gly Gly Asp Glu Trp Gly Gln Gly
                100                 105                 110

Thr Leu Val Thr Val Ser Ser Ala Ser Thr Thr Ala Pro Ser
            115                 120                 125
```

<210> SEQ ID NO 454
<211> LENGTH: 126
<212> TYPE: PRT
<213> ORGANISM: Canis lupus

<400> SEQUENCE: 454

Gly Val Gln Leu Val Glu Ser Gly Gly Asp Leu Val Lys Pro Gly Gly
1               5                   10                  15

Ser Leu Arg Leu Ser Cys Val Ala Ser Gly Phe Asn Phe Ser Ser Ser
            20                  25                  30

Asp Met Ser Trp Val Arg Gln Ser Pro Gly Lys Gly Leu Gln Trp Val
        35                  40                  45

Ala Ile Ile Trp Asn Asp Gly Phe Ser Thr Tyr Tyr Gly Asp Ala Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Ala Ala Met Tyr Tyr Cys
                85                  90                  95

Ala Pro Thr Gly Phe His Asp Arg Phe Leu Ser Tyr Trp Gly Gln Gly
            100                 105                 110

Thr Leu Val Thr Val Ser Ser Ala Ser Thr Thr Ala Pro Ser
        115                 120                 125

<210> SEQ ID NO 455
<211> LENGTH: 130
<212> TYPE: PRT
<213> ORGANISM: Canis lupus

<400> SEQUENCE: 455

Gly Val Gln Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Thr Tyr
            20                  25                  30

Asn Met Gly Trp Val Arg Gln Ser Pro Gly Lys Gly Leu Gln Trp Val
        35                  40                  45

Ala Trp Ile Tyr Tyr Asp Gly Ser Ser Thr Ile Tyr Ser Asp Asp Val
    50                  55                  60

Arg Gly Arg Phe Thr Ile Ser Arg Asp Thr Ala Arg Asn Thr Val His
65                  70                  75                  80

Leu Gln Met Asn Asn Leu Arg Ala Glu Asp Thr Ala Val Tyr Tyr Cys
                85                  90                  95

Ala Thr Gly Thr Tyr Ser Ser Trp Tyr Trp Glu Gly Phe Asp Tyr
            100                 105                 110

Trp Gly Gln Gly Thr Leu Val Thr Val Ser Ser Ala Ser Thr Thr Ala
        115                 120                 125

Pro Ser
    130

<210> SEQ ID NO 456
<211> LENGTH: 131
<212> TYPE: PRT
<213> ORGANISM: Canis lupus

<400> SEQUENCE: 456

Asp Val Gln Leu Val Glu Ser Gly Gly Asp Leu Val Lys Pro Gly Gly
1               5                   10                  15

Ala Leu Arg Leu Ser Cys Gly Ser Gly Asn Thr Leu Asn Ser Tyr
            20                  25                  30

```
Asp Met Asp Trp Val Arg Gln Ala Pro Gly Lys Gly Leu Gln Trp Leu
            35                  40                  45

Ser Glu Ile Ser Ser Gly Ser Ser Thr Tyr Tyr Ala Asp Ala Val
 50                  55                  60

Lys Gly Arg Phe Thr Ile Ser Arg Asp Asn Ala Lys Asn Met Leu Tyr
 65                  70                  75                  80

Leu Gln Met Asn Ser Leu Arg Ala Glu Asp Thr Ala Val Tyr Tyr Cys
                 85                  90                  95

Ala Ala Pro Tyr Ser Ser Ser Trp His Pro Ile Gly Phe Gly Leu Asp
                100                 105                 110

Tyr Trp Gly His Gly Thr Ser Leu Phe Val Ser Ser Ala Ser Thr Thr
                115                 120                 125

Ala Pro Ser
        130

<210> SEQ ID NO 457
<211> LENGTH: 127
<212> TYPE: PRT
<213> ORGANISM: Canis lupus
<220> FEATURE:
<221> NAME/KEY: misc_feature
<222> LOCATION: (40)..(40)
<223> OTHER INFORMATION: Xaa can be any naturally occurring amino acid
<220> FEATURE:
<221> NAME/KEY: misc_feature
<222> LOCATION: (53)..(53)
<223> OTHER INFORMATION: Xaa can be any naturally occurring amino acid
<220> FEATURE:
<221> NAME/KEY: misc_feature
<222> LOCATION: (61)..(61)
<223> OTHER INFORMATION: Xaa can be any naturally occurring amino acid

<400> SEQUENCE: 457

Glu Val Gln Leu Val Glu Ser Gly Gly Asp Gln Val Lys Pro Gly Gly
 1               5                  10                  15

Ser Leu Arg Leu Ser Cys Val Gly Ser Gly Phe Thr Phe Ser Asp Tyr
                 20                  25                  30

Asp Ile Cys Trp Val Arg Gln Xaa Pro Gly Lys Gly Leu Gln Trp Val
            35                  40                  45

Ala Ala Ile Ser Xaa Asp Gly Ser Arg Thr Tyr Val Xaa Asp Ala Val
 50                  55                  60

Lys Gly Arg Phe Thr Val Ser Arg Asp Asn Ala Arg Asn Ala Leu Tyr
 65                  70                  75                  80

Leu Gln Met Asn Ser Leu Arg Ala Glu Asp Thr Ala Val Tyr Tyr Cys
                 85                  90                  95

Val Asp Val Arg Gly Arg Ser Gly Gln Tyr Phe Gly Asp Trp Gly Gln
                100                 105                 110

Gly Thr Leu Val Thr Val Ser Ser Ala Ser Thr Thr Ala Pro Ser
                115                 120                 125

<210> SEQ ID NO 458
<211> LENGTH: 123
<212> TYPE: PRT
<213> ORGANISM: Canis lupus
<220> FEATURE:
<221> NAME/KEY: misc_feature
<222> LOCATION: (29)..(29)
<223> OTHER INFORMATION: Xaa can be any naturally occurring amino acid

<400> SEQUENCE: 458

Gly Val Gln Leu Val Glu Ser Gly Gly Asp Leu Ala Lys Pro Gly Gly
 1               5                  10                  15
```

Ser Leu Arg Leu Ser Cys Val Ala Ser Gly Leu Thr Xaa Asn Asp Tyr
            20                  25                  30

Asp Met Ser Trp Val Arg Gln Ala Pro Gly Lys Gly Leu Gln Trp Val
            35                  40                  45

Ala Ala Ile Ser Tyr Asp Gly Ser Thr Tyr Tyr Thr Asp Ala Val
    50                  55                  60

Lys Gly Arg Phe Thr Ile Ser Arg Asp Asn Ala Arg Asn Thr Val Ser
65                  70                  75                  80

Leu Gln Met Thr Gly Leu Arg Val Glu Asp Thr Ala Val Tyr Tyr Cys
                85                  90                  95

Arg Gly Thr Leu Leu Asn Phe Asp Phe Trp Gly Gln Gly Thr Leu Val
            100                 105                 110

Thr Val Ser Ser Ala Ser Thr Thr Ala Pro Ser
            115                 120

<210> SEQ ID NO 459
<211> LENGTH: 121
<212> TYPE: PRT
<213> ORGANISM: Canis lupus

<400> SEQUENCE: 459

Glu Val Gln Leu Val Glu Ser Gly Gly Asp Leu Val Lys Pro Gly Gly
1               5                   10                  15

Ser Leu Arg Leu Ser Cys Val Ala Pro Gly Phe Thr Phe Ser Ser Tyr
            20                  25                  30

Ser Met Ser Trp Val Arg Gln Ala Pro Gly Lys Gly Leu Gln Trp Val
            35                  40                  45

Thr Gly Ile Asp Tyr Asp Gly Arg Ser Thr Tyr Tyr Thr Ala Ala Val
    50                  55                  60

Lys Gly Arg Phe Thr Ile Ser Arg Asp Asn Ala Arg Asn Thr Val Tyr
65                  70                  75                  80

Leu Gln Met Asn Ser Leu Arg Ala Asp Asp Thr Gly Leu Tyr Tyr Cys
                85                  90                  95

Ala Val Gly Ser Ile Asp Tyr Trp Gly Gln Gly Thr Leu Val Thr Val
            100                 105                 110

Ser Ser Ala Ser Thr Thr Ala Pro Ser
            115                 120

<210> SEQ ID NO 460
<211> LENGTH: 121
<212> TYPE: PRT
<213> ORGANISM: Canis lupus

<400> SEQUENCE: 460

Glu Val Gln Leu Val Glu Ser Gly Gly Asp Leu Val Lys Pro Gly Gly
1               5                   10                  15

Ser Leu Arg Leu Ser Cys Val Ala Ser Gly Phe Ser Ile Gly Asp Ser
            20                  25                  30

Asp Thr Asn Trp Val Arg Leu Ala Pro Gly Lys Arg Leu Gln Trp Val
            35                  40                  45

Ala Gly Ile Ser Val Asp Gly Ile Ser Thr Tyr Tyr Ile Asp Ala Val
    50                  55                  60

Lys Gly Arg Phe Thr Ile Ser Arg Asp Thr Ala Lys Arg Thr Val Tyr
65                  70                  75                  80

Leu Gln Met Asn Ser Leu Arg Ala Glu Asp Thr Ala Val Tyr Tyr Cys
                85                  90                  95

```
Gly Pro Gly Ser Gly Tyr Tyr Trp Gly Gln Gly Thr Leu Val Thr Val
            100                 105                 110

Ser Ser Ala Ser Thr Thr Ala Pro Ser
        115                 120
```

<210> SEQ ID NO 461
<211> LENGTH: 128
<212> TYPE: PRT
<213> ORGANISM: Canis lupus

<400> SEQUENCE: 461

```
Glu Val Arg Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Ser Ser
            20                  25                  30

Gly Met Ser Trp Ile Arg Gln Ala Pro Gly Lys Gly Leu Gln Trp Val
        35                  40                  45

Ala Tyr Ile Gly Pro Tyr Pro Thr Asn Ile Ala Tyr Ala Asp Ala Val
    50                  55                  60

Lys Gly Arg Phe Thr Ile Ser Arg Asp Asn Ala Lys Asn Ala Leu Tyr
65                  70                  75                  80

Leu Gln Met Asp Arg Leu Arg Ala Glu Asp Thr Ala Met Tyr Tyr Cys
                85                  90                  95

Ala Arg Gly Gly Glu Tyr Ile Trp Ile Pro Ser Phe Asp Tyr Trp Gly
            100                 105                 110

Gln Gly Thr Leu Val Thr Val Ser Ser Ala Ser Thr Thr Ala Pro Ser
        115                 120                 125
```

<210> SEQ ID NO 462
<211> LENGTH: 127
<212> TYPE: PRT
<213> ORGANISM: Canis lupus

<400> SEQUENCE: 462

```
Glu Val Gln Leu Val Glu Ser Gly Gly Asp Leu Val Lys Pro Gly Gly
1               5                   10                  15

Ala Leu Lys Leu Ser Cys Val Ala Ser Gly Phe Ala Phe Ser Ser Tyr
            20                  25                  30

Tyr Met Tyr Trp Val Arg Gln Ala Leu Gly Lys Gly Leu Gln Trp Val
        35                  40                  45

Ala Arg Ile Ser Gly Asp Gly Ser Ser Thr Tyr Tyr Ala Asp Ala Met
    50                  55                  60

Lys Gly Arg Phe Thr Ile Ser Arg Asp Asn Ala Lys Lys Thr Leu Tyr
65                  70                  75                  80

Leu Gln Met Asn Ser Leu Arg Asp Glu Asp Thr Ala Val Tyr Tyr Cys
                85                  90                  95

Ala Arg Trp Asp Tyr Thr Ser Tyr Trp Gly Cys Asp Tyr Trp Gly Gln
            100                 105                 110

Gly Thr Leu Val Thr Val Ser Ser Ala Ser Thr Thr Ala Pro Ser
        115                 120                 125
```

<210> SEQ ID NO 463
<211> LENGTH: 125
<212> TYPE: PRT
<213> ORGANISM: Canis lupus

<400> SEQUENCE: 463

```
Glu Gly Gln Leu Ala Glu Ser Gly Gly Asp Leu Val Lys Pro Gly Gly
1               5                   10                  15
```

```
Ser Leu Arg Leu Ser Cys Val Ala Ser Gly Phe Thr Phe Ser Asn Asn
            20                  25                  30

Tyr Met Thr Trp Ile Arg Gln Ala Pro Gly Lys Gly Leu Gln Trp Val
        35                  40                  45

Ser Gln Ile Asn Ser Asp Gly Ser Ser Thr Ser Tyr Ala Asp Ala Val
 50                  55                  60

Lys Gly Arg Phe Thr Ile Ser Arg Asp Asn Ala Arg Asn Thr Leu Tyr
 65                  70                  75                  80

Leu Gln Met Asn Ser Leu Arg Ala Glu Asp Thr Gly Ile Tyr Tyr Cys
                85                  90                  95

Thr Arg Asp Asp Ile Ala Gly Ser Tyr Ser Ala Trp Gly Gln Gly Thr
                100                 105                 110

Leu Val Thr Val Ser Ser Ala Ser Thr Thr Ala Pro Ser
            115                 120                 125

<210> SEQ ID NO 464
<211> LENGTH: 126
<212> TYPE: PRT
<213> ORGANISM: Canis lupus

<400> SEQUENCE: 464

Glu Val Arg Leu Val Glu Ser Gly Gly Asp Leu Val Lys Pro Gly Gly
 1               5                  10                  15

Ser Leu Arg Leu Ser Cys Val Ala Ser Gly Leu Thr Phe Ser Ser Tyr
            20                  25                  30

Tyr Tyr Trp Val Arg Gln Ala Pro Gly Arg Gly Leu Asn Trp Val Ala
        35                  40                  45

Arg Ile Ser Ser Asp Gly Ser Ser Thr Tyr Tyr Ala Asp Ala Val Lys
 50                  55                  60

Gly Arg Phe Thr Ile Ser Arg Asp Asn Ala Lys Asn Thr Leu Tyr Leu
 65                  70                  75                  80

Gln Met Asn Ser Leu Arg Val Glu Asp Thr Gly Leu Tyr Tyr Cys Val
                85                  90                  95

Asp Ile Arg Gly Gly Ser Gly Arg Tyr Phe Gly Ala Trp Gly Gln Gly
                100                 105                 110

Thr Leu Val Thr Val Ser Ser Ala Ser Thr Thr Ala Pro Ser
            115                 120                 125

<210> SEQ ID NO 465
<211> LENGTH: 125
<212> TYPE: PRT
<213> ORGANISM: Canis lupus

<400> SEQUENCE: 465

Glu Val Gln Leu Val Glu Ser Gly Gly Asp Leu Val Lys Pro Gly Gly
 1               5                  10                  15

Ser Leu Thr Leu Ser Cys Val Ala Ser Gly Phe Thr Phe Arg Asp Ser
            20                  25                  30

Thr Met Ser Trp Val Arg Gln Ala Pro Gly Lys Gly Leu Gln Trp Val
        35                  40                  45

Thr Phe Ile Thr Ser Asp Gly Gly Asn Thr Ala Tyr Thr Asp Ala Val
 50                  55                  60

Lys Gly Arg Phe Thr Ile Ser Arg Asp Asn Ala Arg Asn Thr Leu Phe
 65                  70                  75                  80

Leu Gln Met Ser Gly Leu Arg Ala Glu Asp Thr Ala Met Tyr Tyr Cys
                85                  90                  95
```

-continued

```
Val Ala Pro Val Tyr Ala Tyr Gln Phe Asp Tyr Trp Gly Gln Gly Thr
            100                 105                 110

Leu Val Thr Val Ser Ser Ala Ser Thr Thr Ala Pro Ser
        115                 120                 125
```

<210> SEQ ID NO 466
<211> LENGTH: 132
<212> TYPE: PRT
<213> ORGANISM: Canis lupus

<400> SEQUENCE: 466

```
Gly Val Gln Leu Val Glu Ser Gly Gly Asp Leu Val Lys Pro Ala Gly
1               5                   10                  15

Ser Leu Arg Leu Ser Cys Glu Ala Ser Gly Phe Thr Phe Ser Arg Leu
            20                  25                  30

Tyr Ile Tyr Trp Val Arg Gln Ala Pro Gly Lys Gly Leu Gln Trp Val
        35                  40                  45

Ala Arg Ile Ser Ser Asp Gly Phe Thr Thr Ser Tyr Gly Asp Thr Val
    50                  55                  60

Lys Gly Arg Phe Thr Ile Ser Arg Asp Asn Ala Lys Asn Thr Leu Tyr
65                  70                  75                  80

Leu Gln Met Asp Ser Leu Arg Ala Asp Thr Ala Met Tyr Tyr Cys
                85                  90                  95

Ala Lys Val Arg Pro Leu Thr His Tyr Tyr Gly Ser Tyr Ala Tyr Phe
            100                 105                 110

Asp Tyr Trp Gly Gln Gly Thr Leu Val Thr Val Ser Ser Ala Ser Thr
        115                 120                 125

Thr Ala Pro Ser
    130
```

<210> SEQ ID NO 467
<211> LENGTH: 126
<212> TYPE: PRT
<213> ORGANISM: Canis lupus

<400> SEQUENCE: 467

```
Glu Val Gln Leu Val Glu Ser Gly Gly Asp Leu Val Lys Pro Ala Gly
1               5                   10                  15

Ser Leu Arg Leu Ser Cys Val Ala Ser Gly Phe Ala Phe Ser Arg Tyr
            20                  25                  30

Asp Met Ser Trp Val Arg Gln Ala Pro Glu Lys Gly Leu Gln Leu Val
            35                  40                  45

Ala Asn Ile His Ser Gly Gly Tyr Asn Thr Tyr Tyr Thr Asp Ala Val
    50                  55                  60

Lys Gly Arg Phe Thr Ile Ser Arg Asp Asn Gly Lys Asn Thr Val Tyr
65                  70                  75                  80

Leu Gln Met Asn Asp Leu Arg Ala Glu Asp Thr Ala Met Tyr Tyr Cys
                85                  90                  95

Ala Arg Gly Asn Tyr Gly Ser Tyr Ser Leu Asp Tyr Trp Gly Gln Gly
            100                 105                 110

Thr Leu Val Thr Val Ser Ser Ala Ser Thr Thr Ala Pro Ser
        115                 120                 125
```

<210> SEQ ID NO 468
<211> LENGTH: 124
<212> TYPE: PRT
<213> ORGANISM: Canis lupus
<220> FEATURE:
<221> NAME/KEY: misc_feature
<222> LOCATION: (106)..(106)
<223> OTHER INFORMATION: Xaa can be any naturally occurring amino acid

<400> SEQUENCE: 468

Glu Gly Gln Leu Ala Glu Ser Gly Gly Asp Leu Ala Lys Pro Gly Gly
1               5                   10                  15

Ser Leu Arg Leu Ser Cys Val Ala Ser Gly Phe Ile Phe Thr Ser Tyr
            20                  25                  30

Ser Met Ser Trp Val Arg Gln Ala Pro Glu Lys Gly Leu Gln Leu Val
        35                  40                  45

Ala Gly Ile Asn Ser Gly Gly Ser Ser Thr Tyr Tyr Thr Asp Ala Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Arg Gly Glu Asp Thr Ala Val Tyr Tyr Cys
                85                  90                  95

Ala Thr Asn His Leu Ala Asn Leu Asp Xaa Trp Gly Gln Gly Thr Leu
            100                 105                 110

Val Thr Val Ser Ser Ala Ser Thr Thr Ala Pro Ser
        115                 120

<210> SEQ ID NO 469
<211> LENGTH: 127
<212> TYPE: PRT
<213> ORGANISM: Canis lupus
<220> FEATURE:
<221> NAME/KEY: misc_feature
<222> LOCATION: (51)..(51)
<223> OTHER INFORMATION: Xaa can be any naturally occurring amino acid

<400> SEQUENCE: 469

Glu Val Gln Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Ser Pro
            20                  25                  30

Ile Met Ser Trp Val Arg Gln Ala Pro Glu Lys Ala Pro Gln Leu Val
        35                  40                  45

Ala Thr Xaa Asp Ile Asp Gly Ser Arg Thr Phe Tyr Thr Asp Ala Val
    50                  55                  60

Arg Gly Arg Phe Thr Ile Ser Arg Asp Asn Ala Lys Asn Thr Met Tyr
65                  70                  75                  80

Leu Gln Met Asn Ser Leu Arg Ser Glu Asp Thr Ala Val Tyr Tyr Cys
                85                  90                  95

Val Pro Arg Asp Tyr Gly Ser Tyr Tyr Gly Phe Asp Tyr Trp Gly Gln
            100                 105                 110

Gly Thr Leu Val Thr Val Ser Ser Ala Ser Thr Thr Ala Pro Ser
        115                 120                 125

<210> SEQ ID NO 470
<211> LENGTH: 131
<212> TYPE: PRT
<213> ORGANISM: Canis lupus

<400> SEQUENCE: 470

Glu Val Gln Leu Val Glu Leu Gly Gly Asp Leu Val Lys Pro Gly Gly
1               5                   10                  15

Ser Leu Arg Val Ser Cys Val Ala Ser Gly Phe Thr Phe Ser Pro Tyr
            20                  25                  30

Thr Met Asn Trp Val Arg Gln Ala Pro Gly Lys Gly Leu Gln Trp Val

```
                    35                  40                  45
Ala Ser Ile Asn Ser Gly Gly Ser Val Thr Tyr Tyr Ala Asp Ala Val
 50                  55                  60

Lys Gly Arg Phe Thr Ile Ser Arg Asp Asn Asp Arg Asn Thr Leu Tyr
 65                  70                  75                  80

Leu Gln Met Asn Ser Leu Arg Pro Glu Asp Ala Ala Val Tyr Tyr Cys
                 85                  90                  95

Ala Arg Ala Tyr Pro Gly Tyr Ser Thr Tyr Phe His Gly Met Asp
                100                 105                 110

Ser Trp Gly His Gly Thr Ser Leu Phe Val Ser Ser Ala Ser Thr Thr
                115                 120                 125

Ala Pro Ser
    130

<210> SEQ ID NO 471
<211> LENGTH: 129
<212> TYPE: PRT
<213> ORGANISM: Canis lupus

<400> SEQUENCE: 471

Gly Glu Gln Leu Val Glu Ser Gly Gly Asp Leu Val Lys Pro Gly Gly
 1               5                  10                  15

Ser Leu Thr Leu Ser Cys Val Ala Ser Gly Phe Thr Phe Ser Ser Tyr
                 20                  25                  30

Asn Met Ala Trp Val Arg Gln Ala Pro Gly Glu Gly Leu Gln Trp Val
                 35                  40                  45

Ala Trp Ile Tyr Tyr Ala Gly Gly Arg Thr Asp Tyr Ala Asp Asp Val
 50                  55                  60

Lys Gly Arg Phe Thr Val Ser Arg Asp Asn Ala Lys Asn Thr Leu Tyr
 65                  70                  75                  80

Leu Gln Met Asn Ser Leu Arg Ala Glu Asp Thr Ala Met Tyr Tyr Cys
                 85                  90                  95

Ala Lys Asp Asn Ser Ala Trp Ser Val Trp Ser Cys Tyr Asp Tyr Trp
                100                 105                 110

Gly Gln Gly Thr Leu Val Thr Val Ser Ser Ala Ser Thr Thr Ala Pro
                115                 120                 125

Ser

<210> SEQ ID NO 472
<211> LENGTH: 129
<212> TYPE: PRT
<213> ORGANISM: Canis lupus

<400> SEQUENCE: 472

Glu Val Ser Leu Val Glu Ser Gly Gly Asp Leu Val Lys Pro Gly Gly
 1               5                  10                  15

Ser Leu Arg Leu Ser Cys Ala Ala Ser Gly Phe Ala Phe Ser Asn Tyr
                 20                  25                  30

Tyr Met Tyr Trp Val Arg Gln Ala Pro Gly Lys Gly Leu Gln Trp Val
                 35                  40                  45

Ala Arg Ile Ser Ile Asp Gly Lys Thr Thr Tyr Tyr Gly Asp Ala Val
 50                  55                  60

Lys Gly Arg Phe Thr Val Ser Arg Asp Asn Ala Asn Asn Thr Leu Tyr
 65                  70                  75                  80

Leu Arg Met Asn Ser Leu Arg Ala Glu Asp Thr Ala Val Tyr His Cys
                 85                  90                  95
```

Ala Ser Ser Gly Gly Lys Gly Ser Tyr Tyr Arg Phe Asp Tyr Trp
            100                 105                 110

Gly Gln Gly Thr Leu Val Thr Val Ser Ser Ala Ser Thr Thr Ala Pro
        115                 120                 125

Ser

<210> SEQ ID NO 473
<211> LENGTH: 121
<212> TYPE: PRT
<213> ORGANISM: Canis lupus

<400> SEQUENCE: 473

Glu Val Gln Leu Val Glu Ser Gly Gly Asp Leu Val Lys Pro Gly Gly
1               5                   10                  15

Ser Leu Arg Leu Ser Cys Val Ala Pro Gly Phe Thr Phe Lys Asp His
            20                  25                  30

His Met Thr Trp Val Arg Gln Ala Pro Gly Lys Gly Phe Gln Trp Val
        35                  40                  45

Thr Tyr Ile Asn Ser Gly Gly Asp Lys Thr Thr Tyr Ala Asp Ala Val
    50                  55                  60

Arg Gly Arg Phe Thr Val Ser Arg Asp Asn Ala Arg Asn Thr Val Tyr
65                  70                  75                  80

Leu Gln Met Asn Ser Leu Arg Ala Asp Asp Thr Ala Leu Tyr Tyr Cys
                85                  90                  95

Ala Val Gly Ser Ile Asp Tyr Trp Gly Gln Gly Thr Leu Val Thr Val
            100                 105                 110

Ser Ser Ala Ser Thr Thr Ala Pro Ser
        115                 120

<210> SEQ ID NO 474
<211> LENGTH: 127
<212> TYPE: PRT
<213> ORGANISM: Canis lupus

<400> SEQUENCE: 474

Glu Val Gln Leu Val Glu Ser Gly Gly Asp Leu Val Lys Pro Gly Gly
1               5                   10                  15

Ser Leu Arg Leu Ser Cys Val Ala Ser Gly Phe Thr Leu Ser Asp Ser
            20                  25                  30

Asp Thr Asn Trp Val Arg Leu Ala Pro Gly Lys Arg Leu Gln Trp Val
        35                  40                  45

Ala Gly Ile Ser Val Asp Gly Ile Ser Thr Tyr Tyr Ile Asp Ala Val
    50                  55                  60

Lys Gly Arg Phe Thr Ile Ser Arg Asp Thr Ala Arg Lys Thr Val Tyr
65                  70                  75                  80

Leu Gln Met Asn Ser Leu Gly Val Glu Asp Thr Ala Val Tyr Phe Cys
                85                  90                  95

Ser Ser Gly Tyr Ile Tyr Met Asp Thr Ile Ala Asp Asn Trp Gly Gln
            100                 105                 110

Gly Thr Leu Val Thr Val Ser Pro Ala Ser Thr Thr Ala Pro Ser
        115                 120                 125

<210> SEQ ID NO 475
<211> LENGTH: 123
<212> TYPE: PRT
<213> ORGANISM: Canis lupus

<400> SEQUENCE: 475

```
Gly Val Gln Leu Val Glu Ser Gly Gly Asp Leu Ala Lys Pro Gly Gly
1               5                   10                  15

Ser Leu Arg Leu Ser Cys Val Ala Ser Gly Leu Thr Phe Ser Asp His
            20                  25                  30

His Val Asn Trp Val Arg Gln Pro Gly Lys Gly Leu Gln Trp Val
        35                  40                  45

Ala Tyr Ile Asn Asn Asp Gly Lys Asp Ile Ala Phe Ala Asp Ala Val
    50                  55                  60

Lys Gly Arg Phe Thr Ile Ser Arg Asp Asn Ala Lys Asn Thr Val Tyr
65                  70                  75                  80

Leu Gln Met Asp Ser Leu Arg Val Glu Asp Thr Ala Val Tyr Tyr Cys
                85                  90                  95

Arg Gly Thr Leu Leu Asn Phe Asp Phe Trp Gly Gln Gly Thr Leu Val
                100                 105                 110

Thr Val Ser Ser Ala Ser Thr Thr Ala Pro Ser
            115                 120

<210> SEQ ID NO 476
<211> LENGTH: 123
<212> TYPE: PRT
<213> ORGANISM: Canis lupus

<400> SEQUENCE: 476

Gly Val Gln Leu Val Glu Ser Gly Gly Asp Leu Ala Lys Pro Gly Gly
1               5                   10                  15

Ser Leu Arg Leu Ser Cys Val Ala Ser Gly Leu Ala Phe Asn Ser Tyr
            20                  25                  30

Ser Met Ser Trp Val Arg Gln Ala Pro Gly Lys Gly Leu Gln Trp Val
        35                  40                  45

Thr Gly Ile Asp Tyr Asp Gly Arg Ser Thr Tyr Tyr Thr Ala Ala Val
    50                  55                  60

Lys Gly Arg Phe Thr Ile Ser Arg Asp Asn Ala Arg Asn Thr Val Tyr
65                  70                  75                  80

Leu Gln Met Asn Ser Leu Arg Val Glu Asp Thr Ala Val Tyr Tyr Cys
                85                  90                  95

Arg Gly Thr Leu Leu Asn Phe Asp Phe Trp Gly Gln Gly Thr Leu Val
                100                 105                 110

Thr Val Ser Ser Ala Ser Thr Thr Ala Pro Ser
            115                 120

<210> SEQ ID NO 477
<211> LENGTH: 131
<212> TYPE: PRT
<213> ORGANISM: Canis lupus

<400> SEQUENCE: 477

Glu Val Gln Leu Val Glu Ser Gly Gly Asp Leu Val Lys Pro Gly Gly
1               5                   10                  15

Ser Leu Arg Leu Ser Cys Val Ala Ser Gly Phe Ser Ile Gly Ser Tyr
            20                  25                  30

Ser Met Ser Trp Val Arg Gln Ala Pro Gly Lys Gly Leu Gln Trp Val
        35                  40                  45

Thr Gly Ile Asp Tyr Asp Gly Arg Ser Thr Tyr Tyr Thr Ala Ala Val
    50                  55                  60

Lys Gly Arg Phe Thr Ile Ser Arg Asp Asn Ala Arg Asn Thr Val Tyr
65                  70                  75                  80

Leu Gln Met Asn Ser Leu Arg Ala Glu Asp Thr Ala Val Tyr Tyr Cys
```

```
                85                  90                  95
Val Ala Arg Ser Ala Arg Gly Ser Ser Trp Tyr Gly Gly Phe Asp
            100                 105                 110
Tyr Trp Gly Gln Gly Thr Leu Val Thr Val Ser Ser Ala Ser Thr Thr
            115                 120                 125
Ala Pro Ser
            130

<210> SEQ ID NO 478
<211> LENGTH: 130
<212> TYPE: PRT
<213> ORGANISM: Canis lupus

<400> SEQUENCE: 478

Glu Val Gln Leu Val Glu Ser Gly Gly Asp Leu Val Lys Pro Gly Gly
1               5                   10                  15
Ser Leu Arg Leu Ser Cys Leu Val Ser Gly Leu Ser Ile Gly Ser Tyr
            20                  25                  30
His Met Ser Trp Val Arg Gln Ala Pro Gly Lys Gly Leu Gln Trp Val
            35                  40                  45
Ala Tyr Ile Asn Ser Gly Gly Ser Ser Thr Ser Tyr Ala Asp Ala Val
        50                  55                  60
Lys Gly Arg Phe Thr Ile Ser Arg Asp Asn Ala Lys Asn Thr Leu Tyr
65                  70                  75                  80
Leu Gln Met Asn Ser Leu Arg Thr Glu Asp Thr Ala Val Tyr Tyr Cys
                85                  90                  95
Ala Thr Gly Leu Gly Leu Ile Tyr Leu Asn Arg Tyr His Leu Thr Tyr
            100                 105                 110
Trp Gly Gln Gly Thr Leu Val Thr Val Ser Ser Ala Ser Thr Thr Ala
            115                 120                 125
Pro Ser
    130

<210> SEQ ID NO 479
<211> LENGTH: 127
<212> TYPE: PRT
<213> ORGANISM: Canis lupus

<400> SEQUENCE: 479

Glu Val Gln Leu Val Glu Ser Gly Gly Asp Leu Val Lys Pro Gly Gly
1               5                   10                  15
Ser Leu Arg Leu Ser Cys Val Ala Ser Gly Phe Thr Phe Ser Ser His
            20                  25                  30
Asp Met Thr Trp Val Arg Gln Ala Pro Gly Lys Gly Leu Gln Trp Val
            35                  40                  45
Ala Ala Leu Thr Tyr Asp Gly Ile Thr Tyr His Ser Asp Ser Val Lys
        50                  55                  60
Gly Arg Val Thr Val Ser Arg Asp Asn Gly Arg Asn Thr Val Tyr Leu
65                  70                  75                  80
Gln Met Asp Ser Leu Arg Val Glu Asp Thr Ala Val Tyr Tyr Cys Ala
                85                  90                  95
Ala Gly Leu Ala Tyr His Gly Ser Tyr Tyr Gly Asp His Trp Gly Gln
            100                 105                 110
Gly Thr Leu Val Thr Val Ser Ser Ala Ser Thr Thr Ala Pro Ser
            115                 120                 125

<210> SEQ ID NO 480
```

```
<211> LENGTH: 126
<212> TYPE: PRT
<213> ORGANISM: Canis lupus

<400> SEQUENCE: 480

Glu Gly Gln Leu Ala Glu Ser Gly Gly Asp Leu Val Lys Pro Gly Gly
1               5                   10                  15

Ser Leu Arg Leu Ser Cys Val Ala Ser Gly Phe Ala Phe Ser Ala Tyr
            20                  25                  30

His Met Thr Trp Ile Arg Leu Ala Pro Gly Lys Gly Pro Gln Trp Val
        35                  40                  45

Gly Tyr Ile Asn Ser Gly Gly Ala Val Thr Arg Phe Ala Asp Ala Val
    50                  55                  60

Lys Asp Arg Phe Thr Leu Ser Arg Asp Gly Ala Lys Asn Thr Leu Tyr
65                  70                  75                  80

Leu Gln Met Asn Asn Leu Thr Thr Glu Asp Thr Ala Val Tyr Tyr Cys
                85                  90                  95

Ala Asn Asn Phe Gly Thr Asp Tyr Glu Phe Asp Tyr Trp Gly Gln Gly
            100                 105                 110

Thr Leu Val Thr Val Ser Ser Ala Ser Thr Thr Ala Pro Ser
        115                 120                 125

<210> SEQ ID NO 481
<211> LENGTH: 131
<212> TYPE: PRT
<213> ORGANISM: Canis lupus

<400> SEQUENCE: 481

Glu Glu Gln Leu Val Glu Phe Gly Gly Asp Leu Val Lys Pro Gly Gly
1               5                   10                  15

Ser Leu Arg Leu Ser Cys Val Ala Ser Gly Phe Thr Leu Ser Thr Tyr
            20                  25                  30

Asn Met Val Trp Val Arg Gln Ala Pro Gly Lys Gly Leu Gln Trp Val
        35                  40                  45

Ala Trp Ile Tyr Asp Ser Gly Ser Thr Thr Thr Tyr Ala Asp Ala Val
    50                  55                  60

Lys Gly Arg Phe Thr Val Ser Arg Asp Asn Ala Lys Asn Thr Leu Phe
65                  70                  75                  80

Leu His Met Asn Arg Leu Arg Ala Glu Asp Thr Ala Val Tyr Tyr Cys
                85                  90                  95

Val Asn Leu Leu Phe Arg Tyr Ser Gly Arg Tyr Gln Glu Gly Phe Asp
            100                 105                 110

Tyr Trp Gly Gln Gly Ser Leu Val Thr Val Ser Ala Ala Ser Thr Thr
        115                 120                 125

Ala Pro Ser
    130

<210> SEQ ID NO 482
<211> LENGTH: 134
<212> TYPE: PRT
<213> ORGANISM: Canis lupus
<220> FEATURE:
<221> NAME/KEY: misc_feature
<222> LOCATION: (127)..(127)
<223> OTHER INFORMATION: Xaa can be any naturally occurring amino acid

<400> SEQUENCE: 482

Glu Val Ser Leu Val Glu Ser Gly Gly Asp Leu Val Lys Val Gly Gly
1               5                   10                  15
```

```
Ser Leu Arg Leu Ser Cys Val Ala Ser Glu Phe Thr Phe Thr Asn Tyr
        20                  25                  30

Asp Met Asn Trp Val Arg Gln Ala Pro Gly Lys Gly Leu Gln Trp Leu
            35                  40                  45

Ser Glu Ile Asn Ser Ser Gly Ser Ser Thr Tyr Tyr Ala Asp Ala Val
        50                  55                  60

Lys Gly Arg Phe Thr Ile Ser Arg Asp Asp Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Gly Gly Arg Val Trp Cys Thr Asp Asp Tyr Cys Phe Asn Pro
            100                 105                 110

Ala Phe Asp Tyr Trp Gly Gln Gly Thr Leu Val Thr Val Ser Xaa Ala
        115                 120                 125

Ser Thr Thr Ala Pro Ser
        130

<210> SEQ ID NO 483
<211> LENGTH: 109
<212> TYPE: PRT
<213> ORGANISM: Canis lupus

<400> SEQUENCE: 483

Met Met Gln Thr Pro Leu Ser Leu Ser Val Ser Pro Gly Glu Thr Ala
1               5                   10                  15

Ser Ile Ser Cys Lys Ala Ser Gln Ser Leu Leu His Ser Asp Gly Asn
            20                  25                  30

Thr Tyr Leu Asn Trp Phe Arg Gln Lys Pro Gly Gln Ser Pro Gln Arg
        35                  40                  45

Leu Ile Tyr Lys Val Ser Asn Arg Asp Thr Gly Val Pro Asp Arg Phe
    50                  55                  60

Ser Gly Ser Gly Ser Gly Thr Asp Phe Thr Leu Arg Ile Ser Thr Val
65                  70                  75                  80

Glu Ala Asp Asp Thr Gly Ile Tyr Tyr Cys Gly Gln Gly Thr Gln Phe
                85                  90                  95

Pro Leu Thr Phe Gly Gln Gly Thr Lys Leu Glu Ile Lys
            100                 105

<210> SEQ ID NO 484
<211> LENGTH: 109
<212> TYPE: PRT
<213> ORGANISM: Canis lupus

<400> SEQUENCE: 484

Met Met Gln Thr Pro Leu Ser Leu Ser Val Ser Pro Gly Glu Pro Ala
1               5                   10                  15

Ser Ile Ser Cys Lys Ala Ser Gln Ser Leu Leu His Arg Ser Gly Asn
            20                  25                  30

Thr Tyr Leu Tyr Trp Phe Arg Gln Lys Pro Gly Gln Ser Pro Glu Gly
        35                  40                  45

Leu Ile Tyr Gln Val Ser Asn Arg Leu Thr Gly Val Ser Asp Arg Phe
    50                  55                  60

Ser Gly Ser Gly Ser Gly Thr Asp Phe Thr Leu Arg Ile Ser Thr Val
65                  70                  75                  80

Glu Ala Asp Asp Thr Gly Val Tyr Tyr Cys Gly Gln Gly Ala Gln Leu
                85                  90                  95

Pro Trp Thr Phe Gly Ala Gly Thr Lys Val Asp Leu Lys
            100                 105
```

<210> SEQ ID NO 485
<211> LENGTH: 109
<212> TYPE: PRT
<213> ORGANISM: Canis lupus
<220> FEATURE:
<221> NAME/KEY: misc_feature
<222> LOCATION: (11)..(11)
<223> OTHER INFORMATION: Xaa can be any naturally occurring amino acid

<400> SEQUENCE: 485

Met Thr Gln Thr Pro Leu Ser Leu Ser Val Xaa Pro Gly Glu Pro Ala
1               5                   10                  15

Ser Ile Ser Cys Lys Ala Ser Gln Ser Leu Leu His Ser Asn Gly Asn
            20                  25                  30

Thr Tyr Leu Phe Trp Phe Arg Gln Lys Pro Gly Gln Ser Pro Lys Arg
        35                  40                  45

Leu Ile Tyr Glu Val Ser Asp Arg Asp Ser Gly Val Pro Glu Arg Phe
    50                  55                  60

Ser Gly Ser Gly Ser Gly Thr Asp Phe Ala Leu Arg Ile Ser Arg Val
65                  70                  75                  80

Glu Ala Asn Asp Thr Gly Val Tyr Tyr Cys Gly Gln Gly Val Gln Phe
                85                  90                  95

Pro Leu Thr Phe Gly Gln Gly Thr Lys Val Glu Ile Lys
            100                 105

<210> SEQ ID NO 486
<211> LENGTH: 109
<212> TYPE: PRT
<213> ORGANISM: Canis lupus

<400> SEQUENCE: 486

Met Met Gln Thr Pro Leu Ser Leu Ser Ile Ser Pro Gly Glu Thr Ala
1               5                   10                  15

Ser Ile Ser Cys Lys Ala Ser Gln Ser Leu Leu His Ser Asn Gly Asn
            20                  25                  30

Thr Tyr Leu Asn Trp Phe Arg Gln Lys Pro Gly Gln Ser Pro Gln Arg
        35                  40                  45

Leu Ile Tyr Lys Val Ser Ser Arg Asp Ser Gly Val Pro Asp Met Phe
    50                  55                  60

Ser Gly Ser Gly Ser Gly Ala Asp Phe Thr Leu Arg Ile Ser Arg Val
65                  70                  75                  80

Glu Ala Asp Asp Ala Gly Leu Tyr Tyr Cys Gly Gln Gly Thr Gln Asp
                85                  90                  95

Pro Trp Thr Phe Gly Ala Gly Thr Lys Val Asp Leu Lys
            100                 105

<210> SEQ ID NO 487
<211> LENGTH: 109
<212> TYPE: PRT
<213> ORGANISM: Canis lupus

<400> SEQUENCE: 487

Met Met Gln Thr Pro Leu Ser Leu Ser Val Arg Pro Gly Glu Pro Ala
1               5                   10                  15

Ser Ile Ser Cys Lys Ala Ser Gln Ser Leu Leu His Ser Asn Gly Asn
            20                  25                  30

Thr Tyr Leu Phe Trp Phe Arg His Arg Pro Gly Gln Ser Pro Gln Ser
        35                  40                  45

```
Leu Leu Tyr Leu Val Ser Asn Arg Ala Pro Gly Val Pro Asp Arg Phe
        50                  55                  60
Ser Ala Ser Gly Ser Gly Thr Asp Phe Thr Leu Arg Ile Ser Arg Val
65                  70                  75                  80
Glu Ala Asp Asp Ala Gly Val Tyr Tyr Cys Gly His Ile Thr Gln Ser
                85                  90                  95
Pro Pro Thr Phe Gly Gln Gly Thr Lys Leu Glu Ile Lys
                100                 105
```

<210> SEQ ID NO 488
<211> LENGTH: 109
<212> TYPE: PRT
<213> ORGANISM: Canis lupus
<220> FEATURE:
<221> NAME/KEY: misc_feature
<222> LOCATION: (3)..(3)
<223> OTHER INFORMATION: Xaa can be any naturally occurring amino acid

<400> SEQUENCE: 488

```
Met Met Xaa Thr Pro Leu Ser Leu Ser Val Ser Pro Gly Glu Pro Ala
1               5                   10                  15
Ser Ile Ser Cys Lys Ala Ser Gln Asn Leu Leu His Ser Asn Gly Asn
                20                  25                  30
Thr Tyr Leu Tyr Trp Phe Arg Gln Arg Pro Gly Gln Ser Pro Glu Gly
            35                  40                  45
Leu Ile Tyr Lys Val Ser Asn Arg Phe Thr Gly Val Ser Asp Arg Phe
        50                  55                  60
Ser Gly Ser Gly Ser Gly Thr Asp Phe Thr Leu Arg Ile Ser Arg Val
65                  70                  75                  80
Glu Ala Asp Asp Thr Gly Val Tyr Tyr Cys Gly His Gly Ile Glu Phe
                85                  90                  95
Pro Tyr Thr Phe Gly Gln Gly Thr Lys Leu Glu Ile Lys
                100                 105
```

<210> SEQ ID NO 489
<211> LENGTH: 109
<212> TYPE: PRT
<213> ORGANISM: Canis lupus
<220> FEATURE:
<221> NAME/KEY: misc_feature
<222> LOCATION: (3)..(3)
<223> OTHER INFORMATION: Xaa can be any naturally occurring amino acid

<400> SEQUENCE: 489

```
Met Met Xaa Thr Pro Leu Ser Leu Ser Val Ser Pro Gly Glu Pro Ala
1               5                   10                  15
Ser Ile Ser Cys Lys Ala Ser Gln Ser Leu Leu His Arg Asp Gly Asn
                20                  25                  30
Thr Tyr Val Tyr Trp Phe Arg Gln Lys Ser Gly Gln Ser Pro Glu Gly
            35                  40                  45
Leu Ile Tyr Arg Met Ser Asn Arg Phe Thr Gly Val Ser Asp Arg Phe
        50                  55                  60
Ser Gly Ser Gly Ser Gly Thr Asp Phe Thr Leu Arg Ile Ser Arg Val
65                  70                  75                  80
Glu Ala Asp Asp Ala Gly Val Tyr Tyr Cys Gly Gln Gly Leu His Phe
                85                  90                  95
Pro Arg Ala Phe Gly Ala Gly Thr Lys Val Asp Leu Lys
                100                 105
```

```
<210> SEQ ID NO 490
<211> LENGTH: 109
<212> TYPE: PRT
<213> ORGANISM: Canis lupus

<400> SEQUENCE: 490

Met Thr Gln Thr Pro Leu Ser Leu Ser Val Ser Pro Gly Glu Ala Ala
1               5                   10                  15

Ser Ile Ser Cys Lys Ala Ser Gln Ser Leu Leu His Ser Asn Gly Asn
            20                  25                  30

Thr Tyr Phe Tyr Trp Phe Arg Gln Arg Pro Gly Gln Ser Pro Glu Gly
        35                  40                  45

Leu Ile Tyr Lys Val Ser Asn Arg Phe Thr Gly Val Ser Asp Arg Phe
    50                  55                  60

Ser Gly Ser Gly Ser Gly Thr Asp Phe Thr Leu Arg Ile Ser Arg Val
65                  70                  75                  80

Glu Ala Asp Asp Ser Gly Val Tyr Tyr Cys Gly Gln Asn Ile Gln Phe
                85                  90                  95

Pro Leu Thr Phe Gly Gln Gly Thr Lys Leu Glu Ile Lys
            100                 105

<210> SEQ ID NO 491
<211> LENGTH: 108
<212> TYPE: PRT
<213> ORGANISM: Canis lupus
<220> FEATURE:
<221> NAME/KEY: misc_feature
<222> LOCATION: (3)..(3)
<223> OTHER INFORMATION: Xaa can be any naturally occurring amino acid

<400> SEQUENCE: 491

Met Met Xaa Thr Pro Leu Ser Leu Ser Val Ser Pro Gly Glu Thr Ala
1               5                   10                  15

Ser Ile Ser Cys Arg Ala Asn Gln Ser Leu Leu His Ser Asn Gly Asn
            20                  25                  30

Thr Tyr Leu Asp Trp Tyr Ile Gln Arg Pro Gly Gln Ser Pro Gln Ala
        35                  40                  45

Leu Ile Tyr Arg Val Ser Asn Arg Ala Ile Ala Val Ser Asp Arg Phe
    50                  55                  60

Ser Gly Ser Gly Ser Gly Thr Asp Phe Thr Leu Lys Ile Ser Arg Val
65                  70                  75                  80

Glu Ala Gly Asp Ala Gly Leu Tyr Tyr Cys Gly Gln Gly Thr Tyr Ser
                85                  90                  95

Tyr Thr Phe Ser Gln Gly Thr Lys Leu Glu Ile Lys
            100                 105

<210> SEQ ID NO 492
<211> LENGTH: 109
<212> TYPE: PRT
<213> ORGANISM: Canis lupus
<220> FEATURE:
<221> NAME/KEY: misc_feature
<222> LOCATION: (3)..(3)
<223> OTHER INFORMATION: Xaa can be any naturally occurring amino acid

<400> SEQUENCE: 492

Met Met Xaa Thr Pro Leu Ser Leu Ala Val Thr Pro Gly Glu Leu Ala
1               5                   10                  15

Thr Ile Tyr Cys Arg Ala Ser Gln Ser Leu Leu His Ser Asp Gly Lys
            20                  25                  30

Ser Tyr Leu Ser Trp Tyr Leu Gln Lys Pro Gly Gln Thr Pro Arg Pro
```

```
                35                  40                  45
Leu Ile Tyr Glu Ala Ser Lys Arg Phe Ser Gly Val Ser Asp Arg Phe
 50                  55                  60

Ser Gly Ser Gly Ser Gly Thr Asp Phe Thr Leu Lys Ile Ser Gly Val
 65                  70                  75                  80

Glu Ala Gly Asp Val Gly Val Tyr Tyr Cys Gln Gln Ser Leu His Phe
                 85                  90                  95

Pro Gly Thr Phe Ser Gln Gly Thr Lys Leu Glu Ile Lys
            100                 105
```

<210> SEQ ID NO 493
<211> LENGTH: 109
<212> TYPE: PRT
<213> ORGANISM: Canis lupus
<220> FEATURE:
<221> NAME/KEY: misc_feature
<222> LOCATION: (3)..(3)
<223> OTHER INFORMATION: Xaa can be any naturally occurring amino acid

<400> SEQUENCE: 493

```
Met Met Xaa Thr Pro Leu Ser Leu Ala Val Thr Pro Gly Asp Leu Ala
  1               5                  10                  15

Thr Ile Ser Cys Arg Ala Ser Gln Ser Leu Leu Tyr Thr Asp Gly Lys
                 20                  25                  30

Ser Tyr Leu Asn Trp Tyr Leu Gln Arg Pro Gly Gln Thr Pro Arg Pro
                 35                  40                  45

Leu Ile Tyr Glu Thr Ser Lys Arg Phe Ser Gly Val Ser Asp Arg Phe
 50                  55                  60

Ile Gly Ser Gly Ser Gly Thr Asp Phe Thr Leu Thr Ile Ser Arg Val
 65                  70                  75                  80

Glu Ala Glu Asp Val Gly Val Tyr Tyr Cys Gln Gln Ser Val His Phe
                 85                  90                  95

Pro Trp Thr Phe Gly Pro Gly Thr Lys Val Glu Ile Lys
            100                 105
```

<210> SEQ ID NO 494
<211> LENGTH: 107
<212> TYPE: PRT
<213> ORGANISM: Canis lupus

<400> SEQUENCE: 494

```
Arg Ala Asp Ser Ala Ala Ser Val Ser Gly Ser Leu Gly Gln Arg Val
  1               5                  10                  15

Thr Ile Ser Cys Ser Gly Ser Ser Ser Asn Ile Gly Asn His Val Ala
                 20                  25                  30

Trp Phe Gln Gln Leu Pro Gly Thr Gly Pro Arg Thr Leu Ile Tyr Gly
                 35                  40                  45

Asn Asn Asn Arg Pro Ser Gly Val Pro Asp Arg Phe Ser Gly Ser Arg
 50                  55                  60

Ser Gly Ser Thr Ala Thr Leu Thr Ile Ser Gly Leu Gln Thr Glu Asp
 65                  70                  75                  80

Glu Ala Asp Tyr Tyr Cys Ser Ser Trp Asp Thr Ser Leu Ser Gly Tyr
                 85                  90                  95

Val Phe Gly Ser Gly Thr Glu Leu Thr Val Leu
            100                 105
```

<210> SEQ ID NO 495
<211> LENGTH: 108
<212> TYPE: PRT

<213> ORGANISM: Canis lupus

<400> SEQUENCE: 495

Arg Val Asp Gln Ala Ser Ser Val Ser Gly Phe Leu Gly Gln Arg Val
1               5                   10                  15

Thr Ile Ser Cys Thr Gly Ser Ser Lys Ile Gly Arg Gly Phe Val
            20                  25                  30

His Trp Tyr Gln Val Leu Pro Gly Thr Gly Pro Arg Thr Leu Ile Tyr
        35                  40                  45

Gly Val Ser His Arg Pro Ser Gly Val Pro Asp Arg Phe Ser Ala Ser
    50                  55                  60

Lys Ser Gly Lys Thr Ala Thr Leu Thr Ile Ser Gly Leu Gln Ala Glu
65                  70                  75                  80

Asp Glu Ala Asp Tyr Tyr Cys Ser Ser Trp Asp Ser Ser Leu Ser Ser
                85                  90                  95

Leu Val Phe Gly Ser Gly Thr Gln Leu Thr Val Leu
            100                 105

<210> SEQ ID NO 496
<211> LENGTH: 104
<212> TYPE: PRT
<213> ORGANISM: Canis lupus

<400> SEQUENCE: 496

Gly Leu Thr Gln Leu Pro Ser Met Ser Val Ala Leu Arg Gln Thr Ala
1               5                   10                  15

Arg Ile Thr Cys Gly Gly Asn Ile Glu Ser Lys Asn Val His Trp
            20                  25                  30

Tyr Gln Gln Lys Leu Gly Gln Ala Pro Ile Gln Ile Val Tyr Tyr Asp
        35                  40                  45

Thr Arg Arg Pro Val Gly Ile Pro Glu Arg Phe Ser Gly Ala Lys Ser
    50                  55                  60

Gly Asn Thr Ala Thr Leu Thr Ile Ser Gly Ala Leu Ala Glu Asp Glu
65                  70                  75                  80

Ala Asp Tyr Tyr Cys Gln Val Trp Asp Ser Gly Thr Leu Ile Phe Gly
                85                  90                  95

Gly Gly Thr Gln Leu Thr Val Leu
            100

<210> SEQ ID NO 497
<211> LENGTH: 104
<212> TYPE: PRT
<213> ORGANISM: Canis lupus

<400> SEQUENCE: 497

Gly Leu Thr Gln Leu Ala Ser Val Ser Val Asn Pro Gly Gln Thr Ala
1               5                   10                  15

Ile Ile Thr Cys Glu Ala Asp Lys Ile Gly Asp Lys Phe Val His Trp
            20                  25                  30

Tyr Gln Gln Lys Pro Ser Gln Ala Pro Gly Met Ile Val Tyr Glu Asp
        35                  40                  45

His Lys Arg Pro Ser Gly Ile Pro Glu Arg Phe Ser Ala Ser Asn Ser
    50                  55                  60

Gly Asn Thr Ala Thr Leu Thr Ile Ser Gly Ala Arg Ala Glu Asp Glu
65                  70                  75                  80

Ala Asp Tyr Tyr Cys Gln Val Trp Asp Asn Gly Ala Pro Met Phe Gly
                85                  90                  95

```
Gly Gly Thr His Pro Asp Arg Pro
            100
```

<210> SEQ ID NO 498
<211> LENGTH: 106
<212> TYPE: PRT
<213> ORGANISM: Canis lupus
<220> FEATURE:
<221> NAME/KEY: misc_feature
<222> LOCATION: (73)..(73)
<223> OTHER INFORMATION: Xaa can be any naturally occurring amino acid

<400> SEQUENCE: 498

```
Gly Leu Thr Gln Pro Pro Ser Met Ser Val Thr Leu Arg Gln Thr Ala
1               5                   10                  15

Arg Ile Thr Cys Glu Gly Asp Ser Ile Gly Thr Lys Arg Val Tyr Trp
            20                  25                  30

Tyr Gln Gln Lys Leu Gly Gln Val Pro Val Leu Ile Ile Tyr Asp Asp
        35                  40                  45

Ser Ser Arg Pro Ser Gly Ile Pro Glu Arg Phe Ser Gly Ala Asn Ser
    50                  55                  60

Gly Asn Thr Ala Thr Leu Thr Ile Xaa Gly Ala Leu Ala Glu Asp Glu
65                  70                  75                  80

Ala Asp Tyr Tyr Cys Gln Val Trp Asp Ser Ser Thr Lys Ala Ile Val
                85                  90                  95

Phe Gly Gly Gly Thr His Leu Thr Val Leu
            100                 105
```

<210> SEQ ID NO 499
<211> LENGTH: 105
<212> TYPE: PRT
<213> ORGANISM: Canis lupus

<400> SEQUENCE: 499

```
Gly Leu Thr Gln Pro Pro Ser Val Ser Val Ser Leu Gly Gln Thr Ala
1               5                   10                  15

Thr Ile Ser Cys Ser Gly Glu Ser Leu Thr Glu Arg Phe Ala Gln Trp
            20                  25                  30

Phe Gln Gln Lys Pro Gly Gln Ala Pro Val Leu Val Ile Tyr Lys Asp
        35                  40                  45

Thr Glu Arg Pro Ser Gly Ile Pro Asp Arg Phe Ser Gly Ser Ile Ser
    50                  55                  60

Gly Asn Thr His Thr Leu Thr Ile Ser Gly Ala Arg Ala Glu Asp Glu
65                  70                  75                  80

Ala Asp Tyr Tyr Cys Glu Ser Ala Val Thr Ser Asp Thr Tyr Val Phe
                85                  90                  95

Gly Ser Gly Ile Glu Leu Thr Val Leu
            100                 105
```

<210> SEQ ID NO 500
<211> LENGTH: 106
<212> TYPE: PRT
<213> ORGANISM: Canis lupus

<400> SEQUENCE: 500

```
Leu Thr Gln Leu Thr Ser Val Ser Gly Ser Leu Gly Gln Arg Val Thr
1               5                   10                  15

Ile Ser Cys Ser Gly Arg Thr Asn Ile Asp Arg Phe Gly Val Thr Trp
            20                  25                  30

Tyr Gln Gln Phe Pro Gly Lys Ala Pro Arg Leu Leu Val Asp Ser Asp
```

```
                    35                  40                  45

Gly Asp Arg Pro Ser Gly Val Pro Asp Arg Phe Ser Gly Ser Lys Ser
 50                  55                  60

Ala Asn Ser Ala Thr Leu Thr Ile Thr Gly Leu His Ala Glu Asp Glu
 65                  70                  75                  80

Ala Asp Tyr Tyr Cys Leu Ser Ile Gly Pro Thr Leu Gly Val Tyr Val
                 85                  90                  95

Phe Gly Ser Gly Ile Glu Leu Thr Val Leu
            100                 105

<210> SEQ ID NO 501
<211> LENGTH: 108
<212> TYPE: PRT
<213> ORGANISM: Canis lupus

<400> SEQUENCE: 501

Val Leu Thr Gln Leu Thr Ser Val Ser Gly Ser Leu Gly Gln Arg Val
 1               5                  10                  15

Thr Ile Ser Cys Ser Gly Ser Ala Asn Asn Ile Gly Ser Phe Gly Ala
                20                  25                  30

Ile Trp Tyr Gln Gln Phe Pro Gly Lys Ala Pro Lys Leu Leu Ile Tyr
             35                  40                  45

Arg Asp Gly Ser Arg Pro Ser Gly Val Pro Asp Arg Phe Ser Gly Ser
 50                  55                  60

Arg Ser Gly Asn Ser Ala Thr Leu Thr Ile Thr Gly Leu Gln Ala Glu
 65                  70                  75                  80

Asp Glu Ala Asp Phe Tyr Cys Gln Ser Val Asp Pro Thr Leu Gly Ile
                 85                  90                  95

Ala Val Phe Gly Gly Gly Thr His Leu Thr Val Leu
            100                 105

<210> SEQ ID NO 502
<211> LENGTH: 109
<212> TYPE: PRT
<213> ORGANISM: Canis lupus

<400> SEQUENCE: 502

Ala Leu Thr Gln Pro Ala Ser Val Ser Gly Ser Leu Gly Gln Arg Val
 1               5                  10                  15

Thr Ile Ser Cys Ser Gly Thr Thr Asp Asn Ile Gly Ile Val Gly Ala
                20                  25                  30

Asn Trp Tyr Gln Gln Leu Pro Gly Lys Ala Pro Lys Leu Leu Val Tyr
             35                  40                  45

Ser Asp Gly Asn Arg Pro Ala Gly Val Pro Asp Arg Phe Ser Gly Ser
 50                  55                  60

Lys Ser Gly Ser Ser Ala Thr Leu Ile Ile Thr Gly Leu Gln Ala Glu
 65                  70                  75                  80

Asp Glu Ser Asp Tyr Tyr Cys Gln Ser Val Asp Pro Thr Leu Gly Ala
                 85                  90                  95

Arg Tyr Val Phe Gly Ser Gly Ile Glu Leu Thr Val Leu
            100                 105

<210> SEQ ID NO 503
<211> LENGTH: 108
<212> TYPE: PRT
<213> ORGANISM: Canis lupus

<400> SEQUENCE: 503
```

Val Leu Thr Gln Pro Pro Ser Val Ser Gly Ser Leu Gly Gln Lys Ile
1               5                   10                  15

Thr Ile Ser Cys Ser Gly Ser Thr Asn Val Gly Val Gly Ala
            20                  25                  30

Gly Trp Tyr Gln Gln Leu Pro Gly Lys Ala Pro Lys Leu Leu Val Phe
        35                  40                  45

Ser Asp Gly Val Arg Pro Ser Gly Val Pro Asp Arg Phe Ser Gly Ser
        50                  55                  60

Lys Phe Gly Asp Ser His Thr Leu Thr Ile Thr Gly Leu Gln Ala Glu
65                  70                  75                  80

Asp Glu Ala Asp Tyr Tyr Cys Gln Ser Tyr Asp Thr Thr Leu His Thr
                85                  90                  95

Tyr Val Phe Gly Ser Gly Ile Glu Leu Ile Val Leu
            100                 105

<210> SEQ ID NO 504
<211> LENGTH: 106
<212> TYPE: PRT
<213> ORGANISM: Canis lupus

<400> SEQUENCE: 504

Val Leu Thr Gln Pro Pro Ser Val Ser Gly Ser Leu Gly Gln Arg Val
1               5                   10                  15

Thr Ile Ser Cys Ser Gly Ser Thr Asn Asn Ile Gly Ile Val Gly Ala
            20                  25                  30

Ser Trp Tyr Gln Gln Pro Pro Gly Lys Ala Pro Lys Leu Leu Val Tyr
        35                  40                  45

Thr Asn Gly Gly Arg Pro Ser Gly Val Pro Asp Arg Phe Ser Gly Ser
        50                  55                  60

Lys Ser Gly Asn Ser Ala Thr Leu Thr Ile Thr Gly Leu Gln Ala Glu
65                  70                  75                  80

Asp Glu Ala Asp Tyr Tyr Cys Gln Ser Ser Asp Ser Met Leu Ala Val
                85                  90                  95

Phe Gly Gly Gly Thr His Leu Thr Val Leu
            100                 105

<210> SEQ ID NO 505
<211> LENGTH: 108
<212> TYPE: PRT
<213> ORGANISM: Canis lupus

<400> SEQUENCE: 505

Val Leu Thr Gln Pro Pro Ser Val Ser Gly Ser Pro Gly Gln Arg Val
1               5                   10                  15

Thr Ile Ser Cys Ser Gly Arg Thr Asn Asn Ile Gly Ser Val Gly Ala
            20                  25                  30

Thr Trp Tyr Arg Gln Phe Pro Gly Lys Ala Pro Asn Leu Leu Val Tyr
        35                  40                  45

Ser Asp Gly Asn Arg Pro Ser Gly Val Pro Asp Arg Phe Ala Ser
        50                  55                  60

Met Ser Gly Asn Ser Ala Thr Leu Thr Ile Thr Gly Leu Gln Thr Glu
65                  70                  75                  80

Asp Glu Ala Asp Tyr Tyr Cys Gln Ser Tyr Asp Thr Ser Leu Asp Gly
                85                  90                  95

Ala Val Phe Gly Gly Gly Thr His Leu Thr Val Leu
            100                 105

<210> SEQ ID NO 506
<211> LENGTH: 108
<212> TYPE: PRT
<213> ORGANISM: Canis lupus

<400> SEQUENCE: 506

Ala Leu Thr Gln Pro Ser Ser Val Ser Gly Thr Leu Gly Gln Thr Val
1               5                   10                  15

Thr Ile Ser Cys Asp Gly Ser Ser Asp Ile Gly Ser Tyr Ser Tyr
            20                  25                  30

Ile Ala Trp Tyr Gln Gln Phe Pro Gly Thr Ser Pro Lys Leu Leu Ile
            35                  40                  45

Gln Tyr Thr Asp Asn Arg Pro Ser Gly Ile Pro Thr Arg Phe Ser Gly
        50                  55                  60

Ser Lys Ser Gly Asn Thr Ala Ser Leu Thr Ile Pro Gly Leu Gln Ala
65                  70                  75                  80

Glu Asp Glu Ala Asp Tyr Tyr Cys Cys Ala Tyr Ala Gly Ser Asp Thr
                85                  90                  95

Tyr Val Phe Gly Ser Gly Thr Gln Leu Thr Val Leu
            100                 105

<210> SEQ ID NO 507
<211> LENGTH: 108
<212> TYPE: PRT
<213> ORGANISM: Canis lupus

<400> SEQUENCE: 507

Ala Leu Thr Gln Pro Ser Ser Val Ser Gly Thr Leu Gly Gln Thr Val
1               5                   10                  15

Thr Ile Ser Cys Asp Gly Ser Ser Asp Ile Gly Ser Thr Asn Tyr
            20                  25                  30

Ile Glu Trp Tyr Gln Gln Phe Pro Gly Thr Ser Pro Lys Leu Leu Ile
            35                  40                  45

Tyr Tyr Ile Asp Ser Arg Pro Ser Gly Ile Pro Pro Arg Phe Ser Gly
        50                  55                  60

Ser Lys Ser Gly Asn Thr Ala Ser Leu Thr Ile Ser Gly Leu Gln Ala
65                  70                  75                  80

Glu Asp Glu Ala Asp Tyr Tyr Cys Ser Ser Tyr Thr Lys Ser Asp Thr
                85                  90                  95

Phe Val Phe Gly Ser Gly Thr Gln Leu Thr Val Leu
            100                 105

<210> SEQ ID NO 508
<211> LENGTH: 108
<212> TYPE: PRT
<213> ORGANISM: Canis lupus

<400> SEQUENCE: 508

Val Leu Thr Gln Pro Pro Ser Val Ser Gly Phe Leu Gly Gln Arg Val
1               5                   10                  15

Thr Ile Ser Cys Thr Gly Asp Thr Pro Asn Ile Gly Arg Gly Tyr Val
            20                  25                  30

His Trp Tyr Gln Gln Leu Pro Gly Thr Gly Pro Arg Thr Leu Ile Tyr
            35                  40                  45

Gly Val Ser Asn Arg Pro Ser Gly Val Pro Asp Arg Phe Ser Gly Ser
        50                  55                  60

Arg Ser Gly Ser Thr Gly Thr Leu Thr Ile Ser Gly Leu Gln Ala Glu
65                  70                  75                  80

```
Asp Glu Ala Asp Tyr Tyr Cys Ser Ser Trp Asp Thr Thr Leu Ser Ala
                85                  90                  95

Tyr Val Phe Gly Ser Gly Ile Glu Leu Thr Val Leu
            100                 105
```

<210> SEQ ID NO 509
<211> LENGTH: 109
<212> TYPE: PRT
<213> ORGANISM: Canis lupus
<220> FEATURE:
<221> NAME/KEY: misc_feature
<222> LOCATION: (4)..(4)
<223> OTHER INFORMATION: Xaa can be any naturally occurring amino acid

<400> SEQUENCE: 509

```
Thr Leu Thr Xaa Lys Pro Ser Val Ser Gly Ser Leu Gly Gln Arg Val
1               5                   10                  15

Thr Ile Ser Cys Thr Gly Ser Ser Asn Val Gly Tyr Gly Asp Ser
                20                  25                  30

Val Gly Trp Tyr Gln Gln Leu Pro Gly Thr Ser Pro Arg Thr Leu Ile
            35                  40                  45

Tyr Asp Ser Ser Arg Pro Ser Gly Val Pro Asp Arg Phe Ser Gly
    50                  55                  60

Ser Arg Ser Gly Ser Thr Ala Thr Leu Thr Ile Ser Gly Leu Gln Ala
65                  70                  75                  80

Glu Asp Glu Ala Asp Tyr Tyr Cys Ser Ser Tyr Asp Ser Ser Leu Ser
                85                  90                  95

Gly Ala Val Phe Gly Gly Gly Thr His Leu Thr Val Leu
            100                 105
```

<210> SEQ ID NO 510
<211> LENGTH: 108
<212> TYPE: PRT
<213> ORGANISM: Canis lupus
<220> FEATURE:
<221> NAME/KEY: misc_feature
<222> LOCATION: (15)..(15)
<223> OTHER INFORMATION: Xaa can be any naturally occurring amino acid

<400> SEQUENCE: 510

```
Val Leu Thr Gln Leu Ala Ser Val Ser Gly Ser Leu Gly Gln Xaa Val
1               5                   10                  15

Thr Ile Ser Cys Thr Gly Ser Ser Asn Val Gly Tyr Gly Asp Tyr
                20                  25                  30

Val Gly Trp Tyr Gln Gln Leu Pro Gly Thr Gly Pro Arg Thr Leu Ile
            35                  40                  45

His His Thr Thr Ser Arg Pro Ser Gly Val Ser Asp Arg Phe Ser Gly
    50                  55                  60

Ser Arg Ser Gly Asn Thr Ala Thr Leu Thr Ile Ser Gly Leu Gln Ala
65                  70                  75                  80

Glu Asp Glu Ala Asp Tyr Tyr Cys Ser Ser Tyr Asp Thr Gly Leu Asn
                85                  90                  95

Val Val Phe Gly Gly Gly Thr Gln Leu Thr Val Leu
            100                 105
```

<210> SEQ ID NO 511
<211> LENGTH: 109
<212> TYPE: PRT
<213> ORGANISM: Canis lupus

<400> SEQUENCE: 511

Val Leu Thr Gln Leu Ala Ser Val Ser Gly Ser Leu Gly Gln Arg Val
1               5                   10                  15

Thr Ile Ser Cys Ser Gly Ser Ser Asn Val Gly Cys Gly Asp Tyr
            20                  25                  30

Val Gly Trp Phe Gln Gln Leu Pro Gly Thr Gly Pro Arg Thr Leu Ile
        35                  40                  45

Tyr Asp Thr Ser Thr Arg Pro Ser Gly Val Pro Asp Arg Phe Ser Gly
    50                  55                  60

Ser Arg Ser Gly Ser Thr Ala Thr Leu Thr Ile Ser Gly Leu Gln Ala
65              70                  75                  80

Glu Asp Glu Ala Asp Tyr Tyr Cys Ser Ser Tyr Asp Met Thr Leu Arg
                85                  90                  95

Gly Pro Met Phe Gly Gly Gly Thr Gln Leu Thr Val Leu
            100                 105

<210> SEQ ID NO 512
<211> LENGTH: 108
<212> TYPE: PRT
<213> ORGANISM: Canis lupus

<400> SEQUENCE: 512

Val Leu Thr Gln Leu Ala Ser Val Ser Gly Ser Leu Gly Gln Arg Val
1               5                   10                  15

Thr Ile Ser Cys Thr Gly Ser Ser Asn Val Gly Tyr Gly Asn Asp
            20                  25                  30

Val Gly Trp Tyr Gln Gln Leu Pro Gly Thr Gly Pro Arg Thr Leu Ile
        35                  40                  45

Tyr Gly Ser Ser Ile Arg Pro Ser Gly Val Pro Asp Arg Phe Ser Gly
    50                  55                  60

Ser Lys Ser Gly Asn Ser Ala Thr Leu Thr Ile Ser Gly Leu Gln Ala
65              70                  75                  80

Glu Asp Glu Ala Asp Tyr Tyr Cys Ser Ser Tyr Asp Ser Ser Leu Gly
                85                  90                  95

Tyr Val Phe Gly Ser Gly Thr Gln Leu Thr Val Leu
            100                 105

<210> SEQ ID NO 513
<211> LENGTH: 108
<212> TYPE: PRT
<213> ORGANISM: Canis lupus

<400> SEQUENCE: 513

Leu Leu Thr Gln Pro Ala Ser Val Ser Gly Ser Leu Gly Gln Lys Val
1               5                   10                  15

Thr Ile Ser Cys Thr Gly Ser Ser Asn Ile Gly Ser Asn Tyr Val
            20                  25                  30

Ala Trp Tyr Gln Gln Leu Pro Gly Thr Gly Pro Arg Thr Leu Ile Tyr
        35                  40                  45

Ser Asn Thr Asn Arg Phe Ser Gly Val Pro Asp Arg Phe Ser Gly Ser
    50                  55                  60

Arg Ser Gly Ser Thr Ala Thr Leu Thr Ile Ser Gly Leu Gln Ala Glu
65              70                  75                  80

Asp Glu Ala Asp Tyr Tyr Cys Ser Thr Tyr Asp Asn Ser Leu Ser Gly
                85                  90                  95

Leu Val Phe Gly Gly Gly Thr Gln Leu Thr Val Leu
            100                 105

```
<210> SEQ ID NO 514
<211> LENGTH: 108
<212> TYPE: PRT
<213> ORGANISM: Canis lupus

<400> SEQUENCE: 514

Val Leu Thr Gln Leu Ala Ser Val Ser Gly Ser Leu Gly Gln Arg Val
1               5                   10                  15

Thr Ile Ser Cys Thr Gly Ser Thr Ser Asn Ile Gly Arg Gly Tyr Val
            20                  25                  30

Thr Trp Tyr Gln Gln Leu Pro Gly Thr Gly Pro Arg Thr Leu Ile Tyr
        35                  40                  45

Asp Asn Ser Asp Arg Pro Ser Gly Val Pro Asp Arg Phe Ser Gly Ser
    50                  55                  60

Lys Ser Gly Ser Thr Ala Thr Leu Thr Ile Ser Gly Leu Gln Val Glu
65                  70                  75                  80

Asp Glu Ala Asp Tyr His Cys Ser Thr Tyr Asp Ser Ser Leu Gly Gly
                85                  90                  95

Pro Val Phe Gly Gly Gly Thr Gln Leu Thr Val Leu
            100                 105

<210> SEQ ID NO 515
<211> LENGTH: 108
<212> TYPE: PRT
<213> ORGANISM: Canis lupus

<400> SEQUENCE: 515

Ala Leu Thr Gln Pro Ala Ser Val Ser Gly Ser Leu Gly Gln Arg Val
1               5                   10                  15

Thr Val Ser Cys Thr Gly Ser Ser Ser Asn Ile Gly Arg Phe Val Val
            20                  25                  30

Gly Trp Phe Gln Gln Leu Pro Gly Lys Gly Pro Arg Thr Val Ile Tyr
        35                  40                  45

Asn Thr Ser Asn Arg Pro Ser Gly Val Pro Asp Arg Phe Ser Gly Ser
    50                  55                  60

Lys Ser Gly Ser Thr Ala Thr Leu Thr Ile Ser Gly Leu Gln Thr Glu
65                  70                  75                  80

Asp Glu Ala Ala Tyr Tyr Cys Ser Val Tyr Asp Ser Ser Leu Asn Thr
                85                  90                  95

Ile Leu Phe Gly Gly Gly Thr His Leu Thr Val Leu
            100                 105

<210> SEQ ID NO 516
<211> LENGTH: 108
<212> TYPE: PRT
<213> ORGANISM: Canis lupus

<400> SEQUENCE: 516

Val Leu Thr Gln Leu Ala Ser Val Ser Gly Ser Arg Gly Gln Lys Ile
1               5                   10                  15

Thr Ile Ser Cys Thr Gly Ser Phe Ser Asn Ile Gly Asn His Asn Val
            20                  25                  30

Gly Trp Tyr Gln Gln Leu Pro Gly Ser Gly Pro Lys Thr Val Ile Tyr
        35                  40                  45

Asp Thr Asp Ser Arg Pro Ser Gly Val Ser Asp Arg Phe Ser Ala Ser
    50                  55                  60

Lys Ser Gly Ser Thr Ala Thr Leu Thr Ile Ser Gly Leu Gln Thr Glu
65                  70                  75                  80
```

-continued

```
Asp Glu Gly Asp Tyr Tyr Cys Ser Thr Trp Asp Tyr Ser Leu Ser Thr
            85                  90                  95
Ala Val Phe Gly Arg Gly Thr His Leu Thr Val Leu
            100             105
```

SINGLE CHAIN FRAGMENT VARIABLE ANTIBODY LIBRARIES AND USES THEREOF

CROSS-REFERENCE TO RELATED APPLICATIONS

This application is a National Phase Application of PCT International Application PCT/US09/39941, filed Apr. 8, 2009, claiming priority to U.S. Patent Application 61/071,040, filed Apr. 9, 2008, which is incorporated by reference herein in its entirety.

FIELD OF INVENTION

The invention is generally directed to antibody variable domains or antibodies, libraries of antibody variable domains or antibodies, methods of making said antibodies and libraries, and methods of treatment comprising administering the generated antibody variable domains or antibodies. Specifically, the invention is directed to novel primer nucleotide sequences that are used to amplify all rearranged sequences of canine variable heavy (VH) and variable light (VL) immunoglobulin chains that have been used in naturally occurring antibody responses. These novel sequences contain canine framework regions and complementarity determining regions which may be used to canine-ize antibodies. Further, these sequences are useful for the identification and targeting of viral and bacterial pathogens, and tumor-associated antigens.

BACKGROUND OF THE INVENTION

Cancer is the leading cause of death in our current canine pet population. Previous studies have found that 45% of dogs aged 10 years or older, and 23% of dogs of any age, die from different types of cancer.

Recent reports indicate that there are over 74 million dogs in the USA. The estimated cancer incidence rate in dogs in the USA is 243-381/100,000 which is similar to humans, and many of these dogs will be treated with currently available standard chemotherapy protocols. However, chemotherapeutics have significant side effects principally as a result of their actions on non-cancerous tissues and cells. Furthermore, most of these treatments have poor overall efficacy and cancer remains the leading cause of death in the canine pet population. Alternative therapies that specifically target chemotherapeutics to the cancer cells and so increase their efficacy and reduce off-target side effects are needed.

The mainstay of cancer therapy in veterinary medicine is the systemic administration of a combination of chemotherapeutic agents that inhibit cell division and induce cell death. These agents however are not tumor-specific and frequently cause adverse side affects which limit the dose that can be given and the therapeutic efficacy of the agent.

Recent efforts in human cancer therapy have focused on the use of monoclonal antibodies such as trastuzumab (anti-erb2), rituximab (anti-CD20) and bevacizumab (anti-Vascular Endothelial Growth Factor) that directly target tumors and their vasculature providing a specific anti-tumor response that has shown promising results in phase II/III clinical trials. However, the xenogeneic nature of these reagents and the lack of known tumor-associated antigens (TAA) limits their use in the dog.

The use of antibodies and antibody fragments (scFv) that specifically target malignant cells have revolutionized the treatment of certain cancers in humans. Currently, tumor-specific scFvs are being evaluated alone, coupled to cytotoxic agents or expressed in re-directed tumor-specific T cells for the targeted treatment of primary and metastatic cancer in people. Until now, these exciting advances in the targeted therapy of cancer have not been possible in canine cancer patients since monoclonal antibodies or scFvs of canine origin have not been developed, canine TAA have not been identified and in many cases xenogeneic antibodies don't cross react with canine antigens or their efficacy is limited by the development of neutralizing antibody responses.

It would therefore be desirable to have a way of treating cancer in dogs that could be administered systemically and repeatedly if necessary, and that specifically targets cytotoxic agents to malignant cells, thereby reducing the adverse side effects of chemotherapies and improving therapeutic efficacy. In addition, antibody fragments that recognize and neutralize pathogens such as viruses and bacteria also represent a targeted approach to the treatment of infectious disease. Furthermore, antibody fragments that can specifically recognize and neutralize cytokines and other soluble proteins may represent a novel approach to the treatment of infectious and inflammatory diseases.

SUMMARY OF THE INVENTION

In one embodiment, the invention provides an isolated single-chain variable fragment antibody (scFv), comprising an isolated heavy (VH) chain sequence, an isolated light (VL) chain sequence and a flexible linker.

In another embodiment, the invention provides a list of nucleic acids randomly selected from an scFv library of nucleic acids encoding a plurality of antigen binding polypeptides. In another embodiment, the library is made by a method comprising the steps of: isolating RNA encoding an antibody from splenocytes or lymphocytes of a non-immunized canine or a canine, immunized with a specific antigen; generating cDNAs from the isolated RNA; amplifying the variable regions of the antibody's heavy chain and the lambda and kappa light chains using PCR with a set of primers designed for the variable regions, wherein primers for the VH chains are represented by any one of SEQ ID No. 1-8, primers for the VL lambda chains are represented by any one of SEQ ID No. 9-23 and primers for the VL kappa chains are represented by any one of SEQ ID No. 24-31 or their analogues or combination, wherein, the primers are designed to incorporate secondary primer binding sites into the 5' end of the $V_L$ amplicons and the 3' end of the $V_H$ amplicons and a flexible linker into the 3' end of the $V_L$ amplicons and the 5' end of the $V_H$ amplicons; and using the flexible linker, randomly linking the $V_H$ and $V_L$ amplicons; and repeating the step of randomly linking the flexible linker-comprising $V_H$ and $V_L$ amplicons; and forming a library of display packages displaying the scFv chains, wherein a library member comprises a nucleic acid encoding scFv chain. These scFvs may then be expressed on the surface of bacteriophage to generate a phage display library and from this library scFvs may be selected and isolated from the library via their ability to bind to specific antigens of interest. In another embodiment, the splenocyte or lymphocyte is from an immunized or a non-immunized animal. In yet another embodiment, the splenocyte or lymphocyte is from an immunized or a non-immunized canine. In another embodiment, the splenocytes or lymphocytes of a non-immunized canine, is taken from a canine with a cancer.

In one embodiment, the specific antigen is a tumor specific antigen.

In one embodiment, the invention provides libraries of antibodies or antibody variable domains. Specifically, the invention provides single chain Fragment variable antibody libraries for the identification and targeting of tumor-associated antigens.

In one embodiment, the invention provides a nucleic acid sequence encoding a single chain fragment variable antibody (scFv) isolated from the library of nucleic acids encoding a plurality of antigen binding polypeptides, comprising any combination of a VH and VL chain sequence, wherein and in other embodiments, the VH and VL sequences are linked via a flexible linker.

In another embodiment, the invention provides a method of treating a tumor in a subject comprising the step of administering to said subject an effective amount of a single chain fragment variable antibody, wherein in other embodiments, the single chain fragment variable antibody (scFv) is isolated from the library of nucleic acids encoding a plurality of antigen binding polypeptides.

In one embodiment, the invention provides a method of treating a viral infection in a subject comprising the step of administering to said subject an effective amount of a single chain fragment variable antibody, wherein and in other embodiments, the single chain fragment variable antibody is isolated from the library of nucleic acids encoding a plurality of antigen binding polypeptides.

In another embodiment, the invention provides a method of delivering a biologically active agent to cells displaying a target antigen, comprising contacting said cells with a single chain fragment variable antibody isolated from the library of nucleic acids encoding a plurality of antigen binding polypeptides, wherein and in other embodiments, the single chain fragment variable antibody is operably linked to said agent, toxin, radioisotope, or bio-active peptide.

In another embodiment, the invention provides a method of delivering a biologically active agent and a single chain fragment variable antibody isolated from the library of nucleic acids encoding a plurality of antigen binding polypeptides to cells displaying a target antigen, whereby and in other embodiments, the biological agent and the single chain fragment variable antibody are delivered concomitantly but individually.

In one embodiment, the invention provides primer nucleotide sequences that are used to amplify all rearranged sequences of canine variable heavy (VH) and variable light (VL) immunoglobulin chains that have been used in naturally occurring antibody responses.

In another embodiment, the invention provides a method for preparing nucleotides of single-chain variable fragments (scFv) encoding an antigen-specific binding domain, comprising the steps of: isolating RNA encoding an antibody from a splenocyte or lymphocytes of a non-immunized canine, feline, avian, equine, bovine, swine or a canine, immunized with a specific antigen; generating cDNAs from the isolated RNA; amplifying the variable regions of the antibody's heavy chain and the lambda and kappa light chains using PCR with a set of primers designed for the variable regions, wherein primers for the VH chains are represented by any one of SEQ ID No. 1-8, primers for the VL lambda chains are represented by any one of SEQ ID No. 9-23 and primers for the VL kappa chains are represented by any one of SEQ ID No. 24-31 or their analogues or combination, wherein the primers are designed to incorporate secondary primer binding sites into the 5' end of the $V_L$ amplicons and the 3' end of the $V_H$ amplicons and a flexible linker into the 3' end of the $V_L$ amplicons and the 5' end of the $V_H$ amplicons; and using the flexible linker, randomly linking the $V_H$ and $V_L$ amplicons.

Other features and advantages of the present invention become apparent from the following detailed description examples and figures. It should be understood, however, that the detailed description and the specific examples while indicating preferred embodiments of the invention are given by way of illustration only, since various changes and modifications within the spirit and scope of the invention become apparent to those skilled in the art from this detailed description.

BRIEF DESCRIPTION OF THE DRAWINGS

The invention is better understood from a reading of the following detailed description taken in conjunction with the drawings in which like reference designators are used to designate like elements, and in which:

FIG. 3 shows a schematic of the steps involved in the generation of canine scFv libraries from splenic lymphocytes. Green lines represent variable region amplicons and purple lines represent the flexible linker;

FIG. 4 shows Amplification of canine $V_H$ and $V_L$ Ig chains and generation of canine scFv A. $V_L$ lambda PCR products obtained from splenic cDNA. Lane 0 100 bp DNA ladder, Lane 1-13 PCR products obtained using one reverse primer and 13 degenerate forward primers. Prominent bands at ~350 bp represent canine $V_L$ lambda chains. B. $V_H$ PCR products obtained from canine splenic cDNA. Lane 0 100 bp DNA ladder. Lane 1-6 PCR products obtained using VH1-6F primers and $V_H$ IgG rev primer respectively. C. Purified canine $V_H$, $V_L$ and scFv products. Lane 0 100 bp DNA ladder. Lane 1. Purified pooled $V_H$ PCR products. Lane 2. Purified pooled $V_L$ (λ) PCR products. Lane 3. Purified pooled $V_L$ (κ) PCR products. Lane 4. Purified canine scFv product;

FIG. 5 shows Alignment of Ig G heavy chain protein sequences from dog (SEQ ID NO: 445), human (SEQ ID NO: 446), mouse (SEQ ID NO: 447) and rat (SEQ ID NO: 448). The three complementarity determining regions are found between the framework regions and are responsible for specificity of antigen-binding. FR, framework region, CγR, constant gamma region;

DETAILED DESCRIPTION OF THE INVENTION

Figure 2:
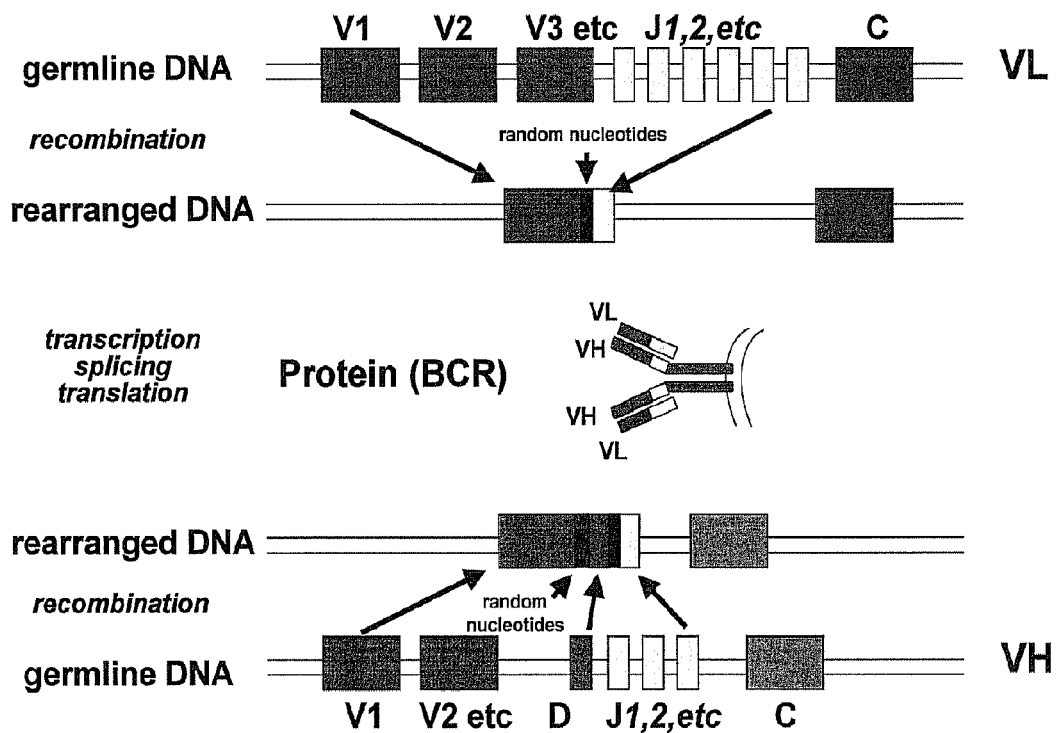
FIG. 2 shows a scheme of generation of diversity in $V_H$ and $V_L$ chains of immunoglobulin.

An animal's immunological repertoire must be extremely diverse in order to recognize the billions of potential pathogens it may be exposed to throughout its lifetime. In order to generate such extreme diversity within the immunoglobulin molecules, the VH and VL chains that together form the antigen-binding site must themselves be highly diverse. The germline DNA that encodes the VH chain of immunoglobulins is comprised of multiple different copies of variable (V), diverse (D) and junctional (J) genes (FIG. 2). During B cell development, one variable (V), one diverse (D) and one junctional (J) gene are randomly selected from the germline DNA, recombined and then transcribed to generate an RNA transcript that encodes for an almost unique VH chain (FIG. 2). To increase diversity further, random nucleotides are inserted between the V, D and J sequences. Similar events occur in the generation of the VL immunoglobulin chains where V and J genes are randomly selected and rearranged, with random nucleotides inserted between the V and J genes, to generate VL chains with almost unique amino acid sequences. Since the antigen-binding site of an immunoglobulin is comprised of the combination of one VH and one VL chain, further diversity in antigen specificity results from this pairing.

In one embodiment, the invention provides an isolated single-chain variable fragment antibody (scFv), comprising an isolated heavy (VH) chain sequence, an isolated light (VL) chain sequence and a flexible linker. In another embodiment, the VH chain is selected from a group of nucleic acid sequences and amino acid sequences encoded thereby set forth in SEQ ID NO: 34-366. In another embodiment, the VL chain is selected from a group of nucleic acid sequences and amino acid sequences encoded thereby set forth in SEQ ID NO: 367-444.

In some embodiments, the term "antibody" refers to intact molecules as well as functional fragments thereof, such as Fab, F(ab')2, and Fv that are capable of specifically interacting with a desired target. In some embodiments, the antibody fragments comprise:

(1) Fab, the fragment which contains a monovalent antigen-binding fragment of an antibody molecule, which can be produced by digestion of whole antibody with the enzyme papain to yield an intact light chain and a portion of one heavy chain;

(2) Fab', the fragment of an antibody molecule that can be obtained by treating whole antibody with papain, followed by reduction, to yield an intact light chain and a portion of the heavy chain; two Fab' fragments are obtained per antibody molecule;

(3) (Fab')2, the fragment of the antibody that can be obtained by treating whole antibody with the enzyme pepsin without subsequent reduction; F(ab')2 is a dimer of two Fab' fragments held together by two disulfide bonds;

(4) Fv, a genetically engineered fragment containing the variable region of the light chain and the variable region of the heavy chain expressed as two chains; and (5) Single chain antibody ("SCA" or scFv), a genetically engineered molecule containing the variable region of the light chain and the variable region of the heavy chain, linked by a suitable polypeptide linker as a genetically fused single chain molecule.

In another embodiment, the terms "antibodies" and "immunoglobulin" include antibodies or immunoglobulins of any isotype, fragments of antibodies which retain specific binding to antigen, including, but not limited to, Fab, Fv, scFv, and Fd fragments, chimeric antibodies, humanized antibodies, single-chain antibodies, and fusion proteins comprising an antigen-binding portion of an antibody and a non-antibody protein. The antibodies may be detectably labeled, e.g., with a radioisotope, an enzyme which generates a detectable product, a fluorescent protein, and the like. The antibodies may be further conjugated to other moieties, such as members of specific binding pairs, e.g., biotin (member of biotin-avidin specific binding pair), a toxin, e.g. tetanus toxoid, and the like. The antibodies may also be bound to a solid support, including, but not limited to, polystyrene plates or beads, and the like. Also encompassed by the term are Fab', Fv, F(ab')$_2$, Fc and or other antibody fragments that retain specific binding to antigen, and monoclonal antibodies. All of this is well know in the arts.

In one embodiment, the term "light chain" (V$_L$) refers to two distinct types, called kappa (k) or lambda (λ) based on the amino acid sequence of the constant domains. In another embodiment, the term "heavy chain" (V$_H$) when used in reference to an antibody refers to five distinct types or "classes", called alpha, delta, epsilon, gamma and mu (IgA, IgD, IgE, IgG, and IgM), based on the amino acid sequence of the heavy chain constant domain and several of these may be further divided into "subclasses" (isotypes), e.g., IgG$_1$, IgG$_2$, IgG$_3$ and IgG$_4$, IgA1, and IgA2. The heavy-chain constant domains that correspond to the different classes of antibodies are called alpha, delta, epsilon, gamma, and mu, respectively. The subunit structures and three-dimensional configurations of different classes of immunoglobulins are well known.

In one embodiment, the term "scFvs" refers to the smallest antibody fragments that maintain the antigen specificity and binding affinity of the whole antibody and are comprised in another embodiment of an immunoglobulin V$_L$ (variable light) and V$_H$ (variable heavy) chain joined by a flexible linker. scFvs are significantly smaller than intact antibodies and can bind to antigens with comparable affinites to the intact antibody molecule. In another embodiment, the flexible linker is one known in the art including but not limited to a serine-glycine linker. In one embodiment, the small size of the scFv chains provided in the libraries described herein that are generated by the methods described herein, endows them with excellent tissue and tumor penetrating properties making them highly attractive as targeting agents for infectious pathogens and tumor cells.

The variability in sequence is concentrated in those regions called complementarity determining regions (CDRs) while the more highly conserved regions within the variable domain are called framework regions (FR). The CDRs of the light and heavy chains contain within them the amino acids which are largely responsible for the interaction of the antibody with antigen and the sequences of which determine the specificity of the antibody or antibody fragment.

The rearranged nucleotide sequences of the VH and VL chains are almost unique and contained within each chain are three complementarity determining regions (CDRs). Folding of the protein chains brings these 3 CDRs together to form the antigen-binding site of each chain. In other embodiments, the term "CDR" will comprise regions as described by Kabat et al., J. Biol. Chem. 252, 6609-6616 (1977) and Kabat et al., *Sequences of protein of immunological interest*. (1991), and Chothia and Lesk, *J. Mol. Biol.* 196:901-917 (1987) and MacCallum et al., *J. Mol. Biol.* 262:732-745 (1996). The amino acids of the CDRs of the variable domains were initially defined by Kabat, based on sequence variability, to consist of amino acid residues 31-35B (H1), 50-65 (H2), and 95-102 (H3) in the human heavy chain variable domain (VH) and amino acid residues 24-34 (L1), 50-56 (L2), and 89-97 (L3) in the human light chain variable domain (VL), using Kabat's numbering system for amino acid residues of an antibody. See Kabat et al., sequences of proteins of immunological interest, US Dept. Health and Human Services, NIH, USA (5th ed. 1991). Surrounding the CDRs are the less diverse framework regions (FR1-FR4) of each chain and these are highly conserved between mammalian species (FIG. 5). In one embodiment, the term "framework region" or "FR" are those variable domain residues other than the hypervariable region residues. The framework regions for humans and mice have been precisely defined. See, e.g., Kabat, E. A. et al., Sequences of Proteins of Immunological Interest, US Dept. Health and Human Services, National Institutes of Health, USA (5.sup.th ed. 1991).

Each variable domain typically has four FRs identified as FR1, FR2, FR3 and FR4. In some embodiments, "FR" also refers to an antibody variable region comprising amino acid residues abutting or proximal to, but outside of the CDR regions i.e. regions which directly interact with the antigen, acting as the recognition element of the antibody molecule within the variable region of an antibody. In one embodiment, the term "framework region" is intended to mean each domain of the framework that is separated by the CDRs. In some embodiments, the sequences of the framework regions of different light or heavy chains are relatively conserved within a species. The combined heavy and light chain framework regions of an antibody serve to position and align the CDRs for proper binding to the antigen.

Figure 1:
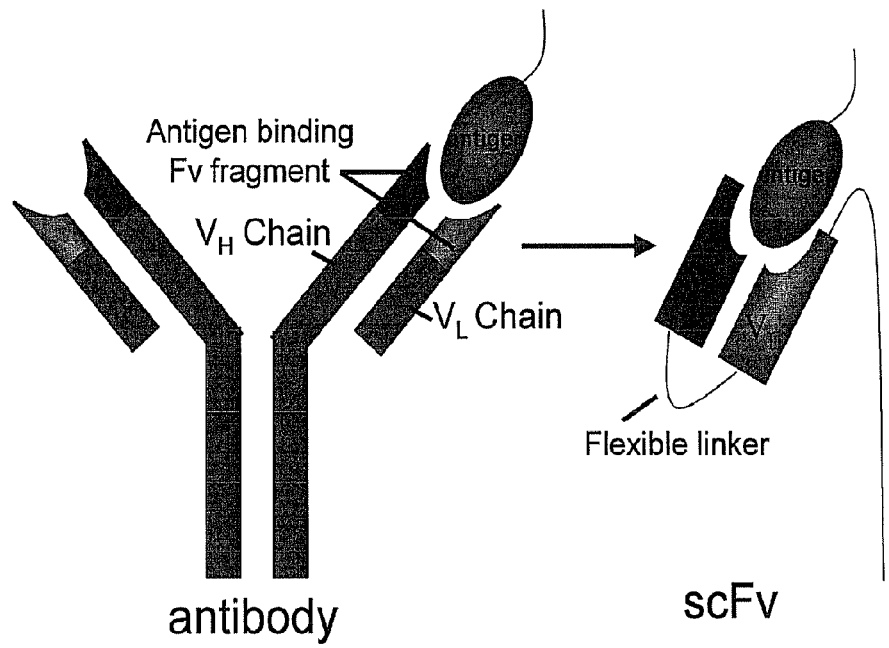
FIG. 1 shows cartoon of a single chain fragment variable (scFv) comprised of the $V_H$ and $V_L$ regions of immunoglobulin linked by a flexible linker.

The term "specific antigen binding domain" or "antigen binding region" refers in one embodiment, to that portion of the selective binding agent (such as an antibody molecule) which contains the amino acid residues that interact with an antigen and confer on the binding agent its specificity and affinity for the antigen. The term "variable region" or "variable domain" refers in another embodiment, to a portion of the light and/or heavy chains of an antibody (see FIG. 1), comprising in certain embodiments the amino-terminal 120 to 130 amino acids in the heavy chain and about 100 to 110 amino acids in the light chain, which differ extensively in sequence among antibodies and which determine the binding and specificity of each particular antibody for its particular antigen.

In one embodiment, the term "binds" or "binding" or grammatical equivalents, refer to the compositions having affinity for each other. "Specific binding" is where the binding is selective between two molecules. A particular example of specific binding is that which occurs between an antibody and an antigen. Typically, specific binding can be distinguished from non-specific when the dissociation constant ($K_D$) is less than about $1\times10^{-5}$ M or less than about $1\times10^{-6}$ M or $1\times10^{-7}$ M. Specific binding can be detected, for example, by ELISA, immunoprecipitation, coprecipitation, with or without chemical crosslinking, two-hybrid assays and the like. Appropriate controls can be used to distinguish between "specific" and "non-specific" binding.

In some embodiments, VH and VL chains are randomly combined to generate single chain molecules that recapitulate the naturally occurring antigen-binding site of the original antibody, where in other embodiments, the synthesized single chain molecules are isolated based on the antigens they recognize and are used therapeutically in a number of targeted therapeutic approaches.

In one embodiment, an isolated antibody, antibody fragment or scFv provided herein finds use in various in vivo and in vitro applications such as, but not limited to diagnostics, antibody imaging, ameliorating symptoms associated with a disease, preventing and treating diseases treatable by antibody-based therapy.

In one embodiment, the term "biological sample" refers to bile, blood, sera, plasma, saliva, sperm, urine, mucous, cerebrospinal fluid, tissue or their combination.

In one embodiment, the isolated scFv, antibody or fragment thereof provided herein is administered for therapeutic treatments to a subject provided herein, such as a canine that is suffering from a tumor or pathologic condition in an amount sufficient to prevent, inhibit, or reduce the progression of the tumor or pathologic condition, wherein the pathologic condition includes but is not limited to a viral or bacterial infection or a tumor. In another embodiment, progression includes, e.g., the growth, invasiveness, metastases and/or recurrence of the tumor or pathologic condition. The composition provided herein that is to be administered contains, in one embodiment, a quantity of the active compound in a therapeutically effective amount for relief of the particular disease or condition being treated. An amount adequate to accomplish this is defined as a therapeutically effective dose. Amounts effective for this use will depend upon the severity of the disease and the general state of the subject's own immune system. Dosing schedules will also vary with the disease state and status of the subject, and will typically range from a single bolus dosage or continuous infusion to multiple administrations per day (e.g., every 4-6 hours), or as indicated by the treating veterinarian and the subject's condition. It should be noted, however, that the present invention is not limited to any particular dose.

In one embodiment, the term "tumor" includes but is not limited to any abnormal or malignant cell growth that affects any member of the canine families Specifically, it includes malignant growths that affect any member of the canine family such as, but not limited to, hemangiosarcoma, osteosarcoma, squamous cell carcinoma, lymphosarcoma, soft tissue sarcoma, bladder tumors, oral tumors, brain tumors, vaccine associated sarcomas, multilobular, tumors of bone, thyroid tumors, nasal tumors, perianal adenoma, lipoma, lymphoma, histiocytoma, insulinomas, transmissible venereal tumors, carcinomas, adenocarcinomas, mammary tumors, mast cell tumors, and pituitary tumors or any other form of epithelial, mesenchymal or hematopoeitic cancer or combination thereof or their metastases.

In one embodiment, "bacterial infections" and "viral infections" include but are not limited to brucellosis, canine coronavirus, canine distemper, canine ehrlichiosis, haemobartonellosis, canine herpesvirus, canine hepatitis, enteritis, canine infectious tracheobronchitis, Leptospirosis, lyme disease, parvovirus infection, plague, rabies, rocky mountain spotted fever, tularemia, rotavirus, parvo virus or any other bacterial or viral infection known in the art to afflict the animals provided herein, such as canines.

In one embodiment, canine cancer patients/subjects generate antibody responses against their own tumor-associated antigens (TAA) and in another embodiment, these naturally occurring responses are used as a molecular template to generate the synthetic antibody-like molecules provided herein, that are then capable of being used therapeutically to deliver a cytotoxic payload to primary and metastatic tumors in vivo.

In one embodiment, the isolated scFv, antibody or fragment thereof provided herein is administered in combination with one or more other anti-neoplastic, anti-viral, or anti-bacterial agents. Any suitable agent can be used, such as a chemotherapeutic agent, radiation, antibiotic, anti-viral or combinations thereof. Such agents are readily known in the art and are readily available, examples include but are not limited to the diptheria toxin, or *pseudomonas* exotoxin for use as anti-neoplastic agents. The anti-neoplastic agent can be an alkylating agent or an anti-metabolite. When the anti-neoplastic agent is radiation, the source of the radiation can be either external (external beam radiation therapy—EBRT) or internal (brachytherapy—BT) to the subject being treated. In another embodiment, treatment involves the use of intravenous (IV) fluids, anti-nausea medications, and antibiotics in order to prevent secondary infections. The dose of anti-neoplastic agent administered depends on numerous factors, including, for example, the type of agent, the type and severity of the tumor being treated and the route of administration of the agent. It should be emphasized, however, that the present invention is not limited to any particular dose.

Targeted delivery of cytotoxic agents reduces in one embodiment, off-target side effects and improves the therapeutic efficacy of the agent.

In another embodiment, the term "isolated" refers to altered "by the hand of man" from the natural state. If an "isolated" composition or substance occurs in nature, it has been changed or removed from its original environment, or both. In another embodiment, a polynucleotide such as an mRNA or a polypeptide naturally present in a living animal is not "isolated," but the same polynucleotide or polypeptide separated from the coexisting materials of its natural state is "isolated", as the term is employed herein. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications has been made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

In one embodiment, the terms "isolated peptide" or "polypeptide" refers to an scFv or antibody or antibody fragment as further described herein. In another embodiment, when in reference to any polypeptide of this invention, the term is meant to include native polypeptides (either degradation products, synthetically synthesized peptides or recombinant peptides) and peptidomimetics (typically, synthetically synthesized peptides), such as peptoids and semipeptoids which are peptide analogs, which may have, for example, modifications rendering the polypeptides more stable while in a body or more capable of penetrating into cells. Such modifications include, but are not limited to N terminal, C terminal or peptide bond modification, including, but not limited to, backbone modifications, and residue modification, each of which represents an additional embodiment of the invention. Methods for preparing peptidomimetic compounds are well known in the art and are specified, for example, in Quantitative Drug Design, C. A. Ramsden Gd., Chapter 17.2, F. Choplin Pergamon Press (1992). In one embodiment, a polypeptide is a full length protein or a variant of a known protein.

In one embodiment the isolated polypeptide of this invention is a fragment of the native protein. In one embodiment, "fragment" refers to a protein or polypeptide that is shorter or comprises fewer amino acids than the full length protein or polypeptide. In another embodiment, fragment refers to a nucleic acid that is shorter or comprises fewer nucleotides than the full length nucleic acid. In another embodiment, the fragment is an N-terminal fragment. In another embodiment, the fragment is a C-terminal fragment. In one embodiment, the fragment of this invention is an intrasequential section of the protein, peptide, or nucleic acid. In another embodiment, the fragment is a functional intrasequential section of the protein, peptide or nucleic acid. In another embodiment, the fragment is a functional intrasequential section within the protein, peptide or nucleic acid. In another embodiment, the fragment is an N-terminal functional fragment. In one embodiment, the fragment is a C-terminal functional fragment.

In one embodiment, an isolated polypeptide of this invention may comprise a derivate of a polypeptide of this invention. "Derivative" is to be understood as referring, in some embodiments, to less than the full-length portion of the native sequence of the protein in question. In some embodiments, a "derivative" may further comprise (at its termini and/or within said sequence itself) non-native sequences, i.e. sequences which do not form part of the native protein in question. The term "derivative" also includes within its scope molecular species produced by conjugating chemical groups to the amino residue side chains of the native proteins or fragments thereof, wherein said chemical groups do not form part of the naturally-occurring amino acid residues present in said native proteins.

In another embodiment, this invention relates to libraries of antibodies or antibody variable domains. In another embodiment, provided herein are single chain Fragment variable antibody libraries comprising the VH and VL sequences linked by a flexible linker for the identification and targeting of tumor-associated antigens.

In another embodiment, expression of scFv libraries on the surface of bacteriophage (a scFv phage display library as the ones described herein) allows for the rapid screening of millions of scFvs and the selection of those scFvs that bind a particular antigen. Antigens bound by scFvs are identified in one embodiment, and isolated in another embodiment, using standard biochemical techniques with the novel primer set described herein. In one embodiment, the resulting phage display is used successfully to discover novel therapeutic targets and isolate antibody fragments that bind them. In one embodiment, scFv phage display libraries generated using the methods described herein, are used to identify and target tumor-associated antigens (TAA). In another embodiment, scFv phage display libraries generated using the methods described herein, are used to identify and target bacteria- or virus-derived antigens wherein said targetting is, in some embodiments, for therapeutic purposes.

In some embodiments, the library is a nucleic acid library, a phage display library or an oligopeptide library. In some embodiments, the process yields an ScFv fragment library, a FR library, a VH library, a VL library, a VH and VL library, a CDR library or an Fab fragment library. In another embodiment, the libraries/methods of the present invention arrive at a canine scFv library, used to identify and target tumor-associated antigens (TAA), infectious pathogens and other target proteins such as cytokines.

In another embodiment, the libraries described herein, further comprise scFv DNA constructs generated from randomly combined VH and VL chains with each scFv chain constituting a library member. In another embodiment, the population of nucleic acids sequences of the scFv DNA constructs generated from randomly combined VH and VL chains are cloned into multiple copies of a phage display vector or bacteriophage that express individual scFv to form phage display libraries expressing the generated scFv constructs.

The libraries produced in accordance with the inventive method described herein, are based in one embodiment, on "source data" comprising annotations of primary sequences determined and/or predicted structures for proteins from which the component peptides are derived. In another embodiment, source data comprise protein sequence resources such as PRINTS, Pfam, SMART, Propom, InterPro, TIGRFAMs, ADDA, CHOP, ProtoNet, SYSTERS, iProClass, SWISSPROT, COG/KOG, and protein structure family resources such as CAMPASS (Cambridge University, UK), CATH database (University College, London, UK), CE (SDSC, La Jolla, Calif., USA), DHS (University College, London, UK), ENTREZ/MMDB (NCBI, Bethesda Md., USA), Structural Classification of Protein Database (SCOP) (Andreeva et al., Nucl. Acid Res. 32:D226-D229, 2004), or the Protein Data Bank (PDB) (Berman et al., Nucleic Acid Res. 28: 235, 2000). It is to be understood that such source data generally need additional refinement to enrich for particular amino acid sequence products capable of independently-forming secondary structures and/or assemblies of secondary structures and/or folds suitable for practical application in drug screening and to ensure that an optimal structural diversity of the library is achieved.

In one embodiment, a library member generated using the methods described herein, further comprises a nucleic acid segment encoding a tag linked to the nucleic acid encoding the scFv chain, wherein the tag is the same in different library members. In another embodiment, the methods described herein further comprise contacting the library members that comprise a nucleic acid segment encoding a tag linked to the nucleic acid with an immobilized receptor having specific affinity for the tag and isolating a subpopulation of library members that bind to immobilized receptor and in yet another embodiment, further comprising contacting the subpopulation of library members with a target lacking specific affinity for the tag, and isolating a further subpopulation of library members that binds to the target, wherein and in other embodiments the target is a tumor antigen. In another embodiment, each embodiment represents a sub population of library members capable of being identified and indexed.

In another embodiment, the term "antigen" includes but is not limited to antigens that originate from tumors, fungi, viral, autoimmune diseases or bacterial infections provided herein. In other embodiments, the antigen is a cytokine, chemokine or other soluble protein that contributes to inflammatory responses.

In one embodiment, the target lacking specific affinity for the tag, is a tumor antigen such as the tumor-associated antigens described herein in certain other discrete embodiments.

The term "filamentous phage" or "filamentous bacteriophage" refers to a viral particle capable of displaying a heterogenous polypeptide on its surface. Although one skilled in the art will appreciate that a variety of bacteriophage may be employed in the present invention, in preferred embodiments the vector is, or is derived from, a filamentous bacteriophage, such as, for example, f1, fd, Pf1, M13, etc. The filamentous phage may contain a selectable marker such as, but not limited to, tetracycline (e.g., "fd-tet"). Various filamentous phage display systems are well known to those of skill in the art (see, e.g., Zacher et al. (1980) Gene 9: 127-140, Smith et al. (1985) Science 228: 1315-1317 (1985); and Parmley and Smith (1988) Gene 73: 305-318).

In some embodiments, the term "nucleic acid" refers to polynucleotide or to oligonucleotides such as deoxyribonucleic acid (DNA), and, where appropriate, ribonucleic acid (RNA) or mimetic thereof. The term should also be understood to include, as equivalents, analogs of either RNA or DNA made from nucleotide analogs, and, as applicable to the embodiment being described, single (sense or antisense) and double-stranded polynucleotides. This term includes oligonucleotides composed of naturally occurring nucleobases, sugars and covalent internucleoside (backbone) linkages as well as oligonucleotides having non-naturally-occurring portions, which function similarly. Such modified or substituted oligonucleotides are often preferred over native forms because of desirable properties such as, for example, enhanced cellular uptake, enhanced affinity for nucleic acid target and increased stability in the presence of nucleases.

As will be appreciated by one skilled in the art, a fragment or derivative of a nucleic acid sequence or gene that encodes for a protein or peptide can still function in the same manner as the entire, wild type gene or sequence. Likewise, forms of nucleic acid sequences can have variations as compared to wild type sequences, nevertheless encoding a protein or peptide, or fragments thereof, retaining wild type function exhibiting the same biological effect, despite these variations. Each of these represents a separate embodiment of this present invention.

The nucleic acids provided herein can be produced by any synthetic or recombinant process such as is well known in the art. Nucleic acids provided herein can further be modified to alter biophysical or biological properties by means of techniques known in the art. For example, the nucleic acid can be modified to increase its stability against nucleases (e.g., "end-capping"), or to modify its lipophilicity, solubility, or binding affinity to complementary sequences.

In one embodiment, cDNA used herein is derived from a source such as but not limited to, peripheral blood lymphocytes, and is used as a template for amplifiying VH and VL chains between FR1 and the constant region or between FR1 and FR4 respectively to produce millions of near unique nucleotide sequences encoding the antigen binding sites of VH and VL chains, thereby reproducing in another embodiment, the immunological repertoire of the individual animal. In another embodiment the cDNA is derived from splenocytes of a healthy canine. In another embodiment the cDNA is derived from splenocytes in a canine that has been exposed to a viral, bacterial or tumor antigen, or their combination. In another embodiment, since the RNA level of plasma cells is approximately 1000 times greater than that of naïve B cells, the immune repertoire (when compared to the non-immune repertoire) is in one embodiment amplified by PCR. In another embodiment, the newly sequenced canine genome enables the design of degenerate primers. In another embodiment, the degenerate set of primers are used in the methods described herein to amplify the rearranged VH and VL immunoglobulin regions from cDNA derived from peripheral blood lymphocytes (PBLs), lymph nodes or splenocytes of healthy donor dogs or their combination. Furthermore, the degenerate set of primers are used in the methods described herein to amplify rearranged VH and VL immunoglobulin regions from cDNA derived from the primary tumor or metastatic lesions of a dog with cancer as well as from the lymph nodes that drain the site where the tumor is present. Amplified VH and VL chains are randomly recombined in one embodiment, using a flexible linker to generate a combinatorial library of scFvs that can be cloned in one embodiment, into a phagemid and expressed on the surface of bacteriophage. The size and diversity of the generated library is evaluated in one embodiment, using cloning and sequencing techniques as will be understood by a skilled artisan.

In one embodiment, this invention relates to primer nucleotide sequences that are used to amplify all rearranged sequences of canine variable heavy (VH) and variable light (VL) immunoglobulin chains that have been used in naturally occurring antibody responses. In another embodiment, provided herein are VH and VL sequences arrived at through amplification of the VH and VL sequences using the primers provided herein. Sequencing of the amplified VH and VL immunoglobulin chains reveals the conserved framework regions of canine VH and VL chains which in some embodiments are utilized to modify the framework regions of human or murine antibodies making them less immunogenic in the dog thereby allowing such "canine-ized" antibodies to be used diagnostically or therapeutically in vivo in the domestic dog population.

In another embodiment, the forward set of primers provided herein used to amplify the variable regions of the IgG heavy chain are based on the predicted nucleotide or amino acid sequence of canine framework region 1 (FR1) and constant IgG region of Ig $V_H$ chains. In another embodiment, the reverse set of primers provided herein used to amplify the lambda and kappa light chains are based on the predicted nucleotide or amino acid sequence of canine framework region 1 (FR1) and framework region 4 (FR4) of $V_L$ lambda (λ) and kappa (k), chains or their combination.

In one embodiment, the isolated polypeptide of this invention may include modification to the original sequence of the native protein. "Modification" is to be understood as comprising non-native amino acid residues and sequences of such non-native residues, which have been introduced as a consequence or mutation of the native sequence (by either random or site-directed processes).

In one embodiment, provided herein is an isolated scFv polypeptide encoded by an isolated nucleic acid sequence encoding the scFv. In another embodiment, the nucleic acid sequence encoding the scFv is isolated from an scFv nucleic acid library. In another embodiment, the scFv is generated from a combinatorial library of VH and VL sequences linked via a flexible linker as provided herein.

Accordingly and in one embodiment, provided herein is an isolated VH sequence selected from the group set forth in SEQ ID NO: X-Y. In another embodiment, provided herein is an isolated VL sequence selected from the group set forth in SEQ ID NO: X-Y. These novel VH and VL set forth in SEQ ID NOs: X-Y contain canine framework regions and complementarity determining regions which may be used to canineize antibodies. In one embodiment, the VH and VL sequences provided herein or homologous sequences are used to arrive at the scFv nucleic acid and polypeptide libraries provided herein. In another embodiment, provided herein is a nucleic acid sequence encoding a single chain fragment variable antibody (scFv) isolated from the scFv nucleic acid library, comprising any combination of a VH and VL chain sequence, wherein in other embodiments, said VH and VL sequences are linked via a flexible linker. In another embodiment, the flexible linker is a flexible serine-glycine linker (GGGG-S-GGGG-S-GGGG-S, SEQ ID No. 33). In some embodiments, the single chain fragment variable antibody comprises a VH chain selected from a group of nucleic acid sequences and amino acid sequences encoded thereby set forth in SEQ ID NO: 34-366. In other embodiments, the single chain fragment variable antibody comprises a VL chain is selected from a group of nucleic acid sequences and amino acid sequences encoded thereby set forth in SEQ ID NO: 367-444. In some embodiments, the single chain fragment variable antibody comprises, or consists of a VH chain selected from a group of nucleic acid sequences and amino acid sequences encoded thereby set forth in SEQ ID NO: 34-366 and a VL chain is selected from a group of nucleic acid sequences and amino acid sequences encoded thereby set forth in SEQ ID NO: 367-444, in any random order, ie—VH-linker-VL, or VL-linker-VH and different VH and VL sequences thereof.

In another embodiment, the antigen-specific binding domain for which a single-chain variable fragments (scFv) encoding polynucleotide is generated using the methods described herein, and incorporated in the libraries provided herein. In one embodiment, the term "tumor-associated antigen" or "TAA" refers to a molecule or complex which is expressed at a higher frequency or density by tumor cells than by non-tumor cells of the same tissue type. In another embodiment, tumor-associated antigens may be antigens not normally expressed by the host; they may be mutated, truncated, misfolded, or otherwise abnormal manifestations of molecules normally expressed by the host; they may be identical to molecules normally expressed but expressed at abnormally high levels; or they may be expressed in a context or milieu that is abnormal. Tumor-associated antigens may be, in one embodiment, proteins or protein fragments, complex carbohydrates, gangliosides, haptens, nucleic acids, or any combination of these or other biological molecules. Knowledge of the existence or characteristics of a particular tumor-associated antigen is not necessary for the practice of the invention. In one embodiment, the tumor-associated antigen, is a canine hemangiosarcoma associated antigen, such as CD31 and Factor VIII-related antigen (vWF). In another embodiment, the cancer is osteosarcoma. In another embodiment the TAA is a parvo virus or a parvo virus-associated antigen.

In one embodiment, an assembly cell is a cell in which a nucleic acid can be packaged into a viral coat protein (capsid). Assembly cells may be infected with one or more different virus particles (e.g. a normal or debilitated phage and a helper phage) that individually or in combination directly package nucleic acids into a viral capsid.

In one embodiment, the invention also provides transformed cells and progeny thereof into which a nucleic acid molecule encoding an antibody, antibody libraries, scFv libraries, antibody fragment, VH or VL libraries has been introduced by means of recombinant DNA techniques in vitro, ex vivo or in vivo. The transformed cells can be propagated and the introduced nucleic acid transcribed, or encoded protein expressed. It is understood that a progeny cell may not be identical to the parental cell, since there may be mutations that occur during replication. Transformed cells include but are not limited to prokaryotic and eukaryotic cells such as bacteria, fungi, plant, insect, and animal (e.g., mammalian, including canine) cells. The cells may be present in culture, in a cell, tissue or organ ex vivo or present in a subject.

In one embodiment, the term "transformed" refers to a genetic change in a cell following incorporation of nucleic acid (e.g., a transgene) exogenous to the cell. Thus, a "transformed cell" is a cell into which, or a progeny of which a nucleic acid molecule has been introduced by means of recombinant DNA techniques. Cell transformation to produce host cells may be carried out as described herein or using techniques known in the art. Accordingly, methods of producing cells containing the nucleic acids and cells expressing the "canine-ized" antibodies of the invention are also provided.

Typically cell transformation employs a vector. The term "vector," refers to, e.g., a plasmid, virus, such as a viral vector, or other vehicle known in the art that can be manipulated by insertion or incorporation of a nucleic acid, for genetic manipulation (i.e., "cloning vectors"), or can be used to transcribe or translate the inserted polynucleotide (i.e., "expression vectors"). Such vectors are useful for introducing nucleic acids, including a nucleic acid that encodes a polypeptide provided herein operably linked with an expression control element, and expressing the encoded protein in vitro (e.g., in solution or in solid phase), in cells or in vivo.

A great variety of vector and/or expression systems can be used for cloning the single chain variable fragment into a DNA construct. Such systems include, among others, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia, viruses, adenoviruses, fowl pox viruses, pseudorabies viruses and retroviruses, and vectors derived from combinations thereof, such as those derived from plasmid and bacteriophage genetic elements, such as cosmids and phagemids.

In another embodiment, the expression systems may contain control regions that regulate as well as engender expression. Generally, any system or vector suitable to maintain, propagate or express polynucleotides to produce a polypeptide in a host may be used. The appropriate nucleotide sequence may be inserted into an expression system by any of a variety of well-known and routine techniques, such as, for example, those set forth in Sambrook et al., Molecular Cloning, A Laboratory Manual.

In one embodiment, provided herein is an expression system as described herein, comprising the scFv obtained by the methods described herein. In another embodiment, the step of randomly linking the flexible linker-comprising $V_H$ and $V_L$ amplicons used to generate the libraries described herein is done using splicing by overlap extension (SOE).

In one embodiment, the flexible linker used to randomly link the $V_H$ and $V_L$ amplicons in the methods described herein, is flexible serine-glycine linker (GGGG-S-GGGG-S-GGGG-S, SEQ ID No. 33). In one embodiment, the term "linker" or "flexible linker" refers to any heterologous polypeptide of at least about 6 amino acids in length, which when inserted between the carboxy-terminal end of $V_H$ and the amino-terminal end of $V_L$ yields a functional protein capable of forming a functional scFV. The term "Flexible linker nucleic acid" refers in another embodiment to a nucleic acid encoding the peptide linker. The term "linker", "linker sequence", "spacer", "tethering sequence" or grammatical equivalents thereof refer to a molecule or group of molecules (such as a monomer or polymer) that connects two molecules and often serves to place the two molecules in a preferred configuration. A number of strategies may be used to covalently link molecules together. These include, but are not limited to polypeptide linkages between N- and C-terminus of proteins or protein domains, linkage via disulfide bonds, and linkage via chemical cross-linking reagents. In one aspect of this embodiment, the linker is a peptide bond, generated by recombinant techniques or peptide synthesis. In another embodiment the linker is a cysteine linker. In yet another embodiment it is a multi-cysteine linker. Choosing a suitable linker for a specific case where two polypeptide chains are to be connected depends on various parameters, including but not limited to the nature of the two polypeptide chains (e.g., whether they naturally oligomerize), the distance between the N- and the C-termini to be connected if known, and/or the stability of the linker towards proteolysis and oxidation. Furthermore, the linker may contain amino acid residues that provide flexibility. Thus, the linker peptide may predominantly include the following amino acid residues: Gly, Ser, Ala, or Thr. The linker peptide should have a length that is adequate to link two molecules in such a way that they assume the correct conformation relative to one another so that they retain the desired activity. Suitable lengths for this purpose include at least one and not more than 30 amino acid residues. In one embodiment, the linker is from about 1 to 30 amino acids in length. In another embodiment, the linker is from about 1 to 15 amino acids in length. In addition, the amino acid residues selected for inclusion in the linker peptide should exhibit properties that do not interfere significantly with the activity of the scFv polypeptide. Thus, the linker peptide on the whole should not exhibit a charge that would be inconsistent with the activity of the polypeptide, or interfere with internal folding, or form bonds or other interactions with amino acid residues in one or more of the monomers that would seriously impede the binding of receptor monomer domains. Useful linkers include glycine-serine polymers, glycine-alanine polymers, alanine-serine polymers, and other flexible linkers such as the tether for the shaker potassium channel, and a large variety of other flexible linkers, as will be appreciated by those in the art. Suitable linkers may also be identified by screening databases of known three-dimensional structures for naturally occurring motifs that can bridge the gap between two polypeptide chains. In one embodiment, the linker is not immunogenic when administered in a human subject. Thus linkers may be chosen such that they have low immunogenicity or are thought to have low immunogenicity. For example, a linker may be chosen that exists naturally in a human. In another embodiment the linker has the sequence of the hinge region of an antibody, that is the sequence that links the antibody Fab and Fc regions; alternatively the linker has a sequence that comprises part of the hinge region, or a sequence that is substantially similar to the hinge region of an antibody. In another embodiment, the linker is an IgG hinge region such as an IgG1, an IgG3 or a fragment thereof. Another way of obtaining a suitable linker is by optimizing a simple linker, e.g., (Gly4Ser)n, through random mutagenesis.

Introduction of nucleic acid encoding polypeptides provided herein can also be carried out by conventional methods known in the art such as osmotic shock (e.g., calcium phosphate), electroporation, microinjection, cell fusion, etc. Introduction of nucleic acid and polypeptide in vitro, ex vivo and in vivo can also be accomplished using other techniques. For example, a polymeric substance, such as polyesters, polyamine acids, hydrogel, polyvinyl pyrrolidone, ethylenevinylacetate, methylcellulose, carboxymethylcellulose, protamine sulfate, or lactide/glycolide copolymers, polylactide/glycolide copolymers, or ethylenevinylacetate copolymers. A nucleic acid can be entrapped in microcapsules prepared by coacervation techniques or by interfacial polymerization, for example, by the use of hydroxymethylcellulose or gelatin-microcapsules, or poly (methylmethacrolate) microcapsules, respectively, or in a colloid drug delivery system. Colloidal dispersion systems include macromolecule complexes, nano-capsules, microspheres, beads, and lipid-based systems, including oil-in-water emulsions, micelles, mixed micelles, and liposomes.

The use of liposomes for introducing various compositions into cells, including nucleic acids, is known to those skilled in the art (see, e.g., U.S. Pat. Nos. 4,844,904, 5,000,959, 4,863, 740, and 4,975,282). A carrier comprising a natural polymer, or a derivative or a hydrolysate of a natural polymer, described in WO 94/20078 and U.S. Pat. No. 6,096,291, is suitable for mucosal delivery of molecules, such as polypeptides and polynucleotides. Piperazine based amphilic cationic lipids useful for gene therapy also are known (see, e.g., U.S. Pat. No. 5,861,397). Cationic lipid systems also are known (see, e.g., U.S. Pat. No. 5,459,127). Accordingly and in one embodiment, viral and non-viral vector means of delivery into cells or tissue, in vitro, in vivo and ex vivo are included. These methods may be employed in the event that a scFv is identified that may inhibit a specific intracellular pathway and as such would be required to be delivered into the cell(s) of interest. In another embodiment, the present invention comprises methods of use of a polynucleotide, vector, polypeptide and/or fragment thereof as herein described and/or compositions comprising the same in treating, inhibiting or preventing a pathologic condition or disease.

In another embodiment, DNA constructs comprise regulatory elements necessary for expression of nucleotides. Such elements include, for example, a promoter, an initiation codon, a stop codon, and a polyadenylation signal. In addition, enhancers are often required for expression of a sequence that encodes an immunogenic target protein. As is known in the art, these elements are preferably operably linked to the sequence that encodes the desired protein. In another embodiment, regulatory elements are selected that are operable in the species to which they are to be administered. Initiation codons and stop codons are included in one embodiment, as part of a nucleotide sequence that encodes the scFv protein. In one embodiment, the initiation and termination codons must be in frame with the coding sequence.

In one embodiment, viral, eukaryotic and prokaryotic promoters are known in the art and are included for use in the methods and compositions provided herein. In another embodiment these promoter sequences regulate expression of the encoded polynucleotide sequences, and in some embodiments of the present invention, are operably linked to polynucleotides encoding the polypeptides of this invention. In additional embodiments of the present invention, these promoters are either constitutive or inducible, and provide a means of high and low levels of expression of the polypeptides of this invention, and in some embodiments, for regulated expression of multiple polypeptides of the invention, which in some embodiments are expressed as a fusion protein.

The promoters will typically control expression, optionally with an operator sequence and may include ribosome binding site sequences for example, for initiating and completing transcription and translation. According to additional embodiments, the vector may also contain expression control sequences, enhancers that may regulate the transcriptional activity of the promoter, appropriate restriction sites to facilitate cloning of inserts adjacent to the promoter and other necessary information processing sites, such as RNA splice sites, polyadenylation sites and transcription termination sequences as well as any other sequence which may facilitate the expression of the inserted nucleic acid.

In one embodiment, the term "homology," "homolog" or "homologous" refers to sequence identity, or refers to structural identity, or functional identity. In another embodiment, by using the term "homology" and the other like forms, it is to be understood that any molecule, whether nucleic acid or peptide, that functions similarly, and/or contains sequence identity, and/or is conserved structurally so that it approximates the reference sequence, is to be considered as part of this invention. In another embodiment, the terms "homology", "homologue" or "homologous", in any instance, indicate that the sequence referred to, whether an amino acid sequence, or a nucleic acid sequence, exhibits at least 76% correspondence with the indicated sequence. In another embodiment, the amino acid sequence or nucleic acid sequence exhibits at least 86-90% correspondence with the indicated sequence. In another embodiment, the amino acid sequence or nucleic acid sequence exhibits at least 91% correspondence with the indicated sequence. In another embodiment, the amino acid sequence or nucleic acid sequence exhibits at least 95% correspondence with the indicated sequence. In another embodiment, the amino acid sequence or nucleic acid sequence exhibits at least 95% or more correspondence with the indicated sequence. In another embodiment, the amino acid sequence or nucleic acid sequence exhibits at least 97% or more correspondence with the indicated sequence. In another embodiment, the amino acid sequence or nucleic acid sequence exhibits 97%-100% correspondence to the indicated sequence. In another embodiment, the amino acid sequence or nucleic acid sequence exhibits 100% correspondence to the indicated sequence. Similarly, in one embodiment, the reference to a correspondence to a particular sequence includes both direct correspondence, as well as homology to that sequence as herein defined. Accordingly and in one embodiment, the term "non-homologous" refers the amino acid sequence or nucleic acid sequence exhibits no more than 75% correspondence with the indicated sequence. In another embodiment, the amino acid sequence or nucleic acid sequence exhibits no more than 65-74% correspondence with the indicated sequence. In another embodiment, the amino acid sequence or nucleic acid sequence exhibits no more than 55-64% correspondence with the indicated sequence. In another embodiment, the amino acid sequence or nucleic acid sequence exhibits no more than 45-54% correspondence with the indicated sequence. In another embodiment, the amino acid sequence or nucleic acid sequence exhibits no more than 35-44% correspondence with the indicated sequence. In another embodiment, the amino acid sequence or nucleic acid sequence exhibits no more than 35-44% correspondence with the indicated sequence. In another embodiment, the amino acid sequence or nucleic acid sequence exhibits no more than 15-34% correspondence with the indicated sequence. In another embodiment, the amino acid sequence or nucleic acid sequence exhibits no more than 5-14% correspondence with the indicated sequence. In another embodiment, the amino acid sequence or nucleic acid sequence exhibits no more than 0.1-4% correspondence with the indicated sequence. In another embodiment, the term "non-homologous" can be used interchangeably with the term "low sequence similarity".

In one embodiment, the scFv, VH, and VL sequences generated using the primers provided herein comprise CDR and framework regions that are canine-ized using similar methods of humanizing antibodies available in the art. In another embodiment, these methods include but are not limited to CDR grafting, CDR shuffling and employ the use of conservative amino acid substitution.

In one embodiment, the term "conservative amino acid substitution" refers to one in which the amino acid residue is replaced with an amino acid residue having a similar side chain. In one embodiment, the polypeptide of this invention comprises an amino acid substitution. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). In another embodiment, the amino acid substitution may not be conservative which may result in enhanced activity of the mutated polypeptide compared to the native polypeptide.

In one embodiment, random recombination of germline DNA genes coupled with random nucleotide insertions ensure that the resulting antigen binding site that consists of 6 highly diverse complimentarity determining sites (CDRs) (3 from VH chain and 3 from VL chain) is almost unique (FIG. 2). The CDRs of VH and VL chains are surrounded by much less diverse framework regions (FR1-FR4) that are highly conserved amongst species.

In one embodiment, the terms "determining," "measuring," and "assessing," and "assaying" are used interchangeably and include both quantitative and qualitative determinations.

In one embodiment, provided herein is a tumor vaccine comprising the tumor specific single chain fragment variable antibody fragments identified by the methods described herein, wherein in another embodiment, the tumor specific single chain fragment variable antibody fragment is operably linked to a toxin. In another embodiment, provided herein is a bacterial, viral, fungal, parasitic vaccine comprising the specific single chain fragment variable antibody fragments identified by the methods described herein, wherein in another embodiment, the specific single chain fragment variable antibody fragment is operably linked to a toxin or biologically active agent. In another embodiment, provided herein is a vaccines comprising the tumor specific single chain fragment variable antibody fragments identified by the methods described herein to neutralize cytokines, chemokines, or a biologically active agent in inflammatory and autoimmune diseases.

In one embodiment, the toxin is a diphtheria toxin, or in yet another embodiment a *Pseudomonas* exotoxin.

In one embodiment, the vaccines used to immunize the animals described herein prior to isolating mRNA encoding IgG antibodies from a splenocyte or lymphocytes, provide an opportunity to immunize against disease states that are not caused by traditional pathogens, such as genetic diseases and cancer. In one embodiment, in a genetic cancer vaccine, antigens to a specific type of tumor cell are isolated and then introduced into the vaccine.

Vaccination refers in one embodiment, to a means of inducing the body's own immune system to seek out and destroy an infecting agent before it causes a pathological response. In another embodiment, vaccines are either live, but attenuated, infectious agents (virus or bacteria) or a killed form of the agent. A vaccine consisting of a live bacteria or virus must be non-pathogenic. Typically, a bacterial or viral culture is attenuated (weakened) by physical or chemical treatment. Although the agent is nonvirulent, it can still elicit an immune response in a subject treated with the vaccine. An immune response is elicited in another embodiment, by antigens, either specific macromolecules, or an infectious agent. These antigens are generally either proteins, polysaccharides, lipids, or glycolipids, which are recognized as "foreign" by lymphocytes known as B cells and T cells. Exposure of both types of lymphocytes to an antigen elicits a rapid cell division and differentiation response, resulting in the formation of clones of the exposed lymphocytes. B cells produce plasma cells, which in turn, produce antibodies (Ab), which selectively bind to the antigens present on the infectious agent, thus neutralizing or inactivating the pathogen (humoral immunity). In another embodiment, B cell response requires the assistance of CD4 helper T cells.

Accordingly and in one embodiment, provided herein, is a method for preparing nucleotides of single-chain variable fragments (scFv) encoding an antigen-specific binding domain, comprising the steps of: isolating RNA encoding an antibody from splenocytes or lymphocytes of a non-immunized canine, or a canine, with a specific antigen; generating cDNAs from the isolated RNA; amplifying the variable regions of the antibody's heavy chain and the lambda and kappa light chains using PCR with a set of primers designed for the variable regions, wherein primers for the VH chains are represented by any one of SEQ ID No. 1-8, primers for the VL lambda chains are represented by any one of SEQ ID No. 9-23 and primers for the VL kappa chains are represented by any one of SEQ ID No. 24-31 or their analogues or combination, wherein the primers are designed to incorporate secondary primer binding sites into the 5' end of the $V_L$ amplicons and the 3' end of the $V_H$ amplicons and a flexible linker into the 3' end of the $V_L$ amplicons and the 5' end of the $V_H$ amplicons; and using the flexible linker, randomly linking the $V_H$ and $V_L$ amplicons.

In one embodiment, the nucleotides of single-chain variable fragments (scFv) encoding an antigen-specific binding domain generated using the methods described herein, are members of the libraries described herein. Accordingly and in one embodiment, provided herein is a library of nucleic acids encoding a plurality of antigen binding polypeptides, the library made by a method comprising the steps of: isolating mRNA encoding an antibody from a splenocyte or lymphocytes of a non-immunized canine or a canine immunized with a specific antigen; generating cDNAs from the isolated mRNA; amplifying the variable regions of the antibody's heavy chain and the lambda and kappa light chains using PCR with a set of primers designed for the variable regions, wherein primers for the VH chains are represented by any one of SEQ ID No. 1-8, primers for the VL lambda chains are represented by any one of SEQ ID No. 9-23 and primers for the VL kappa chains are represented by any one of SEQ ID No. 24-31 or their analogues or combination, wherein the primers are designed to incorporate secondary primer binding sites into the 5' end of the $V_L$ amplicons and the 3' end of the $V_H$ amplicons and a flexible linker into the 3' end of the $V_L$ amplicons and the 5' end of the $V_H$ amplicons; and using the flexible linker, randomly linking the $V_H$ and $V_L$ amplicons; and repeating the step of randomly linking the flexible linker-comprising $V_H$ and $V_L$ amplicons; and forming a library of scFv chains, wherein a library member comprises a nucleic acid encoding scFv chain, and the scFv chain is displayed from the packaging vector.

Methods for modifying nucleic acids to achieve specific purposes are disclosed in the art, for example, in Sambrook et al. (1989). Moreover, the nucleic acid sequences of the invention can include one or more portions of nucleotide sequence that are non-coding for the protein of interest. The invention further provides DNA sequences which encode proteins similar to those encoded by sequences as described herein, but which differ in terms of their codon sequence due to the degeneracy of the genetic code or allelic variations (naturally-occurring base changes in the species population which may or may not result in an amino acid change), which may encode the proteins of the invention described herein, as well. Variations in the DNA sequences, which are caused by point mutations or by induced modifications (including insertion, deletion, and substitution) to enhance the activity, half-life or production of the polypeptides encoded thereby, are also encompassed in the invention.

The polypeptides of this invention can be produced by any synthetic or recombinant process such as is well known in the art. Polypeptides can further be modified to alter biophysical or biological properties by means of techniques known in the art. For example, the polypeptide can be modified to increase its stability against proteases, or to modify its lipophilicity, solubility, or binding affinity to its native receptor/target.

In one embodiment, a skilled artisan when armed with the primers provided herein, can generate scFvs by amplifying canine VH and VL (lambda and kappa) chains from splenocytes of a normal dog and splenocytes of a dog with a tumor, bacterial infection or viral infection as provided herein, and randomly combining the VH and VL chains using a second PCR reaction in order to arrive at the scFvs. In another embodiment, provided herein are randomly selected canine scFvs sequences to confirm that they consist of combined VH and VL (lambda and kappa) immunoglobulin chains. The nucleotide sequences of the VH and VL chains randomly selected from scFv libraries of a normal dog and a dog with hemangiosarcoma together with their amino acid translations are provided herein as set forth in SEQ ID NOs: X-Y.

In one embodiment, a scFv peptide is produced by recombinant means or methods. To facilitate the production of a recombinant peptide or fusion protein nucleic acid encoding same is preferably isolated or synthesized. In this respect, the nucleotide sequence of a nucleic acid encoding the peptide is identified using a method known in the art and/or described herein, e.g., reverse translation. Such a nucleic acid is then produced by synthetic means or recombinant means. In another embodiment, the nucleic acid is isolated using a known method, such as, for example, amplification (e.g., using PCR or splicing by overlap extension). Methods for such isolation will be apparent to the ordinary skilled artisan and/or described in Ausubel et al (In: Current Protocols in Molecular Biology. Wiley Interscience, ISBN 047 150338, 1987), Sambrook et al (In: Molecular Cloning: Molecular Cloning: A Laboratory Manual, Cold Spring Harbor Laboratories, New York, Third Edition 2001). For example, nucleic acid encoding a peptide is isolated using polymerase chain reaction (PCR). Methods of PCR are known in the art and described, for example, in Dieffenbach (ed) and Dveksler (ed) (In: PCR Primer: A Laboratory Manual, Cold Spring Harbour Laboratories, N.Y., 1995). Generally, for PCR two non-complementary, nucleic acid primer molecules comprising at least about 20 nucleotides in length, and in another embodiment at least about 25 nucleotides in length are hybridized to different strands of a nucleic acid template molecule, and specific nucleic acid molecule copies of the template are amplified enzymatically. In one embodiment, the primers provided herein hybridize to nucleic acid within nucleic acid sequences that encoding the peptide, thereby facilitating amplification of the nucleic acid that encodes the subunit, such as a $V_L$ k subunit. Following amplification, the amplified nucleic acid is isolated using a method known in the art and, in certain embodiments, and cloned into a suitable vector.

In another embodiment, the methods provided herein enable a skilled artisan to generate an scFv library and screen the library against tumor, bacterial or viral antigens or any other protein target of interest (such as but not limited to cytokines, chemokines or spermatozoon) to which the sequences of VH and VL chains generated by the methods provided herein specifically bind to, thus allowing the skilled artisan to subsequently isolate a specific scFv and use it diagnostically, therapeutically and prophylcatically in vivo. In another embodiment, the isolated scFv, antibody or fragment thereof comprises a VH and VL region provided herein or homologous regions thereof, in any combination.

In one embodiment, the splenocyte or lymphocyte used in the methods described herein for isolating mRNA encoding IgG antibodies is from dogs that have been actively immunized by vaccination or by natural exposure to antigen. In one embodiment, the term "immunized" refers to any level of protection which is of some benefit in a population of animals, whether in the form of decreased mortality, decreased lesion scores, decreased size and number of primary tumors, decreased invasiveness of metastatic cells and the like. In another embodiment, the animal that is actively immunized is any member of the canine, families.

In one embodiment, the methods described herein for generating the libraries provided, further comprise the step of cloning the single chain variable fragment into a DNA construct. In one embodiment, the term "DNA construct" refers to a specific arrangement of genetic elements in a DNA molecule. In another embodiment, the term "DNA construct" refers to a synthetic DNA structure that can be transcribed in target cells. The construct can comprise a linear nucleic acid such as a purified DNA, or preferably, DNA incorporated in a plasmid vector. The DNA can also be incorporated in a viral or bacterial vector, preferably an attenuated viral or bacterial vector that is non-pathogenic and suitable as a therapeutic composition. In addition to the cloned scFv's described herein, the invention also provides DNA constructs comprising scFv polypeptides from other species, mutant mammals expressing mutated VH or VL or both. In another embodiment, the constructs further comprise a promoter or other regulatory element such as lox-P, and may additionally comprise a reporter or marker element such as enhanced green fluorescent protein (EGFP). In one embodiment, the DNA constructs can be engineered to be operably linked to appropriate expression elements such as promoters or enhancers to allow expression of a genetic element in the DNA construct in an appropriate cell or tissue, for example, an epithelial cell-specific promoter or a lung epithelial cell-specific promoter. The DNA constructs described herein may be incorporated into vectors for propagation, or transfection into appropriate cells to generate TAA-specific scFVs. The DNA constructs may also be incorporated into vectors for transfection into appropriate cells for the development of cell cultures. One skilled in the art can select a vector based on desired properties, for example, for production of a vector in a particular cell such as a mammalian cell or a bacterial cell.

In one embodiment, provided herein is a system to generate combinatorial antibody libraries from canine cDNA derived from sources described herein. In another embodiment, the systems and methods described herein are used to generate libraries from canine patients with hemangiosarcoma and panning these libraries against autologous and allogeneic low passage hemangiosarcoma cell lines thereby identifying TAA-specific scFvs that are, in another embodiment, used to target malignant endothelial cells in vivo, or in another embodiment osteosarcoma, or malignant melanoma, mammary carcinoma, or their combination in other discrete embodiments. In one embodiment, the systems and methods described herein are used to generate libraries from canine patients with bacterial or viral infections. In another embodiment, the systems and methods described herein are used to generate libraries from canine patients with parvo virus. In one embodiment the use of these libraries is effective in the development of revolutionary cancer immunotherapeutics. In another embodiment, the ability to generate canine scFv from the immune repertoire of dogs, or in certain embodiments from non-immunized canine or a canine, immunized with a specific antigen is employed for a wide range of diagnostic and therapeutic purposes including but not limited to diagnostic imaging, bacterial targeting, virus neutralization, cytokine neutralization, targeting of intracellular signaling pathways and alloantigen recognition.

In one embodiment, provided herein is a method of preventing formation of a tumor in a subject, comprising the step of administering an effective amount of a scFv antibody produced by the methods provided herein. In another embodiment, provided herein is a method of treating, preventing, or ameliorating the symptoms associated with a tumor in a subject comprising the step of administering to said subject an effective amount of a single chain fragment variable antibody, wherein in another embodiment, the single chain fragment variable antibody is isolated from the nucleic acid library encoding the scFv antibodies provided herein. In another embodiment, provided herein is a method of treating, preventing, or ameliorating the symptoms associated with a viral infection in a subject comprising the step of administering to said subject an effective amount of a single chain fragment variable antibody, wherein in another embodiment, the single chain fragment variable antibody is isolated from the nucleic acid library encoding the scFv antibodies provided herein. In another embodiment, provided herein is a method of treating, preventing, or ameliorating the symptoms associated with a bacterial infection in a subject comprising the step of administering to said subject an effective amount of a single chain fragment variable antibody, wherein in another embodiment, the single chain fragment variable antibody is isolated from the nucleic acid library encoding the scFv antibodies provided herein. In another embodiment, provided herein is a method of treating, preventing, or ameliorating the symptoms associated with autoimmunity (or an autoimmune disorder) and inflammation in a subject comprising the step of administering to said subject an effective amount of a single chain fragment variable antibody, wherein and in another embodiment, the single chain fragment variable antibody is isolated from the nucleic acid library encoding the scFv antibodies provided herein.

In one embodiment, the "autoimmune disorder" or autoimmunity include but is not limited to the following conditions: autoimmune hemolytic anemia, myasthenia gravis, autoimmune hypothyroidism, immune-mediated thrombocytopenia, idiopathic thrombocytopenic purpura, autoimmune diseases of the skin, systemic lupus erythematosis, polyarthritis, pemphigus vulgaris, addison's disease, canine inflammatory bowel disease, and rheumatoid arthritis.

In one embodiment, provided herein is a method of dianosing the presence of a tumor or an abnormal tissue growth, where the method comprises in another embodiment, the step of contacting a tissue sample with a single chain fragment variable antibody isolated from the nucleic acid library encoding a scFv that binds to a target surface antigen of said tumor or abnormal tissue growth. In another embodiment, the method of diagnosing the presence of a tumor or an abnormal tissue growth comprises locating said bound antibody in said tissue sample. In another embodiment, the dianosing the presence of a tumor or an abnormal tissue growth comprises determining whether said location of said bound antibody indicates the presence of a tumor or abnormal tissue growth in said tissue sample. In another embodiment, the tumor or abnormal tissue growth includes but is not limited to hemangiosarcoma, osteosarcoma, malignant melanoma and mammary carcinoma, or their metastases.

In one embodiment, provided herein is a method of diagnosing a viral infection in a subject, comprising the step of obtaining a biological sample from the subject. In another embodiment, the method of diagnosing a viral infection in a subject comprises the step of contacting the biological sample with a single chain fragment variable antibody isolated from the nucleic acid library encoding the scFv provided herein. In another embodiment, the method of diagnosing a viral infection in a subject comprises the step of analyzing the level of a viral antigen in the biological sample. In another embodiment, the method of diagnosing a viral infection in a subject comprises the step of and comparing the expression of the biological sample to a standard, whereby and in another embodiment, if the standard is taken from a healthy subject or pool of subjects and the level of the viral antigen is different than the standard by a predetermined threshold, the subject has, or is at risk of developing a disease associated with the viral infection. Otherwise and in another embodiment, if the standard is taken from a subject or pool of subjects correctly diagnosed with a viral infection and the level of the viral antigen is different than the standard by more than a predetermined threshold, the subject does not have or is at low risk of developing a disease associated with the viral infection.

In one embodiment, provided herein is a method of dianosing a bacterial infection in a subject, comprising the step of obtaining a biological sample from the subject. In another embodiment, the method of dianosing a bacterial infection in a subject comprises the step of contacting the biological sample with a single chain fragment variable antibody isolated from the nucleic acid library encoding the scFv provided herein. In another embodiment, the method of dianosing a bacterial infection in a subject comprises the step of analyzing the level of a bacterial antigen in the biological sample. In another embodiment, the method of dianosing a bacterial infection in a subject comprises the step of and comparing the expression of the biological sample to a standard, whereby and in another embodiment, if the standard is taken from a healthy subject or pool of subjects and the level of the bacterial antigen is different than the standard by a predetermined threshold, the subject has, or is at risk of developing a disease associated with the bacterial infection. Otherwise and in another embodiment, if the standard is taken from a subject or pool of subjects correctly diagnosed with a bacterial infection and the level of the bacterial antigen is different than the standard by more than a predetermined threshold, the subject does not have or is at low risk of developing a disease associated with the bacterial infection. It is to be understood by a skilled artisan that other methods known in the art, specifically within the field of antibody-based imaging, and antibody-based detection assays that include but are not limited to the use of radio-labeled antibodies or antibodies conjugated to a fluorescent agent or ELISA-based assays are contemplated for use with the methods provided herein.

In one embodiment, a "predetermined threshold" refers to a level, range, or measurement empirically determined. In another embodiment, the threshold depends upon the particular population of subjects. In yet another embodiment, an apparently healthy population will have a different "normal" range or level of the standard than will a population of subjects which have had a prior infection or other condition.

In one embodiment, provided herein is a method of delivering a biologically active agent to cells displaying a target antigen, comprising contacting said cells with a single chain fragment variable antibody isolated from the nucleic acid library encoding the scFv provided herein, wherein in another embodiment, said single chain fragment variable antibody operably linked to said agent.

In one embodiment, provided herein is a method of delivering a biologically active agent and a single chain fragment variable antibody isolated from the nucleic acid library encoding the scFv provided herein, whereby the biologically active agent and the single chain fragment variable antibody are delivered concomitantly but individually.

In one embodiment, the scFvs provided herein are "biologically active", meaning the scFvs are able to exert the biological action or an enhanced action of their corresponding parental antibodies even after modification, in particular in binding to the target antigen, inhibiting binding of ligands to receptors, further in terms of modulation, in particular inhibition of antigen-mediated signal transduction and prophylaxis or therapy of antigen-mediated diseases. The term "biologically active", when used in reference to any of the biologically active agents described herein also refers to the agent's ability to modulate the immune response in a manner that can lead to a preventive, diagnostic, or therapeutic effect as will be understood by a skilled artisan. In another embodiment, the biologically active agent provided herein is a radio-isotope, a toxin, a cytokine, a chemokine or any other molecule that can modulate the immune response in a manner that can lead to a preventive, diagnostic, or therapeutic effect as will be understood by a skilled artisan.

In one embodiment, provided herein is a method of treating a bacterial infection, a viral infection, autoimmunity, or a tumor, comprising the steps of any one of claims 42-43. In another embodiment, the method of treating autoimmunity is accomplished through methods known in the art such as but not limited to cytokine neutralization.

In one embodiment, the libraries described herein, are used in the methods provided. Accordingly, in one embodiment, provided herein is a method of identifying tumor specific single chain fragment variable antibody fragments, comprising the step of panning the libraries described herein against autologous, or allogeneic tumor cells, or their combination; using the display package, identifying tumor specific scFv chains; and isolating the identified tumor specific scFv chains. In one embodiment, the method of identifying tumor specific single chain fragment variable antibody fragments described herein, further comprise the step of increasing affinity between the isolated tumor specific scFv chains and the antigen. In one embodiment, increasing affinity between the isolated tumor specific scFv chains and the antigen is performed by site-specific mutagenesis.

In one embodiment, molecular techniques are used to recapitulate the immune repertoire of canine patients with diseases such as but not limited to, hemangiosarcoma (HSA), osteosarcoma, or parvo virus infection and screen the resulting combinatorial antibody libraries generated using the methods described herein, for single chain fragments that specifically target antigens or cells expressing antigens that characterize these diseases, for example, malignant endothelial cells. In another embodiment, these fragments are isolated, amplified and screened in vitro for their ability to specifically recognize and kill autologous and allogeneic canine HSA cell lines. In another embodiment, the methods described herein are used to develop the first canine-derived, tumor-specific targeting approach for the treatment of HSA in dogs and in another embodiment, provide proof of principle for this approach that can then be employed to generate targeting reagents for many different tumor types.

In one embodiment, such antibody libraries are screened using one or more cell-based or in vitro assays. For such assays, antibodies, purified or unpurified, are typically added exogenously such that cells are exposed to individual variants or groups of variants belonging to a library. These assays are typically, but not always, based on the biology of the ability of the antibody to bind to antigen and mediate some biochemical event, for example effector functions like cellular lysis, phagocytosis, ligand/receptor binding inhibition, inhibition of growth and/or proliferation, apoptosis, etc. Such assays often involve monitoring the response of cells to antibody, for example cell survival, cell death, cellular phagocytosis, cell lysis, change in cellular morphology, or transcriptional activation such as cellular expression of a natural gene or reporter gene. For some assays additional cells or components, that is in addition to the target cells, may need to be added, for example serum complement, or effector cells such as peripheral blood monocytes (PBMCs), NK cells, macrophages, and the like. Such additional cells may be from any organism, e.g., canine, mice, rats, rabbits, monkeys, etc. Crosslinked or monomeric antibodies may cause apoptosis of certain cell lines expressing the antibody's target antigen, or they may mediate attack on target cells by immune cells which have been added to the assay. Methods for monitoring cell death or viability are known in the art, and include the use of dyes, fluorophores, immunochemical, cytochemical, and radioactive reagents. For example, caspase assays or annexin-flourconjugates may enable apoptosis to be measured, and uptake or release of radioactive substrates (e.g. Chromium-51 release assays) or the metabolic reduction of fluorescent dyes such as alamar blue may enable cell growth, proliferation, or activation to be monitored. In one embodiment, the DELFIA® EuTDA-based cytotoxicity assay (Perkin Elmer, Mass.) is used. Alternatively, dead or damaged target cells may be monitored by measuring the release of one or more natural intracellular proteins, for example lactate dehydrogenase. Transcriptional activation may also serve as a method for assaying function in cell-based assays. In this case, response may be monitored by assaying for natural genes or proteins which may be upregulated or down-regulated, for example the release of certain interleukins may be measured, or alternatively readout may be via a luciferase or GFP-reporter construct. Cell-based assays may also involve the measure of morphological changes of cells as a response to the presence of an antibody. Cell types for such assays may be prokaryotic or eukaryotic, and a variety of cell lines that are known in the art may be employed. Alternatively, cell-based screens are performed using cells that have been transformed or transfected with nucleic acids encoding the antibodies.

In some embodiments, the screening of populations of polypeptides such as the altered variable region populations produced by the methods of the invention, involve immobilization of the populations of altered variable regions to filters or other solid substrate. This is particularly advantageous because large numbers of different species can be efficiently screened for antigen binding. Such filter lifts will allow for the identification of altered variable regions that exhibit substantially the same or greater binding affinity. Alternatively, if the populations of altered variable regions are expressed on the surface of a cell or bacteriophage, for example, panning on immobilized antigen can be used to efficiently screen for the relative binding affinity of species within the population.

Another affinity method for screening populations of altered variable regions polypeptides is a capture lift assay that is useful for identifying a binding molecule having selective affinity for a ligand (Watkins et. al., (1997)). This method employs the selective immobilization of altered variable regions to a solid support and then screening of the selectively immobilized altered variable regions for selective binding interactions against the cognate antigen or binding partner. Selective immobilization functions to increase the sensitivity of the binding interaction being measured since initial immobilization of a population of altered variable regions onto a solid support reduces non-specific binding interactions with irrelevant molecules or contaminants which can be present in the reaction.

Another method for screening populations or for measuring the affinity of individual altered variable region polypeptides is through surface plasmon resonance (SPR). This method is based on the phenomenon which occurs when surface plasmon waves are excited at a metal/liquid interface. Light is directed at, and reflected from, the side of the surface not in contact with sample, and SPR causes a reduction in the reflected light intensity at a specific combination of angle and wavelength. Biomolecular binding events cause changes in the refractive index at the surface layer, which are detected as changes in the SPR signal. The binding event can be either binding association or disassociation between a receptor-ligand pair. The changes in refractive index can be measured essentially instantaneously and therefore allows for determination of the individual components of an affinity constant. More specifically, the method enables accurate measurements of association rates (kon) and disassociation rates (koff). Methods for measuring the affinity, including association and disassociation rates using surface plasmon resonance are well known in the arts and can be found described in, for example, Jonsson and Malmquist, Advances in Biosnsors, 2:291-336 (1992) and Wu et al. Proc. Natl. Acad. Sci. USA, 95:6037-6042 (1998). Moreover, one apparatus well known in the art for measuring binding interactions is a BIAcore 2000 instrument which is commercially available through Pharmacia Biosensor, (Uppsala, Sweden).

In one embodiment, the methods described herein are used to remove antibodies which do not exhibit the desired affinity from the library, to arrive at the "optimized" libraries of the invention, or assemble the antibodies based only on the desired characteristics using molecular biology techniques available in the art and as described herein.

In one embodiment, a final antibody, or antibody fragment such as an scFv is generated by the process described herein and is then affinity-purified or isolated after expression. Proteins may be isolated or affinity-purified in a variety of ways known to those skilled in the art. Standard purification methods include chromatographic techniques, electrophoretic, immunological, precipitation, dialysis, filtration, concentration, and chromatofocusing techniques. As is well known in the art, a variety of natural proteins bind antibodies, for example bacterial proteins A, G, and L, and these proteins may find use in the present invention for purification. Purification can often be enabled by a particular fusion partner. For example, proteins may be purified using glutathione resin if a GST fusion is employed, $Ni^{+2}$ affinity chromatography if a His-tag is employed or immobilized anti-flag antibody if a flag-tag is used. For general guidance in suitable purification techniques, see Protein Purification Principles and Practice, $3^{rd}$ Ed., Scopes, Springer-Verlag, N.Y., 1994.

The biophysical properties of antibodies, for example stability and solubility, may be screened using a variety of methods known in the art. Protein stability may be determined by measuring the thermodynamic equilibrium between folded and unfolded states. For example, antibodies of the present invention may be unfolded using chemical denaturant, heat, or pH, and this transition may be monitored using methods including but not limited to circular dichroism spectroscopy, fluorescence spectroscopy, absorbance spectroscopy, NMR spectroscopy, calorimetry, and proteolysis. As will be appreciated by those skilled in the art, the kinetic parameters of the folding and unfolding transitions may also be monitored using these and other techniques. The solubility and overall structural integrity of an antibody may be quantitatively or qualitatively determined using a wide range of methods that are known in the art. Methods which may find use in the present invention for characterizing the biophysical properties of antibodies and antibody fragments include gel electrophoresis, isoelectric focusing, capillary electrophoresis, chromatography such as size exclusion chromatography, ion-exchange chromatography, and reversed-phase high performance liquid chromatography, peptide mapping, oligosaccharide mapping, mass spectrometry, ultraviolet absorbance spectroscopy, fluorescence spectroscopy, circular dichroism spectroscopy, isothermal titration calorimetry, differential scanning calorimetry, analytical ultra-centrifugation, dynamic light scattering, proteolysis, and cross-linking, turbidity measurement, filter retardation assays, immunological assays, fluorescent dye binding assays, protein-staining assays, microscopy, and detection of aggregates via ELISA or other binding assay. Structural analysis employing X-ray crystallographic techniques and NMR spectroscopy may also find use. In one embodiment, stability and/or solubility may be measured by determining the amount of protein solution after some defined period of time. In this assay, the protein may or may not be exposed to some extreme condition, for example elevated temperature, low pH, or the presence of denaturant. Because function typically requires a stable, soluble, and/or well-folded/structured protein, the aforementioned functional and binding assays also provide ways to perform such a measurement. For example, a solution comprising an antibody could be assayed for its ability to bind target antigen, then exposed to elevated temperature for one or more defined periods of time, then assayed for antigen binding again. Because unfolded and aggregated protein is not expected to be capable of binding antigen, the amount of activity remaining provides a measure of the antibody's stability and solubility.

The antibodies of the present invention may find use in a wide range of products. In one embodiment the antibody of the invention is a therapeutic, a diagnostic, or a research reagent. In one embodiment, an antibody of the invention is a therapeutic. In some embodiments, the antibody of the present invention may be used for agricultural or industrial uses. An antibody of the present invention may find use in an antibody composition that is monoclonal or polyclonal. The antibodies of the present invention may be agonists, antagonists, neutralizing, inhibitory, or stimulatory. In one embodiment, the antibodies of the present invention are used to kill target cells that bear the target antigen, for example cancer cells. In an alternate embodiment, the antibodies of the present invention are used to block, antagonize, or agonize the target antigen. In an alternate embodiment, the antibodies of the present invention are used to block, antagonize, or agonize the target antigen and kill the target cells that bear the target antigen.

The antibodies of the invention, including subsequences, modified forms, multimers and nucleic acids encoding them, can be incorporated into pharmaceutical compositions. Such pharmaceutical compositions are useful for administration to a subject in vivo or ex vivo, and for providing therapy for a physiological disorder or condition treatable with an antibody as provided herein.

In one embodiment the compositions of this invention comprise a polypeptide of this invention, alone or in some embodiments, in combination with a second pharmaceutically active or therapeutic agent. In one embodiment, the term "pharmaceutically active agent" refers to any medicament which satisfies the indicated purpose. In some embodiments, the term "agent" of this invention is a decongestant, antibiotic, bronchodilator, anti-inflammatory steroid, leukotriene antagonist or histamine receptor antagonist, and the like.

In one embodiment, the route of administration may be parenteral, or a combination thereof. In another embodiment, the route may be intra-ocular, conjunctival, topical, transdermal, intradermal, subcutaneous, intraperitoneal, intravenous, intra-arterial, vaginal, rectal, intratumoral, transmucosal, intramuscular, intravascular, intraventricular, intracranial, inhalation (aerosol), nasal aspiration (spray), intranasal (drops), sublingual, oral, aerosol or suppository or a combination thereof. In one embodiment, the dosage regimen will be determined by skilled clinicians, based on factors such as exact nature of the condition being treated, the severity of the condition, the age and general physical condition of the patient, body weight, and response of the individual patient.

For intranasal administration or application by inhalation, solutions or suspensions of the compounds mixed and aerosolized or nebulized in the presence of the appropriate carrier suitable. Such an aerosol may comprise any agent described herein.

For parenteral application, particularly suitable are injectable, sterile solutions, preferably oily or aqueous solutions, as well as suspensions, emulsions, or implants, including suppositories and enemas. Ampoules are convenient unit dosages. Such a suppository may comprise any agent described herein.

Sustained or directed release compositions can be formulated, e.g., liposomes or those wherein the active compound is protected with differentially degradable coatings, e.g., by microencapsulation, multiple coatings, etc. Such compositions may be formulated for immediate or slow release. It is also possible to freeze-dry the new compounds and use the lyophilisates obtained, for example, for the preparation of products for injection.

For liquid formulations, pharmaceutically acceptable carriers may be aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of petroleum, animal, vegetable, or synthetic origin, for example, peanut oil, soybean oil, mineral oil, olive oil, sunflower oil, and fish-liver oil.

In one embodiment, a composition of or used in the methods of this invention may be administered alone or within a composition. In another embodiment, compositions of this invention admixted with conventional excipients, i.e., pharmaceutically acceptable organic or inorganic carrier substances suitable for parenteral, enteral (e.g., oral) or topical application which do not deleteriously react with the active compounds may be used. In one embodiment, suitable pharmaceutically acceptable carriers include but are not limited to water, salt solutions, alcohols, gum arabic, vegetable oils, benzyl alcohols, polyethylene glycols, gelatine, carbohydrates such as lactose, amylose or starch, magnesium stearate, talc, silicic acid, viscous paraffin, white paraffin, glycerol, alginates, hyaluronic acid, collagen, perfume oil, fatty acid monoglycerides and diglycerides, pentaerythritol fatty acid esters, hydroxy methylcellulose, polyvinyl pyrrolidone, etc. In another embodiment, the pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds. In another embodiment, they can also be combined where desired with other active agents, e.g., vitamins.

Pharmaceutical compositions include "pharmaceutically acceptable" and "physiologically acceptable" carriers, diluents or excipients. In one embodiment, the terms "pharmaceutically acceptable" and "physiologically acceptable" refers to any formulation which is safe, and provides the appropriate delivery for the desired route of administration of an effective amount of at least one compound for use in the present invention. This term refers to the use of buffered formulations as well, wherein the pH is maintained at a particular desired value, ranging from pH 4.0 to pH 9.0, in accordance with the stability of the compounds and route of administration. The terms include solvents (aqueous or non-aqueous), solutions, emulsions, dispersion media, coatings, isotonic and absorption promoting or delaying agents, compatible with pharmaceutical administration. Such formulations can be contained in a liquid; emulsion, suspension, syrup or elixir, or solid form; tablet (coated or uncoated), capsule (hard or soft), powder, granule, crystal, or microbead. Supplementary active compounds (e.g., preservatives, antibacterial, antiviral and antifungal agents) can also be incorporated into the compositions.

Pharmaceutical compositions can be formulated to be compatible with a particular local or systemic route of administration. Thus, pharmaceutical compositions include carriers, diluents, or excipients suitable for administration by particular routes. Specific non-limiting examples of routes of administration for compositions of the invention are inhalation or intranasal delivery. Additional routes include parenteral, e.g., intravenous, intradermal, subcutaneous, oral, transdermal (topical), transmucosal, and rectal administration.

Solutions or suspensions used for parenteral, intradermal, or subcutaneous application can include: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide.

The term "operably linked" or "operably inserted" refers in one embodiment to a state where the regulatory sequences necessary for expression of the coding sequence are placed in a nucleic acid molecule in the appropriate positions relative to the coding sequence so as to enable expression of the coding sequence. This same definition is sometimes applied to the arrangement of other transcription control elements (e.g. enhancers) in an expression vector.

In one embodiment, the term "treatment" in the compositions and methods provided herein refers to therapeutic treatment. In another embodiment it refers to prophylactic, or suppressive measures for a disease or disorder. Thus, for example, successful administration of an isolated scFv provided herein prior to onset of the disease results in treatment of the disease. "Treatment" also encompasses administration of an isolated scFv polypeptide after the appearance of the disease in order to eradicate the disease. Successful administration of an agent, such as the scFv polypeptide provided herein, after onset and after clinical symptoms have developed, with possible abatement of clinical symptoms and perhaps amelioration of the disease, comprises treatment of the disease. In another embodiment, a skilled artisan would understand that treatment does not necessarily result in the complete absence or removal of symptoms. Treatment also embraces palliative effects: that is, those that reduce the likelihood of a subsequent medical condition. In another embodiment, those "in need of treatment" include animals already having the disease or disorder, as well as those prone to having the disease or disorder, including those in which the disease or disorder is to be prevented. In another embodiment, a subject or animal is successfully "treated" for a cancer if, after receiving a therapeutic amount of an modified molecule provided herein, the subject shows observable and/or measurable reduction in or absence of one or more of the following: reduction in the number of cancer cells or absence of the cancer cells; reduction in the tumor size; inhibition (i.e., slow to some extent and preferably stop) of cancer cell infiltration into peripheral organs including the spread of cancer into soft tissue and bone; inhibition (i.e., slow to some extent and preferably stop) of tumor metastasis; inhibition, to some extent, of tumor growth; and/or relief to some extent, one or more of the symptoms associated with the specific cancer; reduced morbidity and mortality, and improvement in quality of life.

In some embodiments, percentage sequence "identity" refers to a number of identical residues in a pairwise alignment divided by the total number of aligned residues, including the gaps. In other embodiments, percentage sequence "similarity" refers to a number of similar residues in a pairwise alignment divided by the total number of aligned residues, including the gaps. In some embodiments, these residues are ones that have side-chains that share similar biochemical properties, for example hydrophobicity, hydrophilicity, and the like. In other embodiments identical residues are similar but the inverse is not true, therefore identity percentage is smaller than the similarity percentage for sequence pairwise alignments.

In one embodiment, the term "functional fragment" refers to a fragment that maintains a certain degree of biological activity as compared to the wild type despite it being a modified version of the native or wild type antibody or polypeptide. This degree of activity could range from moderate to high as compared to the wild type, where the "activity" refers to its natural biophysical or biochemical characteristics, e.g. binding ability, affinity, half-life, etc.

The term "about" as used herein means in quantitative terms plus or minus 5%, or in another embodiment plus or minus 10%, or in another embodiment plus or minus 15%, or in another embodiment plus or minus 20%.

The term "subject" refers in one embodiment to a mammal including a canine in need of therapy for, or susceptible to, a condition or its sequalae. The subject may include dogs, cats, pigs, cows, sheep, goats, horses, rats, and mice and humans. The term "subject" does not exclude an individual that is normal in all respects.

The following examples are presented in order to more fully illustrate the preferred embodiments of the invention. They should in no way be construed, however, as limiting the broad scope of the invention.

EXAMPLES

Example 1

Design of Degenerate PCR Primers to Generate Single Chain Fragment Variable Antibodies for Targeted Therapy in the Dog A set of degenerate primers that are intended to amplify all known VH and VL (lambda and kappa) chains were designed based on predicted nucleotide sequences and back translated protein sequences. The primers consist of 7 VH forward primers and a single reverse VH primer, located in the constant IgG region such that all amplified VH chains are from the antigen-experienced repertoire (ie IgG). Also designed, were 13 VL lambda forward primers and 2 VL lambda reverse primers that amplify the canine VL lambda chain repertoire and 4 VL kappa forward and 4 VL kappa reverse primers that amplify the canine VL kappa chain repertoire. These primers were shown to reliably amplify VH and VL IgG chains from canine lymphocyte cDNA and that generated amplicons can be "sewn" together using a second PCR reaction to generate scFv constructs. These constructs have been cloned into a phagemid vector and expressed on the surface of bacteriophage where they can now be screened for binding to particular antigens of interest.

57 nucleotide sequences with high sequence homology to FR1 of the reported canine IgG-A nucleotide sequence (AF354264) were identified. These FR1 sequences were aligned and 25 different FR1 sequences were identified within the 57 original sequences. The 25 sequences were assembled into 6 groups, based on sequence homology and six degenerate primers were designed (Canine Single Chain Variable Heavy 1-6-Forward (CSCVH1-6F, SEQ ID NO. 1-6 respectively)) that collectively would be capable of annealing to all 25 unique VH FR1 sequences. In addition, to ensure that all known sequences of immunoglobulin VH regions would be amplified we used the protein sequence of the canine IgG-A to BLAST search the NIH GenBank protein database to identify canine FR1 protein sequences that were not encoded by the previously identified nucleotide sequences. 64 protein sequences were identified that encompassed 18 different FR1 protein sequences (9 amino acids in length) that were not encoded for by the nucleotide sequences previously identified. These sequences were back translated and a single degenerate primer was designed (CSCVH7-F) that would amplify these sequences. It was opted to specifically amplify the "immune" repertoire of canine immunoglobulins and so designed a single non-degenerate VH reverse primer in the IgG constant region rather than in FR4 as originally planned. PCR using CSCG1234 together with CSCVH1-6F consistently results in production of 450 bp amplicons that are consistent with the size of human VH immunoglobulin fragments. However, CSCG1234 together with CSCVH7F only resulted in production of a 450 bp amplicon using splenic cDNA in 1 out of the 2 dogs analyzed. Two more dogs were analyzed, showing similar results, although use of CSCVH7F did not produce a visible amplicon in either of the additional dogs.

The sequences of the canine VH primers are as follows (italics denote previously described flexible linker sequence):

CSCVH1-F;
SEQ ID No. 1
5'-*GGTGGTTCCTCTAGATCTTCCTCCTCTGGTGGCGGTGGCTCGGGCGG*

*TGGTGGGGAG* GTV CAR CTG GTG SAR TCT-3',

CSCVH2-F;
SEQ ID No. 2
5'-*GGTGGTTCCTCTAGATCTTCCTCCTCTGGTGGCGGTGGCTCGGGCGG*

*TGGTGGGGAG* GTR MVD YTG GTG GAR TCT-3',

CSCVH3-F;
SEQ ID No. 3
5'-*GGTGGTTCCTCTAGATCTTCCTCCTCTGGTGGCGGTGGCTCGGGCGG*

*TGGTGGGGRSGTG* CAG CTG GTG GAG TCT-3',.

CSCVH4-F;
SEQ ID No. 4
5'-*GGTGGTTCCTCTAGATCTTCCTCCTCTGGTGGCGGTGGCTCGGGCGG*

*TGGTGGGGAG* GTR CAG CTG STG GAG WMT-3',.

CSCVH5-F;
SEQ ID No. 5
5'-*GGTGGTTCCTCTAGATCTTCCTCCTCTGGTGGCGGTGGCTCGGGCGG*

*TGGTGGGGAR* KWG CAR CTG GTG GAG YTT-3',.

CSCVH6-F;
SEQ ID No. 6
5'-*GGTGGTTCCTCTAGATCTTCCTCCTCTGGTGGCGGTGGCTCGGGCGG*

*TGGTGGGGAG* GGG CAG CTG GCG GAG TCT-3',.

CSCVH7-F;
SEQ ID No. 7
5'-*GGTGGTTCCTCTAGATCTTCCTCCTCTGGTGGCGGTGGCTCGGGCGG*

*TGGTGGGGAR* BTN MAR YTG GTN GAR WSN-3',

CSCG1234-B;
SEQ ID No. 8
5'-CCT GGC CGG CCT GGC CAC TAG AAC CGA GGG GGC

CGT GGT GGA-3',.

Design of VL (Lambda and Kappa) Primers.

8 Degenerate Primers and 1 Non-Degenerate Primer

A similar strategy was employed to design primers that would be capable of amplifying all known nucleotide sequences that encode for the lambda and kappa light chains of the canine immunoglobulin repertoire. For the canine lambda chains, the predicted *Canis familiaris* Ig lambda chain V-I (XM_845300), V-II (XM_543519), V-III (XM_844188) and V-IV (XM_844237) sequences were used in a BLAST search of the canine genome. Highly homologous sequences were grouped within each family and degenerate primers were designed to anneal to all sequences within each group. This resulted in the design of 8 degenerate primers and 1 non-degenerate primer (for the V-II sequence) (designated Canine Single Chain (CSC) CSCLam1a-dF SEQ ID No. 9-12 and CSCLam2-6F SEQ ID No. 13-17). Four protein sequences that were not encoded by the above nucleotide sequences were identified following a BLAST search of the canine database using the 9 amino acid QSVLTQPAS sequence (SEQ ID No. 32), which is highly conserved in FR1 of VL lambda chains across species. These protein sequences were back translated and four highly degenerate primers (CSCLam7-10F, SEQ ID No. 18-21) were designed based on back-translated VL lambda FR1 protein sequences (that would collectively anneal to all unique nucleotide sequences that encode these VL lambda FR1 proteins. Two degenerate reverse VL lambda primers were designed (CSCJLam1-B and CSCJLam2-B, SEQ ID No. 22 and 23, respectively) within the joining (J) region of the canine VL lambda sequence based on aligned nucleotide sequences identified using a BLAST search of the canine genome. In a similar way, to design forward primers that anneal to canine VL kappa sequences, the predicted *Canis familiaris* Ig kappa chain V-I (XM_849621), V-II (XM_844874), V-111 (XM_849629) and V-IV (XM_849668) sequences were used in a BLAST search of the canine genome. One non-degenerate primer (to anneal to the V-I sequence) (designated Canine Single Chain Kappa (CSCK) 1-F) (SEQ ID No. 24) and 3 degenerate primers to anneal to sequences within V-II and V-IV families (designated CSCK24-F) (SEQ No. 25), within VIII and VIV families (designated CSCK34-F) (SEQ No. 26) and within V-IV (designated CSCK4-F) (SEQ No. 27) were designed. Four degenerate reverse primers (Canine Single Chain Joining Kappa (CSCJK) I-4B) (SEQ No. 28-31) were designed in the joining region of kappa chains as identified by sequence alignment with the joining region of human VL kappa chains. Flexible linker sequences complementary to those in the VH forward primers were incorporated into the reverse VL (lambda and kappa) primers. The previously described RSC-F and RSC-B primers that anneal to conserved sequences introduced into the 5' and 3' end of the VH and VL amplicons were used to randomly combine VH and VL chains in a splicing by overlap extension PCR reaction to generate scFv libraries of canine origin.

The designed sequences of the canine VL lambda and kappa primers are as follows (italics denote previously described flexible linker or SOE primer binding sequences incorporated into the designed primers):

```
Canine VλPrimers, 5' Sense
CSCLam1a;
                                           SEQ ID No. 9
5'-GGG CCC AGG CGG CCG AGC TC GTG CTG AMT CMG CYR

SSY TCD-3',.

CSCLam1b;
                                           SEQ ID No. 10
5'-GGG CCC AGG CGG CCG AGC TC RYS CTG ACT CAR MMG

SCC TCM-3',.

CSCLam1c;
                                           SEQ ID No. 11
5'-GGG CCC AGG CGG CCG AGC TC GTS CTG ACT CAG CYD

VCC TCA-3',.

CSCLam1d;
                                           SEQ ID No. 12
5'-GGG CCC AGG CGG CCG AGC TC GYG YTG ACY CAR CYR

GCC TCM-3',.

CSCLam2;
                                           SEQ ID No. 13
5'-GGG CCC AGG CGG CCG AGC TC GCC CTG ACT CAA CCT

TCC TCG-3',.

CSCLam3;
                                           SEQ ID No. 14
5'-GGG CCC AGG CGG CCG AGC TC GTG CTG WCW CAG CYG

CCA TCM-3';.

CSCLam4;
                                           SEQ ID No. 15
5'-GGG CCC AGG CGG CCG AGC TC GTG CTG ACT CAG CCT

CCY TC-3',.

CSCLam5;
                                           SEQ ID No. 16
5'-GGG CCC AGG CGG CCG AGC TC GRG YTG ACT CAG CYR

CCW TC-3',.

CSCLam6;
                                           SEQ ID No. 17
5'-GGG CCC AGG CGG CCG AGC TC GGG YTG AAT CAG SCT

YCC TC-3',.

CSCLam7;
                                           SEQ ID No. 18
5'-GGG CCC AGG CGG CCG AGC TC GTR CTG ACY CAR CCK

CCK TCW-3',.

CSCLam8;
                                           SEQ ID No. 19
5'-GGG CCC AGG CGG CCG AGC TC GTR MGS AAY CAR CCK

CCK TCW-3',.

CSCLam9;
                                           SEQ ID No. 20
5'-GGG CCC AGG CGG CCG AGC TC CTG CTG ACY CAR CCK

GCY TCW-3',.

CSCLam10;
                                           SEQ ID No. 21
5'-GGG CCC AGG CGG CCG AGC TC GTR CTG AAY CAR CCK

CCK TCW-3',.

VλPrimers, 3' Reverse plus linker
CSCJLam1;
                                           SEQ ID No. 22
5'-GGA AGA TCT AGA GGA ACC ACC GCC ACC GAG GAC GGT

CAG STG GGT SCC-3',.

CSCJLam2;
                                           SEQ ID No. 23
5'-GGA AGA TCT AGA GGA ACC ACC GCC ACC WAG GAC GGT

SAG YTS GRT TCC-3',.
```

-continued

```
VκPrimers, 5' Sense
CSCK1-F;
                                    SEQ ID No. 24
5'-GGG CCC AGG CGG CCG AGC TC CAG ATG ACC CAG TCC
CCA A-3',.

CSCK24-F;
                                    SEQ ID No. 25
5'-GGG CCC AGG CGG CCG AGC TC GTS ATG AYR CAG ACY
CCA C-3',.

CSCK34-F;
                                    SEQ ID No. 26
5'-GGG CCC AGG CGG CCG AGC TC GTG ATG ACM CAG TCT
CCA G-3',.

CSCK4-F;
                                    SEQ ID No. 27
5'-GGG CCC AGG CGG CCG AGC TC AYS MTG ACY CAG TKY
CCA G-3';.

VκPrimers, 3' Reverse plus linker
CSCJK1-B;
                                    SEQ ID No. 28
5'-GGA AGA TCT AGA GGA ACC ACC TTT GAG YTC CAC CTK
GGT WCC-3'.

CSCJK2-B;
                                    SEQ ID No. 29
5'-GGA AGA TCT AGA GGA ACC ACC TTT GAG CTC CTC CTT
GGT TCG-3',.

CSCJK3-B;
                                    SEQ ID No. 30
5'-GGA AGA TCT AGA GGA ACC ACC TTT GAG GTC CAC CTT
GGT TCC-3',.

CSCJK4-B;
                                    SEQ ID No. 31
5'-GGA AGA TCT AGA GGA ACC ACC TTT KAT CTC CAV CTT
GGT YCC-3',.
```

All VH and VL (lambda and kappa) primers other than (CSCLam1-F, 8-F and 10-F) and one of the forward and one of the reverse kappa chain primers (CSCK1-F and CSCJK4-B) gave PCR products in the expected 450 bp and 350 bp range respectively. Splenic cDNA from 2 more dogs were analyzed, showing that amplicons of 350 bp were produced from one of these dogs using the CSCLam1-F, 8-F and 10-F primers in combination with the CSCJLam1-B primer but not the CSCJLam2-B primer. However in both of these dogs, the CSCK1-F primer failed to produce any visible amplicon as previously reported for the first two dogs.

These sequences were aligned using the CLUSTALW alignment program and the nucleotide sequences corresponding to the EVQLVESGGD FR1 region (FIG. 5) (GAG GTG CAG TTG GTG GAG TCT GGG GGA GAC) were identified. Using this alignment, 25 different FR1 sequences were identified within the 57 original sequences. Degenerate primers are designed to these FR1 sequences that amplify all known/predicted heavy chain sequences and based on the consensus sequences of the 25 different FR1 regions, it is necessary to design 6 degenerate primers to amplify all VH FR1 nucleotide sequences. In a similar way, the highly conserved constant region of IgG VH chains was identified and a single reverse primer was designed to recognize this sequence in all IgG heavy chains.

Example 2

Generation of Phage Display Combinatorial Antibody Libraries from Dogs with Hemangiosarcoma (HSA)

In order to recapitulate the immune repertoire of dogs with HSA and screen it for tumor-specific antibody responses scFv libraries are generated from splenic lymphocytes of dogs with HSA. Spleen samples are obtained from all canine patients that are undergoing splenectomy for the treatment of suspected HSA. All samples are taken at the time of surgery, divided and placed into RNA later, STD media and formalin. Histopathology is used to confirm or refute the working diagnosis of HSA. Samples in STD media are immediately processed into single cell suspensions, cryopreserved and banked at the PennVet Tumor Tissue Bank. Samples in RNA are then stored at −80° C. until the diagnosis of HSA is confirmed. Splenic samples are collected from 10 dogs with HSA and 10 dogs with non-neoplastic splenic disease (e.g. hematoma, torsion etc). RNA is isolated from the spleens of dogs with HSA using the RNAeasy kit and cDNA is synthesized using random hexamers and Superscript reverse transcriptase. VH and VL (λ and κ) chains are amplified using a set of 30 degenerate primers, products are pooled into 2 groups (VH chains and combined λ and κ VL chains) and gel purified prior to their random recombination using SOE (FIGS. 3 and 4). The resulting scFv products is gel purified, cut with the restriction endonuclease SfiI and cloned into the pCOMB3x phagemid vector for expression as a fusion product with the bacteriophage coat protein p3 using standard cloning techniques).

A set of degenerate primers were designed based on the known and predicted nucleotide and protein sequences (the latter via back-translation) of canine Ig VH and VL chains. There are a total of 7 degenerate forward primers and a single, non degenerate reverse primer that amplify canine VH IgG chains, 13 degenerate forward and 2 degenerate reverse primers that amplify canine VL λ chains and 4 degenerate forward and 4 reverse primers that amplify canine VL κ chains. Using these primers the full complement of antigen-specific IgG antigen-binding regions encoded within canine lymphocytes is reliably amplified. Combinatorial scFv libraries from 3 dogs with non-malignant splenic disease and 3 dogs with splenic HSA were generated.

The resulting library is transformed into electrocompetent E. coli and transformed bacteria is tittered to determine the total number of transformants. This provides an estimation of library size (ie. the number of different scFv in the library) that should be in the $10^7$-$10^8$ range. Library diversity is assessed by BstOI fragment analysis of randomly selected clones. As the pCOMB3x phagemid (which carries a carbenicillin selection marker) does not contain phage replication and assembly genes, the generation of scFv expressing phage requires the addition of helper phage. The VCSM13 helper phage (which contains a kanomycin resistance gene) is added to XL-1 blue cells containing the scFv phagemid libraries and the resulting phage is amplified in culture with carbenicillin and kanamycin overnight. Kanamycin and carbenicillin resistant phage is precipitated using PEG-8000 and the concentration of infectious phage is determined by assessment of the number of plaque-forming units generated per ml. Canine scFv phage display libraries are stored in TBS/1% BSA prior to panning.

Example 3

Identification of Tumor-Specific scFv of Canine Origin that Bind Specifically to Canine HSA Cell Lines Whole cell panning techniques are used to identify scFv constructs expressed by phage that specifically bind to antigens expressed by malignant endothelial cells. The use of whole cell panning techniques enables the isolation of tumor specific scFv binders without the necessity of TAA identification.

To minimize non-specific selection of phage, scFv phage display libraries from each dog with HSA undergo three rounds of subtractive panning against non-neoplastic allogeneic canine spleen cells (obtained from dogs that underwent splenectomy for non-malignant splenic disease e.g. torsion, hematoma). Negatively selected phage are then incubated with single cell suspensions of autologous HSA cell lines generated from cryopreserved cell suspensions. Cell cultures are washed in PBS/1% FCS 5-8 times to remove unbound phage. Bound phage is then eluted from the malignant target cells using an acid wash, amplified in XL-1 blue cells and rescued with VCSM13 helper phage according to standard protocols. Positively selected scFv expressing phage preparations undergo a further 4-8 rounds of positive selection followed by amplification to isolate tumor specific binders. The resulting panned phage pool is analyzed by flow cytometry to confirm binding to autologous and allogeneic HSA cell lines.

Autologous and allogeneic HSA tumor cells and splenocytes from patients with non-malignant disease (negative control) are blocked with goat serum and incubated with either the positively selected scFv phage pool ($2-5 \times 10^{10}$) or the unselected phage pool (negative control). Cells are washed and incubated with an anti-M13 mouse monoclonal antibody, followed by a FITC-labeled goat anti-mouse $F(ab')_2$ fragment specific antibody. Labeled cells are then acquired using a Becton Dickson FACS Calibur flow cytometer and analyzed by FloJo Software. Following confirmation of tumor specific scFv binders in the positively selected pooled phage population, positively selected phage is amplified again in XL-1 blue cells and single clones are analyzed using BstOI fragment analysis to determine whether different scFv sequences exist within this phage pool. DNA sequence analysis of each clone is then performed at the UPenn DNA sequencing core facility to identify the scFv constructs that specifically target malignant endothelial cells.

The binding affinities of all tumor-specific scFv constructs to malignant endothelial cells are determined by BIACore analysis. Each scFv library generated from dogs with HSA are positively selected as described above and screened for scFv sequences that specifically bind tumor cells. scFv constructs that also target allogeneic HSA cell lines are of particular interest since they target universally expressed tumor antigens that could be used to target HSA in all patients.

By screening libraries from 10 dogs with HSA tumor-specific scFv constructs are isolated from one or more dogs. Clearly this is dependent upon 2 factors i) that canine cancer patients make anti-tumor antibody responses ii) that the degenerate primers used are able to amplify all canine VH and VL chain genes. The libraries that have been generated to date have comparable size and complexity to human immune (IgG) scFv libraries and show diversity in the clones that we have sequenced (Tables I and II). Although 90% of the canine Ig utilize the VL λ chain, inclusion of primers that amplify the VL κ chain helps to ensure the capture of all VL sequences in the repertoire.

Table II shows thirty four ampicillin resistant colonies that were randomly picked from XL-1 blue electrocompetent cells transformed with canine combinatorial antibody libraries within the ampicillin resistant pCOMB3X phagemid vector. Plasmid DNA was extracted and sequenced. Sequences were analyzed by nucleotide BLAST to confirm their identity and Immunoglobulin BLAST to locate FRs and CDRs. VH and VL chains are shown separately. The first 11 sequences are VL kappa chains and the remaining sequences are VL lambda chains.

Tables I and II:

TABLE I

Alligned canine VH sequences showing framework regions (FR) and complimentary determining regions (CDR)

| FR1 | CDR1 | FR2 | CDR2 | FR3 | CDR3 | FR4 | CONSTANT | SEQ ID NO: |
|---|---|---|---|---|---|---|---|---|
| DMQLVESGGDLVKPGGSLRLSCVASGFTFS | SYNMG | WVRQAPGKGLQWVA | WIYDSGSNTRYADAVKG | RFTISRDNAKNTLYLQMNSL | RAEDTAVYYCAR DYSTTWGWDFDY | WGQGTLVTVSS | ASTTAPS | 449 |
| EGQLAESGGDLVKPGGSLRLSCVASGFPFS | SYNMG | WVRQAPGKGLQWVA | WIYTGGTRTSYADAVKG | RFTISRDNAKNTLYLQMNNL | RVEDMAQYYCAR DGSSYSSIVEFFPDY | WGQGTLVTVSS | ASTTAPS | 450 |
| EVQLVESGGDLVKPAGSLRLSCVASRATFS | SYNMG | WVRQAPGRGLQWVA | WIYDSGSTRYADAVKG | RFTISRDNARNTLYLQMNRL | RVEDTAMYYCAR ENWSVDA | WGQGTLVTVSS | ASTTAPS | 451 |
| EVSLVESGGNLVKPGGSLRLSCVASGFTFS | AHTMS | WVRQAPETGLQLVA | AIKSDGRKTYYTDAVRG | RFTISRDNVKNTLYLQMNDL | RTEDTAMYYCAT NEGDSRYVGFDY | WGQGTLVTVSP | ASTTAPS | 452 |
| EVSLVESGGDLVKPGGTLRLSCVASGFTFS | FNNMG | WVRQAPGKGLQWVA | WINDGTTTTYADAVKG | RFTISRDNAKNTLYLQMNPL | RAEDTAVYYCVR HGYDITGGDE | WGQGTLVTVSS | ASTTAPS | 453 |
| GVQLVESGGDLVKPGGSLRLSCVASGFNFS | SSDMS | WVRQSPGKGLQWVA | IIWNDGPSTYYGDAVKG | RFTISRDNAKNTLYLQMNSL | RAEDAAMYYCAP TGFHDRFLSY | WGQGTLVTVSS | ASTTAPS | 454 |
| GVQLVESGGDLVKPGGSLRLSCVASGFTFS | TYNMG | WVRQSPGKGLQWVA | WIYDGSSTIYSDDVRG | RFTISRDTARNTVHLQMNNL | RAEDTAVYYCAT GTYSSSWIWEGFDY | WGQGTLVTVSS | ASTTAPS | 455 |
| DVQLVESGGDLVKPGGALRLSCGSSGNTLN | SYDMD | WVRQAPGKGLQWLS | EISSSGSSTYYADAVKG | RFTISRDNAKNMLYLQMNSL | RAEDTAVYYCAA PYSSSWHPIGFGLDY | WGHGTSLFVSS | ASTTAPS | 456 |
| EVQLVESGGDQVKPGGSLRLSCVGSGFTFS | DYDIC | WVRQXPGKGLQWVA | AISXDGSRTYVXDAVKG | RFTVSRDNARNALYLQMNSL | RAEDTAVYYCVD VRGRSGQYFGD | WGQGTLVTVSS | ASTTAPS | 457 |
| GVQLVESGGDLAKPGGSLRLSCVASGLTXN | DYDMS | WVRQAPGKGLQWVA | AISYDGSSTYYTDAVKG | RFTISRDNARNTVSLQMTGL | RVEDTAVYYCRG TLLNPDF | WGQGTLVTVSS | ASTTAPS | 458 |
| EVQLVESGGDLVKPGGSLRLSCVAPGFTFS | SYSMS | WVRQAPGKGLQWVT | GIDYDGRSTYYTAAVKG | RFTISRDNARNTVYLQMNSL | RADDTGLYYCAV GSIDY | WGQGTLVTVSS | ASTTAPS | 459 |
| EVRLVESGGDLVKPGGSLRLSCVASGFSIG | DSDTN | WVRLAPGKRLQWVA | GISVDGISTYYIDAVKG | RFTISRDTAKRTVYLQMNSL | RAEDTAVYYCGP GSGYY | WGQGTLVTVSS | ASTTAPS | 460 |
| GVQLVESGGDLVKPGGSLRLSCVASGFTFS | SSGMS | WIRQAPGKGLQWVA | YIGPYPTNIAYADAVKG | RFTISRDNAKNALYLQMDRL | RAEDTAMYYCAR GGEYIWIPSFDY | WGQGTLVTVSS | ASTTAPS | 461 |
| EVQLVESGGDLVKPAGSLRLSCEASGFTFS | SYYMY | WVRQALGKGLQWVA | RISGDGSSTYYADAMKG | RFTISRDNAKKTLYLQMNSL | RDEDTAVYYCAR WDYTSYWGCDY | WGQGTLVTVSS | ASTTAPS | 462 |
| EGQLAESGGDLAKPGGSLRLSCVASGFAFS | NNYMT | WIRQAPGKGLQWVS | QINSDGSSTSYADAVKG | RFTISRDNARNTLYLQMNSL | RAEDTGIYYCTR DDIAGSYSA | WGQGTLVTVSS | ASTTAPS | 463 |
| EVRLVESGGDLVKPGGSLRLSCVASGLTFS | SYYY | WVRQAPGRGLQWVA | RISSDGSSTYYADAVKG | RFTISRDNAKNTLYLQMNSL | RVEDTGLYYCVD IRGGSGRYFGA | WGQGTLVTVSS | ASTTAPS | 464 |
| EVQLVESGGDLVKPGGSLITLSCVASGFTFR | DSTMS | WVRQAPGKGLQWVT | FITSDGGNTAYTDAVKG | RFTISRDNARNTLFLQMSGL | RAEDTAMYYCVA PVYAYQFDY | WGQGTLVTVSS | ASTTAPS | 465 |
| GVQLVESGGDLVKPAGSLRLSCVCEASGFTFS | RLYIY | WVRQAPGKGLQWVA | RISSDGFTTSYGDTVKG | RFTISRDNAKNTLYLQMDSL | RADDTAMYYCAK VRPLTHYGSYAYPDY | WGQGTLVTVSS | ASTTAPS | 466 |
| EVQLVESGGDLVKPAGSLRLSCVASGFAFS | RYDMS | WVRQAPEKGLQWVA | NIHSGGYNTYYTDAVKG | RFTISRDNGKNTVYLQMNDL | RAEDTAMYYCAR GNYGSYSLDY | WGQGTLVTVSS | ASTTAPS | 467 |
| EGQLAESGGDLAKPGGSLRLSCVASGFIFT | SYSMS | WVRQAPEKGLQLVA | GINSGGSSTYYADAVKG | RFTISRDNAKNTVYLQMNSL | RGEDTAVYYCAT NHLANLDX | WGQGTLVTVSS | ASTTAPS | 468 |
| EVQLVESGGDLVKPGGSLRLSCVASGFNFS | SPIMS | WVRQAPEKAPQLVA | TXDIDGSRTFYTDAVKG | RFTISRDNAKNTMYLQMNSL | RSEDTAVYYCVP RDYGSYYGFDY | WGQGTLVTVSS | ASTTAPS | 469 |
| EVQLVELGGDLVKPGGSLRVSCVASGFTFS | PYTMN | WVRQAPGKGLQWVA | SINSGGSVTYYADAVKG | RFTISRDNDRNTLYLQMNSL | RPEDAAVYYCAR AYPGVSSTYFHGMDS | WGHGTSLFVSS | ASTTAPS | 470 |
| GEQLVESGGDLVKPGGSLITLSCVASGFTFS | SYNMA | WVRQAPGEGLQWVA | WIYYAGGRTDYADDVKG | RFTVSRDNAKNTLYLQMNSL | RAEDTAMYYCAK DNSAWSVWSCYDY | WGQGTLVTVSS | ASTTAPS | 471 |

TABLE I-continued

Aligned canine VH sequences showing framework regions (FR) and complimentary determining regions (CDR)

| FR1 | CDR1 | FR2 | CDR2 | FR3 | CDR3 | FR4 | CONSTANT | SEQ ID NO: |
|---|---|---|---|---|---|---|---|---|
| EVSLVESGGDLVKPGGSLRLSCAASGFAFS | NYYMY | WVRQAPGKGLQWVA | RISIDGKTTYYGDAVKG | RFTVSRDNANNTLYLRMNSL | RAEDTAVYHCAS SGGKGGSYYRFDY | WGQGTLVTVSS | ASTTAPS | 472 |
| EVQLVESGGDLVKPGGSLRLSCVAPGFTFK | DHHMT | WVRQAPGKGFQWVT | YINSGGDKTTYADAVRG | RFTVSRDNARNTVYLQMNSL | RADDTALYYCAV GSIDY | WGQGTLVTVSS | ASTTAPS | 473 |
| EVQLVESGGDLVKPGGSLRLSCVASGFTLS | DSDTN | WVRLAPGKRLQWVA | GISVDGISTYYIDAVKG | RFTISRDTARKTVYLQMNSL | GVEDTAVYFCSS GYIYMDTIADN | WGQGTLVTVSP | ASTTAPS | 474 |
| GVQLVESGGDLVKPGGSLRLSCVASGLTFS | DHHVN | WVRQPPGKGLQWVA | YINNDGKDIAFADAVKG | RFTISRDNAKNTVYLQMDSL | RVEDTAVYYCRG TLLNFDF | WGQGTLVTVSS | ASTTAPS | 475 |
| GVQLVESGGDLAKPGGSLRLSCVASGLAFN | SYSMS | WVRQAPGKGLQWVT | GIDYDGRSTYYTAAVKG | RFTISRDNARNTVYLQMNSL | RVEDTAVYYCRG TLLNFDF | WGQGTLVTVSS | ASTTAPS | 476 |
| EVQLVESGGDLVKPGGSLRLSCVASGFSIG | SYSMS | WVRQAPGKGLQWVT | GIDYDGRSTYYTAAVKG | RFTISRDNARNTVYLQMNSL | RAEDTAVYYCVA RSARGSSWYGGGFDY | WGQGTLVTVSS | ASTTAPS | 477 |
| EVQLVESGGDLVKPGGSLRLSCLVSGLSIG | SYHMS | WVRQAPGKGLQWVA | YINSGGGSTSYADAVKG | RFTISRDNGRNTVYLQMNSL | RTEDTAVYYCAT GLGLIYLNRYHLTY | WGQGTLVTVSS | ASTTAPS | 478 |
| EVQLVESGGDLVKPGGSLRLSCVASGFTFS | SHDMT | WVRQAPGKGLQWVA | ALTYDGITYHSDSVKG | RVTVSRDNGRNTVYLQMDSL | RVEDTAVYYCAA GLAYHGSYYGDH | WGQGTLVTVSS | ASTTAPS | 479 |
| EGQLAESGGDLVKPGGSLRLSCVASGFAFS | AYHMT | WIRLAPGKGPQWVG | YINSGGAVTRFADAVKD | RFTLSRDGAKNTLYLQMNNL | TTEDTAVYYCANN NFGTDYEFDY | WGQGTLVTVSS | ASTTAPS | 480 |
| EEQLVEFGGDLVKPGGSLRLSCVASGFTLS | TYNMV | WVRQAPGKGLQWVA | WIYDSGSTTTYADAVKG | RFTVSRDNAKNTLFLHMNRL | RAEDTAVYYCVN LLFRYSGRYQEGFDY | WGQGSLVTVSA | ASTTAPS | 481 |
| EVSLVESGGDLVKVGGSLRLSCVASEFTFT | NYDMN | WVRQAPGKGLQWLS | EINSSGSSTYYADAVKG | RFTISRDDAKNTLYLQMNSL | RAEDTAVYYCAS GGRVWCTDDYCFNPAFDY | WGQGTLVTVSX | ASTTAPS | 482 |

TABLE II

Aligned canine VL sequences showing framework regions (FR) and complimentarity determining regions (CDR).

| FR1 | CDR1 | FR2 | CDR2 |
|---|---|---|---|
| MMQTPLSLSVSPGETASISC | KASQSLLHSDGNTYLN | WFRQKPGQ | SPQRLIY KVSNRDT |
| MMQTPLSLSVSPGEPASISC | KASQSLLHRSGNTYLY | WFRQKPGQ | SPEGLIY QVSNRLT |
| MTQTPLSLSVXPGEPASISC | KASQSLLHSNGNTYLF | WFRQKPGQ | SPKRLIY EVSDRDS |
| MMQTPLSLSISPGETASISC | KASQSLLHSNGNTYLN | WFRQKPGQ | SPQRLIY KVSSRDS |
| MMQTPLSLSVRPGEPASISC | KASQSLLHSNGNTYLF | WFRHRPGQ | SPQSLLY LVSNRAP |
| MMXTPLSLSVSPGEPASISC | KASQNLLHSNGNTYLY | WFRQRPGQ | SPEGLIY KVSNRFT |
| MMXTPLSLSVSPGEPASISC | KASQSLLHRDGNTYVY | WFRQKSGQ | SPEGLIY RMSNRFT |
| MTQTPLSLSVSPGEAASISC | KASQSLLHSNGNTYFY | WFRQRPGQ | SPEGLIY KVSNRFT |
| MMXTPLSLSVSPGETASISC | RANQSLLHSNGNTYLD | WYIQRPGQ | SPQALIY RVSNRAI |
| MMXTPLSLAVTPGELATIYC | RASQSLLHSDGKSYLS | WYLQKPGQ | TPRPLIY EASKRFS |
| MMXTPLSLAVTPGDLATISC | RASQSLLYTDGKSYLN | WYLQRPGQ | TPRPLIY ETSKRFS |
| RADSAASVSGSLGQRVTISC | SGSSSNIGNHVA | WFQQLPGT | GPRTLIY GNNNRPS |
| RVDQASSVSGFLGQRVTISC | TGSSSKIGRGFVH | WYQVLPGT | GPRTLIY GVSHRPS |
| GLTQLPSMSVALRQTARITC | GGGNIESKNVH | WYQQKLGQ | APIQIVY YDTRRPV |
| GLTQLASVSVNPGQTAIITC | EADKIGDKFVH | WYQQKPSQ | APGMIVY EDHKRPS |
| GLTQPPSMSVTLRQTARITC | EGDSIGTKRVY | WYQQKLGQ | VPVLIIY DDSSRPS |
| GLTQPPSVSVSLGQTATISC | SGESLTERFAQ | WFQQKPGQ | APVLVIY KDTERPS |
| LTQLTSVSGSLGQRVTISC | SGRTNIDRFGVT | WYQQFPGK | APRLLVD SDGDRPS |
| VLTQLTSVSGSLGQRVTISC | SGSANNIGSFGAI | WYQQFPGK | APKLLIY RDGSRPS |
| ALTQPASVSGSLGQRVTISC | SGTTDNIGIVGAN | WYQQLPGK | APKLLVY SDGNRPA |
| VLTQPPSVSGSLGQKITISC | SGSTNNVGVVGAG | WYQQLPGK | APKLLVF SDGVRPS |
| VLTQPPSVSGSLGQRVTISC | SGSTNNIGIVGAS | WYQQPPGK | APKLLVY TNGGRPS |
| VLTQPPSVSGSPGQRVTISC | SGRTNNIGSVGAT | WYRQFPGK | APNLLVY SDGNRPS |
| ALTQPSSVSGTLGQTVTISC | DGSSSDIGSYSYIA | WYQQFPGT | SPKLLIQ YTDNRPS |
| ALTQPSSVSGTLGQTVTISC | DGSSSDIGSTNYIE | WYQQFPGT | SPKLLIY YIDSRPS |
| VLTQPPSVSGFLGQRVTISC | TGDTPNIGRGYVH | WYQQLPGT | GPRTLIY GVSNRPS |
| TLTXKPSVSGSLGQRVTISC | TGSSSNVGYGDSVG | WYQQLPGT | SPRTLIY DSSSRPS |
| VLTQLASVSGSLGQXVTISC | TGSSSNVGYGDYVG | WYQQLPGT | GPRTLIH HTTSRPS |
| VLTQLASVSGSLGQRVTISC | SGSSSNVGCGDYVG | WFQQLPGT | GPRTLIY DTSTRPS |
| VLTQLASVSGSLGQRVTISC | TGSSSNVGYGNDVG | WYQQLPGT | GPRTLIY GSSIRPS |
| LLTQPASVSGSLGQKVTISC | TGSSSNIGSNYVA | WYQQLPGT | GPRTLIY SNTNRFS |
| VLTQLASVSGSLGQRVTISC | TGSTSNIGRGYVT | WYQQLPGT | GPRTLIY DNSDRPS |
| ALTQPASVSGSLGQRVTVSC | TGSSSNIGRFVVG | WFQQLPGK | GPRTVIY NTSNRPS |
| VLTQLASVSGSRGQKITISC | TGSFSNIGNHNVG | WYQQLPGS | GPKTVIY DTDSRPS |

| FR3 | CDR3 | FR4 | SEQ ID NO: |
|---|---|---|---|
| GVPDRFSGSGSGTDFTLRISTVEADDTGIYYC | GQGTQFPLT | FGQGTKLEIK | 483 |
| GVSDRFSGSGSGTDFTLRISTVEADDTGVYYC | GQGAQLPWT | FGAGTKVDLK | 484 |

TABLE II-continued

Aligned canine VL sequences showing framework regions (FR) and complimentarity determining regions (CDR).

| | | | |
|---|---|---|---|
| GVPERFSGSGSGTDFALRISRVEANDTGVYYC | GQGVQFPLT | FGQGTKVEIK | 485 |
| GVPDMFSGSGSGADFTLRISRVEADDAGLYYC | GQGTQDPWT | FGAGTKVDLK | 486 |
| GVPDRFSASGSGTDFTLRISRVEADDAGVYYC | GHITQSPPT | FGQGTKLEIK | 487 |
| GVSDRFSGSGSGTDFTLRISRVEADDTGVYYC | GHGIEFPYT | FGQGTKLEIK | 488 |
| GVSDRFSGSGSGTDFTLRISRVEADDAGVYYC | GQGLHFPRA | FGAGTKVDLK | 489 |
| GVSDRFSGSGSGTDFTLRISRVEADDSGVYYC | GQNIQFPLT | FGQGTKLEIK | 490 |
| AVSDRFSGSGSGTDFTLKISRVEAGDAGLYYC | GQGTYSYT | FSQGTKLEIK | 491 |
| GVSDRFSGSGSGTDFTLKISGVEAGDVGVYYC | QQSLHFPGT | FSQGTKLEIK | 492 |
| GVSDRFIGSGSGTDFTLTISRVEAEDVGVYYC | QQSVHFPWT | FGPGTKVEIK | 493 |
| GVPDRFSGSRSGSTATLTISGLQTEDEADYYC | SSWDTSLSGYV | FGSGTELTVL | 494 |
| GVPDRFSASKSGKTATLTISGLQAEDEADYYC | SSWDSSLSSLV | FGSGTQLTVL | 495 |
| GIPERFSGAKSGNTATLTISGALAEDEADYYC | QVWDSGTLI | FGGGTQLTVL | 496 |
| GIPERFSASNSGNTATLTISGARAEDEADYYC | QVWDNGAPM | FGGGTHPDRP | 497 |
| GIPERFSGANSGNTATLTIXGALAEDEADYYC | QVWDSSTKAIV | FGGGTHLTVL | 498 |
| GIPDRFSGSISGNTHTLTISGARAEDEADYYC | ESAVTSDTYV | FGSGIELTVL | 499 |
| GVPDRFSGSKSANSATLTITGLHAEDEADYYC | LSIGPTLGVYV | FGSGIELTVL | 500 |
| GVPDRFSGSRSGNSATLTITGLQAEDEADFYC | QSVDPTLGIAV | FGGGTHLTVL | 501 |
| GVPDRFSGSKSGSSATLIITGLQAEDESDYYC | QSVDPTLGARYV | FGSGIELTVL | 502 |
| GVPDRFSGSKFGDSHTLTITGLQAEDEADYYC | QSYDTTLHTYV | FGSGIELIVL | 503 |
| GVPDRFSGSKSGNSATLTITGLQAEDEADYYC | QSSDSMLAV | FGGGTHLTVL | 504 |
| GVPDRFSASMSGNSATLTITGLQTEDEADYYC | QSYDTSLDGAV | FGGGTHLTVL | 505 |
| GIPTRFSGSKSGNTASLTIPGLQAEDEADYYC | CAYAGSDTYV | FGSGTQLTVL | 506 |
| GIPPRFSGSKSGNTASLTISGLQAEDEADYYC | SSYTKSDTFV | FGSGTQLTVL | 507 |
| GVPDRFSGSRSGSTGTLTISGLQAEDEADYYC | SSWDTTLSAYV | FGSGIELTVL | 508 |
| GVPDRFSGSRSGSTATLTISGLQAEDEADYYC | SSYDSSLSGAV | FGGGTHLTVL | 509 |
| GVSDRFSGSRSGNTATLTISGLQAEDEADYYC | SSYDTGLNVV | FGGGTQLTVL | 510 |
| GVPDRFSGSRSGSTATLTISGLQAEDEADYYC | SSYDMTLRGPM | FGGGTQLTVL | 511 |
| GVPDRFSGSKSGNSATLTISGLQAEDEADYYC | SSYDSSLGYV | FGSGTQLTVL | 512 |
| GVPDRFSGSRSGSTATLTISGLQAEDEADYYC | STYDNSLSGLV | FGGGTQLTVL | 513 |
| GVPDRFSGSKSGSTATLTISGLQVEDEADYHC | STYDSSLGGPV | FGGGTQLTVL | 514 |
| GVPDRFSGSKSGSTATLTISGLQTEDEAAYYC | SVYDSSLNTIL | FGGGTHLTVL | 515 |
| GVSDRFSASKSGSTATLTISGLQTEDEGDYYC | STWDYSLSTAV | FGRGTHLTVL | 516 |

Cell lines from HSA patients are generated, which can be used for scFv phage selection and assessment of targeted specificity (see Example 3). Allogeneic canine HSA cells lines that are readily available are potentially used for positive selection of phage and assessment of scFv directed killing (Example 3). This approach ensures that isolated scFv recognize common TAAs shared by other dogs with HSA, an important point as the generation of therapeutic scFvs that can target HSA in all affected dogs is accomplished.

Figure 6:
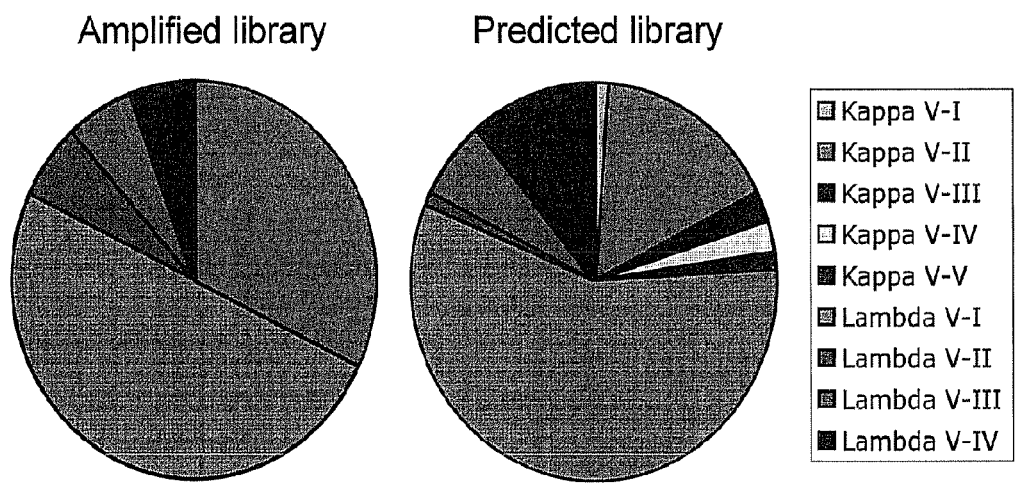
FIG. 6 shows the frequency of VL lambda and kappa chain families in the amplified library versus the predicted library. Thirty four clones were sequenced and the VL lambda and kappa chain families were identified by BLAST search. The frequency of each V chain family represented in the amplified library is shown on the left and on the right the predicted frequency as determined by the numbers of V chains within each family annotated in the canine genome.

As reported for human and murine immunoglobulins, most sequence variation of canine Ig variable regions occurs within the CDR3 region of the VH chain, the hypervariable region that interacts with antigen and assumes greatest responsibility for antigen specificity of the antibody. $V_H$ sequences from these clones were used in a BLAST search to identify which family members ($V_H$-I and/or $V_H$-III) were amplified. All chains were found to be members of the VH-III family which is dominant over the V-I family as predicted by the annotated canine genomic sequence ($V_H$-I 12%; $V_H$-III 88%). $V_L$ sequences from analyzed clones were also subject to a BLAST search to identify which kappa or lambda family members (Kappa V-I through to V-V; Lambda V-I through V-IV) were represented in the amplified library. The frequency of occurrence of each kappa and lambda family amplified in the generated library was then compared with the frequency of each family as predicted from the annotated canine genomic sequence. The results are shown in FIG. 6. Despite the very small sample size of 34 sequenced colonies, all $V_L$ lambda family members were represented in the amplified library at similar frequencies to $V_L$ lambda family members in the predicted library. The kappa chains were over-represented in the amplified library (32% frequency of $V_L$ kappa chains in amplified library versus 22.7% frequency in predicted library) and only members of the V-II family were represented. When a separate VH-VL kappa library was made from the splenocytes of a dog with hemangiosarcoma and light chains amplified were sequenced, 30 of the sequenced VL chains were members of the V-II family and 7 were members of the V-III family. This result confirms that the degenerate primers can amplify both V-II and V-III kappa chain family members and suggests that additional sequencing may reveal other, less commonly employed kappa family members belonging to V-I, V-IV and V-V.

If 100 colonies were picked for sequencing, members of $V_L$ kappa V-I, V-III, V-IV and V-V families would be present in <2 colonies each. As such, many hundreds of colonies would need to be analyzed to confirm the presence or absence of these rare $V_L$ kappa family members in the amplicons.

To determine whether VL kappa primers designed to amplify V-I, V-II, V-III, V-IV and V-V family members do amplifying these chains, products of the first round PCR reaction for VL kappa chains are blunt cloned into TOPO-Blunt Cloning Vector and the plasmid DNA retrieved from transformed bacterial colonies are sequenced. This process is also repeated using the degenerate VH primers that amplify both VH-I and VH-III family members to ensure that VH-I members are represented in the libraries. As the frequency of some of the VL kappa family members is very low then it is potentially more beneficial to generate separate VH-VL lambda and VH-VL kappa scFv libraries in an effort to identify a rare clone that may contain a scFv that recognises an antigen of interest. Currently separate VH-VL lambda and VH-VL kappa libraries are generated from splenic cDNA from a patient with hemangiosarcoma. Clones of this kappa library are then sequenced and analyzed to assess its diversity.

In addition to the generation of scFv libraries that contain VH and VL (lambda and kappa) chains amplified from the splenocytes of a normal dog and a dog with hemangiosarcoma, scFv libraries have also been made from the draining lymph node of a dog with osteosarcoma and from a primary osteosarcoma lesion itself. In both locations, the number of lymphocytes that are likely to encode antibodies that specifically recognize tumor associated antigens should be increased over and above that found in more distant lymphoid tissues such as the spleen. As a result, the scFv libraries generated from such sites are likely to be enriched for tumor-specific scFvs which can be isolated using the phage display technology previously described.

Figure 7:
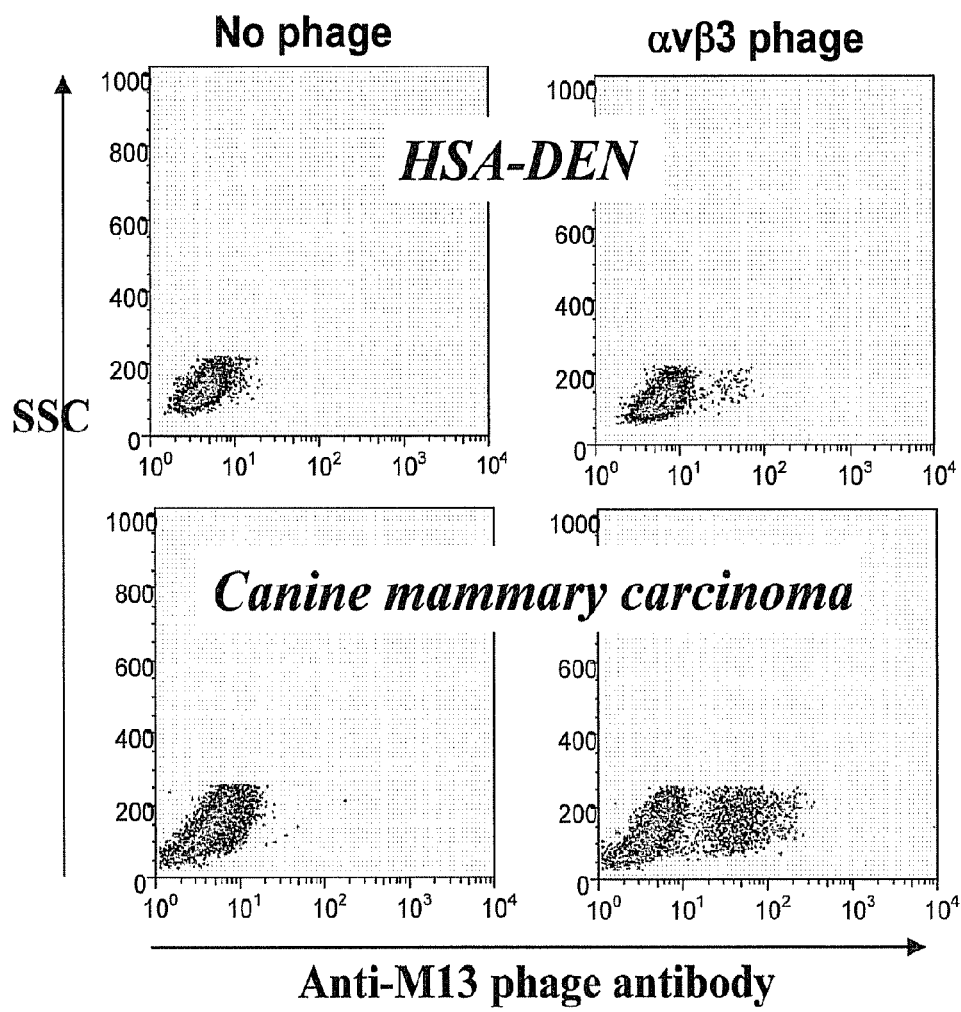
FIG. 7 shows the use of scFv phage display technology and flow cytometry to identify scFv that bind a subset of cells within a canine metastatic mammary carcinoma cell line but not a canine hemangiosarcoma cell line.

For the purpose of using phage display of canine scFvs generated from patients with hemangiosarcoma to identify and target TAA, flow cytometric systems have been optimized for identifying cell surface bound phage (FIG. 7). Briefly, bacteriophage expressing a single human scFv was generated, which recognizes the active form of the integrin αvβ3, (the αvβ3 construct was kindly supplied to us by Dr. Kim Janda of the Scripps Research Institute, La Jolla, Calif.).

Several canine malignant cell lines were screened for the expression of the active form of αvβ3 using phage display and flow cytometry. Interestingly, while the αvβ3 scFv does not bind the HSA-DEN canine hemangiosarcoma cell line (which expresses αvβ3 but not in its active form) it does bind a subset of cells generated from a canine metastatic mammary carcinoma lesion. These techniques of phage display and flow cytometric identification of bound phage are used to identify scFvs from canine combinatorial antibody libraries that bind autologous and allogeneic hemangiosarcoma cell lines, in an attempt to identify TAA and scFvs that are potentially used in vivo to target malignant endothelial cells. Furthermore, this work provides an example of the identification of a human scFv that cross reacts with canine antigens on malignant metastatic cells. Such a cross-reactive scFv could be canine-ized by replacing human FRs with canine FRs, the latter being identified by mass sequencing of canine VH and VL chains amplified using the primers described herein.

Example 4

Evaluation of the Specificity and Cytotoxicity of Canine Tumor-Specific scFv Either Alone or Linked to a Modified *Pseudomonas* Exotoxin Against Canine HSA In Vitro Development of canine scFv to target TAAs and induce apoptosis either directly or when linked to toxic agents aims to circumvent the limitations of xenogeneic antibodies in this species and provides novel immune targeted therapeutics that potentially revolutionize veterinary cancer therapy. In this Example, HSA antigen specific scFv gene fragments (identified in Example 2) are cleaved from the pCOMB3x vector and subcloned into 2 different expression vectors—pET-FLAG that contains a FLAG tag sequence and expresses FLAG-tagged canine scFvs and pBM1.1 that contains a modified *Pseudomonas* exotoxin A (ETA)-gene and expresses canine scFvs linked to ETA. pBM1.1 has been used previously to generate ETA-linked scFv that have shown promising results in murine cancer models and human clinical trials. Both vectors containing a tumor-specific canine scFv are transformed into *E. coli*, subjected to antibiotic selection and treated with IPTG to induce the secretion of the linked scFv constructs into the periplasmic space. scFv-fusion products are purified on anti-FLAG mAb M2 affinity agarose or on Sephacryl-100 by FPLC. Target-specific binding of FLAG-tagged and ETA linked scFv are evaluated on autologous and allogeneic HSA cell lines by flow cytometry using monoclonal antibodies that recognize either the FLAG tag or the ETA moiety (mAb TC-1). Assessment of scFv internalization is determined after a 30 minute incubation by stripping surface bound scFv using a low acid wash, permeabilizing the cells and using anti-FLAG or anti-ETA antibodies for detection. In vitro target-specific cytotoxic activity of each scFv construct is determined by cell proliferation assays and flow cytometric analysis using annexin-V and Propidium Iodide staining. HSA cell lines are incubated with tumor-specific scFv-FLAG or scFv-ETA constructs for 18 hours prior to staining with an Annexin-V/Propidium Iodide apoptosis detection kit. In each set of experiments, a truncated ETA fusion protein expressed from the same vector but lacking the scFv targeting moiety is used to determine specificity of scFv-directed targeting.

It is possible that linking tumor-specific canine scFv to FLAG or the ETA moiety may alter the folding of the scFv and subsequently inhibit its ability to bind to tumor antigen. If scFv antigen recognition is adversely affected, the length of the linker that joins the scFv to the FLAG and ETA moieties is altered (increased) to reduce effects of steric hindrance on the construct.

Example 5

Designed VH and VL Sequences

Below are the nucleotide sequences and protein sequences of a few VH and VL chains we have sequenced from these libraries. These libraries would allow 10^8 or more sequences to be produced.
Total of 66 VH sequences from a dog with hemangiosarcoma VH chains from kappa library

>#1
(SEQ ID NO: 34)
GACGTGCAGCTGGTGGAGTCTGGGGGAGACCTGGTGAAGCCTGGGGGGTC

CCTGAGACTGTCCTGTGTGGCCTCTGGAATCACCCTCAGCAACTACTACA

TGTGCTGGGTCCGCCAGGCTCCAGGGAAGGGGCTTCAGTGGGTCGCACGG

ATTAGTTATGATGGAGGTATCACAGAGTACGCAGACGCTGTGAAGGGCCG

ATTCACCATCTCCAGAGACAATGCCAAGAACACGCTGTATCTGCAGATGA

ACAGCCTGAGAGCCGACGACACGGCTATGTACTACTGTACCCAGGGCATA

GATGGACCCTATTGGGGCCAGGGAACCCTGGTCACCGTCTCCTCAGCCTC

CACCACGGCCCCCTCGGTT (SEQ ID NO: 35)
DVQLVESGGDLVKPGGSLRLSCVASGITLSNYYMCWVRQAPGKGLQWVAR

ISYDGGITEYADAVKGRFTISRDNAKNTLYLQMNSLRADDTAMYYCTQGI

DGPYWGQGTLVTVSSASTTAPSV

>#13
(SEQ ID No: 36)
GAGGGGCAGCTGGCGGAGTCTGGGGGAGACCTGGTGAAGCCTGCGGGGTC

CCTGACTCTGTCCTGTGTGGCCTCTGGAATCACCTTCAGTAAATACGACG

TGATATGGGTCCGCCTGGCTCCTGGGAAGGGACTGCAGTGGGTCGCAGGT

ATTAGCAACAATGGAAACACAGCCTACGCAGACGCTGTGGTGGGGCGATT

CACCACGTCCAGAGACATCGCCAAGAACACAGTGTATCTGCGGATGAACA

GCCTGACAGCCGAGGACACGGCCGTATATTACTGTGTCGCGGGCCTTAAG

TACTGGGGCCAGGGCACCCTGGTCACCGTCTCCTCAGCCTCCACCACGGC

CCCCTCGGTT (SEQ ID NO: 37)
EGQLAESGGDLVKPAGSLTLSCVASGITFSKYDVIWVRLAPGKGLQWVAG

ISNNGNTAYADAVVGRFTTSRDIAKNTVYLRMNSLTAEDTAVYYCVAGLK

YWGQGTLVTVSSASTTAPSV

>#25
(SEQ ID NO: 38)
GAGGGGCAGCTGGCGGAGTCTGGGGGAGACCTGGTGAAGCCTGCGGGGTC

CCTGAGACTGTCCTGTGTGGCCTCTGGATTCACCTTCAGCAGCTACGACA

TGAGCTGGGTCCGCCAGGCTCCTGGGAAGGGGCTGCAGTGGGTCGCAGGT

ATTATGGCCGATGGAAGTACATACTACGCAGACGCTGTGAAGGGCCGATT

CACCATCTCCAGAGACAACGCCAAGAACACAGTGTATCTGCAGATGGACA

GCCTGAGAGCCGAGGACACGGCCATGTATTACTGTGCGAAGGATAGGTTG

AGCTACTACATTTATTGCCTTGAGTACTGGGGCCAGGGCACCCTGGTCAC

CGTCTCCTCAGCCTCCACCACGGCCCCCTCGGTT (SEQ ID NO: 39)
EGQLAESGGDLVKPAGSLRLSCVASGFTFSSYDMSWVRQAPGKGLQWVAG

IMADGSTYYADAVKGRFTISRDNAKNTVYLQMDSLRAEDTAMYYCAKDRL

SYYIYCLEYWGQGTLVTVSSASTTAPSV

>#37
(SEQ ID NO: 40)
GAGGTACAGCTGGTGGAGTCTGGGGGAGACCTGGTGAAGCCGGGGGGGTC

CCTGAGACTGTCCTGTGTGGCCTCTGGATTCGCTTTCAGTAGTTATGGCA

TGAGTTGGGTCCGTCAGTCTCCAGGGAAGGGGCTGCAGTGGGTCGCAGAT

ATTAGGAGTACTGGAGACACATACTACGCAGACGCTGTGAAGGGCCGATT

CACCATCTCCAGAGACAACGCCGAGAACACGCTGTATCTGCAGATGAGCA

GCCTGAGAGTCGAGGACACGGCCATATATTATTGTGCCTCAGGACCAGTA

GATACGACTGAACACTGGGGCCAGGGCACCCTGGTCACCGCCTCCTCAGC

YTCCACCACGGCCCCCTCGGTT (SEQ ID NO: 41)
EVQLVESGGDLVKPGGSLRLSCVASGFAFSSYGMSWVRQSPGKGLQWVAD

IRSTGDTYYADAVKGRFTISRDNAENTLYLQMSSLRVEDTAIYYCASGPV

DTTEHWGQGTLVTASSASTTAPSV

>#2
(SEQ ID NO: 42)
GAGTTGCAACTGGTGGAGCTTGGAGGAAACCTGGTGAAGCCTGGGGGGTC

CCTGAGACTCTCTTGTGTGGCCTCTGGATCCACCTTCAAGAACTATTATA

TGGACTGGGTCCGCCAGGCTCCAGGGAAGACTCTGGAGTGGGTCGCAGGG

ATTAGTAGTGATGGCTATAAGACGTATTATGGACAGGCTGTGCAGGGCCG

TTTCACCATCTCTAGAGACAACGCCAAGAATACACTCTATCTACAAATGG

ACGGCCTGACAGTCGAGGACTCTGCTGTATATTACTGTGCGATGGAAGGG

GGTGTACACAGTGAAAGTTGGTTCGCGGATTTTGACTCTTGGGGCCAGGG

AACCCTGGTCACCGTCTCCTCAGCCTCCACCACGGCCCCCTCGGTT (SEQ ID NO: 43)
ELQLVELGGNLVKPGGSLRLSCVASGSTFKNYYMDWVRQAPGKTLEWVAG

ISSDGYKTYYGQAVQGRFTISRDNAKNTLYLQMDGLTVEDSAVYYCAMEG

GVHSESWFADFDSWGQGTLVTVSSASTTAPSV

>#38
(SEQ ID NO: 44)
GAGGTGCAACTGGTGGAGCTTGGGGGAGACCTGGTGAAGCCTGGAGAATC

CCTAAGACTGTCCTGTTTGGCCTCCGATATCACATTCAGTGCCTATGCGA

TGTTCTGGGTCCGCCAGGCTCCAGGGAAGGGCTTGGACTGGGTCGCGACT

ATTAGTGGAGATGGAGACACCACATACTACGGAGACGCTGTGAAGGGCCG

ATTCACCGTCTCCAGAGACAACGCCCAGAACACAGTTTATCTACAGATGA

ACAGCCTGAGAGCCGAGGACACGGCCGTGTATTACTGTCCCTACTACG

GTGACTACTCAGCTTGCATACTGGGGCCAGGGCACCCTGGTCACCGTCTC

CTCAGCCTCCACCACGGCCCCCTCGGTT

```
                                                     (SEQ ID NO: 45)
EVQLVELGGDLVKPGESLRLSCLASDITFSAYAMFWVRQAPGKGLDWVAT
ISGDGDTTYYGDAVKGRFTVSRDNAQNTVYLQMNSLRAEDTAVYYCVPTT
VTTQLAYWGQGTLVTVSSASTTAPSV

>#3
                                                     (SEQ ID NO: 46)
GAGGTGCAGCTGGTGGAGTCTGGGGGAGACCTGGTGAAGCCTGGGGAGTC
CCTGAGACTCTCCTGTGTGGCCTCTACTTTCACTCTCCGTAAATACGACG
TATATTGGGTCCGCCAGGTTCCAGGGGCAGGCCTAGAATGGGTCGCACGG
ATTTCTGACAGTGGAAGCACCACATTCTATGCAGAATACGTAGAGGGCCG
CTTCACCATTACCAGAGACAACGGCAAGAACATGGCATTTTTACAGATGA
ACAGCCTGAGAGCCGAGGACACGGCCCTTTATTACTGTGCGATCAGTCTC
AGTTGGCGGTGGGGTTTTGACTACTGGGGCCAGGGAACCCTGGTCACCGT
CTCCTCAGCCTCCACCACGGCCCCCTCGGTT (SEQ ID NO: 47)
EVQLVESGGDLVKPGESLRLSCVASTFTLRKYDVYWVRQVPGAGLEWVAR
ISDSGSTTFYAEYVEGRFTITRDNGKNMAFLQMNSLRAEDTALYYCAISL
SWRWGFDYWGQGTLVTVSSASTTAPSV

>#15
                                                     (SEQ ID NO: 48)
CAGCTGGTGGAGCTTGGGGGAGACCTGGTGAAGCCTGCGGGGTCCCTGAG
ACTGTCCTGTGTGGCCTCTGGACTCACCATCAGTAACTACGGCATGAGAT
GGGTCCGCCAGGGTCCTGGGAAGGGGCTGCAGTGGGTCGCAGGTATTAGC
GGCGATGGAACCACAAACTCCGCAGAGCGCTGTGAAGGGCCGATTCACCAT
CTCCAGAGACAACTCTAAGAACACAGTGTATCTGCAGATGCACAGCCTGA
GAGTCGAGGACACGGCCGTGTATTACTGTGTGAGTGGGTCATGGGAGTAC
TGGGGCCAGGGCACCCTGGTCACCGTCTCCTCAGCCTCCACCACGGCCCC
CTCGGTT (SEQ ID NO: 49)
QLVELGGDLVKPAGSLRLSCVASGLTISNYGMRWVRQGPGKGLQWVAGIS
GDGTTNSADAVKGRFTISRDNSKNTVYLQMHSLRVEDTAVYYCVSGSWEY
WGQGTLVTVSSASTTAPSV

>#27
                                                     (SEQ ID NO: 50)
GACGTGCAGCTGGTGGAGTCTGGGGGAGACCTGGTGAAGCCTGGGGGGTC
CTTGAGACTGTCCTGTGTGGCCTCTGGATTCACCTTCAGTAACTATGGCA
TGAGCTGGGTCCGTCAGTCTCCAGGGAAGGGGCTGCAGTCGGTCGCAGTT
ATTAACAATGGTGGAGATTACATACACTACACAGGCGCTGTGAAGGGCCG
ATTCACCATCTCCAGAGACAACGCCAAGAACACGCTGTATCTGCAGATGA
ACAGCCTGAGAGCCGAGGACACGGCCGTCTATTACTGTGCGAAGGCGACG
ATTTTGGGTTTTGGACACGAGTCTTGGGGCCAGGGCACCCTGGTCACCGT
CTCCTCAGCCTCCACCACGGCCCCCTCGGTT (SEQ ID NO: 51)
DVQLVESGGDLVKPGGSLRLSCVASGFTFSNYGMSWVRQSPGKGLQSVAV
INNGGDYIHYTGAVKGRFTISRDNAKNTLYLQMNSLRAEDTAVYYCAKAT
ILGFGHESWGQGTLVTVSSASTTAPSV

>#39
                                                     (SEQ ID NO: 52)
GAGGTGCAGCTGGTGGAGACTGGGGGGGGCCTGGCGAAGCCGGGGGGGTC
CCTAAGACTCTCCTGTGTGGCCTCTGGATTGTCCTTCAGTAGTTATAGTA
TGAGTTGGGTCCGCCAGGCTCCTGGGAAGGGTCTGCAGTGGGTCACAGCC
ATCGACTATCATGGACGTGACACTTTCTACACTGACACTGTGAAGGGCCG
CTTCACCATCTCCAGAGACGATGCCAGGAACACGATGTATCTGCACATGG
ACGGCCTGAGAGCCGAAGACACAGCTGTCTATTACTGTATGGTCTACGGT
AGCCACCTGACCTTTGACTTCTGGGGCCAGGGAACCCTGGTCACCGTCTC
CTCAGCCTCCACCACGGCCCCCTCGGTT (SEQ ID NO: 53)
EVQLVETGGGLAKPGGSLRLSCVASGLSFSSYSMSWVRQAPGKGLQWVTA
IDYHGRDTFYTDTVKGRFTISRDDARNTMYLHMDGLRAEDTAVYYCMVYG
SHLTFDFWGQGTLVTVSSASTTAPSV

>#4
                                                     (SEQ ID NO: 54)
GAGGTGCAGCTGGTGGAGTTTGGAGGAGACCTGGTGAAGCCTGGGGGGTC
CCTGAGACTTTCCTGTGTGGCCTCTGGATTCACCTTCAGTAGCTATGACA
TGGACTGGGTCCGCCAGGCTCCAGGGAAGGGGCTGCAATGGCTCTCAGAA
ATTAGCAGTAGTGGAAGTAGCACATACTACGCAGACGCTGTGAAGGGCCG
ATTCACCATCTCCAGAGACAACGCCAAGAACACACTCTATCTGCACATGA
ACAGCCTGCGACCCGAGGACACGGCCGTGTATTACTGTACAAAGGGCGGG
GTCAAAGCGCCCTATAAAAGTGGTGTGGACTACTGGGGCCCTGGCACCTC
AGTCCTCGTGTCCTCAGCCTCCACCACGGCCCCCTCGGTT (SEQ ID NO: 55)
EVQLVEFGGDLVKPGGSLRLSCVASGFTFSSYDMDWVRQAPGKGLQWLSE
ISSSGSSTYYADAVKGRFTISRDNAKNTLYLHMNSLRPEDTAVYYCTKGG
VKAPYKSGVDYWGPGTSVLVSSASTTAPSV

>#16
                                                     (SEQ ID NO: 56)
GAGGTAAAGCTGGTGGAATCTGGGGGAGACCTGGCGAAGCCTGGGGGGTC
CCTGAGACTCTCCTGTGCGGCCTCTGGACTAGCCTTCAGTAGCCACAGCA
TGAACTGGGTCCGCCAGGCTCCTGGGAAGGGCCTGCAGTGGGTCACTGCT
ATCAGTTATGATGGAAGAAGAATCTACTATAGTGACGATGTGAAGGGCCG
ATTCGCCGTCTCCCGCGATAATGCCAGGAACACCATGTATCTTCAGATGA
CGGGCCTGACAGTCGCGGACACAGGTCTCTATTACTGTGCAATAGTGGGC
TTAGGATGGCAGCTGGCCAATTTTGAGTTCTGGGGCCAGGGAGCCCAGGT
CATCGTCGCCTCAGCCTCCACCACGGCCCCCTCGGTT (SEQ ID NO: 57)
EVKLVESGGDLAKPGGSLRLSCAASGLAFSSHSMNWVRQAPGKGLQWVTA
ISYDGRRIYYSDDVKGRFAVSRDNARNTMYLQMTGLTVADTGLYYCAIVG
LGWQLANFEFWGQGAQVIVASASTTAPSV

>#40
                                                     (SEQ ID NO: 58)
GAGGTGCAGCTGGTGGAGTCTGGGGGAGACCTTGTGAAGCCTGGGGGGTC
CCTGAGACTCTCCTGTGTGGCCTCTGGATTCACCTTTAGTAGCTATGACA
```

TGAGCTGGGTCCGTCAGGCTCCTGGAAAGGGGCTGCAGTGGATCACAGCT
ATTAAGTCAGATGGAACTACTACATACTACATTGACGCTGTGAAGGGCCG
ATTCACCGTCTCCAGAGACAATGCCAGGAACACAGTGTATCTGCAGATGA
ACAGTCTGAGAGCCGAGGACACGGCCATGTATTACTGTGCGAGGGACGAT
ATATTTATGGATAGAGTTGGTATGGACTACTGGGGCCGTGGCACCTCACT
CTTCGTGTCCTCAGCCTCCACCACGGCCCCCTCGGTT (SEQ ID NO: 59)
EVQLVESGGDLVKPGGSLRLSCVASGFTFSSYDMSWVRQAPGKGLQWITA
IKSDGTTTYYIDAVKGRFTVSRDNARNTVYLQMNSLRAEDTAMYYCARDD
IFMDRVGMDYWGRGTSLFVSSASTTAPSV

>#5

(SEQ ID NO: 60)
GAGGTGCGTCTGGTGGAGTCTGGGGGAGACCTGGTGAAGCCGGGGGGGTC
CCTGAGACTCTCCTGTCTAGCCTCTGGATTCACCTTCAGTGACTACGACA
TGAGCTGGGTCCGCCAGGCTCCTGGAAAGGGGCTGCAGTGGGTCGCAGGT
ATTAGCTATGAGGGAAGTAGTACATACTACAATGACGCTGTGAAGGGCCG
ACTCACCATCTCCAGAGACAATGCCAGGAATACATTATATCTGCAGATGA
ATAGCCTGAGAGCCGATGACACGGCTGTTTATTACTGTGCGAGATTTCGA
GCGAACTACGGTAACATCTATGGCAACTCCTATTTTGCCTATTGGGGCCA
GGGAACCCTGGTCACCGTCTCCTCAGCCTCCACCACGGCCCCCTCGGTT (SEQ ID NO: 61)
EVRLVESGGDLVKPGGSLRLSCLASGFTFSDYDMSWVRQAPGKGLQWVAG
ISYEGSSTYYNDAVKGRLTISRDNARNTLYLQMNSLRADDTAVYYCARFR
ANYGNIYGNSYFAYWGQGTLVTVSSASTTAPSV

>#17

(SEQ ID NO: 62)
GGGGTGCAGCTGGTGGAGTCTGGGGGAGACGTGGTGAAGCCTGGGGGGTC
CCTGAGACTCTCCTGTGTGGCCTCTGGATTTACCTTCAGTAGTTACTACA
TGTATTGGGCCCGCCAGGCTCCAGGGAAGGGGCTTCAGTGGGTCTCACAC
ATTAAGAGAGATGGAAGTAGCACAAGCTATGCAGACGCTGTGAAGGGCCG
ATTCACCATCTCCAGAGACAACGCAAAGAACACGCTGTATCTGCAGATGA
ACAGTTTGAGAGCTGAGGACACAGCGGTGTATTACTGTGCAAAGGACCTG
GGGACATATGGATACAACCTTGAGTACTGGGGCCGGGGCACCCTGGTCAC
CGTCTCcTcAGCCTCCACCACGGCCCCCTCGGTT (SEQ ID NO: 63)
GVQLVESGGDVVKPGGSLRLSCVASGFTFSSYYMYWARQAPGKGLQWVSH
IKRDGSSTSYADAVKGRFTISRDNAKNTLYLQMNSLRAEDTAVYYCAKDL
GTYGYNLEYWGRGTLVTVSSASTTAPSV

>#29

(SEQ ID NO: 64)
GAGGTCCAACTGGTGGAGTCTGGGGGGGACCTGGTGAAGCCTGGGGAGTC
CCTGAGGCTGTCGTGTGTGGCCTCTGGTTTCATTCTAAGAAAGTATTATC
TACACTGGGTCCGCCAGGCTCCAGGGAAGGGTCCTCAGTGGGTCGCACGG
ATCAGTGGCGAAGGTTATAAGACCTACTACGCGGACGCGGTGAGGGGCCG
ATTCACCATCTCCAGAGACAATGCCAAGAGCACGATTTATCTACAAATGG

ACACCCTGACAGCCGAGGACGCGGGAATCTATTATTGTGTGAAGGATTCA
GATGCACCTCTTCATAGTTGGGGCGACGGTACCCTGGTTGCCGTCTCTTC
AGCCTCCACCACGGCCCCCTCGGTT (SEQ ID NO: 65)
EVQLVESGGDLVKPGESLRLSCVASGFILRKYYLHWVRQAPGKGPQWVAR
ISGEGYKTYYADAVRGRFTISRDNAKSTIYLQMDTLTAEDAGIYYCVKDS
DAPLHSWGDGTLVAVSSASTTAPSV

>#6

(SEQ ID NO: 66)
GAGGTGCAGCTGCTGGAGTCTGGGGGAGACCTGGTGAAGCCGGGGGGGTC
CCTGAGACTCTCCTGTGTGGCCTCTGGTCTCACCTTCAGTAGTCACGACA
TGGACTGGGTCCGCCAGGCTCCAGGGAAGGGACTGCAGTGGCTCACACGG
ATCACCAATGATGGAAGGAGCACAGACTACGCAGATGCTGTGAAGGGCCG
ATTCACCATCTCCAGAGACAACGCCAAGAACACGCTGTATCTGCAGATGA
ACAGCCTGAGAGCCGAGGACACGGCCCTGTATTACTGTGCGAGGGGCGGC
ACGATGTCTCCTTGGTACTGGGGCCAGGGCACTTTGGTCACCGTCTCCTC
AGCCTCCACCACGGCCCCCTCGGTT (SEQ ID NO: 67)
EVQLLESGGDLVKPGGSLRLSCVASGLTFSSHDMDWVRQAPGKGLQWLTR
ITNDGRSTDYADAVKGRFTISRDNAKNTLYLQMNSLRAEDTALYYCARGG
TMSPWYWGQGTLVTVSSASTTAPSV

>#18

(SEQ ID NO: 68)
GAGGTGCAGCTGCTGGAGTCTGGGGGAGACCTGGTGAGGCCTGGGGAGTC
CCTGAGACTCTCCTGCATAGCCTCTGGATTCACCTTCAATACGTATACCA
TGGCCTGGGTCCGCCAGGGTCCTGGGAAGGGGCTGGAGTGGGTCGCAGGT
ATCAGTTCTGATGGAAGTAGCCCATATCACAGTGCCGCTGTGAAGGGCCG
ATTCACCATCTCCAGGGACAGCGCCAGGAGCACAGTCTATCTGCAGATGA
ACAGCCTGAGAGCCGAGGACACGGCTGTGTATTACTGTGCGAAGGACGCT
CTCAGTAGTTGGGCCCCCATAACTTTGATCATTGGGGCCAGGGAACCCT
GGTCACCGTCTCCTCAGCCTCCACCACGGCCCCCTCGGTT (SEQ ID NO: 69)
EVQLLESGGDLVRPGESLRLSCIASGFTFNTYTMAWVRQGPGKGLEWVAG
ISSDGSSPYHSAAVKGRFTISRDSARSTVYLQMNSLRAEDTAVYYCAKDA
LSSWGPHNFDHWGQGTLVTVSSASTTAPSV

>#42

(SEQ ID NO: 70)
GAGGTGCAGCTGGTGCAGTCTGGGGGAGACCTGGTGAAGCCTGGGGGGCC
CCTGAGACTGTCCTGTGTGGCCTCTGGATTCACCTTCAGTAACTACTACA
TGCACTGGGTCCGCCAGGCTCCAGGGAAGGGACTGCAGTGGGTCGGATAC
ATTAGTAGTGATGGAAGTGGCACATGGTACGCGGACGCTGTGAAGGGCCG
CTTCACCATCTCCAGAGACAACGCCAAGAACACACTGTATCTGCAGATGA
ACAGCCTGAGAGCCGAGGACACGGCCGTGTATTACTGTGCGACCACGGGG
AATACCGTCTCCCACTGGACTATGGAATACTGGGGCCCTGGCACCTCACT
CTTCGTGTCCTCAGCCTCCACCACGGCCCCCTCGGTT (SEQ ID NO: 71)
EVQLVQSGGDLVKPGGPLRLSCVASGFTFSNYYMHWVRQAPGKGLQWVGY
ISSDGSGTWYADAVKGRFTISRDNAKNTLYLQMNSLRAEDTAVYYCATTG
NTVSHWTMEYWGPGTSLFVSSASTTAPSV

>#7
(SEQ ID NO: 72)
GAGGGGCAGCTGGCGGAGTCTGGGGGAGACCTGGTGAAGCCTGCGGGGTC
CCTGAGACTGTCCTGTGTGGCCTCTGGATTCACCTTCAGTACCTACGGCA
TGGACTGGGTCCGCCAGGCTCCTGGGAAGGGGCCGCAATGGGTCGGACAT
ATCAGAACCAGTGGAGACACACGGTACGCAGACGCTGTGAAGGGCCGATT
CACCATCTCCAGAGACAACGCCAAAAACACAGTGTATCTGCAGATGGACA
GCCTGACAGTCGAGGACACGGCCTTCTATTTCTGTGCGAAGGATGGACTA
AGATATGGATACGTCCCTGACTTTGAACACTGGGGCCAGGGTACCCTGGT
CACCGTCTCTTTAGCCTCCACCACGGCCCCCTCGGTT (SEQ ID NO: 73)
EGQLAESGGDLVKPAGSLRLSCVASGFTFSTYGMDWVRQAPGKGPQWVGH
IRTSGDTRYADAVKGRFTISRDNAKNTVYLQMDSLTVEDTAFYFCAKDGL
RYGYVPDFEHWGQGTLVTVSLASTTAPSV

>#19
(SEQ ID NO: 74)
GAGGTGCAACTGGTGGAGTTTGGGGGAGACCTGGTGAAGCCTGCGGGGTC
CCTGAAATTGTCCTGTGTGGCCTCTGGATTCACCTTCAGGCACTACGACA
TACACTGGGTCCGCCAGGCTCCTGGGAGGCGGCTGCAATATGTCGCAGGT
ATTCACTATGATGGAAGTTACATATACTACATTGACGCTGTGAAGGGCCG
ATTCACCATCTCCAGAGACAACGCCAGGAACACAGTGTATCTGCAGATGA
ACAGTCTGAGAGTCGAGGACACGGCTGTGTATTATTGTGTGAAGGCTCCG
GGCCTAGAGTACTGGGGCCAGGGAACCCTGGTCACCGTCTCCTCAGCCTC
CACCACGGCCCCCTCGGTT (SEQ ID NO: 75)
EVQLVEFGGDLVKPAGSLKLSCVASGFTFRHYDIHWVRQAPGRRLQYVAG
IHYDGSYIYYIDAVKGRFTISRDNARNTVYLQMNSLRVEDTAVYYCVKAP
GLEYWGQGTLVTVSSASTTAPSV

>#31
(SEQ ID NO: 76)
GAGGTCCAGCTGGTGGAGTCTGGGGGAGACCTGGTGAAGCCTGGGGGGTC
CCTGAGACTTTCCTGTGTGGCCTCTGGATTCACCTTCGGTGACTATTACA
TGAACTGGGTCCGCCAGGCTCCAGGGAAGGGGCTTCAGTGGGTCGCATAC
ATTCACAGTGGTGGAGGTAGCACGACTTATGCAGACGCTGTGAAGGGCCG
ATTCACCATCTCCAGAGACAACGCCAAAAACACACTATATCTTCAGATGA
ACGGCCTGAGAGCCGAGGACACGGCCCTATATTACTGTGCGAGCGGGTCG
CTGGGAACCTACGGTCGTTACTACTCCTTTGACTACTGGGGCCAGGGAAC
CCTGGTCACCGTCTCCTCAGCCTCCACCACGGCCCCCTCGGTT (SEQ ID NO: 77)
EVQLVESGGDLVKPGGSLRLSCVASGFTFGDYYMNWVRQAPGKGLQWVAY
IHSGGGSTTYADAVKGRFTISRDNAKNTLYLQMNGLRAEDTALYYCASGS
LGTYGRYYSFDYWGQGTLVTVSSASTTAPSV

>#43
(SEQ ID NO: 78)
GAGATACCGCTGGTGGAGTCTGGGGGAGACCTGGTGAAGCCTGCAGGGTC
CCTGAGACTGTCCTGTGTGGCCTCTGGATTCACCTTCTCCAGCTATGTCA
TGAGCTGGGTCCGCCAGACTCCTGGGAAGGGGCTGCAGTGGGTCGCAACT
ATTAACAGTGGTGGAAGTAGCACGAGCTACGCAGACGCTGTGAAGGGCCG
ATTCACCATCTCCAGAGACAATGTCAAGAACACACTGTATCTGCAGATGA
ACAGCCTGAGAGCCGAGGACACGGCCGTGTATTACTGTGTGACGCCGTTA
TATGATAGTTACTACGGCTATGGTATGGACTACTGGGGCCCTGGCACCTC
ACTCTTCGTGTCCTCAGCCTCCACCACGGCCCCCTCGGTT (SEQ ID NO: 79)
EIPLVESGGDLVKPAGSLRLSCVASGFTFSSYVMSWVRQTPGKGLQWVAT
INSGGSSTYADAVKGRFTISRDNVKNTLYLQMNSLRAEDTAVYYCVTPL
YDSYYGYGMDYWGPGTSLFVSSASTTAPSV

>#20
(SEQ ID NO: 80)
GAGGTGCAGCTGGTGGAGTCTGGGGGAGACCTGGTGAAGCCTGGGGGGTC
CCTGAGATTGTCCTGTGTGGCCTCTGGATTCATCTTCAGTAGTTATTATA
TATATTGGGTCCGCCAGAGTCCAGGGAAGGGGCTTCAGTGGGTCGCACGA
ATCAACAATGATGGAAGTAGGATATACTACGCAGACGCTGTGAAGGGCCG
ATTCACCATCTCCAGAGACATCGCCAAGGACACGCTCTACCTGCAGCTGG
ACAGGCTCGGGGCCGAGGACACGGCCGTGTATTATTGTGTCCCGCCGAGA
GTACACGTTTGGTTAGGAGATTTTGACTCCTGGGGCCAGGGGACCCTGGT
CACCGTCTCCTCAGCCTCCACCACGGCCCCCTCGGTT (SEQ ID NO: 81)
EVQLVESGGDLVKPGGSLRLSCVASGFIFSSYYIYWVRQSPGKGLQWVAR
INNDGSRIYYADAVKGRFTISRDIAKDTLYLQLDRLGAEDTAVYYCVPPR
VHVWLGDFDSWGQGTLVTVSSASTTAPSV

>#32
(SEQ ID NO: 82)
GGGGTGCAGCTGGTGGAGTCTGGGGGAGACCGGGTGAACCCTGCGGGGTC
CCTGAGACTGTCCTGTGTGGCCTCTGGATTCACCTTCAGTAGTCACGATA
TGAATTGGGTCCGCCAGGCTCCTGGAAAGGGACTGCAGTGGGTCGCATCT
ATTAACAGTGGTGGCAGCGGTCTGCATTACGCAGACAGTGTGAGGGCCG
ATTCACCGTCTCCAGAGACAACGCCAAGAACACCCTTTATCTGGACTTGA
ACGATGTGAGAGACGAAGACACGGCCATGTATTATTGTACGACAGAGAAG
TTGGGTTACCACAACCCCTTCGGTTTCTGGGATTGGGGCCAGGGCACCCT
GGTCACCGTCTCCTCAGCCTCCACCACGGCCCCCTCGGTT (SEQ ID NO: 83)
GVQLVESGGDRVNPAGSLRLSCVASGFTFSSHDMNWVRQAPGKGLQWVAS
INSGGSGLHYADSVRGRFTVSRDNAKNTLYLDLNDVRDEDTAMYYCTTEK
LGYHNPFGFWDWGQGTLVTVSSASTTAPSV

>#44
(SEQ ID NO: 84)
GAGTTGCAACTGGTGGAGTTTGGGGGAGACCTGGTGAAGCCTGGGGGGTC
CCTGAGACTCTCCTGTGTAGCCTCTGGATTCACCTTCAGTAACTACGACA
TGGCCTGGGTCCGCCAGGCTCCTGGGAAGGGGcTGCAGTGGGTCTCAGCT
ATTAGCTATGATGGAAGGAGTACATATAACACTGACGATGTGAAGGGCCG
ATTCACCATCTCCAGAGACAACGCCAGGAACACACTGTATCTGCAGATGA
ACAGCCTGAGAGCCGAGGACACGGCTGTACATTACTGTGTCCCTACCACC
TGTACTGATGATTACTGTCTCTCTTTTGCCTACTGGGGCCAGGGAACCCT
GGTCACYGTCTCYTCAGCYTCCACCACGGCCCCYTCGGTT (SEQ ID NO: 85)
ELQLVEFGGDLVKPGGSLRLSCVASGFTFSNYDMAWVRQAPGKGLQWVSA
ISYDGRSTYNTDDVKGRFTISRDNARNTLYLQMNSLRAEDTAVHYCVPTT
CTDDYCLSFAYWGQGTLVTVSSASTTAPSV

>#9
(SEQ ID NO: 86)
GAGGGGCAGCTGGCGGAGTCTGGGGGAGACCTGGTGAAGCCTGCGGGGTC
CCTGAGACTGTCCTGTGTGGCCTCTGGATTCACCATCAGCAGCCACGACA
TGAGCTGGGTCCGCCAGGCTCCTGGGAAGGGGCTGCAGTGGGTCGCAGGT
ATTAACAGTGGTGGAACCAGGACAGGCTACACAGACGCTGTGAAGGCCCG
ATTCACCATCTCCAGAGACAACGCCAAGAACACACTGTATCTGCAGATGA
ACAGCCTGAGAGCCGAGGACACGGCCGTATATTACTGTGTGTTGAGTATT
GTAACGACTAATTGGGGCCGGGGAACCCTGGTCACCGTCTCCTCAGCCTC
CACCACGGCCCCCTCGGTT (SEQ ID NO: 87)
EGQLAESGGDLVKPAGSLRLSCVASGFTISSHDMSWVRQAPGKGLQWVAG
INSGGTRTGYTDAVKARFTISRDNAKNTLYLQMNSLRAEDTAVYYCVLSI
VTTNWGRGTLVTVSSASTTAPSV

>#33
(SEQ ID NO: 88)
GAGGTGCAGCTGGTGCAGTCTGGAGGAGACCTGGTGAAGCCTGGGGGGTC
CCTGAGACTTTCCTGTGTGGCCTCTGGATTCACCTTCAGTCGCTATCGCA
TGGCCTGGGTCCGCCAACCACCGGGGAGGGGACTTCAGTGGGTCGCATTC
ATTAATAGTGATGGAGATCGCACGACCTATTCAGACACTGTGAAGGGCCG
ATTCACCATTTCCAGAGACAACGCCAACGACACGCTATATCTTCAGATGA
ACAGCCTGAGAGACGAAGACACGGCCCTTTATTTCTGTGCGAGTGACGCC
CTCTACGGCACCAGTTGGTATTCCATCCTTGACTACTGGGGCCAGGGAAC
CCTGGTCACCGTCTCCTCCGCCTCCACCACGGCCCCCTCGGTT (SEQ ID NO: 89)
EVQLVQSGGDLVKPGGSLRLSCVASGFTFSRYRMAWVRQPPGRGLQWVAF
INSDGDRTTYSDTVKGRFTISRDNANDTLYLQMNSLRDEDTALYFCASDA
LYGTSWYSILDYWGQGTLVTVSSASTTAPSV

>#45
(SEQ ID NO: 90)
GGGGTGCAGCTGGTGGAGTCTGGGGGAGCCCTGGTGAAGCCTGCGGGGTC
CCTGAGACTGTCCTGTGTGACCTCTGGCTTCATCTTCACATACTATGGCA
TGAGCTGGGTCCGCCAGGCTCCTGGGAAGGGGCTGCAGTGGGTCGCGCAT
ATTTACAGTGATGGAAGTGGCACAACTTACGCAGACGCTGTGAAGGGGCG
ATTCACCATATCCAGGGACAACGCCAAGAACACAGTGCATCTGCAAATGA
ACAGCCTGAGAGCCGAGGACACGGCCGTGTATTACTGTGCGAGGGATATG
GACTGGGCGCGTGGGTCGACCTTGAGTACTGGGGCCAGGGCACCCTGGT
CACYGTCTCYTCAGCYTCCACCACGGCCCCYTCGGTT (SEQ ID NO: 91)
GVQLVESGGALVKPAGSLRLSCVTSGFIFTYYGMSWVRQAPGKGLQWVAH
IYSDGSGTTYADAVKGRFTISRDNAKNTVHLQMNSLRAEDTAVYYCARDM
DWGAWVDLEYWGQGTLVTVSSASTTAPSV

>#10
(SEQ ID NO: 92)
GAGGTGCAGCTGGTGGAGTCTGGGGGAGACCTGGTGAAGCCGGGGGGGTC
CCTGAGACTCTCCTGTGTAGCCTCTGGATTCACCTTCAGTAACTACGACA
TGACCTGGGTCCGCCAGGCTCCTGGGAAGGGGCTGCAGTGGGTCGCAGCT
GTTAGTTTTGTTGGAGGTAGTACATATTACACTGACGCTCTGAAGGGCCG
ATTCACCATCTCCAGAGACAACGCCAGGAACACAGTGTATCTGCAGATGA
ACGACCTGAGAGCCGAGGACACGGCTGTGTATTTCTGTGCGGACAATACT
TACAACTGGGGGTGGGGGCGGAATACTGGGGCCAGGGCACCCTGGTCAC
CGTCTCCTCAGCCTCCACCACGGCCCCCTCGGTT (SEQ ID NO: 93)
EVQLVESGGDLVKPGGSLRLSCVASGFTFSNYDMTWVRQAPGKGLQWVAA
VSFVGGSTYYTDALKGRFTISRDNARNTVYLQMNDLRAEDTAVYFCADNT
YNWGWGAEYWGQGTLVTVSSASTTAPSV

>#46
(SEQ ID NO: 94)
GAGTTGCAACTGGTGGAGTTTGGGGGAGACCTGGTGAAGCCTGGGGGGTC
CTTGAGACTGTCCTGTGTGGCCTCTGGATTCACCTTCAGTAGCTATGGCA
TGACCTGGGTCCGTCAGTCTCCAGGGAAGGGGCTACAGTGGGTCGCAGAT
ATTAGCAGTAGTGGAACCACATACCACGCAGACGCTGTGAAGGGCCGATT
TACCATCTCCAGAGACAACGCCAAGAACACGCTGTATCTGCAGATGAACA
GCCTGAGAGCCGAGGACACGGCCGTCTATTACTGTCAAAACAGGTACAG
GGATCCTTGCCACCGGACCACTGGGGCCAGGGCACCCTGGTCACCGTCTC
CTCAGCCTCCACCACGGCCCCCTCGGTT (SEQ ID NO: 95)
ELQLVEFGGDLVKPGGSLRLSCVASGFTFSSYGMTWVRQSPGKGLQWVAD
ISSSGTTYHADAVKGRFTISRDNAKNTLYLQMNSLRAEDTAVYYCAKVQ
GSLPPDHWGQGTLVTVSSASTTAPSV

>#11
(SEQ ID NO: 96)
GAGGTGCAACTGGTGGAATCTGGGGGAGACCTAGTGAAGCCTGGGGGGTC
CTTGAGACTGTCCTGTGTGGCCTCCGGATTCACCTTCAGTGACTATGGCA
TGATCTGGGTCCGTCAGTCTCCAGGGAAGGGGCTGCAGTGGGTCGCGGCT
CTTAGCAGTAGTGGAAGTAGCACATACTACGCAGACGCTGTGAAGGGCCG
ATTCACCATCTCCAGAGACAACGCCGAGAACACGCTGCATCTGCAGATGA
AGAGCCTGAGAGCCGAGGACACGGCCGTCTATTACTGTGCGAAGGGATTC
GGGGGACTATATATACGCATGGATAATATTGAATACTGGGGCCAGGGCAC
CCTGGTCGCCGTCTCCTCAGCCTCCACCACGGCCCCCTCGGTT (SEQ ID NO: 97)
EVQLVESGGDLVKPGGSLRLSCVASGFTFSDYGMIWVRQSPGKGLQWVAA
LSSSGSSTYYADAVKGRFTISRDNAENTLHLQMKSLRAEDTAVYYCAKGF
GGLYIRMDNIEYWGQGTLVAVSSASTTAPSV

>#23
(SEQ ID NO: 98)
GAGGTGCAGCTGGTGGAGTCTGGGGGAGACCTGGTGAAGCCTGGGGGGTC
CCTGAGAGTCTCCTGTGTGGCCTCTGGAATCACCCTCAGTAGTTACAGCA
TGCAATGGGTCCGTCAGGCTCCAGGAAAGGGGCTGCAGTGGGTCGCATAC
ATTAATAGTGGTGGAAGTACCACATACTACGCAGACGCTGTGAAGGGCCG
ATTCACCATCTCCAGAGACAACGCCGAGAACACGGTGTATCTGCAGATGA
ACAGCCTGAGACCCGAAGCACGGCCGTGTATTACTGTAGTCCCCCTGCC
CTTGAGTTCTGGGGCCAGGGCACCCTACTCACCGTCTCCTCAGCCTCCAC
CACGGCCCCCTCGGTT (SEQ ID NO: 99)
EVQLVESGGDLVKPGGSLRVSCVASGITLSSYSMQWVRQAPGKGLQWVAY
INSGGSTTYYADAVKGRFTISRDNAENTVYLQMNSLRPEDTAVYYCSPPA
LEFWGQGTLLTVSSASTTAPSV

>#35
(SEQ ID NO: 100)
GAGGTGCGTTTGGTGGAGTCTGGAGGAGACCTGGTGAAGCCGGGGGGGTC
CCTGAGACTTTCCTGTGTGGCCTCTGGATTCACCTTCAGTGACTATGACA
TGGACTGGGTCCGCCAGGCTCCAGGGAAGGGGCTGCAGTGGCTCTCAGAG
ATCAACAGCAGTGGAAGTAACACATTCTACGCAGACGCTGTGAGGGGCCG
ATTCACCGTCTCCAGAGACAATGCCAAGCATACGGTGTATCTGCAGATGA
ACGGCCTGAGAGCCGAGGACACGGCCGTGTATTATTGTCAAGGGGTTGG
GGCAAGAATACGTTCGCCCCTTTTGACTACTGGGGCCAGGGAACCCTGGT
CACCGTCTCCTCAGCCTCCACCACGGCCCCCTCGGTT (SEQ ID NO: 101)
EVRLVESGGDLVKPGGSLRLSCVASGFTFSDYDMDWVRQAPGKGLQWLSE
INSSGSNTFYADAVRGRFTVSRDNAKHTVYLQMNGLRAEDTAVYYCARGW
GKNTFAPFDYWGQGTLVTVSSASTTAPSV

>#47
(SEQ ID NO: 102)
GAATTGCAACTGGTGGAGTTTGGGGGAGACCTGGTGAAGCCTGGGGGGTC
CCTGAAACTCTCCTGTGTGGCCTCTGGATTCATGCTCGGTAATTACGAGA
TTTACTGGGTCCGCCAGGCTCCAGGGAGAGGTCTGGAGTGGGTCGCAAGG
ATCTATGAGACTGGAACTACCACATACTACGCAGAATCTGTGAATGGCCG
CTTCACCGTGTCCAGAAACAACGCCAATGACATTGCGTACCTACAGATGG
ACAGCCTGAGAGCCGACGACACGGCCGTATATTACTGTGCAAACGACCTA
ACTAGTACTCGGGGCCCCCTCTGGGGCCAGGGAACCCTGGTCACCGTCTC
CTCGGCCTCCACCACGGCCCCCTCGGTT (SEQ ID NO: 103)
ELQLVEFGGDLVKPGGSLKLSCVASGFMLGNYEIYWVRQAPGRGLEWVAR
IYETGTTTYYAESVNGRFTVSRNNANDIAYLQMDSLRADDTAVYYCANDL
TSTRGPLWGQGTLVTVSSASTTAPSV

>#12
(SEQ ID NO: 104)
GACGTGCAGCTGGTGGAGTCTGGGGGAGACTTGGTGAGGCCTGGGGGGTC
CCTGACACTCTCCTGTGTGGCCTCTGGATTCACCTTCACTAACTACGATA
TGTACTGGGTCCGCCAACCTCCAGGGAAAGGACTGGAGTGGGTCGCTAGG
ATTTATGAGACTGGAAGTACCACATACTATGCAGAAGTTGTAAAGGGCCG
ATTCACCATGTCCAGAGACAACGCCAAGAGCATGGCATACCTACAGATGA
ACAGCCTGAGAGCCGAGGACACGGCCGTTTATTACTGTGCGAATCTCACT
CCGCAGCGGGATATCTATGGACCAGGGGACTACTGGGGCCAGGGAACCCT
GGTCACCGTCTCCTCAGCCTCCACCACGGCCCCCTCGGTT (SEQ ID NO: 105)
DVQLVESGGDLVRPGGSLTLSCVASGFTFTNYDMYWVRQPPGKGLEWVAR
IYETGSTTYYAEVVKGRFTMSRDNAKSMAYLQMNSLRAEDTAVYYCANLT
PQRDIYGPGDYWGQGTLVTVSSASTTAPSV

>#36
(SEQ ID NO: 106)
GAGGAGCAACTGGTGGAGTTTGGGGGAGAGCTGGTGAAGCCTGCGGGGTC
CCTGAGACTGTCCTGTGTGGCCTCTGGATTTCCCTTCAGCAATTACGACA
TAAACTGGGTCCGCCAGGCTCCTGGGAAGGGGCTGCAGTGGGTCGCAGGT
ATTAAGAGTGATGGAAGTAGGACATGGTACGCAGACGCTGTGAAGGGCCG
ATTCACCATTTCCAGAGACAATGCCAAGAATACAGTGTATCTGCAGATGA
ACAGCCTGAGAGACGAGGACACGGCCGTGTATTATTGTGTGGACTTAGGA
TGGGGCCCTGATATGGACCACTGGGGCCCTGGCACCTCACTCTTCGTGTC
CTCAGCCTCCACCACGGCCCCCTCGGTT (SEQ ID NO: 107)
EEQLVEFGGELVKPAGSLRLSCVASGFPFSNYDINWVRQAPGKGLQWVAG
IKSDGSRTWYADAVKGRFTISRDNAKNTVYLQMNSLRDEDTAVYYCVDLG
WGPDMDHWGPGTSLFVSSASTTAPSV

>#48
(SEQ ID NO: 108)
GAGGTGCAGCTGGCGGAGTCTGGGGGAGACCTGGTGAAGCCTGGGGGGTC
CCTGAGACTGTCCTGTGTGGCCTCTGGATTCACCTTCAGTAGTTACTACA
TGTACTGGGTCCGCCAGGCTCCTGGGAAGGGGCTTCAGTGGGTCGCACGG
ATTAACACTGATGGAAGTAATACATACTACACAGACGCTGTGAAGGGCCG
CTTCACCATCTCCAGAGACAATGCCAAGAACACGCTGTATCTGCAGATGA
ACAGCCTGAGAGCCGAGGACACGGCTATGTATTTCTGTGCAAAGACCCGG
CCATACGGTACCTCCTGGCTGGGTTTTGACTTCTGGGGCCAGGGAACCCT
GGTCACCGTCTCCTCAGCCTCCACCACGGCCCCCTCGGTT (SEQ ID NO: 109)
EVQLAESGGDLVKPGGSLRLSCVASGFTFSSYYMYWVRQAPGKGLQWVAR
INTDGSNTYYTDAVKGRFTISRDNAKNTLYLQMNSLRAEDTAMYFCAKTR
PYGTSWLGFDFWGQGTLVTVSSASTTAPSV

VH chains from VH-VL Lambda HSA-7 Library

>λ#5
(SEQ ID NO: 110)
GAGGAGCAGCTGGTGGAGCTTGGGGGAGACCTGGTGAAGCCTGGGGGGTC
CTTGAGACTGTCCTGTGTGGCCTCTGAATCGACCTTCGGTGTCTTTGTCA
TGACCTGGGTCCGTCAGTCTCCCGGGAAGGGTCTGCAGTGGGTCGCTGAT
TATAGTAGTACTGGAAGTACCTACTACATGGACGCTGTGAGGGGCCGCTT
CACCATCTCCAGAGACAACGCCAAGAACACGCTGTATCTTCAGATGAACA
GCCTGAGAGCCGAAGACACGGCCGTATATTACTGTGCGAGCCCCCAGGAG
ATGGGACTTTTCACCGCCTCCTGGGGCCAGGGAACCCTGGTCACCGTCTC
CTCAGCCTCCACCACGGCCCCCTCGGTT (SEQ ID NO: 111)
EEQLVELGGDLVKPGGSLRLSCVASESTFGVFVMTWVRQSPGKGLQWVAD
YSSTGSTYYMDAVRGRFTISRDNAKNTLYLQMNSLRAEDTAVYYCASPQE
MGLFTASWGQGTLVTVSSASTTAPSV

>λ#6
(SEQ ID NO: 112)
GAGGTGCAGCTGGTGGAGTCTGGGGGAGACCTGGTGAAGCCTGCGGGGTC
CCTGAGACTGTCCTGTGTGGCCTCCGGATTCACCTTCAGTAGCTCCACCA
TGGCCTGGGTACGCCAGTCTCCTGGGAAGGGGCTGCAGTTGGTCGCTGCT
ATTAACAGAGGTGGAAATAACACATATTACTCAGACGCTGTAAAGGGCCG
ATTCACCATCTCCAGAGACAATGCCAAGAATACAGTGTATCTACAGATGA
ACAGCCTCAGAGACGAGGACACGGCCATGTATTATTGTGCAAAGGGGTGG
GGAAGTGACGACCTTGAGTACTGGGGCCAGGGCACCCTGGTCACCGTCTC
CTCAGCCTCCACCACGGCCCCCTCGGTT (SEQ ID NO: 113)
EVQLVESGGDLVKPAGSLRLSCVASGFTFSSSTMAWVRQSPGKGLQLVAA
INRGGNNTYYSDAVKGRFTISRDNAKNTVYLQMNSLRDEDTAMYYCAKGW
GSDDLEYWGQGTLVTVSSASTTAPSV

>λ#7
(SEQ ID NO: 114)
GAGGGGCAGCTGGCGGAGTCTGGGGGAGCCCTGGTAAAACCTGGGGCATC
CCTGAGACTCTCCTGTGTGGCCTCTGGATTCACCTTCAGTGACTATGACA
TGAGTTGGGTCCGCCAGGCTCCAGGGAAGGGACTACAGTGGGTCGCAGTT
ATTTCGTCTGATGCAAGTACCACATACACCGCAGACGTTGTGAGGGGCCG
ATTCACCATCTCCAGAGACAACGCCAAGAATTCGATGTATCTGGAGATGA
ATGGCCTGAGAGACGAGGACACAGCCGTATATTATTGTGGGAAGGGATCC
CTGACTAGTAACTGGTGGACGGATGGTATGGACTACTGGGGCCCTGGCAC
TTCACTCTTCGTGTCCTCAGCCTCCACCACGGCCCCCTCGGTT (SEQ ID NO: 115)
EGQLAESGGALVKPGASLRLSCVASGFTFSDYDMSWVRQAPGKGLQWVAV
ISSDASTTYTADVVRGRFTISRDNAKNSMYLEMNGLRDEDTAVYYCGKGS
LTSNWWTDGMDYWGPGTSLFVSSASTTAPSV

>λ#8
(SEQ ID NO: 116)
GAGGTGCAGCTGGTGGAGTCTGGGGGAGACCTGGTGAAGCCTGCGGGGTC
CCTGAGACTGTCCTGTGTGGCCTCTGGATTCACCTTCAGTAGCTACAGTA
TGAGCTGGGTACGCCAGGCTCCTGGGAAGGGGCTGCAATTGGTCGCAGGT
ATTATCAGCGGTGGAAGTAGCACATACTACACAGACGCTGTGAAGGGCCG
ATTCACCGTCTCCAGAGACAACGCCAAGAACACAGTGTTTCTGCAGATGA
ACAGCCTGAGAGCCGAGGACACGGCCATGTATTACTGTGCAAAGGAGAAG
TATACATATGGATACGGGGCCGGACTTGAGTACTGGGGCCAGGGCACCCT
GGTCACCGTCTCCTCAGCCTCCACCACGGCCCCCTCGGTT (SEQ ID NO: 117)
EVQLVESGGDLVKPAGSLRLSCVASGFTFSSYSMSWVRQAPGKGLQLVAG
IISGGSSTYYTDAVKGRFTVSRDNAKNTVFLQMNSLRAEDTAMYYCAKEK
YTYGYGAGLEYWGQGTLVTVSSASTTAPSV

>λ#14
(SEQ ID NO: 118)
GGGGTGCAGCTGGTGGAGTCTGGGGGAGACCTGGTGAAGCCTGGGGGGTC
CTTGAGATTGTCCTGTGTAGTCTCTGGAATCACCATCAATACATATACCT
ATGGCATGAGTTGGGTCCGTCTGTCCCCAGGGAGGGGACTGCAGTCCGTC
GCTCATCTTAGTCGGGCTGGTTACACATACTACGCGGACGCTGTAAAGGG
CCGATTCACCATCTCCAGAGACAACGGCAAGAGTACGCTATATTTACAGA
TGAACAGCCTGACAGTCGAGGACACGGCCGTATATTATTGTGTGAAGGCC
CCCCTTAGGTCCGGTGGCGTCGACTACTGGGGCCAGGGCACCCTGGTCAC
CGTCTCCTCAGCCTCCACCACGGCCCCCTCGGTT (SEQ ID NO: 119)
GVQLVESGGDLVKPGGSLRLSCVVSGITINTYTYGMSWVRLSPGRGLQSV
AHLSRAGYTYYADAVKGRFTISRDNGKSTLYLQMNSLTVEDTAVYYCVKA
PLRSGGVDYWGQGTLVTVSSASTTAPSV

>λ#15

(SEQ ID NO: 120)
GAGGGGCAGCTGGCGGAGTCTGGGGGAGACCTGGTGAAGCCTGGGGGGTC
CCTGAGACTCTCCTGTGTAGCCTCTGGATTCACCTTCAGTAACTACGACA
TGACCTGGGTCCGCCAGGCTCCTGGGAAGGGGCTGCAGTGGGTCGCAGCT
ATTAGCTATGATGGAAGTAGTACATATTACACTGACGCTGTGAAGGGCCG
ATTCACCATCTCCAGAGACAACGCCAGGAACACACTGTATCTGCAGATGA
ACAGCCTGAGAGCCGAGGACACGGCTGTATATTACTGTGTCCCTACCACC
TGTACTGATGATTACTGTCTCTCTTTTGCCTACTGGGGCCAGGGAACCCT
GGTCACCGTCTCCTCAGCCTCCACCACGGCCCCCTCGGTT (SEQ ID NO: 121)
EGQLAESGGDLVKPGGSLRLSCVASGFTFSNYDMTWVRQAPGKGLQWVAA
ISYDGSSTYYTDAVKGRFTISRDNARNTLYLQMNSLRAEDTAVYYCVPTT
CTDDYCLSFAYWGQGTLVTVSSASTTAPSV

>λ#16

(SEQ ID NO: 122)
GGGGTGCAGCTGGTGCAATCTGGGGGAGACCTGGTGAAGCCTGGGGGGTC
CTTGAGACTCTCCTGTGTGGCCTCTGGTTTCACCTTCAGTAGCAACCACA
TGGACTGGGTCCGCCAGGCTCCAGGGAAGGGGCTGCAGTGGCTCACACGG
ATTCGCAGTGATGGAGACATAGGCTACGCAGATGTTGTGAAGGGCCGCTT
CACCATCTCCAGAGACAACGCCAAGAACACACTGTATCTGCAGATGGACA
GCCTGAGATCTGAGGACACGGCTGTATATTATTGTGCGAGACACTGGGAT
CTGGACTATTGGGGCCAGGGAACCCGGGTGACCGTCTCCTCAGCCTCCAC
CACGGCCCCCTCGGTT (SEQ ID NO: 123)
GVQLVQSGGDLVKPGGSLRLSCVASGFTFSSNHMDWVRQAPGKGLQWLTR
IRSDGDIGYADVVKGRFTISRDNAKNTLYLQMDSLRSEDTAVYYCARHWD
LDYWGQGTRVTVSSASTTAPSV

>λ#21

(SEQ ID NO: 124)
GACGTGCAGCTGGTGGAGTCTGGGGGAGACCTGGTGAAGCCTGGGGGGTC
CCTGAGACTCTCCTGTGTGGCCTCTGGATTCACCTTCAATAATTATGAGA
TCTACTGGGTCCGCCAGGCTCCAGGGAAAGGACTGGAGTGGGTCGCAAAG
ATCTATGAGAGTGGACGTACCACATCCTACGCAGAAGCTGTAAAGGGCCG
ATTCACCATTTCCAGAGACAACGGCGAGAACATGGCGTCTTTGCAGATGA
ATAGCCTGAGAGCCGAGGACACGGCCGTGTATTACTGTGCGAGTGCTCTC
GACGGTAGCCTTTATCCCAATTACTGGGGCCAGGGAACCCTGGTCACCGT
TTCCTCCGCCTCCACCACGGCCCCCTCGGTT (SEQ ID NO: 125)
DVQLVESGGDLVKPGGSLRLSCVASGFTFNNYEIYWVRQAPGKGLEWVAK
IYESGRTTSYAEAVKGRFTISRDNGENMASLQMNSLRAEDTAVYYCASAL
DGSLYPNYWGQGTLVTVSSASTTAPSV

>λ#23

(SEQ ID NO: 126)
GAGGTACAACTGGTGCAGTCTGGGGGAGACCTGGTGAAGCCTGGGGGGTC
CCTGAGACTCTCCTGTGTGGCCTCTGGATTCACCCTCAGTAACTTCGACA
TGCAATGGGTCCGTCAGGCTCCAGGGAAGGGGCTGCAATGGGTCGCTTAC
ATTAATAGTGGTGCAAATACCACATACTACGCAGACGCTGTGAGGGGCCG
ATTCACCGTCTCCAGAGACAACGCCAAGAACACACTCTATCTGCAGATGA
ACAGCCTGACAGCCGAGGACACGGCCGTTTATTACTGTACTGATCGGGGG
GGACACTGGGGCCAGGGCACCCTGGTCACCGTCTCCTCAGCCTCCACCAC
GGCCCCCTCGGTT (SEQ ID NO: 127)
EVQLVQSGGDLVKPGGSLRLSCVASGFTLSNFDMQWVRQAPGKGLQWVAY
INSGANTTYYADAVRGRFTVSRDNAKNTLYLQMNSLTAEDTAVYYCTDRG
GHWGQGTLVTVSSASTTAPSV

>λ#29

(SEQ ID NO: 128)
CAACTGGTGGAGCTTGGGGGAGACCTGGTGAAGCCTGCGGGTCCCTGAG
ACTGTCCTGTGTGGCCTCTGGATTCACCTTCAGTTCGTACAGCATGAGCT
GGGTACGCCAGGCTCCTGGGAAGGGGCTGCAGTTGGTCGCAGGTATTAAC
AGTGGTGGAACAAGTATATATTATACAGACGTTGTGAAGGGCCGATTCAC
CATCTCCAGAGACAATGCCAAGAACACAGTTTATCTGCAGATGAACAGCC
TGAGAGCCGAGGACACGGCTATGTATTACTGTGTAAAGGACGCGTACTAC
TGTAATTCTTATTACTGTCCCGCGACTTATGGTTGGGACTACTGGGGCCC
AGGCACTTCAATATTCGTGTCCTCCGCCTCCACCACGGCCCCCTCGGTT (SEQ ID NO: 129)
QLVELGGDLVKPAGSLRLSCVASGFTFSSYSMSWVRQAPGKGLQLVAGIN
SGGTSIYYTDVVKGRFTISRDNAKNTVYLQMNSLRAEDTAMYYCVKDAYY
CNSYYCPATYGWDYWGPGTSIFVSSASTTAPSV

>λ#30

(SEQ ID NO: 130)
GAGGGGCAGCTGGCGGAGTCTGGGGGAGACCTGGTGAAGCCTGGGGGGTC
CCTGAGACTGTCCTGTGTGGCCTCTGGATTCACCTTCAGTGACTATTATA
TGTATTGGGTCCGTCTGGCTCCAGGGAAGGGGCTGCAGTGGGTCGCACGG
ATTAAGAATGATGGAACTTACACATCCTACGCAGACGCTGTGGAGGGCCA
CTTCACCATCTCCAGAGACAATGCCAAGAACACAGTGTATCTGCAGATGA
ACAGCCTGAGAGCCGAGGACACGGCCATGTATTACTGTGGACAATGGGA
GTTGTTCTAGTGGTTGGCCCTTGGGAATACTTGGGCCAGGGCACCCTGGT
CACCGTCTCCTCAGCCTCCACCACGGCCCCCTCGGTT (SEQ ID NO: 131)
EGQLAESGGDLVKPGGSLRLSCVASGFTFSDYYMYWVRLAPGKGLQWVAR
IKNDGTYTSYADAVEGHFTISRDNAKNTVYLQMNSLRAEDTAMYYCGQWG
VVLVVGPWEYLGQGTLVTVSSASTTAPSV

>λ#32

(SEQ ID NO: 132)
GAGGTGAGTTTGGTGGAGTCTGGGGGAGACCTGGTGAAGCCTGCGGGGTC
CCTGAGACTGTCCTGTGTGGCCTCTGGATTCACCTTCAGTGACTACGACA
TGTACTGGGTCCGCCAGGCTCCGGGGAAGGGGCTGCAGTGGGTCGCAGTT
ATCAGTTATGGAGGAATTGACACATACAGTGACACTGTGAAGGGCCGATT
CACCATCTCCAGAGACAACGCCAGGAACACAGTATATTTGCAGATGAACA

GTCTGAGAGCCGAGGACACGGCTGTGTATTTCTGTGCGAGGTCTTCCTTC
AGAACTGACCTTAACTATTGGGGCCAGGGCACCCTGGTCATTGTCTCCTC
AGCCTCCACCACGGCCCCCTCGGTTA (SEQ ID NO: 133)
EVSLVESGGDLVKPAGSLRLSCVASGFTFSDYDMYWVRQAPGKGLQWVAV
ISYGGIDTYSDTVKGRFTISRDNARNTVYLQMNSLRAEDTAVYFCARSSF
RTDLNYWGQGTLVIVSSASTTAPSV

>λ#38
(SEQ ID NO: 134)
GAGGTGCAGCTGGTGGAGCTTGGGGGAGACCTGGTGAAGCCTGGGGGGTC
CTTGAGACTGTCCTGTGTGGCCTCTGGATTCACCTTCAGTAACTATGGCA
TGATCTGGGTCCGTCAGTCTCCAGGGAAGGGGCTGCAGTGGGTCGCAGCT
ATTAGCGAAAATGGAATTAGTACATACTACGCAGACGCTGTGAAGGGCCG
ATTCACCATCTCCAAAGACAACGCCAAGAGCACGCTGTATCTGCAGATGA
ACGCCCTGAGAGCCGAGGACACGGCCGTATATTACTGTGGGAAGGCCCAG
AAAATAGTAGCAACTGGAAATGAGTACTGGGGCCAGGGCACCCTGGTCAC
CGTCTCcTCAGCCTCCACCACGGCCCCCTCGGTT (SEQ ID NO: 135)
EVQLVELGGDLVKPGGSLRLSCVASGFTFSNYGMIWVRQSPGKGLQWVAA
ISENGISTYYADAVKGRFTISKDNAKSTLYLQMNALRAEDTAVYYCGKAQ
KIVATGNEYWGQGTLVTVSSASTTAPSV

>λ#39
(SEQ ID NO: 136)
GAGGTGCAGCTGGTGGAGACTGGGGGAGATTTGGTGAAACCTGGGGGGTC
CCTGAGAATTTCCTGTGTGGCCTCTGGGTTCGACTTTCATTCATCCCACA
TGACCTGGGTCCGCCAGACTCCAGGGAAGGGACTGCAGTGGGTCGCAAGT
ATTAACAGCGGTAGAGGAACAGGCTACGCAGACGCTGTGAAGGGCCGATT
CACCATCTCCAGAGACAACGCCAAGAATACAGTGTATCTGCGGATGAACA
GCCTGACAGCCAAGGACACGGCCGTGTATTACTGTGCGAAGGGGCGTATC
GCCGTTGAGTCCTGGGGCCAGGGCACCCTGGTCACCGTCTCCTCAGCCTC
CACCACGGCCCCCTCGGTT (SEQ ID NO: 137)
EVQLVETGGDLVKPGGSLRISCVASGFDFHSSHMTWVRQTPGKGLQWVAS
INSGRGTGYADAVKGRFTISRDNAKNTVYLRMNSLTAKDTAVYYCAKGRI
AVESWGQGTLVTVSSASTTAPSV

>λ#47
(SEQ ID NO: 138)
GAGGGGCAGCTGGCGGAGTCTGGGGGAGACCTGGTGAAGCCTGGGGGGTC
CCTGAGACTCTCCTGTGTAGGCTCTGGATTCACCTTCAGTACCTATGTCA
TGACCTGGGTCCGCCAGGCTCCTGGGAAGGGGCCGCAGTGGGTCGCAAGT
ATTAACAGTGGTGGAACTAGCGCTACCTACGCAGACGCTGTGAAGGGCCG
ATTCACCATCTCCAGAGACAACGCCAAAAACACACTTTATCTACAGATAA
ACAGCCTGAGAGCCGAGGACACGGCCGTATATCACTGTGCGGGCCTTTAT
ATGTATAGTCCATCTCGCGCGCTTGAATTCTGGGGCCAGGGCACCCTGGT
CACCGTCTCCTCAGCCTCCACCACGGCCCCCTCGGTT (SEQ ID NO: 139)
EGQLAESGGDLVKPGGSLRLSCVGSGFTFSTYVMTWVRQAPGKGPQWVAS
INSGGTSATYADAVKGRFTISRDNAKNTLYLQINSLRAEDTAVYHCAGLY
MYSPSRALEFWGQGTLVTVSSASTTAPSV

>λ#53
(SEQ ID NO: 140)
GAGGAGCAGCTGGTGGAGCTTGGGGGAGACCTGGTGAAGCCTGGGGGGTC
CCTGAGACTGTCCTGTGTGGCCTCTGGATTCACCTTCAGTAGCTATTACA
TGTTCTGGGTCCGCCAGGCTCCAGGGAAGAGACTACAATGGGTCGCAGAT
ATTACCTATGCTGAACCGTATATTACGCAGACATTACAGAGGGCCGATT
CACCATTTCCAGAGACAACGCCAAAAATACGGTGTATCTGCAGATGGCCA
GCCTGACGGCCGAGGACACGGCCGTCTATTACTGTACGAAATTAGGGGGT
TCTAGTGCCTGGGGGGACTATTGGGGCCCTGGCACGTCAGTCTTCGTGTC
GTCAGCCTCCACCACGGCCCCCTCGGTT (SEQ ID NO: 141)
EEQLVELGGDLVKPGGSLRLSCVASGFTFSSYYMFWVRQAPGKRLQWVAD
ITYAGTVYYADITEGRFTISRDNAKNTVYLQMASLTAEDTAVYYCTKLGG
SSAWGDYWGPGTSVFVSSASTTAPSV

>λ#56
(SEQ ID NO: 142)
GAAGAGCAACTGGTGGAGCTTGGGGGAGACCTGGTGAAGCCTGGGGGGTC
CTTGAGACTGTCCTGTGTGGCCTCNGGATTCACCTTCAATAACTATGGCA
TGAGCTGGGTCCGTCAGTCTCCAGGGAAGGGGCTGCAGTGGGCCGCAACT
ATTAGTCTTCGTGGAAGTACCACATACTACGCAGACGCTGTGAAGGGCCG
ATGCACCATCTCCAGAGACGACGCCAAGAACACACTGTATCTGCAGATGA
GCAGCCTGAGAGCCGAAGACACGGCCGTGTATTACTGTGCGAAGGGAGCG
GACGCTACCTATTATTATAATATGGAGGACTGGGGCCCTGGCACCTCACT
CTTCGTGTCNTGGGCNTCCACCACGGCCCCCTCGGTT (SEQ ID NO: 143)
EEQLVELGGDLVKPGGSLRLSCVASGFTFNNYGMSWVRQSPGKGLQWAAT
ISLRGSTTYYADAVKGRCTISRDDAKNTLYLQMSSLRAEDTAVYYCAKGA
DATYYYNMEDWGPGTSLFVSWASTTAPSV

>λ#61
(SEQ ID NO: 144)
GAGGAGCAGCTGGTGGAGCTTGGGGGAGACCTGGTGAAGCCTGGGGGGTC
CCTGAGACTGTCCTGTGTGGCCTCTGGATTCACCTTCAGTAGCTATTACA
TGTTCTGGGTCCGCCAGGCTCCAGGGAAGAGACTACAATGGGTCGCAGAT
ATTACCTATGCTGAACCGTATATTACGCAGACATTACAGAGGGCCGATT
CACCATTTCCAGAGACAACGCCAAAAATACGGTGTATCTGCAGATGGCCA
GCCTGACGGCCGAGGACACGGCCGTCTATTACTGTACGAAATTAGGGGGT
TCTAGTGCCTGGGGGGACTATTGGGGCCCTGGCACGTCAGTCTTCGTGTC
GTCAGCCTCCACCACGGCCCCCTCGGTT (SEQ ID NO: 145)
EEQLVELGGDLVKPGGSLRLSCVASGFTFSSYYMFWVRQAPGKRLQWVAD
ITYAGTVYYADITEGRFTISRDNAKNTVYLQMASLTAEDTAVYYCTKLGG
SSAWGDYWGPGTSVFVSSASTTAPSV

>λ# 63

(SEQ ID NO: 145)
GAGGGGCAGCTGGCGGAGTCTGGGGGAGACCTGGTGAAGCCTGCGGGGTC
CCTGAGACTCTCCTGTGTAGCCTCTGGATTCACCTTCAGTGACTACGACA
TGAGTTGGGTCCGCCAGGCTCCTGGGAAGGGGCTGCAGTGGGTCGCAGGT
ATTAGTTATGATGGAAGGAGCACATACTACACTGACGCTGTGAAGGGCCG
ATTCACCGTGTCCAGAGACAACGCCAGGAACACGTTGTTTCTGCAGATGA
ACAGCCTGAGAGCTGAGGACACGGCCATGTATTATTGTGCGAAGGTCGAC
TGGTTTACTAGGAATTGGTACATTGACTTCTGGGGCCAGGGCACCCTGGT
CACCGTCTCCTCAGCCTCCACCACGGCCCCCTCGGTT (SEQ ID NO: 146)
EGQLAESGGDLVKPAGSLRLSCVASGFTFSDYDMSWVRQAPGKGLQWVAG
ISYDGRSTYYTDAVKGRFTVSRDNARNTLFLQMNSLRAEDTAMYYCAKVD
WFTRNWYIDFWGQGTLVTVSSASTTAPSV

>λ#64

(SEQ ID NO: 147)
GAGGTGCCTTTGGTGGAATCTGGGGGAGGGTTGGTGAAGCCGGGGGGCTT
CCTGAGACTGTCCTGTGTGGCCTCCGGATTCACCTTCAGTAACTCCACCA
TGACCTGGCTACGCCAGGCTCCTGGGAAGGGGCTGCAGTTGGTCGCATAT
ATTTCCTATGGTGGAGGTACCACATACTATGTAGAGGATGTTAAGGGCCG
GTTCACCATCTCCAGAGACAACGCCAAGAACACGCTCTCTCTGCAGATGG
ACAGCCTGAGAGCCGAGGACACGGCCGTATATTTTTGTGCGGCACAGAGT
TCTAGTGGTTGGGGCTATTTCGTCAGTGAGTACTGGGGCCAGGGCACCCT
GGTCACCGTCTCATCGGCCTCCACCACGGCCCCCTCGGTTT (SEQ ID NO: 148)
EVPLVESGGGLVKPGGFLRLSCVASGFTFSNSTMTWLRQAPGKGLQLVAY
ISYGGGTTYYVEDVKGRFTISRDNAKNTLSLQMDSLRAEDTAVYFCAAQS
SSGWGYFVSEYWGQGTLVTVSSASTTAPSV

>λ#69

(SEQ ID NO: 149)
GAGGTGCAGCTGGTGGAGTCTGGGGGAGACCTGGTGAAGCCTGGGGGGTC
CCTAAGACTCTCCTGTGCGGCCTCTGGATTCACCTTCAGTACCTACTTCA
TGTCCTGGGTCCGCCAGGCTCCAGGGAAGGGGCTTCAGTGGGTCGCACGG
ATAACCGAGGATGGAAGTAGCGCAAACTACGCAGACGCTGTGAGGGGCCG
ATTCACCATCTCCAGAGACAACGCCGAAAACACGCTCTATCTTCAGATGA
ACAGCCTGAGAGCCGACGACACGGCCGTGTATTACTGTGTGAAACTGGTA
CCTGGTTCTTATCGTCTCTTCTATGGTGTGGACTACTGGGGCCCTGGCAC
CTCACTCTTCGTGTCCTCGGCCTCCACCACGGCCCCCTCGGTT (SEQ ID NO: 150)
EVQLVESGGDLVKPGGSLRLSCAASGFTFSTYFMSWVRQAPGKGLQWVAR
ITEDGSSANYADAVRGRFTISRDNAENTLYLQMNSLRADDTAVYYCVKLV
PGSYRLFYGVDYWGPGTSLFVSSASTTAPSV

>λ#70

(SEQ ID NO: 151)
GAGGTACAGCTGGTGCAGTCTGGGGGAGACCTGGTAAACCCTGGGGGGTC
CTTGAGACTGTCCTGTCTGGCCTCTGGATTCGCCTTTAGTTCTCATGCCA
TGAGCTGGGTCCGTCAGTCTCCAGGGAAGGGGCTGCAGTGGGTCGCAGCC
ATTTGGAATAATGGACATACTGCACATTACACCGACGCTGTCAAGGGCCG
ATTCACCATCTCCAGGGACGACGCCAAGAACACGGTATATCTCCAGATGA
ACAGCCTGAGAGCCGAGGACACAGCCGTATATTACTGTGTGGCCCGGGGG
GGTAATTGGCAACCTTTTGACTACTGGGGCCAGGGAACCCAGGTCACCGT
CTCCTCAGCCTCCACCACGGCCCCCTCGGTT (SEQ ID NO: 152)
EVQLVQSGGDLVNPGGSLRLSCLASGFAFSSHAMSWVRQSPGKGLQWVAA
IWNNGHTAHYTDAVKGRFTISRDDAKNTVYLQMNSLRAEDTAVYYCVARG
GNWQPFDYWGQGTQVTVSSASTTAPSV

>λ#71

(SEQ ID NO: 153)
GAGGGGCAGCTGGCGGAGTCTGGGGGAGACCTGGTGAAGCCTGCGGGGTC
CCTGAGACTCTCCTGTGTAGCCTCTGGATTCACCTTCAGTGACTACGACA
TGAGTTGGGTCCGCCAGGCTCCTGGGAAGGGGCTGCAGTGGGTCGCAGGT
ATTAGTTATGATGGAAGGAGCACATACTACACTGACGCTGTGAAGGGCCG
ATTCACCGTGTCCAGAGACAACGCCAGGAACACGTTGTTTCTGCAGATGA
ACAGCCTGAGAGCTGAGGACACGGCCATGTATTATTGTGCGAAGGTCGAC
TGGTTTACTAGGAATTGGTACATTGACTTCTGGGGCCAGGGCACCCTGGT
CACCGTCTCCTCAGCCTCCACCACGGCCCCCTCGGTT (SEQ ID NO: 154)
EGQLAESGGDLVKPAGSLRLSCVASGFTFSDYDMSWVRQAPGKGLQWVAG
ISYDGRSTYYTDAVKGRFTVSRDNARNTLFLQMNSLRAEDTAMYYCAKVD
WFTRNWYIDFWGQGTLVTVSSASTTAPSV

>λ#78

(SEQ ID NO: 155)
GAGGTGCGTTTGGTGGAGTCTGGGGGAGACCTGGTGAAGCCTGGGGGGTC
CCTGAGACTCTCCTGTGTGGCCTCTGGATTCACCTTCAGTAGATACGGCA
TGAGTTGGGTCCGCCAGGCTCCTGGGAAGGGGCTGCAGTGGGTCACGATT
ATTAACCATGATGGAAGTAGCACATTCTACACTGACGCTGTGAAGGGCCG
ATTCACCATCTCCAGAGACAACGCCAGGAACACAGTGGTTCTGCAGATGA
GCAGCCTGAGAGCCGAGGACACGGCTGTGTATTACTGTGTGGCTTCGGGT
TCTTTTGGTCATTGGGGCCAGGGCACCCTGGTCACTGTCTCCTCAGCCTC
CACCACGGCCCCCTCGGTT (SEQ ID NO: 156)
EVRLVESGGDLVKPGGSLRLSCVASGFTFSRYGMSWVRQAPGKGLQWVTI
INHDGSSTFYTDAVKGRFTISRDNARNTVVLQMSSLRAEDTAVYYCVASG
SFGHWGQGTLVTVSSASTTAPSV

>λ#79

(SEQ ID NO: 157)
GAGGTGCAGCTGCTGGAGTATGGGGGAGACCTGGTGAAGCCTGGGGGGTC
CCTGAGACTCTCCTGTGTGGCCTCTGGATTCACCTTCAGTCAGTACGAAA
TGTACTGGGTCCGCCAGGCTCCAGGGAAGGGCTGGAGTGGGTCGCAAGG
ATTTATGGGAATGGAAAGACCACATACTATGGAGAATCTGTAAAGGGCCG
ATTCACCATTTCCAGAGACGACGCCAACAACATGGCGTTTCTGCAGATGA

ACAGCCTGCGAGCCGAGGACACGGCCGTATATTACTGTGCGAGTGGTAGA

TATTTCGGTAGTTTCGCCCATCCCAGTTTTGACTATTGGGGCCAGGGAAC

CCTGGTCACCGTCTCCTCAGCCTCCACCACGGCCCCCTCGGTT (SEQ ID NO: 158)
EVQLLEYGGDLVKPGGSLRLSCVASGFTFSQYEMYWVRQAPGKGLEWVAR

IYGNGKTTYYGESVKGRFTISRDDANNMAFLQMNSLRAEDTAVYYCASGR

YFGSFAHPSFDYWGQGTLVTVSSASTTAPSV

>λ#80

(SEQ ID NO: 159)
GAGGTACGATTGGTGGAATCTGGGGGAGACCTGGTGAAGCCTGGGGGGTC

CCTGAGACTCTCCTGTGTGGCCTCTGGATTCACCTTCAGTGAATATAACA

TGGGCTGGGTCCGCCAGGGTCCAGGGAAGGGACTGCAATGGGTCGCGTGG

ATTTATGCCAGTGGAACTAGTACAAGGTATGCAGACACTGTGCAGGGCCG

CCTCACCATATCCAGAGACAACGCCAAGAACACGTTGTATCTACAGATGG

ACAGGTTGAGAGGTGAAGCACGGCTGTGTATTATTGTGCGAGGAGTCAT

CATACATTTGGATTTGGATACAACCTTGACTATTGGGGCCAGGGCAACCC

TGGTCACCGTCTCCTCAGCCTCCACCACGGCCCCCTCGGTT (SEQ ID NO: 160)
EVRLVESGGDLVKPGGSLRLSCVASGFTFSEYNMGWVRQGPGKGLQWVAW

IYASGTSTRYADTVQGRLTISRDNAKNTLYLQMDRLRGEDTAVYYCARSH

HTFGFGYNLDYWGQGNPGHRLLSLHHGPLG

>λ#85

(SEQ ID NO: 161)
GAGGTGCAGCTGCTGGAGACTGGGGGAGACCTGGTGAAGCCTGGGGAGTC

CCTGAGACTTTCCTGTGTGGCCTCTGGATTCAGTTTTAGTAATTATTACA

TGACCTGGGTCCGCCAGGCTCCAGGGAAGGGTCTTCAGTGGGTCGGATAT

ATTGACAATGATGGCAGCGGCACGGACTATGCAGACTCTGTGAAGGGCCG

ATTCACCATCTCCAGAGACAACGCCAGGAACACGCTATATCTTCAGATGA

CCAGCCTGAGAGTCGAGGATACGGCCGTTTATTACTGTGCGAGTGACCTT

TGGGGACACTACGGTAGTTATCGTGGTCCCAGACTACTTCTTGACAACTG

GGGACAGGGAACCCTGGTCACCGTCTCNTCGGCCTCCACCACGGCCCCCT

CGGTT (SEQ ID NO: 162)
EVQLLETGGDLVKPGESLRLSCVASGFSFSNYYMTWVRQAPGKGLQWVGY

IDNDGSGTDYADSVKGRFTISRDNARNTLYLQMTSLRVEDTAVYYCASDL

WGHYGSYRGPRLLLDNWGQGTLVTVSSASTTAPSV

>λ#87

(SEQ ID NO: 163)
GAGGTGAGGTTGGTGGAGTCTGGGGGAGACCTGGTGAAGCCTGCGGGGTC

CCTGAGACTGTCCTGTGTGGCCTCTGGATTCACCTTCAGTAGCTACACCA

TGAGCTGGGTACGCCAGGCTCCTGGGAAGGGCCTGCAGTTGGTCGCTAAT

ATTAAGAGCGGTGGAACTTACACATACTACAGACGCTGTGCAGGGCCG

ATTCACCATCTCCAGAGACAATGCCAAGAACACAGTGTATCTCCAGATGA

ACAGCCTGAGAGCCGAGGACACGGCCATGTATTACTGTACAAAGGAGGGC

TACTACGATACTTTCTTTGACTGCTGGGGCCAGGGCACCCTGGTCACCGT

CTCCTCAGCCTCCACCACGGCCCCCTCGGTT (SEQ ID NO: 164)
EVRLVESGGDLVKPAGSLRLSCVASGFTFSSYTMSWVRQAPGKGLQLVAN

IKSGGTYTYYTDAVQGRFTISRDNAKNTVYLQMNSLRAEDTAMYYCTKEG

YYDTFFDCWGQGTLVTVSSASTTAPSV

>λ#93

(SEQ ID NO: 165)
GAGTTGCAACTGGTGGAGCTTGGGGGAGACCTGGTGAAGCCTGGGGGATC

CCTGACACTGTCCTGTGTGACCTCTGGATTCACCTTCAGTGACTATGCCA

TGACCTGGGTCCGCCAGGCTCCAGGGAAGGGGCTGCAGTGGGTCGCATAC

ATTAACACTGGTGGGACTACAACATACTACGCAGATGCTGTGAAGGGCCG

CTTCACCATTTCCAGAGACGATGCCAGGAACACACTGTATCTGCAAATGA

ACAGCCTGAGATCCGAGGATACAGCCGTTTATTACTGTCTGGGGGCTACG

GTGGCTTATTTCTATGGTCTGGACTACTGGGGCCATGGCACCTCAGTCTT

CGTGTCCTCAGCCTCCACCACGGCCCCCTCGGTT (SEQ ID NO: 166)
ELQLVELGGDLVKPGGSLTLSCVTSGFTFSDYAMTWVRQAPGKGLQWVAY

INTGGTTTYYADAVKGRFTISRDDARNTLYLQMNSLRSEDTAVYYCLGAT

VAYFYGLDYWGHGTSVFVSSASTTAPSV

>λ#95

(SEQ ID NO: 167)
GAGGGGCAGCTGGCGGAGTCTGGGGGAGACCTGGTGAAGCCTGGGGGGTC

CTTGAGACTGTCCTGTGTGGCCTCTGGATTCACCTTCAGTAAGGACATGA

CCTGGGTCCGTCAGTCTCCAGGGCAGGGCCTGCAATGGGTCGCAGATATC

ACCCCTGATGGAAGGACGGACTATTCAGACGCTGTCAGGGGCCGATTCAC

CATCTCCAGCGACATCGCCAAGACCACGCTCTATCTGCAGATGGACAGTC

TGAGAGTCGAAGACTCGGCCGTCTATTATTGTGCCTCGGGGCCATTAGAC

CTCTGGGGCCAGGGCACCCTGGTCACCGTCTCCTCAGCCTCCACCACGGC

CCCCTCGGTT (SEQ ID NO: 168)
EGQLAESGGDLVKPGGSLRLSCVASGFTFSKDMTWVRQSPGQGLQWVADI

TPDGRTDYSDAVRGRFTISSDIAKTTLYLQMDSLRVEDSAVYYCASGPLD

LWGQGTLVTVSSASTTAPSV

VH Chains from VH-VL scFv Library of a Normal Dog—Total of 29 Sequences

>VHn11

(SEQ ID NO: 169)
AACCGAGGGGCCGTGGTGGAGGCTGAG-
GAGACGGTGACCAGGGTTCCCTGG

CCCCAATAGTCAATGCTCCCCACCGCA-
CAGTAATAAAGACCCGTGTCGTCGG

CTCTCAGGCTGTTCATCTGCAGATA-
GACTGTCCTTTTGGCGGTGTCTCTGGA

AATGGTGAATCGGCCCTTCACAGCGT-
CAATATAGTATGTGCTGATTCCATCA

ACACTGATTCCAGCGACCCACTG-
TAGTCGCTTCCCAGGAGCCAGGCGGACCC

-continued

AGTTCGTGTCGGAGTCAGAGAAGGT-
GAATCCAGGGGCTACACAGGAGAGTCT

CAGGGACCCCCCCGGCTTCACCAG-
GTCTCCCCCAGATTCCACCAGCTGCaCC

TCCCC (SEQ ID NO: 170)

GEVQLVESGGDLVKPGGSLRLSCVAPG-
FTFSDSDTNWVRLAPGKRLQWVAGI

SVDGISTYYIDAVKGRFTISRD-
TAKRTVYLQMNSLRADDTGLYYCAVGSIDY

WGQGTLVTVSSASTTAPSV

>VHn12

(SEQ ID NO: 171)

AACCGAGGGGCCGTGGTGGAGGCTGAG-
GACACGAAGAGTGAGGTGCCATGG

CCCCAGTAGTCAAAAGCCACCGCCCGC-
CTCGCACAGTAATACACAGCCGTGT

CCTCAGCTCTCAAGCTGTTCATCTGCA-
GATACAGTGTGTTCTTGGCGTTGTC

TCTGGAGATGGTGAATCGGCCCTTCA-
CAGCGTCTGCATACCTTGTGTTACTT

CCACTATCATAAATCCATGCGACCCACT-
GCAGTCCCTTCCCTGGAGCCTGGC

GGACCCAGCCCATGTTGTAGCTACT-
GAAGGGGAATCAGAGGCCACACAGGA

GAGTCTCAGGGACCCCCCAGGCCTCAC-
CAAGTCTCCCCCAGACTCCGCCAGC

TGCCCCTCCCCA (SEQ ID NO: 172)

GEGQLAESGGDLVRPGGSLRLSCVASGF-
PFSSYNMGWVRQAPGKGLQWVAWI

YDSGSNTRYADAVKGRFTISRDNAKNT-
LYLQMNSLRAEDTAVYYCARRAVAF

DYWGHGTSLFVSSASTTAPSV

> VHn 13

(SEQ ID NO: 173)

AACCGAGGGGCCGTGGTGGAGGCTGAR-
GAGACGGTGACCAGGGTTCCCTGG

CTCCAATACCTCCAGGTAGCGGGGGCA-
CAGTAATATACGGCCGTGTCCTCGA

CTTTCAGGCTGTTCATCTGGAGATAT-
AGCGTGTTTTTGGCGTCGTCTCTGGA

AATGGTGAATCGGCCCTTCACAGCGTCT-
GCGTAGTATGTGGTACTTCCATCA

TACCAAATACTTGCGACCCACTGCAGTC-
CCTTTCCTGGAGACTGACGGACCC

AGCTCATGTCAGAGCCACTAAAGGT-
GAATCCAGAGGCCACACAGGACAGTCT

CAAGGTCCCCCCAGGCTTCACCAG-
GTCTCCCCCAGACTCCACCAGCTGCACC

TC (SEQ ID NO: 174)

EVQLVESGGDLVKPGGTLRLSCVASG-
FTFSGSDMSWVRQSPGKGLQWVASIW

YDGSTTYYADAVKGRFTISRDDAKNT-
LYLQMNSLKVEDTAVYYCAPATWRYW

SQGTLVTVSSASTTAPSV

-continued

> VHn 14

(SEQ ID NO: 175)

AACCGAGGGGCCGTGGTGGAGGCAGAG-
GAGACGGTGACCAGGGTTCCATGG

CCCCAGTAGGTCAGATGATATCTAT-
TCAAATATATCAGACCAAGCCCAGTCG

CACAGTAGTAGACAGCCGTGTCCTCGGT-
TCTCAGACTGTCCATCTGCAGATA

CACTGTGTTCCGGCCATTGTCTCTG-
GAGACGGTGACTCGGCCCTTCACAGAG

TCACTATGATAAGTGATTCCATCATAAG-
TAAGAGCTGCGACCCACTGCAGCC

CCTTCCCAGGAGCCTGGCGGACCCAGGT-
CATGTCGTGGGAACTGAAGGCGAG

TCCAGAGACTAGACAGGAGAGTCTCAGG-
GACCCCCCAGGCTTCACCAGGTCT

CCCCCAGACTCCACCAGCTGCACCTC (SEQ ID NO: 176)

EVQLVESGGDLVKPGGSLRLSCLVS-
GLAFSSHDMTWVRQAPGKGLQWVAALT

YDGITYHSDSVKGRVTVSRDNGRN-
TVYLQMDSLRTEDTAVYYCATGLGLIYL

NRYHLTYWGHGTLVTVSSASTTAPSV

> VHn15

(SEQ ID NO: 177)

AACCGAGGGGCCGTGGTGGAGGCTGAG-
GAGACGGTGACCAGAGTTCCCTGG

CCCCAGTAGTCAAACTCATAGTCGGTAC-
CGAAATTGTTCGCACAGTAATATA

CAGCCGTGTCCTCAGTGGTCAACCTGT-
TCATATGCAAAAACAGTGTGTTCTT

GGCGTTGTCTCTGGAGACGGTGAATCG-
GCCCTTCACAGCGTCTGCATAGGTT

GTGGTACTTCCACTATCATAAATCCAT-
GCGACCCACTGCAGTCCCTTCCCTG

GAGCCTGGCGGACCCAGACCATGTTG-
TAGGTAGTGAAGGTGAATCCAGAGGC

CACACAGGAGAGTCTCAGGGAC-
CCCCCAGGCTTCACCAAGTCTCCCCCAGAC

TCCGCCAGCTGCCCCTC (SEQ ID NO: 178)

EGQLAESGGDLVKPGGSLRLSCVASGFT-
FTTYNMVWVRQAPGKGLQWVAWIY

DSGSTTTYADAVKGRFTVSRD-
NAKNTLFLHMNRLTTEDTAVYYCANNFGTDY

EFDYWGQGTLVTVSSASTTAPSV

> VHn16

(SEQ ID NO: 179)

AACCGAGGGGCCGTGGTGGAGGCTGAG-
GAGACGGTGACCAGGGTTCCCTGG

CCCCAGTAGTCAAATCCCTCCCAGTAC-
CAGCTGCTACTATACGTTCCGGTTG

CACAGTAATACACGGCCGTGTCCTCG-
GCTCTCAGGCTGTTCATCTGCAGATA

CAGCATGTTCTTGGCGTTGTCTCTG-
GAGATGGTGAATCGGCCCTTCACAGCG

```
TCTGCGTAGTATGTGCTACTTCCAC-
TACTGCTAATTTCTGAGAGCCACTGCA

GCCCCTTCCCTGGAGCCTGGCGGAC-
CCAGTCCATGTCATAGCTACTGAAGGT

GAATCCAGAGGCCACACAGGAAAGTCT-
CAGGGACCCCCCAGGCTTCACCAGG

TCTCCTCCAGACTCCACCAGCTGCACCCC
```
(SEQ ID NO: 180)
```
GVQLVESGGDLVKPGGSLRLSCVASG-
FTFSSYDMDWVRQAPGKGLQWLSEIS

SSGSSTYYADAVKGRFTISRDNAKNM-
LYLQMNSLRAEDTAVYYCATGTYSSS

WYWEGFDYWGQGTLVTVSSASTTAPSV

> VHn 17
```
(SEQ ID NO: 181)
```
AACCGAGGGGCCGTGGTGGAGGCTGCG-
GAGACGGTGACCAGGCTTCCCTGG

CCCCAGTAGTCAAAACCCTCTTGGTAGC-
GACCGGAGTAGCGGAACAGAAGGT

TTACACAGTAATATACGGCCGTGTCT-
TCGGCTCTCAGGCTGTTCATCTGCAG

ATACAGCGTGTTCTTGGCGTCGTCTCTG-
GAGATGGTGAATCGGCCCTTCACA

GCGTCTGCGTAGTATGTGCTACTTCCAC-
TACTGTTAATTTCCGAGAGCCACT

GCAGCCCCTTCCCTGGAGCCTGGCGGAC-
CCAGTTCATGTCATAGTTATTAAA

GGTGAATCCAGAGGCCACACAG-
GAAAGTCTCAGGGACCCCCAGGCTTCACC

AGGTCTCCTCCAAACTCCACCAGCTGCTCCTC
```
(SEQ ID NO: 182)
```
EEQLVEFGGDLVKPGGSLRLSCVASGFT-
FNNYDMNWVRQAPGKGLQWLSEIN

SSGSSTYYADAVKGRFTISRDDAKNT-
LYLQMNSLRAEDTAVYYCVNLLFRYS

GRYQEGFDYWGQGSLVTVSAASTTAPSV

> VHn 19
```
(SEQ ID NO: 183)
```
AACCGAGGGGCCGTGGTGGAGGCTGAG-
GAGACGATGACCAGGGTTCCCTGG

CCCCAATAGTCAAAACGGTAATAACTC-
CCTCCTTTTCCCCCGGAACTCGCAC

AATGATACACGGCCGTGTCCTCGGCTCT-
CAGACTGTTCATCTGAAGATACAC

CGTATTCCTGGCATTGTCTCTGGAGACG-
GTGAATCGGCCCCTCACAGCGTCT

GCATAGGTTGTCTTATCTCCACCACTAT-
TAATGTATGTGACCCACTGAAACC

CCTTCCCTGGAGCCTGGCGGACCCAGGT-
CATGTGATGGTCACTGAGGGTGAA

TCCAGAGGCCGCACAGGAAAGTCTCAGGGACCCCCCAGGCTTCACCAGGTC
```
(SEQ ID NO: 184)
```
DLVKPGGSLRLSCAASGFTLSDHH-
MTWVRQAPGKGFQWVTYINSGGDKTTYA

DAVRGRFTVSRDNARNTVYLQMNSL-
RAEDTAVYHCASSGGKGGSYYRFDYWG

QGTLVIVSSASTTAPSV

> VHn 20
```
(SEQ ID NO: 185)
```
AACCGAGGGGCCGTGGTGGAGGCTGAG-
GAGACGGTGACCAGGGTTCCCTGG

CCCCACTCGTCCCCCCCTGTAATGTCG-
TAGCCATGCCGGACACAGTAATACA

CGGCCGTGTCCTCGGCTCTCAGGCTGT-
TCATCTGCAGATACAGCGTGTTCTT

GGCGTTGTCTCTGGAGATGGTGAATCG-
GCCCTTCACAGCGTCTCCATAATAT

GTGCTAAATCCATCATTC-
CAAATAATCGCGACCCACTGCAGCCCCTTCCCTG

GAGACTGACGGACCCAGCTCATGTCA-
GAGCTACTAAAGGTGAATCCAGAGGC

CACACAGGACAGTCTCAAGGTC-
CCCCCAGGCTTCACCAGGTCTCCCCCAGAT

TCCACCAAACTCACCTC
```
(SEQ ID NO: 186)
```
EVSLVESGGDLVKPGGTLRLSCVASG-
FTFSSSDMSWVRQSPGKGLQWVAIIW

NDGFSTYYGDAVKGRFTISRDNAKNT-
LYLQMNSLRAEDTAVYYCVRHGYDIT

GGDEWGQGTLVTVSSASTTAPSV

> VHn 21
```
(SEQ ID NO: 187)
```
AACCGAGGGGCCGTGGTGGAGGCGGAG-
GAGACGGTGACCAGGGTTCCCTGG

CCCCAGTAGTCAAAGTACCAGGAACCAC-
CATAGCCCAATTTCCTCGCGCAGT

AATAGACGGCCGTGTCTTCGGCTCTCA-
GACTGTTCATCTGCAGATACAGGGT

GTTCCTGGCGTTGTCTCTGGAGATGGT-
GAATCGGCCCTTCACAGCGTCTCCA

TATTTTGTGAGAGATCCATCACTC-
CAAATAAGTGCGACCCATTGCAGCCCCT

CCCCTGGAGACTGACGGACCCAGTTCAT-
GTCAGAACTACTGAAGGTGAATCC

AGAGGCCACACAGGACAGTCTCAAGGTC-
CCCCCAGGCTTCACCAGGTCTCCC

CCAGATTCCACCAGTTGTACCTCCCCA
```
(SEQ ID NO: 188)
```
GEVQLVESGGDLVKPGGTLRLSCVASG-
FTFSSSDMNWVRQSPGEGLQWVALI

WSDGSLTKYGDAVKGRFTISRDNARN-
TLYLQMNSLRAEDTAVYYCARKLGYG

GSWYFDYWGQGTLVTVSSASTTAPSV

> VHn 22
```
(SEQ ID NO: 189)
```
AACCGAGGGGCCGTGGTGGAGGCTGAG-
GAGACGGTGACCAGGGTTCCCTGG

CCCCAATAGTCAATGCTCCCCACCGCA-
CAGTAATACAGAGCCGTGTCGTCGG

CTCTCAGGCTGTTCATCTGTAGATA-
GACTGTCTTTCTGGCGGTGTCTCTGGA

AATGGTGAATCGGCCCTTCACAGCGT-
CAATATAGTATGTGCTGATTCCATCG
```

```
ACACTGATTCCAGCGACCCACTGCAGC-
CGCTTCCCAGGAGCCAGGCGGACCC

AGTTCGTGTCGGAGTCAGAGAAGGT-
GAATCCAGGGGCTACACAGGAGAGTCT

CAGGGACCCCCCGGCTTCACCAGGTCTCCCCAGACTCCACCAGCTG
```
(SEQ ID NO: 190)
```
QLVESGGDLVKPGGSLRLSCVAPGFTFS-
DSDTNWVRLAPGKRLQWVAGISVD

GISTYYIDAVKGRFTISRDTARK-
TVYLQMNSLRADDTALYYCAVGSIDYWGQ

GTLVTVSSASTTAPSV

> VHn 23
```
(SEQ ID NO: 191)
```
AACCGAGGGGCCGTGGTGGAGGCTGAG-
GAGACGGTGACCAGGGTGCCCTGG

CCCCAGTAGTCATAACAGGACCAGACG-
GACCAGGCACTATTATCCTTGGCAC

AGTAATACATAGCCGTGTCCTCGGCTCT-
CAGACTGTTCATCCGCAGATACAG

TGTGTTGTTGGCATTGTCTCTGGAGACG-
GTGAATCGGCCCTTCACAGCGTCT

CCATAATATGTAGTCTTTCCATCAATAC-
TAATCCGTGCGACCCACTGAAGCC

CCTTCCCTGGAGCCTGGCGGACCCAATA-
CATATAATAATTCTTGAAGGTAAA

TCCAGAGGCCACACAGGACAGTGTCAGGGACCCCCCAGGCTTCACCAGGTC
```
(SEQ ID NO: 192)
```
DLVKPGGSLTLSCVASGFTFKNYYMY-
WVRQAPGKGLQWVARISIDGKTTYYG

DAVKGRFTVSRDNANNTLYLRMNSL-
RAEDTAMYYCAKDNSAWSVWSCYDYWG

QGTLVTVSSASTTAPSVv

> VHn 24
```
(SEQ ID NO: 193)
```
AACCGAGGGGCCGTGGTGGAGGCTGAR-
GAGACGGTGACCAGGGTTCCCTGG

CCCCAGTACACCGGGACCTGCTCCTTTG-
CACAGTAATACATAGCCGTGTCCT

CGGCTCTCAGGCTGTTCATCTGCAGATA-
CAGCGTGTTTTTGGCATTGTCTCT

GGAGATGGTGAATCGGCCCTTCA-
CAGCGTCTGTATTATATGTGCTACTCCCA

TCACTGCTAATCCGTGCGACCCACT-
GAAGCCCCTTCCCTGGAGCCTGGCGGA

CCCAGTAGTAGTAACTTCTGAAGG-
TAAATCCAGAGGCCACACAGGACAGTCT

CAGGGACCCCCCAGGCTTCACCAG-
GTCTCCCCAGACTCCACCAGCTGCACC

TC
```
(SEQ ID NO: 194)
```
EVQLVESGGDLVKPGGSLRLSCVASGFT-
FRSYYYWVRQAPGKGLQWVARISS

DGSSTYNTDAVKGRFTISRDNAKNT-
LYLQMNSLRAEDTAMYYCAKEQVPVYW

GQGTLVTVSSASTTAPSV

> VHn 25
```
(SEQ ID NO: 195)
```
AACCGAGGGGCCGTGGTGGAGGCTGAG-
GAGACGGTGACCAGGGTTCCCTGG

CCCCAGTAGTCAAAAAACTCCACTATC-
GAAGAGTAGCTGCTACCCCATCCC

TCGCACAGTAATATTGAGCCATGTCCT-
CAACTCTCAATCTGTTCATCTGCAG

ATATAATGTGTTCCTGGCGTTGTCTCTG-
GAGATGGTGAATCGGCCCTTCACA

GCGTCTGCATACCTTGTGCCACTTCCAC-
TATCATAAATCCAAGCGACCCACT

GCAGTCCCCTCCCTGGAGCCTGGCGGAC-
CCAGCCCATGTTGTAGCTACTGAA

GGTGAATCCAGAGGCCACACAG-
GAGAGTCTCAGGGACCCCCAGGCTTCACC

AGGTCTCCCCCAGACTCCGCCAGCTGCCCCTC
```
(SEQ ID NO: 196)
```
EGQLAESGGDLVKPGGSLRLSCVASG-
FTFSSYNMGWVRQAPGRGLQWVAWIY

DSGSGTRYADAVKGRFTISRDNARN-
TLYLQMNRLRVEDMAQYYCARDGGSSY

SSIVEFFDYWGQGTLVTVSSASTTAPSV

> VHn 28
```
(SEQ ID NO: 197)
```
AACCGAGGGGCCGTGGTGGARGCTGAG-
GAGACGGTGACCAGGGTTCCCTGG

CCCCAGGCGGAATAACTACCGGCAATAT-
CATCCCTCGTACAGTAATAAATGC

CCGTGTCCTCGGCTCTCAGGCTGTT-
CATCTGCAGATAAAGCGTGTTCTTGGC

GTTGTCTCTGGAGATGGTGAATCGGC-
CCTTCACAGCGTCTGCGTAGTATGTG

CTACTTCCATCACTGCTAATCCGTGC-
GACCCACTGAAGCCCCCTCCCTGGAG

CCTGGCGGACCCAGTAGTAgTAACTTCT-
GAAGGTAAATCCAGAGGCCACACA

GGACAGTCTCAGGGACCCCCCAGGCTTCACCAGGTC
```
(SEQ ID NO: 198)
```
DLVKPGGSLRLSCVASGFTFRSYYY-
WVRQAPGRGLQWVARISSDGSSTYYAD

AVKGRFTISRDNAKNTLYLQMNSL-
RAEDTGIYYCTRDDIAGSYSAWGQGTLV

TVSSASTTAPSV

> VHn 29
```
(SEQ ID NO: 199)
```
AACCGAGGGGCCGTGGTGGAGGCTGAG-
GAGACGGTGACCAGGGTTCCCTGG

CCCCAAAAGTCAAAATTCAACAAGGTGC-
CCCGACAGTAATACACAGCTGTGT

CCTCGACTCTCAGGCTGTTCATCTGCA-
GATACACTGTGTTCCTGGCGTTGTC

TCTGGAAATGGTGAATCGGCCCTTCA-
CAGCGGCAGTGTAGTATGTACTTCTC

CCATCATAGTCAATACCTGTGACCCACT-
GCAGCCCCTTCCCAGGGGCCTGGC
```

```
GGACCCAGGACATGCTGTAGCTTC-
CgATACTTAATCCAGAGGCCACACAGGA

GAGTCTCAGGGACCCCCCAgGCTTCgC-
CAGGTCTCCCCCAGACTCCACCAGC

TGCACGCC
```
(SEQ ID NO: 200)
```
GVQLVESGGDLAKPGGSLRLSCVAS-
GLSIGSYSMSWVRQAPGKGLQWVTGID

YDGRSTYYTAAVKGRFTISRDNARN-
TVYLQMNSLRVEDTAVYYCRGTLLNFD

FWGQGTLVTVSSASTTAPSV

> VHn 30
AACCGAGGGGCCGTGGTGGAGGCTGAR-
GAGACGGTGACCAGGGTTCCCTGG

CCCCAAAAGTCAAAATTCAACAAGGTGC-
CCCGACAGTAATACACAGCTGTGT

CCTCGACTCTCAGGCTGTTCATCTGCA-
GATACACTGTGTTCCTGGCGTTGTC

TCTGGAAATGGTGAATCGGCCCTTCA-
CAGCGGCAGTGTAGTATGTACTTCTC

CCATCATAGTCAATACCTGTGACCCACT-
GCAGCCCCTTCCCAGGGGCCTGGC

GGACCCAGGACATGCTGTAGCTTC-
CgATACTTAATCCAGAGGCCACACAGGA gAGTCTCAGGGACCCCCCAgGCTTCgC-
CAGgTCTCCCCCAgACTCCACCAGC

TGCACGCC
```
(SEQ ID NO: 201)
```
GVQLVESGGDLAKPGGSLRLSCVAS-
GLSIGSYSMSWVRQAPGKGLQWVTGID

YDGRSTYYTAAVKGRFTISRDNARN-
TVYLQMNSLRVEDTAVYYCRGTLLNFD

FWGQGTLVTVSSASTTAPSV

> VHn 33
AACCGAGGGGCCGTGGTGGAGGCTGAG-
GAGACGGTGACCAGGGTTCCCTGG

CCCCAGTAGTCAAATCCCTCCCAGTAC-
CAGCTGCTACTATACGTTCCGGTTG

CACAGTAATACACGGCCGTGTCCTCG-
GCTCTCAGGCTGTTCATCTGCAGATA

CAGCATGTTCTTGGCGTTGTCTCTG-
GAGATGGTGAATCGGCCCTTCACAGCG

TCTGCGTAGTATGTGCTACTTCCAC-
TACTGCTAATTTCTGAGAGCCACTGCA

GCCCCTTCCCTGGAGCCTGGCGGAC-
CCAGTCCATGTCATAGCTACTGAAGGT

GAATCCAGAGGCCACACAGGAAAGTCT-
CAGGGACCCCCCAGGCTTCACCAGG

TCTCCTCCAGACTCCACCAGCTGCACCCC
```
(SEQ ID NO: 202)
```
GVQLVESGGDLVKPGGSLRLSCVASG-
FTFSSYDMDWVRQAPGKGLQWLSEIS

SSGSSTYYADAVKGRFTISRDNAKNM-
LYLQMNSLRAEDTAVYYCATGTYSSS

WYWEGFDYWGQGTLVTVSSASTTAPSV

> VHn 34
AACCGAGGGGCCGTGGTGGAGGCTGAR-
GAGACGGTGACCAGGGTTCCCTGG

CCCCAGTAGTCAAAGCCGTAGTAGCTAC-
CGTAATCTCTAGGGACACAGTAAT

ACACGGCTGTGTCCTCGGATCTCAGGCT-
GTTCATCTGCAGATACAGTGTGTT

CCTGTCATTGTCTCTGGAGATGGTGAAC-
CGGCCCTTCACAGCATCTGCGTAG

TATGTGACACTTCCACCACTGTTAATG-
GATGCGACCCACTGCAGCCCCTTCC

CTGGAGCCTGGCGGACCCAGTTCATGG-
TATAGGGACTGAAGGTGAATCCAGA

GGCCACACAGGACAGTCTCAGGGATC-
CCCCAGgCTTCACCAGGTCTCCCCa gATTCCACCAGCTGCACCTC
```
(SEQ ID NO: 205)

(SEQ ID NO: 206)
```
EVQLVESGGDLVKPGGSLRLSCVASG-
FTFSPYTMNWVRQAPGKGLQWVASIN

SGGSVTYYADAVKGRFTISRDNDRN-
TLYLQMNSLRSEDTAVYYCVPRDYGSY

YGFDYWGQGTLVTVSSASTTAPSV

> VHn 38
AACCGAGGGGCCGTGGTGGAGGCTGAG-
GAGACGGTGACCAGGGTTCCCTGG

CCCCAGTAGTCAAAAGATGGTATC-
CATATATATTCACCCCCTCGTGCACAGT

AATACATAGCCGTGTCCTCGGCTCTCAG-
GCTGTTCATCTGCAGATACAGCGT

TTTCTTGGCATTGTCTCTGGAGATGGT-
GAATCGGCCCTTCATAGCGTCTGCA

TAGTATGTGCTACTTCCATCAC-
CGCTAATCCGTGCGACCCACTGAAGCCCCT

TCCCTAGAGCCTGGCGGACCCAGTACAT-
GTAGTAGCTGCTGAAGGTGAATCC

AGAGGCCACACAGGACAGTCTCAGGGAC-
CCCCAgGCTTCACCAGGTCTCCC

CCAgATTCCacCAaTCTTACCTC
```
(SEQ ID NO: 207)

(SEQ ID NO: 208)
```
EVRLVESGGDLVKPGGSLRLSCVASG-
FTFSSYYMYWVRQALGKGLQWVARIS

GDGSSTYYADAMKGRFTISRDNAKKT-
LYLQMNSLRAEDTAMYYCARGGEYIW

IPSFDYWGQGTLVTVSSASTTAPSV

> VHn 39
AACCGAGGGGCCGTGGTGGARGCTGAG-
GAGACGGTGACCAGGGTTCCCTGG

CCCCAGTCGCAAAGTATTGGCCACTTC-
TACCCCGGACATCCACACAGTAAT

ATACAGCTGTGTCCTCGGCTCTCAGGC-
CGGTCATCTGCAGAGAAACTGTGTT

CCTGGCGTTGTCTCTGGAGATGGT-
GAATCGGCCCTTCACAGCGTCAGTGTAG
```
(SEQ ID NO: 209)

```
TATGTGCTACTTCCATCATAGCTAAT-
AGCTGCGACCCACTGCAGCCCCTTCC

CAGGAGCCTGGCGGACCCAGCTCAT-
GTCGTAATCACTGAAGGTGAATCCAGA

GCCTACACAGGAGAGTCTCAGGGAC-
CCCCCCGGCTTCACCTGGTCTCCCCCA

GATTCCACCAgCTGCACCTC
```
(SEQ ID NO: 210)
```
EVQLVESGGDQVKPGGSLRLSCVGSG-
FTFSDYDMSWVRQAPGKGLQWVAAIS

YDGSSTYYTDAVKGRFTISRDNARNTVS-
LQMTGLRAEDTAVYYCVDVRGRSG

QYFGDWGQGTLVTVSSASTTAPSV

> VHn 40
```
(SEQ ID NO: 211)
```
AACCGAGGGGCCGTGGTGGAGGCTGAG-
GAGACGGTGACCAGGGTTCCCTGG

CCCCAGTAGTCAAAATCCCAGCCCAAG-
TAGTAGAATAATCCCTCGCACAGT

AATACACAGCCGTGTCCTCAGCTCT-
CAAGTTGTTCATCTGCAGATACAGTGT

GTTCTTGGCATTGTCTCTGGAGATGGT-
GAATCGGCCCTTCACAGCGTCTGCG

TAGCTTGTCCTAGTTCCACCAG-
TATAAATCCATGCGACCCACTGCAGTCCCT

TCCCTGGAGCCTGGCGGACCCAGCCCAT-
GTTGTAGCTACTGAAGGTGAATCC

AGAGGCCACACAGGAGAGTCTCAGGGAC-
CCCCCCGGCTTCACCAGGTCTCCC

CCAGACTCCACCAGCTGCATGTC
```
(SEQ ID NO: 212)
```
DMQLVESGGDLVKPGGSLRLSCVASG-
FTFSSYNMGWVRQAPGKGLQWVAWIY

TGGTRTSYADAVKGRFTISRDNAKNT-
LYLQMNNLRAEDTAVYYCARDYSTTW

GWDFDYWGQGTLVTVSSASTTAPSV

> VHn 41
```
(SEQ ID NO: 213)
```
AACCGAGGGGCCGTGGTGGAGGCTGAG-
GAGACGGTGACCAGGGTTCCCTGG

CCCCAGTAGTAGCCACTGCGGGTCCA-
CAATAATATACGGCCGTGTCCTCGG

CTCTGAGGCGGTCCATCTGCAGATA-
GAGCGCGTTCTTGGCGTTGTCTCTGGA

GATGGTGAATCGGCCCTTCACAGCGTCT-
GCGTAGGCTATGTTAGTTGGATAA

GGGCCTATGTATGCGACCCACTGAAGC-
CCCTTTCCTGGAGCCTGGCGGATCC

AGCTCATGCCGGAACTACTGAAGGC-
GAATCCAGAGGCTACACAGGAGAGTCT

CAGGGACCCCCCAGGCTTCWCCAG-
GTCTCCCCCAGACTCCACCAGCTGCACC

TC
```
(SEQ ID NO: 214)
```
EVQLVESGGDLXKPGGSLRLSCVASG-
FAFSSSGMSWIRQAPGKGLQWVAYIG

PYPTNIAYADAVKGRFTISRDNAKNA-
LYLQMDRLRAEDTAVYYCGPGSGYYW

GQGTLVTVSSASTTAPSV

> VHn 42
```
(SEQ ID NO: 215)
```
AACCGAGGGGCCGTGGTGGAGGCTGAG-
GAGACGGTGACCAGGGTTCCCTGG

CCCCAGTAGTCAAATTGATATGCGTA-
GACTGGGGCGACACAATAATACATAG

CCGTGTCCTCGGCTCTCAGGCTGTC-
CATCTGCAGATACAGCGTGTTCTTGGC

GTTGTCTCTGGAGATGGTGAATCGGC-
CCTTCACAGTGTCTCCGTAGGATGTG

GTAAATCCATCACTGCTAATTCGTGC-
GACCCACTGAAGCCCCTTCCCAGGAG

CCTGGCGGACCCAGTATATGTACAAGC-
GACTGAAGGCGAATCCAGAGGCCAC

ACAGGACAGTGTCAGAGACCCCCCAG-
GCTTCACCAGGTCTCCCCCAGATTCC

ACCAGCTGCACCTC
```
(SEQ ID NO: 216)
```
EVQLVESGGDLVKPGGSLTLSCVASG-
FAFSRLYIYWVRQAPGKGLQWVARIS

SDGFTTSYGDTVKGRFTISRDNAKNT-
LYLQMDSLRAEDTAMYYCVAPVYAYQ

FDYWGQGTLVTVSSASTTAPSV

> VHn 45
```
(SEQ ID NO: 217)
```
AACCGAGGGGCCGTGGTGGAGGCTGAG-
GAGACGGTGACCAGGGTTCCCTGG

CCCCAGGAGTCAAAAAAGTTGTAGTCG-
GCACCGGTCAGGACCTTCGCACAGT

AATAGACAGCCGTGTCCTCGGCTTTCA-
GACTGTCCATCTGCAGATACACCGT

GTTCCTGGAATTGTCTCTGGAAATGGT-
GAATCGGCCCTTCACAGCGTCAGTG

TAGTATGTTATAGTTCCATCATCCT-
TAATAGTAGCGACCCACTGCAGTCCCT

TCCCAGGAGCCTGGCGGACCCAGGTCAT-
GTAACGGTTTTTGAAGGTGAGACT

AGTGAGTCCAGAGGCTACACAG-
GAGAGTCTCAGGGACCCCCCAGGCTTCACC

AGGTCTCCCCCAGACTCCACCAGCTGTACCTC
```
(SEQ ID NO: 218)
```
EVQLVESGGDLVKPGGSLRLSCVAS-
GLTSLTFKNRYMTWVRQAPGKGLQWVA

TIKDDGTITYYTDAVKGRFTISRDNSRN-
TVYLQMDSLKAEDTAVYYCAKVLT

GADYNFFDSWGQGTLVTVSSASTTAPSV

> VHn 48
```
(SEQ ID NO: 219)
```
AACCGAGGGGCCGTGGTGGAGGCTGAg-
GAgACGGTGACCAGGGTTCCCTGG

CCCCAGTGGTCACCGTAATAGCTAC-
CGTGGTAGGCCAGTCCAGCCGCACaAT

AATACACGCCGTGTCCTCGACTCTCA-
GATTGTTCATCTGCAGATACAGCGT
```

```
GTTCTTGGCGCCGTCTCTGGAGAGAGT-
GAATCGGTCCTTCACAGCGTCTGCA

AACCTCGTCACAGCTCCACCACTGT-
TAATGTAGCCGACCCACTGAGGCCCCT

TCCCGGGAGCCAGGCGGATCCAGGTCAT-
GTGGTAGGCACTGAGGGTGAATCC aGAGGCCACACAGGAAAGTCTCAGGGAC-
CCCCCAGGCTTCACCAGGTCTCCC

CCAgACTCCACCAgCTGCaCCTC
```

(SEQ ID NO: 220)
```
EVQLVESGGDLVKPGGSLRLSCVASG-
FTLSAYHMTWIRLAPGKGPQWVGYIN

SGGAVTRFADAVKDRFTLSRDGAKNT-
LYLQMNNLRVEDTAVYYCAAGLAYHG

SYYGDHWGQGTLVTVSSASTTAPSV

> VHn 50
```

(SEQ ID NO: 221)
```
AACCGAGGGGGCCGTGGTGGARGCTGAR-
GAGACGGTGACCAGRGTTCCCTGG

CCCCAAAAGTCAAAATTCAACAAGGTGC-
CCCCGACAGTAATACACAGCTGTGT

CCTCGACTCTCAGGCTGTTCATCTGCA-
GATACACTGTGTTCCTGGCGTTGTC

TCTGGAAATGGTGAATCGGCCCTTCA-
CAGCGGCAGTGTAGTATGTACTTCTC

CCATCATAGTCAATACCTGTGACCCACT-
GCAGCCCCTTCCCAGGGGCCTGGC

GGACCCAGGACATGCTGTAGCTTC-
CGATACTTAATCCAGAGGCCACACAGGA gAGTCTCAGGGACCCCCCtGGCTTCgC-
CAGGTCTCCCCCAGACTCCACCAGC

TGCACCCC
```

(SEQ ID NO: 222)
```
GVQLVESGGDLAKPGGSLRLSCVAS-
GLSIGSYSMSWVRQAPGKGLQWVTGID

YDGRSTYYTAAVKGRFTISRDNARN-
TVYLQMNSLRVEDTAVYYCRGTLLNFD

FWGQGTLVTVSSASTTAPSV

> VHn 52
```

(SEQ ID NO: 223)
```
AACCGAGGGGGCCGTGGTGGAGGCTGGG-
GAGACGGTGACCAGGGTTCCCTGG

CCCCAGTTGTCCGCGATCGTATC-
CATATATATATAACCGCTCGAACAGAAAT

ACACGGCCGTGTCTTCGACTCCCAGGCT-
GTCCATCTGAAGATACACCGTGTT

CTTGGCGTTGTCTCTGGAGATGGT-
GAATCGGCCCTTCACAGCGTCTGCAAAG

GCTATGTCCTTTCCATCATTGTTGATG-
TAAGCGACCCACTGAAGCCCCTTCC

CAGGAGGCTGGCGGACCCAGTTGACGTG-
GTGGTCATTGAAGGCGAATCCAGA

GGCCACACAGGAAAGTCTCAGGGAC-
CCCCAGGCTTCACGAGGTCTCCCCCA

GATTCCACCAGCTGCACCTC
```

(SEQ ID NO: 224)
```
EVQLVESGGDLVKPGGSLRLSCVASG-
FAFNDHHVNWVRQPPGKGLQWVAYIN

NDGKDIAFADAVKGRFTISRD-
NAKNTVYLQMDSLGVEDTAVYFCSSGYIYMD

TIADNWGQGTLVTVSPASTTAPSV

> VHn 53
```

(SEQ ID NO: 225)
```
AACCGAGGGGCCGTGGTGGAGGCTGAG-
GAGACGGTGACCAGGGTTCCCTGG

CCCCAGTAAGACACGTATC-
CATATATATATATATCCCCCGCCACACAGTAAT

ACACAGCTGTGTCCTCGGCTCTCAGGCT-
GTTCATCTGCAGATACACTGTGTT

CCTGGCGTTGTCTCTGGAGATGGT-
GAATCGGCCCTTCACAGCGTCACTATAG

TATGTGTTACTTCCATCATAGCTAAT-
AGTTGTGACCCACTGCAGCCCCTTCC

CAGGAGCCTGGCGACCCAGTTCATGCT-
GTAGCTACTGAAGGTTAATCCAGA

GGCCACACAGGAGAGTCTCAGGGACCC
```

(SEQ ID NO: 226)
```
GSLRLSCVASGLTFSSYSMN-
WVRQAPGKGLQWVTTISYDGSNTYYSDAVKGR

FTISRDNARNTVYLQMNSLRAEDTAVYY-
CVAGDIYIYGYVSYWGQGTLVTVS

SASTTAPSV
```

VL Kappa Chains from HSA-7 Library (37 Sequences)

>#1

(SEQ ID NO: 227)
```
GTGATGATGCAGACTCCACTGTCCCT-
GTCCGTCAGCCCTGGAGAGCCGGCCT

CCATCTCCTGCAAGGCCAGTCAGAGC-
CTCCTGTACAGTAACGGGAACACCTA

TTTGTATTGGTTCCGACAGAAGCCAGGC-
CAGTCTCCACAGCGCCTGATCTAT

TTGGTTTCCAATAGAGACGCTGGGGTC-
CCAGACAGGTTCAGTGGCAGCGGGT

CAGGGACAGATTTCACTCTGACAATCAG-
CAGAGTGGAGGCTGATGATGCTGG

AGTTTATTATTGCGGGCAAGGTATACAA-
GATCCTCCTACTTTCAGCCAGGAA

CCAAGCTGGAGATAAAA
```

(SEQ ID NO: 228)
```
VMMQTPLSLSVSPGEPASISCKASQS-
LLYSNGNTYLYWFRQKPGQSPQRLIY

LVSNRDAGVPDRFSGSGSGTD-
FTLTISRVEADDAGVYYCGQGIQDPPTFSQE

PSWR-
```
>#13

(SEQ ID NO: 229)
```
GTGATGACACAGTCTCCAGCCTC-
CCTCTCCTTGTCTCAGGAGGAAAAAGTCA

CCATCACCTGCCGGGCCAGTCAGAGTGT-
TAGCAGCTACTTAGCCTGGTACCA
```

```
GCAAAAACCTGGGCAGGCTCCCAAGCTC-
CTCATCTATGGTACATCCAACAGG

GCCACTGGTGTCCCATCCCGGTTCAGTG-
GCAGTGGGTCTGGGACAGACTTCA

GCTTCACCATCAGCAGCCTGGAGCCT-
GAAGATGTTGCAGTTTATTACTGTCA

GCAGTATAATAGCGGGTGGACGTTCG-
GAGCAGGAACCAAGGTGGACCTCAAA

VMTQSPASLSLSQEEKVTITCRASQSVS-
SYLAWYQQKPGQAPKLLIYGTSNR

ATGVPSRFSGSGSGTDFSFTISSLEPED-
VAVYYCQQYNSGWTFGAGTKVDLK

>#25

GTGATGATGCAGACCCCACTGTCCCT-
GTCCGTCAGCCCTGGGGAACCGGCCT

CCATCTCCTGCAAGGCCAGTCAGAGC-
CTCCTGTCAAGTAATGGGAACACCTA

TTTGTATTGGTTCCGACAGAAGCCAGGC-
CAGTCTCCGCAGCGTTTGATTTAT

GAGGTCTCCAACAGAGACCCTGGGGTTC-
CAGACAGGTTCAGTGGCAGCGGGT

CAGGGACAGATTTCACCCTGAGAAT-
CAGCGGAGTGGAGGCTGATGATGCTGG

AATTTATTACTGCGGGCAAGGTATACAG-
GATCCGTGGACGTTCGGAGCAGGA

ACCAAGGTGGACCTCAAA

VMMQTPLSLSVSPGEPASISCKASQS-
LLSSNGNTYLYWFRQKPGQSPQRLIY

EVSNRDPGVPDRFSGSGSGTDFTLRIS-
GVEADDAGIYYCGQGIQDPWTFGAG

TKVDLK

>#37

GTGATGATGCAGACTCCACTGTCCCT-
GTCCGTCAGCCCTGGAGAGACTGCCT

CCATCTCCTGCAAGGCCAGTCAGAGC-
CTCCTGCACAGTAACGGGAACACCTA

TTTGTTTTGGTTGCGACAGAGGCCAGGC-
CAGTCTCCACAGCGCCTGATCAAC

TTGGTTTCCAACAGAGACCCTGGGGTC-
CCAGACAGGTTCAGTGGCAGCGGGT

CAGGGACAGATTTCACCCTGAGAATCAG-
CAGAGTGGAGGCTGACGATGCTGG

AGTTTATTACTGCGGGCAAGGTATA-
CAAGGTTATAGTTTCAGCCAGGGAACC

AAGCTGGAGATCAAA

VMMQTPLSVSPGETASISCKASQS-
LLHSNGNTYLFWLRQRPGQSPQRLIN

LVSNRDPGVPDRFSGSGSGTDFTLRIS-
RVEADDAGVYYCGQGIQGYSFSQGT

KLEIK
```

(SEQ ID NO: 230)

(SEQ ID NO: 231)

(SEQ ID NO: 232)

(SEQ ID NO: 233)

(SEQ ID NO: 234)

```
>#15

GTGATGATGCAGACTCCACTGTCCCT-
GTCCGTCAGCCCTGGAGAGCCGGCCT

CCATCTCCTGCAAGGCCAGTCAGAGC-
CTCCTGCACAGTAATGGGAACACCTA

TTTGTATTGGTTCCGACAGAAGCCAGGC-
CAGTCTCCACAGCGTTTGATCTAT

GGGGTCTCCAACAGAGACCCTGGGGTC-
CCAGACAGGTTCAGTGGCAGCGGGT

CAGGGACAGATTTCACCCTGAGAAT-
CAGCGGAGTGGAGGCTGATGATGCTGG

AGTTTATTACTGCGGGCAAGGTATACAA-
GATCCGTGGACGTTCGGAGCAGGA

ACCAA

VMMQTPLSLSVSPGEPASISCKASQS-
LLHSNGNTYLYWFRQKPGQSPQRLIY

GVSNRDPGVPDRFSGSGSGTDFTLRIS-
GVEADDAGVYYCGQGIQDPWTFGAG

T

>#2

GTGATGATGCAGACTCCACTGTCCCT-
GTCCGTCAGCCCTGGAGAGCCGGCCT

CCATCTCCTGCAAGGCCAGTCAGAGC-
CTCCTGGACAGTAATGGAAACACCTT

TTTGTCTTGGTTCCGACAGAAGCCAGGC-
CAGTCTCCACAGCGTTTGATCTAT

AAGGTCTCCAACAGAGACCCTGGGGTC-
CCAGACAGGTTCAGTGGCAGCGGGT

CAGGGACAGATTTCACCCTGAGAAT-
CAGCGGAGTGGAGGCTGATGATGCTGG

AATTTATTACTGCGGGCAAGGTTTACAA-
GATCCGTGGACGTTCGGAGCAGGA

ACCCA

VMMQTPLSLSVSPGEPASISCKASQS-
LLDSNGNTFLSWFRQKPGQSPQRLIY

KVSNRDPGVPDRFSGSGSGTDFTLRIS-
GVEADDAGIYYCGQGLQDPWTFGAG

T

>#38

GTGATGATACAGACTCCACTGTCCCT-
GTCCGTCAGCCCTGGAGAGCCGGCCT

CCATCTCCTGCAAGGCCAGTCAGAGC-
CTCCTGGACAGTAATGGAAACACCTT

TTTGTCTTGGTTCCGACAGAAGCCAGGC-
CAGTCTCCACAGCGTTTGATCTAT

AAGGTCTCCAACAGAGACCCTGGGGTC-
CCAGACAGGTTCAGTGGCAGCGGGT

CAGGGACAGATTTCACCCTGAGAAT-
CAGCGGAGTGGAGGCTGATGATGCTGG

AATTTATTACTGCGGGCAAGGTATACAG-
GATCCGTGGACGTTCGGAGCAGGA

ACCAA
```

(SEQ ID NO: 235)

(SEQ ID NO: 236)

(SEQ ID NO: 237)

(SEQ ID NO: 238)

(SEQ ID NO: 239)

```
VMIQTPLSLSVSPGEPASISCKASQS-
LLDSNGNTFLSWFRQKPGQSPQRLIY

KVSNRDPGVPDRFSGSGSGTDFTLRIS-
GVEADDAGIYYCGQGIQDPWTFGAG

T

>#3
                                                    (SEQ ID NO: 241)
GTGATGACCCAGTCTCCAGCCTC-
CCTCTCCTTGTCTCAGGAGGAAAAAGTCA

CCATCACCTGCCGGGCCAGTCAAAGTCT-
TAACAATTACTTGGCCTGGTACCA

GCAAAAACCTGGGCAGGCTCCCAAGCTC-
CTCATCTATGATACATTTAAAAGG

GCCACTGGTGTCCCATCCCGGTTCAGTG-
GCAGTGGGTCTGGGCAGAGTTCA

CCTTCACCATCAGCAGCCTGGAGCCT-
GAAGATGTTGCAGTTTATTACTGTCA

GCAATATTATGACGGTTGCACGTTCG-
GACCAGGAACCAAGGTGGACCTCAAA

VMTQSPASLSLSQEEKVTITCRASQSLN-
NYLAWYQQKPGQAPKLLIYDTFKR

ATGVPSRFSGSGSGAEFTFTISSLEPED-
VAVYYCQQYYDGCTFGPGTKVDLK

>#15
                                                    (SEQ ID NO: 243)
GTGATGATGCAGACTCCACTGTCCCT-
GTCCGTCAGCCCTGGAGAGCCGGCCT

CCATCTCCTGCAAGGCCAGTCAGAGC-
CTCCTGCACAGTAATGGGAACACCTA

TTTGTATTGGTTCCGACAGAAGCCAGGC-
CAGTCTCCACAGCGTTTGATCTAT

GGGGTCTCCAACAGAGACCCTGGGGTC-
CCAGACAGGTTCAGTGGCAGCGGGT

CAGGGACAGATTTCACCCTGAGAAT-
CAGCGGAGTGGAGGCTGATGATGCTGG

AGTTTATTACTGCGGGCAAGGTATACAA-
GATCCGTGGACGTTCGGAGCAGGA

ACCAAGGTGGACCTCAAA

VMMQTPLSLSVSPGEPASISCKASQS-
LLHSNGNTYLYWFRQKPGQSPQRLIY

GVSNRDPGVPDRFSGSGSGTDFTLRIS-
GVEADDAGVYYCGQGIQDPWTFGAG

TKVDLK

>#27
                                                    (SEQ ID NO: 245)
GTCATGATGCAGACTCCACTGTCCCT-
GTCCGTCAGCCCTGGAGAGCCGGCCT

CCATCTCCTGCAAGGCCAGTCAGAGC-
CTCCTGGAAAGTGATGGGAACACCTT

TTTGTCTTGGTTCCGACAGAAGCCAGGC-
CAGTCTCCACAGCGTTTGATCTAT

AAGGTCTCCAACAGAGACCCTGGGGTC-
CCAGACAGGTTCAGTGGCAGCGGGT

CAGGGACAGATTTCACCCTGAGAATCAG-
CAGAGTGGAGGCTGACGATGCTGG

AGTTTATTACTGCATGCAAGGTACT-
CAGTTTCCTCGGACGTTCGGAGCAGGA

ACCAAGGTGGACCTCAAA (SEQ ID NO: 246)
VMMQTPLSLSVSPGEPASISCKASQS-
LLESDGNTFLSWFRQKPGQSPQRLIY

KVSNRDPGVPDRFSGSGSGTDFTLRIS-
RVEADDAGVYYCMQGTQFPRTFGAG

TKVDLK

>#39
                                                    (SEQ ID NO: 247)
GTGATGATGCAGACCCCACTGTCCCT-
GTCCGTCAGCCCTGGGGAACCGGCCT

CCATCCCTGCAAGGCCAGTCAGAGC-
CTCCTGTCAAGTAATGGGAACACCTA

TTTGTATTGGTTCCGACAGAAGCCAGGC-
CAGTCTCCGCAGCGTTTGATTTAT

GAGGTCTCCAACAGAGACCCTGGGGTTC-
CAGACAGGTTCAGTGGCAGCGGGT

CAGGGACAGATTTCACCCTGAGAAT-
CAGCGGAGTGGAGGCTGATGATGCTGG

AATTTATTACTGCGGGCAAGGTATACAG-
GATCCGTGGACGTTCGGAGCAGGA

ACCAAGGTGGACCTCAAA (SEQ ID NO: 248)
VMMQTPLSLSVSPGEPASISCKASQS-
LLSSNGNTYLYWFRQKPGQSPQRLIY

EVSNRDPGVPDRFSGSGSGTDFTLRIS-
GVEADDAGIYYCGQGIQDPWTFGAG

TKVDLK

>#4
                                                    (SEQ ID NO: 249)
GTCATGACGCAGACTCCACTGTCCCTG-
GCCGTCACCCCTGGAGAGCTGGCCA

CTATCTCCTGCAGGGCCAGTCA-
GAGTCTCCTGCGCAGTGATGGAAAATCCTA

TTTGAATTGGTACCTACAGAAGCCAGGC-
CAGACTCCTCGGCCGCTGATTTAT

GAGGCTTCCAAGCGTTTCTCTGGGGTCT-
CAGACAGGTTCAGTGGCAGCGGGT

CAGGGACAGATTTCACCCTTAAAATCAG-
CAGGGTGGAGGCTGAGGATGTTGG

AGTTTATTACTGCCAGCAAAGTCTA-
CATTTTCCTCCGACGTTCGGAGCAGGA

ACCAAGGTGGAGCTCAAA (SEQ ID NO: 250)
VMTQTPLSLAVTPGELATISCRASQSLL-
RSDGKSYLNWYLQKPGQTPRPLIY

EASKRFSGVSDRFSGSGSGTD-
FTLKISRVEAEDVGVYYCQQSLHFPPTFGAG

TKVELK

>#40
                                                    (SEQ ID NO: 251)
GTGATGATGCAGACTCCACTGTCCCT-
GTCCGTCAGCCCTGGAGAGCCGGCCT

CCATCTCCTGCAAGGCCAGTCAGAGC-
CTCCTGCACAGTAGCGGGAACACCTA
```

-continued

TTTGTATTGGTTTCGACAGAAGCCAGGC-
CAGTCTCCACAGCGTTTGATCTAT

AAGGTCTCCAACAGAGACCCTGGGGTC-
CCAGACAGGTTCAGTGGCAGCGGGT

CAGGGACAGATTTCACCCTGAGAAT-
CAGCGGAGTGGAGGCTGATGATGCTGG

AATTTATTACTGCGGGCAAGGTATACAG-
GATCCGTGGACGTTCGGAGCAGGA

ACCAAGGTGGACCTCAAA (SEQ ID NO: 252)

VMMQTPLSLSVSPGEPASISCKASQS-
LLHSSGNTYLYWFRQKPGQSPQRLIY

KVSNRDPGVPDRFSGSGSGTDFTLRIS-
GVEADDAGIYYCGQGIQDPWTFGAG

TKVDLK

>#5

GTGATGACACAGTCTCCAGCCTC-
CCTCTCCTTGTCTCAGGACGAAAAAGTCA

CCATCACCTGCCGGGCCAGTCAGAG-
TATTAGCAGCTACTTAGCCTGGTATCA

GCAAAAACCTGGGCAGGCTCCCAAGCTC-
CTCATCTATGGTACATCCAACAGG

GCCACTGGTGTCCCATCCCGGTTCAGTG-
GCAGTGGGTCTGGGACAGACTTCA

GCCTCACCATCAGCACCCTGGAGCCT-
GAGGATGTTGCAGTTTATTACTGTCA

ACAGTATTATATCTGGTGGACGTTCG-
GAGCAGGAACCCAGGTGGAACTCAAA (SEQ ID NO: 253)

VMTQSPASLSLSQDEKVTITCRASQSIS-
SYLAWYQQKPGQAPKLLIYGTSNR

ATGVPSRFSGSGSGTDFSLTISTLEPED-
VAVYYCQQYYIWWTFGAGTQVELK

>#17

GTGATGATGCAGACTCCACTGTCCCT-
GTCCGTCAGCCCTGGAGAGCCGGCCT

CCATCTCCTGCAAGGCCAGTCAGAGC-
CTCCTGCACAGTAATGGGAACACCTA

TTTGTATTGGTTCCGACAGAAGCCAGGC-
CAGTCTCCACAGCGTTTGATCTCT

AATGTCTCCAACAGAGACCCTGGGGTC-
CCAGACAGGGTCAGTGGCAGCGGGT

CAGGGACAGATTTCACCCTGAGAATCAG-
CAGAGTGGAGGCTGATGATGCTGG

AGTTTATTACTGCGGGCAAGCTATACAG-
GATCCGCGGACGTTCGGAGCAGGA

ACCAAGGTGGACCTCAAA (SEQ ID NO: 255)

VMMQTPLSLSVSPGEPASISCKASQS-
LLHSNGNTYLYWFRQKPGQSPQRLIS

NVSNRDPGVPDRVSGSGSGTDFTLRIS-
RVEADDAGVYYCGQAIQDPRTFGAG

TKVDLK

>#29

GTGATGATGCAGACTCCACTGTCCCT-
GTCCGTCAGCCCTGGAGAGACTGCCT

CCATCTCCTGCAAGGCCAGTCAGAGC-
CTCCTGTATAGTGATGGAAACACGTA

TTTGCATTGGTTCCGACAGAAGCCAGGC-
CAGCCTCCACAGCGTTTGATCTTT

CAGGTCTCCAAAAGAGACCCTGGGGTC-
CCAGACAGGCTCAGTGGCAGCGGGT

CAGGGACAGACTTCACCCTGAGAATCAG-
CAGAGTGGAGGCTGGCGATACTGG

AGTTTATTACTGCATGCAAGCAA-
CAAAGTCTCCTCTCACTTTCAGCCAGGGG

ACCAAGGTGGAGATAAAA (SEQ ID NO: 257)

VMMQTPLSLSVSPGETASISCKASQS-
LLYSDGNTYLHWFRQKPGQPPQRLIF

QVSKRDPGVPDRLSGSGSGTDFTLRIS-
RVEAGDTGVYYCMQATKSPLTFSQG

TKVEIK

>#6

GTGATGACCCAGTCTCCAGCCTC-
CCTCTCCTTGTCTCAGGAGGAAAAAGTCA

CCATCACCTGCCGGGCCAGTCAGAGTGT-
TAGCAGCTACTTAGCCTGGTACCA

GCAAAAACCTGGGCAGGCTCCCAAGCTC-
CTCATCTATGGTACATCCAACAGG

GCCACTGGTGTCCCATCCCGGTTCAGTG-
GCAGTGGGTCTGGGACAGACTTCA

GCTTCACCATCAGCAGCCTGGAGCCT-
GAAGATGTTGCAGTTTATTACTGTCA

GCAGTATAATAGCGGATATACGTTCGGC-
CAAGGAACCAAGGTGGAGCTCAAA (SEQ ID NO: 259)

VMTQSPASLSLSQEEKVTITCRASQSVS-
SYLAWYQQKPGQAPKLLIYGTSNR

ATGVPSRFSGSGSGTDFSFTISSLEPED-
VAVYYCQQYNSGYTFGQGTKVELK

>#18

GTCATGATGCAGACTCCACTGTCCCT-
GTCCGTCAGCCCTGGAGAGCCGGCCT

CCATCTCCTGCAAGGCCAGTCAGAGC-
CTCCTGGACAGTAATGGAAACACCTT

TTTGTCTTGGTTCCGACAGAAGCCAGGC-
CAGTCTCCACAGCGTTTGATCTAT

AAGGTCTCCAACAGAGACCCTGGGGTC-
CCAGACAGGTTCAGTGGCAGCGGGT

CAGGGACAGATTTCACCCTGAGAAT-
CAGCGGAGTGGAGGCTGATGATGCTGG

AATTTATTACTGCGGGCAAGGTTACAA-
GATCCGTGGACGTTCGGAGCAGGA

ACCAAGGTGGACCTCAAA (SEQ ID NO: 261)

VMMQTPLSLSVSPGEPASISCKASQS-
LLDSNGNTFLSWFRQKPGQSPQRLIY (SEQ ID NO: 254)

(SEQ ID NO: 256)

(SEQ ID NO: 258)

(SEQ ID NO: 260)

(SEQ ID NO: 262)

KVSNRDPGVPDRFSGSGSGTDFTLRIS-
GVEADDAGIYYCGQGLQDPWTFGAG

TKVDLK

>#42

GTGATGATGCAGACTCCACTGTCCCT-
GTCCGTCAGCCCTGGAGAGCCGGCCT

CCATCTCCTGCAAGGCCAGTCAGAGC-
CTCCTACACAGTAATGGGAACATCTT

GTTGTATTGGTTCCGACAGAAGCCAGGC-
CAGTCTCCACAGCCTTTGATCTAT

AAGGTCTCCAACAGAGACCCTGGGGTC-
CCAGACAGGTTCAGTGGCAGCGGGT

CAGGGACAGATTTCACCCTGAGAATCAG-
CAGAGTGGAGGCTGACGATACTGG

AATTTATTACTGCGGGCAAATTATA-
CAGTTTCCTCGGACGTTCGGAGCAGGT

ACCCAGGTGGAACTCAAA (SEQ ID NO: 264)

VMMQTPLSLSVSPGEPASISCKASQS-
LLHSNGNILLYWFRQKPGQSPQPLIY

KVSNRDPGVPDRFSGSGSGTDFTLRIS-
RVEADDTGIYYCGQIIQFPRTFGAG

TQVELK

>#7

GTGATGATGCAGACTCCACTGTCCCT-
GTCCGTCAGCCCTGGAGAGCCGGCCT

CCATCTCCTGCAAGGCCAGTCAGAGC-
CTCGTGGACAGTAATGGAAACACCTT

TTTGTCTTGGTTCCGACAGAAGCCAGGC-
CAGTCTCCACAGCGTTTGATCTAT

AAGGTCTCCAACAGAGACCCTGGGGTC-
CCAGACAGGTTCAGTGGCAGCGGGT

CAGGGACAGATTTCACCCTGAGAAT-
CAGCGGAGTGGAGGCTGATGATGGTGG

AATTTATTACTGCGGGCAAGGTTTACAA-
GATCCGTGGACGTTCGGAGCAGGA

ACCAAGGTGGACCTCAAA (SEQ ID NO: 266)

VMMQTPLSLSVSPGEPASISCKASQS-
LVDSNGNTFLSWFRQKPGQSPQRLIY

KVSNRDPGVPDRFSGSGSGTDFTLRIS-
GVEADDGGIYYCGQGLQDPWTFGAG

TKVDLK

>#19

GTGATGACCCAGTCTCCAGCCTC-
CCTCTCCTTGTCTCGGGAGGAAGAGGTCA

CCATCACCTGCCGGGCCAGTCAGACTAT-
TACCAACTCCTTAGCCTGGTACCA

GCAAAAACCTGGGCAGGCTCCCAAGCTC-
CTCATCTATGCTACATCCAACAGG

GCCACTGGTGTCCCATCCCGGTTCAGTG-
GCAGTGGGTCTGGGACAGACTTCA

GGTTCACCATCAGCAGCCTGGAGCCT-
GAAGATGTTGGAGTTTATTACTGTCA (SEQ ID NO: 263)

VMTQSPASLSLSREEEVTITCRASQTIT-
NSLAWYQQKPGQAPKLLIYATSNR

ATGVPSRFSGSGSGTDFRFTISSLEPED-
VGVYYCQQYNSGWTFGAGTKVEIK

>#31

GTCATGATGCAGACCCCACTGTCCCT-
GTCCGTCAgCCCTGGAGAGCTGGCCT

CCATCTCCTGCAAGGCCAGTCAGAGC-
CTCCTGGACAGTAATGGAAACACCTT

TTTGTCTTGGTTCCGACAGAAGCCAGGC-
CAGTCTCCACAGCGTTTGATCTAT

AAGGTCTCCAACAGAGACCCTGGGGTC-
CCAGACAGGTTCAGTGGCAGCGGGT

CAGGGACAGATTTCACCCTGAGAAT-
CAGCGGAGTGGAGGCTGATGATGCTGG

AATTTATTACTGCGGGCAAGGTATACAG-
GATCCGTGGACGTTCGGAGCAGGA

ACCAAGGTGGACCTCAAA (SEQ ID NO: 270)

VMMQTPLSLSVSPGELASISCKASQS-
LLDSNGNTFLSWFRQKPGQSPQRLIY

KVSNRDPGVPDRFSGSGSGTDFTLRIS-
GVEADDAGIYYCGQGIQDPWTFGAG

TKVDLK

>#43

GTGATGATGCAGACTCCACTGTCCCT-
GTCCGTCAGCCCTGGAGAGACTGTCT

CCATCTCCTGCAAGGCCAGTCAGAGC-
CTCCTGCACAGTAACGGGAACACCCA

TTTGTTTTGGTTCCGACAGAAGCCAGGC-
CAGTCTCCACAGCGCCTGATCAAC

TTGGTTTCCAACAGAGACCCTGGGGTC-
CCAGACAGGTTCAGTGGCAGCGGGT

CAGGGACAGATTTCACCCTGAGAATCAG-
CAGAGTGGAGGCTGACGATGCTGG

TGTTTATTACTGCGGGCAAGGTACACAA-
GATCCTCCGACGTTCGGAGCAGGA

ACCAAGGTGGACCTCAAA (SEQ ID NO: 272)

VMMQTPLSLSVSPGETVSISCKASQS-
LLHSNGNTHLFWERQKPGQSPQRLIN

LVSNRDPGVPDRFSGSGSGTDFTLRIS-
RVEADDAGVYYCGQGTQDPPTFGAG

TKVDLK

>#20

GTGATGATGCAGACTCCACTGTCCCT-
GTCCGTCAGCCCTGGAGAGCCGGCCT

CCATCTCCTGCAAGGCCAGTCAGAGC-
CTCCTGCACAGTAACGGGAACACCTA

TTTGTCTTGGTTTCGACAGAAGCCAGGC-
CAGTCTCCACAGTCTTTGATCTAT (SEQ ID NO: 265)

(SEQ ID NO: 267)

(SEQ ID NO: 268)

(SEQ ID NO: 269)

(SEQ ID NO: 271)

(SEQ ID NO: 273)

-continued

AAGGTCTCCAACAGAGACCCTGGGGC-
CCCAGACAGGTTCAGTGGCAGCGGGT

CAGGGACAGATTTCACCCTGAGAAT-
CAGCGGAGTGGAGGCTGATGATGTTGG

AATTTATTACTGCGGGCAAGGTATACAG-
GATCCGTGGACGTTCGGAGCAGGA

ACCAAGGTGGACCTCAAA (SEQ ID NO: 274)

VMMQTPLSLSVSPGEPASISCKASQS-
LLHSNGNTYLSWFRQKPGQSPQSLIY

KVSNRDPGAPDRFSGSGSGTDFTLRIS-
GVEADDVGIYYCGQGIQDPWTFGAG

TKVDLK

>#32

(SEQ ID NO: 275)

GTGATGATGCAGACTCCACTGTCCCT-
GTCCGTCAGCCCTGGAGAGCCGGCCT

CCATCTCCTGCAAGGCCAGTCAGAGC-
CTCCTGGACAGTAATGGAAACACCTT

TTTGTCTTGGTTCCGACAGAAGCCAGGC-
CAGTCTCCACAGCGTTTGATCTAT

AAGGTCTCCAACAGAGACCCTGGGGTC-
CCAGACAGGTTCAGTGGCAGCGGGT

CAGGGACAGATTTCACCCTGAGAAT-
CAGCGGAGTGGAGGCTGATGATGCTGG

AATTTATTACTGTGGGCAAGGTATACAG-
GATCCGTGGACGTTCGGAGCAGGA

ACCAAGGTGGACCTCAAA (SEQ ID NO: 276)

VMMQTPLSLSVSPGEPASISCKASQS-
LLDSNGNTFLSWFRQKPGQSPQRLIY

KVSNRDPGVPDRFSGSGSGTDFTLRIS-
GVEADDAGIYYCGQGIQDPWTFGAG

TKVDLK

>#9

(SEQ ID NO: 277)

GTGATGATGCAGACTCCACTGTCCCT-
GTCCGTCAGCCCTGGAGAGCCGGCCT

CCATCTCCTGCAAGGCCAGTCAGAGC-
CTCCTGGACAGTAATGGAAACACCTT

TTTGTCTTGGTTCCGACAGAAGCCAGGC-
CAGTCTCCACAGCGTTTGATCTAT

AAGGTCTCCAACAGAGACCCTGGGGTC-
CCAGACAGGTTCAGTGGCAGCGGGT

CAGGGGCAGATTTCACCCTGAGAAT-
CAGCGGAGTGGAGGCTGACGATACTGG

AGTTTATTACTGCATGCAAGGTATA-
CAGTTTCCTCGGACGTTCGGAGCAGGA

ACCAAGGTGGACCTCAAA (SEQ ID NO: 278)

VMMQTPLSLSVSPGEPASISCKASQS-
LLDSNGNTFLSWFRQKPGQSPQRLIY

KVSNRDPGVPDRFSGSGSGADFTLRIS-
GVEADDTGVYYCMQGIQFPRTFGAG

TKVDLK

-continued

>#33

(SEQ ID NO: 279)

GTGATGACGCAGACCCCACTGTCCCT-
GTCCGTCAGCCCTGGAGAGCCGGCCT

CCATCTCCTGCAAGGCCAGTCAGAGC-
CTCCTGGACAGTAATGGAAACACCTT

TTTGTCTTGGTTCCGACAGAAGCCAGGC-
CAGTCTCCACAGCGTTTGATCTTT

AAGGTCTCCAACAGAGACCCTGGGGTC-
CCAGACAGGTTCAGTGGCAGCGGGT

CAGGGACAGATTTCACCCTGAGAAT-
CAGCGGAGTGGAGGCTGATGATGTTGG

AATTTATTACTGCGGGCAAGGTATACAG-
GATCCGTGGACGTTCGGAGCAGGT

ACCCAGGTGGAACTCAAA (SEQ ID NO: 280)

VMTQTPLSLSVSPGEPASISCKASQS-
LLDSNGNTFLSWFRQKPGQSPQRLIF

KVSNRDPGVPDRFSGSGSGTDFTLRIS-
GVEADDVGIYYCGQGIQDPWTFGAG

TQVELK

>#45

(SEQ ID NO: 281)

GTCATGACGCAGACCCCACTGTCCCT-
GTCCGTCASCCCTGGAGAGCCGGCCT

CCATCTCCTGCAAGGCCAGTCAGAGC-
CTCCTGGACAGTAATGGAAACACCTT

TTTGTCTTGGTTCCGACAGAAGCCAGGC-
CAGTCTCCACAGCGTTTGATCTAT

AAGGTCTCCAACAGAGACCCTGGGGTC-
CCAGACAGGTTCAGTGGCAGCGGGT

CAGGGACAGATTTCACCCTGAGAAT-
CAGCGGAGTGGAGGCTGATGATGCTGG

AATTTATTACTGCGGGCAAGGTATACAG-
GATCCGTGGACGTTCGGAGCAGGT

ACCCAGGTGGAGCTCAAA (SEQ ID NO: 282)

VMTQTPLSLSVXPGEPASISCKASQS-
LLDSNGNTFLSWFRQKPGQSPQRLIY

KVSNRDPGVPDRFSGSGSGTDFTLRIS-
GVEADDAGIYYCGQGIQDPWTFGAG

TQVELK

>#10

(SEQ ID NO: 283)

GTGATGACACAGTCTCCAGCCTC-
CCTCTCCTTGTCTCAGGAGGAAGAAGTCA

CCATCACCTGCCGGGCCAGTCAGAGTGT-
TAGCAGCTACTTAGCCTGGTACCA

GCAAAAACCTGGGCAGGCTCCCAAGCTC-
CTCATCTATGGTACATCCAACAGG

GCCACTGGTGTCCCATCCCGGTTCAGTG-
GCAGTGGGTCTGGGACAGACTTCA

GCTTCACCATCAGCAGCCTGGAGCCT-
GAAGATGTTGCAGTTTATTACTGTCA

GCACTATAATGGCGGGTGGACGTTCG-
GAGCAGGAACCAAGGTGGAACTCAAA

VMTQSPASLSLSQEEEVTITCRASQSVS-
SYLAWYQQKPGQAPKLLIYGTSNR

ATGVPSRFSGSGSGTDFSFTISSLEPED-
VAVYYCQHYNGGWTFGAGTKVELK

>#46

(SEQ ID NO: 284)
GTGATGATGCAGACTCCACTGTCCCT-
GTCCGTCAGCCCTGGAGAGCCGGCCT

CCATCTCCTGCAAGGCCAGTCAGAGC-
CTCCTGGACAGTAATGGAAACACCTT

TTTGTCTTGGTTCCGACAGAAGCCAGGC-
CAGTCTCCACAGCGTTTGATCTAT

AAGGTCTCCAACAGAGACCCTGGGGTC-
CCAGACAGGTTCAGTGGCAGCGGGT

CAGGGACAGATTTCACCCTGAGAAT-
CAGCGGAGTGGAGGCTGATGATGCTGG

AATTTATTACTGCGGGCAAGGTATACAG-
GATCCGTGGACGTTCGGAGCAGGA

ACCAAGGTGGACCTCAAA (SEQ ID NO: 285)
VMMQTPLSLSVSPGEPASISCKASQS-
LLDSNGNTFLSWFRQKPGQSPQRLIY

KVSNRDPGVPDRFSGSGSGTDFTLRIS-
GVEADDAGIYYCGQGIQDPWTFGAG

TKVDLK

>#23

(SEQ ID NO: 286)
GTGATGACACAGACCCCACTGTCCCT-
GTCCGTCAGCCCTGGAGAGCCGGCCT

CCATCTCCTGCAAGGCCAGTCAGAGC-
CTCCTGCACAGTAATGGGAACACCTA

TTTGTATTGGTTCCGACAGAAGCCAGGC-
CAGTCTCCACAGCGTTTGATCTAT

AAGGTCTCCAACAGAGACCCTGGGGTC-
CCAGACAGGTTCAGTGGCAGCGGGT

CAGGGACAGATTTCACCCTGAGAATCAG-
CAGAGTGGAGGCTGATGATGCTGG

AGTTTATTACTGCGGGCAAGGTTTCCAA-
GATCCGTGGACGTTCGGAGCAGGA

ACCAAGGTGGACCTCAAA (SEQ ID NO: 287)
VMTQTPLSLSVSPGEPASISCKASQS-
LLHSNGNTYLYWFRQKPGQSPQRLIY

KVSNRDPGVPDRFSGSGSGTDFTLRIS-
RVEADDAGVYYCGQGFQDPWTFGAG

TKVDLK

>#35

(SEQ ID NO: 288)
GTGATGATACAGACTCCACTGTCCCTG-
GCCGTCACCCCTGGAGAGCTGGCCA

CTATCTCCTGCAGGGCCAGTCA-
GAGTCTCCTGCACAGTGATGGAAAATCCTA

TTTGAATTGGTACCTGCAGAAGCCAGGC-
CAGACTCCTCGGCCGCTGATTTAT

GAGGCTTCCAAGCGTTTCTCTGGGGTCT-
CAGACAGGTTCAGTGGCAGCGGGT (SEQ ID NO: 289)
CAGGGACAGATTTCACCCTTAAAATCAG-
CAGGGTGGAGGCTGAGGATGTTGG

AGTTTATTACTGCCAGCAAAGTCTA-
CATTTTCCTCCTGCGTTCGGAGCAGGA

ACCAAGGTGGACCTCAAA (SEQ ID NO: 290)
VMIQTPLSLAVTPGELATISCRASQS-
LLHSDGKSYLNWYLQKPGQTPRPLIY

EASKRFSGVSDRFSGSGSGTD-
FTLKISRVEAEDVGVYYCQQSLHFPPAFGAG

TKVDLK

>#47

(SEQ ID NO: 291)
GTCATGATGCAGACTCCACTGTCCCT-
GTCCGTCAGCCCTGGAGAGCCGGCCT

CCATCTCCTGCAAGGCCAGTCAGAGC-
CTCCTGCACAGTAACGGGAACACCTA

TTTGTTTTGGTTTCGACAGAAGCCAGGC-
CAGTCTCCACAGCGTTTGATCTAT

AAGGTCTCCAACAGAGACCCTGGGGTC-
CCAGACAGGTTCAGTGGCAGCGGGT

CAGGGACAGATTTCACCCTGACAATCAG-
CAGAGTGGAGGCTGACGATACTGG

AGTTTATTACTGCGGGCAAGGTATA-
CAGTTTCCTCGGACGTTCGGAGCAGGT

ACCCAGGTGGAGCTCAAA (SEQ ID NO: 292)
VMMQTPLSLSVSPGEPASISCKASQS-
LLHSNGNTYLFWFRQKPGQSPQRLIY

KVSNRDPGVPDRFSGSGSGTD-
FTLTISRVEADDTGVYYCGQGIQFPRTFGAG

TQVELK

>#12

(SEQ ID NO: 293)
GTGATGATGCAGACTCCACTGTCCCT-
GTCCGTCAGCCCTGGAGAGACTGCCT

CCATTTCCTGCACGGCCAGTCAGAGC-
CTCCTCCACAGTGATGGAAACACGTA

TTTGAATTGGATCCGACAGAAGCCAGGC-
CAGTCTCCACAGCGTTTGATCGAA

AAGGTCTCCAAGAGAGACCCTGGGGTC-
CCAGACAGGTTCAGTGGCAGCGGGT

CAGGGACAGATTTCACCCTGAGAATCAG-
CAGAGTGGAGGCTGGCGATGTTGG

AGTTTATTACTGCCTGCAAGGCACA-
CAGTCTCCGTGACGTTCGGAACAGGG

ACCAAGCTGGAGATCAAA (SEQ ID NO: 294)
VMMQTPLSLSVSPGETASISCTASQS-
LLHSDGNTYLNWIRQKPGQSPQRLIE

KVSKRDPGVPDRFSGSGSGTDFTLRIS-
RVEAGDVGVYYCLQGTQSPWTFGTG

TKLEIK

>#24

(SEQ ID NO: 295)
GTCATGATGCAGACTCCACTGTCCCT-
GTCCGTCAGCCCTGGAGAGCCGGCCT

```
CCATCTCCTACAAGGCCAGTCAGAGC-
CTCCTGGAAAGTGATGGGAACACCTT

TTTGTCTTGGTTCCGACAGAAGCCAGGC-
CAGTCTCCACAGCGTTTGATCTAT

AAGGTCTCCAACAGAGACCCTGGGGTC-
CCAGACAGGTTCAGTGGCAGCGGGT

CAGGGACAGATTTCACCCTGAGAAT-
CAGCGGAGTGGAGGCTGATGATGCTGG

AATTTATTACTGCGGGCAAGGTATACAG-
GATCCGTGGACGTTCGGAGCAGGA

ACCAAGGTGGACCTCAAA
```
(SEQ ID NO: 296)
```
VMMQTPLSLSVSPGEPASISYKASQS-
LLESDGNTFLSWFRQKPGQSPQRLIY

KVSNRDPGVPDRFSGSGSGTDFTLRIS-
GVEADDAGIYYCGQGIQDPWTFGAG

TKVDLK

>#36
```
(SEQ ID NO: 297)
```
GTGATGATGCAGACCCCACTGTCCCT-
GTCCGTCAGCCCTGGAGAGCCGGCCT

CCATCTCCTGCAAGGCCAGTCA-
GAGTCTCCTGCGCAGTGATGGAAAATCCTA

TTTGAATTGGTACCTGCAGAAGCCAGAC-
CAGACTCCTCGGCCGCTGATTTAT

GAGGCTTCCAAGCGTTTCTCTGGGGTCT-
CAGACAGGTTCAGTGGCAGCGGGT

CAGGGACAGATTTCACCCTGAGAATCAG-
CAGAGTGGAGGCTGACGATACTGG

AGTTTATTATTGTGGGCAAGTTATAGAA-
GATCCGTGGACGTTCGGAGCAGGA

ACCAAGGTGGACCTCAAA
```
(SEQ ID NO: 298)
```
VMMQTPLSLSVSPGEPASISCKASQSLL-
RSDGKSYLNWYLQKPDQTPRPLIY

EASKRFSGVSDRFSGSGSGTDFTLRIS-
RVEADDTGVYYCGQVIEDPWTFGAG

TKVDLK

>#48
```
(SEQ ID NO: 299)
```
GTCATGACACAGACTCCACTGTCCCT-
GTCCGTCAGCCCTGGAGAGCCGGCCT

CCATCTCCTGCAAGGCCAGTCAGAGC-
CTCCTGCACAGTAATGGGAACACCTA

TTTGTATTGGTTTCGACAGAAGGCAGGC-
CAGTCTCCACAGCGTTTGATCTAT

AAGGTCTCCAACAGAGACCCTGGGGTC-
CCAGACAGGTTCAGTGGCAGCGGGT

CAGGGACAGATTTCACCCTGAGAATCAG-
CAGAGTGGAGGCTGATGATGCTGG

AGTTTATTATTGCGGGCAAGGTATACAA-
GATCCTCCGACGTTCGGAGCAGGA

ACCCAGGTGGAGCTCAAA
```
(SEQ ID NO: 300)
```
VMTQTPLSLSVSPGEPASISCKASQS-
LLHSNGNTYLYWFRQKAGQSPQRLIY

KVSNRDPGVPDRFSGSGSGTDFTLRIS-
RVEADDAGVYYCGQGIQDPPTFGAG

TQVELK
```

VL Lambda Chains from HSA-7 Library

>#1
(SEQ ID NO: 301)
```
GGGTTGACTCAGCTGCCTTCCGTGAAT-
GTGACCCTGAGGCAGACGGCCCACA

TCACCTGTGGGGGAGACAGGATTGGAAG-
TAAATATGTTCAATGGACCCAGCA

GAATCCAGGCCAGGCCCCCGTGGTGAT-
TATCTATAAGGATACCAACAGGCCG

AGAGGGATCCCTGAGCGATTCTCTG-
GCGCCAACTCAGGGAACACGGCTACCC

TGACCATCAGCGGGGCCCTCGCCGAA-
GACGAGGCTGACTATTACTGCCAGGT

GTGGGACACCAGTGCTAAGGCTGTGT-
TCGGCGGAGGCACCCACCTGACCGTC

CTT
```
(SEQ ID NO: 302)
```
GLTQLPSVNVTLRQTAHITCGGDRIG-
SKYVQWTQQNPGQAPVVIIYKDTNRP

RGIPERFSGANSGN-
TATLTISGALAEDEADYYCQVWDTSAKAVFGGGTHLTV

L

>#2
```
(SEQ ID NO: 303)
```
GTGTTGAcTCAGCTGGCCTCAGT-
GTCTGGGTCCCTGWgGcCAGAGGGTCACC

ATCTCCTGCACTGGCAGCAGCTCCAA-
CATCGGTAGATTTAGTGTTGGCTGGT

TCCAGCAACTCCCGGGAAAAGGCCCCA-
GAACCGTCATCTATAGTAGTAGTAA

CCGACCCTCAGGGGTCCCTGATCGAT-
TCTCTGGCTCCAAGTCAGGCAGCACA

ACCACCCTGACTATCTCTGGGCTCCAG-
GCTGAGGACGAGGCTGATTATTACT

GTTCAACATACGACGACAGTCTCACTAT-
TACTGTGTTCGGCGGAGGCACCCA

CCTGACCGTCCTC
```
(SEQ ID NO: 304)
```
C-
LSWPQCLGPXGQRVTISCTGSSSNI-
GRFSVGWFQQLPGKGPRTVIYSSNRP

SGVPDRFSGSKSGSTT-
TLTISGLQAEDEADYYCSTYDDSLTITVFGGGTHLT

VL

>#3
```
(SEQ ID NO: 305)
```
GTGCTGACTCAGCTGGCCTCAGTG-
GCTGGGTCCCtGgGcCAGAGGGTCACCA

TCTCCTGCACTGGAAGCAGTTCCAA-
CATCGGTGGATATCATGTTGGCTGGTT

CCAGCAGGTCCCGGAAACAGGCCCCA-
GAATCGTCATCTATAGTAGTGGTCAG
```

```
CGACCCTCGGGGGTCCCAGATCGAT-
TCTCTGGCTCCAGGTCAGGCAGCACAG

CCACCCTGACCATATCTGGGCTCCAG-
GCTGAGGACGAGGCTGAGTATTACTG

CTCAACATGGGACGACAGTCT-
CAAAGCGCCTGTGTTCGGCAGAGGCACCCAG

CTGACCGTCCTC
```
(SEQ ID NO: 306)
```
VLTQLASVAGSLGQRVTISCTGSSSNIG-
GYHVGWFQQVPETGPRIVIYSSGQ

RPSGVPDRFSGSRSG-
STATLTISGLQAEDEAEYYCSTWDDSLKAPVFGRGTQ

LTVL
```

>#4
(SEQ ID NO: 307)
```
GTGCTGACTCAGCTTACCTCAGT-
GTCTGGGTCCCTGGGCAGAgGCTCACCA

TCTCCTGCACTGGAAGCAGT-
TCTAACGTCGGTCGATATAATGTTGGCTGGTT

CCAGCAGGTCCCGGGAAAAGGC-
CCCAAAACCGTCATCTATAATACTTCTACC

CGACCCTCAGGGGTCCCTGATCGAT-
TCTCTGGGTCCAAGTCAGGCAATACCG

CCACCCTGACCATCTCTGGCCTCCAAC-
CTGAGGACGAAGCTGATTATTACTG

CTCAACATACGACAGCTTTCTCATTACT-
GTCTTCGGCGGAGGCACCCACCTG

ACCGTCCTC
```
(SEQ ID NO: 308)
```
VLTQLTSVSGSLGQRLTISCTGSSSN-
VGRYNVGWFQQVPGKGPKTVIYNTST

RPSGVPDRFSGSKSGNTATLTISGLQ-
PEDEADYYCSTYDSFLITVFGGGTHL

TVL
```

>#9
(SEQ ID NO: 309)
```
GTGCTGACTCAGCTGACCTCAGT-
GTCGGGGTCCCTtggccAgAGGGTCACCC

TGTCCTGCTCTGGAAGCACGAACAA-
CATCGGTCTTTTTGGTGCGACCTGGTA

CCAACAGTTCCCAGGAAAGGC-
CCCTAAACTCCTCATGTACACTGATGGGGAT

CGACCGTCCGGGGTCCCTGACCG-
TTTTCCGGCTCCAaGTCAGGCGACTCAG

CCACCCTGACCATCACTGGGCTTCAG-
GCTGAGGACGAGGCTGATTATCACTG

TCAATCCGCTGATCCCACGCTTAGAGTT-
TATGTGTTCGGCTCAGGCACCCAg

CTGACCGTCCTC
```
(SEQ ID NO: 310)
```
VLTQLTSVSGSLGQRVTLSCSGST-
NNIGLFGATWYQQFPGKAPKLLMYTDGD

RPSGVPDRFSGSKSGDSATLTIT-
GLQAEDEADYHCQSADPTLRVYVFGSGTQ

LTVL
```

>#10
(SEQ ID NO: 311)
```
GTGCTGACTCAGCCTCCTTCAGTGTC-
CCGGTACCtgggCCAGAGTGTCACCA

TCTCTTGTAATGGAAGCTCTTC-
CAATATCGGTCGACCTTATGTACACTGGTA

CCAACAATTCCCGGGAACCGCCCCCA-
GAACCCTCATCTATGGTGTTAGTAAT

CGACTCTCAGGGGTCCCCGATCGAT-
TCTCTGCCTCCAGGTCGGGCACTACAG

CGACTCTGACGATCTTTGGGCTCCAG-
GCTGAGGATGAGACTGATTATTATTG

TTCATCCTGGGACAGCAGTCTCAATGGT-
TACGTGTTCGGCTCGGGAATCGAA

CTCACCGTCCTA
```
(SEQ ID NO: 312)
```
VLTQPPSVSRYLGQSVTISCNGSSSNI-
GRPYVHWYQQFPGTAPRTLIYGVSN

RLSGVPDRFSASRSGTTATLTIFGLQAE-
DETDYYCSSWDSSLNGYVFGSGIE

LTVL
```

>#11
(SEQ ID NO: 313)
```
GTGTTGACTCAGCTGGCCTCAGT-
GTCTGGGTCCCTGGGCCAGAAGGTCACCA

TCTCCTGCTCTGGAAACACCTCCAA-
CATCGGAACTAATTCAGTGGGCTGGTA

TCAACAGTTGCCAGGCAGAGGCCCTA-
GAACCGTCATCTATGGTGATGATTAC

CGCCCTTCAGGGGTCCCCGATCGAT-
TCTCTGCCTCCAAGTCAGGCAGTTCAG

GCTCCCTGACCATCTCTGGCCTCCAGC-
CTGAGGACGAGGCTGCCTATTACTG

CTCATCCTGGGATGATAATCTCAGAGGT-
GTTGTATTCGGTGGAGGCACCCAG

CTGACCGTCCTC
```
(SEQ ID NO: 314)
```
VLTQLASVSGSLGQKVTISCS-
GNTSNIGTNSVGWYQQLPGRGPRTVIYGDDY

RPSGVPDR FSASKSGSSGSLTISGLQ-
PEDEAAYYCSSWDDNLRGVVFGGGT

QLTVL
```

>#12
(SEQ ID NO: 315)
```
CTGCTGACTCAGCCTGCTTCTGT-
GTCTGGGTCCCTGGGcCAGAGGGTCACCA

TCTCCTGCACTGGAAGCAGTTCCAA-
CATCGGTGGATATCATGTTGGCTGGTT

CCAGCAGGTCCCGGAAACAGGCCCCA-
GAATCGTCATCCATAGTAGTGGTCAG

CGACCCTCGGGGGTCCCAGATCGAT-
TCTCTGGCTCCAGGTCAGGCAGCACAG

CCACCCTGACCATCTCTGGGCTCCAG-
GCTGAGGACGAGGCTGAGTATTACTG

TTCAACATGGGACGACAGTCT-
CAAAGCGCCTGTGTTCGGCGGAGGCACCCAC

CTGACCGTCCTC
```

(SEQ ID NO: 316)
LLTQPASVSGSLGQRVTISCTGSSSNIG-
GYHVGWFQQVPETGPRIVIHSSGQ

RPSGVPDRFSGSRSG-
STATLTISGLQAEDEAEYYCSTWDDSLKAPVFGGGTH

LTVL

>#17
(SEQ ID NO: 317)
GTGCTGACTCAGCCTCCTTCTGTGTCTG-
CAGCCCTGGGACAGAGGGTCACCA

TCTCCTGCACTGGAAGTGACACCAA-
CATCGGCAGTGGTTATGAGGTACAGTG

GTACCAACTCCTCCCAGGAAAGTC-
CCCGAAGACTATCATCTATGGTAATATC

AATCGACCCTCGGGGGTCCCGGTTCGAT-
TCTCTGGCTCCAAGTCAGGCACTA

TAGTCACCCTGTCCATCACTGGGATC-
CAGGCTGAGGATGAGGCTGATTATTA

CTGCCAGTCCTATGATGACAACGTC-
GATGGTTACGTGTTCGGCTCAGGAACC

GAACTCACCGTCCTT (SEQ ID NO: 318)
VLTQPPSVSAALGQRVTISCTGSDT-
NIGSGYEVQWYQLLPGKSPKTIIYGNI

NRPSGVPVRFSGSKSGTIVTLSIT-
GIQAEDEADYYCQSYDDNVDGYVFGSGT

ELTVL

>#19
(SEQ ID NO: 319)
GGGCTGACTCAGCCGCCATCCGTGAAT-
GTGACCCTGAGGCAGACGGCCCACA

TCACCTGTGGGGGAGACAGTATTGGAAG-
TAAATATGTTCAATGGATCCAGCA

GAGTCCAGGCCAGGCCCCCCTACTTAT-
CATCTATAAAGATAGTCACAGGGCG

ACAGGGATCCCTGAGCGATTCTCTGC-
CGCCAACTCAGGGAGCACGGCTACCC

TGACCATCGCCGGGGCCCTGGCCGAA-
GACGAGGCTGACTATTACTGCCAGGT

GTGGGACAACAGTGTCATTGCGTTCG-
GCGGAGGCACCCACCTGACCGTCCTC (SEQ ID NO: 320)
GLTQPPSVNVTLRQTAHITCGGDSIG-
SKYVQWIQQSPGQAPLLIIYKDSHRA

TGIPERFSAANSGSTATLTIA-
GALAEDEADYYCQVWDNSVIAFGGGTHLTVL

>#20
(SEQ ID NO: 321)
GCGTTGACTCAGCTAGCCTCAGTGTCTG-
GATCCCTGGGCCAAAGGGTCACCA

TCTCCTGCACTGTAAGCACAGGCAAT-
GTCGGTGGTTATAATTATGTACACTG

GTACCAGCAACTCCCAGGAAAGGCAC-
CCAGTCCTCATCTATGGTGATCAT

AACAGAGATTCTAGGGCCCCTGAACGAT-
TCTCTGGCTCCAAGTCAGGCAGCT

CAGCCACTCTGACCATCACTGGCCTC-
CAGGCTGAGGACGAGGCTGATTATTA

TTGCCAGTCCTACGATGACAGTTTCAAT-
GCTGTGTTCGGCGGAGGCACCCAC

CTGACCGTCCTC (SEQ ID NO: 322)
ALTQLASVSGSLGQRVTISCTVSTGN-
VGGYNYVHWYQQLPGKAPSLLIYGDH

NRDSRAPERFSGSKSGSSATLTIT-
GLQAEDEADYYCQSYDDSFNAVFGGGTH

LTVL

>#25
(SEQ ID NO: 323)
GCGCTGACTCAGAAGGCCTCAGT-
GTCTGGGTCCCTGGGCCAGAGGGTCACCA

TCTCCTGCACTGGAAGCAGCTCCAA-
CATCGGTAGATATAGTGTTGGTTGGTT

CCAGCAGCTCCCGGGAAAAGGCCCCA-
GAACCGTCATCCAAAGTAGTAGTGAC

CGACCCTCAGGGGTCCCTGATCGAT-
TCTCTGGCTCCAAGTCAGGCAGCACAG

CCACCCTGACCATCTCTGGGCTCCAG-
GCTGAGGACGAGGCTGATTATTATTG

TTCAACATACGATAGCAGTCTCAGTGGT-
TGGGTATCCGGTGAAGGGACCCAG

CTGACCGTCCTC (SEQ ID NO: 324)
ALTQKASVSGSLGQRVTISCTGSSSNI-
GRYSVGWFQQLPGKGPRTVIQSSSD

RPSGVPDRFSGSKSG-
STATLTISGLQAEDEADYYCSTYDSSLSGWVSGEGTQ

LTVL

>#26
(SEQ ID NO: 325)
GTGCTGACTCAGCTACCCTCAGT-
GTCTGGGTCCCTGGGcCAGAGGGTCACCA

TCTCCTGCACTGGAAGCAGCTCCAATGT-
TGGTTATGCGCTTATGTGGGCTG

GTGGCAGCAGCTCCCAGGAACAAGGC-
CCAGAATCCTCATCTATGATATAACT

AACCGACCCTCGGGGGTCCCTGATCGAT-
TCTCTGGCTCCAGGTCAGGCTACA

CAGCTACCCTGACCATCTCTGGGCTC-
CCGGCTGAGGATGAAGCCGATTATTA

CTGCTCAACCTATGACAGCAGTCT-
CAAAGGTTACGTGTTCGGCGGAGGCACC

CAGCTGACCGTCCTC (SEQ ID NO: 326)
VLTQLPSVSGSLGQRVTISCTGSSSN-
VGYGAYVGWWQQLPGTRPRILIYDIT

NRPSGVPDRFSGSRS-
GYTATLTISGLPAEDEADYYCSTYDSSLKGYVFGGGT

QLTVL

>#28
(SEQ ID NO: 327)
fam 3,

GGGCTGAATCAGCCTCCCTCGGTAT-
CAGTGTCTCTGGGACAGACAGCAACCA

```
TCTCCTGCTCTGGAGAGAGTCTGAG-
TAAATATTATGCACAATGGTTCCAGCA

GAAGGCAGGCCAAGCCCCTGTTGGT-
CATATATAAGGACACTGAGCGGCCC

TCTGGGATCCCTGACCGATTCTCTG-
GCTCCAGTTCAGGGAACACACACACCC

TGACCATCAGCGGGGCTCGGGCCGAG-
GACGAGGCTGACTATTACTGCGAGTC

AGCAGTCAGTACTGATACTGCTATGT-
TCGGCGGAGGGACCCAGCTGACCGTC

CTC
```
(SEQ ID NO: 328)

```
GLNQPPSVSVSLGQTATISCSGESL-
SKYYAQWFQQKAGQAPVLVIYKDTERP

SGIPDRFSGSSSGNTHTLTISGA-
RAEDEADYYCESAVSTDTAMFGGGTQLTV

L
```

>#33
(SEQ ID NO: 329)
```
GTGCTGACTCAGAAGGCCTCAGT-
TGTCTGGGTCCCTGTgGCACANACGGTCA

CCATCTCCTGCACTGGAAGCCTGTCCAA-
CATCCGTGCATTCGGTGTTGGCTG

GTTCCAGCAGGTCCCGGGAAGAGGC-
CCCAgAACCGTCATCTATAgtACGCGT

AACCGACCCTCAGGGGTCCCTGATCGAT-
TCTCTGGCTCCAAGTCAGGCAGCA

CAGCCACCCTGACCATCTCTGGGCTC-
CAgGCTGAGGACAAGGCTGATTATTA

CTGTTCAGTCTATGACAGCAGTCTCAC-
TAATGGTCTGTTCGGCGGAGGGACC

CACCTGACCGTCCTC
```
(SEQ ID NO: 330)
```
VLTQKASVVWVPVAXTVTISCTGSL-
SNIRAFGVGWFQQVPGRGPRTVIYSTR

NRPSGVPDRFSGSKSG-
STATLTISGLQAEDKADYYCSVYDSSLTNGLFGGGT

HLTVL
```

>#34 partial sequence
(SEQ ID NO: 331)
```
CTCAGCTGGCCTCAGATGTTGGGGTC-
CCCTTGgCcAGAGGGTCTCCATCTCCT

GTTCTGGAAGCACGAACAGTATCG-
GTTTTCTTGGTGCGAGTTGGTACCAACA

GCTCCCAGGAAAGGCCCCTAAACTC-
CTCGTGTACACTGATGGGAATCGACCG

TCAGGGGTCCCTGACCGGTTTTCCG-
GCTCCAGGTCTGGCGACTCAGGCACCC

TGACCATCACTGGGCTCCAGGCTGAG-
GACGAGGCTGATTATTACTGTCAGTC

TGTTGATTCCACGTCTAGTGCTAT-
TATATTCGGCGGAGGGACCCACCTGACC

GTCCTC
```
(SEQ ID NO: 332)
```
LSWPQMLGSLGQRVSISCSGSTNSIGFL-
GASWYQQLPGKAPKLLVYTDGNRP

SGVPDRFSGSRSGDSGTLTIT-
GLQAEDEADYYCQSVDSTSSAIIFGGGTHLT

VL
```

>#41
(SEQ ID NO: 333)
```
GGGTTGAATCAGCCTTCCTCGGT-
GTCTGGGACTTTGGGCCAGACTGTCACCA

TCTCCTGTGATGGAAGCAGCAGTAACAT-
TGGCAGTCATAATTGGATCGAATG

GTACCAGCAGTTCCCAGGCACCTC-
CCCCAAACTCCTGATTTACTATACCAAT

AATCGGCCATCAGGGATCCCTGCTCGCT-
TCTCTGGCTCCAAGTCTGGGAATA

CGGCCTCCTTGACCATCTCTGGCCTC-
CAGGCTGAAGATGAGGCTGATTATTA

CTGCAGCGCATTTGCTGGTAG-
TAATAACGCTGCTCTGTTCGGCGGAGGCACC

CAGCTGACCGTCCTC
```
(SEQ ID NO: 334)
```
GLNQPSSVSGTLGQTVTISCDGSSSNIG-
SHNWIEWYQQFPGTSPKLLIYYTN

NRPSGIPARFSGSKSGN-
TASLTISGLQAEDEADYYCSAFAGSNNAALFGGGT

QLTVL
```

>#42
(SEQ ID NO: 335)
```
GTCTGACTCAGCCGGCCTCCGT-
GACTGGGTCCCTGGGCCAGAGGGTCACTAT

CTCCTGCACTGGAAGCAGTTCCAA-
CATCGGTGGATATCATGTTGGCTGGTTC

CAGCAGGTCCCGGGAAACAGGCCCCA-
GAATCGTCATCCATAGTAGTGGTCAGC

GACCCTCGGGGGTCCCAGATCGAT-
TCTCTGGCTCCAGGTCAGGCAGCACAGC

CACCCTGACCATCTCTGGGCTCCAGACT-
GAGGACGAGGCTGAGTATTACTGC

TCAACATGGGACGACAGTCTCAAAGCGC-
CTGTGTTCGGCAGAGGCACCCACC

TGACCGTCCTC
```
(SEQ ID NO: 336)
```
LTQPASVTGSLGQRVTISCTGSSSNIG-
GYHVGWFQQVPETGPRIVIHSSGQR

PSGVPDRFSGSRSGSTATLTISGLQT-
EDEAEYYCSTWDDSLKAPVFGRGTHL

TVL
```

>#43
(SEQ ID NO: 337)
```
GTGCTGACTCAGCCGCCCTCAGT-
GTCGGGGTCCCTCGGCCAGAgGGTCACCA

TGTCCTGCACTGGAAGCAGATCCAATGT-
TGGTTATGGCAACAGATATGTGGG

CTGGTACCAATTGGTCCCAGGGACAGGC-
CCCAAAACCCTCATCTATGAAGAT

AGTAGACGACCCTCGGGGGTCCCTGATC-
GATTCTCAGGCTCCAGGTCAGGCA

GCACAGCAACCCTGAC-
TATCTCTGGGCTCCAGGCTGAGGATGAAGCCGATTA
```

```
                                                      (SEQ ID NO: 338)
VLTQPPSVSGSLGQRVTMSCTGSRSN-
VGYGNRYVGWYQLVPGTPKTLIYED

SRRPSGVPDRFSGSRSG-
STATLTISGLQAEDEADYFCSSYDTSLLAGVFGGG

THLTVL

>#49
                                                      (SEQ ID NO: 339)
GTGCTGACTCAgCCGGCCTCAGT-
GTCTGGGTCCCTGGGCCAGAGGGTCACCA

TCTCCTGCACTGGAAGCAGCTCCAA-
CATCGGTTGGGGTGATGTGGGCTGGTA

CCAACAGTACCCAGGAACAGGCCCCA-
GAACCCTCATCTATGATACTAGTCGC

CGACCCTCGGGGTCCCTGATC-
GATTTTCTGGCTCCAGGTCAGGCAGCACAG

CAACCCTGACCATCTCTGGGCTCCAG-
GCTGAGGACGAGGCTGATTATTACTG

TTCATCCTCTGACAGCACAACCAGTG-
GTGGCGTGTTCGGCTCAGGAATCCAA

CTCACCGTCCTT
                                                      (SEQ ID NO: 340)
VLTQPASVSGSLGQRVTISCTGSSSNIG-
WGDVGWYQQYPGTPRTLIYDTSR

RPSGVPDRFSGSRSG-
STATLTISGLQAEDEADYYCSSSDSTTSGGVFGSGIQ

LTVL

>#51
                                                      (SEQ ID NO: 341)
GTGCTGTCACAGCTGCCATCCGTGTCT-
GCGGtCCTGgGACAGAGGGTCACCA

TCTCCTGCACTGGAAGTAGCACCAACAT-
TGGCAAGGATTATGATGTACAATG

GTACCAGCAGCTCCCAGGAAAAGTC-
CCCTAAAACTATCGTCTATGGTAATAGC

AATCGACCCTCAGGGGTCCCGGATCGCT-
TCTCTGGCTCCAAGTCAGGCAGCA

CAGCCTCTCTGACCATCACTGGGCTC-
CAGGCTGAGGACGAGGCTGATTATTA

CTGCCAGTCCTCTGATGACAATGTCGAT-
GATTATATTGTGTTCGGCAGAGGC

ACCCACCTGACCGTCCTC
                                                      (SEQ ID NO: 342)
VLSQLPSVSAVLGQRVTISCTGSST-
NIGKDYDVQWYQQLPGKSPKTIVYGNS

NRPSGVPDRFSGSKSGSTASLTIT-
GLQAEDEADYYCQSSDDNVDDYIVFGRG

THLTVL

>#60
                                                      (SEQ ID NO: 343)
CTGCTGACCCAGCCGGCCTCAGT-
GTCTGGGTCCCTGGGCCAGAGGGTCACCA

TCTCCTGCACTGGAAGCAGCTCCAA-
CATCGGTAGAGGTTATGTGGGCTGGTA

CCAGCAGCTCCCAGGAACAGGCCCCA-
GAACCCTCATCTATGATAGTAGTAGT

CGACCCTCGGGGTCCCTGATCGAT-
TCTCTGGCTCCAGGTCAGGCAGCACAG

CAACCCTGACCATCTCTGGGCTCCAG-
GCTGAGGACGAGGCTGATTATTACTG

CTCATCCTATGACAGCAGTCTCAGTGCT-
GTGTTCGGCGGAGGCACCCACCTG

ACCGTCCTC
                                                      (SEQ ID NO: 344)
LLTQPASVSGSLGQRVTISCTGSSSNI-
GRGYVGWYQQLPGTGPRTLIYDSSS

RPSGVPDRFSGSRSG-
STATLTISGLQAEDEADYYCSSYDSSLSAVFGGGTHL

TVL

>#65
                                                      (SEQ ID NO: 345)
ATGCTGACTCAACAGGCCTCAGT-
GTCTGGGTCCCTGGgCcAGACGGTCACCA

TCTCCTGCACTGGAAGCACCTCCAACAT-
TGGTAGGAGTCATGTGGCCTGGTA

CCAGCAGCTCCCAGGAGCAAGCCCCA-
GAACCCTCATCTATGATAGTACTAGC

CGACCCTCGGGGTCCCTGATCGAT-
TCTCTGGCTCCAGGTCAGGCAGCACAG

CAACCCTGACCATCTCTGGGCTC-
CAGTCTGAGGACGAGGCTGAATATTTTTG

TTCATCATGGGATAATCGTCTCAGAGGT-
GTTCTGTTCGGCGGAGGGACCCAG

CTGACCGTCCTC
                                                      (SEQ ID NO: 346)
MLTQQASVSGSLGQTVTISCTGSTSNI-
GRSHVAWYQQLPGASPRTLIYDSTS

RPSGVPDRFSGSRSG-
STATLTISGLQSEDEAEYFCSSWDNRLRGVLFGGGTQ

LTVL

>#66
                                                      (SEQ ID NO: 347)
CTGCTGACTCAACCGGCCTCAGTGTC-
CGGGTTCCTGGGCCAGACGGTCACCA

TCTCCTGCACTGGAAGCAGCTCCAA-
CATCGAAACAGGTTATGTACACTGGTA

CCAACAGTTCCCAGGAACAGGCCCCA-
GAACCCTCATCTATGATCTTCATGAC

CGACCCTCAGGGGTCCCCGATCGCT-
TCTCTGGCTCCAGGTCCGGCAACACAG

CCACTCTTACAATCTCTGGACTCCAG-
GCTGAGGATGAGGCTGATTATTACTG

CTCAGCCTGGGACACCAGTCTCAGTGCG-
TACTTGTTCGGCGCAGGAATCCAG

CTCACCGTCCTA
                                                      (SEQ ID NO: 348)
LLTQPASVSGFLGQTVTISCTGSSSNI-
ETGYVHWYQQFPGTGPRTLIYDLHD

RPSGVPDRFSGSRSGN-
TATLTISGLQAEDEADYYCSAWDTSLSAYLFGAGIQ

LTVL
```

-continued

>#68
(SEQ ID NO: 349)
GTGCTGACTCAGCCTCCTTCTGTGTCTG-
CAGCCCTGGGGCAGAGGGTCACCA

TCTCCTGCACTGGAAGTAACACCAA-
CATCGGCAGTGGTTCTGATGTACAGTG

GTACCAGCAGTTCCCAGGAAAGTC-
CCCTAAACCTATCATTTATGGTAATAGG

GATCGACCCTCGGGGGTCCCGGCTCGAT-
TCTCTGGCTCCAAGTCAGGCAACA

CAGCCACCCTGACCATCACTGGGATC-
CAGGCTGAGGATGAGGCTGATTATTA

CTGCCAGTCCTATGATGACAACCTC-
GATGGTCATTGCGTGTTCGGCTCAGGA

ACCCAACTCACCGTCCTC (SEQ ID NO: 350)
VLTQPPSVSAALGQRVTISCTGSNT-
NIGSGSDVQWYQQFPGKSPKPIIYGNR

DRPSGVPARFSGSKSGNTATLTIT-
GIQAEDEADYYCQSYDDNLDGHCVFGSG

TQLTVL

>#73
(SEQ ID NO: 351)
GCGTTGACCCAACCAGCCTCCGTGTC-
CGGGTCCCTGGGNCAGAAAGTCACCA

TCTCCTGCACTGGAAGCAACTCCAA-
CATCGGTGATAATTTTGTGGGCTGGTA

CCAACAACTCCCAGGAATAGGCCCTA-
GAACCGTCATCTATGGTGATGATTAC

CGACCTTCAGGCATCCCCGATCGAT-
TCTCTGGCTCCAAGTCAGGCAGTTCAG

CCACCCTGACCATCTCTGGGCTCCAG-
GCTGAGGACGAGGCTGATTATTACTG

CTCATCATGGGACTATAGTCTCAGAG-
GTCCTGTGTTCGGCGGAGGCACCCAC

CTGACCGTCCTC (SEQ ID NO: 352)
ALTQPASVSGSLGQKVTISCTGSN-
SNIGDNFVGWYQQLPGIGPRTVIYGDDY

RPSGIPDRFSGSKSGSS-
ATLTISGLQAEDEADYYCSSWDYSLRGPVFGGGTH

LTVL

>#74
(SEQ ID NO: 353)
GGGTTGAATCAGCCTCCCTCTGTGTCTG-
CAGCCCTGGGGCAGAGGGTCACCA

TTTCCTGCACTGGAAGTGACACCAA-
CATCGGCGGTGATCATGATGTTCAGTG

GTACCGCCAACTCCCAGGAAAGTCCCCT-
GAAGCTATCATTTACGGTAATACC

AATCGACCCTCGGGGGTCTCGGTTCGAT-
TCTCTGGCTCCAAGTCAGGCAACA

CAGCCACCCTGACCATCAGTGGGATC-
CAGGCTGAGGATGAGGCTGATTATTA

CTGCCAGTCCTATGATGACAACTTC-
GATGGTTGGTATTCGGTGAAGGGACC

CACCTGACCGTCCTC (SEQ ID NO: 354)
GLNQPPSVSAALGQRVTISCTGSDTNIG-
GDHDVQWYRQLPGKSPEAIIYGNT

NRPSGVSVRFSGSKSGN-
TATLTISGIQAEDEADYYCQSYDDNFDGWVFGEGT

HLTVL

>#75
(SEQ ID NO: 355)
GTGCTGACTCAGCTTGCCTCAGT-
GACTGGGTCCCTGGGCCAGAGGGTCACCA

TCTCCTGCACTGGAAGCAGCGCCAA-
CATCGGTACATATAATGTTGGCTGGTT

CCAGCAGCTCCCGGGAGCAGGCCCCA-
GAACCGTCATTAATAGAAGTGATAAC

CGACCCTCGGGGGTCCCGGATCGAT-
TCTCTGGTTCCAGGTCAGGCAGCACAG

CCACCCTGACCATCTCTGGGCTCCAG-
GCTGAGGACGAGGCTGAGTATTACTG

CTCAACATGGGACAAGGATCTCAATAC-
CTACGTCTTCGGCTCAGGAATCGAG

CTGACCGTCCTA (SEQ ID NO: 356)
VLTQLASVTGSLGQRVTISCTGSSANIG-
TYNVGWFQQLPGAGPRTVINRSDN

RPSGVPDRFSGSRSG-
STATLTISGLQAEDEAEYYCSTWDKDLNTYVFGSGIE

LTVL

>#76
(SEQ ID NO: 357)
GTGCTGACTCAGCCTCCTTCAGT-
GTCGGGGTCCCTTGGCCAGAGGGTCACCA

TTTCCTGCTCCGGAACTATGAATAA-
CATCGGGACTGTTGGTGCGAGTTGGTA

CCAACAGGTCCCAGGAAAGGC-
CCCTAAACTCATCGCGAACAGTGGTGGGAGT

CGACCGTCAGGGGTCCCTGACCG-
GTTTTCCGGCGCCGACTCAGGCGATTCAG

CCACCCTGACCATCACTGGACTCCAG-
GCTGAGGACGAGGCTGATTATTTCTG

TCAGTCTATTGATTCCGCGCTTGATGAG-
TACGTGTTCGGCTCAGGAACCCAA

CTGACCGTCCTT (SEQ ID NO: 358)
VLTQPPSVSGSLGQRVTISCSGTMN-
NIGTVGASWYQQVPGKAPKLIANSGGS

RPSGVPDRFSGADSGDSATLTIT-
GLQAEDEADYFCQSIDSALDEYVFGSGTQ

LTVL

>#82
(SEQ ID NO: 359)
GTGCTGACTCAGCCTCCCTCAGTAT-
CAGTCTCTCTGGGACAGACAGCAACCA

TCTCCTGCTCTGGAGAGAGTCTGAG-
TAAATATTATGCACAATGGTTCCAGCA

GAGGGCAGGCCAAGTCCCTGTGTTGGT-
CATATATAAGGACACTGAGCGGCCC

```
TCTGGGATCCCTGACCGATTCTCCG-
GCTCCAGTTCAGGGAACACACACACCC

TGACCATCAGCGGGGCTCGGGCCGAG-
GACGAGGCTGACTATTACTGCGAGTC

AGAAGTCAGTACTGGTACTGCTGTGT-
TCGGCGGAGGCACCCACCTGACCGTC

CTC
```
(SEQ ID NO: 360)
```
VLTQPPSVSVSLGQTATISCSGESL-
SKYYAQWFQQRAGQVPVLVIYKDTERP

SGIPDRFSGSSSGNTHTLTISGA-
RAEDEADYYCESEVSTGTAVFGGGTHLTV

L
```

>#83
(SEQ ID NO: 361)
```
CTGCTGACCCAACCGGCCTCAGT-
GTCTGGGTCCCTGGGACAGAGGGTCACCA

TCTCCTGCACTGGAAGCACCTC-
CAATTTTGGTAGCTCTTATGTGGGCTGGTA

CCAACGACTCCCAGGAACAGGC-
CCCCGAACCCTCATATATAGTACTAATATC

CGACCCCCGGGGGTCCCCGATC-
GATTTTCTGGCTCCGGGTCAGGCAATACAG

CGACCCTGACCATATCTGGACTCCAG-
GCTGAGGACGAGGGTGATTATTACTG

CTCAGCATATGACAGCAATCTCAGTAGT-
GAGATCGTGTTTGGCGGAGGCACC

CACCTGACCGTCCTC
```
(SEQ ID NO: 362)
```
LLTQPASVSGSLGQRVTISCTGSTSN-
FGSSYVGWYQRLPGTGPRTLIYSTNI

RPPGVPDRFSGSGSGN-
TATLTISGLQAEDEGDYYCSAYDSNLSSEIVFGGGT

HLTVL
```
>#89
(SEQ ID NO: 363)
```
GTGCTGACTCAGCCTCCCTCAGTGTCT-
GCGGtCCTGGGACAGACGGTCACCA

TCTCCTGCACTGGAAGCAGCACCAACAT-
TGGCAGTGGTTATGATGTACATTG

GTACCAACAGGCCCCAGGAAAGTC-
CCCTAAGACTATCATCTATGGTAATAGT

AAACGACCCTCAGGGGTCCCGGATCGCT-
TCTCTGGCTCCAAGTCAGGCAGCA

CAGCCTCTCTGACCATCACTGGGCTC-
CAGGCTGAGGACGAGGCTGATTATTA

CTGCCAGTCCTCTGATGACAACGTCCAT-
AATTACGTGTTCGGCTCAGGAACC

CAACTGACCGTCCTA
```
(SEQ ID NO: 364)
```
VLTQPPSVSAVLGQTVTISCTGSST-
NIGSGYDVHWYQQAPGKSPKTIIYGNS

KRPSGVPDRFSGSKSGSTASLTIT-
GLQAEDEADYYCQSSDDNVHNYVFGSGT

QLTVL
```

>#90
(SEQ ID NO: 365)
```
CTGCTGACTCAGCCTGCCTCAGT-
GTCTGGGTCCCTGGGCCAGAAGGTCACCC

TCTCCTGCACTGGGAGCAGCTCCAA-
CATCGGTGGTAATTATGTGGGCTGGTA

CCAACAACTTCCAGGAGTAGGCCCTA-
GAACCGTCATCTATGATAATGATAAC

CGACCTTTAGGGGTCCCCGATCGAT-
TCTCTGGCTCCAAGTCAGGGAGTTCAG

CCACCCTGACCATCTCTGGGCTCCAG-
GCTGAGGACGAGGCTGAATATTATTG

TTCGTCATGGGATGATAGTCTCAGTCA-
GACTGTATTCGGCGGAGGCACCCAC

CTGACCGTCCTC
```
(SEQ ID NO: 366)
```
LLTQPASVSGSLGQKVTLSCTGSSSNIG-
GNYVGWYQQLPGVGPRTVIYDNDN

RPLGVPDRFSGSKSGSS-
ATLTISGLQAEDEAEYYCSSWDDSLSQTVFGGGTH

LTVL
```

VL Lambda Chains from a Normal Dog Library (25 Sequences)

ScFV5b
(SEQ ID NO: 367)
```
GTGCTGACTCAGCTGCCTCAGTGTC-
CGGGTCCCTGGGCCAGAGGGTCACCAT

CTCCTGCTCTGGAAGCAGCTCCAA-
CATCGGTAACCATGTGGCCTGGTTCCAA

CAGCTCCCGGGAACAGGCCCCAGAAC-
CCTCATCTATGGTAATAATAACCGAC

CCTCAGGGGTCCCCGATCGGTTCTCTG-
GCTCCAGGTCAGGCAGCACAGCCAC

CCTGACCATCTCTGGGCTCCAGACTGAG-
GATGAGGCTGATTATTACTGCTCA

TCGTGGGACACCAGTCTCAGCGGT-
TACGTGTTCGGCTCAGGAACCGAGCTGA

CCGTCCTTGGC
```
(SEQ ID NO: 368)
```
ADSAASVSGSLGQRVTISCSGSSSNIGN-
HVAWFQQLPGTGPRTLIYGNNNRP

SGVPDRFSGSRSGSTATLTISGLQT-
EDEADYYCSSWDTSLSGYVFGSGTELT

VLG
```

7b V1
(SEQ ID NO: 369)
```
CTGCTGACCCAACCGGCTTCAGT-
GTCTGGGTCCCTGGGACAGAAGGTCACCA

TCTCCTGCACTGGAAGCAGCTCCAACAT-
TGGTAGTAATTATGTGGCCTGGTA

CCAGCAGCTCCCAGGAACAGGCCCCA-
GAACCCTCATCTATAGTAATACTAAT

CGATTTTCGGGGGTCCCCGATCGAT-
TCTCTGGCTCCAGGTCAGGCAGCACAG

CAACCCTGACCATCTCTGGGCTCCAG-
GCTGAGGACGAGGCTGATTATTACTG
```

CTCAACATATGACAACAGTCTCAGTG-
GTCTTGTGTTCGGCGGGGGCACCCAG

CTGACCGTCCTCGGC (SEQ ID NO: 370)

LLTQPASVSGSLGQKVTISCTGSSSNIG-
SNYVAWYQQLPGTGPRTLIYSNTN

RFSGVPDRFSGSRSG-
STATLTISGLQAEDEADYYCSTYDNSLSGLVFGGGTQ

LTVLG

8b VL3

(SEQ ID NO: 371)

GGGTTGACTCAGCTGCCTTCCATGAGT-
GTGGCCCtGAGGCAGACGGCCCGCA

TCACCTGTGGGGAGGCAACATCGAAAG-
TAAAAATGTTCATTGGTACCAACA

GAAACTGGGCCAGGCCCCTATACA-
GATCGTCTATTATGATACCCGGAGGCCG

GTAGGGATCCCTGAACGATTCTCTG-
GCGCCAAGTCGGGGAACACGGCCACCC

TGACCATCAGCGGGGCCCTGGCCGAG-
GACGAGGCTGACTATTACTGTCAGGT

GTGGGACAGCGGCACTCTCATATTCG-
GCGGAGGCACCCAGCTGACCGTCCTC

GGC (SEQ ID NO: 372)

GLTQLPSMSVALRQ-
TARITCGGGNIESKNVHWYQQKLGQAPIQIVYYDTRRP

VGIPERFSGAKSGN-
TATLTISGALAEDEADYYCQVWDSGTLIFGGGTQLTVL

G 9b vlam (SEQ ID NO: 373)

GTGCTGACTCAGCTTGCCTCAGT-
GTCTGGGTCCCTGGGCCAGAGGGTCACCA

TCTCCTGCACTGGAAGCAGCTCCAATGT-
TGGGTATGGCAATGATGTGGGCTG

GTACCAGCAGCTCCCAGGAACAGGC-
CCCAGAACCCTCATCTATGGTAGCAGT

ATCCGACCCTCGGGGGTCCCTGATCGAT-
TCTCTGGCTCCAAATCAGGCAACT

CAgCCACACTGACCATCTCTGGGCTC-
CAGGCTGAGGATGAAGCTGATTATTA

CTGTTCATCCTATGACAGCAGTCTCGGT-
TACGTGTTCGGCTCAGGAATCGAG

CTCACCGTCCTTGGC (SEQ ID NO: 374)

VLTQLASVSGSLGQRVTISCTGSSSN-
VGYGNDVGWYQQLPGTGPRTLIYGSS

IRPSGVPDRFSGSKSGNS-
ATLTISGLQAEDEADYYCSSYDSSLGYVFGSGIE

LTVLG

12b Vlam (SEQ ID NO: 375)

GTGCTGACTCAGCTAACCTCAGT-
GTCGGGGTCCCTGGGCCAGAGAGTCACCA

TCTCCTGCTCTGGAAgGACAAACATC-
GATAGGTTTGGTGTGACTTGGTATCA

GCAGTTCCCAGGAAAGGCCCCTAGACTC-
CTCGTGGACAGTGATGGGGATCGA

CCGTCAGGTGTCCCTGACCGATTTTCCG-
GCTCCAAGTCTGCCAACTCGGCCA

CTCTGACCATCACTGGTCTCCATGCT-
GAGGACGAGGCTGATTATTATTGTCT

GTCTATTGGTCCCACACTTGGTGTT-
TACGTGTTCGGCTCAGGAATCGAGCTG

ACCGTCCTAGGC (SEQ ID NO: 376)

VLTQLTSVSGSLGQRVTISCSGRT-
NIDRFGVTWYQQFPGKAPRLLVDSDGDR

PSGYPDRFSGSKSANSATLTITGL-
HAEDEADYYCLSIGPTLGVYVFGSGIEL

TVLG

14b Vlam (SEQ ID NO: 377)

GTGCTGACTCAGCCACCCTCAGT-
GTCGGGGTCCCTTGGCCAGAGGGTCACCA

TTTCCTGCTCTGGAAGCACGAACAA-
CATCGGCATTGTTGGTGCGAGCTGGTA

CCAACAGCCCCCAGGAAAGGC-
CCCTAAACTCCTCGTATACACTAATGGGGT

CGACCGTCAGGGGTCCCTGACCG-
GTTTTCCGGCTCCAAGTCTGGCAACTCAG

CCACCCTGACCATCACTGGCCTTCAG-
GCTGAGGACGAGGCTGATTATTACTG

CCAGTCCTCTGATTCCATGCTTGCTGT-
GTTCGGCGGAGGCACCCACCTGACC

GTCCTCGGC (SEQ ID NO: 378)

VLTQPPSVSGSLGQRVTISCSGSTNNI-
GIVGASWYQQPPGKAPKLLVYTNGG

RPSGVPDRFSGSKSGNSATLTIT-
GLQAEDEADYYCQSSDSMLAVFGGGTHLT

VLG

15b Vlam (SEQ ID NO: 379)

GTGCTGACTCAGCCTCCTTCAGT-
GTCGGGGTCCCTTGGCCAGAAGATCACCA

TCTCCTGTTCTGGAAGCACGAA-
CAACGTCGGTGTTGTTGGTGCGGGCTGGTA

CCAACAGCTCCCAGGAAAGGC-
CCCTAAACTCCTCGTATTTAGTGATGGGGTT

CGACCGTCAGGGGTCCCTGACCG-
GTTTTCCGGCTCCAAGTTTGGCGACTCAC

ACACCCTGACCATCACTGGACTTCAG-
GCTGAGGACGAGGCTGATTATTATTG

CCAGTCGT (SEQ ID NO: 380)

VLTQPPSVSGSLGQKITISCSGST-
NNVGVVGAGWYQQLPGKAPKLLVFSDGV

RPSGVPDRFSGSKFGDSHTLTIT-
GLQAEDEADYYCQSYDTTLHTYVFGSGIE

LIVLG

-continued 17b vlam (SEQ ID NO: 381)
GCGCTGACCCAGCCTGCCTCAGT-
GTCGGGGTCCCTTGGCCAGAGGGTCACCA

TTTCCTGCTCTGGAACCACGGA-
CAATATCGGTATTGTTGGTGCAACTGGTA

CCAACAACTCCCAGGAAAGGC-
CCCTAAACTCCTCGTGTACAGTGATGGGAAT

CGACCGGCAGGGGTCCCTGACCG-
GTTTTCCGGCTCCAAGTCTGGCAGCTCAG

CCACCCTGATCATCACTGGGCTTCAG-
GCTGAGGACGAGTCTGATTATTACTG

TCAGTCTGTTGATCCCACGCTTGGT-
GCTCGGTACGTCTTCGGCTCAGGAATC

GAGCTGACCGTCCTAGGC (SEQ ID NO: 382)
ALTQPASVSGSLGQRVTISCSGTTDNI-
GIVGANWYQQLPGKAPKLLVYSDGN

RPAGVPDRFSGSKSGSSATLIIT-
GLQAEDESDYYCQSVDPTLGARYVFGSGI

ELTVLG

19b (SEQ ID NO: 383)
GTGCTGACTCAGCCTCCCTCAGTGTC-
CGGGTTCCTGGGCCAGAGGGTCACCA

TCTCCTGCACTGGAGACACCCCCAA-
CATCGGTAGAGGTTATGTGCACTGGTA

CCAACAGCTCCCAGGAACAGGCCCCA-
GAACCCTCATCTATGGTGTTAGTAAC

CGACCCTCAGGGGTCCCCGATCGAT-
TCTCTGGCTCCAGGTCAGGCAGCACAG

GCACTCTGACAATCTCTGGGCTCCAG-
GCTGAGGATGAGGCTGATTATTATTG

CTCGTCCTGGGACACCACTCTCAGTGCT-
TACGTGTTCGGCTCAGGAATCGAG

CTGACCGTCCTTGGC (SEQ ID NO: 384)
VLTQPPSVSGFLGQRVTISCTGDTPNI-
GRGYVHWYQQLPGTGPRTLIYGVSN

RPSGVPDRFSGSRSGST-
GTLTISGLQAEDEADYYCSSWDTTLSAYVFGSGIE

LTVLG

21b Vlam (SEQ ID NO: 385)
GTGTTGACTCAGCCAGCCTCAGT-
GTCTGGGTCCCTGGGCCAGAGGGTCACCA

TCTCCTGCACTGGAAGCAGTTCCAATGT-
TGGTTATGGCAATTCTGTGGGTTG

GTATCAGCAGCTCCCAGGAACAAGTC-
CCAGAACCCTCATCATTGATAGTAAT

AACCGACCCTCGGGGGTCCCTGATCGGT-
TCTCTAGCTCCAGGTCAGGCAACA

TAGGAACCCTGACCATATCTGGGCTC-
CAGGCTGAGGATGAAGCCGATTATTG

CTGTACATGTTTTGACAGCAGTCT-
CAATGGTGGTGTTTTCGGCGGAGGCACC

CAGCTGACCGTCCTCGGC (SEQ ID NO: 386)
VLTQPASVSGSLGQRVTISCTGSSSN-
VGYGNSVGWYQQLPGTSPRTLIIDSN

NRPSGVPDRFSSSRS-
GNIGTLTISGLQAEDEADYCCTCFDSSLNGGVFGGGT

QLTVLG

22b L1

(SEQ ID NO: 387)
GCGTTGACCCAACCGGCCTCAGT-
GTCTGGGTCCCTGGGCCAGAGGGTCACCG

TCTCCTGCACTGGGAGCAGCTCCAA-
CATCGGTAGATTTGTTGTTGGCTGGTT

CCAGCAGCTCCCGGGAAAAGGCCCCA-
GAACCGTCATCTATAATCAAGTAAC

CGACCCTCAGGGGTCCCTGATC-
GATTTTCTGGCTCCAAGTCAGGCAGCACAG

CCACCCTGACCATCTCTGGGCTCCA-
GACTGAGGACGAGGCTGCTTATTACTG

CTCAGTATATGACAGTAGTCTCAATAC-
TATTCTGTTTGGCGGAGGCACCCAC

CTGACCGTCCTCGGC (SEQ ID NO: 388)
ALTQPASVSGSLGQRVTVSCTGSSSNI-
GRFVVGWFQQLPGKGPRTVIYNTSN

RPSGVPDRFSGSKSGSTATLTISGLQT-
EDEAAYYCSVYDSSLNTILFGGGTH

LTVLG scFv24b_F08_054.seq L3

(SEQ ID NO: 389)
GGGCTGACTCAGCTGCCTTCCGTGAAT-
GTGACCCTGAGGCAGACGGCCCACA

TCACCTGTGGGGGAGACAGCATTGGAAG-
TAAATATGTTCAATGGATCCAGCA

GAATCCAGGCCAGGCCCCCGTGATGAT-
TATCTATAAAGATACCAACAGGCCG

ACAGGGATCCCTGAGCGATTCTCTG-
GCGCCAACTCAGGGAACACGGCTACCC

TGACCATCAGCGGGGCCCTGGCCGAA-
GACGAGGCTGACTATTACTGCCAGGT

GTGGGACAGCAATACTAAGAGGATTGT-
GTTCGGCGGAGGCACCCACCCTGACC

GTCCTGGG (SEQ ID NO: 390)
GLTQLPSVNVTLRQTAHITCGGDSIG-
SKYVQWIQQNPGQAPVMIIYKDTNRP

TGIPERFSGANSGN-
TATLTISGALAEDEADYYCQVWDSNTKRIVFGGGTHLT

VLG 23b vlam (SEQ ID NO: 391)
GGGTTGATCAGGCTTCCTCAGTGTC-
CGGGTTCCTGGGCCAGAGGGTCACCAT

CTCCTGCACTGGGAGTAGCTCCAA-
GATCGGTAGAGGTTTTGTTCACTGGTAC

CAGGTACTCCCAGGAACAGGCCCCA-
GAACCCTCATCTATGGTGTTAGTCACC

-continued

GACCCTCAGGGGTCCCCGATCGAT-
TCTCTGCCTCCAAGTCAGGCAAGACAGC

CACTCTGACAATCTCTGGGCTCCAGGCT-
GAGGATGAGGCTGATTATTACTGC

TCATCCTGGGACAGCAGTCTCAG-
TAGTCTCGTGTTCGGCTCAGGAACCCAGC

TCACCGTCCTTGGC (SEQ ID NO: 392)

VDQASSVSGFLGQRVTISCTGSSSKI-
GRGFVHWYQVLPGTGPRTLIYGVSHR

PSGVPDRFSASKSGK-
TATLTISGLQAEDEADYYCSSWDSSLSSLVFGSGTQL

TVLG

26b L1

(SEQ ID NO: 393)

ACCCTGACTCAgAAGCCCTCCGT-
GTCTGGGTCCCTGGGCCAGAGGGTCACCA

TCTCCTGCACTGGAAGCAGCTCCAATGT-
TGGTTATGGCGATTCTGTGGGCTG

GTACCAGCAGCTCCCAGGAACAAGC-
CCCAGAACCCTCATCTATGATAGTAGT

AGCCGACCCTCGGGGGTCCCTGATCGAT-
TCTCTGGCTCCAGGTCAGGCAGCA

CAGCAACCCTGACCATCTCTGGGCTC-
CAGGCTGAGGATGAAGCCGATTATTA

CTGCTCATCCTATGACAGCAGTCT-
CAGTGGTGCTGTGTTCGGCGGAGGCACC

CACCTGACCGTCCTCGGC (SEQ ID NO: 394)

TLTQKPSVSGSLGQRVTISCTGSSSN-
VGYGDSVGWYQQLPGTSPRTLIYDSS

SRPSGVPDRFSGSRSG-
STATLTISGLQAEDEADYYCSSYDSSLSGAVFGGGT

HLTVLG

28b Vlam 1

(SEQ ID NO: 395)

GTGCTGACTCAGCCTCCCTCAGT-
GTCGGGGTCCCCTGGCCAGAGGGTCACCA

TCTCCTGCTCTGGAAgGACGAA-
CAATATCGGTAGTGTTGGTGCGACCTGGTA

CCGACAATTCCCAGGAAAGGCCCCTAAC-
CTCCTCGTATACAGTGATGGGAAT

CGACCGTCGGGGGTCCCTGACCG-
GTTTTCCGCCTCCATGTCTGGCAACTCAG

CCACCCTGACCATCACTGGGCTTCA-
GACTGAGGACGAGGCTGATTATTACTG

CCAGTCCTATGACACCTCGCTTGATGGT-
GCTGTGTTCGGCGGAGGCACCCAC

CTGACCGTCCTCGGC (SEQ ID NO: 396)

VLTQPPSVSGSPGQRVTISCSGRT-
NNIGSVGATWYRQFPGKAPNLLVYSDGN

RPSGVPDRFSASMSGNSATLTITGLQT-
EDEADYYCQSYDTSLDGAVFGGGTH

LTVLG 30b seq Vlam 2

(SEQ ID NO: 397)

GCCCTGACTCAACCTTCCTCGGT-
GTCTGGGACTTTGGGCCAGACTGTCACCA

TCTCCTGTGATGGAAGCAGCAGTGACAT-
TGGCAGTTATAGTTATATCGCTTG

GTACCAGCAGTTCCCAGGCACCTC-
CCCCAAACTCCTGATTCAATACACCGAT

AATCGGCCATCAGGGATCCCTACTCGCT-
TCTCTGGCTCCAAGTCTGGGAACA

CGGCCTCCTTGACCATCCCTGGTCTC-
CAGGCTGAAGATGAGGCTGATTATTA

CTGCTGCGCATATGCTGGTAGTGATACT-
TACGTATTCGGCTCAGGAACCCAA

CTCACCGTCCTAGGC (SEQ ID NO: 398)

ALTQPSSVSGTLGQTVTISCDGSSSDIG-
SYSYIAWYQQFPGTSPKLLIQYTD

NRPSGIPTRFSGSKSGN-
TASLTIPGLQAEDEADYYCCAYAGSDTYVFGSGTQ

LTVLG

34b L1

(SEQ ID NO: 399)

GTGTTGACTCAGCTGGCCTCCGT-
GTCTGGGTCCCTGGGCCAGAGGGTCACCA

TCTCCTGCACTGGAAGCAGCTCCAATGT-
TGGGTATGGCAATGATGTGGGCTG

GTACCAGCAGCTCCCAGGAACAGGC-
CCCAGAACCCTCATCTATGGTAGCAGT

ATCCGACCCTCGGGGGTCCCTGATCGAT-
TCTCTGGCTCCAAATCAGGCAACT

CAGCCACACTGACCATCTCTGGGCTC-
CAGGCTGAGGATGAAGCTGATTATTA

CTGTTCATCCTATGACAGCAGTCTCGGT-
TACGTGTTCGGCTCAGGAACCCAA

CTCACCGTCCTTGGC (SEQ ID NO: 400)

VLTQLASVSGSLGQRVTISCTGSSSN-
VGYGNDVGWYQQLPGTGPRTLIYGSS

IRPSGVPDRFSGSKSGNS-
ATLTISGLQAEDEADYYCSSYDSSLGYVFGSGTQ

LTVLG

35b Vlam 1

(SEQ ID NO: 401)

GTGCTGACTCAGCTTGCCTCAGT-
GTCTGGGTCCCTGGGCCAAAGGGTCACCA

TCTCCTGCTCTGGAAGCAGCTCCAATGT-
TGGTTGTGGCGATTATGTGGGCTG

GTTCCAGCAACTCCCAGGAACGGGC-
CCCAGAACCCTCATCTATGATACTAGT

ACCCGACCCTCGGGGGTCCCTGATCGAT-
TCTCTGGCTCCAGGTCTGGCAGCA

CAGCAACCCTGACCATCTCTGGGCTC-
CAGGCTGAGGATGAGGCCGATTACTA

CTGCTCATCCTATGACATGACTCTCA-
GAGGTCCTATGTTCGGCGGAGGGACC

CAGCTGACCGTCCTCGGC (SEQ ID NO: 402)
VLTQLASVSGSLGQRVTISCSGSSSN-
VGCGDYVGWFQQLPGTGPRTLIYDTS

TRPSGVPDRFSGSRSG-
STATLTISGLQAEDEADYYCSSYDMTLRGPMFGGGT

QLTVLG

36b L1
(SEQ ID NO: 403)
GTCCTGACTCAGCTGCCCTCAGt-
GTCGGGGTCCCTTGGCCAGAgGGTCACCA

TCTCCTGCTCTGGAAGCACGAACAA-
CATCGGTATTACTGGTGCGACCTGGTA

CCAACAACTCCCAGGAAAGGCCCCTA-
CACTCCTCGTATACAGTGATGGGGAT

CGACCGTCAGGGGTCCCTGACCG-
GTTTTCCAGTTCCAACTCTGACTTCTCAG

ACACCCTGACCATCACTGGTCTTCAG-
GCTGAGGACGAGGCTGATTATTACTG

CCAGTCCTTTGATACCACGCTTGATGCT-
TACgTGTTCGGTTCAgGAATCgAg

CTGACCGTCCTTGGC (SEQ ID NO: 404)
VLTQLPSVSGSLGQRVTISCSGSTNNIG-
ITGATWYQQLPGKAPTLLVYSDGD

RPSGVPDRFSSSNSDFSDTLTIT-
GLQAEDEADYYCQSFDTTLDAYVFGSGIE

LTVLG

42b Vlam1
(SEQ ID NO: 405)
GTGCTGACTCAGCTTGCCTCAGT-
GTCTGGGTCCCTGGGCCAGAGGGTCACCA

TCTCCTGCACTGGAAGCACCTCCAA-
CATCGGTAGAGGTTATGTGACCTGGTA

CCAGCAGCTCCCAGGAACAGGCCCCA-
GAACCCTCATCTATGATAATAGTGAC

CGACCCTCGGGGGTCCCTGATCGCT-
TCTCTGGCTCCAAGTCAGGCAGCACAG

CCACCCTGACCATATCCGGCCTCCAGGT-
TGAGGACGAGGCTGATTATCACTG

CTCAACATATGACAGCAGTCTCGGTG-
GTCCTGTGTTCGGCGGAGGCACCCAG

CTGACCGTCCTCGGC (SEQ ID NO: 406)
VLTQLASVSGSLGQRVTISCTGSTSNI-
GRGYVTWYQQLPGTGPRTLIYDNSD

RPSGVPDRFSGSKSG-
STATLTISGLQVEDEADYHCSTYDSSLGGPVFGGGTQ

LTVLG

46b Vlam 3
(SEQ ID NO: 407)
GTGTTGACTCAGCTGGCCTCCGTGT-
CAGTGAACCCGGGACAGACAGCCATCA

TCACCTGTGAGGCAGATAAAATAGGG-
GATAAATTTGTTCACTGGTACCAACA

GAAGCCTAGTCAGGCCCCCGGAATGAT-
TGTTTATGAGGATCACAAGCGCCCC

TCAGGGATCCCTGAGCGATTCTCTGC-
CTCCAACTCGGGGAACACGGCCACCC

TGACCATCAGCGGGGCCAGGGCCGAG-
GATGAGGCTGACTATTACTGTCAGGT

GTGGGACAACGGTGCTCCGATGTTCG-
GCGGAGGCACCCACCCTGACCGTCCT

CGGC (SEQ ID NO: 408)
VLTQLASVSVNPGQTAIITCEADKIGDK-
FVHWYQQKPSQAPGMIVYEDHKRP

SGIPERFSASNSGNTATLTISGA-
RAEDEADYYCQVWDNGAPMFGGGTHPDRP

R

47b Vlam1
(SEQ ID NO: 409)
GTGCTGACTCAGCTTGCCTCAGT-
GTCTGGGTCCCTGGGCCAGAgGGTCACCA

TCTCCTGCACTGGAAGCAGCTCCAATGT-
TGGTTATGGCGATTATGTGGGCTG

GTATCAGCAGCTCCCAGGAACAGGC-
CCCAGAACCCTCATCCATCATACTACT

AGCCGACCCTCGGGAGTCTCCGATCGAT-
TCTCTGGCTCCAGGTCAGGCAACA

CAGCAACCCTGACCATCTCTGGACTC-
CAGGCTGAGGATGAAGCCGATTATTA

CTGCTCATCTTATGACACAGGTCTCAAT-
GTTGTGTTCGGCGGAGGCACCCAG

CTGACCGTCCTCGGC (SEQ ID NO: 410)
VLTQLASVSGSLGQRVTISCTGSSSN-
VGYGDYVGWYQQLPGTGPRTLIHHTT

SRPSGVSDRFSGSRSGN-
TATLTISGLQAEDEADYYCSSYDTGLNVVFGGGTQ

LTVLG

48b VLam1
(SEQ ID NO: 411)
GTGCTGACTCAGCTGACCTCAGT-
GTCGGGGTCCCTTGGCCAGAGGGTCACCA

TTTCCTGCTCTGGAAGCGCGAACAA-
CATCGGTAGTTTTGGTGCGATCTGGTA

CCAACAGTTCCCAGGAAAGGC-
CCCTAAACTCCTCATATACAGGGATGGGAGT

CGACCGTCAGGGGTCCCTGACCG-
GTTTTCCGGCTCCAGGTCTGGCAACTCAG

CCACCCTGACCATCACTGGGCTTCAG-
GCTGAGGACGAGGCTGATTTTTACTG

TCAGTCTGTTGATCCCACGCTTGGTAT-
TGCTGTGTTCGGCGGAGGCACCCAC

CTGACCGTCCTCGGC (SEQ ID NO: 412)
VLTQLTSVSGSLGQRVTISCSGSAN-
NIGSFGAIWYQQFPGKAPKLLIYRDGS

RPSGVPDRFSGSRSGNSATLTIT-
GLQAEDEADFYCQSVDPTLGIAVFGGGTH

LTVLG

49b Vlam 1

(SEQ ID NO: 413)

GTGCTGACCCAGCCAGCCTCCGT-
GTCTGGGTCCCTGGGCCAGAGGGTCACCA

TCTCCCGCACTGGAAGCAGCTCCAATGT-
TGGGTATGGCAATGATGTGGGCTG

GTACCAGCAGCTCCCAGGAACAGGC-
CCCAGAACCCTCATCTATGGTAGCAGT

ATCCGACCCTCGGGGGTCCCTGATCGAT-
TCTCTGGCTCCAAATCAGGCAACT

CAGCCACACTGACCATCTCTGGGCTC-
CAGGCTGAGGATGAAGCTGATTATTA

CTGTTCATCCTATGACAGCAGTCTCGGT-
TACGTGTTCGGCTCAGGAACCCAA

CTGACCgTCCTTGGC (SEQ ID NO: 414)

VLTQPASVSGSLGQRVTISRTGSSSN-
VGYGNDVGWYQQLPGTGPRTLIYGSS

IRPSGVPDRFSGSKSGNS-
ATLTISGLQAEDEADYYCSSYDSSLGYVFGSGTQ

LTVLG

53b Vlam 1

(SEQ ID NO: 415)

GTGCTGACTCAGCTAACCTCAGT-
GTCTGGGTCCCTGGGCCAGAGGGTCACCA

TCTCCTGCTCTGGAAGTGAATTCAATGT-
TGGTGGTGGCAATCATGTGGCCTG

GTACCGGCAGATCCCAGGGACAGGTC-
CCAKAACCCTCATCTTTGATACTAAT

GGTCGACCCTCGGGGGTCCCTGATCGCT-
TCTCTGCCTCCAGGTCAGACAATA

CAGCGACCCTGACCATCTCTGAACTC-
CAGGCTGACGATGAGGCCGATTACTA

CTGTTCATCCTATGACAAGTCTTTCAGT-
GTTGTTTTCGGCGGARGCACCCAC

CTWACCGTCCTCGGC (SEQ ID NO: 416)

VLTQLTSVSGSLGQRVTISCSGSEFN-
VGGGNHVAWYRQIPGTGPXTLIFDTN

GRPSGVPDRFSASRSDNTATL-
TISELQADDEADYYCSSYDKSFSVVFGGXTH

LTVLG

VL Kappa Chains from a Normal Dog Library (14 Sequences)

50b VKappa2

(SEQ ID NO: 417)

GTCATGATGCAKACCCCACTGTCCCT-
GTCTGTCAGCCCTGGAGAGACGGCCT

CCATCTCCTGCAGGGCCAATCAGAGC-
CTCCTGCACAGTAACGGGAACACCTA

TTTAGATTGGTACATACAGAGGCCAGGC-
CAGTCTCCCCAGGCCCTGATCTAC

AGGGTGTCCAACCGCGCCATCGCCACT-
GCCGTGTCAGACAGATTTAGTGGCA

GCGGGTCAGGGACAGATTTCACCCTGAA-
GATCAGCAGAGTGGAGGCTGGCGA

TGCTGGACTTTATTACTGCGGGCAAGG-
TACATACTCTTATACTTTCAGCCAG

GGAACCAAGCTGGAGATCAAA (SEQ ID NO: 418)

VMMXTPLSLSVSPGETASISCRANQS-
LLHSNGNTYLDWYIQRPGQSPQALIY

RVSNRAIATAVSDRFSGSGSGTD-
FTLKISRVEAGDAGLYYCGQGTYSYTFSQ

GTKLEIK 51b k2

(SEQ ID NO: 419)

GTCATGATGcAgACCCcACTGTCCCT-
GTCTGTCAGCCCTGGAGAGACGGCCT

CCATCTCCTGCAgGGCCAATCAGAGC-
CTCCTGCACAGTAACGGGAACACCTA

TTTAGATTGGTACATACAGAGGCCAGGC-
CAGTCTCCCCAGGCCCTGATCTAC

AGGGTGTCCAACCGCGCCATCGCCACT-
GCCGTGTCAGACAGATTTAGTGGCA

GCGGGTCAGGGACAGATTTCACCCTGAA-
GATCAGCAGAGTGGAGGCTGGCGA

TGCTGGACTTTATTACTGCGGGCAAGG-
TACATACTCTTATACTTTCAGCCAG

GGAACCAAGCTGGAGATCAAA (SEQ ID NO: 420)

1VMMQTPLSLSVSPGETASISCRANQS-
LLHSNGNTYLDWYIQRPGQSPQALI

YRVSNRAIATAVSDRFSGSGSGTD-
FTLKISRVEAGDAGLYYCGQGTYSYTFS

QGTKLEIK

43b (SEQ ID NO: 421)

GTGATGATGCAGACTCCACTGTCCCT-
GTCCGTCAGCCCTGGAGAGACGGCCT

CCATCTCCTGCAAGGCCAGTCAGAGC-
CCCCTGCACACTAATGGGAACACCTA

TTTGTTTTGGTTTCGACGAAGCCAGGC-
CAGTCTCCACAGCGCTTGATCTCT

TCGGTCTCCAATAGAGACCCTGGGGTC-
CCAGACAGGTTCAGTGGCAGCGGGT

CAGGGACAGATTTCACCCTGAGAATCAG-
CAGAGTGGAGGCTAACGATACTGG

AGTTTATTACTGCGGGCAAGGTATACG-
GTCTCCTTATACTTTCAGCCAGGGG

ACCAAGCTGGAGATAAAA (SEQ ID NO: 422)

VMMQTPLSLSVSPGETASISCKASQS-
PLHTNGNTYLFWFRQKPGQSPQRLIS

SVSNRDPGVPDRFSGSGSGTDFTLRIS-
RVEANDTGVYYCGQGIRSPYTFSQG

TKLEIK 44b kappa 2

(SEQ ID NO: 423)

GTCATGATGCAGACTCCACCGTCCCT-
GTCCGTCAGCCCTGGAGAGCCGGCCT

CCATCTCCTGTAAGGCCAGTCAGAGC-
CTCCTGCACATTAATGGGATCAACTA

```
TTTGTCTTGGTTCCAACAAAAGCCAGGC-
CAGTCTCCACAGCGTCTGATCGTT

AGGGCCTCCAACAGAGAACCTGGAGTC-
CCAGACAGGTTCAGTGGCAGCGGGT

CAGGGACAGATTTCACCCTGAGAATCAG-
CAGAGTGGAGGCTGATGATGTTGG

AGTTTATTACTGCGGACAATATCTATCA-
CATCCGTACACGTTCGGACCAGGA

ACCAAGGTGGACCTCAAA
```
                                                (SEQ ID NO: 424)

```
VMMQTPPSLSVSPGEPASISCKASQSLL-
HINGINYLSWFQQKPGQSPQRLIV

RASNREPGVPDRFSGSGSGTDFTLRIS-
RVEADDVGVYYCGQYLSHPYTFGPG

TKVDLK 45b vkappa2
```
                                                (SEQ ID NO: 425)

```
GTGATGATGCAGACTCCACTGTCCCT-
GTCCGTCAGCCCTGGAGAGACTGCCT

CCATCTCCTGCAAGGCCAGTCAGAGC-
CTCCTGCACAGTGATGAAACACGTA

TTTGAATTGGTTCCGACAGAAGCCAGGC-
CAGTCTCCACAGCGTTTGATCTAT

AAGGTCTCCAACAGAGACACTGGGGTC-
CCAGACAGGTTCAGTGGCAGCGGGT

CAGGGACAGATTTCACCCTGAGAATCAG-
CACAGTGGAGGCTGACGATACTGG

AATTTATTACTGCGGGCAAGGTACA-
CAGTTTCCGCTTACGTTCGGCCAAGGA

ACCAAGCTGGAGATCAAA
```
                                                (SEQ ID NO: 426)

```
VMMQTPLSLSVSPGETASISCKASQS-
LLHSDGNTYLNWFRQKPGQSPQRLIY

KVSNRDTGVPDRFSGSGSGTDFTL-
RISTVEADDTGIYYCGQGTQFPLTFGQG

TKLEIK 37b k2
```
                                                (SEQ ID NO: 427)

```
GTGATGATGCAgACTCCACTGTCCCT-
GTCCGTCAGTCCTGGAGAGCCGGCCT

CCATCTCCTGCAAGGCCAGTCAGAGC-
CTCCTGCACCGTAGTGGGAACACCTA

TTTGTATTGGTTTCGACAGAAGCCAGGC-
CAGTCTCCAGAGGGCCTGATTTAT

CAGGTGTCCAACCGCCTCACTGGCGTGT-
CAGACAGGTTCAGTGGCAGCGGGT

CAGGGACAGATTTCACCCTGAGGATCAG-
CACAGTGGAGGCTGACGATACTGG

AGTTTATTACTGCGGGCAAGGTGCA-
CAGCTTCCGTGGACGTTCGGAGCAGGA

ACCAAGGTGGACCTCAAA
```
                                                (SEQ ID NO: 428)

```
VMMQTPLSLSVSPGEPASISCKASQSLL-
HRSGNTYLYWFRQKPGQSPEGLIY
```

```
QVSNRLTGVSDRFSGSGSGTDFTL-
RISTVEADDTGVYYCGQGAQLPWTFGAG

TKVDLK

39B K2
```
                                                (SEQ ID NO: 429)

```
GTGATGATGCAGACTCCACTGTCCCT-
GTCCGTCAGACCTGGAGAGCCGGCCT

CCATCTCCTGCAAGGCCAGTCAGAGC-
CTCCTGCACAGTAACGGGAACACCTA

TTTGTTTTGGTTTCGACACAGGCCAGGC-
CAGTCTCCACAGAGTTTGTTGTAT

CTGGTCTCCAACGAGCCCCTGGGGTC-
CCAGACAGGTTCAGTGCCAGCGGGT

CAGGGACAGATTTCACCCTGAGAATCAG-
CAGAGTGGAGGCTGACGATGCTGG

AGTTTATTACTGCGGGCATATTACA-
CAGTCTCCTCCTACGTTCGGCCAAGGG

ACCAAGCTGGAGATAAAA
```
                                                (SEQ ID NO: 430)

```
VMMQTPLSLSVRPGEPASISCKASQS-
LLHSNGNTYLFWFRHRPGQSPQSLLY

LVSNRAPGVPDRFSASGSGTDFTLRIS-
RVEADDAGVYYCGHITQSPPTFGQG

TKLEIK 41b vkappa 2
```
                                                (SEQ ID NO: 431)

```
GTGATGATGCAgACTCCACTGTCCCTG-
GCCGTCACCCCTGGAGACCTGGCCA

CTATTTCCTGCAGGGCCAGTCA-
GAGTCTCCTATACACTGATGGAAAATCCTA

TTTGAATTGGTACCTGCAGAGGCCAGGC-
CAGACTCCTCGGCCGCTGATCTAT

GAGACTTCCAAGCGTTTCTCTGGGGTCT-
CAGACAGGTTCATTGGCAGCGGGT

CAGGGACAGATTTCACCCTAACAATCAG-
CAGGGTGGAGGCTGAGGATGTTGG

AGTCTATTACTGCCAGCAAAGTGTA-
CATTTTCCGTGGACGTTCGGACCAGGA

ACCAAGGTGGAGATCAAA
```
                                                (SEQ ID NO: 432)

```
VMMQTPLSLAVTPGDLATISCRASQS-
LLYTDGKSYLNWYLQRPGQTPRPLIY

ETSKRFSGVSDRFIGSGSGTD-
FTLTISRVEAEDVGVYYCQQSVHFPWTFGPG

TKVEIK

31b Vkappa2
```
                                                (SEQ ID NO: 433)

```
GTCATGACGCAGACCCCACTGTCCCT-
GTCCGTCAGTCCTGGAGAGGCGGCCT

CCATCTCCTGCAAGGCCAGTCAGAGC-
CTCCTGCACAGCAATGGGAATACCTA

TTTCTATTGGTTCCGACAGAGGCCAGGC-
CAGTCTCCAGAGGGCCTGATCTAT

AAGGTCTCCAACCGCTTCACTGGCGT-
GTCGGACAGGTTCAGTGGCAGCGGGT

CAGGGACAGACTTCACTCTGAGAATCAG-
CAGAGTGGAGGCTGACGATTCTGG
```

-continued

```
AGTTTATTACTGCGGGCAGAATATA-
CAGTTTCCTCTTACGTTCGGCCAAGGA

ACCAAGCTGGAGATCAAA
```
(SEQ ID NO: 434)

```
VMTQTPLSLSVSPGEAASISCKASQS-
LLHSNGNTYFYWFRQRPGQSPEGLIY

KVSNRFTGVSDRFSGSGSGTDFTLRIS-
RVEADDSGVYYCGQNIQFPLTFGQG

TKLEIK
```

33b Kappa 2 (SEQ ID NO: 435)

```
GTGATGATGCAgACTCCACTGTCCCT-
GTCCGTCAGCCCTGGAGAGCCGGCCT

CCATCTCCTGCAAGGCCAGTCAGAGC-
CTCCTGCACAGGGATGGGAACACCTA

TGTGTATTGGTTCCGACAGAAGTCAGGC-
CAGTCTCCAGAGGGCCTGATCTAT

AGGATGTCCAACCGCTTCACTGGCGTGT-
CAGACAGGTTCAGTGGCAGCGGGT

CAGGGACGGATTTCACCCTGAGAATCAG-
CAGAGTGGAGGCTGACGATGCTGG

AGTTTATTACTGCGGGCAAGGTCTA-
CACTTTCCTCGGGCATTCGGAGCAGGA

ACCAAGGTGGACCTCAAA
```
(SEQ ID NO: 436)

```
VMMQTPLSLSVSPGEPASISCKASQSLL-
HRDGNTYVYWFRQKSGQSPEGLIY

RMSNRFTGVSDRFSGSGSGTDFTLRIS-
RVEADDAGVYYCGQGLHFPRAFGAG

TKVDLK
```

27b Vkap2 (SEQ ID NO: 437)

```
GTGATGATGCAGACTCCACTGTCCCT-
GTCCGTCAGCCCTGGAGAGACTGCCT

CCATCTCTTGTAAGGCCAGTCAGAGC-
CTCCTGCACAGTGATGGGAACACGTA

TTTGAATTGGTTCCGACAGAAGCCAGGC-
CAGTCTCCACAGCGTTTGATCTAT

AAGGTCTCCAACAGAGACACCGGGGTC-
CCAGACAGGTTCAGTGGCAGCGGGT

CAGGGACAGATTTCACCCTGAGAAATCAG-
CACAGTGGAGGCTATCGATACTGG

AATTTATTACTGTGGACAAAATATC-
CACTTTCCTCTTACGTTCGGCCAAGGG

ACCAAGCTGGAGATCAAA
```
(SEQ ID NO: 438)

```
VMMQTPLSLSVSPGETASISCKASQS-
LLHSDGNTYLNWERQKPGQSPQRLIY

KVSNRDTG VPDRFSGSGSGTDFTLKI-
STVEAIDTGIYYCGQNIHFPLTFGQ

GTKLEIK
```

20b K2 (SEQ ID NO: 439)

```
GTGATGATGCAgACCCCACTGTCCCT-
GTCCGTCAGCCCTGGAGAGCCGGCCT

CCATCTCCTGCAAGGCCAGTCAGAAC-
CTCCTGCACAGTAATGGGAACACCTA

TTTGTATTGGTTCCGACAGAGGCCAGGC-
CAGTCTCCAGAGGGCCTGATCTAT

AAGGTGTCCAACCGCTTCACTGGCGTGT-
CAGACAGGTTCAGTGGCAGCGGGT

CAGGGACAGATTTCACCCTGAGAATCAG-
CAGAGTGGAGGCTGACGATACTGG

AGTTTATTACTGCGGGCACGGTATA-
GAGTTTCCTTATACTTTCGGCCAGGGA

ACCAAGCTGGAGATCAAA
```
(SEQ ID NO: 440)

```
VMMQTPLSLSVSPGEPASISCKASQN-
LLHSNGNTYLYWFRQRPGQSPEGLIY

KVSNRFTGVSDRFSGSGSGTDFTLRIS-
RVEADDTGVYYCGHGIEFPYTFGQG

TKLEIK
```

16b K2 (SEQ ID NO: 441)

```
GTGATGATGCAGACTCCACTGTCCCT-
GTCCGTCAGCCCTGGAGAGCCGGCCT

CCATCTCCTGCAAGGCCAGTCAGAGC-
CTCCTGCACAGGGATGGGAACACCTA

TGTGTATTGGTTCCGACAGAAGTCAGGC-
CAGTCTCCAGAGGGCCTGATCTAT

AGGATGTCCAACCGCTTCACTGGCGTGT-
CAGACAGGTTCAGTGGCAGCGGGT

CAGGGACGGATTTCACCCTGAGAATCAG-
CAGAGTGGAGGCTGACGATGCTGG

AGTTTATTACTGCGGGCAAGGTCTA-
CACTTTCCTCGGGCATTCGGAGCAGGA

ACCAAGGTGGACCTCAAA
```
(SEQ ID NO: 442)

```
VMMQTPLSLSVSPGEPASISCKASQSLL-
HRDGNTYVYWFRQKSGQSPEGLIY

RMSNRFTGVSDRFSGSGSGTDFTLRIS-
RVEADDAGVYYCGQGLHFPRAFGAG

TKVDLK
```

11b K2 (SEQ ID NO: 443)

```
GTGATGATGCAgACTCCACTGTCCCTG-
GCCGTCACCCCTGGAGAGCTGGCCA

CTATCTACTGCAGGGCCAGTCA-
GAGTCTCCTGCACAGTGATGGAAAATCCTA

TTTGAGTTGGTACCTGCAGAAGCCAGGC-
CAGACTCCTCGGCCGCTGATTTAT

GAGGCTTCCAAGCGTTTCTCTGGGGTCT-
CAGACAGGTTCAGTGGCAGCGGGT

CAGGGACAGATTTCACCCTTAAAAT-
CAGCGGGGTGGAGGCTGGGGATGTTGG

AGTTTATTACTGCCAGCAAAGTCTA-
CATTTTCCGGGGACTTTCAgCCAGGGA

ACCAAGCTGGAgATCAAA
```
(SEQ ID NO: 444)

```
VMMQTPLSLAVTPGELATIYCRASQS-
LLHSDGKSYLSWYLQKPGQTPRPLIY
```

-continued

EASKRFSGVSDRFSGSGSGTDFTLKIS-
GVEAGDVGVYYCQQSLHFPGTFSQG

TKLEIK

Having described preferred embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

What is claimed is:

1. A method for preparing nucleotides of single-chain variable fragments (scFv) encoding an antigen-specific binding domain, comprising the steps of:
   a) isolating RNA encoding an antibody from splenocytes or lymphocytes of a non-immunized canine, or a canine immunized with a specific antigen;
   b) generating cDNAs of the isolated RNA;
   c) amplifying the variable regions of the antibody's heavy chain and the lambda and kappa light chains to generate $V_L$ and $V_H$ amplicons using PCR with a set of primers designed for the variable regions,
   wherein the set of primers include at least one pair of $V_H$ chain primers, at least one pair of $V_L$ lambda chain primers and at least one pair of $V_L$ kappa chain primers,
   wherein the at least one pair of $V_H$ chain primers comprises at least one VH chain forward primer and one $V_H$ chain reverse primer, wherein the at least one pair of $V_L$ lambda chain primers comprises at least one $V_L$ lambda chain forward primer and at least one $V_L$ lambda chain reverse primer, wherein the at least one pair of $V_L$ kappa chain primers comprises at least one $V_L$ kappa chain forward primer and at least one $V_L$ kappa chain reverse primer,
   wherein the at least one $V_H$ chain forward primer is selected from the group consisting of SEQ ID Nos. 1-7, wherein the one $V_H$ chain reverse primer is SEQ ID No. 8,
   wherein the at least one $V_L$ lambda chain forward primer is selected from the group consisting of SEQ ID Nos. 9-21, wherein the at least one $V_L$ lambda chain reverse primer is selected from the group consisting of SEQ ID Nos. 22-23,
   wherein the at least one $V_L$ kappa chain forward primer is selected from the group consisting of SEQ ID Nos. 24-27, wherein the at least one $V_L$ kappa chain reverse primer is selected from the group consisting of SEQ ID Nos. 28-31,
   wherein the primers are designed to incorporate secondary primer binding sites into the 5' end of the $V_L$ amplicons and the 3' end of the $V_H$ amplicons and a flexible linker into the 3' end of the $V_L$ amplicons and the 5' end of the $V_H$ amplicons; and
   d) using the flexible linker, randomly linking the $V_H$ and $V_L$ amplicons, thereby generating nucleotides encoding single-chain variable fragments.

2. The method of claim 1, whereby splenocytes or lymphocytes are from dogs that have been actively immunized by vaccination or by natural exposure to antigen.

3. The method of claim 1, whereby said forward primers are based on the predicted nucleotide or amino acid sequence of canine framework region 1 (FR1) and constant IgG region of Ig VH chains.

4. The method of claim 1, whereby said reverse primers are based on the predicted nucleotide or amino acid sequence of canine framework region 1 (FR1) and framework region 4 (FR4) of VL lambda (λ) and kappa (κ), chains or their combination.

5. The method of claim 1, further comprising the step of cloning the nucleotides encoding the single-chain variable fragments into DNA constructs.

6. The method of claim 5, whereby the DNA constructs are plasmids, phagemids, or expression cassettes.

7. The method of claim 1, whereby splenocytes or lymphocytes of a non-immunized canine, are taken from a canine afflicted with a cancer.

8. The method of claim 7, whereby the cancer is hemangiosarcoma, osteosarcoma, malignant melanoma, mammary carcinoma, or any other form of epithelial, mesenchymal or hematopoeitic cancer or combination thereof.

9. The method of claim 1, whereby the antigen is a tumor associated antigen, (TAA).

10. The method of claim 1 whereby the antigen is a bacterial, fungal, parasitic or viral antigen.

11. The method of claim 1 whereby the antigen is a cytokine, chemokine or other soluble protein that contributes to inflammatory responses.

* * * * *